US011584751B1

(12) United States Patent
Ren et al.

(10) Patent No.: US 11,584,751 B1
(45) Date of Patent: Feb. 21, 2023

(54) SUBSTITUTED IMIDAZOLES AS GLP-1 RECEPTOR AGONISTS

(71) Applicant: Eccogene (Shanghai) Co., Ltd., Shanghai (CN)

(72) Inventors: Zaifang Ren, Shanghai (CN); Xuefeng Sun, Shanghai (CN); Jingye Zhou, Shanghai (CN); Qing Xu, Shanghai (CN)

(73) Assignee: Eccogene (Shanghai) Co., Ltd., Shanghai (CN)

( * ) Notice: Subject to any disclaimer, the term of this patent is extended or adjusted under 35 U.S.C. 154(b) by 67 days.

(21) Appl. No.: 17/516,932

(22) Filed: Nov. 2, 2021

Related U.S. Application Data

(63) Continuation of application No. 17/380,084, filed on Jul. 20, 2021.

(30) Foreign Application Priority Data

Jul. 20, 2020 (WO) ................ PCT/CN2020/102955
Jan. 4, 2021 (WO) ................ PCT/CN2021/070120

(51) Int. Cl.

| | |
|---|---|
| *A61K 31/4166* | (2006.01) |
| *C07D 233/04* | (2006.01) |
| *C07D 487/04* | (2006.01) |
| *C07D 519/00* | (2006.01) |

(52) U.S. Cl.

CPC ......... *C07D 487/04* (2013.01); *C07D 519/00* (2013.01)

(58) Field of Classification Search

CPC .......................... A61K 31/4166; C07D 233/04
USPC ........................................ 514/398; 548/347.1
See application file for complete search history.

(56) References Cited

U.S. PATENT DOCUMENTS

2019/0225604 A1* 7/2019 Yoshino .................. A61P 25/28

FOREIGN PATENT DOCUMENTS

WO WO 2019/166951 A1 9/2019

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Wolff, Manfred E., Ed. Burger's Medicinal Chemistry and Drug Discovery—Fifth Edition, vol. 1: Principles and Practice, New York: John Wiley & Sons, 1994, 975-977.*
Hackam, et al. JAMA, 296(14), 2006, 1731-1732.*

* cited by examiner

*Primary Examiner* — Douglas M Willis
(74) *Attorney, Agent, or Firm* — Cooley LLP; Chen Chen; Heng Zhang

(57) ABSTRACT

The application relates to a compound of Formula (I):

(I)

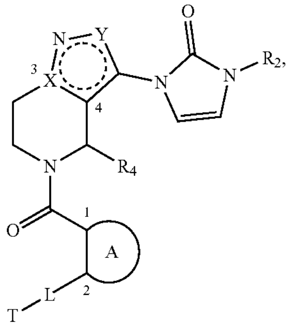

or a pharmaceutically acceptable salt, hydrate, solvate, prodrug, stereoisomer, or tautomer thereof, which modulates the activity of GLP-1 receptor, a pharmaceutical composition comprising a compound of Formula (I), and a method of treating or preventing a disease in which GLP-1 receptor plays a role.

25 Claims, No Drawings

SUBSTITUTED IMIDAZOLES AS GLP-1 RECEPTOR AGONISTS

RELATED APPLICATIONS

This application is a continuation of U.S. application Ser. No. 17/380,084, filed on Jul. 20, 2021, which claims the benefit of and priority to International Application No. PCT/CN2020/102955, filed on Jul. 20, 2020, and International Application No. PCT/CN2021/070120, filed on Jan. 4, 2021, the entire contents of each of which are incorporated herein by reference in their entireties.

BACKGROUND

Glucagon-like peptide-1 (GLP-1) is an incretin of 30 or 31 amino acids, secreted from L cells in the small intestine. GLP-1 exerts a wide range of effects through the GLP-1 receptor, such as promotion of glucose dependent insulin secretion, inhibition of glucagon secretion, delay of gastric emptying, and suppression of feeding. Accordingly, GLP-1 analogs display potent effects in HbA1c reduction and weight loss, and have been developed as effective therapeutic agents for treatment of diabetes and obesity. GLP-1 analogs also demonstrate efficacy on improving cardiovascular outcomes and retaining renal functions in diabetic patients, thus providing therapeutic opportunities for a variety of metabolic disorders and related comorbidities. Recently, Liraglutide and Semaglutide treatment is shown to decrease liver fat and boost NASH resolution in clinical trials, suggesting potential utility for NASH. However, most of these GLP-1 analogs require an invasive subcutaneous administration. Semaglutide in specific formulation can be administrated via oral route, but still suffers from inconvenient dosing regimen and poor bioavailability. Improving metabolic stability and bioavailability of GLP-1 analogs is challenging, likely due to their peptidic nature.

Currently, there is no approved small molecule GLP-1 receptor agonist for the treatment of diabetes or other metabolic disorders where GLP-1 receptor plays a role. Thus, there is a need for small molecule GLP-1 receptor agonists as therapeutic options for the treatment of these disorders. The present application addresses the need.

SUMMARY

The present application provides novel GLP-1 receptor ligands which are useful in the treatment of a disease or disorder in which GLP-1 receptor plays a role, such as those described herein, including but not limited to diabetes, obesity, overweight condition, hyperlipidemia, hypercholesteremia, hypertriglyceridemia, atherosclerosis, hypertension, stroke, coronary heart disease, congestive heart failure, cardiac arrhythmias, diabetic kidney disease, dementia, Parkinson's disease, Alzheimer's disease, and liver diseases such as nonalcoholic fatty liver disease (NAFLD) and nonalcoholic steatohepatitis (NASH).

A first aspect of the application relates to a compound of Formula (I):

(I)

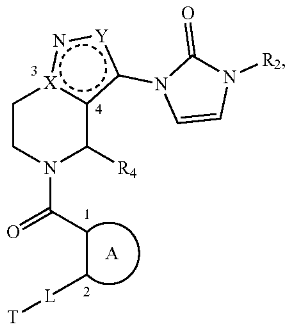

or a pharmaceutically acceptable salt, solvate, prodrug, stereoisomer, or tautomer thereof, wherein A, X, Y, T, L, $R_2$, and $R_4$ are as described in detail below.

Another aspect of the application relates to a pharmaceutical composition comprising a compound of Formula (I) or a compound described herein, or a pharmaceutically acceptable salt, solvate, prodrug, stereoisomer, or tautomer thereof, and a pharmaceutically acceptable diluent, excipient, or carrier.

Another aspect of the application relates to a method of treating or preventing a GLP-1 receptor-mediated disease or disorder (e.g., a disease or disorder in which GLP-1 receptor plays a role or which is associated with modulation of GLP-1 receptor), as described herein (e.g., diabetes, obesity, overweight condition, hyperlipidemia, hypercholesteremia, hypertriglyceridemia, atherosclerosis, hypertension, stroke, coronary heart disease, congestive heart failure, cardiac arrhythmias, diabetic kidney disease, dementia, Parkinson's disease, Alzheimer's disease, and liver diseases such as NAFLD and NASH). The method comprises administering to a subject in need of such a treatment a therapeutically effective amount of a compound of Formula (I) or a compound described herein, or a pharmaceutically acceptable salt, solvate, prodrug, stereoisomer, or tautomer thereof, or a therapeutically effective amount of a pharmaceutical composition comprising a compound of Formula (I) or a compound described herein, or a pharmaceutically acceptable salt, solvate, prodrug, stereoisomer, or tautomer thereof, and a pharmaceutically acceptable diluent, excipient, or carrier.

Another aspect of the application relates to a method of modulating (e.g., activating or stimulating) GLP-1 receptor. The method comprises administering to a subject in need of such modulation a therapeutically effective amount of a compound of Formula (I) or a compound described herein, or a pharmaceutically acceptable salt, solvate, prodrug, stereoisomer, or tautomer thereof, or a therapeutically effective amount of a pharmaceutical composition comprising a compound of Formula (I) or a compound described herein, or a pharmaceutically acceptable salt, solvate, prodrug, stereoisomer, or tautomer thereof, and a pharmaceutically acceptable diluent, excipient, or carrier.

Another aspect of the application relates to a compound of Formula (I) or a compound described herein, or a pharmaceutically acceptable salt, solvate, prodrug, stereoisomer, or tautomer thereof, or a pharmaceutical composition comprising a compound of Formula (I) or a compound described herein, or a pharmaceutically acceptable salt, solvate, prodrug, stereoisomer, or tautomer thereof, and a pharmaceutically acceptable diluent, excipient, or carrier, for use in a method of treating or preventing a GLP-1 receptor-mediated disease or disorder or of modulating (e.g., activating or stimulating) GLP-1 receptor.

Another aspect of the application relates to use of a compound of Formula (I) or a compound described herein, or a pharmaceutically acceptable salt, solvate, prodrug, stereoisomer, or tautomer thereof, or a pharmaceutical composition comprising a compound of Formula (I) or a compound described herein, or a pharmaceutically acceptable salt, solvate, prodrug, stereoisomer, or tautomer thereof, and a pharmaceutically acceptable diluent, excipient, or carrier, in the manufacture of a medicament for treating or preventing a GLP-1 receptor-mediated disease or disorder or for modulating (e.g., activating or stimulating) GLP-1 receptor.

The present application provides modulators (e.g., agonists) of GLP-1 receptor that are therapeutic agents in the treatment of diseases such as diabetes, obesity, metabolic diseases, cardiovascular diseases, liver diseases, NASH, kidney diseases, neurodegenerative diseases, and other diseases or disorders associated with the modulation of GLP-1 receptor.

The present application further provides compounds and compositions with an improved therapeutic profile (e.g., efficacy, pharmacodynamics, safety) relative to known GLP-1 receptor agonists and alternative routes of administration, toward the treatment of various types of diseases including diabetes, obesity, metabolic diseases, cardiovascular diseases, liver diseases, NASH, kidney diseases, neurodegenerative diseases, and other diseases associated with the modulation of GLP-1 receptor.

DETAILED DESCRIPTION

Compounds of the Application

The present application relates to compounds and compositions thereof that are capable of modulating the activity of GLP-1 receptor. The application features methods of treating, preventing, or ameliorating a disease or disorder in which GLP-1 receptor plays a role by administering to a subject in need thereof a therapeutically effective amount of a compound of the present application, or a pharmaceutically acceptable salt, solvate, prodrug, stereoisomer, or tautomer thereof. The compounds of the present application can be used in the treatment of a variety of GLP-1-mediated diseases and disorders by stimulating GLP-1 receptor. Activation or stimulation of GLP-1 receptor provides treatment, prevention, or amelioration of diseases including, but not limited to, diabetes, obesity, metabolic diseases, cardiovascular diseases, liver diseases, nonalcoholic steatohepatitis (NASH), and other diseases associated with the modulation of GLP-1 receptor.

In a first aspect of the application, a compound of Formula (I) is described:

(I)

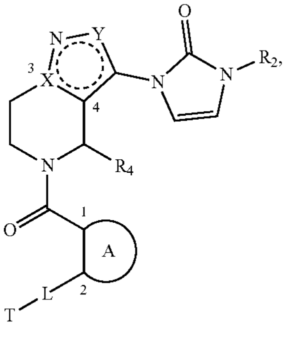

or a pharmaceutically acceptable salt, solvate, prodrug, stereoisomer, or tautomer thereof, wherein:

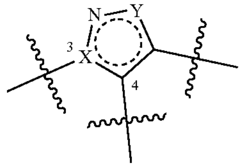

is

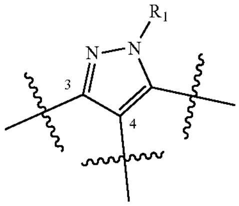

or

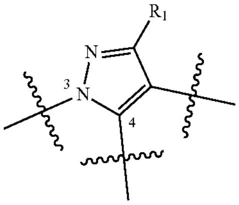

;

$R_1$ is $(CR_CR_C)_{0-2}$—$C_3$-$C_6$ cycloalkyl, $(CR_CR_C)_{0-2}$-phenyl, or $(CR_CR_C)_{0-2}$-heteroaryl comprising one 5- or 6-membered ring and 1-3 heteroatoms selected from N, O, and S, wherein the cycloalkyl, phenyl, or heteroaryl is optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy, OH, halogen, $NH_2$, NH—($C_1$-$C_6$ alkyl), N($C_1$-$C_6$ alkyl)$_2$, CN, $NO_2$, and $C_3$-$C_6$ cycloalkyl, wherein the cycloalkyl is a spiro-, bridged-, or mono-cycloalkyl;

each $R_C$ is independently H, $C_1$-$C_3$ alkyl, or $C_1$-$C_3$ haloalkyl;

$R_2$ is $C_3$-$C_{10}$ cycloalkyl, phenyl, heterocyclyl comprising one or two 5- or 6-membered rings and 1-3 heteroatoms selected from N, O, and S, or heteroaryl comprising one or two 5- or 6-membered rings and 1-3 heteroatoms selected from N, O, and S, wherein the cycloalkyl, phenyl, heterocyclyl, or heteroaryl is optionally substituted with one or more substituents independently selected from $C_1$-$C_6$ alkyl optionally substituted with $C_1$-$C_6$ alkoxy, $C_1$-$C_6$ haloalkyl, $C_1$-$C_6$ alkoxy, $C_1$-$C_6$ haloalkoxy, OH, halogen, $NH_2$, NH—($C_1$-$C_6$ alkyl), N($C_1$-$C_6$ alkyl)$_2$, CN, and $NO_2$, wherein the cycloalkyl is a spiro-, bridged-, or mono-cycloalkyl;

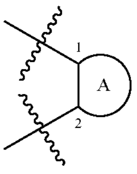

is a bicyclic heteroaryl ring selected from

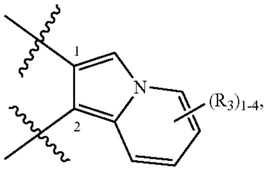

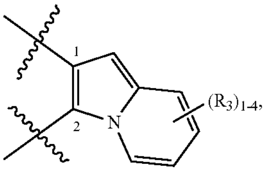

-continued

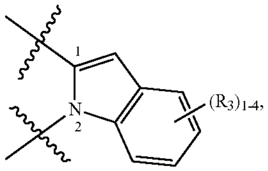
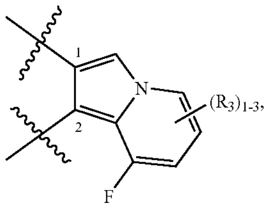
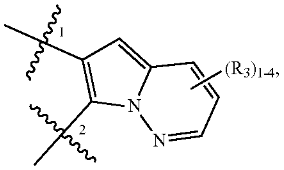
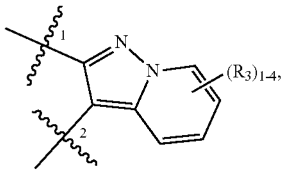
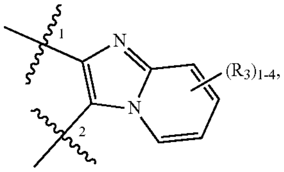
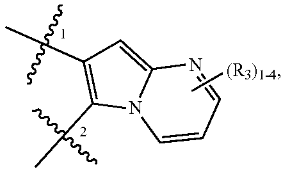
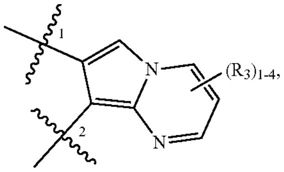
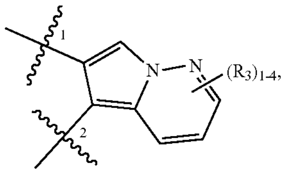
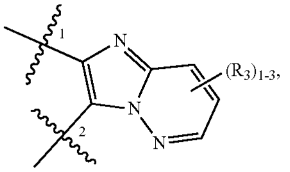
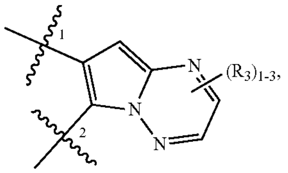
and
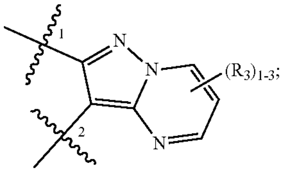

each $R_3$ is independently halogen, $C_3$-$C_{10}$ cycloalkyl, phenyl, heterocyclyl comprising one or two 3- to 6-membered rings and 1-3 heteroatoms selected from N, O, and S, or heteroaryl comprising one or two 5- or 6-membered rings and 1-3 heteroatoms selected from N, O, and S, wherein the cycloalkyl, phenyl, heterocyclyl, or heteroaryl is optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy, OH, halogen, $NH_2$, NH—($C_1$-$C_6$ alkyl), N($C_1$-$C_6$ alkyl)$_2$, CN, and $NO_2$, wherein the cycloalkyl is a spiro-, bridged-, or mono-cycloalkyl, provided that at least one $R_3$ is cycloalkyl, phenyl, heterocyclyl, or heteroaryl;

$R_4$ is $C_1$-$C_6$ alkyl, $C_1$-$C_6$ haloalkyl, $C_1$-$C_6$ alkoxy, $C_1$-$C_6$ haloalkoxy, NH—($C_1$-$C_6$ alkyl), N($C_1$-$C_6$ alkyl)$_2$ or CN;

L is

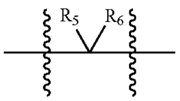

or phenylenyl, wherein the phenylenyl is optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy, and halogen, or wherein when the phenylenyl is substituted with two substituents attached to adjacent carbon atoms in the phenylenyl ring, the two substituents, together with the carbon atoms to which they are attached, may form a 5- or 6-membered ring optionally comprising 1-3 heteroatoms selected from N, O, and S;

$R_5$ and $R_6$ are each independently H, $C_1$-$C_6$ alkyl, $C_1$-$C_6$ haloalkyl, $C_1$-$C_6$ alkoxy, $C_1$-$C_6$ haloalkoxy, OH, or halogen, or $R_5$ and $R_6$, together with the carbon atom to which they are attached, form $C_3$-$C_6$ cycloalkyl optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy, OH, and halogen; and T is C(O)OH, ($CH_2$)NHS(O)$_2$—($C_1$-$C_6$ alkyl), or heteroaryl comprising one 5- or 6-membered ring and 1-3 heteroatoms selected from N, O, and S, wherein the heteroaryl is optionally substituted with $C_1$-$C_6$ alkyl, $C_1$-$C_6$ haloalkyl, $C_1$-$C_6$ alkoxy, $C_1$-$C_6$ haloalkoxy, OH, halogen, or oxo, and when L is

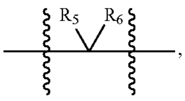,

T is not C(O)OH, or when L is phenylenyl substituted with two substituents attached to adjacent carbon atoms in the phenylenyl ring, and the two substituents, together with the carbon atoms to which they are attached, form a 5- or 6-membered ring, T is H, provided that when

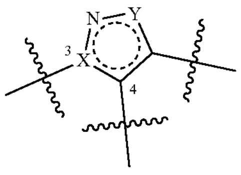
is
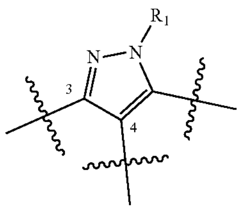,
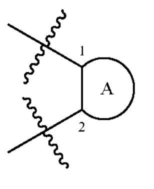
is
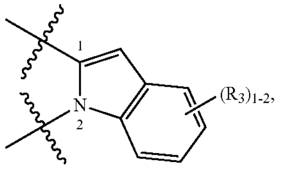

T is oxadiazolonyl, each $R_3$ is independently F, heterocyclyl comprising one or two 3- to 6-membered rings and 1-3 heteroatoms selected from N, O, and S, or heteroaryl comprising one or two 5- or 6-membered rings and 1-3 heteroatoms selected from N, O, and S, wherein the heterocyclyl or heteroaryl is optionally substituted, L is

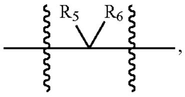, and $R_5$ and $R_6$, together with the carbon atom to which they are attached, form $C_3$-$C_6$ cycloalkyl, then the $C_3$-$C_6$ cycloalkyl is unsubstituted;

provided that when

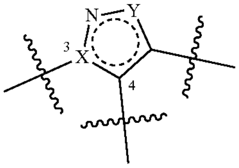 is 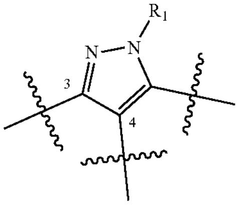,

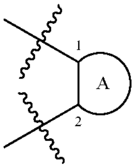 is 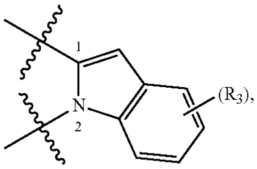

T is oxadiazolonyl, L is

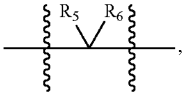, and $R_5$ and $R_6$, together with the carbon atom to which they are attached, form unsubstituted $C_3$-$C_6$ cycloalkyl, and $R_3$ is heterocyclyl comprising one 6-membered ring and 1-3 heteroatoms selected from N, O, and S, then $R_3$ is substituted;

provided that when

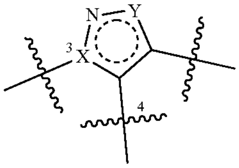 is 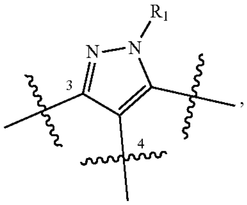,

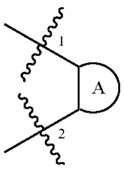 is 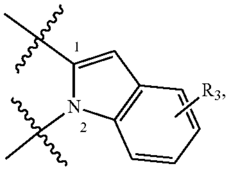

T is oxadiazolonyl, L is

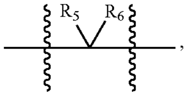, and $R_5$ and $R_6$ are each methyl, then $R_3$ is not heteroaryl comprising one 6-membered ring and 1-3 heteroatoms selected from N, O, and S; and provided that when

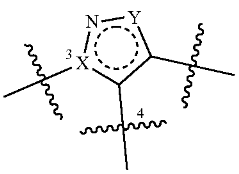 is 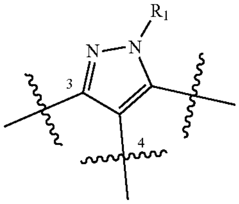,

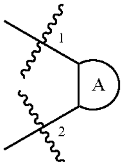 is 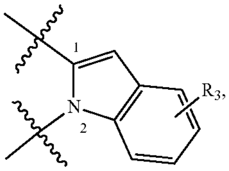

L is

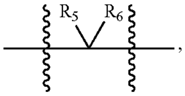, $R_5$ and $R_6$ are each H, and $R_3$ is heterocyclyl comprising one 6-membered ring and 1-3 heteroatoms selected from N, O, and S, then $R_3$ is substituted.

In some embodiments, the compounds of Formula (I) have the structure of Formula (Ia1), (Ia2), (Ia3), (Ia4), (Ia5), (Ia6), (Ia7), (Ia8), (Ia9), (Ia10), or (Ia11):

(Ia1)

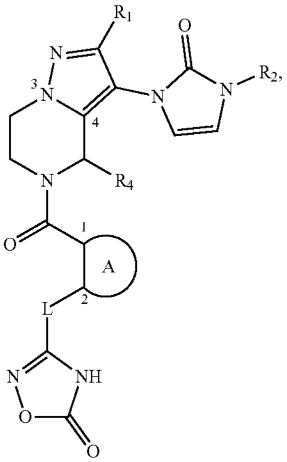

-continued
(Ia2)
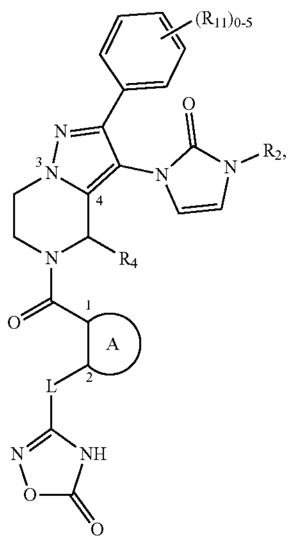
(Ia3)
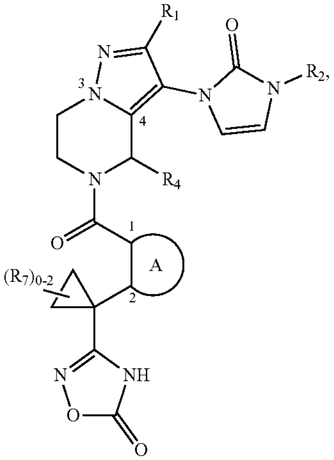
(Ia4)
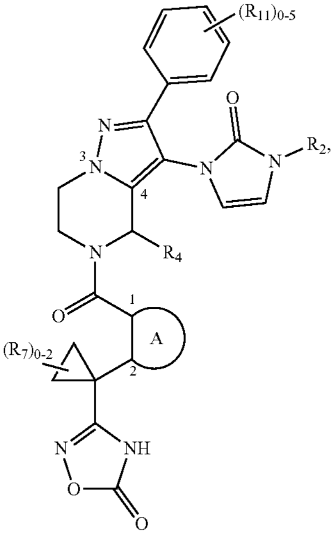
-continued
(Ia5)
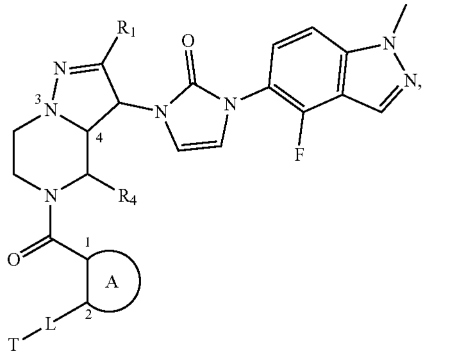
(Ia6)
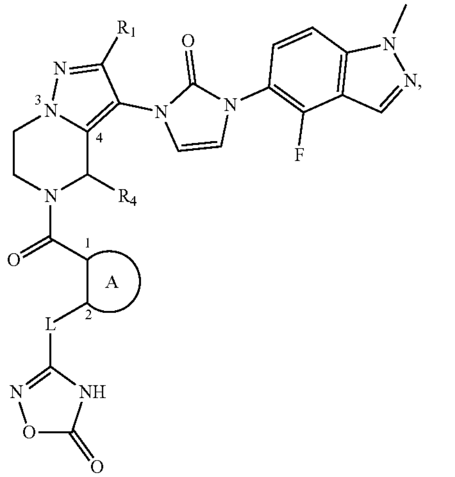
(Ia7)
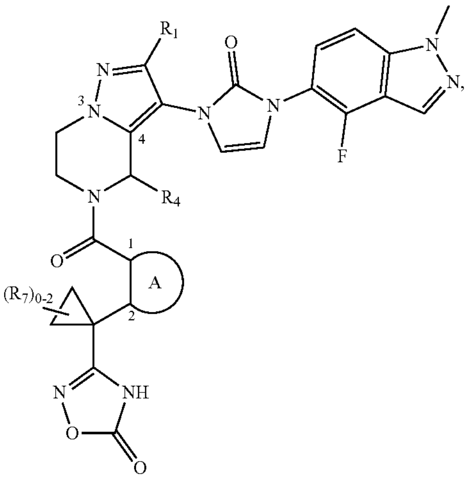

-continued (Ia8)

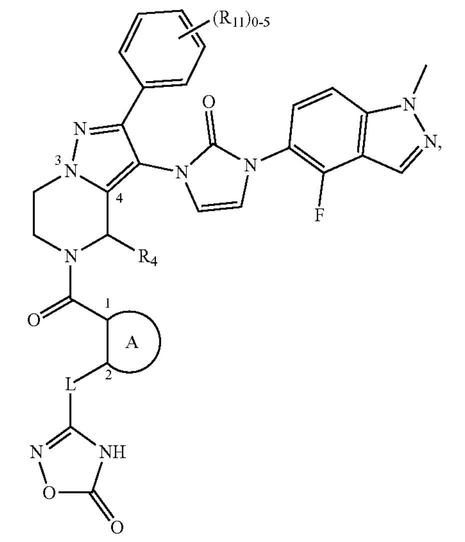

(Ia9)

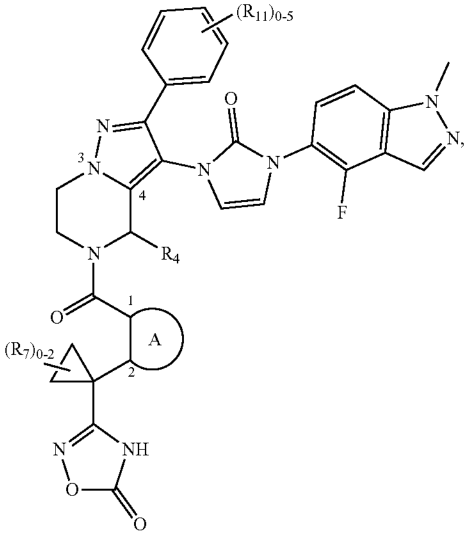

(Ia10)

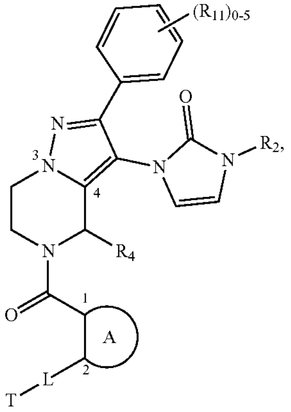

or

-continued (Ia11)

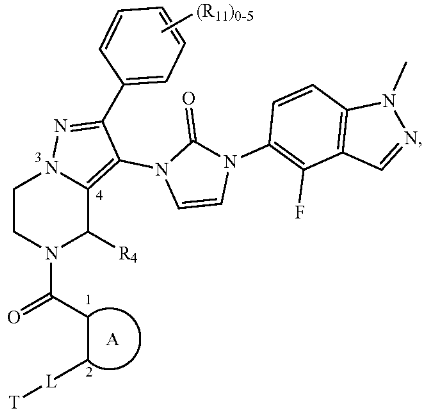

or a pharmaceutically acceptable salt, solvate, prodrug, stereoisomer, or tautomer thereof, wherein:

each $R_7$ is independently $C_1$-$C_6$ alkyl, $C_1$-$C_6$ haloalkyl, $C_1$-$C_6$ alkoxy, $C_1$-$C_6$ haloalkoxy, OH, or halogen; and each $R_{11}$ is independently $C_1$-$C_6$ alkyl, $C_1$-$C_6$ haloalkyl, $C_1$-$C_6$ alkoxy, $C_1$-$C_6$ haloalkoxy, OH, halogen, $NH_2$, NH—($C_1$-$C_6$ alkyl), N($C_1$-$C_6$ alkyl)$_2$, CN, $NO_2$, or $C_3$-$C_6$ cycloalkyl.

In some embodiments, the compounds of Formula (I) have the structure of Formula (Ib1), (Ib2), (Ib3), (Ib4), (Ib5), (Ib6), (Ib7), (Ib8), (Ib9), (Ib10), or (Ib11):

(Ib1)

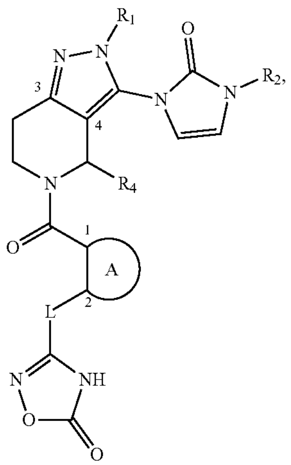

-continued
(Ib2)
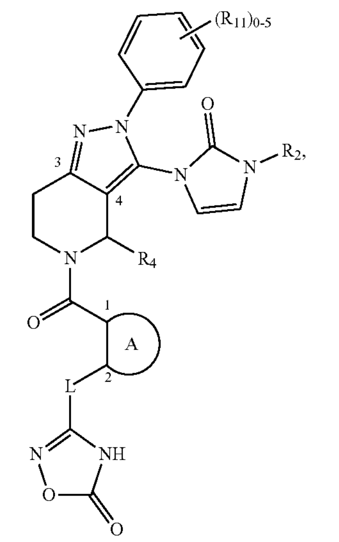
(Ib3)
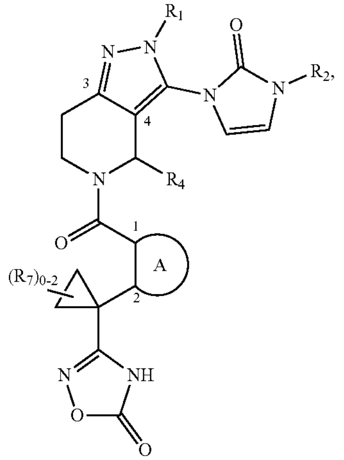
(Ib4)
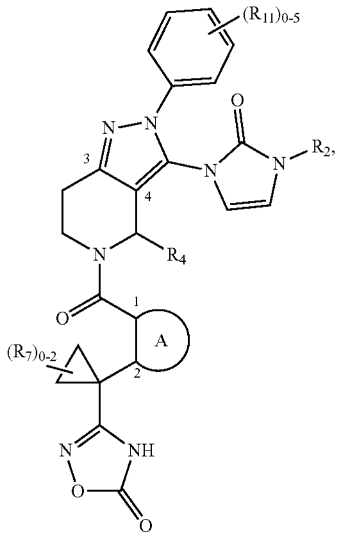
-continued
(Ib5)
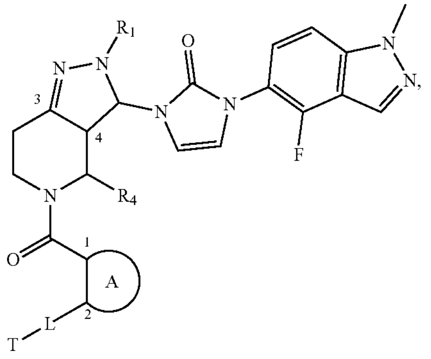
(Ib6)
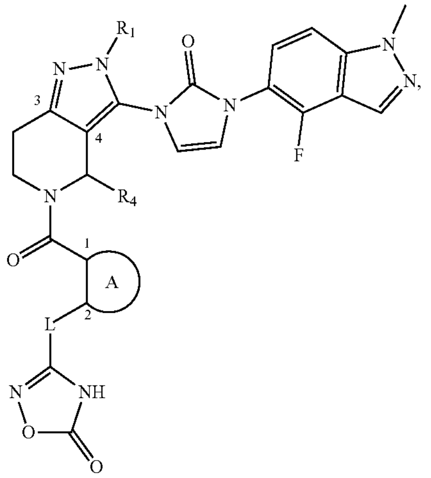
(Ib7)
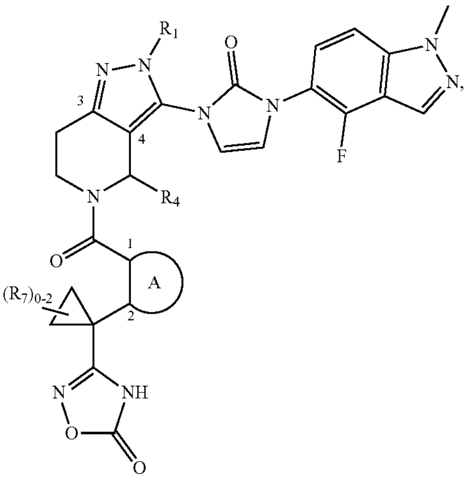

-continued (Ib8)

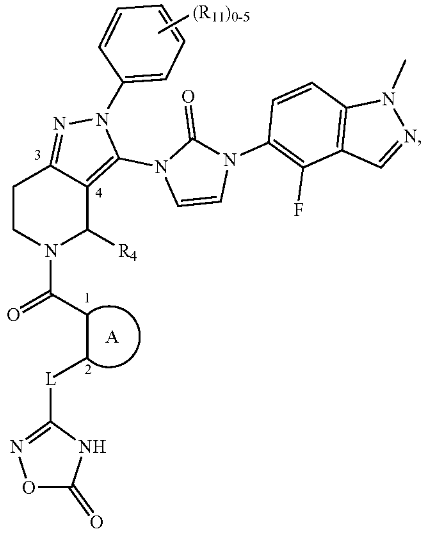

(Ib9)

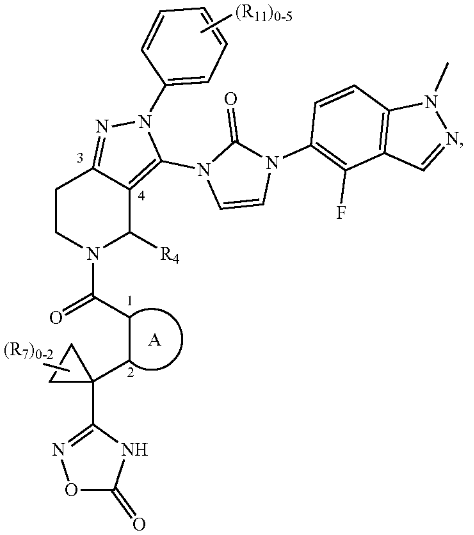

(Ib10)

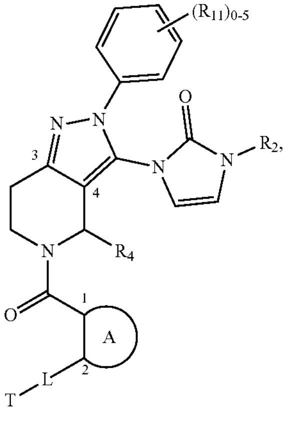

or

-continued (Ib11)

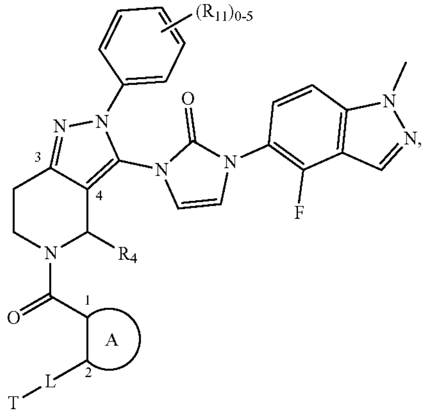

or a pharmaceutically acceptable salt, solvate, prodrug, stereoisomer, or tautomer thereof, wherein:

each $R_7$ is independently $C_1$-$C_6$ alkyl, $C_1$-$C_6$ haloalkyl, $C_1$-$C_6$ alkoxy, $C_1$-$C_6$ haloalkoxy, OH, or halogen; and each $R_{11}$ is independently $C_1$-$C_6$ alkyl, $C_1$-$C_6$ haloalkyl, $C_1$-$C_6$ alkoxy, $C_1$-$C_6$ haloalkoxy, OH, halogen, $NH_2$, NH—($C_1$-$C_6$ alkyl), $N(C_1$-$C_6$ alkyl$)_2$, CN, $O_2$, or $C_3$-$C_6$ cycloalkyl.

For each of the formulae described herein, where applicable:

In some embodiments,

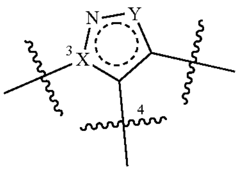

is

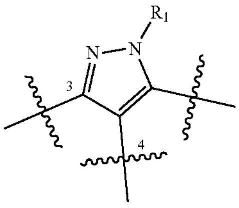

,

In some embodiments,

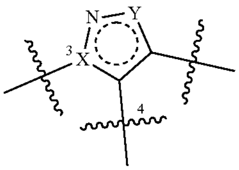

is

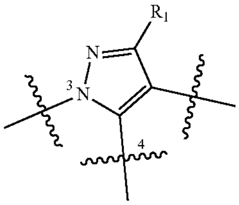

,

In some embodiments, $R_1$ is $(CR_CR_C)_{0-2}$-phenyl substituted with one or more substituents independently selected from straight-chain $C_1$-$C_6$ alkyl or branched $C_3$-$C_6$ alkyl (e.g., methyl, ethyl, propyl, i-propyl, n-butyl, i-butyl, s-butyl, t-butyl, pentyl, or hexyl), straight-chain $C_1$-$C_6$ haloalkyl or branched $C_3$-$C_6$ haloalkyl (e.g., methyl, ethyl, propyl, i-propyl, n-butyl, i-butyl, s-butyl, t-butyl, pentyl, or hexyl, each of which is substituted with one or more halogen (e.g., F, Cl)), straight-chain $C_1$-$C_6$ alkoxy or branched $C_3$-$C_6$ alkoxy (e.g., methoxy, ethoxy, propoxy, i-propoxy, n-butoxy, i-butoxy, s-butoxy, t-butoxy, pentoxy, or hexyloxy), straight-chain $C_1$-$C_6$ haloalkoxy or branched $C_3$-$C_6$ haloalkoxy (e.g., methoxy, ethoxy, propoxy, i-propoxy, n-butoxy, i-butoxy, s-butoxy, t-butoxy, pentoxy, or hexyloxy, each of which is substituted with one or more halogen (e.g., F, Cl)), OH, halogen (e.g., F, Cl, Br, or I), $NH_2$, NH—($C_1$-$C_6$ alkyl) (e.g., methyl, ethyl, propyl, i-propyl, n-butyl, i-butyl, s-butyl, t-butyl, pentyl, or hexyl), N($C_1$-$C_6$ alkyl)$_2$ (e.g., methyl, ethyl, propyl, i-propyl, n-butyl, i-butyl, s-butyl, t-butyl, pentyl, or hexyl), CN, $NO_2$, and $C_3$-$C_6$ cycloalkyl ((e.g., cyclopropyl, cyclobutyl, cyclopentyl, or cyclohexyl).

In some embodiments, $R_1$ is $(CR_CR_C)_{0-2}$-phenyl substituted with one or more substituents independently selected from straight-chain $C_1$-$C_4$ alkyl or branched $C_3$-$C_4$ alkyl (e.g., methyl, ethyl, propyl, i-propyl, n-butyl, i-butyl, s-butyl, or t-butyl), straight-chain $C_1$-$C_4$ haloalkyl or branched $C_3$-$C_4$ haloalkyl (e.g., methyl, ethyl, propyl, i-propyl, n-butyl, i-butyl, s-butyl, or t-butyl, each of which is substituted with one or more halogen (e.g., F, Cl)), straight-chain $C_1$-$C_4$ alkoxy or branched $C_3$-$C_4$ alkoxy (e.g., methoxy, ethoxy, propoxy, i-propoxy, n-butoxy, i-butoxy, s-butoxy, or t-butoxy), straight-chain $C_1$-$C_4$ haloalkoxy or branched $C_3$-$C_4$ haloalkoxy (e.g., methoxy, ethoxy, propoxy, i-propoxy, n-butoxy, i-butoxy, s-butoxy, or t-butoxy, each of which is substituted with one or more halogen (e.g., F, Cl)), OH, halogen (e.g., F, Cl, Br, or I), $NH_2$, NH—($C_1$-$C_4$ alkyl) (e.g., methyl, ethyl, propyl, i-propyl, n-butyl, i-butyl, s-butyl, or t-butyl), N($C_1$-$C_4$ alkyl)$_2$ (e.g., methyl, ethyl, propyl, i-propyl, n-butyl, i-butyl, s-butyl, or t-butyl), CN, $NO_2$, and $C_3$-$C_6$ cycloalkyl ((e.g., cyclopropyl, cyclobutyl, cyclopentyl, or cyclohexyl).

In some embodiments, $R_1$ is $(CR_CR_C)_{0-2}$-phenyl substituted with one or more substituents independently selected from straight-chain $C_1$-$C_4$ alkyl or branched $C_3$-$C_4$ alkyl (e.g., methyl, ethyl, propyl, i-propyl, n-butyl, i-butyl, s-butyl, or t-butyl), straight-chain $C_1$-$C_4$ haloalkyl or branched $C_3$-$C_4$ haloalkyl (e.g., methyl, ethyl, propyl, i-propyl, n-butyl, i-butyl, s-butyl, or t-butyl, each of which is substituted with one or more halogen (e.g., F, Cl)), straight-chain $C_1$-$C_4$ alkoxy or branched $C_3$-$C_4$ alkoxy (e.g., methoxy, ethoxy, propoxy, i-propoxy, n-butoxy, i-butoxy, s-butoxy, or t-butoxy), straight-chain $C_1$-$C_4$ haloalkoxy or branched $C_3$-$C_4$ haloalkoxy (e.g., methoxy, ethoxy, propoxy, i-propoxy, n-butoxy, i-butoxy, s-butoxy, or t-butoxy, each of which is substituted with one or more halogen (e.g., F, Cl)), and halogen (e.g., F, Cl, Br, or I).

In some embodiments, $R_1$ is $(CR_CR_C)_{0-2}$-phenyl substituted with one, two, or three substituents as described herein.

In some embodiments, $R_1$ is $(CR_CR_C)_{0-2}$-phenyl substituted with one, two, or three substituents selected from methyl, methoxy, $CF_3$, F, and Cl.

In some embodiments, $R_1$ is $(CR_CR_C)_{0-1}$-phenyl substituted with one or more substituents as described herein.

In some embodiments, $R_1$ is $(CR_CR_C)_{0-1}$-phenyl substituted with one, two, or three substituents as described herein.

In some embodiments, $R_1$ is $(CR_CR_C)_{0-1}$-phenyl substituted with one, two, or three substituents selected from methyl, methoxy, $CF_3$, F, and Cl.

In some embodiments, $R_1$ is phenyl substituted with one or more substituents as described herein.

In some embodiments, $R_1$ is phenyl substituted with one, two, or three substituents as described herein.

In some embodiments, $R_1$ is phenyl substituted with one, two, or three substituents selected from methyl, methoxy, $CF_3$, F, and Cl.

In some embodiments, $R_1$ is $CR_CR_C$-phenyl substituted with one or more substituents as described herein.

In some embodiments, $R_1$ is $CR_CR_C$-phenyl substituted with one, two, or three substituents as described herein.

In some embodiments, $R_1$ is $CR_CR_C$-phenyl substituted with one, two, or three substituents selected from methyl, $CF_3$, F, and Cl.

In some embodiments, $R_1$ is $(CR_CR_C)_{0-2}$—$C_3$-$C_6$ cycloalkyl (e.g., cyclopropyl, cyclobutyl, cyclopentyl, cyclohexyl, bicyclobutanyl, bicyclopentanyl, or bicyclohexanyl) optionally substituted with one or more substituents independently selected from straight-chain $C_1$-$C_6$ alkyl or branched $C_3$-$C_6$ alkyl (e.g., methyl, ethyl, propyl, i-propyl, n-butyl, i-butyl, s-butyl, t-butyl, pentyl, or hexyl), straight-chain $C_1$-$C_6$ haloalkyl or branched $C_3$-$C_6$ haloalkyl (e.g., methyl, ethyl, propyl, i-propyl, n-butyl, i-butyl, s-butyl, t-butyl, pentyl, or hexyl, each of which is substituted with one or more halogen (e.g., F, Cl)), straight-chain $C_1$-$C_6$ alkoxy or branched $C_3$-$C_6$ alkoxy (e.g., methoxy, ethoxy, propoxy, i-propoxy, n-butoxy, i-butoxy, s-butoxy, t-butoxy, pentoxy, or hexyloxy), straight-chain $C_1$-$C_6$ haloalkoxy or branched $C_3$-$C_6$ haloalkoxy (e.g., methoxy, ethoxy, propoxy, i-propoxy, n-butoxy, i-butoxy, s-butoxy, t-butoxy, pentoxy, or hexyloxy, each of which is substituted with one or more halogen (e.g., F, Cl)), OH, halogen (e.g., F, Cl, Br, or I), $NH_2$, NH—($C_1$-$C_6$ alkyl) (e.g., methyl, ethyl, propyl, i-propyl, n-butyl, i-butyl, s-butyl, t-butyl, pentyl, or hexyl), N($C_1$-$C_6$ alkyl)$_2$ (e.g., methyl, ethyl, propyl, i-propyl, n-butyl, i-butyl, s-butyl, t-butyl, pentyl, or hexyl), CN, $NO_2$, and $C_3$-$C_6$ cycloalkyl ((e.g., cyclopropyl, cyclobutyl, cyclopentyl, or cyclohexyl).

In some embodiments, $R_1$ is $(CR_CR_C)_{0-2}$—$C_3$-$C_6$ cycloalkyl (e.g., cyclopropyl, cyclobutyl, cyclopentyl, cyclohexyl, bicyclobutanyl, bicyclopentanyl, or bicyclohexanyl) optionally substituted with one or more substituents independently selected from straight-chain $C_1$-$C_4$ alkyl or branched $C_3$-$C_4$ alkyl (e.g., methyl, ethyl, propyl, i-propyl, n-butyl, i-butyl, s-butyl, or t-butyl), straight-chain $C_1$-$C_4$ haloalkyl or branched $C_3$-$C_4$ haloalkyl (e.g., methyl, ethyl, propyl, i-propyl, n-butyl, i-butyl, s-butyl, or t-butyl, each of which is substituted with one or more halogen (e.g., F, Cl)), straight-chain $C_1$-$C_4$ alkoxy or branched $C_3$-$C_4$ alkoxy (e.g., methoxy, ethoxy, propoxy, i-propoxy, n-butoxy, i-butoxy, s-butoxy, or t-butoxy), straight-chain $C_1$-$C_4$ haloalkoxy or branched $C_3$-$C_4$ haloalkoxy (e.g., methoxy, ethoxy, propoxy, i-propoxy, n-butoxy, i-butoxy, s-butoxy, or t-butoxy, each of which is substituted with one or more halogen (e.g., F, Cl)), OH, halogen (e.g., F, Cl, Br, or I), $NH_2$, NH—($C_1$-$C_4$ alkyl) (e.g., methyl, ethyl, propyl, i-propyl, n-butyl, i-butyl, s-butyl, or t-butyl), N($C_1$-$C_4$ alkyl)$_2$ (e.g., methyl, ethyl, propyl, i-propyl, n-butyl, i-butyl, s-butyl, or t-butyl), CN, $NO_2$, and $C_3$-$C_6$ cycloalkyl ((e.g., cyclopropyl, cyclobutyl, cyclopentyl, or cyclohexyl).

In some embodiments, $R_1$ is $(CR_CR_C)_{0-2}$—$C_3$-$C_6$ cycloalkyl (e.g., cyclopropyl, cyclobutyl, cyclopentyl, cyclohexyl, bicyclobutanyl, bicyclopentanyl, or bicyclohexanyl) optionally substituted with one, two, or three substituents as described herein.

In some embodiments, $R_1$ is $(CR_CR_C)_{0-2}$—$C_3$-$C_6$ cycloalkyl (e.g., cyclopropyl, cyclobutyl, cyclopentyl, cyclohexyl, bicyclobutanyl, bicyclopentanyl, or bicyclohexanyl) optionally substituted with one, two, or three substituents selected from methyl, methoxy, $CF_3$, F, and $C_1$.

In some embodiments, $R_1$ is $(CR_CR_C)_{0-1}$—$C_3$-$C_6$ cycloalkyl (e.g., cyclopropyl, cyclobutyl, cyclopentyl, cyclohexyl, bicyclobutanyl, bicyclopentanyl, or bicyclohexanyl) optionally substituted with one or more substituents as described herein.

In some embodiments, $R_1$ is $(CR_CR_C)_{0-1}$—$C_3$-$C_6$ cycloalkyl (e.g., cyclopropyl, cyclobutyl, cyclopentyl, cyclohexyl, bicyclobutanyl, bicyclopentanyl, or bicyclohexanyl) optionally substituted with one, two, or three substituents as described herein.

In some embodiments, $R_1$ is $(CR_CR_C)_{0-1}$—$C_3$-$C_6$ cycloalkyl (e.g., cyclopropyl, cyclobutyl, cyclopentyl, cyclohexyl, bicyclobutanyl, bicyclopentanyl, or bicyclohexanyl) optionally substituted with one, two, or three substituents selected from methyl, methoxy, $CF_3$, F, and Cl.

In some embodiments, $R_1$ is cyclohexyl or bicyclopentanyl, each of which is optionally substituted with one or more substituents as described herein.

In some embodiments, $R_1$ is cyclohexyl or bicyclopentanyl, each of which is optionally substituted with one, two, or three substituents as described herein.

In some embodiments, $R_1$ is cyclohexyl or bicyclopentanyl, each of which is optionally substituted with one, two, or three substituents selected from methyl, methoxy, $CF_3$, F, and Cl.

In some embodiments, $R_1$ is $(CR_CR_C)_{0-2}$-heteroaryl comprising one 5- or 6-membered ring and 1-3 heteroatoms selected from N, O, and S, optionally substituted with one or more substituents independently selected from straight-chain $C_1$-$C_6$ alkyl or branched $C_3$-$C_6$ alkyl (e.g., methyl, ethyl, propyl, i-propyl, n-butyl, i-butyl, s-butyl, t-butyl, pentyl, or hexyl), straight-chain $C_1$-$C_6$ haloalkyl or branched $C_3$-$C_6$ haloalkyl (e.g., methyl, ethyl, propyl, i-propyl, n-butyl, i-butyl, s-butyl, t-butyl, pentyl, or hexyl, each of which is substituted with one or more halogen (e.g., F, Cl)), straight-chain $C_1$-$C_6$ alkoxy or branched $C_3$-$C_6$ alkoxy (e.g., methoxy, ethoxy, propoxy, i-propoxy, n-butoxy, i-butoxy, s-butoxy, t-butoxy, pentoxy, or hexyloxy), straight-chain $C_1$-$C_6$ haloalkoxy or branched $C_3$-$C_6$ haloalkoxy (e.g., methoxy, ethoxy, propoxy, i-propoxy, n-butoxy, i-butoxy, s-butoxy, t-butoxy, pentoxy, or hexyloxy, each of which is substituted with one or more halogen (e.g., F, Cl)), OH, halogen (e.g., F, Cl, Br, or I), $NH_2$, NH—($C_1$-$C_6$ alkyl) (e.g., methyl, ethyl, propyl, i-propyl, n-butyl, i-butyl, s-butyl, t-butyl, pentyl, or hexyl), N($C_1$-$C_6$ alkyl)$_2$ (e.g., methyl, ethyl, propyl, i-propyl, n-butyl, i-butyl, s-butyl, t-butyl, pentyl, or hexyl), CN, $NO_2$, and $C_3$-$C_6$ cycloalkyl ((e.g., cyclopropyl, cyclobutyl, cyclopentyl, or cyclohexyl).

In some embodiments, $R_1$ is $(CR_CR_C)_{0-2}$-heteroaryl comprising one 5- or 6-membered ring and 1-3 heteroatoms selected from N, O, and S, optionally substituted with one or more substituents independently selected from straight-chain $C_1$-$C_4$ alkyl or branched $C_3$-$C_4$ alkyl (e.g., methyl, ethyl, propyl, i-propyl, n-butyl, i-butyl, s-butyl, or t-butyl), straight-chain $C_1$-$C_4$ haloalkyl or branched $C_3$-$C_4$ haloalkyl (e.g., methyl, ethyl, propyl, i-propyl, n-butyl, i-butyl, s-butyl, or t-butyl, each of which is substituted with one or more halogen (e.g., F, Cl)), straight-chain $C_1$-$C_4$ alkoxy or branched $C_3$-$C_4$ alkoxy (e.g., methoxy, ethoxy, propoxy, i-propoxy, n-butoxy, i-butoxy, s-butoxy, or t-butoxy), straight-chain $C_1$-$C_4$ haloalkoxy or branched $C_3$-$C_4$ haloalkoxy (e.g., methoxy, ethoxy, propoxy, i-propoxy, n-butoxy, i-butoxy, s-butoxy, or t-butoxy, each of which is substituted with one or more halogen (e.g., F, Cl)), OH, halogen (e.g., F, Cl, Br, or I), $NH_2$, NH—($C_1$-$C_4$ alkyl) (e.g., methyl, ethyl, propyl, i-propyl, n-butyl, i-butyl, s-butyl, or t-butyl), N($C_1$-$C_4$ alkyl)$_2$ (e.g., methyl, ethyl, propyl, i-propyl, n-butyl, i-butyl, s-butyl, or t-butyl), CN, $NO_2$, and $C_3$-$C_6$ cycloalkyl ((e.g., cyclopropyl, cyclobutyl, cyclopentyl, or cyclohexyl).

In some embodiments, $R_1$ is $(CR_CR_C)_{0-2}$-heteroaryl comprising one 5-membered ring and 1-3 heteroatoms selected from N, O, and S, optionally substituted as described herein.

In some embodiments, $R_1$ is $(CR_CR_C)_{0-1}$-heteroaryl comprising one 5-membered ring and 1-3 heteroatoms selected from N, O, and S, optionally substituted as described herein.

In some embodiments, $R_1$ is heteroaryl comprising one 5-membered ring and 1-3 heteroatoms selected from N, O, and S, optionally substituted as described herein.

In some embodiments, $R_1$ is $(CR_CR_C)_{0-2}$-heteroaryl comprising one 6-membered ring and 1-3 heteroatoms selected from N, O, and S, optionally substituted as described herein.

In some embodiments, $R_1$ is $(CR_CR_C)_{0-1}$-heteroaryl comprising one 6-membered ring and 1-3 heteroatoms selected from N, O, and S, optionally substituted as described herein.

In some embodiments, $R_1$ is heteroaryl comprising one 6-membered ring and 1-3 heteroatoms selected from N, O, and S, optionally substituted as described herein.

In some embodiments, each $R_C$ is H.

In some embodiments, at least one $R_C$ is $C_1$-$C_3$ alkyl (e.g., methyl, ethyl, propyl, or i-propyl) or $C_1$-$C_3$ haloalkyl (e.g., methyl, ethyl, propyl, or i-propyl, each of which is substituted one or more halogen (e.g., F, Cl)).

In some embodiments, each $R_C$ is independently $C_1$-$C_3$ alkyl (e.g., methyl, ethyl, propyl, or i-propyl) or $C_1$-$C_3$ haloalkyl (e.g., methyl, ethyl, propyl, or i-propyl, each of which is substituted one or more halogen (e.g., F, Cl)).

In some embodiments, $R_2$ is heterocyclyl comprising one or two 5- or 6-membered rings and 1-3 heteroatoms selected from N, O, and S, or heteroaryl comprising one or two 5- or 6-membered rings and 1-3 heteroatoms selected from N, O, and S, wherein the heterocyclyl or heteroaryl is optionally substituted with one or more substituents independently selected from $C_1$-$C_6$ alkyl (e.g., methyl, ethyl, propyl, i-propyl, n-butyl, i-butyl, s-butyl, t-butyl, pentyl, or hexyl) optionally substituted with straight-chain $C_1$-$C_6$ alkoxy or branched $C_3$-$C_6$ alkoxy (e.g., methoxy, ethoxy, propoxy, i-propoxy, n-butoxy, i-butoxy, s-butoxy, t-butoxy, pentoxy, or hexyloxy), straight-chain $C_1$-$C_6$ haloalkyl or branched $C_3$-$C_6$ haloalkyl (e.g., methyl, ethyl, propyl, i-propyl, n-butyl, i-butyl, s-butyl, t-butyl, pentyl, or hexyl, each of which is substituted with one or more halogen (e.g., F, Cl)), straight-chain $C_1$-$C_6$ alkoxy or branched $C_3$-$C_6$ alkoxy (e.g., methoxy, ethoxy, propoxy, i-propoxy, n-butoxy, i-butoxy, s-butoxy, t-butoxy, pentoxy, or hexyloxy), straight-chain $C_1$-$C_6$ haloalkoxy or branched $C_3$-$C_6$ haloalkoxy (e.g., methoxy, ethoxy, propoxy, i-propoxy, n-butoxy, i-butoxy, s-butoxy, t-butoxy, pentoxy, or hexyloxy, each of which is substituted with one or more halogen (e.g., F, Cl)), OH, halogen (e.g., F, Cl, Br, or I), $NH_2$, NH—($C_1$-$C_6$ alkyl) (e.g., methyl, ethyl, propyl, i-propyl, n-butyl, i-butyl, s-butyl, t-butyl, pentyl, or hexyl), N($C_1$-$C_6$ alkyl)$_2$ (e.g., methyl, ethyl, propyl, i-propyl, n-butyl, i-butyl, s-butyl, t-butyl, pentyl, or hexyl), CN, and $NO_2$.

In some embodiments, $R_2$ is heterocyclyl comprising one or two 5- or 6-membered rings and 1-3 heteroatoms selected from N, O, and S, wherein the heterocyclyl is optionally substituted with one or more substituents independently selected from $C_1$-$C_6$ alkyl (e.g., methyl, ethyl, propyl, i-propyl, n-butyl, i-butyl, s-butyl, t-butyl, pentyl, or hexyl) optionally substituted with straight-chain $C_1$-$C_6$ alkoxy or branched $C_3$-$C_6$ alkoxy (e.g., methoxy, ethoxy, propoxy, i-propoxy, n-butoxy, i-butoxy, s-butoxy, t-butoxy, pentoxy, or hexyloxy), straight-chain $C_1$-$C_6$ haloalkyl or branched $C_3$-$C_6$ haloalkyl (e.g., methyl, ethyl, propyl, i-propyl, n-butyl, i-butyl, s-butyl, t-butyl, pentyl, or hexyl, each of which is substituted with one or more halogen (e.g., F, Cl)), straight-chain $C_1$-$C_6$ alkoxy or branched $C_3$-$C_6$ alkoxy (e.g., methoxy, ethoxy, propoxy, i-propoxy, n-butoxy, i-butoxy, s-butoxy, t-butoxy, pentoxy, or hexyloxy), straight-chain $C_1$-$C_6$ haloalkoxy or branched $C_3$-$C_6$ haloalkoxy (e.g., methoxy, ethoxy, propoxy, i-propoxy, n-butoxy, i-butoxy, s-butoxy, t-butoxy, pentoxy, or hexyloxy, each of which is substituted with one or more halogen (e.g., F, Cl)), OH, halogen (e.g., F, Cl, Br, or I), $NH_2$, NH—($C_1$-$C_6$ alkyl) (e.g., methyl, ethyl, propyl, i-propyl, n-butyl, i-butyl, s-butyl, t-butyl, pentyl, or hexyl), $N(C_1-C_6\ alkyl)_2$ (e.g., methyl, ethyl, propyl, i-propyl, n-butyl, i-butyl, s-butyl, t-butyl, pentyl, or hexyl), CN, and $NO_2$.

In some embodiments, $R_2$ is heterocyclyl comprising one 5- or 6-membered ring and 1-3 heteroatoms selected from N, O, and S, wherein the heterocyclyl is optionally substituted with one or more substituents as described herein.

In some embodiments, $R_2$ is heterocyclyl comprising one 5-membered ring and 1-3 heteroatoms selected from N, O, and S, wherein the heterocyclyl is optionally substituted with one or more substituents as described herein.

In some embodiments, $R_2$ is heterocyclyl comprising one 6-membered ring and 1-3 heteroatoms selected from N, O, and S, wherein the heterocyclyl is optionally substituted with one or more substituents as described herein.

In some embodiments, $R_2$ is heteroaryl comprising one or two 5- or 6-membered rings and 1-3 heteroatoms selected from N, O, and S, wherein the heteroaryl is optionally substituted with one or more substituents independently selected from $C_1$-$C_6$ alkyl (e.g., methyl, ethyl, propyl, i-propyl, n-butyl, i-butyl, s-butyl, t-butyl, pentyl, or hexyl) optionally substituted with straight-chain $C_1$-$C_6$ alkoxy or branched $C_3$-$C_6$ alkoxy (e.g., methoxy, ethoxy, propoxy, i-propoxy, n-butoxy, i-butoxy, s-butoxy, t-butoxy, pentoxy, or hexyloxy), straight-chain $C_1$-$C_6$ haloalkyl or branched $C_3$-$C_6$ haloalkyl (e.g., methyl, ethyl, propyl, i-propyl, n-butyl, i-butyl, s-butyl, t-butyl, pentyl, or hexyl, each of which is substituted with one or more halogen (e.g., F, Cl)), straight-chain $C_1$-$C_6$ alkoxy or branched $C_3$-$C_6$ alkoxy (e.g., methoxy, ethoxy, propoxy, i-propoxy, n-butoxy, i-butoxy, s-butoxy, t-butoxy, pentoxy, or hexyloxy), straight-chain $C_1$-$C_6$ haloalkoxy or branched $C_3$-$C_6$ haloalkoxy (e.g., methoxy, ethoxy, propoxy, i-propoxy, n-butoxy, i-butoxy, s-butoxy, t-butoxy, pentoxy, or hexyloxy, each of which is substituted with one or more halogen (e.g., F, Cl)), OH, halogen (e.g., F, Cl, Br, or I), $NH_2$, NH—($C_1$-$C_6$ alkyl) (e.g., methyl, ethyl, propyl, i-propyl, n-butyl, i-butyl, s-butyl, t-butyl, pentyl, or hexyl), $N(C_1-C_6\ alkyl)_2$ (e.g., methyl, ethyl, propyl, i-propyl, n-butyl, i-butyl, s-butyl, t-butyl, pentyl, or hexyl), CN, and $NO_2$.

In some embodiments, $R_2$ is heteroaryl comprising two 5- or 6-membered rings and 1-3 heteroatoms selected from N, O, and S, wherein the heteroaryl is optionally substituted with one or more substituents as described herein.

In some embodiments, $R_2$ is heteroaryl comprising two 5- or 6-membered rings and 1-3 heteroatoms selected from N and O, wherein the heteroaryl is optionally substituted with one or more substituents as described herein.

In some embodiments, $R_2$ is heteroaryl comprising two 5- or 6-membered rings and 1-3 heteroatoms selected from N, wherein the heteroaryl is optionally substituted with one or more substituents as described herein.

In some embodiments, $R_2$ is heteroaryl comprising one 5- or 6-membered ring and 1-3 heteroatoms selected from N, O, and S, wherein the heteroaryl is optionally substituted with one or more substituents as described herein.

In some embodiments, $R_2$ is heteroaryl comprising one 5-membered ring and 1-3 heteroatoms selected from N, O, and S, wherein the heteroaryl is optionally substituted with one or more substituents as described herein.

In some embodiments, $R_2$ is heteroaryl comprising one 6-membered ring and 1-3 heteroatoms selected from N, O, and S, wherein the heteroaryl is optionally substituted with one or more substituents as described herein.

In some embodiments, $R_2$ is indazolyl or imidazopyridinyl, each of which is optionally substituted with one or more substituents independently selected from $C_1$-$C_6$ alkyl (e.g., methyl, ethyl, propyl, i-propyl, n-butyl, i-butyl, s-butyl, t-butyl, pentyl, or hexyl) optionally substituted with straight-chain $C_1$-$C_6$ alkoxy or branched $C_3$-$C_6$ alkoxy (e.g., methoxy, ethoxy, propoxy, i-propoxy, n-butoxy, i-butoxy, s-butoxy, t-butoxy, pentoxy, or hexyloxy), straight-chain $C_1$-$C_6$ haloalkyl or branched $C_3$-$C_6$ haloalkyl (e.g., methyl, ethyl, propyl, i-propyl, n-butyl, i-butyl, s-butyl, t-butyl, pentyl, or hexyl, each of which is substituted with one or more halogen (e.g., F, Cl)), straight-chain $C_1$-$C_6$ alkoxy or branched $C_3$-$C_6$ alkoxy (e.g., methoxy, ethoxy, propoxy, i-propoxy, n-butoxy, i-butoxy, s-butoxy, t-butoxy, pentoxy, or hexyloxy), straight-chain $C_1$-$C_6$ haloalkoxy or branched $C_3$-$C_6$ haloalkoxy (e.g., methoxy, ethoxy, propoxy, i-propoxy, n-butoxy, i-butoxy, s-butoxy, t-butoxy, pentoxy, or hexyloxy, each of which is substituted with one or more halogen (e.g., F, Cl)), OH, halogen (e.g., F, Cl, Br, or I), $NH_2$, NH—($C_1$-$C_6$ alkyl) (e.g., methyl, ethyl, propyl, i-propyl, n-butyl, i-butyl, s-butyl, t-butyl, pentyl, or hexyl), $N(C_1-C_6\ alkyl)_2$ (e.g., methyl, ethyl, propyl, i-propyl, n-butyl, i-butyl, s-butyl, t-butyl, pentyl, or hexyl), CN, and $NO_2$.

In some embodiments, $R_2$ is indazolyl or imidazopyridinyl, each of which is optionally substituted with one or more substituents independently selected from $C_1$-$C_6$ alkyl (e.g., methyl, ethyl, propyl, i-propyl, n-butyl, i-butyl, s-butyl, t-butyl, pentyl, or hexyl) optionally substituted with straight-chain $C_1$-$C_6$ alkoxy or branched $C_3$-$C_6$ alkoxy (e.g., methoxy, ethoxy, propoxy, i-propoxy, n-butoxy, i-butoxy, s-butoxy, t-butoxy, pentoxy, or hexyloxy), straight-chain $C_1$-$C_6$ haloalkyl or branched $C_3$-$C_6$ haloalkyl (e.g., methyl, ethyl, propyl, i-propyl, n-butyl, i-butyl, s-butyl, t-butyl, pentyl, or hexyl, each of which is substituted with one or more halogen (e.g., F, Cl)), straight-chain $C_1$-$C_6$ alkoxy or branched $C_3$-$C_6$ alkoxy (e.g., methoxy, ethoxy, propoxy, i-propoxy, n-butoxy, i-butoxy, s-butoxy, t-butoxy, pentoxy, or hexyloxy), straight-chain $C_1$-$C_6$ haloalkoxy or branched $C_3$-$C_6$ haloalkoxy (e.g., methoxy, ethoxy, propoxy, i-propoxy, n-butoxy, i-butoxy, s-butoxy, t-butoxy, pentoxy, or hexyloxy, each of which is substituted with one or more halogen (e.g., F, Cl)), OH, and halogen (e.g., F, Cl, Br, or I).

In some embodiments, $R_2$ is indazolyl or imidazopyridinyl, each of which is optionally substituted with one or more substituents independently selected from $C_1$-$C_6$ alkyl (e.g., methyl, ethyl, propyl, i-propyl, n-butyl, i-butyl, s-butyl, t-butyl, pentyl, or hexyl) optionally substituted with straight-chain $C_1$-$C_6$ alkoxy or branched $C_3$-$C_6$ alkoxy (e.g., methoxy, ethoxy, propoxy, i-propoxy, n-butoxy, i-butoxy, s-butoxy, t-butoxy, pentoxy, or hexyloxy), straight-chain $C_1$-$C_6$ haloalkyl or branched $C_3$-$C_6$ haloalkyl (e.g., methyl, ethyl, propyl, i-propyl, n-butyl, i-butyl, s-butyl, t-butyl, pentyl, or hexyl, each of which is substituted with one or more halogen (e.g., F, Cl)), and halogen (e.g., F, Cl, Br, or I).

In some embodiments, $R_2$ is indazolyl or imidazopyridinyl, each of which is optionally substituted with one, two, or three substituents as described herein.

In some embodiments, $R_2$ is spiro-, bridged-, or mono-$C_3$-$C_{10}$ cycloalkyl (e.g., cyclopropyl, cyclobutyl, cyclopentyl, cyclohexyl, cycloheptyl, cyclooctyl, each of which can be spiro-, bridged-, or mono-cycloalkyl) optionally substituted with one or more substituents independently selected from $C_1$-$C_6$ alkyl (e.g., methyl, ethyl, propyl, i-propyl, n-butyl, i-butyl, s-butyl, t-butyl, pentyl, or hexyl) optionally substituted with straight-chain $C_1$-$C_6$ alkoxy or branched $C_3$-$C_6$ alkoxy (e.g., methoxy, ethoxy, propoxy, i-propoxy, n-butoxy, i-butoxy, s-butoxy, t-butoxy, pentoxy, or hexyloxy), straight-chain $C_1$-$C_6$ haloalkyl or branched $C_3$-$C_6$ haloalkyl (e.g., methyl, ethyl, propyl, i-propyl, n-butyl, i-butyl, s-butyl, t-butyl, pentyl, or hexyl, each of which is substituted with one or more halogen (e.g., F, Cl)), straight-chain $C_1$-$C_6$ alkoxy or branched $C_3$-$C_6$ alkoxy (e.g., methoxy, ethoxy, propoxy, i-propoxy, n-butoxy, i-butoxy, s-butoxy, t-butoxy, pentoxy, or hexyloxy), straight-chain $C_1$-$C_6$ haloalkoxy or branched $C_3$-$C_6$ haloalkoxy (e.g., methoxy, ethoxy, propoxy, i-propoxy, n-butoxy, i-butoxy, s-butoxy, t-butoxy, pentoxy, or hexyloxy, each of which is substituted with one or more halogen (e.g., F, Cl)), OH, halogen (e.g., F, Cl, Br, or I), $NH_2$, NH—($C_1$-$C_6$ alkyl) (e.g., methyl, ethyl, propyl, i-propyl, n-butyl, i-butyl, s-butyl, t-butyl, pentyl, or hexyl), N($C_1$-$C_6$ alkyl)$_2$ (e.g., methyl, ethyl, propyl, i-propyl, n-butyl, i-butyl, s-butyl, t-butyl, pentyl, or hexyl), CN, and $NO_2$.

In some embodiments, $R_2$ is bicyclooctanyl substituted with one or more substituents independently selected from $C_1$-$C_6$ alkyl (e.g., methyl, ethyl, propyl, i-propyl, n-butyl, i-butyl, s-butyl, t-butyl, pentyl, or hexyl) optionally substituted with straight-chain $C_1$-$C_6$ alkoxy or branched $C_3$-$C_6$ alkoxy (e.g., methoxy, ethoxy, propoxy, i-propoxy, n-butoxy, i-butoxy, s-butoxy, t-butoxy, pentoxy, or hexyloxy), straight-chain $C_1$-$C_6$ haloalkyl or branched $C_3$-$C_6$ haloalkyl (e.g., methyl, ethyl, propyl, i-propyl, n-butyl, i-butyl, s-butyl, t-butyl, pentyl, or hexyl, each of which is substituted with one or more halogen (e.g., F, Cl)), straight-chain $C_1$-$C_6$ alkoxy or branched $C_3$-$C_6$ alkoxy (e.g., methoxy, ethoxy, propoxy, i-propoxy, n-butoxy, i-butoxy, s-butoxy, t-butoxy, pentoxy, or hexyloxy), straight-chain $C_1$-$C_6$ haloalkoxy or branched $C_3$-$C_6$ haloalkoxy (e.g., methoxy, ethoxy, propoxy, i-propoxy, n-butoxy, i-butoxy, s-butoxy, t-butoxy, pentoxy, or hexyloxy, each of which is substituted with one or more halogen (e.g., F, Cl)), OH, halogen (e.g., F, Cl, Br, or I), $NH_2$, NH—($C_1$-$C_6$ alkyl) (e.g., methyl, ethyl, propyl, i-propyl, n-butyl, i-butyl, s-butyl, t-butyl, pentyl, or hexyl), N($C_1$-$C_6$ alkyl)$_2$ (e.g., methyl, ethyl, propyl, i-propyl, n-butyl, i-butyl, s-butyl, t-butyl, pentyl, or hexyl), CN, and $NO_2$.

In some embodiments, $R_2$ is phenyl substituted with one or more substituents independently selected from $C_1$-$C_6$ alkyl (e.g., methyl, ethyl, propyl, i-propyl, n-butyl, i-butyl, s-butyl, t-butyl, pentyl, or hexyl) optionally substituted with straight-chain $C_1$-$C_6$ alkoxy or branched $C_3$-$C_6$ alkoxy (e.g., methoxy, ethoxy, propoxy, i-propoxy, n-butoxy, i-butoxy, s-butoxy, t-butoxy, pentoxy, or hexyloxy), straight-chain $C_1$-$C_6$ haloalkyl or branched $C_3$-$C_6$ haloalkyl (e.g., methyl, ethyl, propyl, i-propyl, n-butyl, i-butyl, s-butyl, t-butyl, pentyl, or hexyl, each of which is substituted with one or more halogen (e.g., F, Cl)), straight-chain $C_1$-$C_6$ alkoxy or branched $C_3$-$C_6$ alkoxy (e.g., methoxy, ethoxy, propoxy, i-propoxy, n-butoxy, i-butoxy, s-butoxy, t-butoxy, pentoxy, or hexyloxy), straight-chain $C_1$-$C_6$ haloalkoxy or branched $C_3$-$C_6$ haloalkoxy (e.g., methoxy, ethoxy, propoxy, i-propoxy, n-butoxy, i-butoxy, s-butoxy, t-butoxy, pentoxy, or hexyloxy, each of which is substituted with one or more halogen (e.g., F, Cl)), OH, halogen (e.g., F, Cl, Br, or I), $NH_2$, NH—($C_1$-$C_6$ alkyl) (e.g., methyl, ethyl, propyl, i-propyl, n-butyl, i-butyl, s-butyl, t-butyl, pentyl, or hexyl), N($C_1$-$C_6$ alkyl)$_2$ (e.g., methyl, ethyl, propyl, i-propyl, n-butyl, i-butyl, s-butyl, t-butyl, pentyl, or hexyl), CN, and $NO_2$.

In some embodiments, $R_2$ is indazolyl, imidazopyridinyl, phenyl, or bicyclooctanyl, each of which is optionally independently substituted with one or more substituents independently selected from $C_1$-$C_6$ alkyl (e.g., methyl, ethyl, propyl, i-propyl, n-butyl, i-butyl, s-butyl, t-butyl, pentyl, or hexyl) optionally substituted with straight-chain $C_1$-$C_6$ alkoxy or branched $C_3$-$C_6$ alkoxy (e.g., methoxy, ethoxy, propoxy, i-propoxy, n-butoxy, i-butoxy, s-butoxy, t-butoxy, pentoxy, or hexyloxy), straight-chain $C_1$-$C_6$ haloalkyl or branched $C_3$-$C_6$ haloalkyl (e.g., methyl, ethyl, propyl, i-propyl, n-butyl, i-butyl, s-butyl, t-butyl, pentyl, or hexyl, each of which is substituted with one or more halogen (e.g., F, Cl)), straight-chain $C_1$-$C_6$ alkoxy or branched $C_3$-$C_6$ alkoxy (e.g., methoxy, ethoxy, propoxy, i-propoxy, n-butoxy, i-butoxy, s-butoxy, t-butoxy, pentoxy, or hexyloxy), straight-chain $C_1$-$C_6$ haloalkoxy or branched $C_3$-$C_6$ haloalkoxy (e.g., methoxy, ethoxy, propoxy, i-propoxy, n-butoxy, i-butoxy, s-butoxy, t-butoxy, pentoxy, or hexyloxy, each of which is substituted with one or more halogen (e.g., F, Cl)), OH, halogen (e.g., F, Cl, Br, or I), $NH_2$, NH—($C_1$-$C_6$ alkyl) (e.g., methyl, ethyl, propyl, i-propyl, n-butyl, i-butyl, s-butyl, t-butyl, pentyl, or hexyl), N($C_1$-$C_6$ alkyl)$_2$ (e.g., methyl, ethyl, propyl, i-propyl, n-butyl, i-butyl, s-butyl, t-butyl, pentyl, or hexyl), CN, and $NO_2$.

In some embodiments, $R_2$ is indazolyl, imidazopyridinyl, phenyl, or bicyclooctanyl, each of which is optionally independently substituted with one or more substituents independently selected from $C_1$-$C_6$ alkyl (e.g., methyl, ethyl, propyl, i-propyl, n-butyl, i-butyl, s-butyl, t-butyl, pentyl, or hexyl) optionally substituted with straight-chain $C_1$-$C_6$ alkoxy or branched $C_3$-$C_6$ alkoxy (e.g., methoxy, ethoxy, propoxy, i-propoxy, n-butoxy, i-butoxy, s-butoxy, t-butoxy, pentoxy, or hexyloxy), straight-chain $C_1$-$C_6$ haloalkyl or branched $C_3$-$C_6$ haloalkyl (e.g., methyl, ethyl, propyl, i-propyl, n-butyl, i-butyl, s-butyl, t-butyl, pentyl, or hexyl, each of which is substituted with one or more halogen (e.g., F, Cl)), straight-chain $C_1$-$C_6$ alkoxy or branched $C_3$-$C_6$ alkoxy (e.g., methoxy, ethoxy, propoxy, i-propoxy, n-butoxy, i-butoxy, s-butoxy, t-butoxy, pentoxy, or hexyloxy), straight-chain $C_1$-$C_6$ haloalkoxy or branched $C_3$-$C_6$ haloalkoxy (e.g., methoxy, ethoxy, propoxy, i-propoxy, n-butoxy, i-butoxy, s-butoxy, t-butoxy, pentoxy, or hexyloxy, each of which is substituted with one or more halogen (e.g., F, Cl)), OH, and halogen (e.g., F, Cl, Br, or I).

In some embodiments, $R_2$ is indazolyl, imidazopyridinyl, phenyl, or bicyclooctanyl, each of which is optionally independently substituted with one, two, or three substituents as described herein.

In some embodiments,

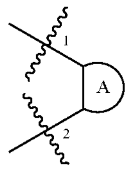

is a bicyclic heteroaryl ring selected from

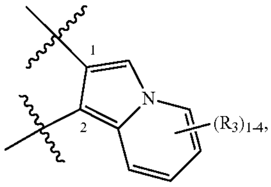

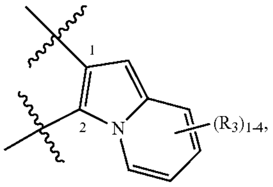

-continued
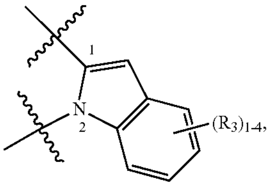,
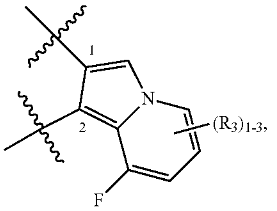,
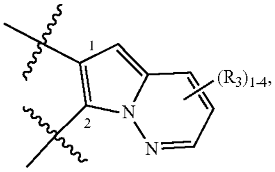,
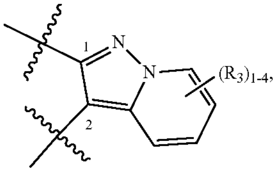,
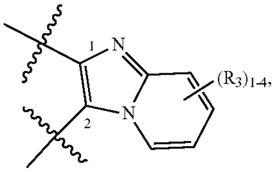,
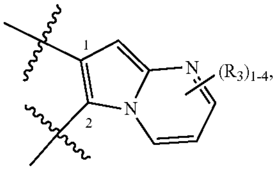,
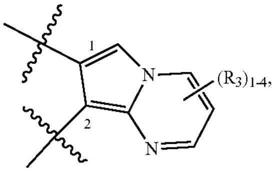,
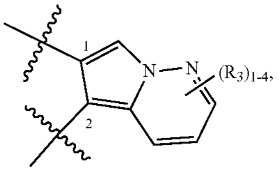,
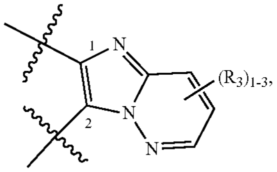, and
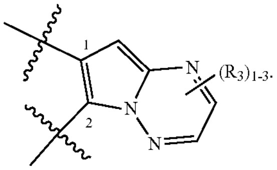.
In some embodiments,
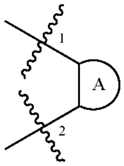
is a bicyclic heteroaryl ring selected from
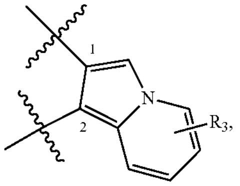,
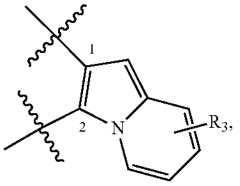,
-continued
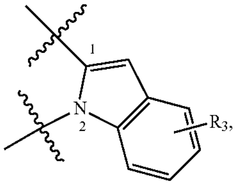,
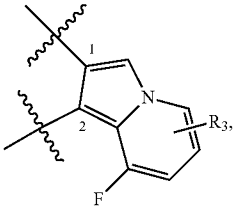,
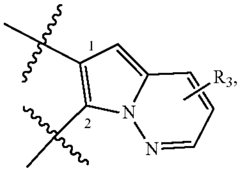,
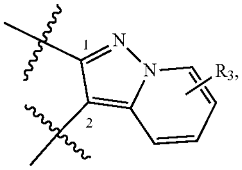,
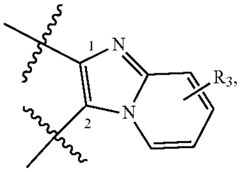,
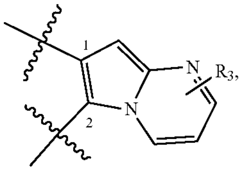,
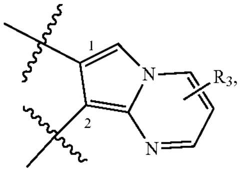,
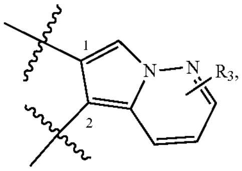,
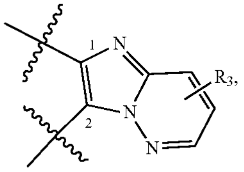,
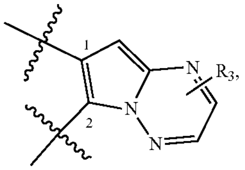, and
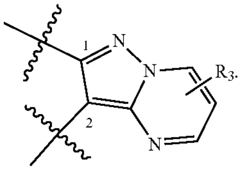.
In some embodiments,
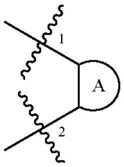

is a bicyclic heteroaryl ring selected from
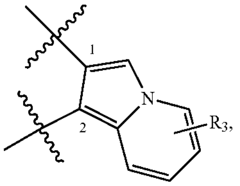
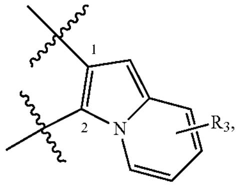
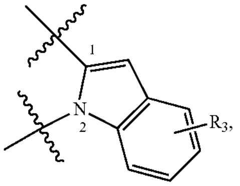
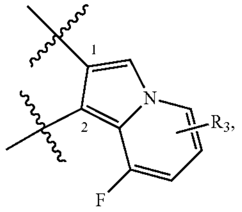
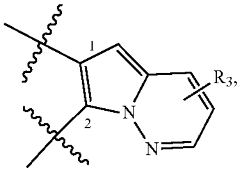
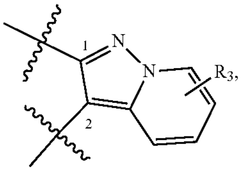
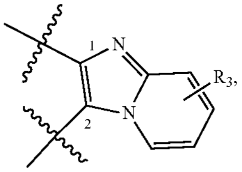
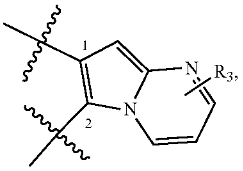
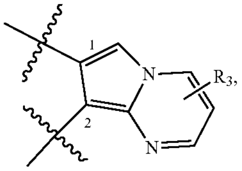
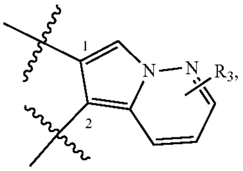
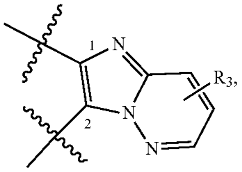
and
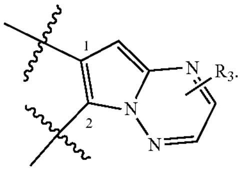
In some embodiments,
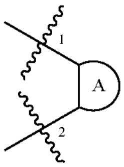
is a bicyclic heteroaryl ring selected from
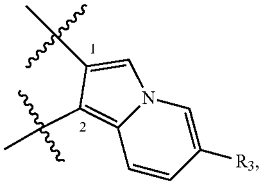
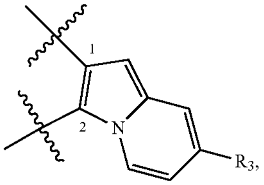
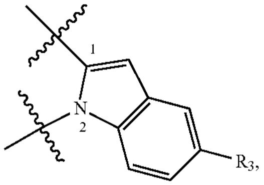
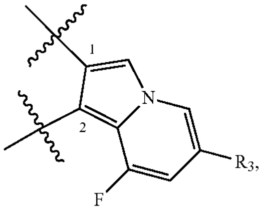
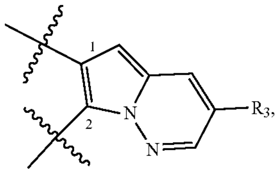
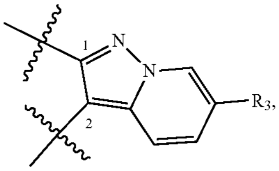
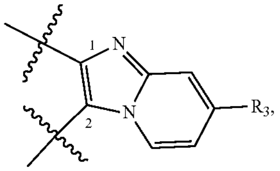
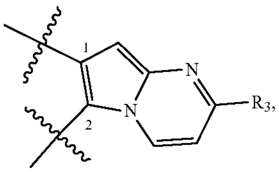
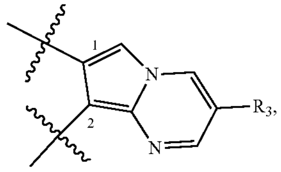
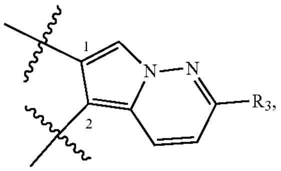
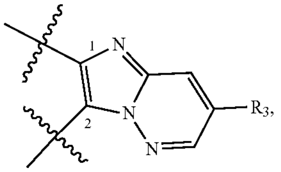
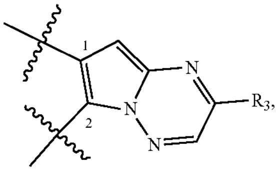
and
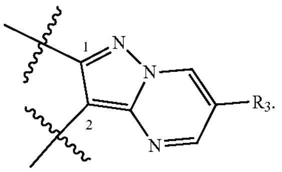

In some embodiments,
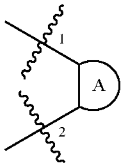
is a bicyclic heteroaryl ring selected from
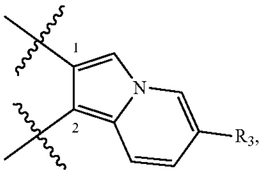
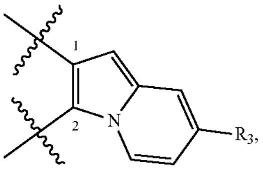
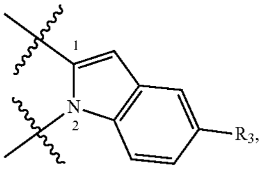
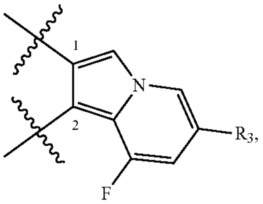
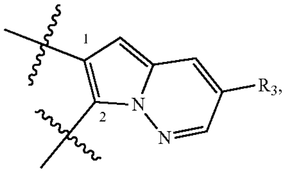
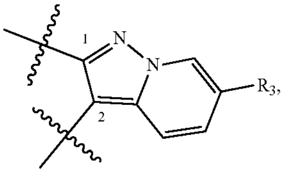
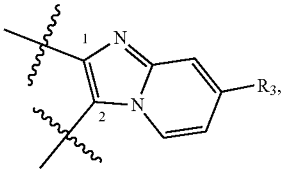
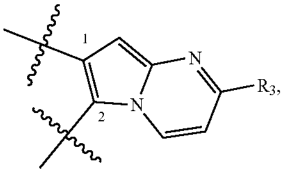
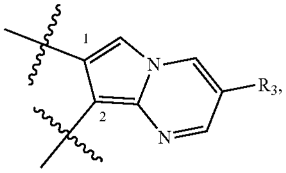
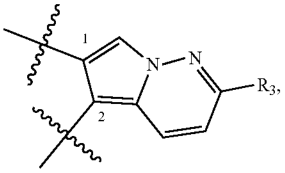
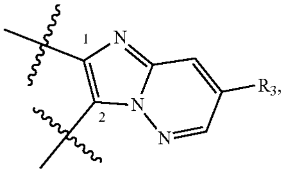
and
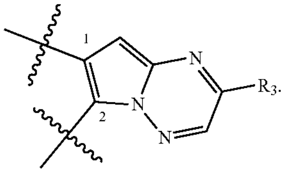
In some embodiments,
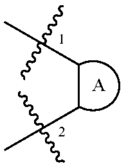
is a bicyclic heteroaryl ring selected from
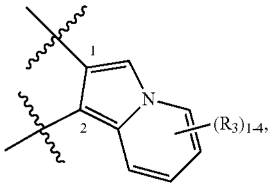
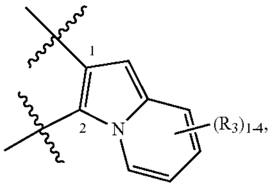
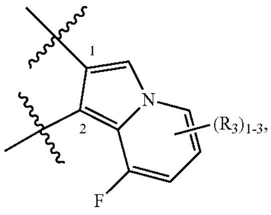
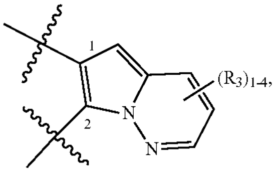
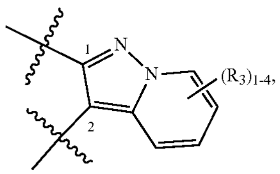
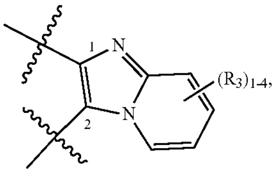
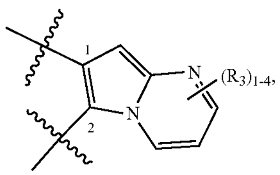
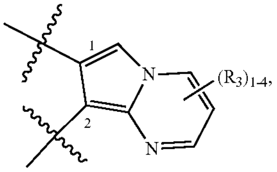
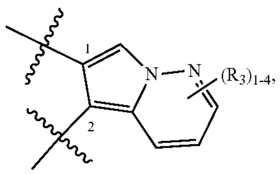
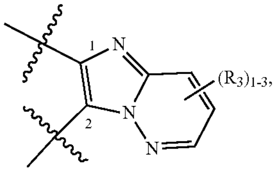
and
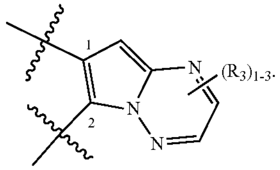

In some embodiments,
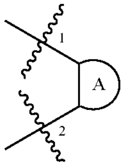
is a bicyclic heteroaryl ring selected from
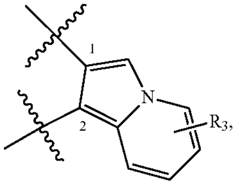
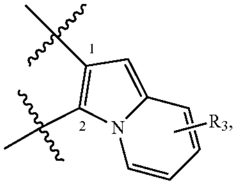
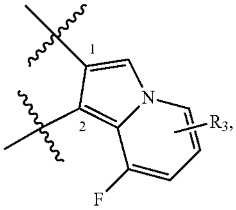
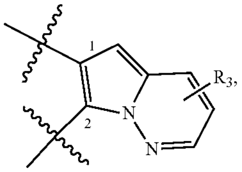
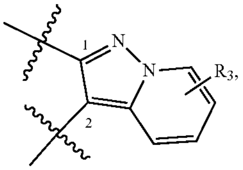
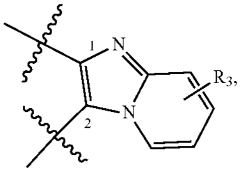
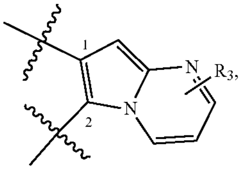
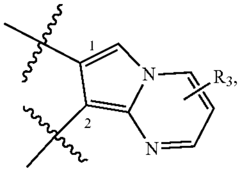
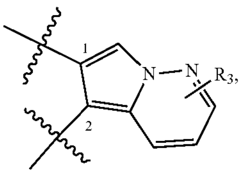
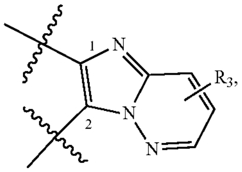
and
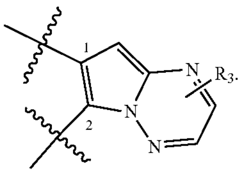
In some embodiments,
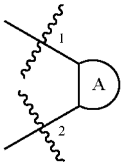
is a bicyclic heteroaryl ring selected from
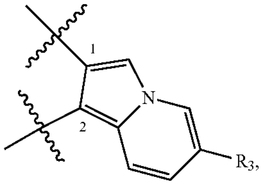
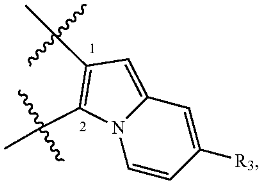
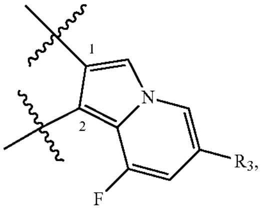
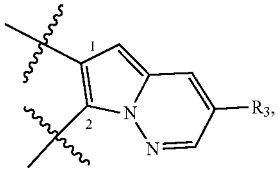
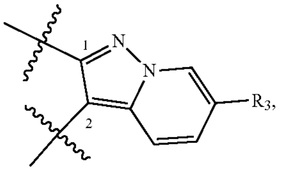
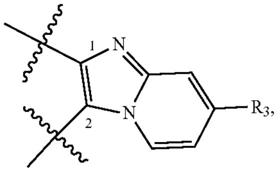
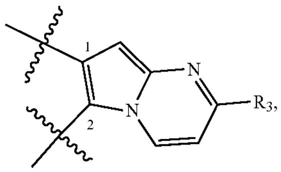
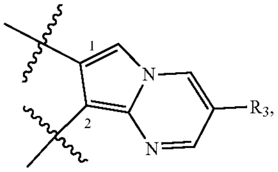
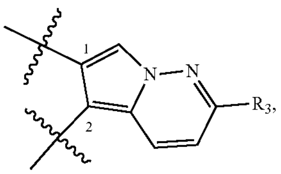
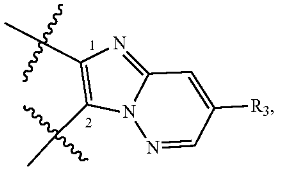
and
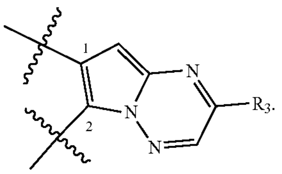

In some embodiments,
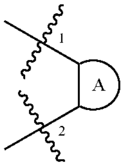
is a bicyclic heteroaryl ring selected from
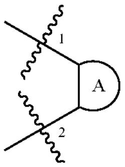
In some embodiments,
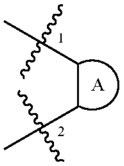
is a bicyclic heteroaryl ring selected from
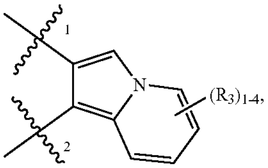
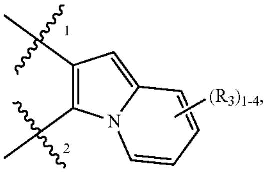
and
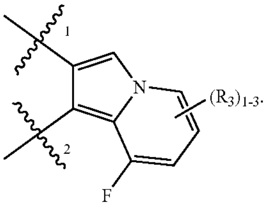
In some embodiments,
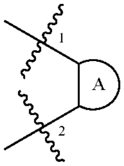
is a bicyclic heteroaryl ring selected from
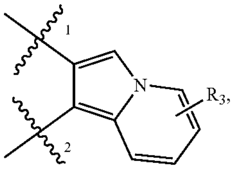
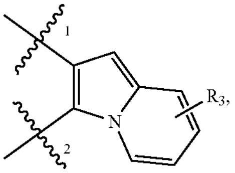
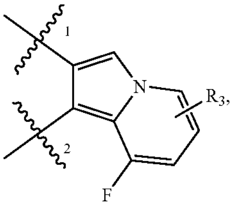
and
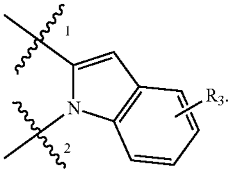
In some embodiments,
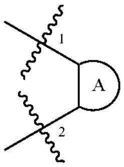
is a bicyclic heteroaryl ring selected from
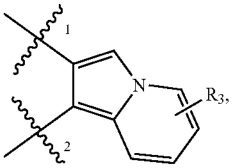
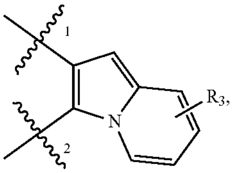
and -continued
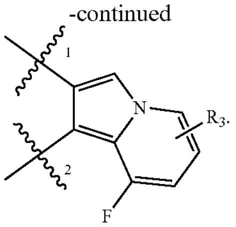
In some embodiments,
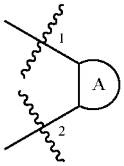
is a bicyclic heteroaryl ring selected from
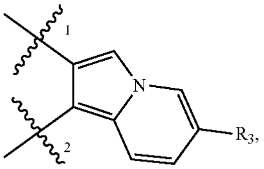
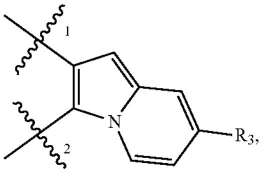
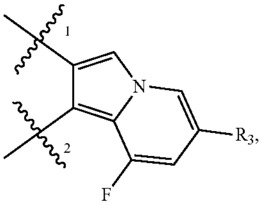
and
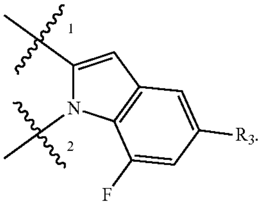
In some embodiments,
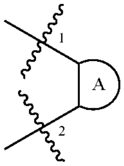
is a bicyclic heteroaryl ring selected from
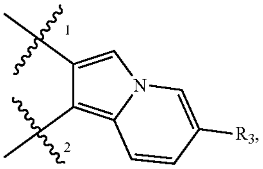
-continued
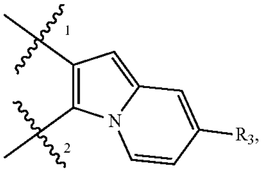
and
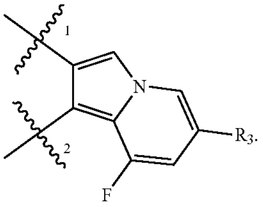
In some embodiments,
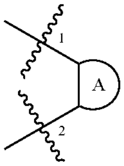
is a bicyclic heteroaryl ring selected from
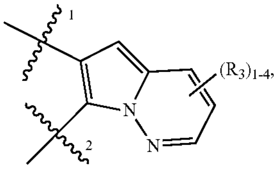
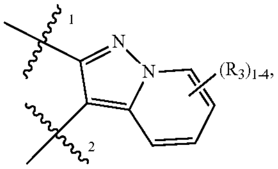
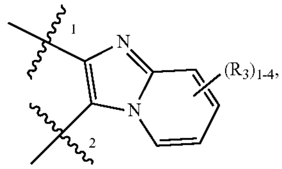
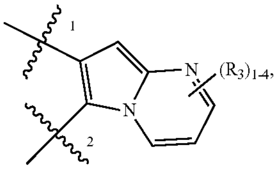
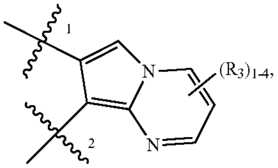
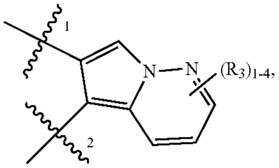
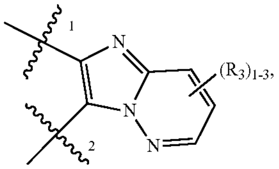

-continued
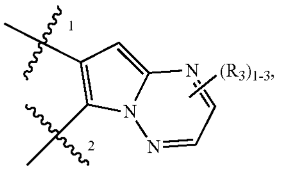
and
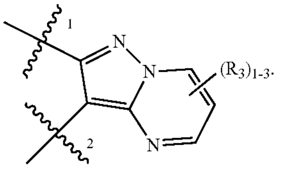
In some embodiments,
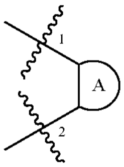
is a bicyclic heteroaryl ring selected from
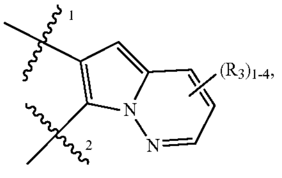
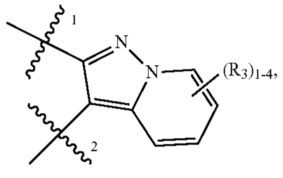
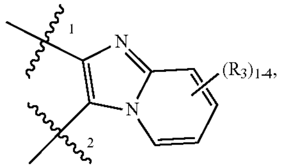
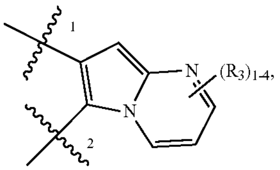
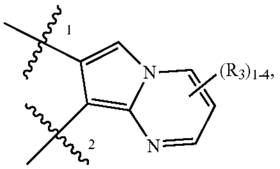
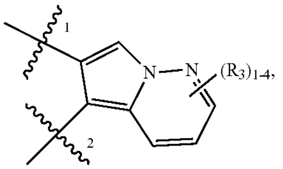
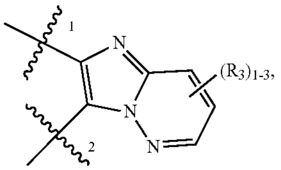
and
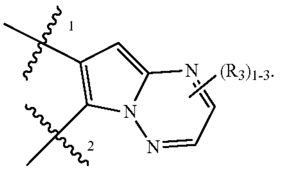
In some embodiments,
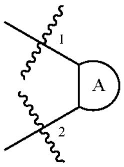
is a bicyclic heteroaryl ring selected from
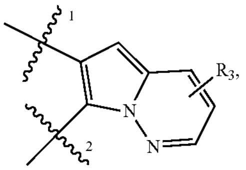
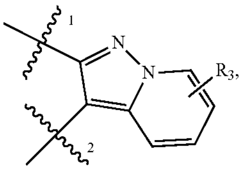
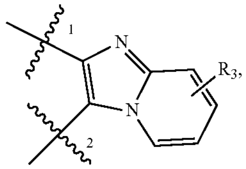
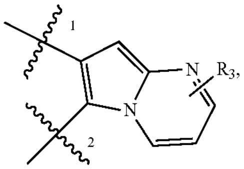
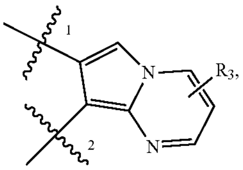
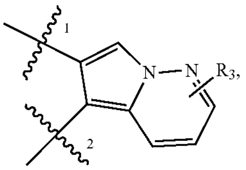
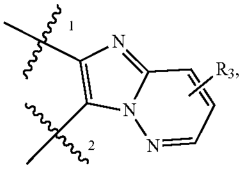
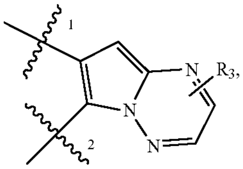
and
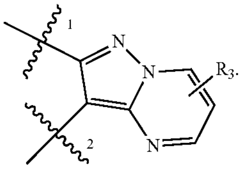
In some embodiments,
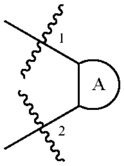

is a bicyclic heteroaryl ring selected from
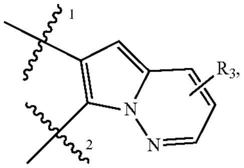
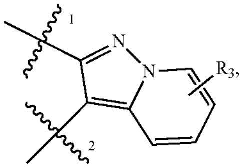
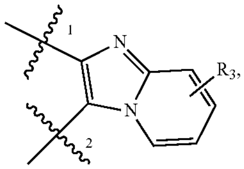
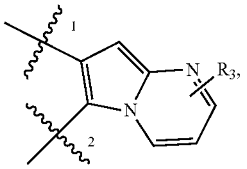
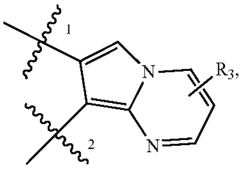
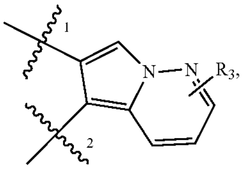
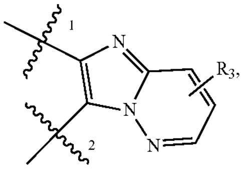
and
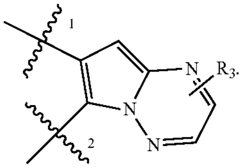
In some embodiments,
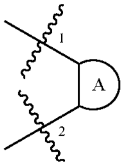
is a bicyclic heteroaryl ring selected from
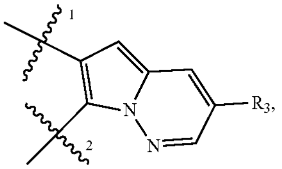
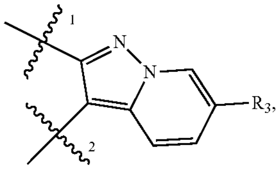
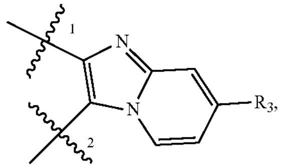
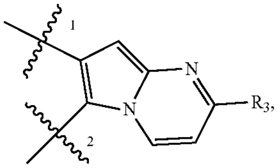
-continued
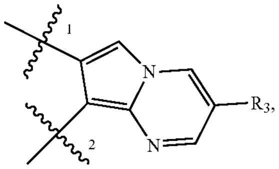
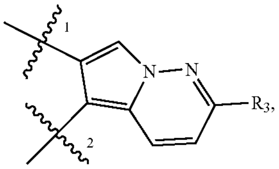
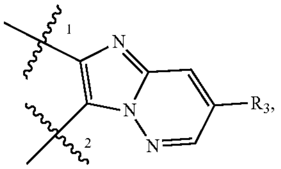
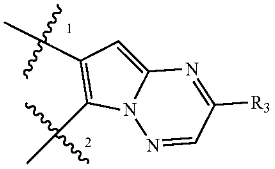
and
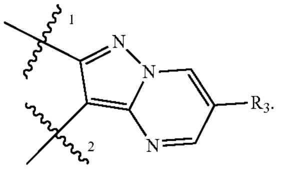
In some embodiments,
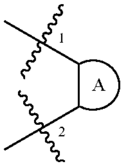
is a bicyclic heteroaryl ring selected from
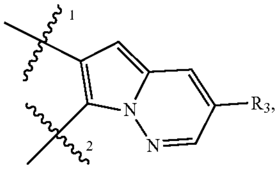
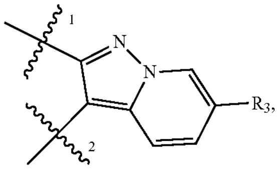
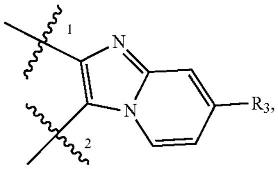
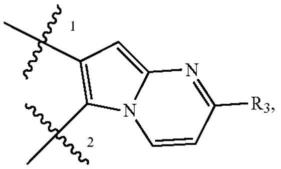
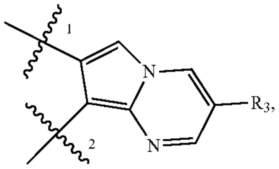
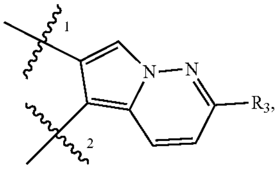

-continued
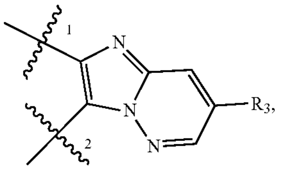
and
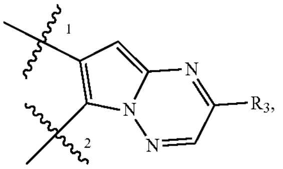
In some embodiments,
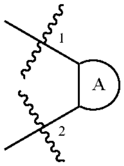
is a bicyclic heteroaryl ring selected from
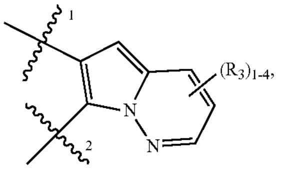
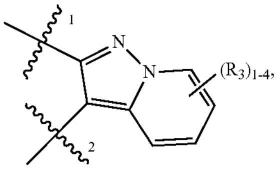
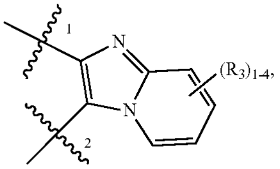
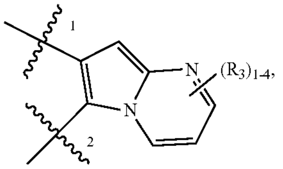
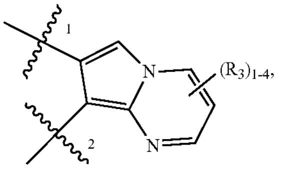
and
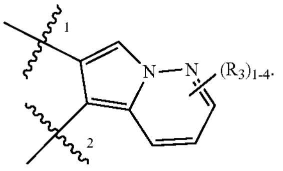
In some embodiments,
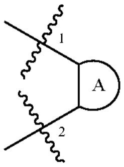
is a bicyclic heteroaryl ring selected from
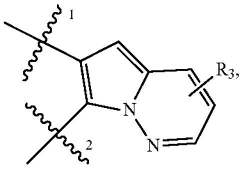
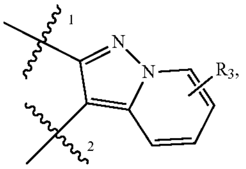
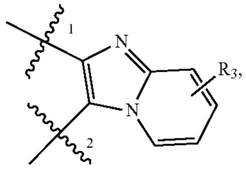
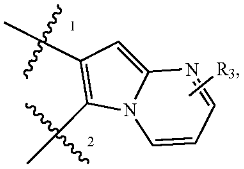
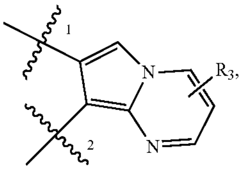
and
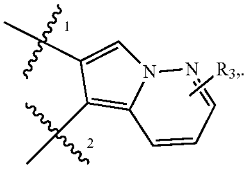
In some embodiments,
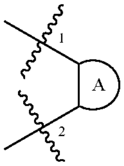
is a bicyclic heteroaryl ring selected from
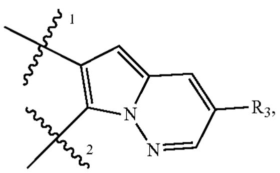
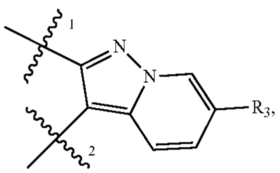
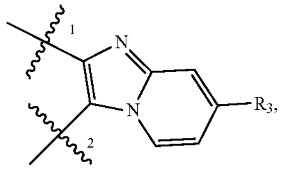
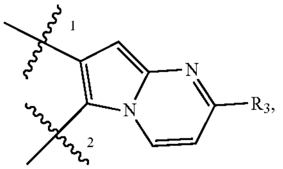

-continued
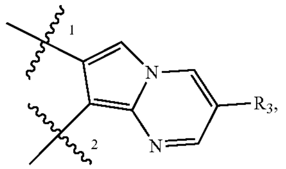
and
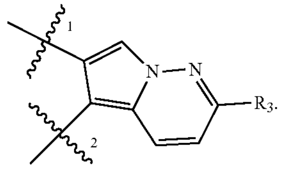
In some embodiments,
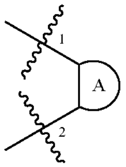
is a bicyclic heteroaryl ring selected from,
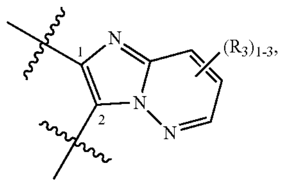
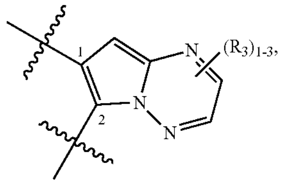
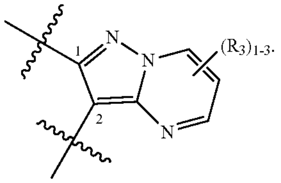
In some embodiments,
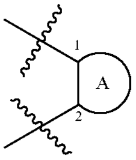
is a bicyclic heteroaryl ring selected from
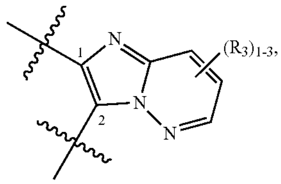
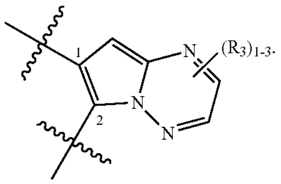
In some embodiments,
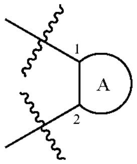
is a bicyclic heteroaryl ring selected from
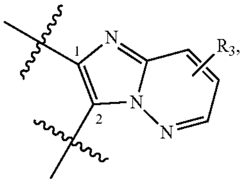
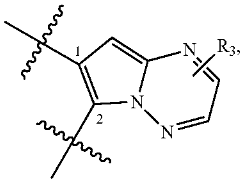
and
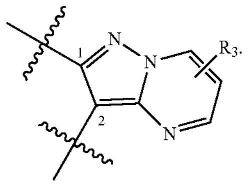
In some embodiments,
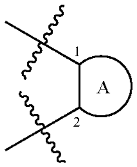
is a bicyclic heteroaryl ring selected from
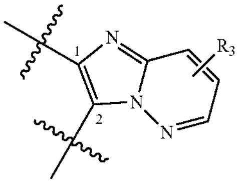
and
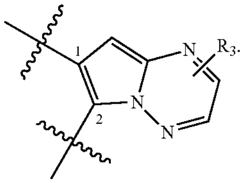
In some embodiments,
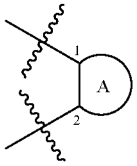

is a bicyclic heteroaryl ring selected from

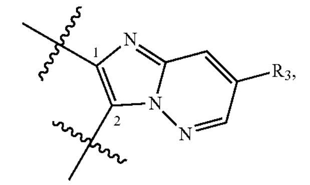

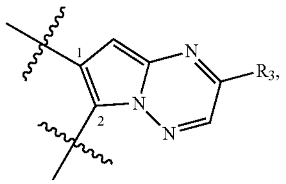

and

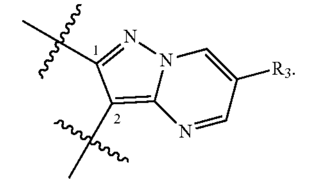

In some embodiments,

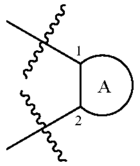

is a bicyclic heteroaryl ring selected from

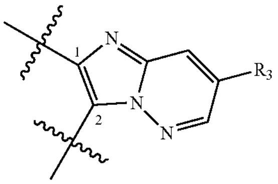

and

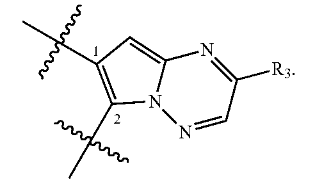

In some embodiments, at least one $R_3$ is spiro-, bridged-, or mono-$C_3$-$C_{10}$ cycloalkyl (e.g., cyclopropyl, cyclobutyl, cyclopentyl, cyclohexyl, cycloheptyl, cyclooctyl, each of which can be spiro-, bridged-, or mono-cycloalkyl) optionally substituted with one or more substituents independently selected from straight-chain $C_1$-$C_6$ alkyl or branched $C_3$-$C_6$ alkyl (e.g., methyl, ethyl, propyl, i-propyl, n-butyl, i-butyl, s-butyl, t-butyl, pentyl, or hexyl), straight-chain $C_1$-$C_6$ haloalkyl or branched $C_3$-$C_6$ haloalkyl (e.g., methyl, ethyl, propyl, i-propyl, n-butyl, i-butyl, s-butyl, t-butyl, pentyl, or hexyl, each of which is substituted with one or more halogen (e.g., F, Cl)), straight-chain $C_1$-$C_6$ alkoxy or branched $C_3$-$C_6$ alkoxy (e.g., methoxy, ethoxy, propoxy, i-propoxy, n-butoxy, i-butoxy, s-butoxy, t-butoxy, pentoxy, or hexyloxy), straight-chain $C_1$-$C_6$ haloalkoxy or branched $C_3$-$C_6$ haloalkoxy (e.g., methoxy, ethoxy, propoxy, i-propoxy, n-butoxy, i-butoxy, s-butoxy, t-butoxy, pentoxy, or hexyloxy, each of which is substituted with one or more halogen (e.g., F, Cl)), OH, halogen (e.g., F, Cl, Br, or I), $NH_2$, NH—($C_1$-$C_6$ alkyl) (e.g., methyl, ethyl, propyl, i-propyl, n-butyl, i-butyl, s-butyl, t-butyl, pentyl, or hexyl), N($C_1$-$C_6$ alkyl)$_2$ (e.g., methyl, ethyl, propyl, i-propyl, n-butyl, i-butyl, s-butyl, t-butyl, pentyl, or hexyl), CN, and $NO_2$.

In some embodiments, at least one $R_3$ is spiro-, bridged-, or mono-$C_3$-$C_{10}$ cycloalkyl (e.g., cyclopropyl, cyclobutyl, cyclopentyl, cyclohexyl, cycloheptyl, cyclooctyl, each of which can be spiro-, bridged-, or mono-cycloalkyl) optionally substituted with one or more substituents independently selected from straight-chain $C_1$-$C_6$ alkyl or branched $C_3$-$C_6$ alkyl (e.g., methyl, ethyl, propyl, i-propyl, n-butyl, i-butyl, s-butyl, t-butyl, pentyl, or hexyl), straight-chain $C_1$-$C_6$ haloalkyl or branched $C_3$-$C_6$ haloalkyl (e.g., methyl, ethyl, propyl, i-propyl, n-butyl, i-butyl, s-butyl, t-butyl, pentyl, or hexyl, each of which is substituted with one or more halogen (e.g., F, Cl)), straight-chain $C_1$-$C_6$ alkoxy or branched $C_3$-$C_6$ alkoxy (e.g., methoxy, ethoxy, propoxy, i-propoxy, n-butoxy, i-butoxy, s-butoxy, t-butoxy, pentoxy, or hexyloxy), straight-chain $C_1$-$C_6$ haloalkoxy or branched $C_3$-$C_6$ haloalkoxy (e.g., methoxy, ethoxy, propoxy, i-propoxy, n-butoxy, i-butoxy, s-butoxy, t-butoxy, pentoxy, or hexyloxy, each of which is substituted with one or more halogen (e.g., F, Cl)), and halogen (e.g., F, Cl, Br, or I).

In some embodiments, at least one $R_3$ is spiro-, bridged-, or mono-$C_3$-$C_{10}$ cycloalkyl (e.g., cyclopropyl, cyclobutyl, cyclopentyl, cyclohexyl, cycloheptyl, cyclooctyl, each of which can be spiro-, bridged-, or mono-cycloalkyl) optionally substituted with one or more substituents independently selected from straight-chain $C_1$-$C_4$ alkyl or branched $C_3$-$C_4$ alkyl (e.g., methyl, ethyl, propyl, i-propyl, n-butyl, i-butyl, s-butyl, or t-butyl), straight-chain $C_1$-$C_4$ haloalkyl or branched $C_3$-$C_4$ haloalkyl (e.g., methyl, ethyl, propyl, i-propyl, n-butyl, i-butyl, s-butyl, or t-butyl, each of which is substituted with one or more halogen (e.g., F, Cl)), straight-chain $C_1$-$C_4$ alkoxy or branched $C_3$-$C_4$ alkoxy (e.g., methoxy, ethoxy, propoxy, i-propoxy, n-butoxy, i-butoxy, s-butoxy, or t-butoxy), straight-chain $C_1$-$C_4$ haloalkoxy or branched $C_3$-$C_4$ haloalkoxy (e.g., methoxy, ethoxy, propoxy, i-propoxy, n-butoxy, i-butoxy, s-butoxy, or t-butoxy, each of which is substituted with one or more halogen (e.g., F, Cl)), and halogen (e.g., F, Cl, Br, or I).

In some embodiments, at least one $R_3$ is spiro-, bridged-, or mono-$C_3$-$C_{10}$ cycloalkyl (e.g., cyclopropyl, cyclobutyl, cyclopentyl, cyclohexyl, cycloheptyl, cyclooctyl, each of which can be spiro-, bridged-, or mono-cycloalkyl) optionally substituted with one or more substituents independently selected from straight-chain $C_1$-$C_4$ alkyl or branched $C_3$-$C_4$ alkyl (e.g., methyl, ethyl, propyl, i-propyl, n-butyl, i-butyl, s-butyl, or t-butyl), straight-chain $C_1$-$C_4$ haloalkyl or branched $C_3$-$C_4$ haloalkyl (e.g., methyl, ethyl, propyl, i-propyl, n-butyl, i-butyl, s-butyl, or t-butyl, each of which is substituted with one or more halogen (e.g., F, Cl)), and halogen (e.g., F, Cl, Br, or I).

In some embodiments, at least one $R_3$ is spiro-, bridged-, or mono-$C_3$-$C_{10}$ cycloalkyl (e.g., cyclopropyl, cyclobutyl, cyclopentyl, cyclohexyl, cycloheptyl, cyclooctyl, each of which can be spiro-, bridged-, or mono-cycloalkyl) optionally substituted with one or two substituents as described herein.

In some embodiments, at least one $R_3$ is phenyl optionally substituted with one or more substituents independently selected from straight-chain $C_1$-$C_6$ alkyl or branched $C_3$-$C_6$ alkyl (e.g., methyl, ethyl, propyl, i-propyl, n-butyl, i-butyl, s-butyl, t-butyl, pentyl, or hexyl), straight-chain $C_1$-$C_6$ haloalkyl or branched $C_3$-$C_6$ haloalkyl (e.g., methyl, ethyl, propyl, i-propyl, n-butyl, i-butyl, s-butyl, t-butyl, pentyl, or hexyl, each of which is substituted with one or more halogen (e.g., F, Cl)), straight-chain $C_1$-$C_6$ alkoxy or branched $C_3$-$C_6$ alkoxy (e.g., methoxy, ethoxy, propoxy, i-propoxy, n-butoxy, i-butoxy, s-butoxy, t-butoxy, pentoxy, or hexyloxy), straight-chain $C_1$-$C_6$ haloalkoxy or branched $C_3$-$C_6$ haloalkoxy (e.g., methoxy, ethoxy, propoxy, i-propoxy, n-butoxy, i-butoxy, s-butoxy, t-butoxy, pentoxy, or hexyloxy, each of which is substituted with one or more halogen (e.g., F, Cl)), OH, halogen (e.g., F, Cl, Br, or I), $NH_2$, NH—($C_1$-$C_6$ alkyl) (e.g., methyl, ethyl, propyl, i-propyl, n-butyl, i-butyl, s-butyl, t-butyl, pentyl, or hexyl), N($C_1$-$C_6$ alkyl)$_2$ (e.g., methyl, ethyl, propyl, i-propyl, n-butyl, i-butyl, s-butyl, t-butyl, pentyl, or hexyl), CN, and $NO_2$.

In some embodiments, at least one $R_3$ is phenyl optionally substituted with one or more substituents independently selected from straight-chain $C_1$-$C_6$ alkyl or branched $C_3$-$C_6$ alkyl (e.g., methyl, ethyl, propyl, i-propyl, n-butyl, i-butyl, s-butyl, t-butyl, pentyl, or hexyl), straight-chain $C_1$-$C_6$ haloalkyl or branched $C_3$-$C_6$ haloalkyl (e.g., methyl, ethyl, propyl, i-propyl, n-butyl, i-butyl, s-butyl, t-butyl, pentyl, or hexyl, each of which is substituted with one or more halogen (e.g., F, Cl)), straight-chain $C_1$-$C_6$ alkoxy or branched $C_3$-$C_6$ alkoxy (e.g., methoxy, ethoxy, propoxy, i-propoxy, n-butoxy, i-butoxy, s-butoxy, t-butoxy, pentoxy, or hexyloxy), straight-chain $C_1$-$C_6$ haloalkoxy or branched $C_3$-$C_6$ haloalkoxy (e.g., methoxy, ethoxy, propoxy, i-propoxy, n-butoxy, i-butoxy, s-butoxy, t-butoxy, pentoxy, or hexyloxy, each of which is substituted with one or more halogen (e.g., F, Cl)), and halogen (e.g., F, Cl, Br, or I).

In some embodiments, at least one $R_3$ is phenyl optionally substituted with one or more substituents independently selected from straight-chain $C_1$-$C_4$ alkyl or branched $C_3$-$C_4$ alkyl (e.g., methyl, ethyl, propyl, i-propyl, n-butyl, i-butyl, s-butyl, or t-butyl), straight-chain $C_1$-$C_4$ haloalkyl or branched $C_3$-$C_4$ haloalkyl (e.g., methyl, ethyl, propyl, i-propyl, n-butyl, i-butyl, s-butyl, or t-butyl, each of which is substituted with one or more halogen (e.g., F, Cl)), straight-chain $C_1$-$C_4$ alkoxy or branched $C_3$-$C_4$ alkoxy (e.g., methoxy, ethoxy, propoxy, i-propoxy, n-butoxy, i-butoxy, s-butoxy, or t-butoxy), straight-chain $C_1$-$C_4$ haloalkoxy or branched $C_3$-$C_4$ haloalkoxy (e.g., methoxy, ethoxy, propoxy, i-propoxy, n-butoxy, i-butoxy, s-butoxy, or t-butoxy, each of which is substituted with one or more halogen (e.g., F, Cl)), and halogen (e.g., F, Cl, Br, or I).

In some embodiments, at least one $R_3$ is phenyl optionally substituted with one or more substituents independently selected from straight-chain $C_1$-$C_4$ alkyl or branched $C_3$-$C_4$ alkyl (e.g., methyl, ethyl, propyl, i-propyl, n-butyl, i-butyl, s-butyl, or t-butyl), straight-chain $C_1$-$C_4$ haloalkyl or branched $C_3$-$C_4$ haloalkyl (e.g., methyl, ethyl, propyl, i-propyl, n-butyl, i-butyl, s-butyl, or t-butyl, each of which is substituted with one or more halogen (e.g., F, Cl)), and halogen (e.g., F, Cl, Br, or I).

In some embodiments, at least one $R_3$ is phenyl optionally substituted with one or two substituents as described herein.

In some embodiments, at least one $R_3$ is phenyl substituted with one or two substituents as described herein.

In some embodiments, at least one $R_3$ is heterocyclyl comprising one or two 3- to 6-membered rings and 1-3 heteroatoms selected from N, O, and S, optionally substituted with one or more substituents independently selected from straight-chain $C_1$-$C_6$ alkyl or branched $C_3$-$C_6$ alkyl (e.g., methyl, ethyl, propyl, i-propyl, n-butyl, i-butyl, s-butyl, t-butyl, pentyl, or hexyl), straight-chain $C_1$-$C_6$ haloalkyl or branched $C_3$-$C_6$ haloalkyl (e.g., methyl, ethyl, propyl, i-propyl, n-butyl, i-butyl, s-butyl, t-butyl, pentyl, or hexyl, each of which is substituted with one or more halogen (e.g., F, Cl)), straight-chain $C_1$-$C_6$ alkoxy or branched $C_3$-$C_6$ alkoxy (e.g., methoxy, ethoxy, propoxy, i-propoxy, n-butoxy, i-butoxy, s-butoxy, t-butoxy, pentoxy, or hexyloxy), straight-chain $C_1$-$C_6$ haloalkoxy or branched $C_3$-$C_6$ haloalkoxy (e.g., methoxy, ethoxy, propoxy, i-propoxy, n-butoxy, i-butoxy, s-butoxy, t-butoxy, pentoxy, or hexyloxy, each of which is substituted with one or more halogen (e.g., F, Cl)), OH, halogen (e.g., F, Cl, Br, or I), $NH_2$, NH—($C_1$-$C_6$ alkyl) (e.g., methyl, ethyl, propyl, i-propyl, n-butyl, i-butyl, s-butyl, t-butyl, pentyl, or hexyl), N($C_1$-$C_6$ alkyl)$_2$ (e.g., methyl, ethyl, propyl, i-propyl, n-butyl, i-butyl, s-butyl, t-butyl, pentyl, or hexyl), CN, and $NO_2$, wherein the heterocyclyl comprising two 3- to 6-membered rings and 1-3 heteroatoms selected from N, O, and S may be a spiro- or fused-ring heterocyclyl.

In some embodiments, at least one $R_3$ is heterocyclyl comprising one or two 3- to 6-membered rings and 1-3 heteroatoms selected from N, O, and S, optionally substituted with one or more substituents independently selected from straight-chain $C_1$-$C_6$ alkyl or branched $C_3$-$C_6$ alkyl (e.g., methyl, ethyl, propyl, i-propyl, n-butyl, i-butyl, s-butyl, t-butyl, pentyl, or hexyl), straight-chain $C_1$-$C_6$ haloalkyl or branched $C_3$-$C_6$ haloalkyl (e.g., methyl, ethyl, propyl, i-propyl, n-butyl, i-butyl, s-butyl, t-butyl, pentyl, or hexyl, each of which is substituted with one or more halogen (e.g., F, Cl)), straight-chain $C_1$-$C_6$ alkoxy or branched $C_3$-$C_6$ alkoxy (e.g., methoxy, ethoxy, propoxy, i-propoxy, n-butoxy, i-butoxy, s-butoxy, t-butoxy, pentoxy, or hexyloxy), straight-chain $C_1$-$C_6$ haloalkoxy or branched $C_3$-$C_6$ haloalkoxy (e.g., methoxy, ethoxy, propoxy, i-propoxy, n-butoxy, i-butoxy, s-butoxy, t-butoxy, pentoxy, or hexyloxy, each of which is substituted with one or more halogen (e.g., F, Cl)), and halogen (e.g., F, Cl, Br, or I), wherein the heterocyclyl comprising two 3- to 6-membered rings and 1-3 heteroatoms selected from N, O, and S may be a spiro- or fused-ring heterocyclyl.

In some embodiments, at least one $R_3$ is heterocyclyl comprising one or two 3- to 6-membered rings and 1-3 heteroatoms selected from N, O, and S, optionally substituted with one or more substituents independently selected from straight-chain $C_1$-$C_4$ alkyl or branched $C_3$-$C_4$ alkyl (e.g., methyl, ethyl, propyl, i-propyl, n-butyl, i-butyl, s-butyl, or t-butyl), straight-chain $C_1$-$C_4$ haloalkyl or branched $C_3$-$C_4$ haloalkyl (e.g., methyl, ethyl, propyl, i-propyl, n-butyl, i-butyl, s-butyl, or t-butyl, each of which is substituted with one or more halogen (e.g., F, Cl)), straight-chain $C_1$-$C_4$ alkoxy or branched $C_3$-$C_4$ alkoxy (e.g., methoxy, ethoxy, propoxy, i-propoxy, n-butoxy, i-butoxy, s-butoxy, or t-butoxy), straight-chain $C_1$-$C_4$ haloalkoxy or branched $C_3$-$C_4$ haloalkoxy (e.g., methoxy, ethoxy, propoxy, i-propoxy, n-butoxy, i-butoxy, s-butoxy, or t-butoxy, each of which is substituted with one or more halogen (e.g., F, Cl)), and halogen (e.g., F, Cl, Br, or I), wherein the heterocyclyl comprising two 3- to 6-membered rings and 1-3 heteroatoms selected from N, O, and S may be a spiro- or fused-ring heterocyclyl.

In some embodiments, at least one $R_3$ is heterocyclyl comprising one or two 3- to 6-membered rings and 1-3 heteroatoms selected from N, O, and S, optionally substituted with one or more substituents independently selected from straight-chain $C_1$-$C_4$ alkyl or branched $C_3$-$C_4$ alkyl (e.g., methyl, ethyl, propyl, i-propyl, n-butyl, i-butyl, s-butyl, or t-butyl), straight-chain $C_1$-$C_4$ haloalkyl or branched $C_3$-$C_4$ haloalkyl (e.g., methyl, ethyl, propyl, i-propyl, n-butyl, i-butyl, s-butyl, or t-butyl, each of which is substituted with one or more halogen (e.g., F, Cl)), and halogen (e.g., F, Cl, Br, or I), wherein the heterocyclyl comprising two 3- to 6-membered rings and 1-3 heteroatoms selected from N, O, and S may be a spiro- or fused-ring heterocyclyl.

In some embodiments, at least one $R_3$ is heterocyclyl comprising one or two 3- to 6-membered rings and 1-3 heteroatoms selected from N, O, and S, optionally substituted with one or two substituents as described herein, wherein the heterocyclyl comprising two 3- to 6-membered rings and 1-3 heteroatoms selected from N, O, and S may be a spiro- or fused-ring heterocyclyl.

In some embodiments, at least one $R_3$ is heterocyclyl comprising one or two 3- to 6-membered rings and 1-3 heteroatoms selected from N, O, and S, substituted with one or two substituents as described herein, wherein the heterocyclyl comprising two 3- to 6-membered rings and 1-3 heteroatoms selected from N, O, and S may be a spiro- or fused-ring heterocyclyl.

In some embodiments, at least one $R_3$ is heterocyclyl comprising one or two 5- or 6-membered rings and 1-3 heteroatoms selected from N, O, and S, optionally substituted with one or more substituents independently selected from straight-chain $C_1$-$C_6$ alkyl or branched $C_3$-$C_6$ alkyl (e.g., methyl, ethyl, propyl, i-propyl, n-butyl, i-butyl, s-butyl, t-butyl, pentyl, or hexyl), straight-chain $C_1$-$C_6$ haloalkyl or branched $C_3$-$C_6$ haloalkyl (e.g., methyl, ethyl, propyl, i-propyl, n-butyl, i-butyl, s-butyl, t-butyl, pentyl, or hexyl, each of which is substituted with one or more halogen (e.g., F, Cl)), straight-chain $C_1$-$C_6$ alkoxy or branched $C_3$-$C_6$ alkoxy (e.g., methoxy, ethoxy, propoxy, i-propoxy, n-butoxy, i-butoxy, s-butoxy, t-butoxy, pentoxy, or hexyloxy), straight-chain $C_1$-$C_6$ haloalkoxy or branched $C_3$-$C_6$ haloalkoxy (e.g., methoxy, ethoxy, propoxy, i-propoxy, n-butoxy, i-butoxy, s-butoxy, t-butoxy, pentoxy, or hexyloxy, each of which is substituted with one or more halogen (e.g., F, Cl)), OH, halogen (e.g., F, Cl, Br, or I), $NH_2$, NH—($C_1$-$C_6$ alkyl) (e.g., methyl, ethyl, propyl, i-propyl, n-butyl, i-butyl, s-butyl, t-butyl, pentyl, or hexyl), $N(C_1$-$C_6$ alkyl$)_2$ (e.g., methyl, ethyl, propyl, i-propyl, n-butyl, i-butyl, s-butyl, t-butyl, pentyl, or hexyl), CN, and $NO_2$.

In some embodiments, at least one $R_3$ is heterocyclyl comprising one or two 5- or 6-membered rings and 1-3 heteroatoms selected from N, O, and S, optionally substituted with one or more substituents independently selected from straight-chain $C_1$-$C_6$ alkyl or branched $C_3$-$C_6$ alkyl (e.g., methyl, ethyl, propyl, i-propyl, n-butyl, i-butyl, s-butyl, t-butyl, pentyl, or hexyl), straight-chain $C_1$-$C_6$ haloalkyl or branched $C_3$-$C_6$ haloalkyl (e.g., methyl, ethyl, propyl, i-propyl, n-butyl, i-butyl, s-butyl, t-butyl, pentyl, or hexyl, each of which is substituted with one or more halogen (e.g., F, Cl)), straight-chain $C_1$-$C_6$ alkoxy or branched $C_3$-$C_6$ alkoxy (e.g., methoxy, ethoxy, propoxy, i-propoxy, n-butoxy, i-butoxy, s-butoxy, t-butoxy, pentoxy, or hexyloxy), straight-chain $C_1$-$C_6$ haloalkoxy or branched $C_3$-$C_6$ haloalkoxy (e.g., methoxy, ethoxy, propoxy, i-propoxy, n-butoxy, i-butoxy, s-butoxy, t-butoxy, pentoxy, or hexyloxy, each of which is substituted with one or more halogen (e.g., F, Cl)), and halogen (e.g., F, Cl, Br, or I).

In some embodiments, at least one $R_3$ is heterocyclyl comprising one or two 5- or 6-membered rings and 1-3 heteroatoms selected from N, O, and S, optionally substituted with one or more substituents independently selected from straight-chain $C_1$-$C_4$ alkyl or branched $C_3$-$C_4$ alkyl (e.g., methyl, ethyl, propyl, i-propyl, n-butyl, i-butyl, s-butyl, or t-butyl), straight-chain $C_1$-$C_4$ haloalkyl or branched $C_3$-$C_4$ haloalkyl (e.g., methyl, ethyl, propyl, i-propyl, n-butyl, i-butyl, s-butyl, or t-butyl, each of which is substituted with one or more halogen (e.g., F, Cl)), straight-chain $C_1$-$C_4$ alkoxy or branched $C_3$-$C_4$ alkoxy (e.g., methoxy, ethoxy, propoxy, i-propoxy, n-butoxy, i-butoxy, s-butoxy, or t-butoxy), straight-chain $C_1$-$C_4$ haloalkoxy or branched $C_3$-$C_4$ haloalkoxy (e.g., methoxy, ethoxy, propoxy, i-propoxy, n-butoxy, i-butoxy, s-butoxy, or t-butoxy, each of which is substituted with one or more halogen (e.g., F, Cl)), and halogen (e.g., F, Cl, Br, or I).

In some embodiments, at least one $R_3$ is heterocyclyl comprising one or two 5- or 6-membered rings and 1-3 heteroatoms selected from N, O, and S, optionally substituted with one or more substituents independently selected from straight-chain $C_1$-$C_4$ alkyl or branched $C_3$-$C_4$ alkyl (e.g., methyl, ethyl, propyl, i-propyl, n-butyl, i-butyl, s-butyl, or t-butyl), straight-chain $C_1$-$C_4$ haloalkyl or branched $C_3$-$C_4$ haloalkyl (e.g., methyl, ethyl, propyl, i-propyl, n-butyl, i-butyl, s-butyl, or t-butyl, each of which is substituted with one or more halogen (e.g., F, Cl)), and halogen (e.g., F, Cl, Br, or I).

In some embodiments, at least one $R_3$ is heterocyclyl comprising one or two 5- or 6-membered rings and 1-3 heteroatoms selected from N, O, and S, optionally substituted with one or two substituents as described herein.

In some embodiments, at least one $R_3$ is heterocyclyl comprising one or two 5- or 6-membered rings and 1-3 heteroatoms selected from N, O, and S, substituted with one or two substituents as described herein.

In some embodiments, at least one $R_3$ is heterocyclyl comprising one 5- or 6-membered ring and 1-3 heteroatoms selected from N, O, and S, optionally substituted with one or more substituents as described herein.

In some embodiments, at least one $R_3$ is heterocyclyl comprising one 5- or 6-membered ring and 1-3 heteroatoms selected from N, O, and S, optionally substituted with one or two substituents as described herein.

In some embodiments, at least one $R_3$ is heterocyclyl comprising one 5- or 6-membered ring and 1-3 heteroatoms selected from N, O, and S, substituted with one or two substituents as described herein.

In some embodiments, at least one $R_3$ is heterocyclyl comprising one 5-membered ring and 1-3 heteroatoms selected from N, O, and S, optionally substituted with one or more substituents as described herein.

In some embodiments, at least one $R_3$ is heterocyclyl comprising one 5-membered ring and 1-3 heteroatoms selected from N, O, and S, optionally substituted with one or two substituents as described herein.

In some embodiments, at least one $R_3$ is heterocyclyl comprising one 5-membered ring and 1-3 heteroatoms selected from N, O, and S, substituted with one or two substituents as described herein.

In some embodiments, at least one $R_3$ is heterocyclyl comprising one 6-membered ring and 1-3 heteroatoms selected from N, O, and S, optionally substituted with one or more substituents as described herein.

In some embodiments, at least one $R_3$ is heterocyclyl comprising one 6-membered ring and 1-3 heteroatoms selected from N, O, and S, optionally substituted with one or two substituents as described herein.

In some embodiments, at least one $R_3$ is heterocyclyl comprising one 6-membered ring and 1-3 heteroatoms selected from N, O, and S, substituted with one or two substituents as described herein.

In some embodiments, at least one $R_3$ is tetrahydropyranyl optionally substituted with one or more substituents as described herein.

In some embodiments, at least one $R_3$ is tetrahydropyranyl optionally substituted with one or two substituents as described herein.

In some embodiments, at least one $R_3$ is tetrahydropyranyl substituted with one or two substituents as described herein.

In some embodiments, at least one $R_3$ is heteroaryl comprising one or two 5- or 6-membered rings and 1-3 heteroatoms selected from N, O, and S, optionally substituted with one or more substituents independently selected from straight-chain $C_1$-$C_6$ alkyl or branched $C_3$-$C_6$ alkyl (e.g., methyl, ethyl, propyl, i-propyl, n-butyl, i-butyl, s-butyl, t-butyl, pentyl, or hexyl), straight-chain $C_1$-$C_6$ haloalkyl or branched $C_3$-$C_6$ haloalkyl (e.g., methyl, ethyl, propyl, i-propyl, n-butyl, i-butyl, s-butyl, t-butyl, pentyl, or hexyl, each of which is substituted with one or more halogen (e.g., F, Cl)), straight-chain $C_1$-$C_6$ alkoxy or branched $C_3$-$C_6$ alkoxy (e.g., methoxy, ethoxy, propoxy, i-propoxy, n-butoxy, i-butoxy, s-butoxy, t-butoxy, pentoxy, or hexyloxy), straight-chain $C_1$-$C_6$ haloalkoxy or branched $C_3$-$C_6$ haloalkoxy (e.g., methoxy, ethoxy, propoxy, i-propoxy, n-butoxy, i-butoxy, s-butoxy, t-butoxy, pentoxy, or hexyloxy, each of which is substituted with one or more halogen (e.g., F, Cl)), OH, halogen (e.g., F, Cl, Br, or I), $NH_2$, NH—($C_1$-$C_6$ alkyl) (e.g., methyl, ethyl, propyl, i-propyl, n-butyl, i-butyl, s-butyl, t-butyl, pentyl, or hexyl), N($C_1$-$C_6$ alkyl)$_2$ (e.g., methyl, ethyl, propyl, i-propyl, n-butyl, i-butyl, s-butyl, t-butyl, pentyl, or hexyl), CN, and $NO_2$.

In some embodiments, at least one $R_3$ is heteroaryl comprising one or two 5- or 6-membered rings and 1-3 heteroatoms selected from N, O, and S, optionally substituted with one or more substituents independently selected from straight-chain $C_1$-$C_6$ alkyl or branched $C_3$-$C_6$ alkyl (e.g., methyl, ethyl, propyl, i-propyl, n-butyl, i-butyl, s-butyl, t-butyl, pentyl, or hexyl), straight-chain $C_1$-$C_6$ haloalkyl or branched $C_3$-$C_6$ haloalkyl (e.g., methyl, ethyl, propyl, i-propyl, n-butyl, i-butyl, s-butyl, t-butyl, pentyl, or hexyl, each of which is substituted with one or more halogen (e.g., F, Cl)), straight-chain $C_1$-$C_6$ alkoxy or branched $C_3$-$C_6$ alkoxy (e.g., methoxy, ethoxy, propoxy, i-propoxy, n-butoxy, i-butoxy, s-butoxy, t-butoxy, pentoxy, or hexyloxy), straight-chain $C_1$-$C_6$ haloalkoxy or branched $C_3$-$C_6$ haloalkoxy (e.g., methoxy, ethoxy, propoxy, i-propoxy, n-butoxy, i-butoxy, s-butoxy, t-butoxy, pentoxy, or hexyloxy, each of which is substituted with one or more halogen (e.g., F, Cl)), and halogen (e.g., F, Cl, Br, or I).

In some embodiments, at least one $R_3$ is heteroaryl comprising one or two 5- or 6-membered rings and 1-3 heteroatoms selected from N, O, and S, optionally substituted with one or more substituents independently selected from straight-chain $C_1$-$C_4$ alkyl or branched $C_3$-$C_4$ alkyl (e.g., methyl, ethyl, propyl, i-propyl, n-butyl, i-butyl, s-butyl, or t-butyl), straight-chain $C_1$-$C_4$ haloalkyl or branched $C_3$-$C_4$ haloalkyl (e.g., methyl, ethyl, propyl, i-propyl, n-butyl, i-butyl, s-butyl, or t-butyl, each of which is substituted with one or more halogen (e.g., F, Cl)), straight-chain $C_1$-$C_4$ alkoxy or branched $C_3$-$C_4$ alkoxy (e.g., methoxy, ethoxy, propoxy, i-propoxy, n-butoxy, i-butoxy, s-butoxy, or t-butoxy), straight-chain $C_1$-$C_4$ haloalkoxy or branched $C_3$-$C_4$ haloalkoxy (e.g., methoxy, ethoxy, propoxy, i-propoxy, n-butoxy, i-butoxy, s-butoxy, or t-butoxy, each of which is substituted with one or more halogen (e.g., F, Cl)), and halogen (e.g., F, Cl, Br, or I).

In some embodiments, at least one $R_3$ is heteroaryl comprising one or two 5- or 6-membered rings and 1-3 heteroatoms selected from N, O, and S, optionally substituted with one or more substituents independently selected from straight-chain $C_1$-$C_4$ alkyl or branched $C_3$-$C_4$ alkyl (e.g., methyl, ethyl, propyl, i-propyl, n-butyl, i-butyl, s-butyl, or t-butyl), straight-chain $C_1$-$C_4$ haloalkyl or branched $C_3$-$C_4$ haloalkyl (e.g., methyl, ethyl, propyl, i-propyl, n-butyl, i-butyl, s-butyl, or t-butyl, each of which is substituted with one or more halogen (e.g., F, Cl)), and halogen (e.g., F, Cl, Br, or I).

In some embodiments, at least one $R_3$ is heteroaryl comprising one or two 5- or 6-membered rings and 1-3 heteroatoms selected from N, O, and S, optionally substituted with one or two substituents as described herein.

In some embodiments, at least one $R_3$ is heteroaryl comprising one or two 5- or 6-membered rings and 1-3 heteroatoms selected from N, O, and S, substituted with one or two substituents as described herein.

In some embodiments, at least one $R_3$ is heteroaryl comprising one 5- or 6-membered ring and 1-3 heteroatoms selected from N, O, and S, optionally substituted with one or more substituents as described herein.

In some embodiments, at least one $R_3$ is heteroaryl comprising one 5- or 6-membered ring and 1-3 heteroatoms selected from N, O, and S, optionally substituted with one or two substituents as described herein.

In some embodiments, at least one $R_3$ is heteroaryl comprising one 5- or 6-membered ring and 1-3 heteroatoms selected from N, O, and S, substituted with one or two substituents as described herein.

In some embodiments, at least one $R_3$ is heteroaryl comprising one 5-membered ring and 1-3 heteroatoms selected from N, O, and S, optionally substituted with one or more substituents as described herein.

In some embodiments, at least one $R_3$ is heteroaryl comprising one 5-membered ring and 1-3 heteroatoms selected from N, O, and S, optionally substituted with one or two substituents as described herein.

In some embodiments, at least one $R_3$ is heteroaryl comprising one 5-membered ring and 1-3 heteroatoms selected from N, O, and S, substituted with one or two substituents as described herein.

In some embodiments, at least one $R_3$ is heteroaryl comprising one 6-membered ring and 1-3 heteroatoms selected from N, O, and S, optionally substituted with one or more substituents as described herein.

In some embodiments, at least one $R_3$ is heteroaryl comprising one 6-membered ring and 1-3 heteroatoms selected from N, O, and S, optionally substituted with one or two substituents as described herein.

In some embodiments, at least one $R_3$ is heteroaryl comprising one 6-membered ring and 1-3 heteroatoms selected from N, O, and S, substituted with one or two substituents as described herein.

In some embodiments, at least one $R_3$ is pyridyl optionally substituted with one or more substituents as described herein.

In some embodiments, at least one $R_3$ is pyridyl optionally substituted with one or two substituents as described herein.

In some embodiments, at least one $R_3$ is pyridyl substituted with one or two substituents as described herein.

In some embodiments, $R_4$ is straight-chain $C_1$-$C_6$ alkyl or branched $C_3$-$C_6$ alkyl (e.g., methyl, ethyl, propyl, i-propyl, n-butyl, i-butyl, s-butyl, t-butyl, pentyl, or hexyl), straight-chain $C_1$-$C_6$ haloalkyl or branched $C_3$-$C_6$ haloalkyl (e.g., methyl, ethyl, propyl, i-propyl, n-butyl, i-butyl, s-butyl, t-butyl, pentyl, or hexyl, each of which is substituted with one or more halogen (e.g., F, Cl)), straight-chain $C_1$-$C_6$ alkoxy or branched $C_3$-$C_6$ alkoxy (e.g., methoxy, ethoxy, propoxy, i-propoxy, n-butoxy, i-butoxy, s-butoxy, t-butoxy, pentoxy, or hexyloxy), straight-chain $C_1$-$C_6$ haloalkoxy or branched $C_3$-$C_6$ haloalkoxy (e.g., methoxy, ethoxy, propoxy, i-propoxy, n-butoxy, i-butoxy, s-butoxy, t-butoxy, pentoxy, or hexyloxy, each of which is substituted with one or more halogen (e.g., F, Cl)), OH, or halogen (e.g., F, Cl, Br, or I).

In some embodiments, $R_4$ is straight-chain $C_1$-$C_6$ alkyl or branched $C_3$-$C_6$ alkyl (e.g., methyl, ethyl, propyl, i-propyl, n-butyl, i-butyl, s-butyl, t-butyl, pentyl, or hexyl), straight-chain $C_1$-$C_6$ haloalkyl or branched $C_3$-$C_6$ haloalkyl (e.g., methyl, ethyl, propyl, i-propyl, n-butyl, i-butyl, s-butyl, t-butyl, pentyl, or hexyl, each of which is substituted with one or more halogen (e.g., F, Cl)), or halogen (e.g., F, Cl, Br, or I).

In some embodiments, $R_4$ is straight-chain $C_1$-$C_6$ alkyl or branched $C_3$-$C_6$ alkyl (e.g., methyl, ethyl, propyl, i-propyl, n-butyl, i-butyl, s-butyl, t-butyl, pentyl, or hexyl).

In some embodiments, $R_4$ is straight-chain $C_1$-$C_4$ alkyl or branched $C_3$-$C_4$ alkyl (e.g., methyl, ethyl, propyl, i-propyl, n-butyl, i-butyl, s-butyl, or t-butyl).

In some embodiments, L is

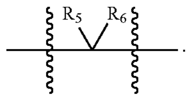

In some embodiments, L is phenylenyl optionally substituted with one or more substituents independently selected from straight-chain $C_1$-$C_6$ alkyl or branched $C_3$-$C_6$ alkyl (e.g., methyl, ethyl, propyl, i-propyl, n-butyl, i-butyl, s-butyl, t-butyl, pentyl, or hexyl), straight-chain $C_1$-$C_6$ haloalkyl or branched $C_3$-$C_6$ haloalkyl (e.g., methyl, ethyl, propyl, i-propyl, n-butyl, i-butyl, s-butyl, t-butyl, pentyl, or hexyl, each of which is substituted with one or more halogen (e.g., F, Cl)), straight-chain $C_1$-$C_6$ alkoxy or branched $C_3$-$C_6$ alkoxy (e.g., methoxy, ethoxy, propoxy, i-propoxy, n-butoxy, i-butoxy, s-butoxy, t-butoxy, pentoxy, or hexyloxy), straight-chain $C_1$-$C_6$ haloalkoxy or branched $C_3$-$C_6$ haloalkoxy (e.g., methoxy, ethoxy, propoxy, i-propoxy, n-butoxy, i-butoxy, s-butoxy, t-butoxy, pentoxy, or hexyloxy, each of which is substituted with one or more halogen (e.g., F, Cl)), OH, or halogen (e.g., F, Cl, Br, or I).

In some embodiments, L is phenylenyl substituted with two substituents attached to adjacent carbon atoms in the phenylenyl ring, and the two substituents, together with the carbon atoms to which they are attached, may form a 5- or 6-membered ring optionally comprising 1-3 heteroatoms selected from N, O, and S.

In some embodiments, $R_5$ and $R_6$ are each H.

In some embodiments, one of $R_5$ and $R_6$ is straight-chain $C_1$-$C_6$ alkyl or branched $C_3$-$C_6$ alkyl (e.g., methyl, ethyl, propyl, i-propyl, n-butyl, i-butyl, s-butyl, t-butyl, pentyl, or hexyl), straight-chain $C_1$-$C_6$ haloalkyl or branched $C_3$-$C_6$ haloalkyl (e.g., methyl, ethyl, propyl, i-propyl, n-butyl, i-butyl, s-butyl, t-butyl, pentyl, or hexyl, each of which is substituted with one or more halogen (e.g., F, Cl)), straight-chain $C_1$-$C_6$ alkoxy or branched $C_3$-$C_6$ alkoxy (e.g., methoxy, ethoxy, propoxy, i-propoxy, n-butoxy, i-butoxy, s-butoxy, t-butoxy, pentoxy, or hexyloxy), straight-chain $C_1$-$C_6$ haloalkoxy or branched $C_3$-$C_6$ haloalkoxy (e.g., methoxy, ethoxy, propoxy, i-propoxy, n-butoxy, i-butoxy, s-butoxy, t-butoxy, pentoxy, or hexyloxy, each of which is substituted with one or more halogen (e.g., F, Cl)), OH, or halogen (e.g., F, Cl, Br, or I).

In some embodiments, $R_5$ and $R_6$, together with the carbon atom to which they are attached, form $C_3$-$C_6$ cycloalkyl (e.g., cyclopropyl, cyclobutyl, cyclopentyl, or cyclohexyl) optionally substituted with one or more substituents independently selected from straight-chain $C_1$-$C_6$ alkyl or branched $C_3$-$C_6$ alkyl (e.g., methyl, ethyl, propyl, i-propyl, n-butyl, i-butyl, s-butyl, t-butyl, pentyl, or hexyl), straight-chain $C_1$-$C_6$ haloalkyl or branched $C_3$-$C_6$ haloalkyl (e.g., methyl, ethyl, propyl, i-propyl, n-butyl, i-butyl, s-butyl, t-butyl, pentyl, or hexyl, each of which is substituted with one or more halogen (e.g., F, Cl)), straight-chain $C_1$-$C_6$ alkoxy or branched $C_3$-$C_6$ alkoxy (e.g., methoxy, ethoxy, propoxy, i-propoxy, n-butoxy, i-butoxy, s-butoxy, t-butoxy, pentoxy, or hexyloxy), straight-chain $C_1$-$C_6$ haloalkoxy or branched $C_3$-$C_6$ haloalkoxy (e.g., methoxy, ethoxy, propoxy, i-propoxy, n-butoxy, i-butoxy, s-butoxy, t-butoxy, pentoxy, or hexyloxy, each of which is substituted with one or more halogen (e.g., F, Cl)), OH, and halogen (e.g., F, Cl, Br, or I).

In some embodiments, $R_5$ and $R_6$, together with the carbon atom to which they are attached, form $C_3$-$C_6$ cycloalkyl (e.g., cyclopropyl, cyclobutyl, cyclopentyl, or cyclohexyl) optionally substituted with one or more substituents independently selected from straight-chain $C_1$-$C_4$ alkyl or branched $C_3$-$C_4$ alkyl (e.g., methyl, ethyl, propyl, i-propyl, n-butyl, i-butyl, s-butyl, or t-butyl), straight-chain $C_1$-$C_4$ haloalkyl or branched $C_3$-$C_4$ haloalkyl (e.g., methyl, ethyl, propyl, i-propyl, n-butyl, i-butyl, s-butyl, or t-butyl, each of which is substituted with one or more halogen (e.g., F, Cl)), straight-chain $C_1$-$C_4$ alkoxy or branched $C_3$-$C_4$ alkoxy (e.g., methoxy, ethoxy, propoxy, i-propoxy, n-butoxy, i-butoxy, s-butoxy, or t-butoxy), straight-chain $C_1$-$C_4$ haloalkoxy or branched $C_3$-$C_4$ haloalkoxy (e.g., methoxy, ethoxy, propoxy, i-propoxy, n-butoxy, i-butoxy, s-butoxy, or t-butoxy, each of which is substituted with one or more halogen (e.g., F, Cl)), OH, and halogen (e.g., F, Cl, Br, or I).

In some embodiments, $R_5$ and $R_6$, together with the carbon atom to which they are attached, form $C_3$-$C_6$ cycloalkyl (e.g., cyclopropyl, cyclobutyl, cyclopentyl, or cyclohexyl) optionally substituted with one or more straight-chain $C_1$-$C_4$ alkyl or branched $C_3$-$C_4$ alkyl (e.g., methyl, ethyl, propyl, i-propyl, n-butyl, i-butyl, s-butyl, or t-butyl).

In some embodiments, $R_5$ and $R_6$, together with the carbon atom to which they are attached, form cyclopropyl optionally substituted with one or two straight-chain $C_1$-$C_6$ alkyl or branched $C_3$-$C_6$ alkyl (e.g., methyl, ethyl, propyl, i-propyl, n-butyl, i-butyl, s-butyl, t-butyl, pentyl, or hexyl).

In some embodiments, $R_5$ and $R_6$, together with the carbon atom to which they are attached, form cyclopropyl optionally substituted with one or two straight-chain $C_1$-$C_4$ alkyl or branched $C_3$-$C_4$ alkyl (e.g., methyl, ethyl, propyl, i-propyl, n-butyl, i-butyl, s-butyl, or t-butyl).

In some embodiments, $R_5$ and $R_6$, together with the carbon atom to which they are attached, form cyclopropyl.

In some embodiments, T is C(O)OH.

In some embodiments, T is $(CH_2)NHS(O)_2$—($C_1$-$C_6$ alkyl).

In some embodiments, T is heteroaryl comprising one 5- or 6-membered ring and 1-3 heteroatoms selected from N, O, and S, optionally substituted with one or more substituents independently selected from straight-chain $C_1$-$C_6$ alkyl or branched $C_3$-$C_6$ alkyl (e.g., methyl, ethyl, propyl, i-propyl, n-butyl, i-butyl, s-butyl, t-butyl, pentyl, or hexyl), straight-chain $C_1$-$C_6$ haloalkyl or branched $C_3$-$C_6$ haloalkyl (e.g., methyl, ethyl, propyl, i-propyl, n-butyl, i-butyl, s-butyl, t-butyl, pentyl, or hexyl, each of which is substituted with one or more halogen (e.g., F, Cl)), straight-chain $C_1$-$C_6$ alkoxy or branched $C_3$-$C_6$ alkoxy (e.g., methoxy, ethoxy, propoxy, i-propoxy, n-butoxy, i-butoxy, s-butoxy, t-butoxy, pentoxy, or hexyloxy), straight-chain $C_1$-$C_6$ haloalkoxy or branched $C_3$-$C_6$ haloalkoxy (e.g., methoxy, ethoxy, propoxy, i-propoxy, n-butoxy, i-butoxy, s-butoxy, t-butoxy, pentoxy, or hexyloxy, each of which is substituted with one or more halogen (e.g., F, Cl)), OH, halogen (e.g., F, Cl, Br, or I), and oxo (i.e., =O).

In some embodiments, T is heteroaryl comprising one 5- or 6-membered ring and 1-3 heteroatoms selected from N, O, and S, optionally substituted with one or more substituents independently selected from straight-chain $C_1$-$C_4$ alkyl or branched $C_3$-$C_4$ alkyl (e.g., methyl, ethyl, propyl, i-propyl, n-butyl, i-butyl, s-butyl, or t-butyl), straight-chain $C_1$-$C_4$ haloalkyl or branched $C_3$-$C_4$ haloalkyl (e.g., methyl, ethyl, propyl, i-propyl, n-butyl, i-butyl, s-butyl, or t-butyl, each of which is substituted with one or more halogen (e.g., F, Cl)), straight-chain $C_1$-$C_4$ alkoxy or branched $C_3$-$C_4$ alkoxy (e.g., methoxy, ethoxy, propoxy, i-propoxy, n-butoxy, i-butoxy, s-butoxy, or t-butoxy), straight-chain $C_1$-$C_4$ haloalkoxy or branched $C_3$-$C_4$ haloalkoxy (e.g., methoxy, ethoxy, propoxy, i-propoxy, n-butoxy, i-butoxy, s-butoxy, or t-butoxy, each of which is substituted with one or more halogen (e.g., F, Cl)), OH, halogen (e.g., F, Cl, Br, or I), and oxo (i.e., =O).

In some embodiments, T is heteroaryl comprising one 5-membered ring and 1-3 heteroatoms selected from N, O, and S, optionally substituted with one or more substituents as described herein.

In some embodiments, T is heteroaryl comprising one 6-membered ring and 1-3 heteroatoms selected from N, O, and S, optionally substituted with one or more substituents as described herein.

In some embodiments, T is heteroaryl selected from oxazolyl, isoxazolyl, thiazolyl, isothiazolyl, oxadiazolyl, thiadiazolyl, oxadiazolonyl, and thiadiazolonyl, each of which is optionally substituted with one or more substituents as described herein.

In some embodiments, at least one $R_7$ is straight-chain $C_1$-$C_6$ alkyl or branched $C_3$-$C_6$ alkyl (e.g., methyl, ethyl, propyl, i-propyl, n-butyl, i-butyl, s-butyl, t-butyl, pentyl, or hexyl), straight-chain $C_1$-$C_6$ haloalkyl or branched $C_3$-$C_6$ haloalkyl (e.g., methyl, ethyl, propyl, i-propyl, n-butyl, i-butyl, s-butyl, t-butyl, pentyl, or hexyl, each of which is substituted with one or more halogen (e.g., F, Cl)), straight-chain $C_1$-$C_6$ alkoxy or branched $C_3$-$C_6$ alkoxy (e.g., methoxy, ethoxy, propoxy, i-propoxy, n-butoxy, i-butoxy, s-butoxy, t-butoxy, pentoxy, or hexyloxy), straight-chain $C_1$-$C_6$ haloalkoxy or branched $C_3$-$C_6$ haloalkoxy (e.g., methoxy, ethoxy, propoxy, i-propoxy, n-butoxy, i-butoxy, s-butoxy, t-butoxy, pentoxy, or hexyloxy, each of which is substituted with one or more halogen (e.g., F, Cl)), OH, or halogen (e.g., F, Cl, Br, or I).

In some embodiments, at least one $R_7$ is straight-chain $C_1$-$C_4$ alkyl or branched $C_3$-$C_4$ alkyl (e.g., methyl, ethyl, propyl, i-propyl, n-butyl, i-butyl, s-butyl, or t-butyl), straight-chain $C_1$-$C_4$ haloalkyl or branched $C_3$-$C_4$ haloalkyl (e.g., methyl, ethyl, propyl, i-propyl, n-butyl, i-butyl, s-butyl, or t-butyl, each of which is substituted with one or more halogen (e.g., F, Cl)), straight-chain $C_1$-$C_4$ alkoxy or branched $C_3$-$C_4$ alkoxy (e.g., methoxy, ethoxy, propoxy, i-propoxy, n-butoxy, i-butoxy, s-butoxy, or t-butoxy), straight-chain $C_1$-$C_4$ haloalkoxy or branched $C_3$-$C_4$ haloalkoxy (e.g., methoxy, ethoxy, propoxy, i-propoxy, n-butoxy, i-butoxy, s-butoxy, or t-butoxy, each of which is substituted with one or more halogen (e.g., F, Cl)), OH, or halogen (e.g., F, Cl, Br, or I).

In some embodiments, at least one $R_7$ is straight-chain $C_1$-$C_4$ alkyl or branched $C_3$-$C_4$ alkyl (e.g., methyl, ethyl, propyl, i-propyl, n-butyl, i-butyl, s-butyl, or t-butyl).

In some embodiments, at least one $R_{11}$ is straight-chain $C_1$-$C_6$ alkyl or branched $C_3$-$C_6$ alkyl (e.g., methyl, ethyl, propyl, i-propyl, n-butyl, i-butyl, s-butyl, t-butyl, pentyl, or hexyl), straight-chain $C_1$-$C_6$ haloalkyl or branched $C_3$-$C_6$ haloalkyl (e.g., methyl, ethyl, propyl, i-propyl, n-butyl, i-butyl, s-butyl, t-butyl, pentyl, or hexyl, each of which is substituted with one or more halogen (e.g., F, Cl)), straight-chain $C_1$-$C_6$ alkoxy or branched $C_3$-$C_6$ alkoxy (e.g., methoxy, ethoxy, propoxy, i-propoxy, n-butoxy, i-butoxy, s-butoxy, t-butoxy, pentoxy, or hexyloxy), straight-chain $C_1$-$C_6$ haloalkoxy or branched $C_3$-$C_6$ haloalkoxy (e.g., methoxy, ethoxy, propoxy, i-propoxy, n-butoxy, i-butoxy, s-butoxy, t-butoxy, pentoxy, or hexyloxy, each of which is substituted with one or more halogen (e.g., F, Cl)), OH, halogen (e.g., F, Cl, Br, or I), $NH_2$, NH—($C_1$-$C_6$ alkyl) (e.g., methyl, ethyl, propyl, i-propyl, n-butyl, i-butyl, s-butyl, t-butyl, pentyl, or hexyl), N($C_1$-$C_6$ alkyl)$_2$ (e.g., methyl, ethyl, propyl, i-propyl, n-butyl, i-butyl, s-butyl, t-butyl, pentyl, or hexyl), CN, $NO_2$, or $C_3$-$C_6$ cycloalkyl (e.g., cyclopropyl, cyclobutyl, cyclopentyl, or cyclohexyl).

In some embodiments, at least one $R_{11}$ is straight-chain $C_1$-$C_4$ alkyl or branched $C_3$-$C_4$ alkyl (e.g., methyl, ethyl, propyl, i-propyl, n-butyl, i-butyl, s-butyl, or t-butyl), straight-chain $C_1$-$C_4$ haloalkyl or branched $C_3$-$C_4$ haloalkyl (e.g., methyl, ethyl, propyl, i-propyl, n-butyl, i-butyl, s-butyl, or t-butyl, each of which is substituted with one or more halogen (e.g., F, Cl)), straight-chain $C_1$-$C_4$ alkoxy or branched $C_3$-$C_4$ alkoxy (e.g., methoxy, ethoxy, propoxy, i-propoxy, n-butoxy, i-butoxy, s-butoxy, or t-butoxy), straight-chain $C_1$-$C_4$ haloalkoxy or branched $C_3$-$C_4$ haloalkoxy (e.g., methoxy, ethoxy, propoxy, i-propoxy, n-butoxy, i-butoxy, s-butoxy, or t-butoxy, each of which is substituted with one or more halogen (e.g., F, Cl)), OH, halogen (e.g., F, Cl, Br, or I), $NH_2$, NH—($C_1$-$C_4$ alkyl) (e.g., methyl, ethyl, propyl, i-propyl, n-butyl, i-butyl, s-butyl, or t-butyl), N($C_1$-$C_4$ alkyl)$_2$ (e.g., methyl, ethyl, propyl, i-propyl, n-butyl, i-butyl, s-butyl, or t-butyl), CN, $O_2$, or $C_3$-$C_6$ cycloalkyl (e.g., cyclopropyl, cyclobutyl, cyclopentyl, or cyclohexyl).

In some embodiments, at least one $R_{11}$ is straight-chain $C_1$-$C_4$ alkyl or branched $C_3$-$C_4$ alkyl (e.g., methyl, ethyl, propyl, i-propyl, n-butyl, i-butyl, s-butyl, or t-butyl), straight-chain $C_1$-$C_4$ haloalkyl or branched $C_3$-$C_4$ haloalkyl (e.g., methyl, ethyl, propyl, i-propyl, n-butyl, i-butyl, s-butyl, or t-butyl, each of which is substituted with one or more halogen (e.g., F, Cl)), straight-chain $C_1$-$C_4$ alkoxy or branched $C_3$-$C_4$ alkoxy (e.g., methoxy, ethoxy, propoxy, i-propoxy, n-butoxy, i-butoxy, s-butoxy, or t-butoxy), straight-chain $C_1$-$C_4$ haloalkoxy or branched $C_3$-$C_4$ haloalkoxy (e.g., methoxy, ethoxy, propoxy, i-propoxy, n-butoxy, i-butoxy, s-butoxy, or t-butoxy, each of which is substituted with one or more halogen (e.g., F, Cl)), or halogen (e.g., F, Cl, Br, or I).

In some embodiments, at least one $R_{11}$ is F.

In some embodiments, at least one $R_{11}$ is F and at least one $R_{11}$ is methyl.

Any of the moieties described herein for any one of

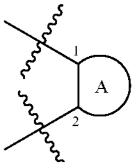,
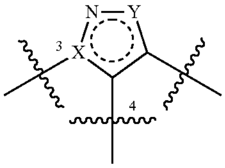,

L, T, $R_1$, $R_C$, $R_{11}$, $R_2$, $R_3$, $R_4$, $R_5$, $R_6$, and $R_7$ can be combined with any of the moieties described herein for one or more of the remainder of

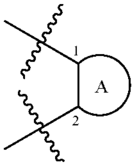,
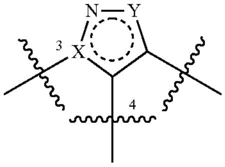,

L, T, $R_1$, $R_C$, $R_{11}$, $R_2$, $R_3$, $R_4$, $R_5$, $R_6$, and $R_7$.

In some embodiments,

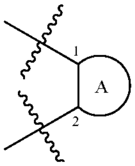,
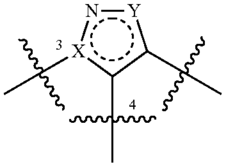,

L, T, $R_1$, $R_C$, $R_{11}$, $R_2$, $R_3$, $R_4$, $R_5$, $R_6$, and $R_7$ can be combined as follows:

(A-1') In some embodiments,

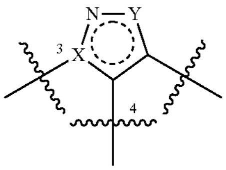
is
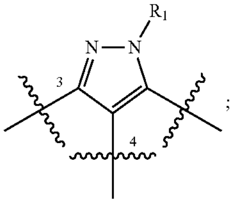
; and

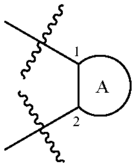

is a bicyclic heteroaryl ring selected from

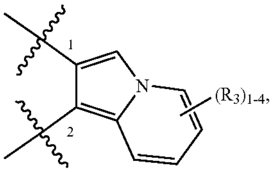

-continued

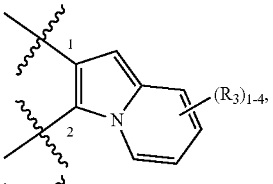

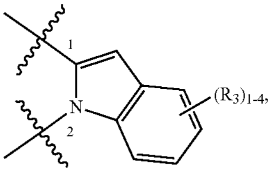

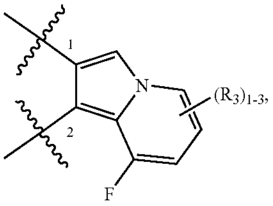

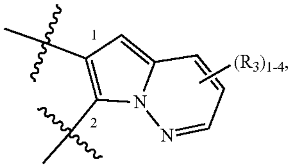

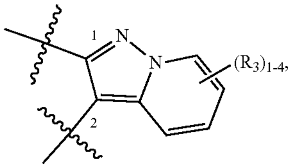

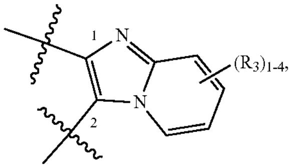

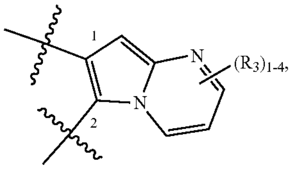

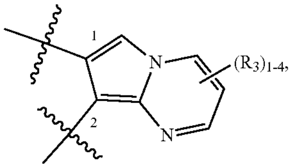

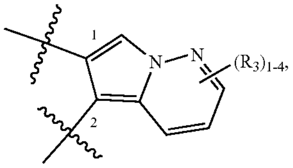

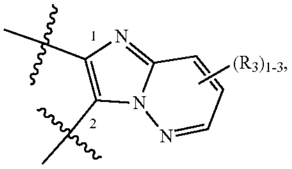

-continued
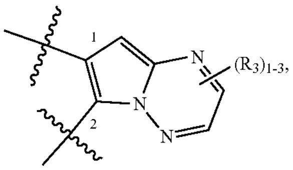
and
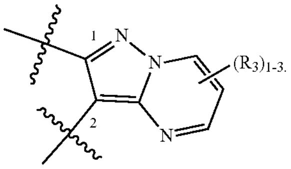
(A-1) In some embodiments,
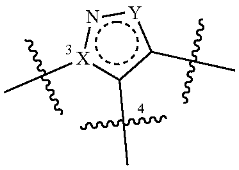
is
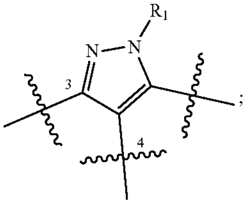
; and
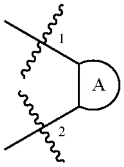
is a bicyclic heteroaryl ring selected from
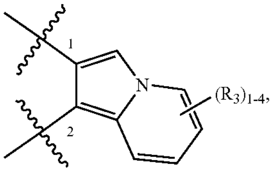
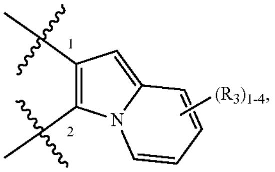
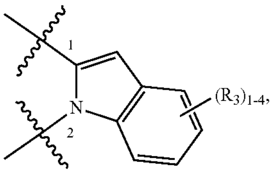
-continued
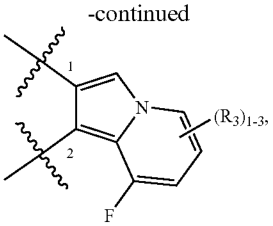
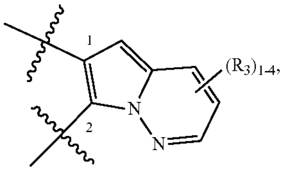
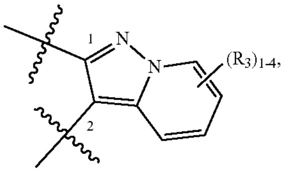
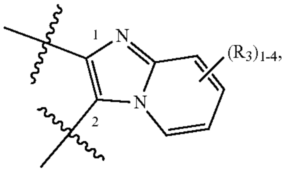
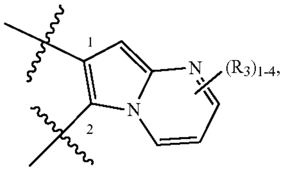
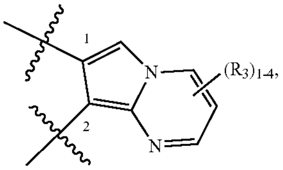
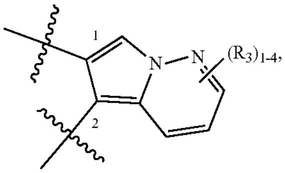
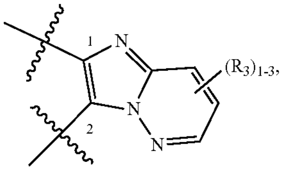
and
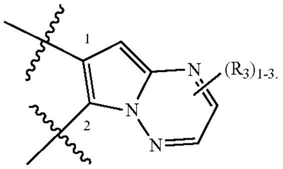

(A-2) In some embodiments,
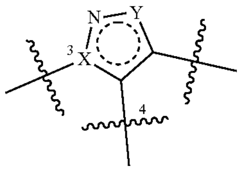
is
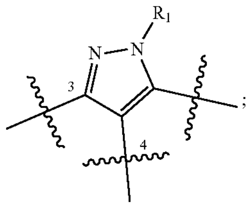
and
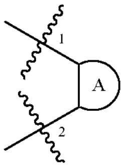
is a bicyclic heteroaryl ring selected from
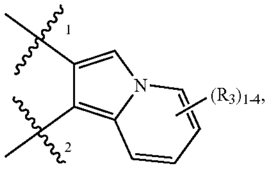
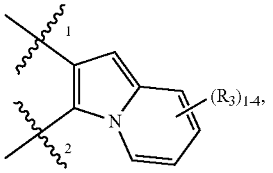
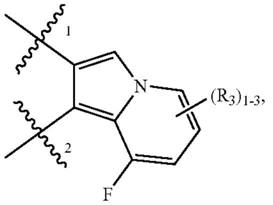
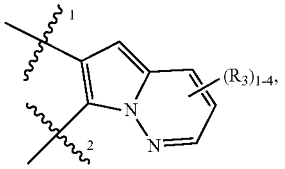
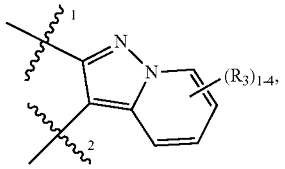
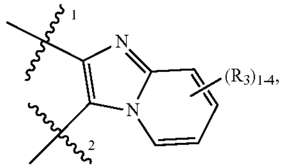
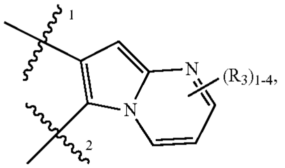
-continued
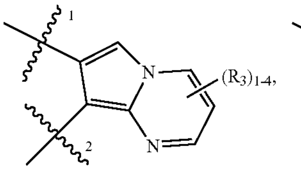
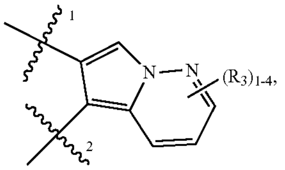
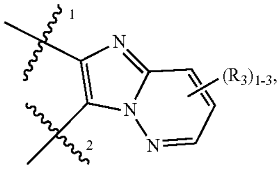
and
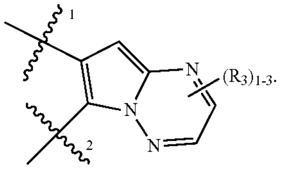
(A-3') In some embodiments,
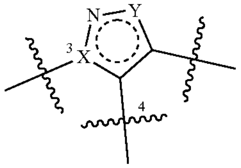
is
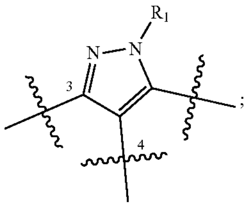
and
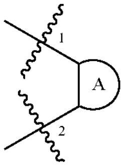
is a bicyclic heteroaryl ring selected from
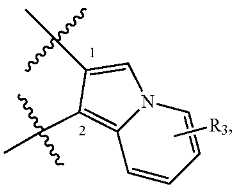
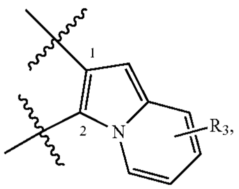
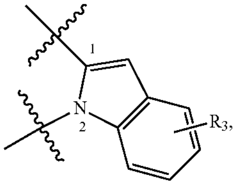
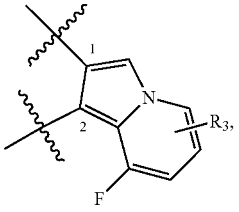

-continued
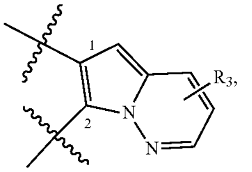
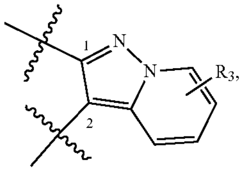
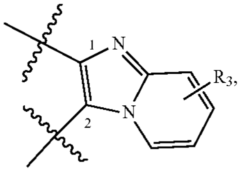
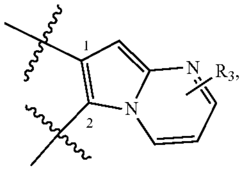
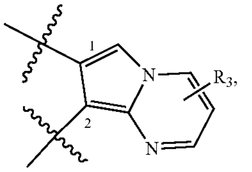
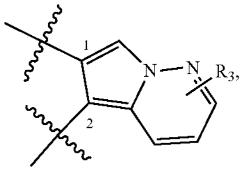
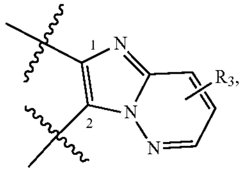
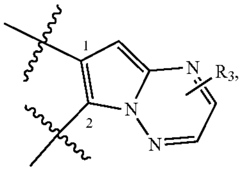
and
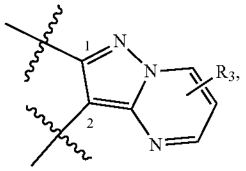
(A-3) In some embodiments,
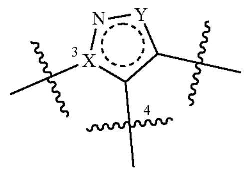
is
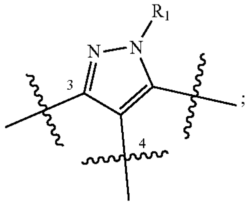
; and
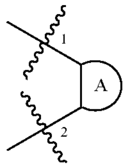
is a bicyclic heteroaryl ring selected from
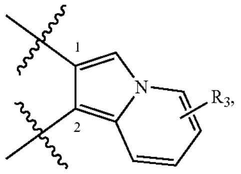
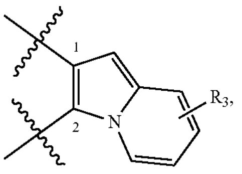
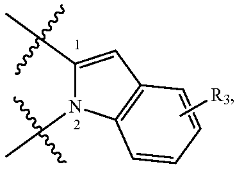
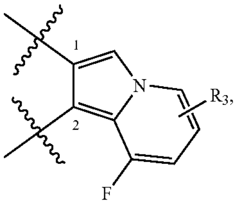
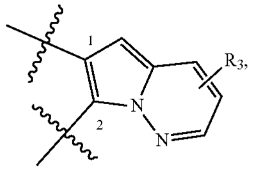
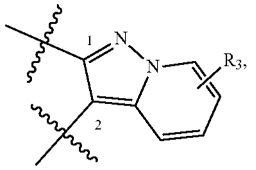
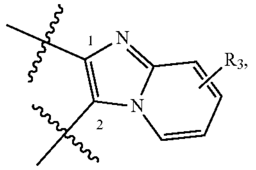
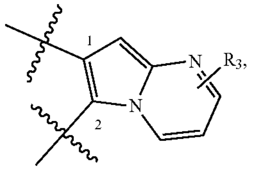
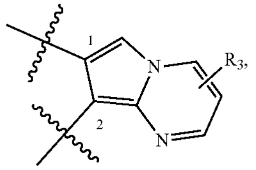
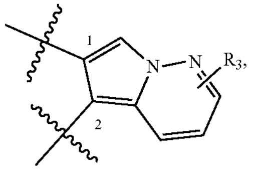
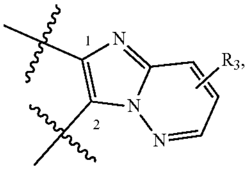
and
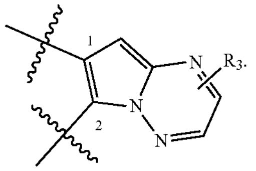
(A-4) In some embodiments,
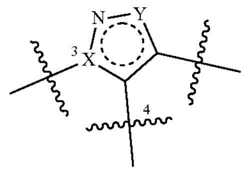
is
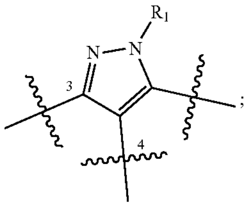
; and -continued
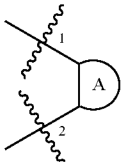
is a bicyclic heteroaryl ring selected from
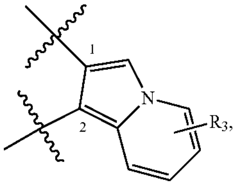
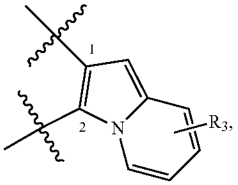
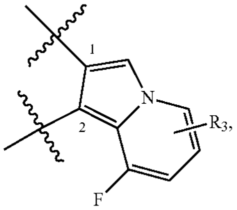
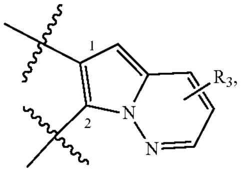
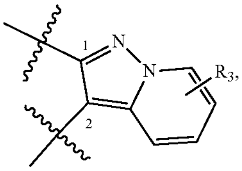
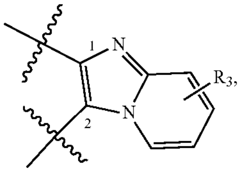
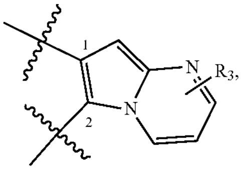
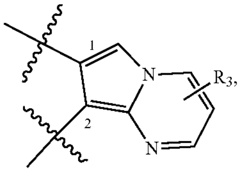
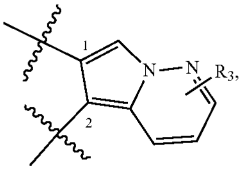
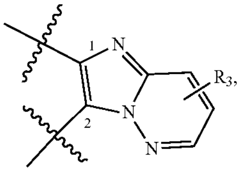
and
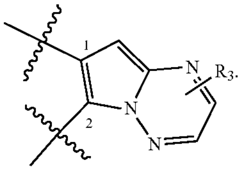
(A-5') In some embodiments,
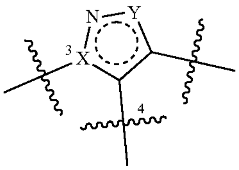
is
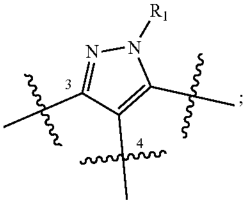
; and
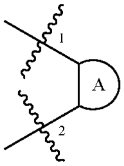
is a bicyclic heteroaryl ring selected from
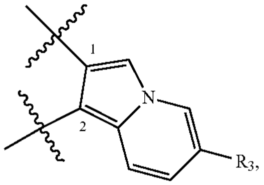
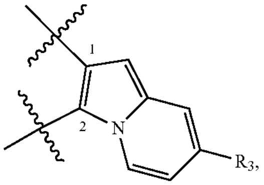
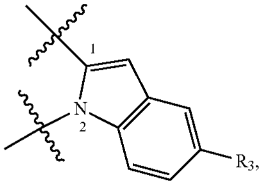
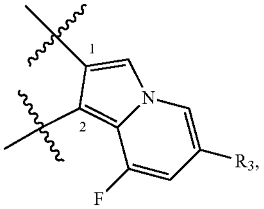
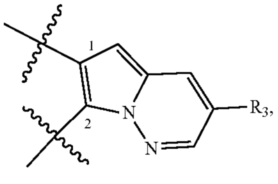
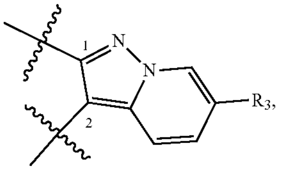
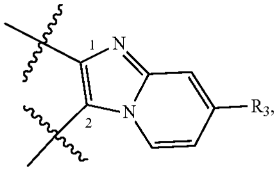
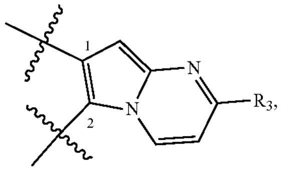
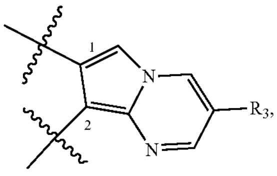
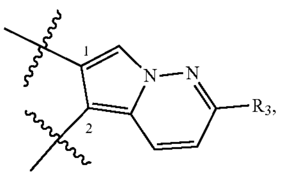

-continued
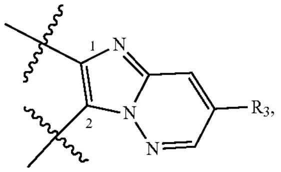
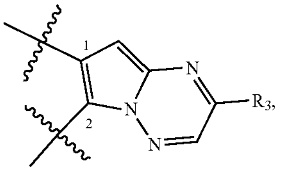
and
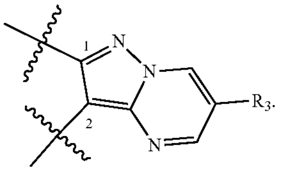
(A-5) In some embodiments,
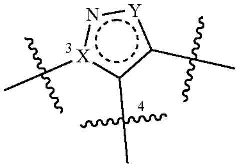
is
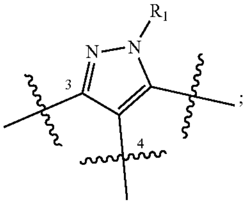
; and
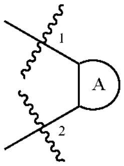
is a bicyclic heteroaryl ring selected from
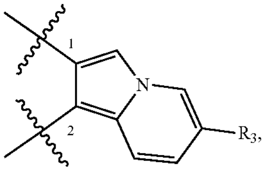
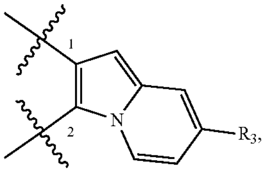
-continued
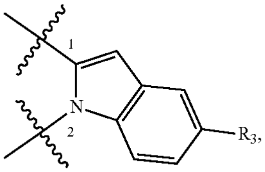
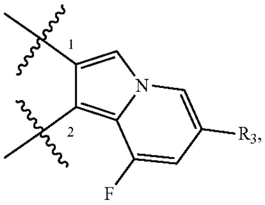
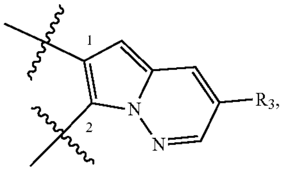
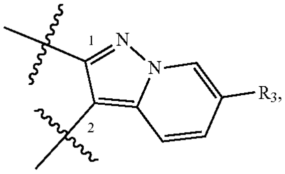
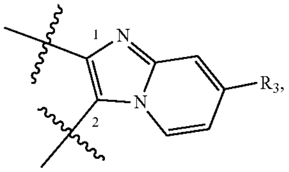
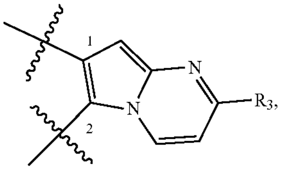
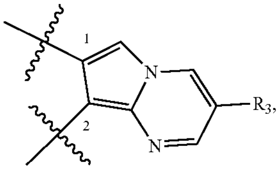
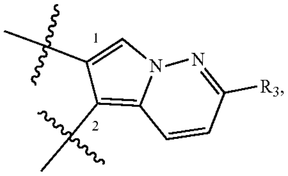
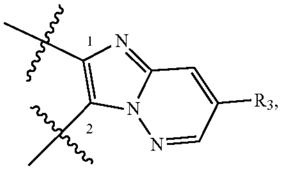
and -continued
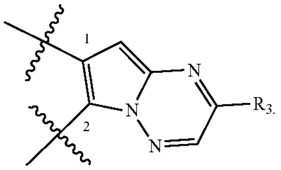
(A-6) In some embodiments,
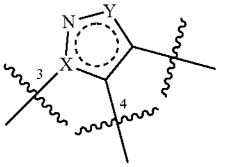 is 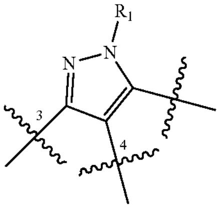 ; and
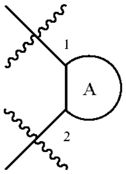
is a bicyclic heteroaryl ring selected from
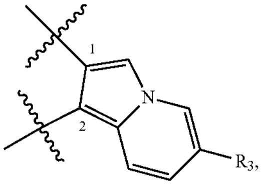
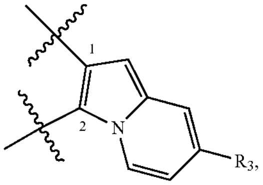
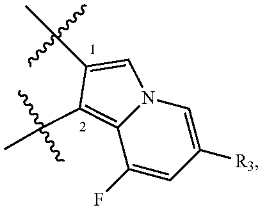
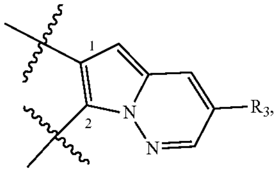
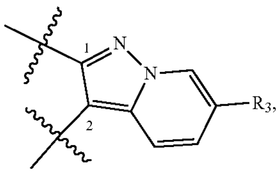
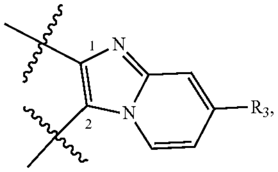
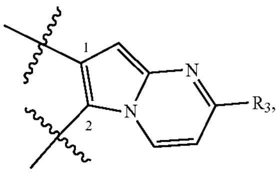
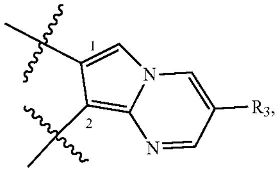
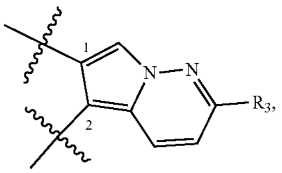
-continued
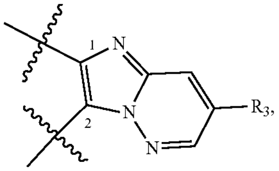 and
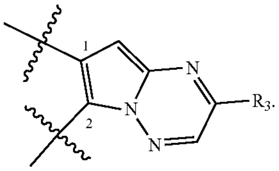
(A-7) In some embodiments,
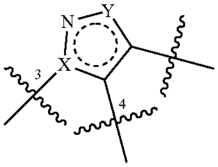 is 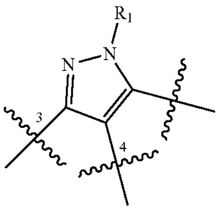 ; and
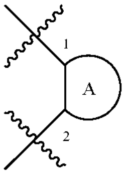
is a bicyclic heteroaryl ring selected from
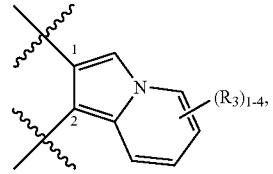
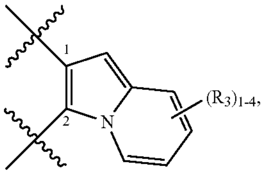
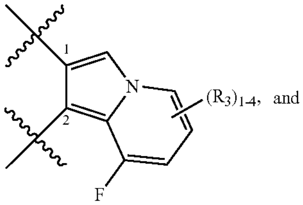 and
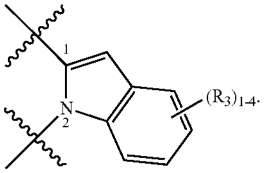
(A-8) In some embodiments,
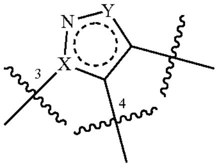 is 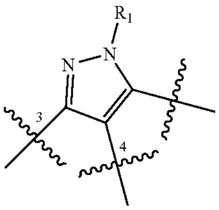 ; and -continued
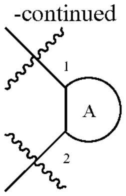
is a bicyclic heteroaryl ring selected from
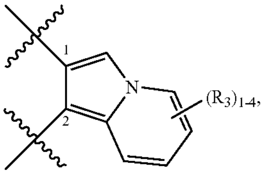
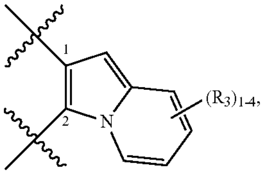
and
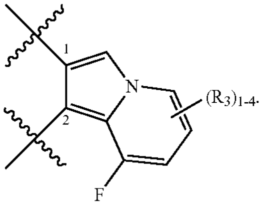
(A-9) In some embodiments,
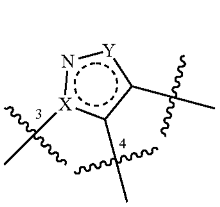
is
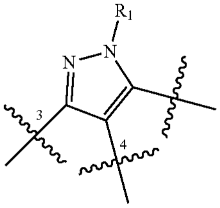
; and
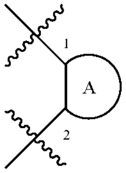
is a bicyclic heteroaryl ring selected from
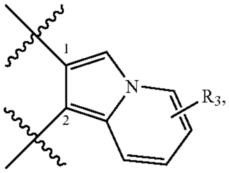
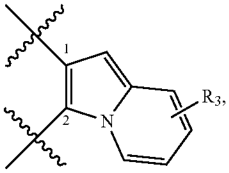
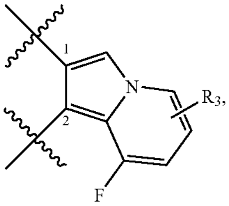
and
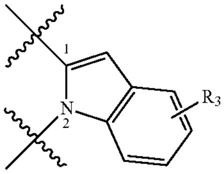
(A-10) In some embodiments,
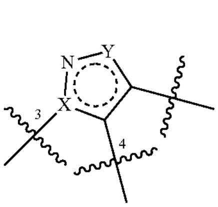
is
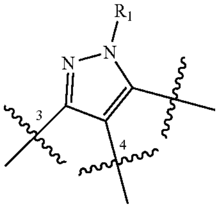
; and
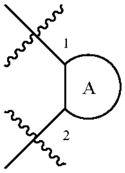
is a bicyclic heteroaryl ring selected from
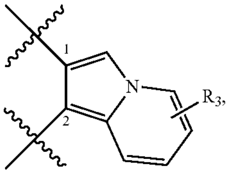
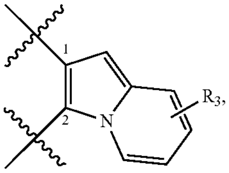
and
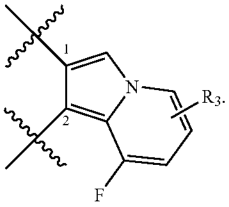
(A-11) In some embodiments,
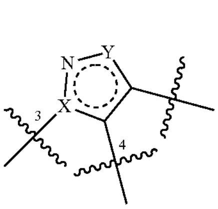
is
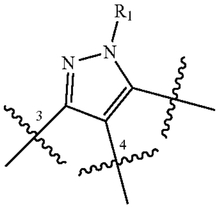
; and
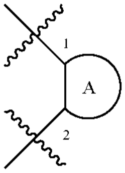
is a bicyclic heteroaryl ring selected from
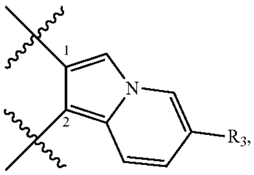
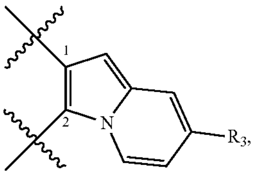

-continued
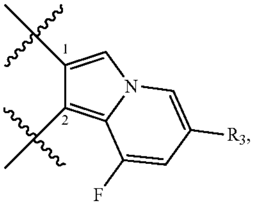
and
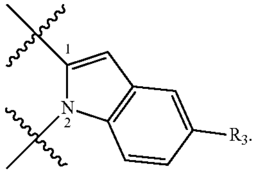
(A-12) In some embodiments,
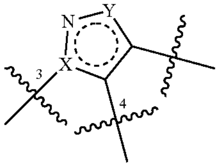
is
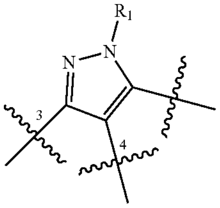
; and
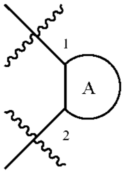
is a bicyclic heteroaryl ring selected from
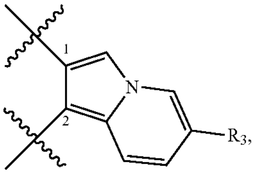
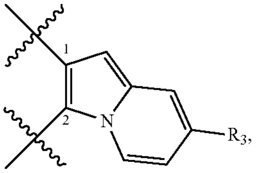
and
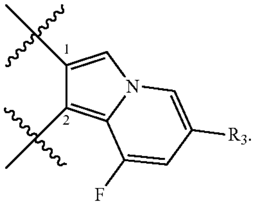
(A-13) In some embodiments,
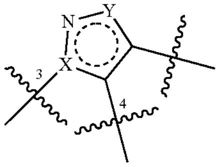
is
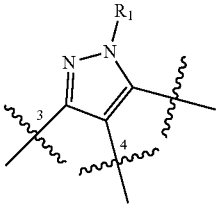
; and
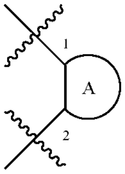
is a bicyclic heteroaryl ring selected from
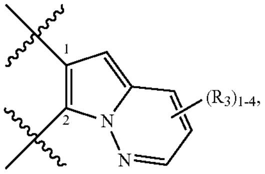
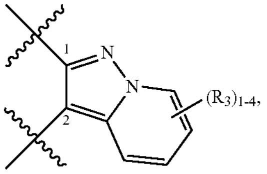
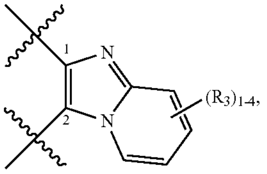
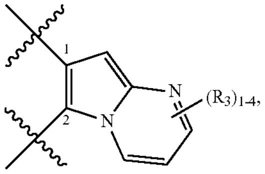
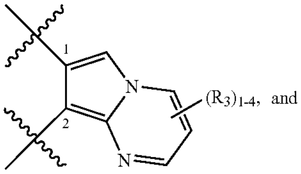
and
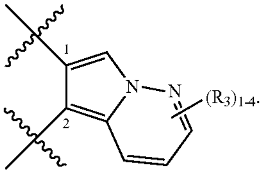
(A-14) In some embodiments,
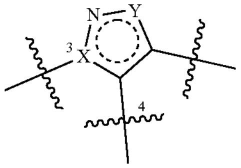
is
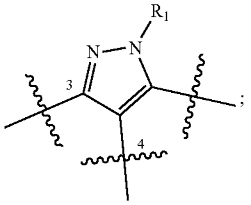
; and
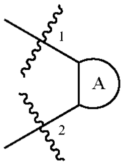
is a bicyclic heteroaryl ring selected from
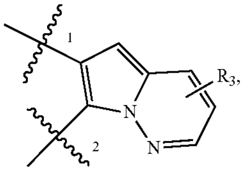
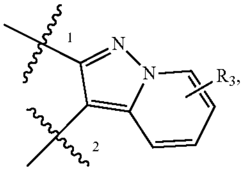
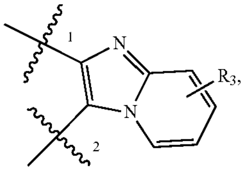
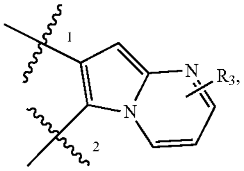

-continued
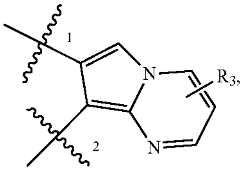
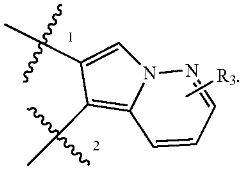
(A-15) In some embodiments,
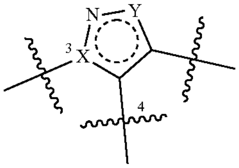
is
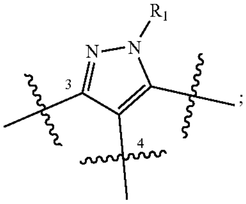
; and
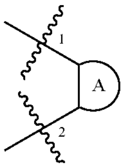
is a bicyclic heteroaryl ring selected from
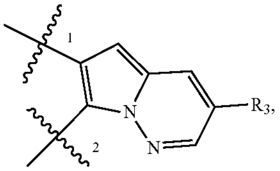
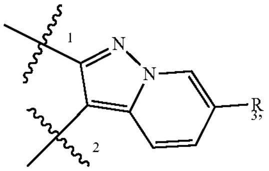
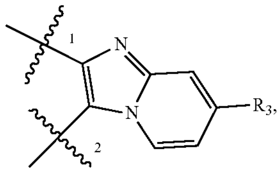
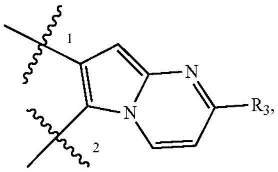
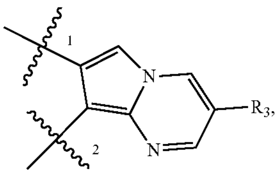
and
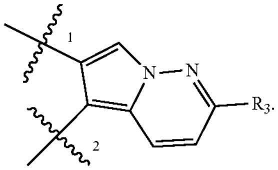
(A-16') In some embodiments,
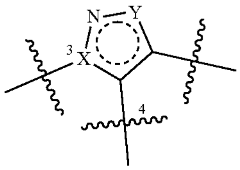
is
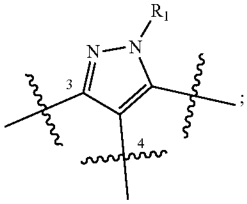
; and
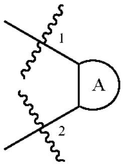
is a bicyclic heteroaryl ring selected from
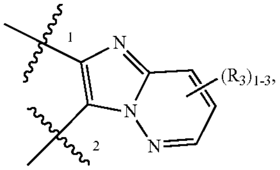
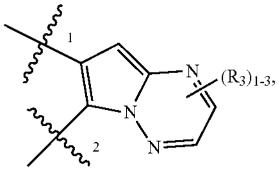
and
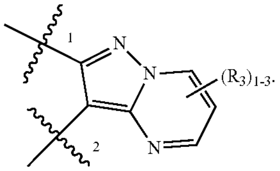
(A-16) In some embodiments,
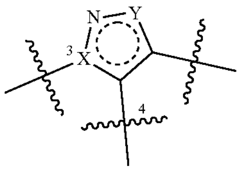
is
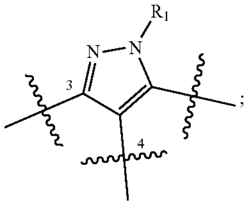
; and -continued
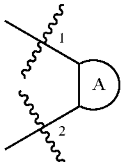
is a bicyclic heteroaryl ring selected from
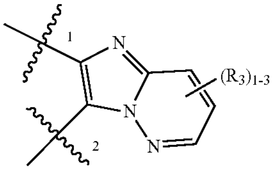
and
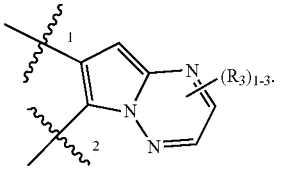
(A-17') In some embodiments,
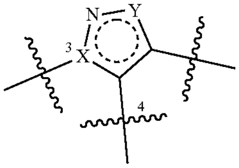
is
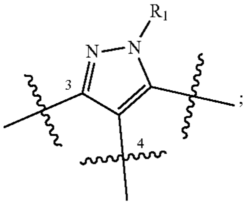
; and
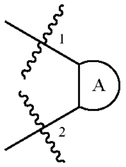
is a bicyclic heteroaryl ring selected from
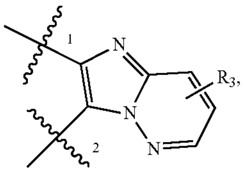
-continued
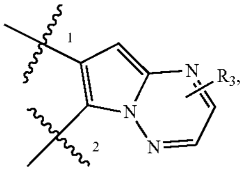
and
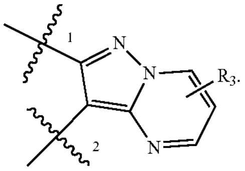
(A-17) In some embodiments,
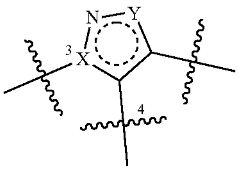
is
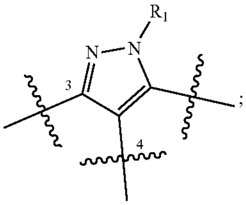
; and
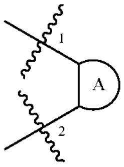
is a bicyclic heteroaryl ring selected from
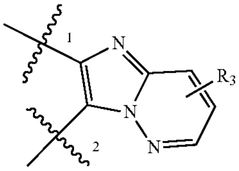
and
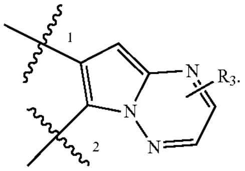

(A-18') In some embodiments,
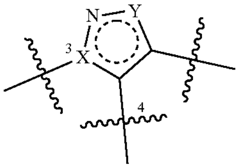
is
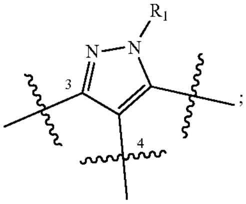
; and
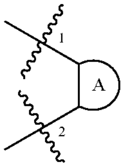
is a bicyclic heteroaryl ring selected from
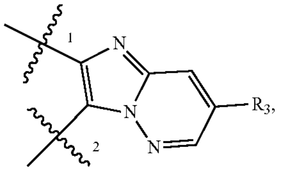
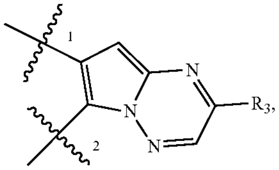
and
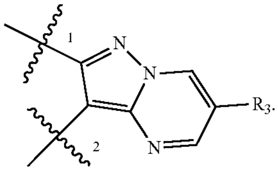
(A-18) In some embodiments,
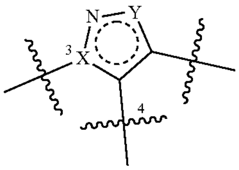
is
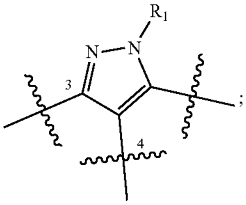
; and
-continued
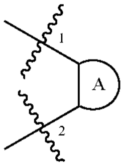
is a bicyclic heteroaryl ring selected from
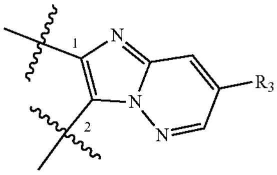
and
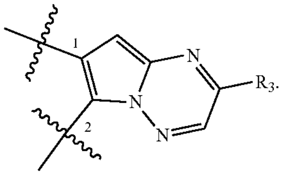
(B-1') In some embodiments,
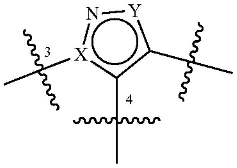
is
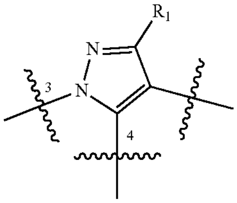
; and
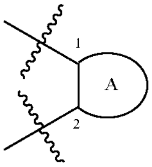
is a bicyclic heteroaryl ring selected from
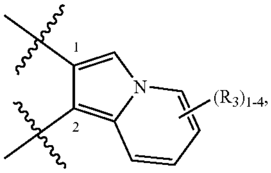
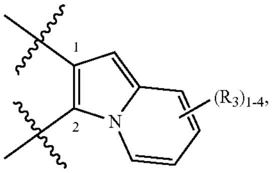
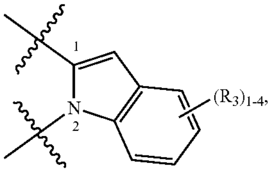
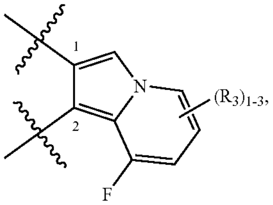

-continued
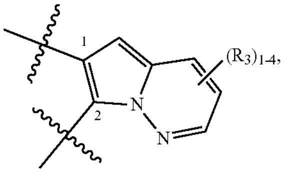,
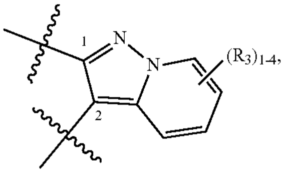,
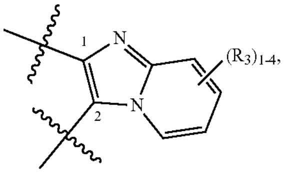,
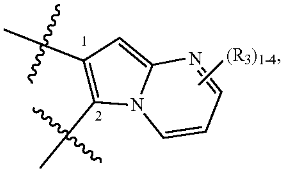,
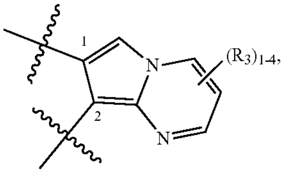,
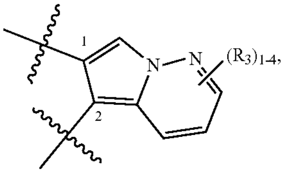,
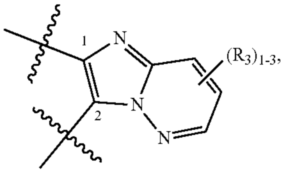,
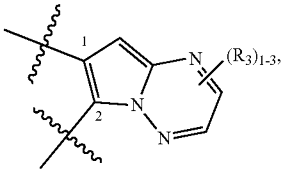 and
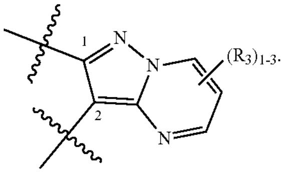.
(B-1) In some embodiments,
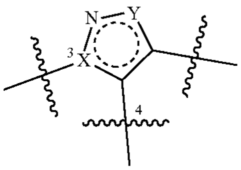
is
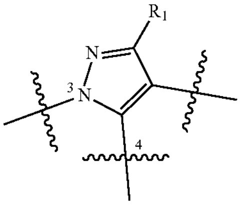
; and
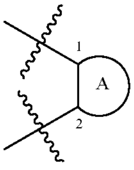
is a bicyclic heteroaryl ring selected from
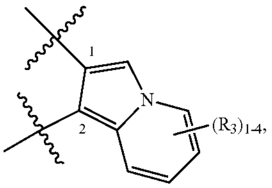,
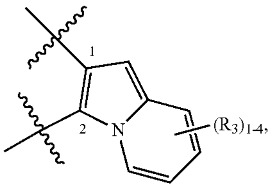,
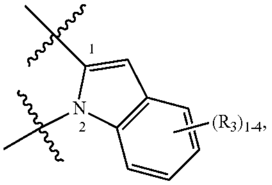,
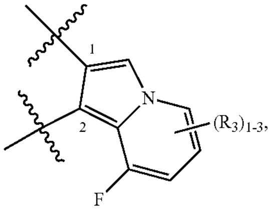,
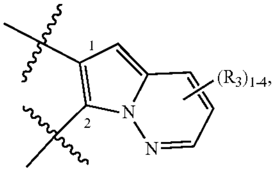,
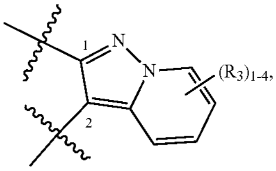,
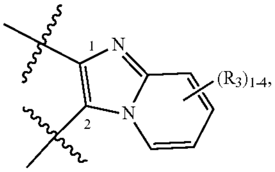,
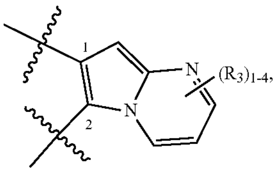,
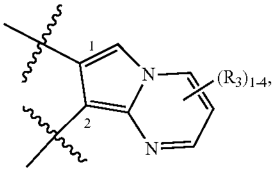,
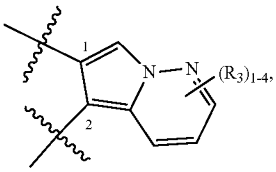,
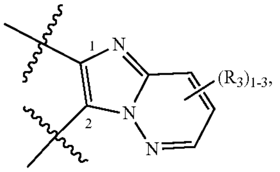 and
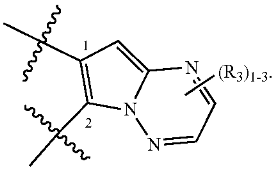.
(B-2') In some embodiments,
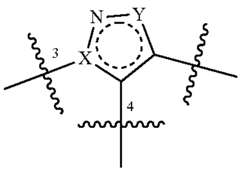
is -continued
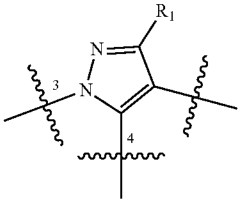
; and
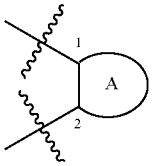
is a bicyclic heteroaryl ring selected from
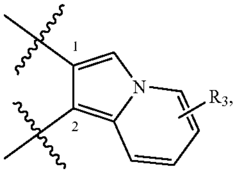
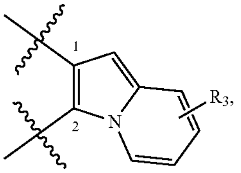
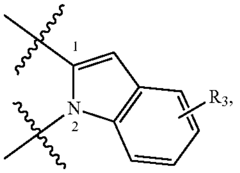
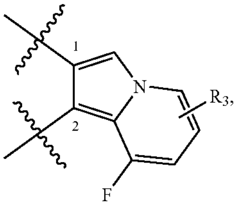
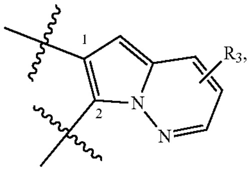
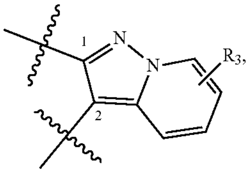
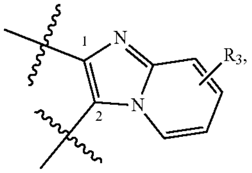
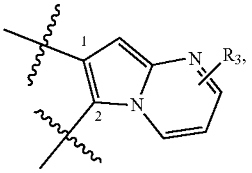
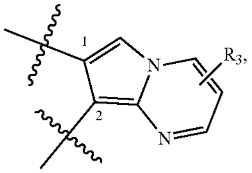
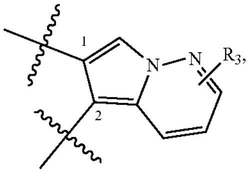
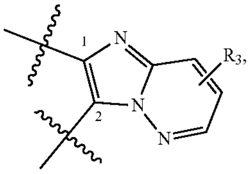
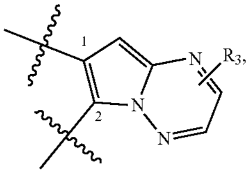
and
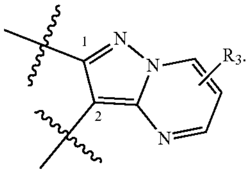
(B-2) In some embodiments,
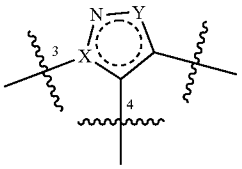
is
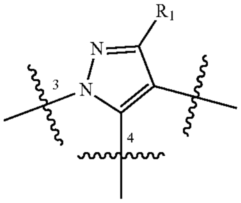
; and
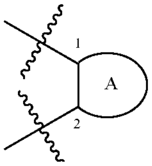
is a bicyclic heteroaryl ring selected from
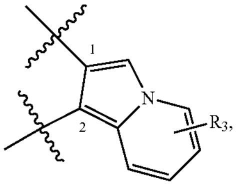
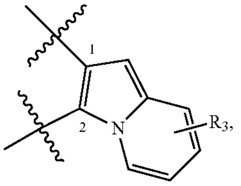
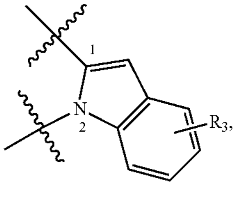
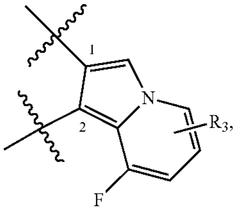
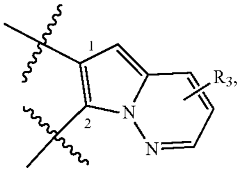
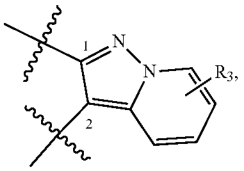
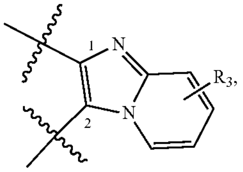
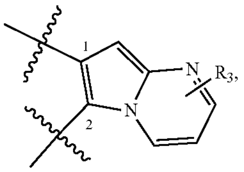
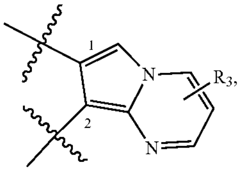
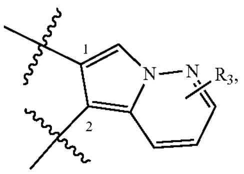
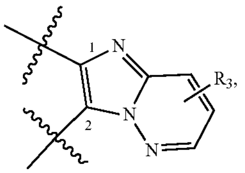
and -continued
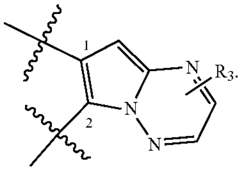
(B3') In some embodiments
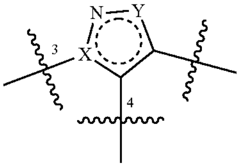
is
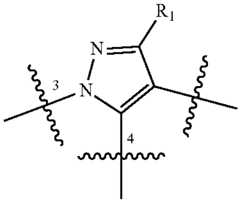
; and
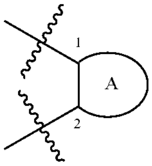
is a bicyclic heteroaryl ring selected from
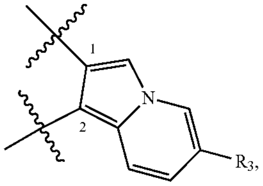
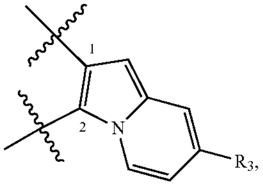
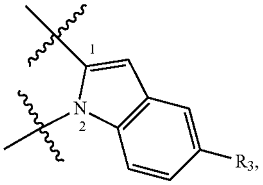
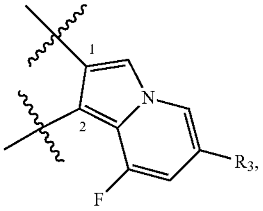
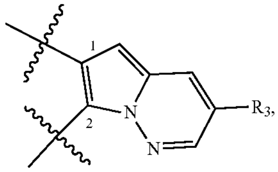
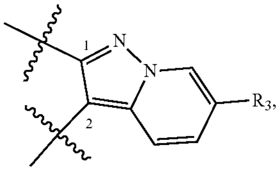
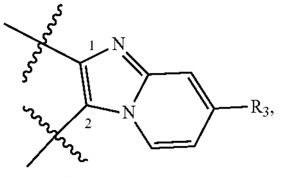
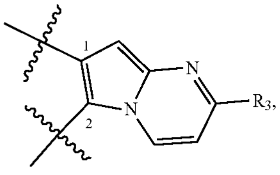
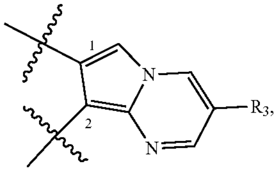
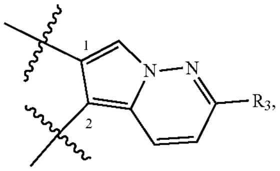
-continued
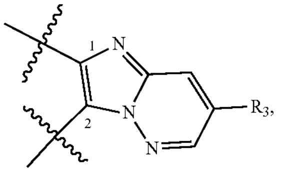
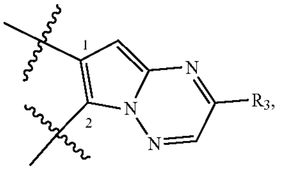
and
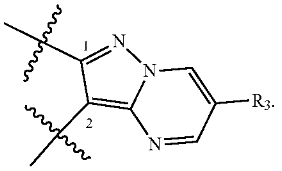
(B-3) In some embodiments,
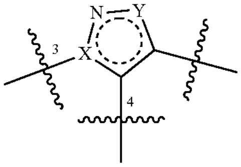
is
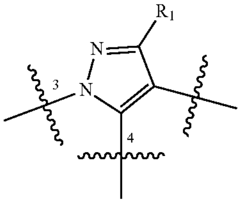
; and
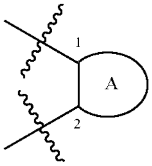
is a bicyclic heteroaryl ring selected from
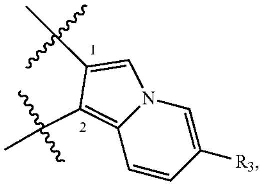
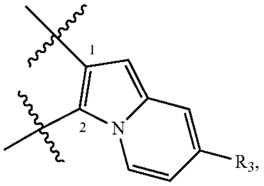
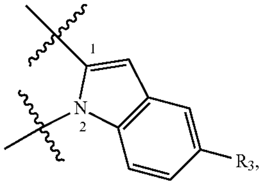
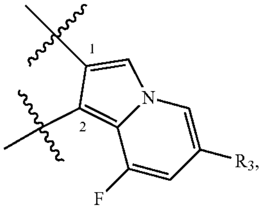
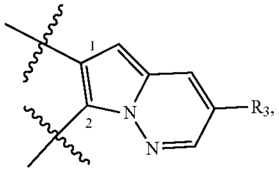
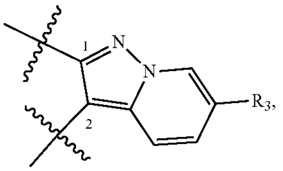

-continued
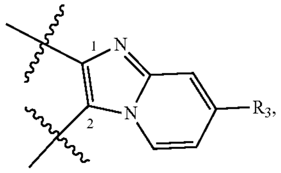
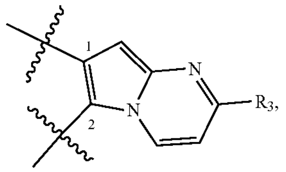
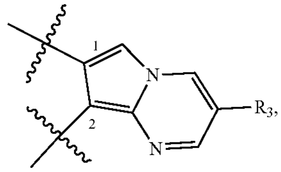
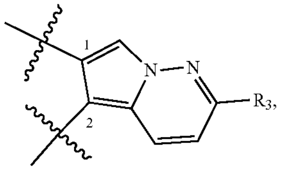
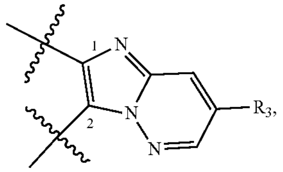
and
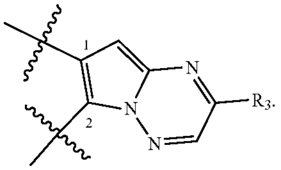
(B-4) In some embodiments,
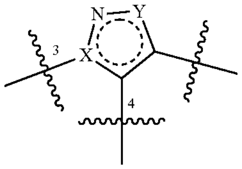
is
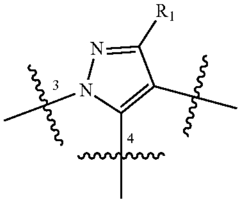
; and
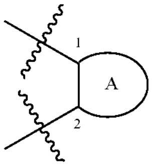
is a bicyclic heteroaryl ring selected from
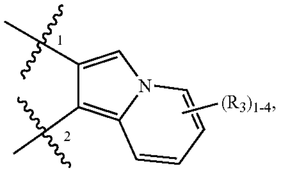
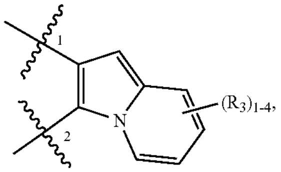
-continued
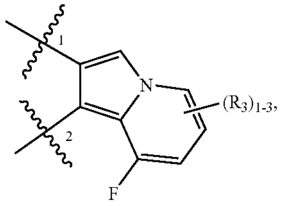
and
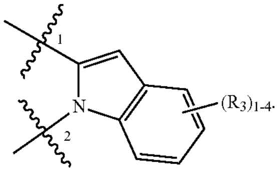
(B-5) In some embodiments,
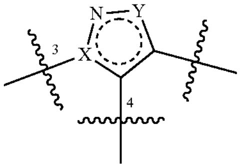
is
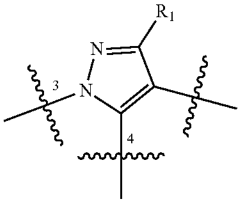
; and
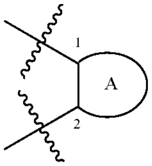
is a bicyclic heteroaryl ring selected from
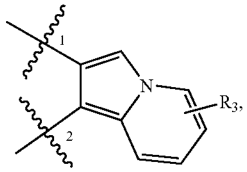
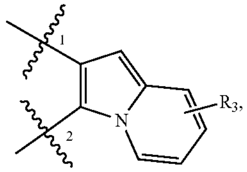
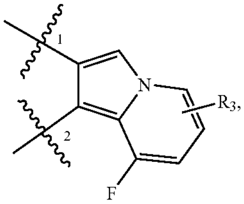
and -continued
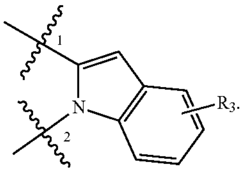
(B-6) In some embodiments,
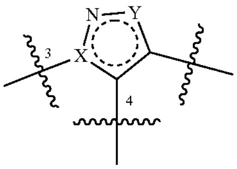
is
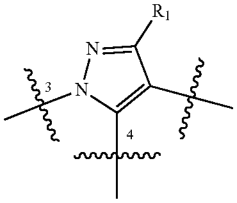
; and
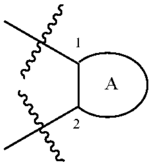
is a bicyclic heteroaryl ring selected from
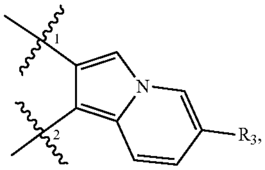
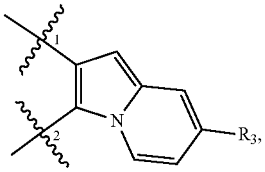
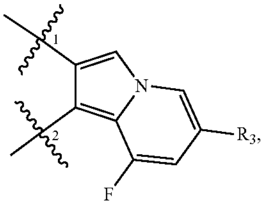
and
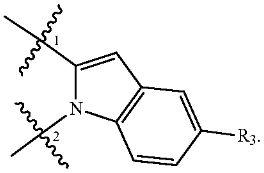
(B-7) In some embodiments,
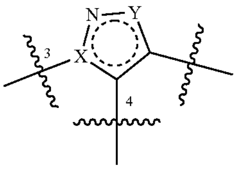
is
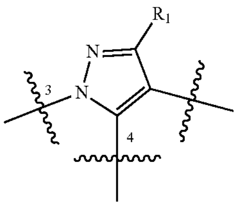
; and
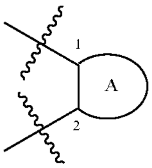
is a bicyclic heteroaryl ring selected from
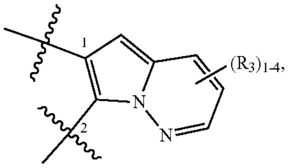
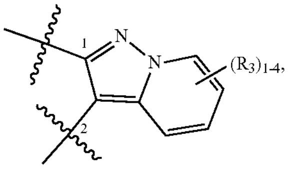
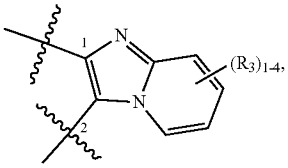
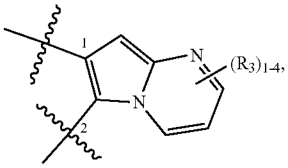
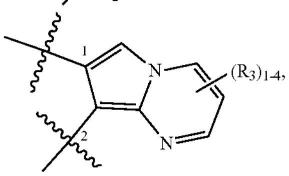
and
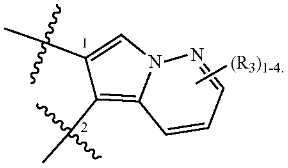

(B-8) In some embodiments,
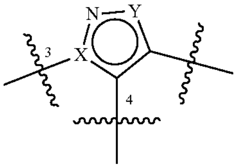
is
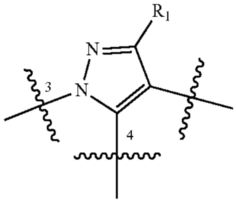
; and
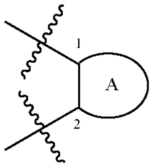
is a bicyclic heteroaryl ring selected from
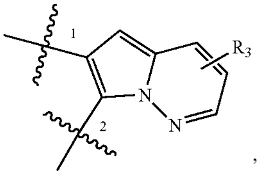
,
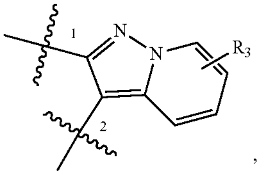
,
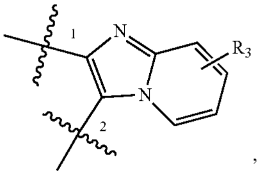
,
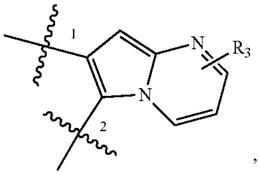
,
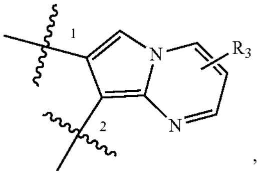
,
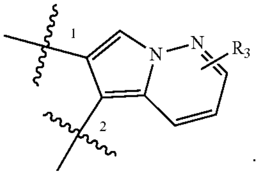
.
(B-9) In some embodiments,
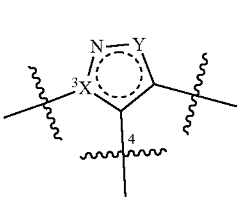
is
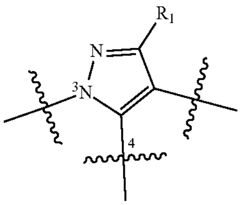
;
and
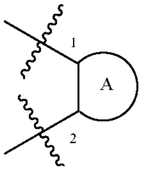
is a bicyclic heteroaryl ring selected from
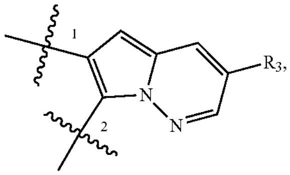
,
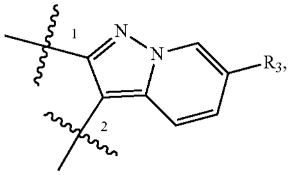
,
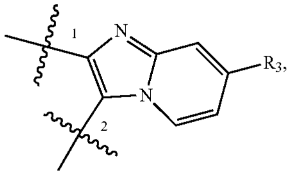
,
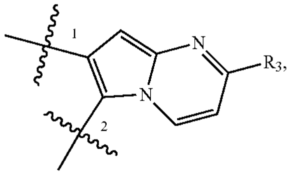
,
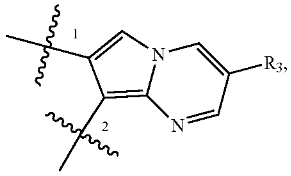
, and
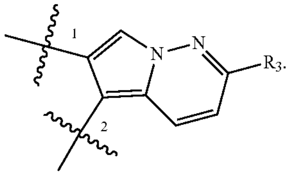
.
(B-10') In some embodiments,
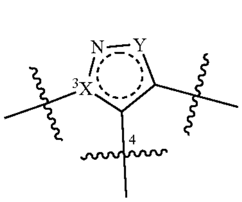
is
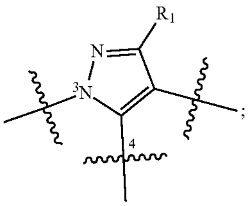
;
and
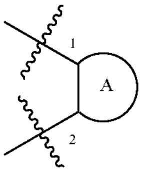

is a bicyclic heteroaryl ring selected from
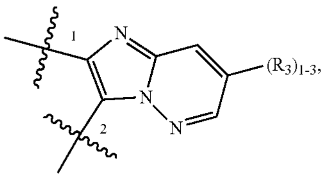
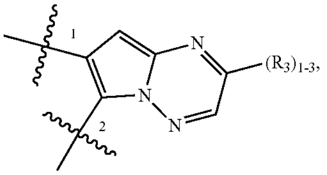
and
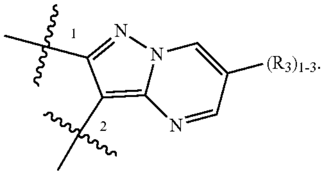
(B-10) In some embodiments,
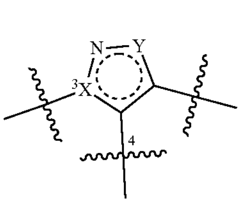
is
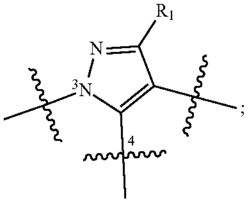
and
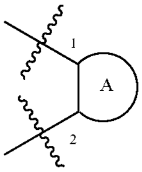
is a bicyclic heteroaryl ring selected from
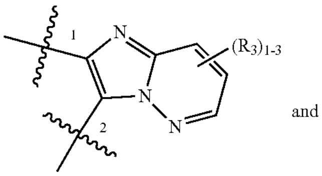
and
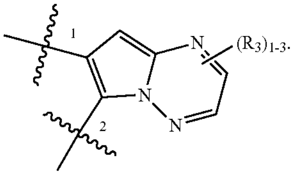
(B-11') In some embodiments,
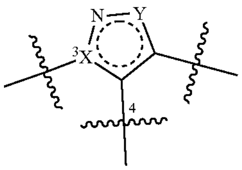
is
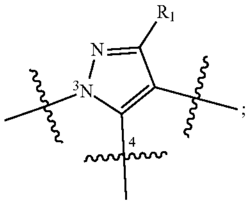
and
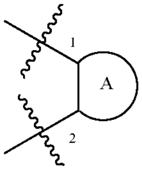
is a bicyclic heteroaryl ring selected from
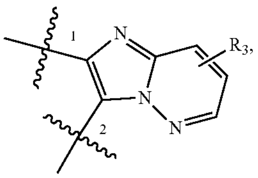
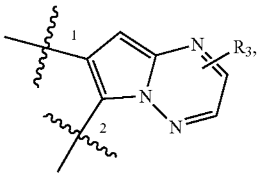
and
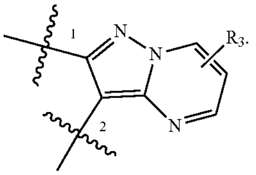
(B-11) In some embodiments,
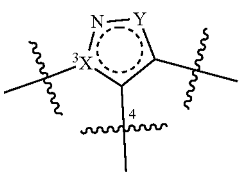
is
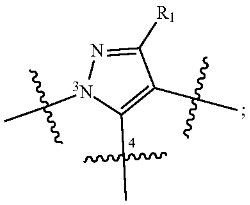
and
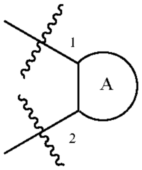

is a bicyclic heteroaryl ring selected from

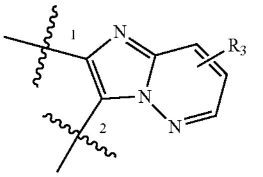

and

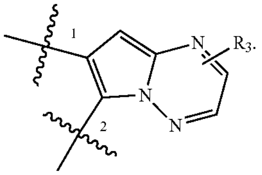

(B-12') In some embodiments,

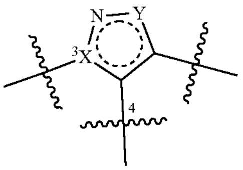

is

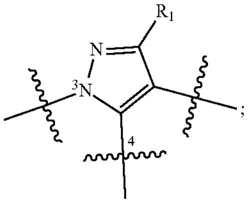

and

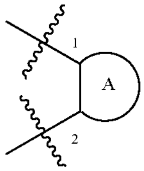

is a bicyclic heteroaryl ring selected from

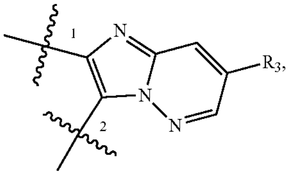

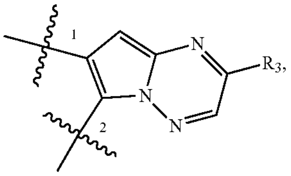

and

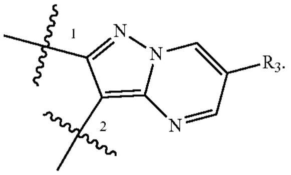

(B-12) In some embodiments,

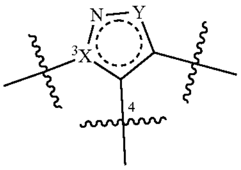

is

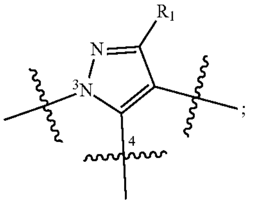

and

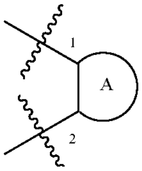

is a bicyclic heteroaryl ring selected from

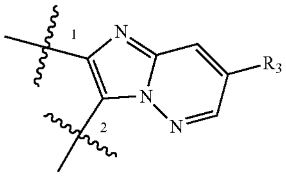

and

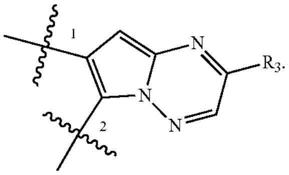

(C-1) In some embodiments,

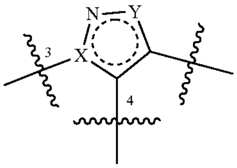

and

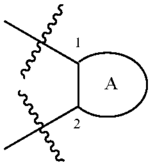

are as described in any one of (A-1')-(B-12), and $R_1$ is $(CR_CR_C)_{0-2}$-phenyl substituted with one or more substituents as described herein.

(C-2) In some embodiments,

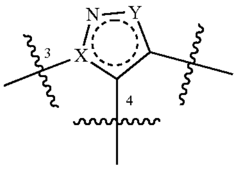

and

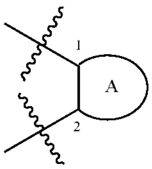

are as described in any one of (A-1')-(B-12), and $R_1$ is $(CR_CR_C)_{0-2}$-phenyl substituted with one, two, or three substituents as described herein.

(C-3) In some embodiments,

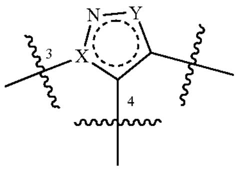

and

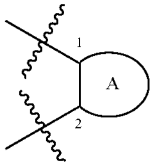

are as described in any one of (A-1')-(B-12), and $R_1$ is $(CR_CR_C)_{0-2}$-phenyl substituted with one, two, or three substituents selected from methyl, methoxy, $CF_3$, F, and Cl.

(C-4) In some embodiments,

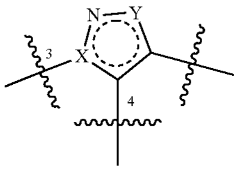

and

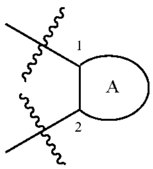

are as described in any one of (A-1')-(B-12), and $R_1$ is phenyl substituted with one or more substituents as described herein.

(C-5) In some embodiments,

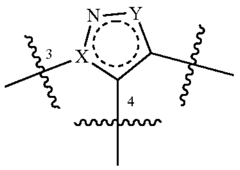

and

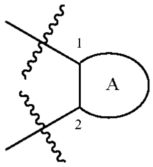

are as described in any one of (A-1')-(B-12), and $R_1$ is phenyl substituted with one, two, or three substituents as described herein.

(C-6) In some embodiments,

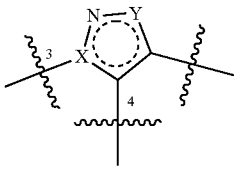

and

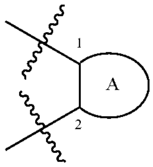

are as described in any one of (A-1')-(B-12), and $R_1$ is phenyl substituted with one, two, or three substituents selected from methyl, methoxy, $CF_3$, F, and Cl.

(C-7) In some embodiments,

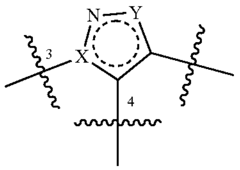

and

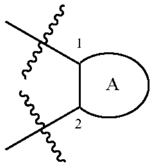

are as described in any one of (A-1')-(B-12), and $R_1$ is $CR_CR_C$-phenyl substituted with one or more substituents as described herein.

(C-8) In some embodiments,

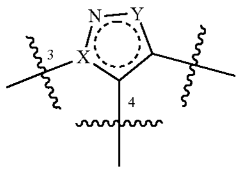

and

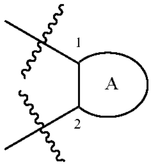

are as described in any one of (A-1')-(B-12), and $R_1$ is $CR_CR_C$-phenyl substituted with one, two, or three substituents as described herein.

(C-9) In some embodiments,

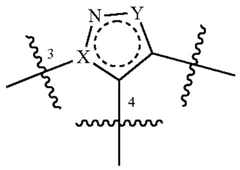

and

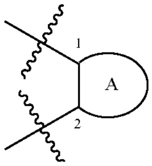

are as described in any one of (A-1')-(B-12), and $R_1$ is $CR_CR_C$-phenyl substituted with one, two, or three substituents selected from methyl, $CF_3$, F, and Cl.

(C-10) In some embodiments,

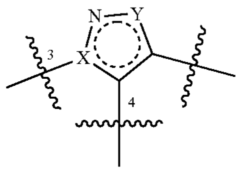

and

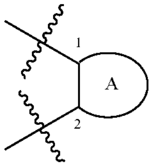

are as described in any one of (A-1')-(B-12), and $R_1$ is $(CR_CR_C)_{0-2}$—$C_3$-$C_6$ cycloalkyl (e.g., cyclopropyl, cyclobutyl, cyclopentyl, cyclohexyl, bicyclobutanyl, bicyclopentanyl, or bicyclohexanyl) optionally substituted with one or more substituents as described herein.

(C-11) In some embodiments,

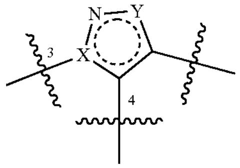

and

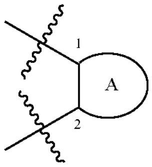

are as described in any one of (A-1')-(B-12), and $R_1$ is $(CR_CR_C)_{0-2}$—$C_3$-$C_6$ cycloalkyl (e.g., cyclopropyl, cyclobutyl, cyclopentyl, cyclohexyl, bicyclobutanyl, bicyclopentanyl, or bicyclohexanyl) optionally substituted with one, two, or three substituents as described herein.

(C-12) In some embodiments,

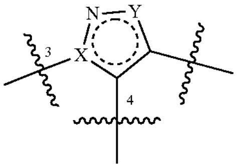

and

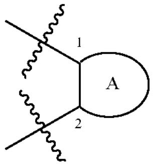

are as described in any one of (A-1')-(B-12), and $R_1$ is $(CR_CR_C)_{0-2}$—$C_3$-$C_6$ cycloalkyl (e.g., cyclopropyl, cyclobutyl, cyclopentyl, cyclohexyl, bicyclobutanyl, bicyclopentanyl, or bicyclohexanyl) optionally substituted with one, two, or three substituents selected from methyl, methoxy, $CF_3$, F, and Cl.

(C-13) In some embodiments,

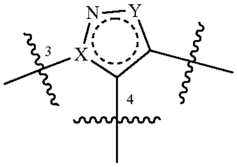

and

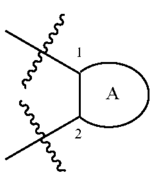

are as described in any one of (A-1')-(B-12), and $R_1$ is cyclohexyl or bicyclopentanyl, each of which is optionally substituted with one or more substituents as described herein.

(C-14) In some embodiments,

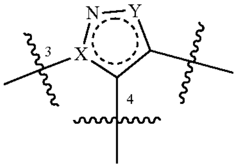

and

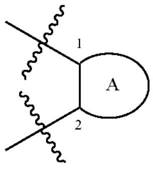

are as described in any one of (A-1')-(B-12), and $R_1$ is cyclohexyl or bicyclopentanyl, each of which is optionally substituted with one, two, or three substituents as described herein.

(C-15) In some embodiments,

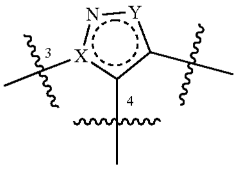

and

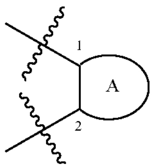

are as described in any one of (A-1')-(B-12), and $R_1$ is cyclohexyl or bicyclopentanyl, each of which is optionally substituted with one, two, or three substituents selected from methyl, methoxy, $CF_3$, F, and Cl.

(C-16) In some embodiments,

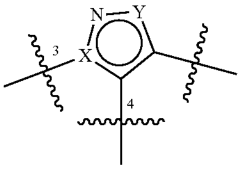

and

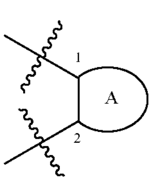

are as described in any one of (A-1')-(B-12), and $R_1$ is $(CR_CR_C)_{0-2}$-heteroaryl comprising one 5-membered ring and 1-3 heteroatoms selected from N, O, and S, optionally substituted as described herein.

(C-17) In some embodiments,

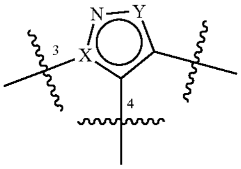

and

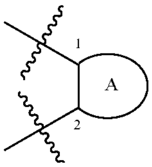

are as described in any one of (A-1')-(B-12), and $R_1$ is heteroaryl comprising one 5-membered ring and 1-3 heteroatoms selected from N, O, and S, optionally substituted as described herein.

(C-18) In some embodiments,

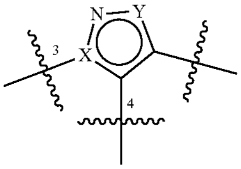

and

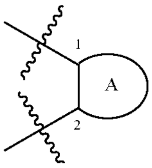

are as described in any one of (A-1')-(B-12), and $R_1$ is $(CR_CR_C)_{0-2}$-heteroaryl comprising one 6-membered ring and 1-3 heteroatoms selected from N, O, and S, optionally substituted as described herein.

(C-19) In some embodiments,

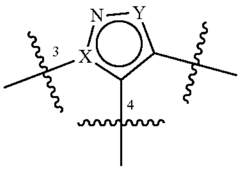

and

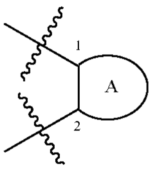

are as described in any one of (A-1')-(B-12), and $R_1$ is heteroaryl comprising one 6-membered ring and 1-3 heteroatoms selected from N, O, and S, optionally substituted as described herein.

(D-1) In some embodiments,

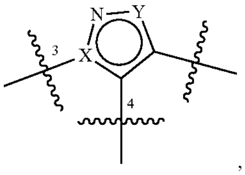,
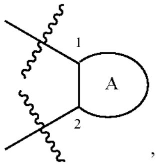, and $R_1$ are as described, as applicable, in any one of (A-1')-(C-19), and $R_2$ is heterocyclyl comprising one or two 5- or 6-membered rings and 1-3 heteroatoms selected from N, O, and S, optionally substituted with one or more substituents as described herein.

(D-2) In some embodiments,

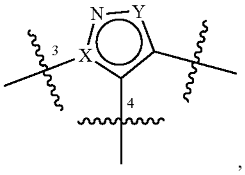,
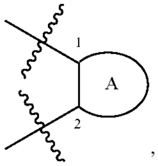, and $R_1$ are as described, as applicable, in any one of (A-1')-(C-19), and $R_2$ is heterocyclyl comprising one 5-membered ring and 1-3 heteroatoms selected from N, O, and S, optionally substituted with one or more substituents as described herein.

(D-3) In some embodiments,

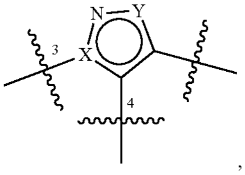,
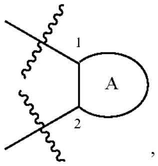, and $R_1$ are as described, as applicable, in any one of (A-1')-(C-19), and $R_2$ is heterocyclyl comprising one 6-membered ring and 1-3 heteroatoms selected from N, O, and S, optionally substituted with one or more substituents as described herein.

(D-4) In some embodiments,

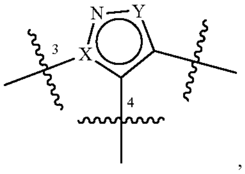,
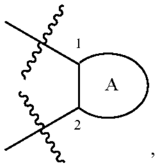, and $R_1$ are as described, as applicable, in any one of (A-1')-(C-19), and $R_2$ is heteroaryl comprising one or two 5- or 6-membered rings and 1-3 heteroatoms selected from N, O, and S, optionally substituted with one or more substituents as described herein.

(D-5) In some embodiments,

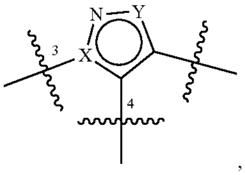,
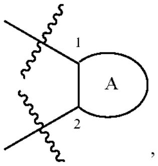, and $R_1$ are as described, as applicable, in any one of (A-1')-(C-19), and $R_2$ is heteroaryl comprising one 5-membered ring and 1-3 heteroatoms selected from N, O, and S, optionally substituted with one or more substituents as described herein.

(D-6) In some embodiments,

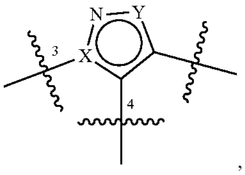,
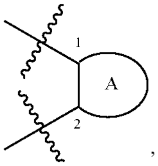, and $R_1$ are as described, as applicable, in any one of (A-1')-(C-19), and $R_2$ is heteroaryl comprising one 6-membered ring and 1-3 heteroatoms selected from N, O, and S, optionally substituted with one or more substituents as described herein.

(D-7) In some embodiments,

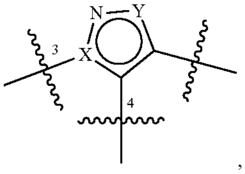,
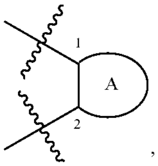, and $R_1$ are as described, as applicable, in any one of (A-1')-(C-19), and $R_2$ is heteroaryl comprising two 5- or 6-membered rings and 1-3 heteroatoms selected from N, O, and S, optionally substituted with one or more substituents as described herein.

(D-8) In some embodiments,

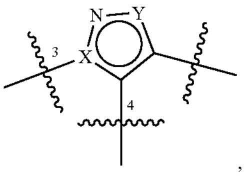,
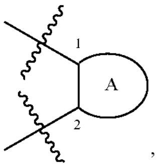, and $R_1$ are as described, as applicable, in any one of (A-1')-(C-19), and $R_2$ is indazolyl or imidazopyridinyl, each of which is optionally substituted with one or more substituents as described herein.

(D-9) In some embodiments,

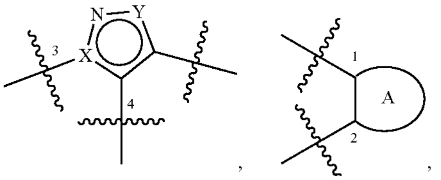

and $R_1$ are as described, as applicable, in any one of (A-1')-(C-19), and $R_2$ is spiro-, bridged-, or mono-$C_3$-$C_{10}$ cycloalkyl (e.g., cyclopropyl, cyclobutyl, cyclopentyl, cyclohexyl, cycloheptyl, cyclooctyl, each of which can be spiro-, bridged-, or mono-cycloalkyl) optionally substituted with one or more substituents as described herein.

(D-10) In some embodiments,

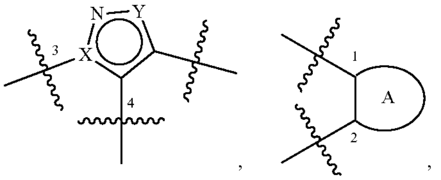

and $R_1$ are as described, as applicable, in any one of (A-1')-(C-19), and $R_2$ is bicyclooctanyl optionally substituted with one or more substituents as described herein.

(D-11) In some embodiments,

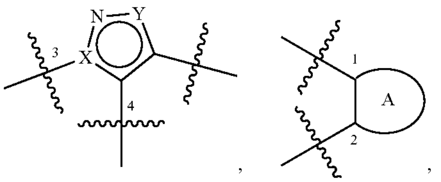

and $R_1$ are as described, as applicable, in any one of (A-1')-(C-19), and $R_2$ is phenyl optionally substituted with one or more substituents as described herein.

(E-1) In some embodiments,

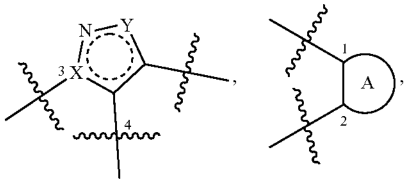

$R_1$, and $R_2$ are as described, as applicable, in any one of (A-1')-(D-11), and at least one $R_3$ is spiro-, bridged-, or mono-$C_3$-$C_{10}$ cycloalkyl (e.g., cyclopropyl, cyclobutyl, cyclopentyl, cyclohexyl, cycloheptyl, cyclooctyl, each of which can be spiro-, bridged-, or mono-cycloalkyl) optionally substituted with one or more substituents as described herein.

(E-2) In some embodiments,

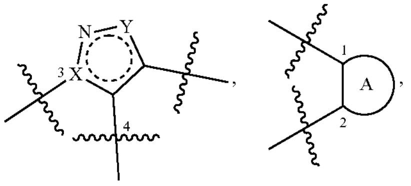

$R_1$, and $R_2$ are as described, as applicable, in any one of (A-1')-(D-11), and at least one $R_3$ is phenyl optionally substituted with one or more substituents as described herein.

(E-3) In some embodiments,

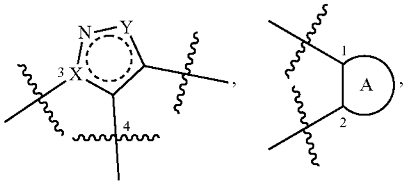

$R_1$, and $R_2$ are as described, as applicable, in any one of (A-1')-(D-11), and at least one $R_3$ is heterocyclyl comprising one or two 3- to 6-membered rings and 1-3 heteroatoms selected from N, O, and S, optionally substituted with one or more substituents as described herein.

(E-4) In some embodiments,

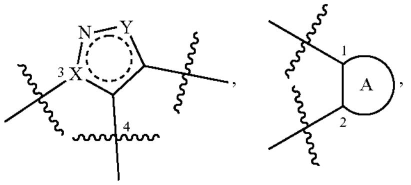

$R_1$, and $R_2$ are as described, as applicable, in any one of (A-1')-(D-11), and at least one $R_3$ is heterocyclyl comprising one 5- or 6-membered ring and 1-3 heteroatoms selected from N, O, and S, optionally substituted with one or more substituents as described herein.

(E-5) In some embodiments,

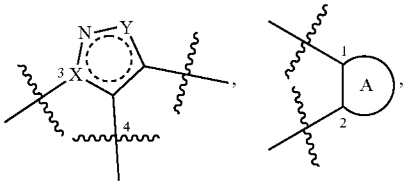

$R_1$, and $R_2$ are as described, as applicable, in any one of (A-1')-(D-11), and at least one $R_3$ is heterocyclyl comprising one 5-membered ring and 1-3 heteroatoms selected from N, O, and S, optionally substituted with one or more substituents as described herein.

(E-6) In some embodiments,

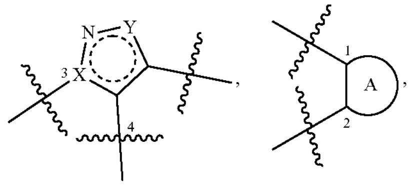

$R_1$, and $R_2$ are as described, as applicable, in any one of (A-1')-(D-11), and at least one $R_3$ is heterocyclyl comprising one 6-membered ring and 1-3 heteroatoms selected from N, O, and S, optionally substituted with one or more substituents as described herein.

(E-7) In some embodiments,

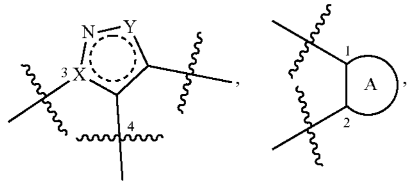

$R_1$, and $R_2$ are as described, as applicable, in any one of (A-1')-(D-11), and at least one $R_3$ is tetrahydropyranyl optionally substituted with one or more substituents as described herein.

(E-8) In some embodiments,

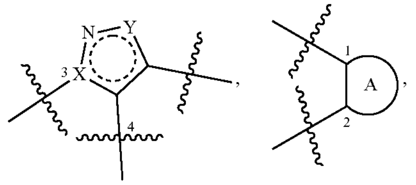

$R_1$, and $R_2$ are as described, as applicable, in any one of (A-1')-(D-11), and at least one $R_3$ is heteroaryl comprising one or two 5- or 6-membered rings and 1-3 heteroatoms selected from N, O, and S, optionally substituted with one or more substituents as described herein.

(E-9) In some embodiments,

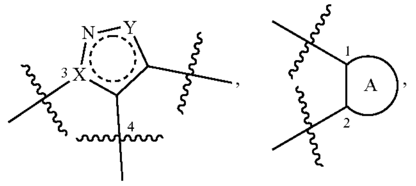

$R_1$, and $R_2$ are as described, as applicable, in any one of (A-1')-(D-11), and at least one $R_3$ is heteroaryl comprising one 5- or 6-membered ring and 1-3 heteroatoms selected from N, O, and S, optionally substituted with one or more substituents as described herein.

(E-10) In some embodiments,

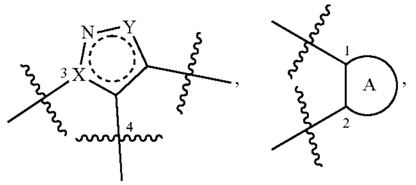

$R_1$, and $R_2$ are as described, as applicable, in any one of (A-1')-(D-11), and at least one $R_3$ is heteroaryl comprising one 5-membered ring and 1-3 heteroatoms selected from N, O, and S, optionally substituted with one or more substituents as described herein.

(E-11) In some embodiments,

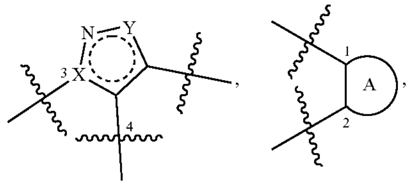

$R_1$, and $R_2$ are as described, as applicable, in any one of (A-1')-(D-11), and at least one $R_3$ is heteroaryl comprising one 6-membered ring and 1-3 heteroatoms selected from N, O, and S, optionally substituted with one or more substituents as described herein.

(E-12) In some embodiments,

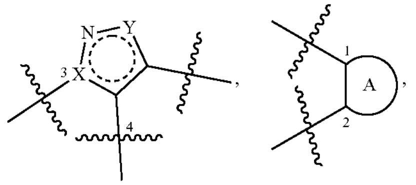

$R_1$, and $R_2$ are as described, as applicable, in any one of (A-1')-(D-11), and at least one $R_3$ is pyridyl optionally substituted with one or more substituents as described herein.

(F-1) In some embodiments,

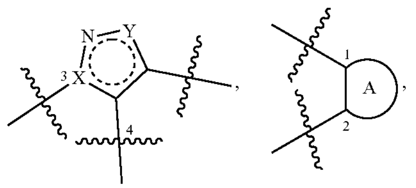

$R_1$, $R_2$, and $R_3$ are as described, as applicable, in any one of (A-1')-(E-12), and L is

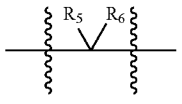

and $R_5$ and $R_6$ are each H.

(F-2) In some embodiments,

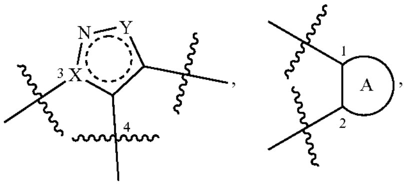

$R_1$, $R_2$, and $R_3$ are as described, as applicable, in any one of (A-1')-(E-12), and L is

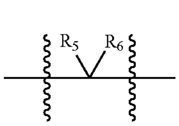

and $R_5$ and $R_6$, together with the carbon atom to which they are attached, form $C_3$-$C_6$ cycloalkyl (e.g., cyclopropyl, cyclobutyl, cyclopentyl, or cyclohexyl) optionally substituted with one or more substituents as described herein.

(F-3) In some embodiments,

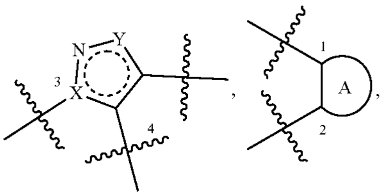

$R_1$, $R_2$, and $R_3$ are as described, as applicable, in any one of (A-1')-(E-12), and L is

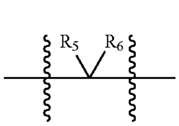

and $R_5$ and $R_6$, together with the carbon atom to which they are attached, form cyclopropyl optionally substituted with one or more substituents as described herein.

(G-1) In some embodiments,

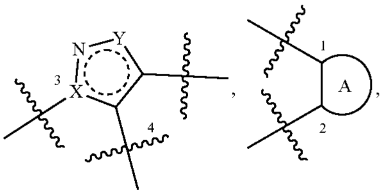

$R_1$, $R_2$, $R_3$, $R_5$, $R_6$, and L are as described, as applicable, in any one of (A-1')-(F-3), and T is heteroaryl comprising one 5- or 6-membered ring and 1-3 heteroatoms selected from N, O, and S, optionally substituted with one or more substituents as described herein.

(G-2) In some embodiments,

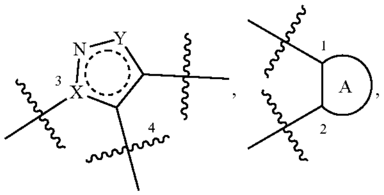

$R_1$, $R_2$, $R_3$, $R_5$, $R_6$, and L are as described, as applicable, in any one of (A-1')-(F-3), and T is heteroaryl comprising one 5-membered ring and 1-3 heteroatoms selected from N, O, and S, optionally substituted with one or more substituents as described herein.

(G-3) In some embodiments,

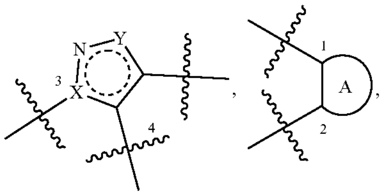

$R_1$, $R_2$, $R_3$, $R_5$, $R_6$, and L are as described, as applicable, in any one of (A-1')-(F-3), and T is heteroaryl comprising one 6-membered ring and 1-3 heteroatoms selected from N, O, and S, optionally substituted with one or more substituents as described herein.

(G-4) In some embodiments,

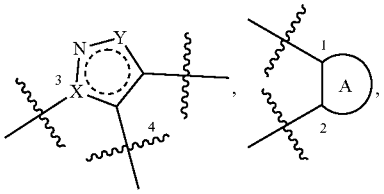

$R_1$, $R_2$, $R_3$, $R_5$, $R_6$, and L are as described, as applicable, in any one of (A-1')-(F-3), and T is heteroaryl selected from oxazolyl, isoxazolyl, thiazolyl, isothiazolyl, oxadiazolyl, thiadiazolyl, oxadiazolonyl, and thiadiazolonyl, each of which is optionally substituted with one or more substituents as described herein.

Non-limiting illustrative compounds of the application are listed in Table A. As shown in Table A, other tables of compounds, examples, schemes, and compounds throughout the present application, "or 1" (or "Or 1") and "or 2" (or "Or 2") indicate a single stereoisomeric configuration although the absolute stereochemistry of the indicated chiral carbon atom is not determined, and "&1" indicates a mixture of the stereoisomers of the indicated chiral carbon atom.

TABLE A

| Cmpd No. | Structure | Chemical name |
|---|---|---|
| 1 | 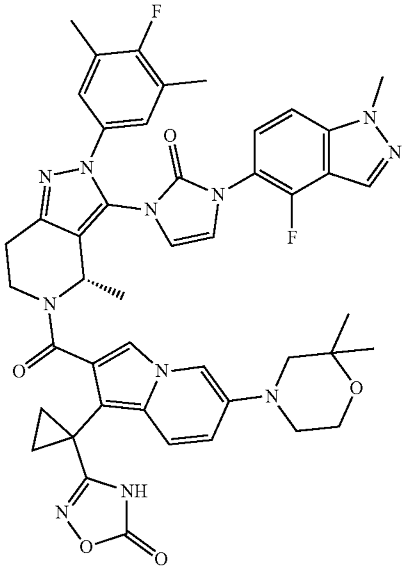 [SMILES: Cc1cc(-n2nc3c(c2-n2ccn(-c4ccc5c(cnn5C)c4F)c2=O)[C@H](C)N(C(=O)c2cn4cc(N5CCOC(C)(C)C5)ccc4c2C2(c4noc(=O)[nH]4)CC2)CC3)cc(C)c1F] | (S)-3-(1-(6-(2,2-dimethylmorpholino)-2-(3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)indolizin-1-yl)cyclopropyl)-1,2,4-oxadiazol-5(4H)-one |
| 2 | 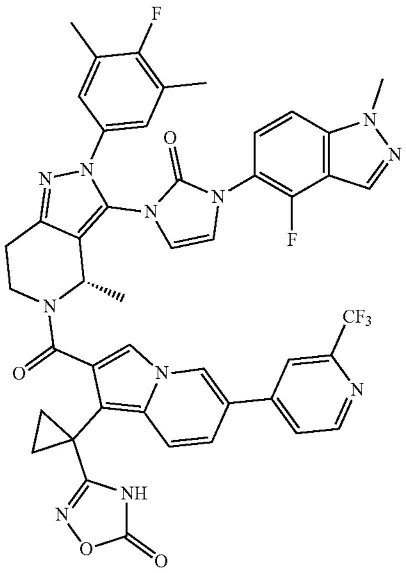 [SMILES: Cc1cc(-n2nc3c(c2-n2ccn(-c4ccc5c(cnn5C)c4F)c2=O)[C@H](C)N(C(=O)c2cn4cc(-c5ccnc(C(F)(F)F)c5)ccc4c2C2(c4noc(=O)[nH]4)CC2)CC3)cc(C)c1F] | (S)-3-(1-(2-(3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-6-(2-(trifluoromethyl)pyridin-4-yl)indolizin-1-yl)cyclopropyl)-1,2,4-oxadiazol-5(4H)-one |

TABLE A-continued

| Cmpd No. | Structure | Chemical name |
| --- | --- | --- |
| 3 | 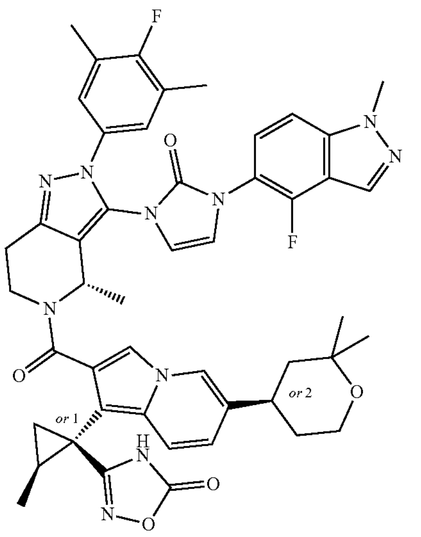 [SMILES: Cc1cc(-n2nc3c(c2-n2ccn(-c4ccc5c(cnn5C)c4F)c2=O)[C@H](C)N(C(=O)c2cn4cc([C@@H]5CCOC(C)(C)C5)ccc4c2[C@@]2(c4noc(=O)[nH]4)C[C@@H]2C)CC3)cc(C)c1F] | 3-((1R,2S)-1-(6-((R)-2,2-dimethyltetrahydro-2H-pyran-4-yl)-2-{(S)-3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)indolizin-1-yl)-2-methylcyclopropyl)-1,2,4-oxadiazol-5(4H)-one |
| 4 | 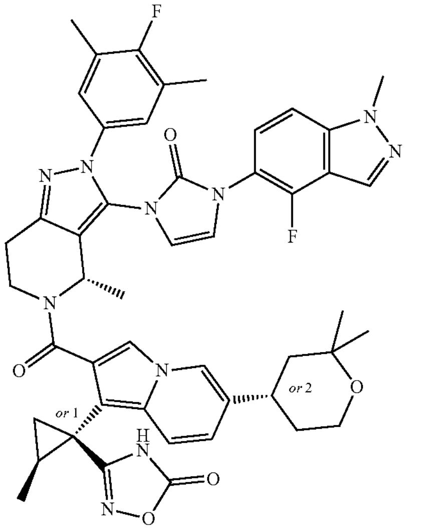 [SMILES: Cc1cc(-n2nc3c(c2-n2ccn(-c4ccc5c(cnn5C)c4F)c2=O)[C@H](C)N(C(=O)c2cn4cc([C@H]5CCOC(C)(C)C5)ccc4c2[C@@]2(c4noc(=O)[nH]4)C[C@@H]2C)CC3)cc(C)c1F] | 3-((1R,2S)-1-(6-((S)-2,2-dimethyltetrahydro-2H-pyran-4-yl)-2-((S)-3-(3-(4-fluoro-1-methyl-1H-indazol-5-yl)-2-oxo-2,3-dihydro-1H-imidazol-1-yl)-2-(4-fluoro-3.5-dimethylphenyl)-4-methyl-4,5,6,7-tetrahydro-2H-pyrazolo[4,3-c]pyridine-5-carbonyl)indolizin-1-yl)-2-methylcyclopropyl)-1,2,4-oxadiazol-5(4H)-one |
| 5 | 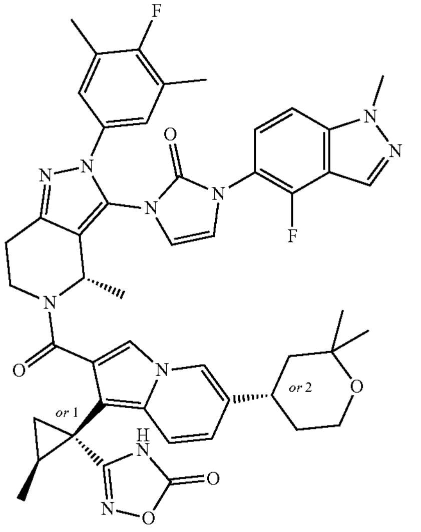 [SMILES: Cc1cc(-n2nc3c(c2-n2ccn(-c4ccc5c(cnn5C)c4F)c2=O)[C@H](C)N(C(=O)c2cn4cc([C@H]5CCOC(C)(C)C5)ccc4c2[C@]2(c4noc(=O)[nH]4)C[C@@H]2C)CC3)cc(C)c1F] | 3-((1S,2S)-1-(6-((S)-2,2-dimethyltetrahydro-2H-pyran-4-yl)-2-((S)-3-(3-(4-fluoro-1-methyl-1H-indazol-5-yl)-2-oxo-2,3-dihydro-1H-imidazol-1-yl)-2-(4-fluoro-3,5-dimcthylphenyl)-4-methyl-4,5,6,7-tetrahydro-2H-pyrazolo[4,3-c]pyridine-5-carbonyl)indolizin-1-yl)-2-methylcyclopropyl)-1,2,4-oxadiazol-5(4H)-one |

TABLE A-continued

| Cmpd No. | Structure | Chemical name |
| --- | --- | --- |
| 6 | 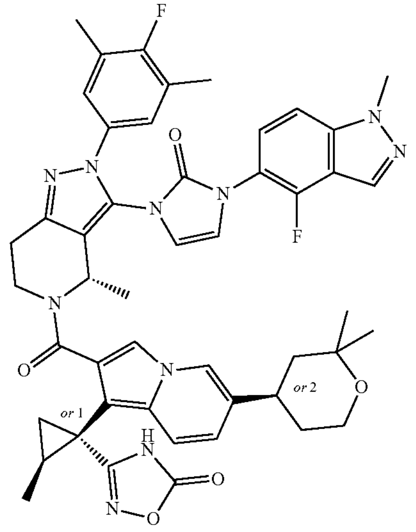 [SMILES: Cc1cc(-n2nc3c(c2-n2ccn(-c4ccc5c(cnn5C)c4F)c2=O)[C@H](C)N(C(=O)c2cn4cc([C@@H]5CCOC(C)(C)C5)ccc4c2[C@]2(c4noc(=O)[nH]4)C[C@@H]2C)CC3)cc(C)c1F] | 3-((1S,2S)-1-(6-((R)-2,2-dimethyltetrahydro-2H-pyran-4-yl)-2-((S)-3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)indolizin-1-yl)-2-methylcyclopropyl)-1,2,4-oxadiazol-5(4H)-one |
| 7 | 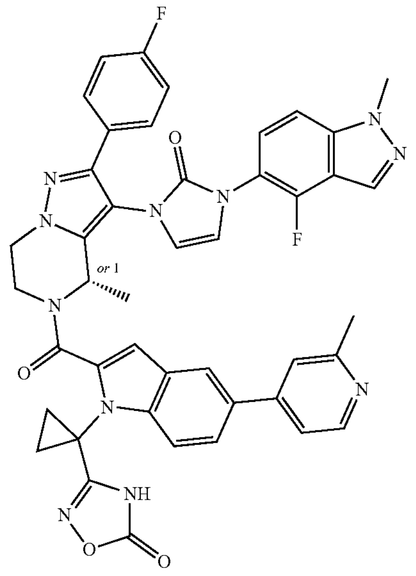 [SMILES: Cc1cc(-c2ccc3c(c2)cc(C(=O)N2CCn4nc(-c5ccc(F)cc5)c(-n5ccn(-c6ccc7c(cnn7C)c6F)c5=O)c4[C@@H]2C)n3C2(c3noc(=O)[nH]3)CC2)ccn1] | (S)-3-(1-(2-(3-(3-(4-fluoro-1-methyl-1H-indazol-5-yl)-2-oxo-2,3-dihydro-1H-imidazol-1-yl)-2-(4-fluorophenyl)-4-methyl-4,5,6,7-tetrahydropyrazolo[1,5-a]pyrazine-5-carbonyl)-5-(2-methylpyridin-4-yl)-1H-indol-1-yl)cyclopropyl)-1,2,4-oxadiazol-5(4H)-one |

TABLE A-continued

| Cmpd No. | Structure | Chemical name |
|---|---|---|
| 8 | 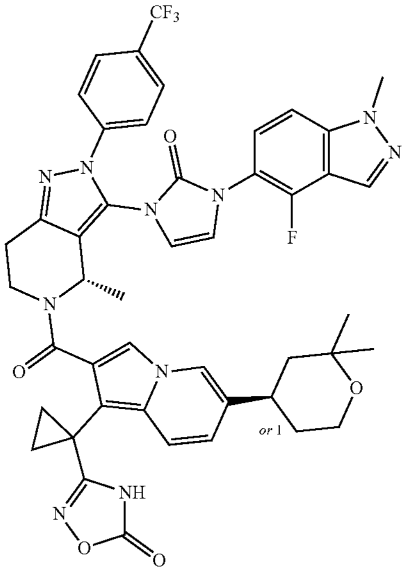 | 3-(1-(6-((R)-2,2-dimethyltetrahydro-2H-pyran-4-yl)-2-((S)-3-(3-(4-fluoro-1-methyl-1H-indazol-5-yl)-2-oxo-2,3-dihydro-1H-imidazol-1-yl)-4-methyl-2-(4-(trifluoromethyl)phenyl)-4,5,6,7-tetrahydro-2H-pyrazolo[4,3-c]pyridine-5-carbonyl)indolizin-1-yl)cyclopropyl)-1,2,4-oxadiazol-5(4H)-one |
| 9 | 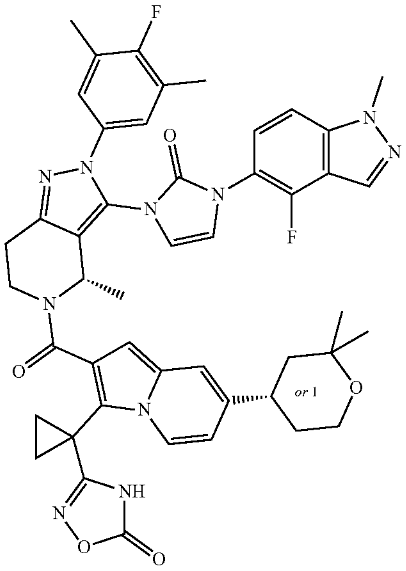 [SMILES: Cc1cc(-n2nc3c(c2-n2ccn(-c4ccc5c(cnn5C)c4F)c2=O)[C@H](C)N(C(=O)c2cc4cc([C@H]5CCOC(C)(C)C5)ccn4c2C2(c4noc(=O)[nH]4)CC2)CC3)cc(C)c1F] | 3-(1-(7-((S)-2,2-dimethyltetrahydro-2H-pyran-4-yl)-2-((S)-3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)indolizin-3-yl)cyclopropyl)-1,2,4-oxadiazol-5(4H)-one |

TABLE A-continued

| Cmpd No. | Structure | Chemical name |
| --- | --- | --- |
| 10 | 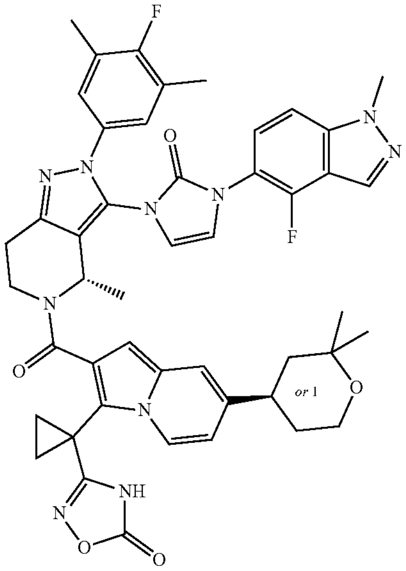 [SMILES: Cc1cc(-n2nc3c(c2-n2ccn(-c4ccc5c(cnn5C)c4F)c2=O)[C@H](C)N(C(=O)c2cc4cc([C@@H]5CCOC(C)(C)C5)ccn4c2C2(c4noc(=O)[nH]4)CC2)CC3)cc(C)c1F] | 3-(1-(7-((R)-2,2-dimethyltetrahydro-2H-pyran-4-yl)-2-((S)-3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)indolizin-3-yl)cyclopropyl)-1,2,4-oxadiazol-5(4H)-one |
| 11 | 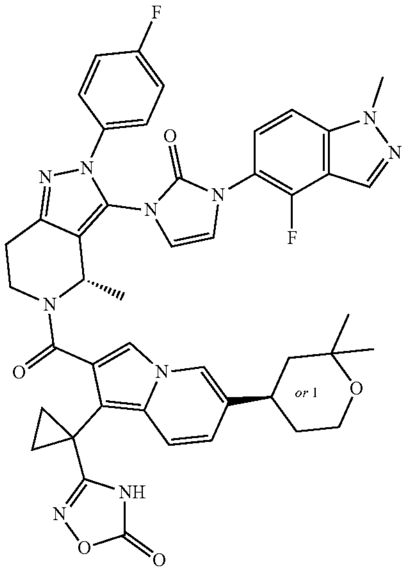 [SMILES: C[C@H]1c2c(nn(-c3ccc(F)cc3)c2-n2ccn(-c3ccc4c(cnn4C)c3F)c2=O)CCN1C(=O)c1cn2cc([C@@H]3CCOC(C)(C)C3)ccc2c1C1(c2noc(=O)[nH]2)CC1] | 3-(1-(6-((R)-2,2-dimethyltetrahydro-2H-pyran-4-yl)-2-((S)-3-(3-(4-fluoro-1-methyl-1H-indazol-5-yl)-2-oxo-2,3-dihydro-1H-imidazol-1-yl)-2-(4-fluorophenyl)-4-methyl-4,5,6,7-tetrahydro-2H-pyrazolo[4,3-c]pyridine-5-carbonyl)indolizin-1-yl)cyclopropyl)-1,2,4-oxadiazol-5(4H)-one |

TABLE A-continued

| Cmpd No. | Structure | Chemical name |
|---|---|---|
| 12 | 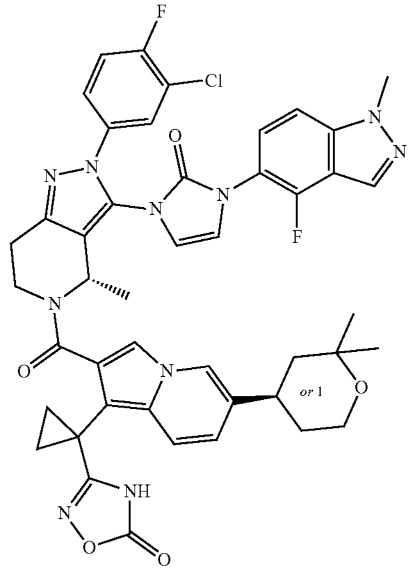 [SMILES: C[C@H]1c2c(nn(-c3ccc(F)c(Cl)c3)c2-n2ccn(-c3ccc4c(cnn4C)c3F)c2=O)CCN1C(=O)c1cn2cc([C@@H]3CCOC(C)(C)C3)ccc2c1C1(c2noc(=O)[nH]2)CC1] | 3-(1-(2-((S)-2-(3-chloro-4-fluorophenyl)-3-(3-(4-fluoro-1-methyl-1H-indazol-5-yl)-2-oxo-2,3-dihydro-1H-imidazol-1-yl)-4-methyl-4,5,6,7-tetrahydro-2H-pyrazolo[4,3-c]pyridine-5-carbonyl)-6-((R)-2,2-dimethyltetrahydro-2H-pyran-4-yl)indolizin-1-yl)cyclopropyl)-1,2,4-oxadiazol-5(4H)-one |
| 13 | 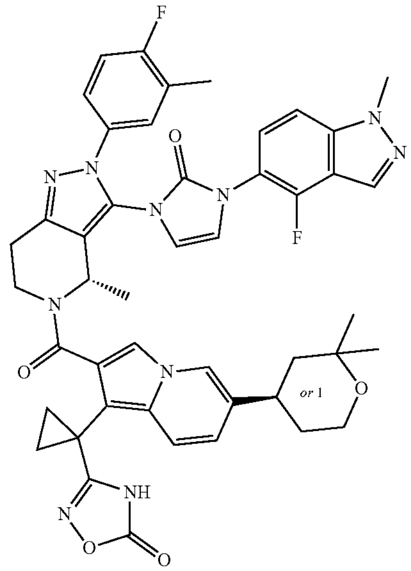 [SMILES: Cc1cc(-n2nc3c(c2-n2ccn(-c4ccc5c(cnn5C)c4F)c2=O)[C@H](C)N(C(=O)c2cn4cc([C@@H]5CCOC(C)(C)C5)ccc4c2C2(c4noc(=O)[nH]4)CC2)CC3)ccc1F] | 3-(1-(6-((R)-2,2-dimethyltetrahydro-2H-pyran-4-yl)-2-((S)-3-(3-(4-fluoro-1-methyl-1H-indazol-5-yl)-2-oxo-2,3-dihydro-1H-imidazol-1-yl)-2-(4-fluoro-3-methylphenyl)-4-methyl-4,5,6,7-tetrahydro-2H-pyrazolo[4,3-c]pyridine-5-carbonyl)indolizin-1-yl)cyclopropyl)-1,2,4-oxadiazol-5(4H)-one |

TABLE A-continued

| Cmpd No. | Structure | Chemical name |
|---|---|---|
| 14 | 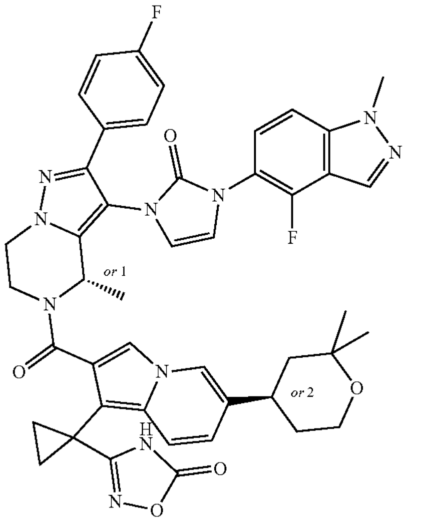 [SMILES: C[C@H]1c2c(-n3ccn(-c4ccc5c(cnn5C)c4F)c3=O)c(-c3ccc(F)cc3)nn2CCN1C(=O)c1cn2cc([C@@H]3CCOC(C)(C)C3)ccc2c1C1(c2noc(=O)[nH]2)CC1] | 3-(1-(6-((R)-2,2-dimethyltetrahydro-2H-pyran-4-yl)-2-((S)-3-(3-(4-fluoro-1-methyl-1H-indazol-5-yl)-2-oxo-2,3-dihydro-1H-imidazol-1-yl)-2-(4-fluorophenyl)-4-methyl-4,5,6,7-tetrahydropyrazolo[1,5-a]pyrazine-5-carbonyl)indolizin-1-yl)cyclopropyl)-1,2,4-oxadiazol-5(4H)-one |
| 15 | 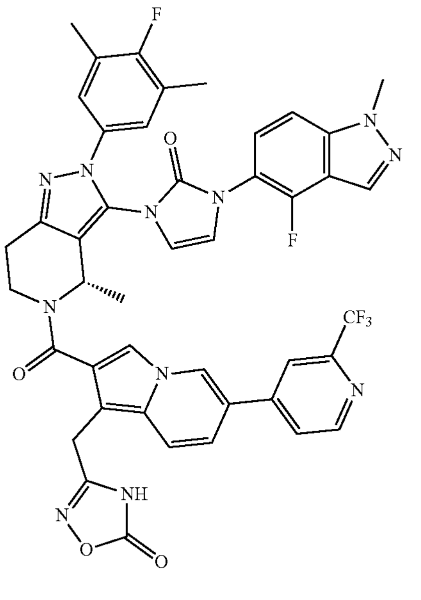 [SMILES: Cc1cc(-n2nc3c(c2-n2ccn(-c4ccc5c(cnn5C)c4F)c2=O)[C@H](C)N(C(=O)c2cn4cc(-c5ccnc(C(F)(F)F)c5)ccc4c2Cc2noc(=O)[nH]2)CC3)cc(C)c1F] | (S)-3-((2-(3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-6-(2-(trifluoromethyl)pyridin-4-yl)indolizin-1-yl)methyl)-1,2,4-oxadiazol-5(4H)-one |

TABLE A-continued

| Cmpd No. | Structure | Chemical name |
|---|---|---|
| 16 | 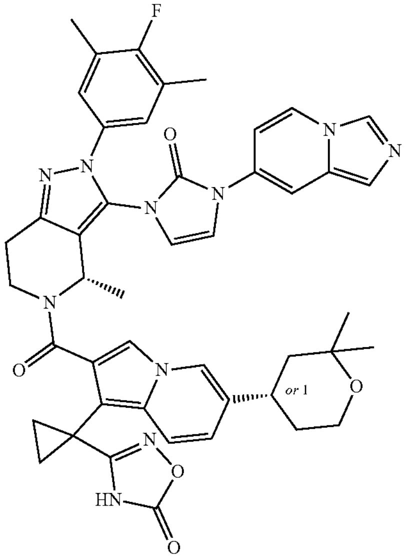 [SMILES: Cc1cc(-n2nc3c(c2-n2ccn(-c4ccn5cncc5c4)c2=O)[C@H](C)N(C(=O)c2cn4cc([C@H]5CCOC(C)(C)C5)ccc4c2C2(c4noc(=O)[nH]4)CC2)CC3)cc(C)c1F] | 3-(1-(6-((S)-2,2-dimethyltetrahydro-2H-pyran-4-yl)-2-((S)-2-(4-fluoro-3,5-dimethylphenyl)-3-(3-(imidazo[1,5-a]pyridin-7-yl)-2-oxo-2,3-dihydro-1H-imidazol-1-yl)-4-methyl-4,5,6,7-tetrahydro-2H-pyrazolo[4,3-c]pyridine-5-carbonyl)indolizin-1-yl)cyclopropyl)-1,2,4-oxadiazol-5(4H)-one |
| 17 | 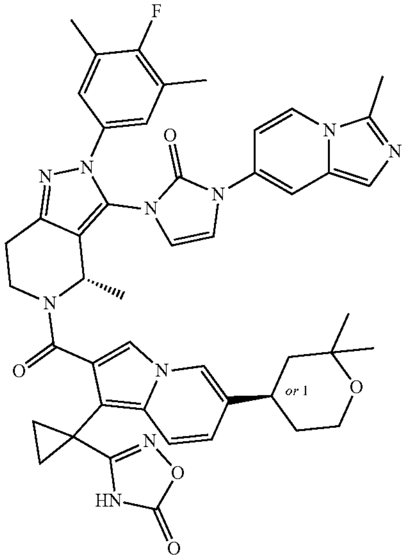 [SMILES: Cc1cc(-n2nc3c(c2-n2ccn(-c4ccn5c(C)ncc5c4)c2=O)[C@H](C)N(C(=O)c2cn4cc([C@@H]5CCOC(C)(C)C5)ccc4c2C2(c4noc(=O)[nH]4)CC2)CC3)cc(C)c1F] | 3-(1-(6-((R)-2,2-dimethyltetrahydro-2H-pyran-4 yl)-2-((S)-2-(4-fluoro-3,5-dimethylphenyl)-4-methyl-3-(3-(3-methylimidazo[1,5-a]pyridin-7-yl)-2-oxo-2,3-dihydro-1H-imidazol-1-yl)-4,5,6,7-tetrahydro-2H-pyrazolo[4,3-c]pyridine-5 carbonyl)indolizin-1-yl)cyclopropyl)-1,2,4-oxadiazol-5(4H)-onc |

TABLE A-continued

| Cmpd No. | Structure | Chemical name |
|---|---|---|
| 18 | 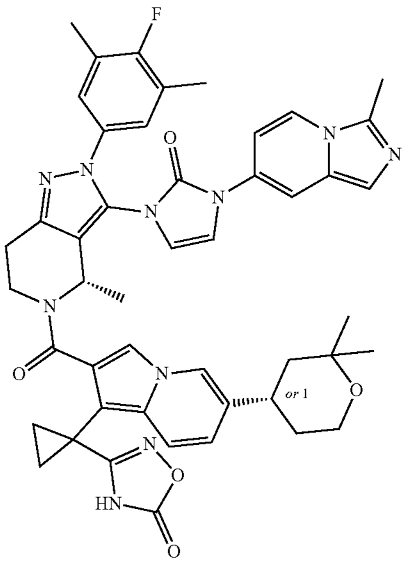 [SMILES: Cc1cc(-n2nc3c(c2-n2ccn(-c4ccn5c(C)ncc5c4)c2=O)[C@H](C)N(C(=O)c2cn4cc([C@H]5CCOC(C)(C)C5)ccc4c2C2(c4noc(=O)[nH]4)CC2)CC3)cc(C)c1F] | 3-(1-(6-((S)-2,2-dimethyltetrahydro-2H-pyran-4-yl)-2-((S)-2-(4-fluoro-3,5-dimethylphenyl)-4-methyl-3-(3-(3-methylimidazo[1,5-a]pyridin-7-yl)-2-oxo-2,3-dihydro-1H-imidazol-1-yl)-4,5,6,7-tetrahydro-2H-pyrazolo[4,3-c]pyridine-5-carbonyl)indolizin-1-yl)cyclopropyl)-1,2,4-oxadiazol-5(4H)-onc |
| 19 | 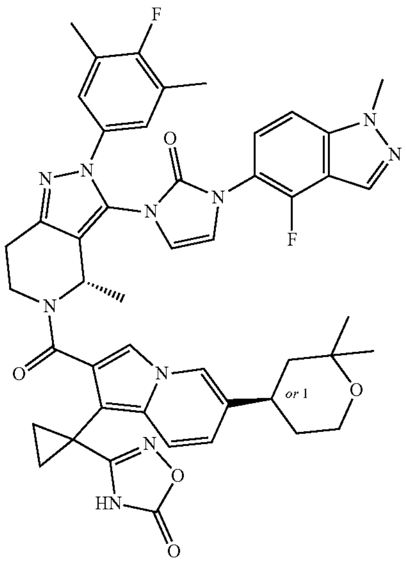 [SMILES: Cc1cc(-n2nc3c(c2-n2ccn(-c4ccc5c(cnn5C)c4F)c2=O)[C@H](C)N(C(=O)c2cn4cc([C@@H]5CCOC(C)(C)C5)ccc4c2C2(c4noc(=O)[nH]4)CC2)CC3)cc(C)c1F] | 3-(1-(6-((R)-2,2-dimethyltetrahydro-2H-pyran-4-yl)-2-((S)-3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)indolizin-1-yl)cyclopropyl)-1,2,4-oxadiazol-5(4H)-one |

TABLE A-continued

| Cmpd No. | Structure | Chemical name |
|---|---|---|
| 20 | 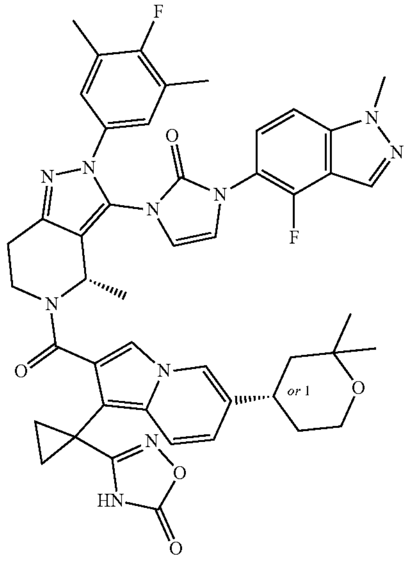 [SMILES: Cc1cc(-n2nc3c(c2-n2ccn(-c4ccc5c(cnn5C)c4F)c2=O)[C@H](C)N(C(=O)c2cn4cc([C@H]5CCOC(C)(C)C5)ccc4c2C2(c4noc(=O)[nH]4)CC2)CC3)cc(C)c1F] | 3-(1-(6-((S)-2,2-dimethyltetrahydro-2H-pyran-4-yl)-2-((S)-3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)indolizin-1-yl)cyclopropyl)-1,2,4-oxadiazol-5(4H)-onc |
| 21 | 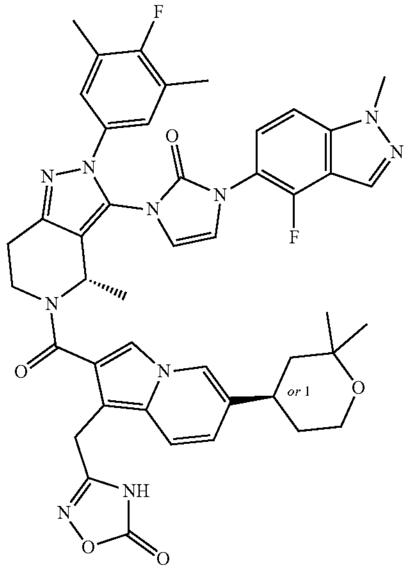 [SMILES: Cc1cc(-n2nc3c(c2-n2ccn(-c4ccc5c(cnn5C)c4F)c2=O)[C@H](C)N(C(=O)c2cn4cc([C@@H]5CCOC(C)(C)C5)ccc4c2Cc2noc(=O)[nH]2)CC3)cc(C)c1F] | 3-((6-((R)-2,2-dimethyltetrahydro-2H-pyran-4-yl)-2-((S)-3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)indolizin-1-yl)methyl)-1,2,4-oxadiazol-5(4H)-one |

TABLE A-continued

| Cmpd No. | Structure | Chemical name |
|---|---|---|
| 22 | 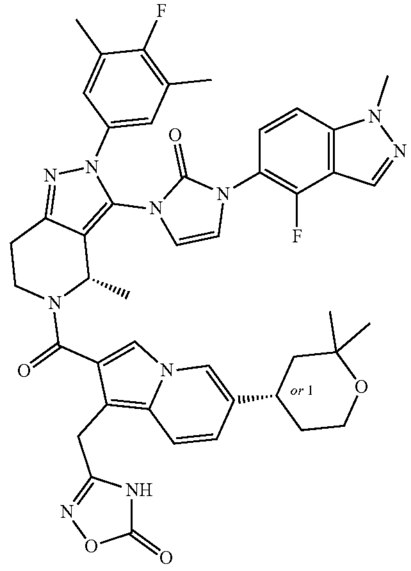 [SMILES: Cc1cc(-n2nc3c(c2-n2ccn(-c4ccc5c(cnn5C)c4F)c2=O)[C@H](C)N(C(=O)c2cn4cc([C@H]5CCOC(C)(C)C5)ccc4c2Cc2noc(=O)[nH]2)CC3)cc(C)c1F] | 3-((6-((S)-2,2-dimethyltetrahydro-2H-pyran-4-yl)-2-((S)-3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)indolizin-1-yl)methyl)-1,2,4-oxadiazol-5(4H)-one |
| 23 | 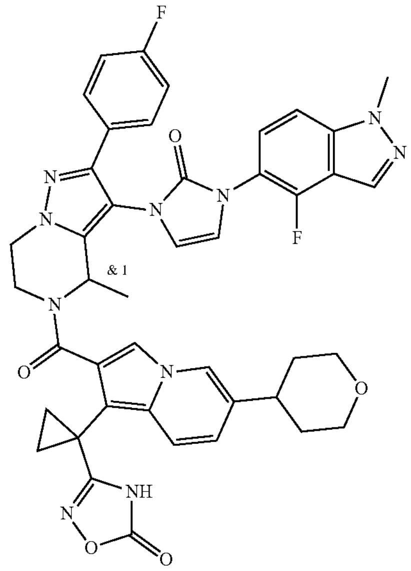 [SMILES: CC1c2c(-n3ccn(-c4ccc5c(cnn5C)c4F)c3=O)c(-c3ccc(F)cc3)nn2CCN1C(=O)c1cn2cc(C3CCOCC3)ccc2c1C1(c2noc(=O)[nH]2)CC1] | 3-(1-(2-(3-(3-(4-fluoro-1-methyl-1H-indazol-5-yl)-2-oxo-2,3-dihydro-1H-imidazol-1-yl)-2-(4-fluorophenyl)-4-methyl-4,5,6,7-tetrahydropyrazolo[1,5-a]pyrazine-5-carbonyl)-6-(tetrahydro-2H-pyran-4-yl)indolizin-1-yl)cyclopropyl)-1,2,4-oxadiazol-5(4H)-one |

TABLE A-continued

| Cmpd No. | Structure | Chemical name |
|---|---|---|
| 24 | 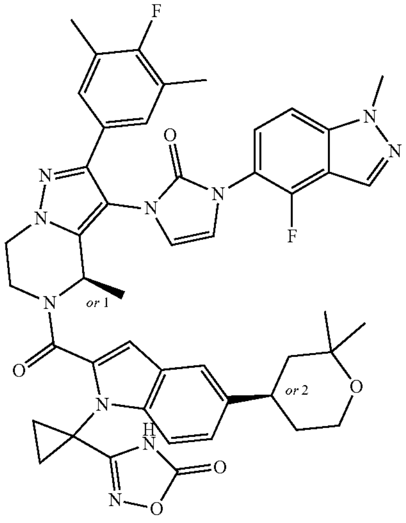 [SMILES: Cc1cc(-c2nn3c(c2-n2ccn(-c4ccc5c(cnn5C)c4F)c2=O)[C@@H](C)N(C(=O)c2cc4cc([C@@H]5CCOC(C)(C)C5)ccc4n2C2(c4noc(=O)[nH]4)CC2)CC3)cc(C)c1F] | 3-(1-(5-((R)-2,2-dimethyltetrahydro-2H-pyran-4-yl)-2-((R)-3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-4,5,6,7-tetrahydropyrazolo[1,5-a]pyrazine-5-carbonyl)-1H-indol-1-yl)cyclopropyl)-1,2,4-oxadiazol-5(4H)-one |
| 25 | 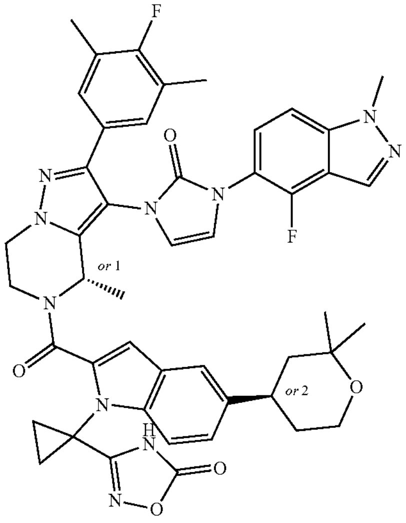 [SMILES: Cc1cc(-c2nn3c(c2-n2ccn(-c4ccc5c(cnn5C)c4F)c2=O)[C@H](C)N(C(=O)c2cc4cc([C@@H]5CCOC(C)(C)C5)ccc4n2C2(c4noc(=O)[nH]4)CC2)CC3)cc(C)c1F] | 3-(1-(5-((R)-2,2-dimethyltetrahydro-2H-pyran-4-yl)-2-((S)-3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-4,5,6,7-tetrahydropyrazolo[1,5-a]pyrazine-5-carbonyl)-1H-indol-1-yl)cyclopropyl)-1,2,4-oxadiazol-5(4H)-one |
| 26 | 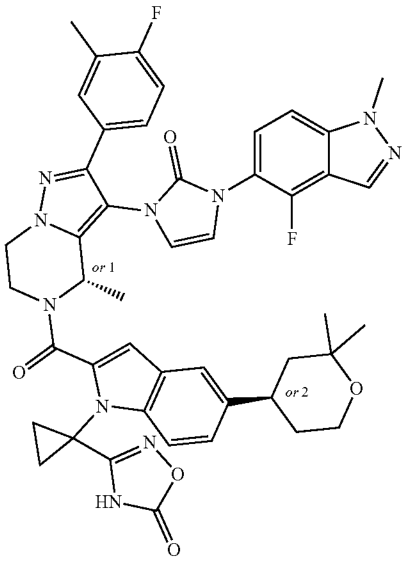 [SMILES: Cc1cc(-c2nn3c(c2-n2ccn(-c4ccc5c(cnn5C)c4F)c2=O)[C@H](C)N(C(=O)c2cc4cc([C@@H]5CCOC(C)(C)C5)ccc4n2C2(c4noc(=O)[nH]4)CC2)CC3)ccc1F] | 3-(1-(5-((R)-2,2-dimethyltetrahydro-2H-pyran-4-yl)-2-((S)-3-(3-(4-fluoro-1-methyl-1H-indazol-5-yl)-2-oxo-2,3-dihydro-1H-imidazol-1-yl)-2-(4-fluoro-3-methylphenyl)-4-methyl-4,5,6,7-tetrahydropyrazolo[1,5-a]pyrazine-5-carbonyl)-1H-indol-1-yl)cyclopropyl)-1,2,4-oxadiazol-5(4H)-one |

TABLE A-continued

| Cmpd No. | Structure | Chemical name |
|---|---|---|
| 27 | 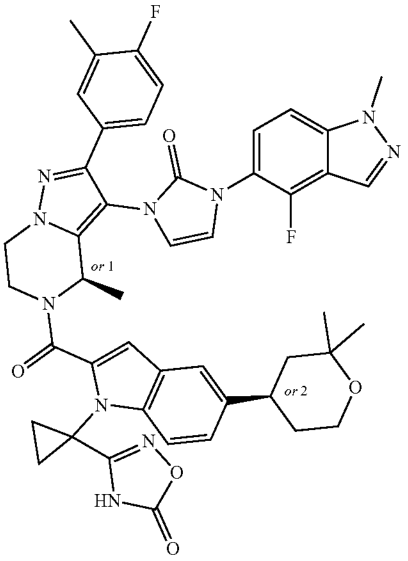 [SMILES: Cc1cc(-c2nn3c(c2-n2ccn(-c4ccc5c(cnn5C)c4F)c2=O)[C@@H](C)N(C(=O)c2cc4cc([C@@H]5CCOC(C)(C)C5)ccc4n2C2(c4noc(=O)[nH]4)CC2)CC3)ccc1F] | 3-(1-(5-((R)-2,2-dimethyltetrahydro-2H-pyran-4-yl)-2-((R)-3-(3-(4-fluoro-1-methyl-1H-indazol-5-yl)-2-oxo-2,3-dihydro-1H-imidazol-1-yl)-2-(4-fluoro-3-methylphenyl)-4-methyl-4,5,6,7-tetrahydropyrazolo[1,5-a]pyrazine-5-carbonyl)-1H-indol-1-yl)cyclopropyl)-1,2,4-oxadiazol-5(4H)-one |
| 28 | 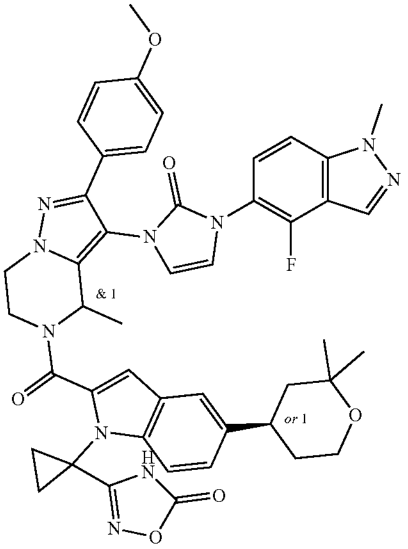 [SMILES: COc1ccc(-c2nn3c(c2-n2ccn(-c4ccc5c(cnn5C)c4F)c2=O)C(C)N(C(=O)c2cc4cc([C@@H]5CCOC(C)(C)C5)ccc4n2C2(c4noc(=O)[nH]4)CC2)CC3)cc1] | 3-(1-(5-((R)-2,2-dimethyltetrahydro-2H-pyran-4-yl)-2-(3-(3-(4-fluoro-1-methyl-1H-indazol-5-yl)-2-oxo-2,3-dihydro-1H-imidazol-1-yl)-2-(4-methoxyphenyl)-4-methyl-4,5,6,7-tetrahydropyrazolo[1,5-a]pyrazine-5-carbonyl)-1H-indol-1-yl)cyclopropyl)-1,2,4-oxadiazol-5(4H)-one |

TABLE A-continued

| Cmpd No. | Structure | Chemical name |
| --- | --- | --- |
| 29 | 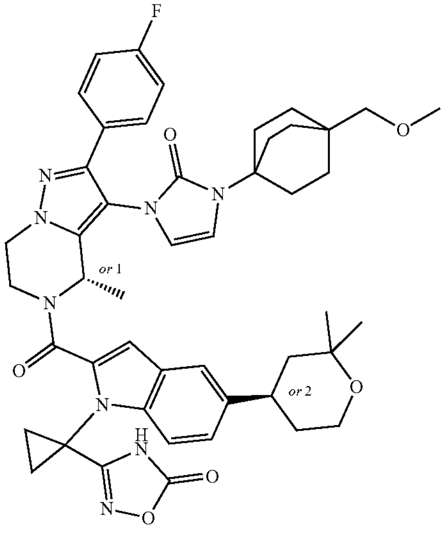 [SMILES: COCC12CCC(n3ccn(-c4c(-c5ccc(F)cc5)nn5c4[C@H](C)N(C(=O)c4cc6cc([C@@H]7CCOC(C)(C)C7)ccc6n4C4(c6noc(=O)[nH]6)CC4)CC5)c3=O)(CC1)CC2] | 3-(1-(5-((R)-2,2-dimethyltetrahydro-2H-pyran-4-yl)-2-((S)-2-(4-fluorophenyl)-3-(3-(4-(methoxymethyl)bicyclo[2.2.2]octan-1-yl)-2-oxo-2,3-dihydro-1H-imidazol-1-yl)-4-methyl-4,5,6,7-tetrahydropyrazolo[1,5-a]pyrazine-5-carbonyl)-1H-indol-1-yl)cyclopropyl)-1,2,4-oxadiazol-5(4H)-one |
| 30 | 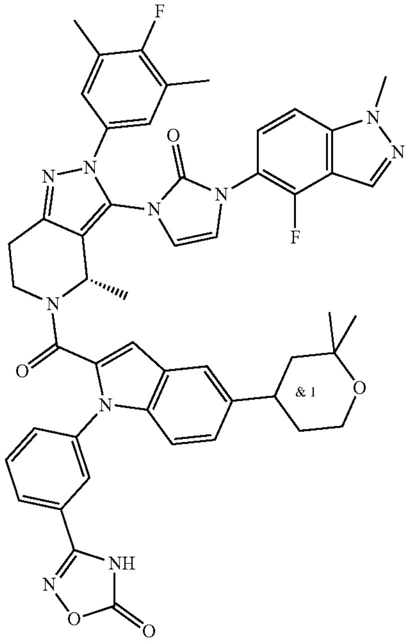 [SMILES: Cc1cc(-n2nc3c(c2-n2ccn(-c4ccc5c(cnn5C)c4F)c2=O)[C@H](C)N(C(=O)c2cc4cc(C5CCOC(C)(C)C5)ccc4n2-c2cccc(-c4noc(=O)[nH]4)c2)CC3)cc(C)c1F] | 3-(3-(5-(2,2-dimethyltetrahydro-2H-pyran-4-yl)-2-((S)-3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-1H-indol-1-yl)phenyl)-1,2,4-oxadiazol-5(4H)-one |

TABLE A-continued

| Cmpd No. | Structure | Chemical name |
| --- | --- | --- |
| 31 | 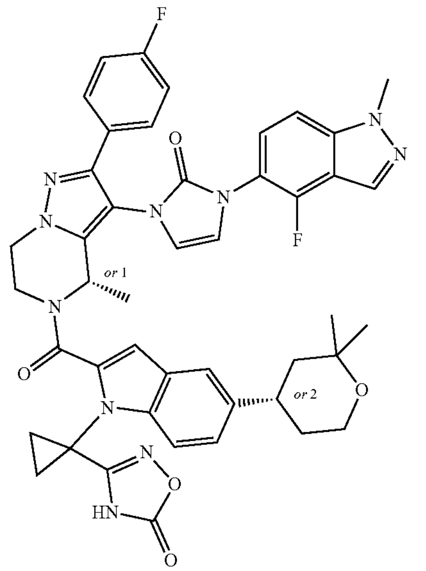 [SMILES: C[C@H]1c2c(-n3ccn(-c4ccc5c(cnn5C)c4F)c3=O)c(-c3ccc(F)cc3)nn2CCN1C(=O)c1cc2cc([C@H]3CCOC(C)(C)C3)ccc2n1C1(c2noc(=O)[nH]2)CC1] | 3-(1-(5-((S)-2,2-dimethyltetrahydro-2H-pyran-4-yl)-2-((S)-3-(3-(4-fluoro-1-methyl-1H-indazol-5-yl)-2-oxo-2,3-dihydro-1H-imidazol-1-yl)-2-(4-fluorophenyl)-4-methyl-4,5,6,7-tetrahydropyrazolo[1,5-a]pyrazine-5-carbonyl)-1H-indol-1-yl)cyclopropyl)-1,2,4-oxadiazol-5(4H)-one |
| 32 | 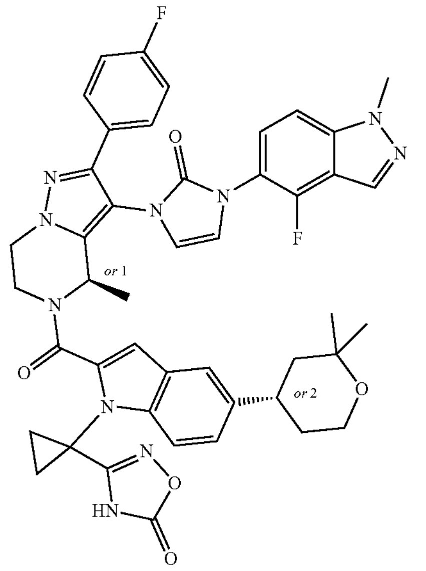 [SMILES: C[C@@H]1c2c(-n3ccn(-c4ccc5c(cnn5C)c4F)c3=O)c(-c3ccc(F)cc3)nn2CCN1C(=O)c1cc2cc([C@H]3CCOC(C)(C)C3)ccc2n1C1(c2noc(=O)[nH]2)CC1] | 3-(1-(5-((S)-2,2-dimethyltetrahydro-2H-pyran-4-yl)-2-((R)-3-(3-(4-fluoro-1-methyl-1H-indazol-5-yl)-2-oxo-2,3-dihydro-1H-imidazol-1-yl)-2-(4-fluorophenyl)-4-methyl-4,5,6,7-tetrahydropyrazolo[1,5-a]pyrazine-5-carbonyl)-1H-indol-1-yl)cyclopropyl)-1,2,4-oxadiazol-5(4H)-one |

TABLE A-continued

| Cmpd No. | Structure | Chemical name |
|---|---|---|
| 33 | 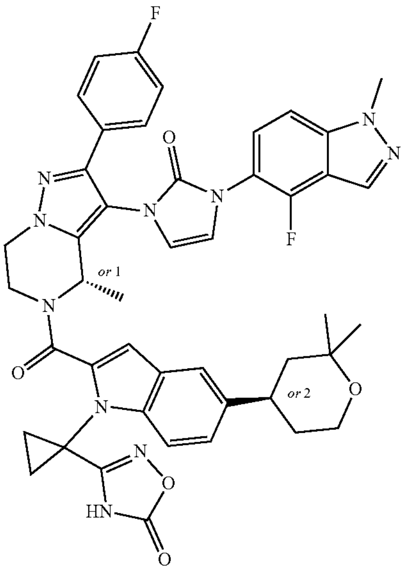 [SMILES: C[C@H]1c2c(-n3ccn(-c4ccc5c(cnn5C)c4F)c3=O)c(-c3ccc(F)cc3)nn2CCN1C(=O)c1cc2cc([C@@H]3CCOC(C)(C)C3)ccc2n1C1(c2noc(=O)[nH]2)CC1] | 3-(1-(5-((R)-2,2-dimethyltetrahydro-2H-pyran-4-yl)-2-((S)-3-(3-(4-fluoro-1-methyl-1H-indazol-5-yl)-2-oxo-2,3-dihydro-1H-imidazol-1-yl)-2-(4-fluorophenyl)-4-methyl-4,5,6,7-tetrahydropyrazolo[1,5-a]pyrazine-5-carbonyl)-1H-indol-1-yl)cyclopropyl)-1,2,4-oxadiazol-5(4H)-one |
| 34 | 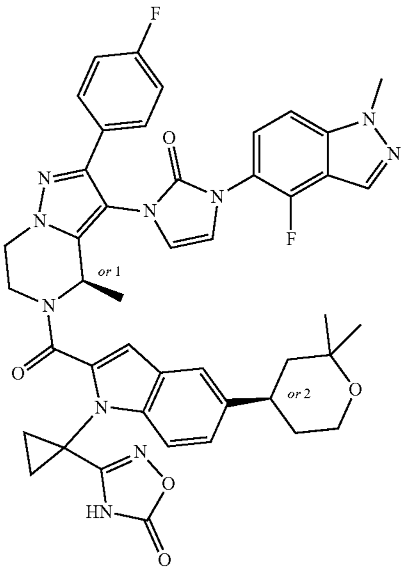 [SMILES: C[C@@H]1c2c(-n3ccn(-c4ccc5c(cnn5C)c4F)c3=O)c(-c3ccc(F)cc3)nn2CCN1C(=O)c1cc2cc([C@@H]3CCOC(C)(C)C3)ccc2n1C1(c2noc(=O)[nH]2)CC1] | 3-(1-(5-((R)-2,2-dimethyltetrahydro-2H-pyran-4-yl)-2-((R)-3-(3-(4-fluoro-1-methyl-1H-indazol-5-yl)-2-oxo-2,3-dihydro-1H-imidazol-1-yl)-2-(4-fluorophenyl)-4-methyl-4,5,6,7-tetrahydropyrazolo[1,5-a]pyrazine-5-carbonyl)-1H-indol-1-yl)cyclopropyl)-1,2,4-oxadiazol-5(4H)-one |

TABLE A-continued

| Cmpd No. | Structure | Chemical name |
|---|---|---|
| 35 | 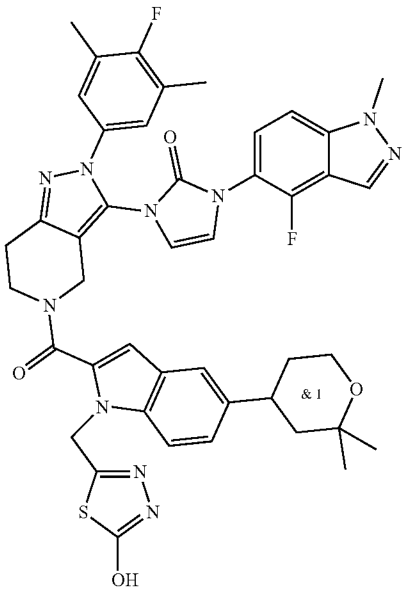 [SMILES: Cc1cc(-n2nc3c(c2-n2ccn(-c4ccc5c(cnn5C)c4F)c2=O)CN(C(=O)c2cc4cc(C5CCOC(C)(C)C5)ccc4n2Cc2nnc(O)s2)CC3)cc(C)c1F] | l-(5-(5-(2,2-dimethyltetrahydro-2H-pyran-4-yl)-1-((5-hydroxy-1,3,4-thiadiazol-2-yl)methyl)-1H-indole-2-carbonyl)-2-(4-fluoro-3,5-dimethylphenyl)-4,5,6,7-tetrahydro-2H-pyrazolo[4,3-c]pyridin-3-yl)-3-(4-fluoro-1-methyl-1H-indazol-5-yl)-l,3-dihydro-2H-imidazol-2-one |
| 36 | 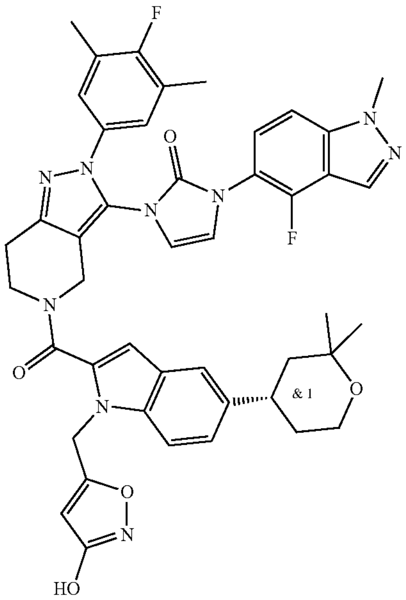 [SMILES: Cc1cc(-n2nc3c(c2-n2ccn(-c4ccc5c(cnn5C)c4F)c2=O)CN(C(=O)c2cc4cc([C@H]5CCOC(C)(C)C5)ccc4n2Cc2cc(O)no2)CC3)cc(C)c1F] | l-(5-(5-(2,2-dimethyltetrahydro-2H-pyran-4-yl)-1-((3-hydroxyisoxazol-5-yl)methyl)-1H-indole-2-carbonyl)-2-(4-fluoro-3,5-dimethylphenyl)-4,5,6,7-tetrahydro-2H-pyrazolo[4,3-c]pyridin-3-yl)-3-(4-fluoro-1-methyl-1H-indazol-5-yl)-1,3-dihydro-2H-imidazol-2-one |

TABLE A-continued

| Cmpd No. | Structure | Chemical name |
| --- | --- | --- |
| 37 | 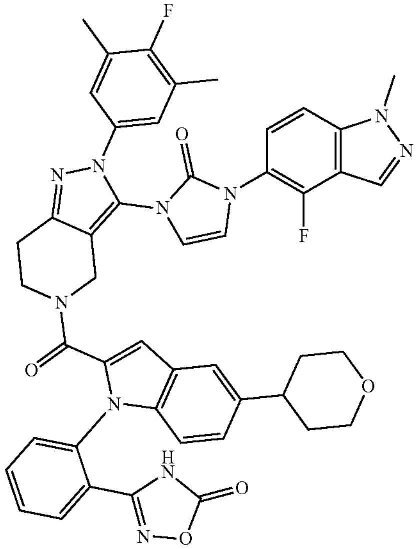 [SMILES: Cc1cc(-n2nc3c(c2-n2ccn(-c4ccc5c(cnn5C)c4F)c2=O)CN(C(=O)c2cc4cc(C5CCOCC5)ccc4n2-c2ccccc2-c2noc(=O)[nH]2)CC3)cc(C)c1F] | 3-(2-(2-(3-(3-(4-fluoro-1-methyl-1H-indazol-5-yl)-2-oxo-2,3-dihydro-1H-imidazol-1-yl)-2-(4-fluoro-3,5-dimethylphenyl)-4,5,6,7-tetrahydro-2H-pyrazolo[4,3-c]pyridine-5-carbonyl)-5-(tetrahydro-2H-pyran-4-yl)-1H-indol-1-yl)phenyl)-1,2,4-oxadiazol-5(4H)-one |
| 38 | 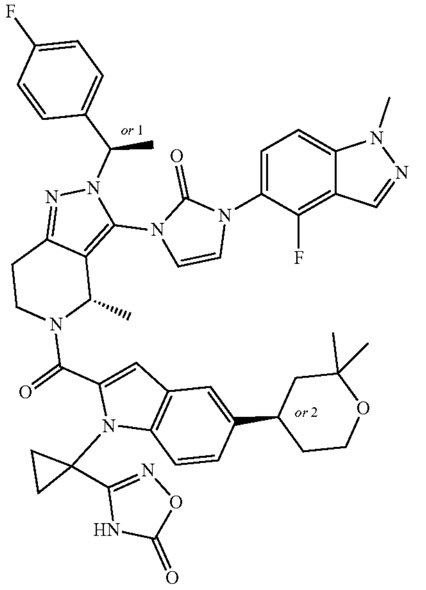 [SMILES: C[C@H](c1ccc(F)cc1)n1nc2c(c1-n1ccn(-c3ccc4c(cnn4C)c3F)c1=O)[C@H](C)N(C(=O)c1cc3cc([C@@H]4CCOC(C)(C)C4)ccc3n1C1(c3noc(=O)[nH]3)CC1)CC2] | 3-(1-(5-((R)-2,2-dimethyltetrahydro-2H-pyran-4-yl)-2-((S)-3-(3-(4-fluoro-1-methyl-1H-indazol-5-yl)-2-oxo-2,3-dihydro-1H-imidazol-1-yl)-2-((R)-1-(4-fluorophenyl)ethyl)-4-methyl-4,5,6,7-tetrahydro-2H-pyrazolo[4,3-c]pyridine-5-carbonyl)-1H-indol-1-yl)cyclopropyl)-1,2,4-oxadiazol-5(4H)-one |

TABLE A-continued

| Cmpd No. | Structure | Chemical name |
| --- | --- | --- |
| 39 | 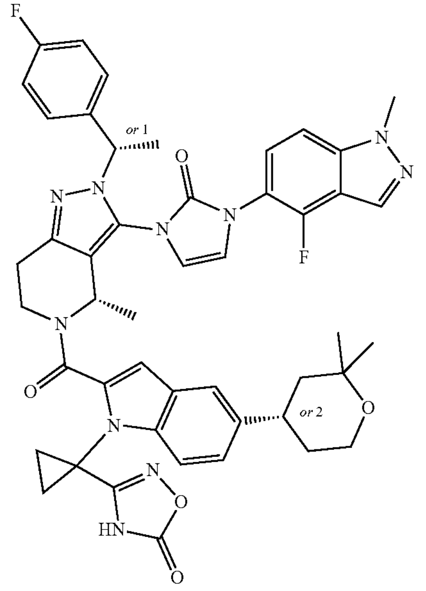 [SMILES: C[C@H]1c2c(nn([C@@H](C)c3ccc(F)cc3)c2-n2ccn(-c3ccc4c(cnn4C)c3F)c2=O)CCN1C(=O)c1cc2cc([C@H]3CCOC(C)(C)C3)ccc2n1C1(c2noc(=O)[nH]2)CC1] | 3-(1-(5-((S)-2,2-dimethyltetrahydro-2H-pyran-4-yl)-2-((S)-3-(3-(4-fluoro-1-methyl-1H-indazol-5-yl)-2-oxo-2,3-dihydro-1H-imidazol-1-yl)-2-((S)-1-(4-fluorophenyl)ethyl)-4-methyl-4,5,6,7-tetrahydro-2H-pyrazolo[4,3-c]pyridine-5-carbonyl)-1H-indol-1-yl)cyclopropyl)-1,2,4-oxadiazol-5(4H)-onc |
| 40 | 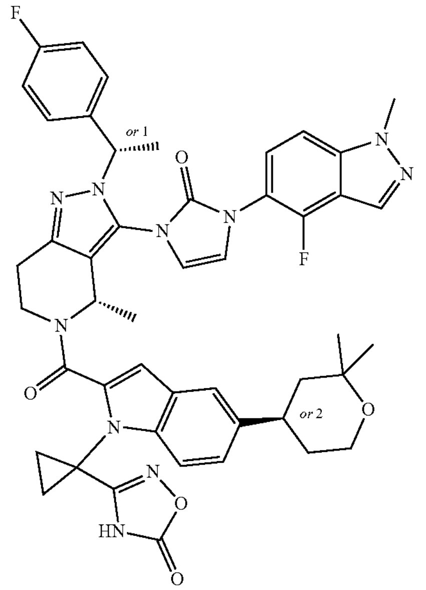 [SMILES: C[C@H]1c2c(nn([C@@H](C)c3ccc(F)cc3)c2-n2ccn(-c3ccc4c(cnn4C)c3F)c2=O)CCN1C(=O)c1cc2cc([C@@H]3CCOC(C)(C)C3)ccc2n1C1(c2noc(=O)[nH]2)CC1] | 3-(1-(5-((R)-2,2-dimethyltetrahydro-2H-pyran-4-yl)-2-((S)-3-(3-(4-fluoro-1-methyl-1H-indazol-5-yl)-2-oxo-2,3-dihydro-1H-imidazol-1-yl)-2-((S)-1-(4-fluorophenyl)ethyl)-4-methyl-4,5,6,7-tetrahydro-2H-pyrazolo[4,3-c]pyridine-5-carbonyl)-1H-indol-1-yl)cyclopropyl)-1,2,4-oxadiazol-5(4H)-one |

TABLE A-continued

| Cmpd No. | Structure | Chemical name |
|---|---|---|
| 41 | 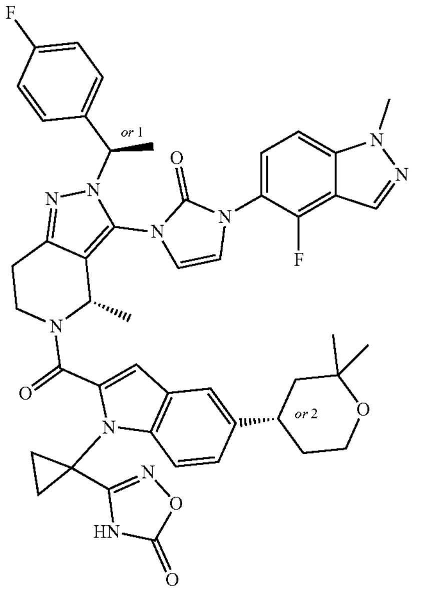 [SMILES: C[C@H](c1ccc(F)cc1)n1nc2c(c1-n1ccn(-c3ccc4c(cnn4C)c3F)c1=O)[C@H](C)N(C(=O)c1cc3cc([C@H]4CCOC(C)(C)C4)ccc3n1C1(c3noc(=O)[nH]3)CC1)CC2] | 3-(1-(5-((S)-2,2-dimethyltetrahydro-2H-pyran-4-yl)-2-((S)-3-(3-(4-fluoro-1-methyl-1H-indazol-5-yl)-2-oxo-2,3-dihydro-1H-imidazol-1-yl)-2-((R)-1-(4-fluorophenyl)ethyl)-4-methyl-4,5,6,7-tetrahydro-2H-pyrazolo[4,3-c]pyridine-5-carbonyl)-1H-indol-1-yl)cyclopropyl)-1,2,4-oxadiazol-5(4H)-one |
| 42 | 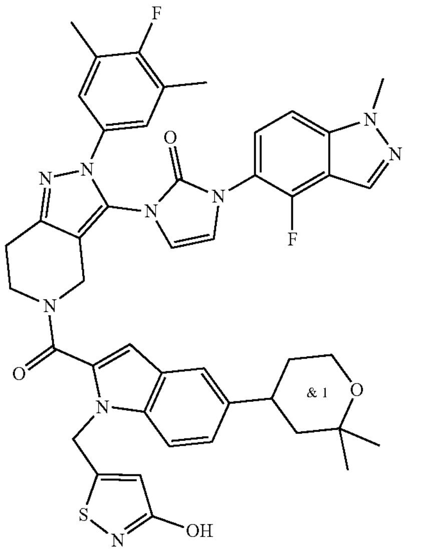 [SMILES: Cc1cc(-n2nc3c(c2-n2ccn(-c4ccc5c(cnn5C)c4F)c2=O)CN(C(=O)c2cc4cc(C5CCOC(C)(C)C5)ccc4n2Cc2cc(O)ns2)CC3)cc(C)c1F] | 1-(5-(5-(2,2-dimethyltetrahydro-2H-pyran-4-yl)-1-((3-hydroxyisothiazol-5-yl)methyl)-1H-indole-2-carbonyl)-2-(4-fluoro-3,5-dimethylphenyl)-4,5,6,7-tetrahydro-2H-pyrazolo[4,3-c]pyridin-3-yl)-3-(4-fluoro-1-methyl-1H-indazol-5-yl)-1,3-dihydro-2H-imidazol-2-one |

TABLE A-continued

| Cmpd No. | Structure | Chemical name |
| --- | --- | --- |
| 43 | 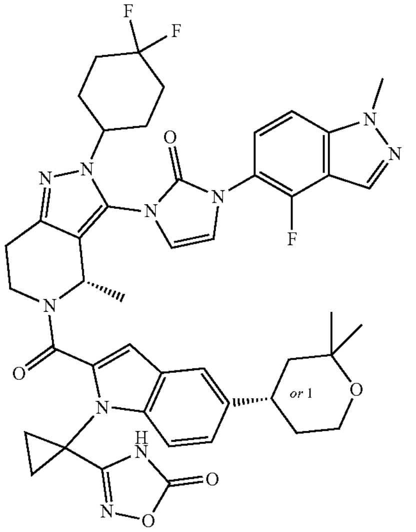 [SMILES: C[C@H]1c2c(nn(C3CCC(F)(F)CC3)c2-n2ccn(-c3ccc4c(cnn4C)c3F)c2=O)CCN1C(=O)c1cc2cc([C@H]3CCOC(C)(C)C3)ccc2n1C1(c2noc(=O)[nH]2)CC1] | 3-(1-(2-((S)-2-(4,4-difluorocyclohexyl)-3-(3-(4-fluoro-1-methyl-1H-indazol-5-yl)-2-oxo-2,3-dihydro-1H-imidazol-1-yl)-4-methyl-4,5,6,7-tetrahydro-2H-pyrazolo[4,3-c]pyridine-5-carbonyl)-5-((S)-2,2-dimethyltetrahydro-2H-pyran-4-yl)-1H-indol-1-yl)cyclopropyl)-1,2,4-oxadiazol-5(4H)-one |
| 44 | 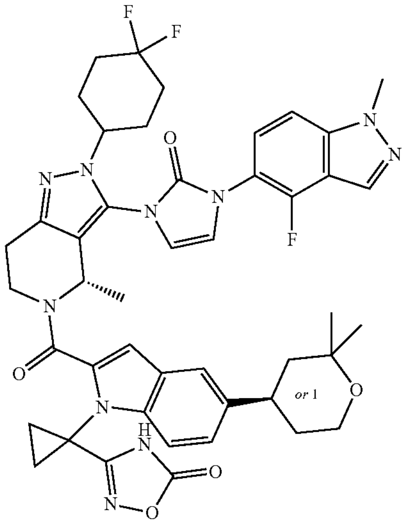 [SMILES: C[C@H]1c2c(nn(C3CCC(F)(F)CC3)c2-n2ccn(-c3ccc4c(cnn4C)c3F)c2=O)CCN1C(=O)c1cc2cc([C@@H]3CCOC(C)(C)C3)ccc2n1C1(c2noc(=O)[nH]2)CC1] | 3-(1-(2-((S)-2-(4,4-difluorocyclohexyl)-3-(3-(4-fluoro-1-methyl-1H-indazol-5-yl)-2-oxo-2,3-dihydro-1H-imidazol-1-yl)-4-methyl-4,5,6,7-tetrahydro-2H-pyrazolo[4,3-c]pyridine-5-carbonyl)-5-((R)-2,2-dimethyltetrahydro-2H-pyran-4-yl)-1H-indol-1-yl)cyclopropyl)-1,2,4-oxadiazol-5(4H)-one |
| 45 | 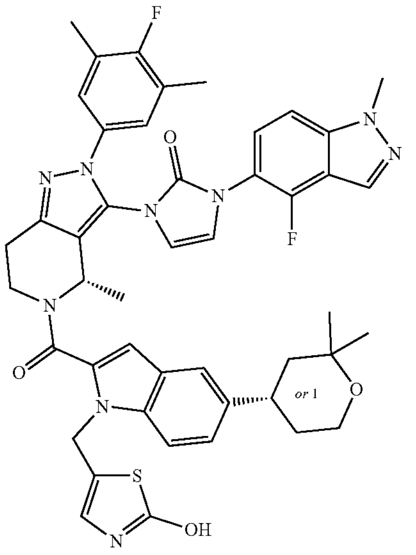 [SMILES: Cc1cc(-n2nc3c(c2-n2ccn(-c4ccc5c(cnn5C)c4F)c2=O)[C@H](C)N(C(=O)c2cc4cc([C@H]5CCOC(C)(C)C5)ccc4n2Cc2cnc(O)s2)CC3)cc(C)c1F] | 1-((S)-5-(5-((S)-2,2-dimethyltetrahydro-2H-pyran-4-yl)-1-((2-hydroxythiazol-5-yl)methyl)-1H-indole-2-carbonyl)-2-(4-fluoro-3,5-dimethylphenyl)-4-methyl-4,5,6,7-tetrahydro-2H-pyrazolo[4,3-c]pyridin-3-yl)-3-(4-fluoro-1-methyl-1H-indazol-5-yl)-l,3-dihydro-2H-imidazol-2-one |

TABLE A-continued

| Cmpd No. | Structure | Chemical name |
|---|---|---|
| 46 | 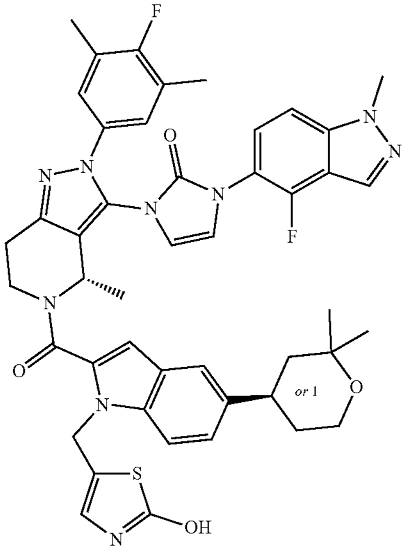 [SMILES: Cc1cc(-n2nc3c(c2-n2ccn(-c4ccc5c(cnn5C)c4F)c2=O)[C@H](C)N(C(=O)c2cc4cc([C@@H]5CCOC(C)(C)C5)ccc4n2Cc2cnc(O)s2)CC3)cc(C)c1F] | 1-((S)-5-(5-((R)-2,2-dimethyltetrahydro-2H-pyran-4-yl)-1-((2-hydroxythiazol-5-yl)methyl)-1H-indole-2-carbonyl)-2-(4-fluoro-3,5-dimethylphenyl)-4-methyl-4,5,6,7-tetrahydro-2H-pyrazolo[4,3-c]pyridin-3-yl)-3-(4-fluoro-1-methyl-1H-indazol-5-yl)-1,3-dihydro-2H-imidazol-2-one |
| 47 | 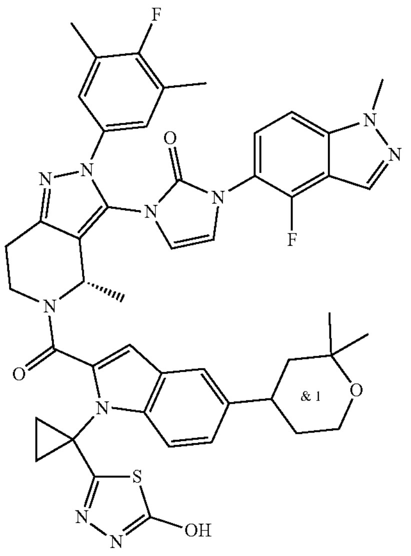 [SMILES: Cc1cc(-n2nc3c(c2-n2ccn(-c4ccc5c(cnn5C)c4F)c2=O)[C@H](C)N(C(=O)c2cc4cc(C5CCOC(C)(C)C5)ccc4n2C2(c4nnc(O)s4)CC2)CC3)cc(C)c1F] | 1-((4S)-5-(5-(2,2-dimethyltetrahydro-2H-pyran-4-yl)-1-(1-(5-hydroxy-1,3,4-thiadiazol-2-yl)cyclopropyl)-1H-indole-2-carbonyl)-2-(4-fluoro-3,5-dimethylphenyl)-4-methyl-4,5,6,7-tetrahydro-2H-pyrazolo[4,3-c]pyridin-3-yl)-3-(4-fluoro-1-methyl-1H-indazol-5-yl)-1,3-dihydro-2H-imidazol-2-one |

TABLE A-continued

| Cmpd No. | Structure | Chemical name |
|---|---|---|
| 48 | 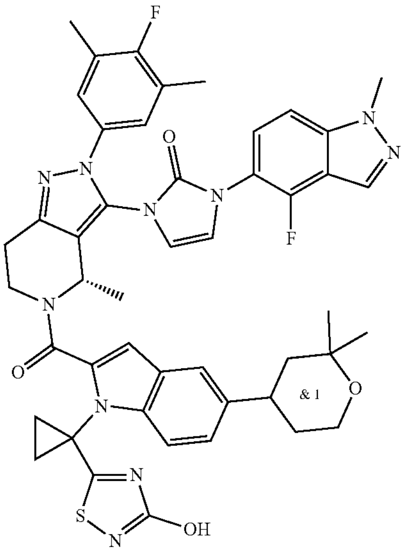 [SMILES: Cc1cc(-n2nc3c(c2-n2ccn(-c4ccc5c(cnn5C)c4F)c2=O)[C@H](C)N(C(=O)c2cc4cc(C5CCOC(C)(C)C5)ccc4n2C2(c4nc(O)ns4)CC2)CC3)cc(C)c1F] | 1-((4S)-5-(5-(2,2-dimethyltetrahydro-2H-pyran-4-yl)-1-(1-(3-hydroxy-1,2,4-thiadiazol-5-yl)cyclopropyl)-1H-indole-2-carbonyl)-2-(4-fluoro-3,5-dimethylphenyl)-4-methyl-4,5,6,7-tetrahydro-2H-pyrazolo[4,3-c]pyridin-3-yl)-3-(4-fluoro-1-methyl-1H-indazol-5-yl)-1,3-dihydro-2H-imidazol-2-one |
| 49 | 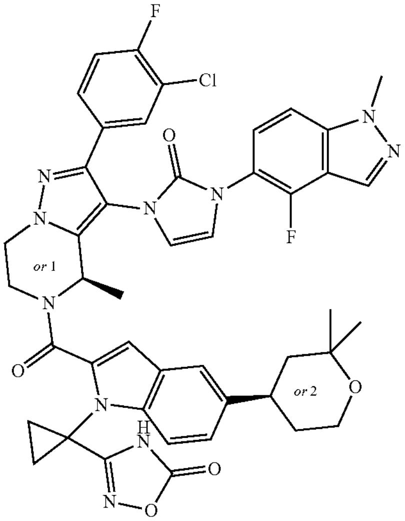 [SMILES: C[C@@H]1c2c(-n3ccn(-c4ccc5c(cnn5C)c4F)c3=O)c(-c3ccc(F)c(Cl)c3)nn2CCN1C(=O)c1cc2cc([C@@H]3CCOC(C)(C)C3)ccc2n1C1(c2noc(=O)[nH]2)CC1] | 3-(1-(2-((R)-2-(3-chloro-4-fluorophenyl)-3-(3-(4-fluoro-1-methyl-1H-indazol-5-yl)-2-oxo-2,3-dihydro-1H-imidazol-1-yl)-4-methyl-4,5,6,7-tetrahydropyrazolo[1,5-a]pyrazine-5-carbonyl)-5-((R)-2,2-dimethyltetrahydro-2H-pyran-4-yl)-1H-indol-1-yl)cyclopropyl)-1,2,4-oxadiazol-5(4H)-one |
| 50 | 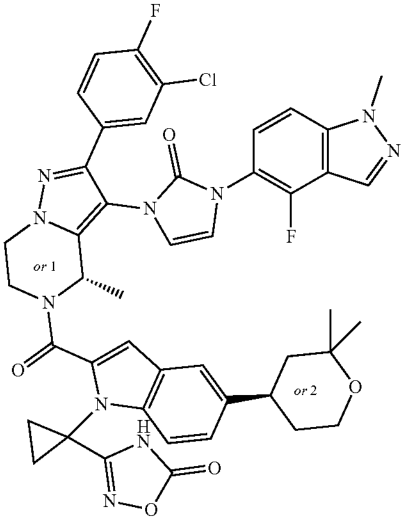 [SMILES: C[C@H]1c2c(-n3ccn(-c4ccc5c(cnn5C)c4F)c3=O)c(-c3ccc(F)c(Cl)c3)nn2CCN1C(=O)c1cc2cc([C@@H]3CCOC(C)(C)C3)ccc2n1C1(c2noc(=O)[nH]2)CC1] | 3-(1-(2-((S)-2-(3-chloro-4-fluorophenyl)-3-(3-(4-fluoro-1-methyl-1H-indazol-5-yl)-2-oxo-2,3-dihydro-1H-imidazol-1-yl)-4-methyl-4,5,6,7-tetrahydropyrazolo[1,5-a]pyrazine-5-carbonyl)-5-((R)-2,2-dimethyltetrahydro-2H-pyran-4-yl)-1H-indol-1-yl)cyclopropyl)-1,2,4-oxadiazol-5(4H)-one |

TABLE A-continued

| Cmpd No. | Structure | Chemical name |
|---|---|---|
| 51 | 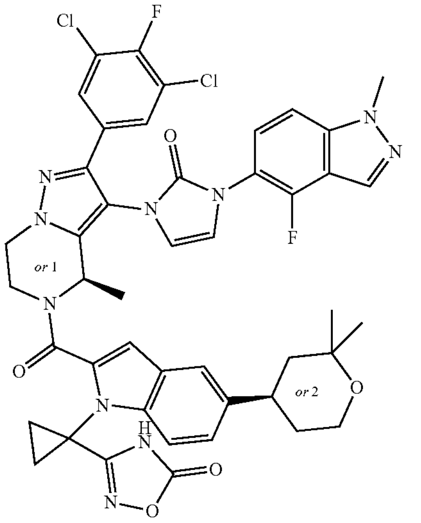 [SMILES: C[C@@H]1c2c(-n3ccn(-c4ccc5c(cnn5C)c4F)c3=O)c(-c3cc(Cl)c(F)c(Cl)c3)nn2CCN1C(=O)c1cc2cc([C@@H]3CCOC(C)(C)C3)ccc2n1C1(c2noc(=O)[nH]2)CC1] | 3-(1-(2-((R)-2-(3,5-dichloro-4-fluorophenyl)-3-(3-(4-fluoro-1-methyl-1H-indazol-5-yl)-2-oxo-2,3-dihydro-1H-imidazol-1-yl)-4-methyl-4,5,6,7-tetrahydropyrazolo[1,5-a]pyrazine-5-carbonyl)-5-((R)-2,2-dimethyltetrahydro-2H-pyran-4-yl)-1H-indol-1-yl)cyclopropyl)-1,2,4-oxadiazol-5(4H)-one |
| 52 | 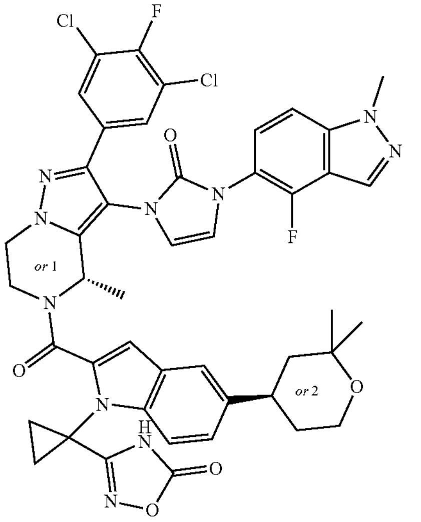 [SMILES: C[C@H]1c2c(-n3ccn(-c4ccc5c(cnn5C)c4F)c3=O)c(-c3cc(Cl)c(F)c(Cl)c3)nn2CCN1C(=O)c1cc2cc([C@@H]3CCOC(C)(C)C3)ccc2n1C1(c2noc(=O)[nH]2)CC1] | 3-(1-(2-((S)-2-(3,5-dichloro-4-fluorophenyl)-3-(3-(4-fluoro-1-methyl-1H-indazol-5-yl)-2-oxo-2,3-dihydro-1H-imidazol-1-yl)-4-methyl-4,5,6,7-tetrahydropyrazolo[1,5-a]pyrazine-5-carbonyl)-5-((R)-2,2-dimethyltetrahydro-2H-pyran-4-yl)-1H-indol-1-yl)cyclopropyl)-1,2,4-oxadiazol-5(4H)-one |

TABLE A-continued

| Cmpd No. | Structure | Chemical name |
|---|---|---|
| 53 | 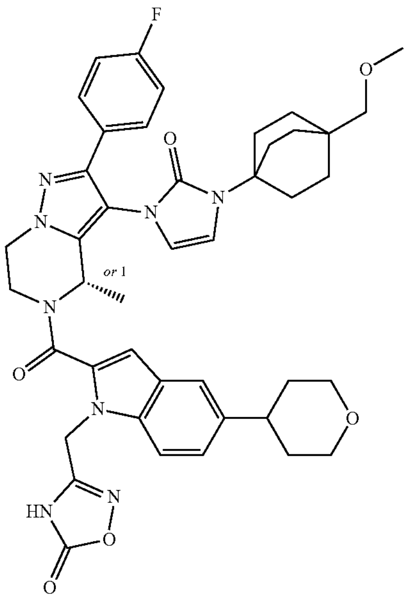 [SMILES: COCC12CCC(n3ccn(-c4c(-c5ccc(F)cc5)nn5c4[C@H](C)N(C(=O)c4cc6cc(C7CCOCC7)ccc6n4Cc4noc(=O)[nH]4)CC5)c3=O)(CC1)CC2] | (S)-3-((2-(2-(4-fluorophenyl)-3-(3-(4-(methoxymethyl)bicyclo[2.2.2]octan-1-yl)-2-oxo-2,3-dihydro-1H-imidazol-1-yl)-4-methyl-4,5,6,7-tetrahydropyrazolo[1,5-a]pyrazine-5-carbonyl)-5-(tetrahydro-2H-pyran-4-yl)-1H-indol-1-yl)methyl)-1,2,4-oxadiazol-5(4H)-one |
| 54 | 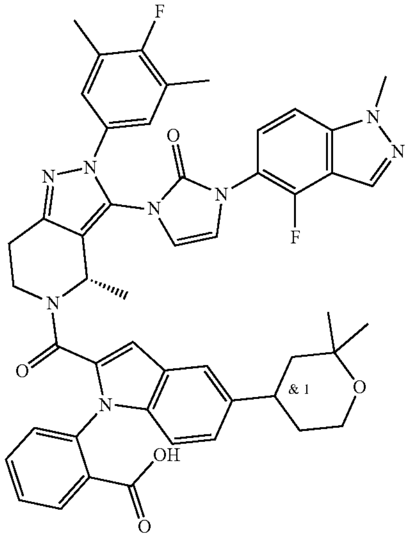 [SMILES: Cc1cc(-n2nc3c(c2-n2ccn(-c4ccc5c(cnn5C)c4F)c2=O)[C@H](C)N(C(=O)c2cc4cc(C5CCOC(C)(C)C5)ccc4n2-c2ccccc2C(=O)O)CC3)cc(C)c1F] | 2-(5-(2,2-dimethyltetrahydro-2H-pyran-4-yl)-2-((S)-3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-1H-indol-1-yl)benzoic acid |

TABLE A-continued

| Cmpd No. | Structure | Chemical name |
|---|---|---|
| 55 | 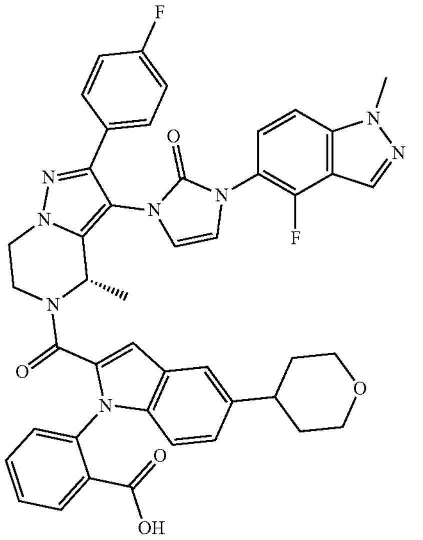 [SMILES: C[C@H]1c2c(-n3ccn(-c4ccc5c(cnn5C)c4F)c3=O)c(-c3ccc(F)cc3)nn2CCN1C(=O)c1cc2cc(C3CCOCC3)ccc2n1-c1ccccc1C(=O)O] | 2-(2-(3-(3-(4-fluoro-1-methyl-1H-indazol-5-yl) 2-oxo-2,3-dihydro-1H-imidazol-1-yl)-2-(4-fluorophenyl)-4,5,6,7-tetrahydropyrazolo[1,5-a]pyrazine-5-carbonyl)-5-(tetrahydro-2H-pyran 4-yl)-1H-indol-1-yl)benzoic acid |
| 56 | 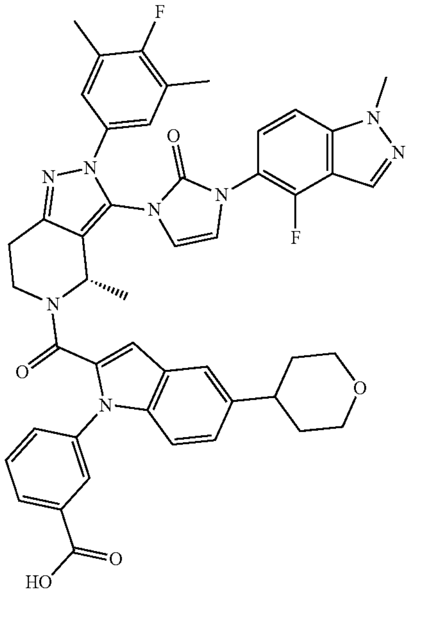 [SMILES: Cc1cc(-n2nc3c(c2-n2ccn(-c4ccc5c(cnn5C)c4F)c2=O)[C@H](C)N(C(=O)c2cc4cc(C5CCOCC5)ccc4n2-c2cccc(C(=O)O)c2)CC3)cc(C)c1F] | (S)-3-(2-(3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-5-(tetrahydro-2H-pyran-4-yl)-1H-indol-1-yl)benzoic acid |

TABLE A-continued

| Cmpd No. | Structure | Chemical name |
| --- | --- | --- |
| 57 | 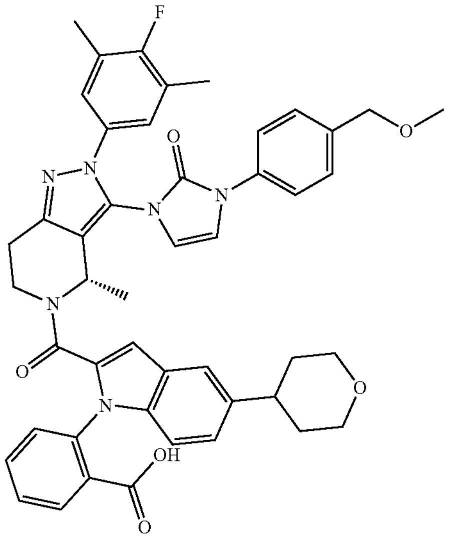 [SMILES: COCc1ccc(-n2ccn(-c3c4c(nn3-c3cc(C)c(F)c(C)c3)CCN(C(=O)c3cc5cc(C6CCOCC6)ccc5n3-c3ccccc3C(=O)O)[C@H]4C)c2=O)cc1] | (S)-2-(2-(2-(4-fluoro-3,5-dimethylphenyl)-3-(3-(4-(methoxymethyl)phenyl)-2-oxo-2,3-dihydro-1H-imidazol-1-yl)-4-metliyl-4,5,6,7-tetrahydro-2H-pyrazolo[4,3-c]pyridine-5-carbonyl)-5-(tetrahydro-2H-pyran-4-yl)-1H-indol-1-yl)benzoic acid |
| 58 | 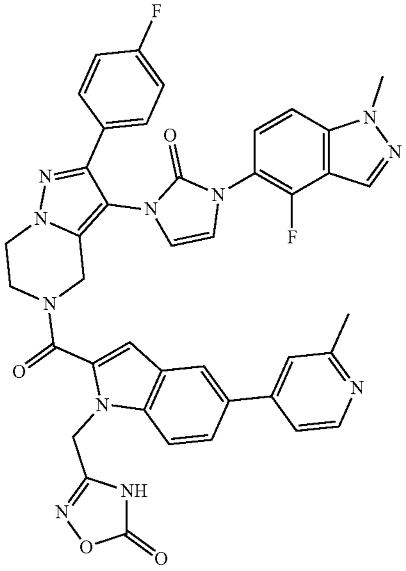 [SMILES: Cc1cc(-c2ccc3c(c2)cc(C(=O)N2CCn4nc(-c5ccc(F)cc5)c(-n5ccn(-c6ccc7c(cnn7C)c6F)c5=O)c4C2)n3Cc2noc(=O)[nH]2)ccn1] | 3-((2-(3-(3-(4-fluoro-1-methyl-1H-indazol-5-yl)-2-oxo-2,3-dihydro-1H-imidazol-1-yl)-2-(4-fluorophenyl)-4,5,6,7-tetrahydropyrazolo[1,5-a]pyrazine-5-carbonyl)-5-(2-methylpyridin-4-yl)-1H-indol-1-yl)methyl)-1,2,4-oxadiazol-5(4H)-one |

TABLE A-continued

| Cmpd No. | Structure | Chemical name |
|---|---|---|
| 59 | 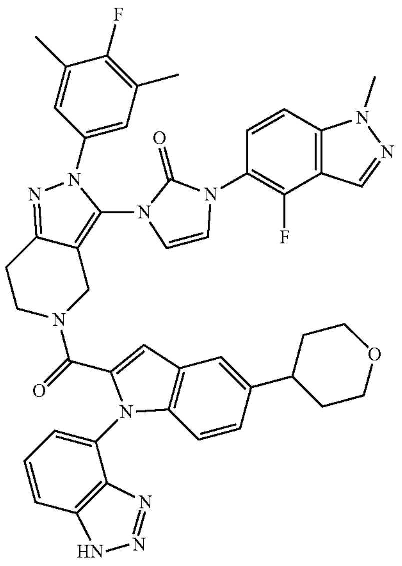 [SMILES: Cc1cc(-n2nc3c(c2-n2ccn(-c4ccc5c(cnn5C)c4F)c2=O)CN(C(=O)c2cc4cc(C5CCOCC5)ccc4n2-c2cccc4[nH]nnc24)CC3)cc(C)c1F] | 1-(5-(1-(1H-benzo[d][1,2,3]triazol-4-yl)-5-(tetrahydro-2H-pyran-4-yl)-1H-indole-2-carbonyl)-2-(4-fluoro-3,5-dimethylphenyl)-4,5,6,7-tetrahydro-2H-pyrazolo[4,3-c]pyridin-3-yl)-3-(4-fluoro-1-methyl-1H-indazol-5-yl)-1,3-dihydro-2H-imidazol-2-one |
| 60 | 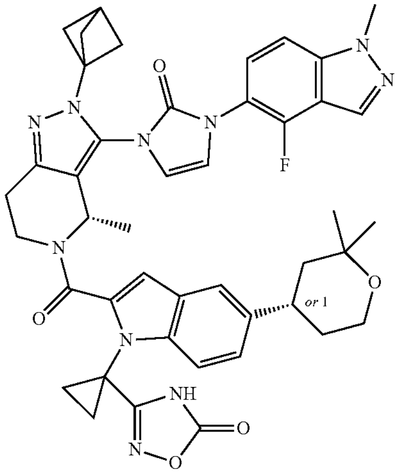 [SMILES: C[C@H]1c2c(nn(C34CC(C3)C4)c2-n2ccn(-c3ccc4c(cnn4C)c3F)c2=O)CCN1C(=O)c1cc2cc([C@H]3CCOC(C)(C)C3)ccc2n1C1(c2noc(=O)[nH]2)CC1] | 3-(1-(2-((S)-2-(bicyclo[1.1.1]pentan-1-yl)-3-(3-(4-fluoro-1-methyl-1H-indazol-5-yl)-2-oxo-2,3-dihydro-1H-imidazol-1-yl)-4-methyl-4,5,6,7-tetrahydro-2H-pyrazolo[4,3-c]pyridine-5-carbonyl)-5-((S)-2,2-dimethyltetrahydro-2H-pyran-4-yl)-1H-indol-1-yl)cyclopropyl)-1,2,4-oxadiazol-5(4H)-one |
| 61 | 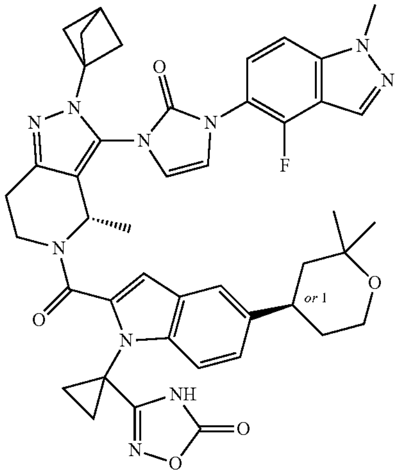 [SMILES: C[C@H]1c2c(nn(C34CC(C3)C4)c2-n2ccn(-c3ccc4c(cnn4C)c3F)c2=O)CCN1C(=O)c1cc2cc([C@@H]3CCOC(C)(C)C3)ccc2n1C1(c2noc(=O)[nH]2)CC1] | 3-(1-(2-((S)-2-(bicyclo[1.1.1]pentan-1-yl)-3-(3-(4-fluoro-1-methyl-1H-indazol-5-yl)-2-oxo-2,3-dihydro-1H-imidazol-1-yl)-4-methyl-4,5,6,7-tetrahydro-2H-pyrazolo[4,3-c]pyridine-5-carbonyl)-5-((R)-2,2-dimethyltetrahydro-2H-pyran-4-yl)-1H-indol-1-yl)cyclopropyl)-1,2,4-oxadiazol-5(4H)-one |

TABLE A-continued

| Cmpd No. | Structure | Chemical name |
| --- | --- | --- |
| 62 | 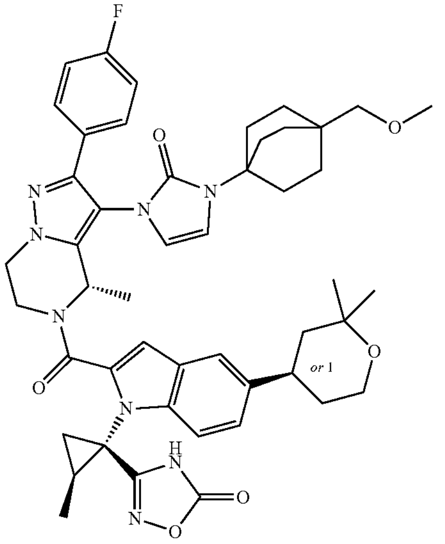 [SMILES: COCC12CCC(n3ccn(-c4c(-c5ccc(F)cc5)nn5c4[C@H](C)N(C(=O)c4cc6cc([C@@H]7CCOC(C)(C)C7)ccc6n4[C@@]4(c6noc(=O)[nH]6)C[C@@H]4C)CC5)c3=O)(CC1)CC2] | 3-((1S,2S)-1-(5-((R)-2,2-dimethyltetrahydro-2H-pyran-4-yl)-2-((S)-2-(4-fluorophenyl)-3-(3-(4-(methoxymethyl)bicyclo[2.2.2]octan-1-yl)-2-oxo-2,3-dihydro-1H-imidazol-1-yl)-4-methyl-4,5,6,7-telrahydropyrazolo[1,5-a]pyrazine-5-carbonyl)-1H-indol-1-yl)-2-methylcyclopropyl)-1,2,4-oxadiazol-5(4H)-one |
| 63 | 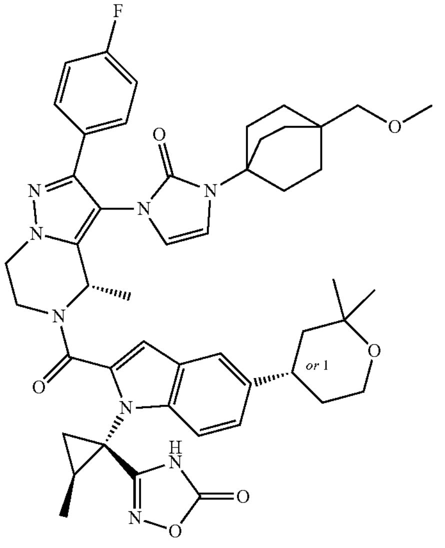 [SMILES: COCC12CCC(n3ccn(-c4c(-c5ccc(F)cc5)nn5c4[C@H](C)N(C(=O)c4cc6cc([C@H]7CCOC(C)(C)C7)ccc6n4[C@@]4(c6noc(=O)[nH]6)C[C@@H]4C)CC5)c3=O)(CC1)CC2] | 3-((1S,2S)-1-(5-((S)-2,2-dimethyltetrahydro-2H-pyran-4-yl)-2-((S)-2-(4-fluorophenyl)-3-(3-(4-(methoxymethyl)bicyclo[2.2.2]octan-1-yl)-2-oxo-2,3-dihydro-1H-imidazol-1-yl)-4-methyl-4,5,6,7-tetrahydropyrazolo[1,5-a]pyrazine-5-carbonyl)-1H-indol-1-yl)-2-methylcyclopropyl)-1,2,4-oxadiazol-5(4H)-one |
| 64 | 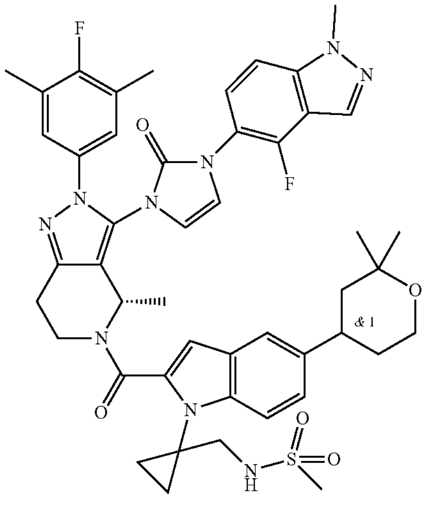 [SMILES: Cc1cc(-n2nc3c(c2-n2ccn(-c4ccc5c(cnn5C)c4F)c2=O)[C@H](C)N(C(=O)c2cc4cc(C5CCOC(C)(C)C5)ccc4n2C2(CNS(C)(=O)=O)CC2)CC3)cc(C)c1F] | N-((1-(5-(2,2-dimethyltetrahydro-2H-pyran-4-yl)-2-((S)-3-(3-(4-fluoro-1-methyl-1H-indazol-5-yl)-2-oxo-2,3-dihydro-1H-lmidazol-1-yl)-2-(4-fluoro-3,5-dimethylphenyl)-4-methyl-4,5,6,7-tetrahydro-2H-pyrazolo[4,3-c]pyridine-5-carbonyl)-1H-indol-1-yl)cyclopropyl)methyl)methanesulfonamide |

TABLE A-continued

| Cmpd No. | Structure | Chemical name |
| --- | --- | --- |
| 65 | 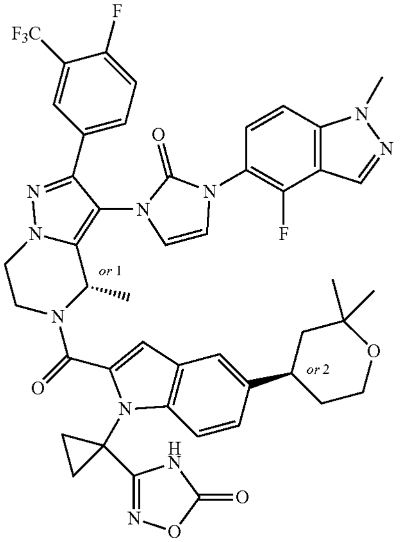 [SMILES: C[C@H]1c2c(-n3ccn(-c4ccc5c(cnn5C)c4F)c3=O)c(-c3ccc(F)c(C(F)(F)F)c3)nn2CCN1C(=O)c1cc2cc([C@@H]3CCOC(C)(C)C3)ccc2n1C1(c2noc(=O)[nH]2)CC1] | 3-(1-(5-((R)-2,2-dimethyltetrahydro-2H-pyran-4-yl)-2-((S)-3-(3-(4-fluoro-1-methyl-1H-indazol-5-yl)-2-oxo-2,3-dihydro-1H-imidazol-1-yl)-2-(4-fluoro-3-(trifluoromelhyl)phenyl)-4-methyl-4,5,6,7-telrahydropyrazolo[1,5-a]pyrazine-5-carbonyl)-1H-indol-1-yl)cyclopropyl)-1,2,4-oxadiazol-5(4H)-one |
| 66 | 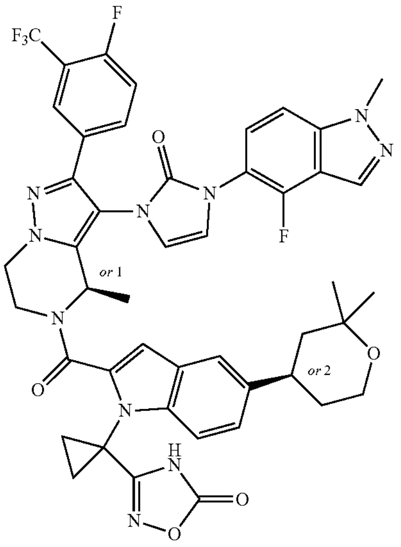 [SMILES: C[C@@H]1c2c(-n3ccn(-c4ccc5c(cnn5C)c4F)c3=O)c(-c3ccc(F)c(C(F)(F)F)c3)nn2CCN1C(=O)c1cc2cc([C@@H]3CCOC(C)(C)C3)ccc2n1C1(c2noc(=O)[nH]2)CC1] | 3-(1-(5-((R)-2,2-dimethyltetrahydro-2H-pyran-4-yl)-2-((R)-3-(3-(4-fluoro-1-methyl-1H-indazol-5-yl)-2-oxo-2,3-dihydro-1H-imidazol-1-yl)-2-(4-fluoro-3-(trifluoroinethyl)phenyl)-4-methyl-4,5,6,7-tetrahydropyrazolo[1,5-a]pyrazine-5-carbonyl)-1H-indol-1-yl)cyclopropyl)-1,2,4-oxadiazol-5(4H)-one |

TABLE A-continued

| Cmpd No. | Structure | Chemical name |
|---|---|---|
| 67 | 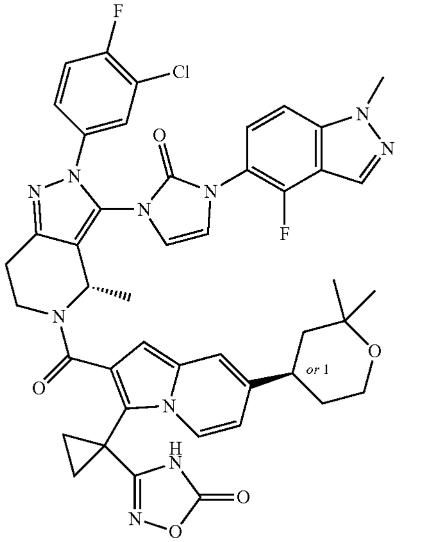 [SMILES: C[C@H]1c2c(nn(-c3ccc(F)c(Cl)c3)c2-n2ccn(-c3ccc4c(cnn4C)c3F)c2=O)CCN1C(=O)c1cc2cc([C@@H]3CCOC(C)(C)C3)ccn2c1C1(c2noc(=O)[nH]2)CC1] | 3-(1-(2-((S)-2-(3-chloro-4-fluorophenyl)-3-(3-(4-fluoro-1-methyl-1H-indazol-5-yl)-2-oxo-2,3-dihydro-1H-imidazol-1-yl)-4-methyl-4,5,6,7-tetrahydro-2H-pyrazolo[4,3-c]pyridine-5-caibonyl)-7-((R)-2,2-dimethyltetrahydro-2H-pyran-4-yl)indolizin-3-yl)cyclopropyl)-1,2,4-oxadiazol-5(4H)-one |
| 68 | 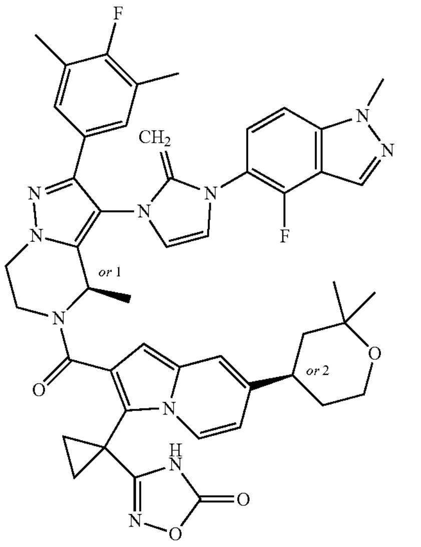 [SMILES: C=C1N(c2ccc3c(cnn3C)c2F)C=CN1c1c(-c2cc(C)c(F)c(C)c2)nn2c1[C@@H](C)N(C(=O)c1cc3cc([C@@H]4CCOC(C)(C)C4)ccn3c1C1(c3noc(=O)[nH]3)CC1)CC2] | 3-(1-(7-((R)-2,2-dimethyltetrahydro-2H-pyran-4-yl)-2-((R)-3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-4,5,6,7-tetrahydropyrazolo[1,5-a]pyrazine-5-carbonyl)indolizin-3-yl)cyclopropyl)-1,2,4-oxadiazol-5(4H)-one |

TABLE A-continued

| Cmpd No. | Structure | Chemical name |
|---|---|---|
| 69 | 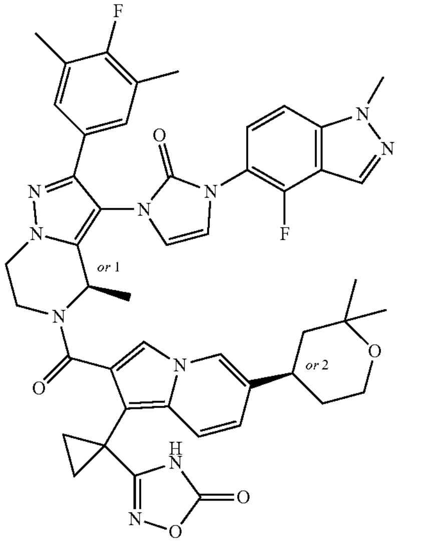 [SMILES: Cc1cc(-c2nn3c(c2-n2ccn(-c4ccc5c(cnn5C)c4F)c2=O)[C@@H](C)N(C(=O)c2cn4cc([C@@H]5CCOC(C)(C)C5)ccc4c2C2(c4noc(=O)[nH]4)CC2)CC3)cc(C)c1F] | 3-(1-(6-((R)-2,2-dimethyltetrahydro-2H-pyran-4-yl)-2-((R)-3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-4,5,6,7-tetrahydropyrazolo[1,5-a]pyrazine-5-carbonyl)indolizin-1-yl)cyclopropyl)-1,2,4-oxadiazol-5(4H)-one |
| 70 | 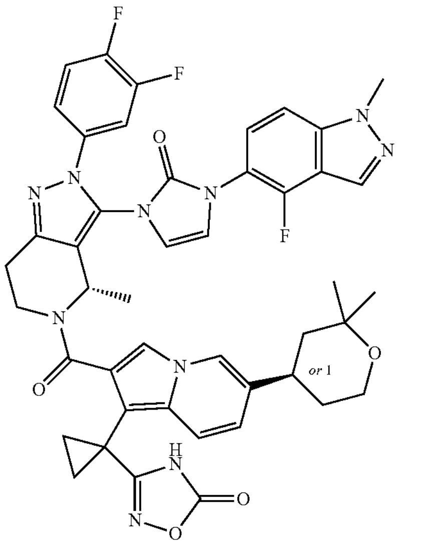 [SMILES: C[C@H]1c2c(nn(-c3ccc(F)c(F)c3)c2-n2ccn(-c3ccc4c(cnn4C)c3F)c2=O)CCN1C(=O)c1cn2cc([C@@H]3CCOC(C)(C)C3)ccc2c1C1(c2noc(=O)[nH]2)CC1] | 3-(1-(2-((S)-2-(3,4-difluorophenyl)-3-(3-(4-fluoro-1-methyl-1H-indazol-5-yl)-2-oxo-2,3-dihydro-1H-imidazol-1-yl)-4-methyl-4,5,6,7-tetrahydro-2H-pyrazolo[4,3-c]pyridine-5-carbonyl)-6-((R)-2,2-dimethyltetrahydro-2H-pyran-4-yl)indolizin-1-yl)cyclopropyl)-1,2,4-oxadiazol-5(4H)-one |

TABLE A-continued

| Cmpd No. | Structure | Chemical name |
|---|---|---|
| 71 | 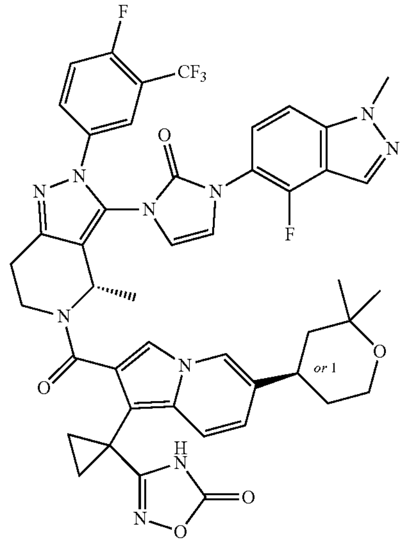 [SMILES: C[C@H]1c2c(nn(-c3ccc(F)c(C(F)(F)F)c3)c2-n2ccn(-c3ccc4c(cnn4C)c3F)c2=O)CCN1C(=O)c1cn2cc([C@@H]3CCOC(C)(C)C3)ccc2c1C1(c2noc(=O)[nH]2)CC1] | 3-(1-(6-((R)-2,2-dimethyltetrahydro-2H-pyran-4-yl)-2-((S)-3-(3-(4-fluoro-1-methyl-1H-indazol-5-yl)-2-oxo-2,3-dihydro-1H-imidazol-1-yl)-2-(4-fluoro-3-(trifluoromethyl)phenyl)-4-methyl-4,5,6,7-tetrahydro-2H-pyrazolo[4,3-c]pyridine-5-carbonyI)indolizin-1-yl)cyclopropyl)-1,2,4-oxadiazol-5(4H)-one |
| 72 | 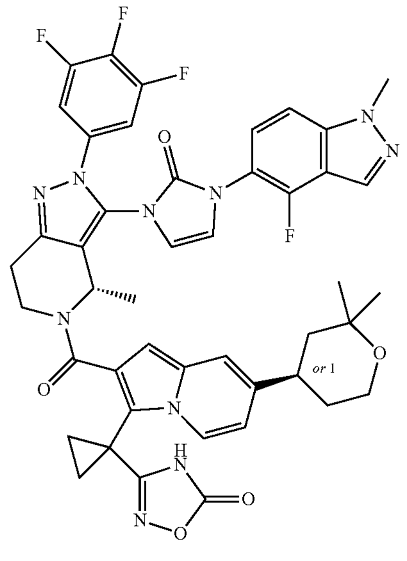 [SMILES: C[C@H]1c2c(nn(-c3cc(F)c(F)c(F)c3)c2-n2ccn(-c3ccc4c(cnn4C)c3F)c2=O)CCN1C(=O)c1cc2cc([C@@H]3CCOC(C)(C)C3)ccn2c1C1(c2noc(=O)[nH]2)CC1] | 3-(1-(7-((R)-2,2-dimethyltetrahydro-2H-pyran-4-yl)-2-((S)-3-(3-(4-fluoro-1-methyl-1H-indazol-5-yl)-2-oxo-2,3-dihydro-1H-imidazol-1-yl)-4-methyl-2-(3,4,5-trifluorophenyl)-4,5,6,7-tetrahydro-2H-pyrazolo[4,3-c]pyridine-5-carbonyl)indolizin-3-yl)cyclopropyl)-1,2,4-oxadiazol-5(4H)-one |

TABLE A-continued

| Cmpd No. | Structure | Chemical name |
|---|---|---|
| 73 | 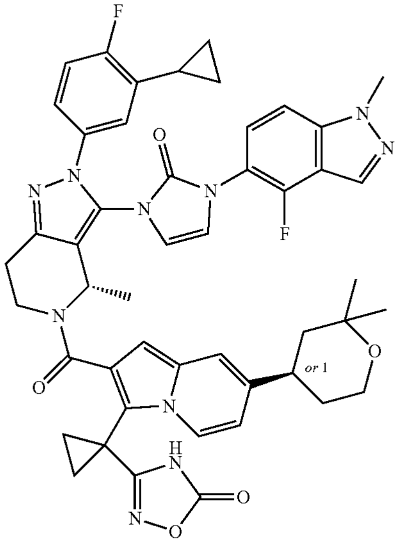 [SMILES: C[C@H]1c2c(nn(-c3ccc(F)c(C4CC4)c3)c2-n2ccn(-c3ccc4c(cnn4C)c3F)c2=O)CCN1C(=O)c1cc2cc([C@@H]3CCOC(C)(C)C3)ccn2c1C1(c2noc(=O)[nH]2)CC1] | 3-(1-(2-((S)-2-(3-cyclopropyl-4-fluorophenyl)-3-(3-(4-fluoro-1-methyl-1H-indazol-5-yl)-2-oxo-2,3-dihydro-1H-imidazol-1-yl)-4-methyl-4,5,6,7-tetrahydro-2H-pyrazolo[4,3-c]pyridine-5-carbonyl)-7-((R)-2,2-dimethyltetrahydro-2H-pyran-4-yl)indolizin-3-yl)cyclopropyl)-1,2,4-oxadiazol-5(4H)-one |
| 74 | 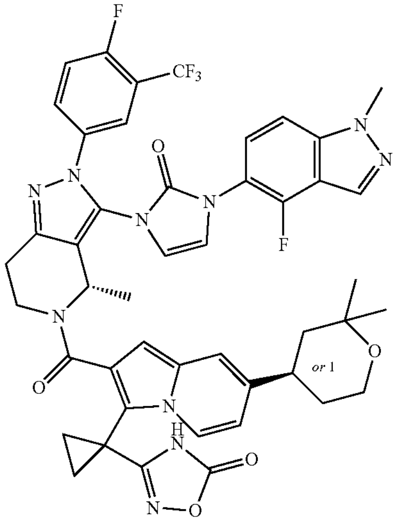 [SMILES: C[C@H]1c2c(nn(-c3ccc(F)c(C(F)(F)F)c3)c2-n2ccn(-c3ccc4c(cnn4C)c3F)c2=O)CCN1C(=O)c1cc2cc([C@@H]3CCOC(C)(C)C3)ccn2c1C1(c2noc(=O)[nH]2)CC1] | 3-(1-(7-((R)-2,2-dimethyltetrahydro-2H-pyran-4-yl)-2-((S)-3-(3-(4-fluoro-1-methyl-1H-indazol-5-yl)-2-oxo-2,3-dihydro-1H-imidazol-1-yl)-2-(4-fluoro-3-(trifluoromethyl)phenyl)-4-methyl-4,5,6,7-tetrahydro-2H-pyrazolo[4,3-c]pyridine-5-carbonyl)indolizin-3-yl)cyclopropyl)-1,2,4-oxadiazol-5(4H)-one |
| 75 | 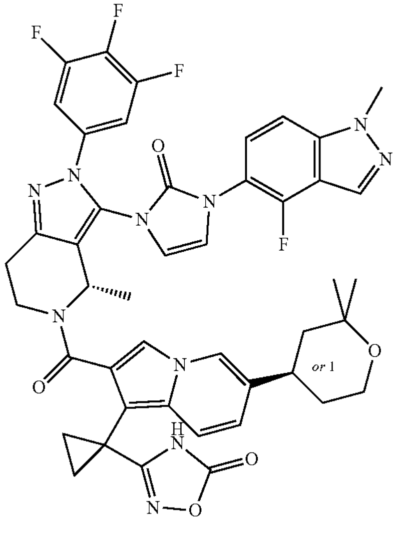 [SMILES: C[C@H]1c2c(nn(-c3cc(F)c(F)c(F)c3)c2-n2ccn(-c3ccc4c(cnn4C)c3F)c2=O)CCN1C(=O)c1cn2cc([C@@H]3CCOC(C)(C)C3)ccc2c1C1(c2noc(=O)[nH]2)CC1] | 3-(1-(6-((R)-2,2-dimethyltetrahydro-2H-pyran-4-yl)-2-((S)-3-(3-(4-fluoro-1-methyl-1H-indazol-5-yl)-2-oxo-2,3-dihydro-1H-imidazol-1-yl)-4-methyl-2-(3,4,5-trifluorophenyl)-4,5,6,7-tetrahydro-2H-pyrazolo[4,3-c]pyridine-5-carbonyl)indolizin-1-yl)cyclopropyl)-1,2,4-oxadiazol-5(4H)-one |

TABLE A-continued

| Cmpd No. | Structure | Chemical name |
|---|---|---|
| 76 | 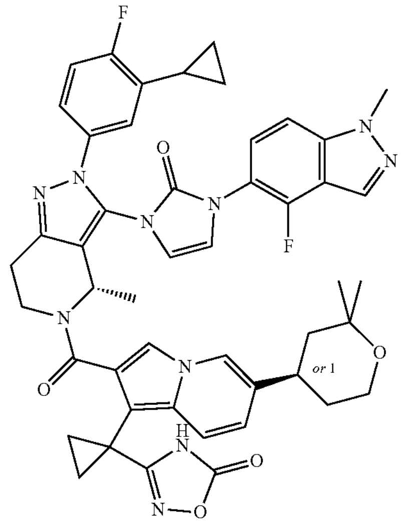 [SMILES: C[C@H]1c2c(nn(-c3ccc(F)c(C4CC4)c3)c2-n2ccn(-c3ccc4c(cnn4C)c3F)c2=O)CCN1C(=O)c1cn2cc([C@@H]3CCOC(C)(C)C3)ccc2c1C1(c2noc(=O)[nH]2)CC1] | 3-(1-(2-((S)-2-(3-cyclopropyl-4-fluorophenyl)-3-(3-(4-fluoro-1-methyl-1H-indazol-5-yl)-2-oxo-2,3-dihydro-1H-imidazol-1-yl)-4-methyl-4,5,6,7-tetrahydro-2H-pyrazolo[4,3-c]pyridine-5-carbonyl)-6-((R)-2,2-dimethyltetrahydro-2H-pyran-4-yl)indolizin-1-yl)cyclopropyl)-1,2,4-oxadiazol-5(4H)-one |
| 77 | 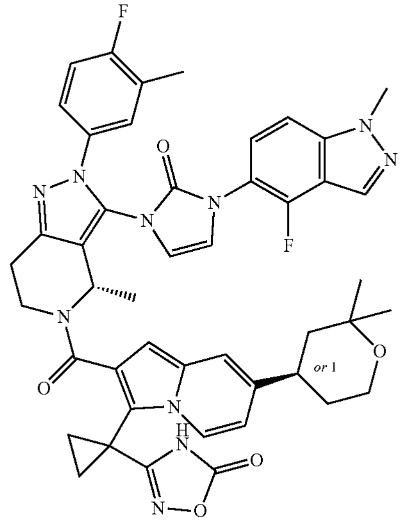 [SMILES: Cc1cc(-n2nc3c(c2-n2ccn(-c4ccc5c(cnn5C)c4F)c2=O)[C@H](C)N(C(=O)c2cc4cc([C@@H]5CCOC(C)(C)C5)ccn4c2C2(c4noc(=O)[nH]4)CC2)CC3)ccc1F] | 3-(1-(7-((R)-2,2-dimethyltetrahydro-2H-pyran-4-yl)-2-((S)-3-(3-(4-fluoro-1-methyl-1H-indazol-5-yl)-2-oxo-2,3-dihydro-1H-imidazol-1-yl)-2-(4-fluoro-3-methylphenyl)-4-methyl-4,5,6,7-tetrahydro-2H-pyrazolo[4,3-c]pyridine-5-carbonyl)indolizin-3-yl)cyclopropyl)-1,2,4-oxadiazol-5(4H)-one |
| 78 | 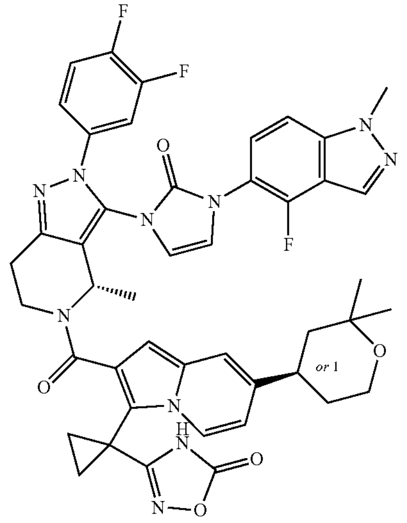 [SMILES: C[C@H]1c2c(nn(-c3ccc(F)c(F)c3)c2-n2ccn(-c3ccc4c(cnn4C)c3F)c2=O)CCN1C(=O)c1cc2cc([C@@H]3CCOC(C)(C)C3)ccn2c1C1(c2noc(=O)[nH]2)CC1] | 3-(1-(2-((S)-2-(3,4-difluorophenyl)-3-(3-(4-fluoro-1-methyl-1H-indazol-5-yl)-2-oxo-2,3-dihydro-1H-imidazol-1-yl)-4-methyl-4,5,6,7-tetrahydro-2H-pyrazolo[4,3-c]pyridine-5-carbonyl)-7-((R)-2,2-dimethyltetrahydro-2H-pyran-4-yl)indolizin-3-yl)cyclopropyl)-1,2,4-oxadiazol-5(4H)-one |

TABLE A-continued

| Cmpd No. | Structure | Chemical name |
|---|---|---|
| 79 | 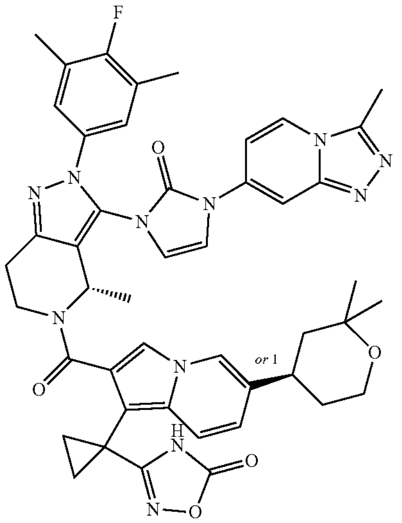 [SMILES: Cc1cc(-n2nc3c(c2-n2ccn(-c4ccn5c(C)nnc5c4)c2=O)[C@H](C)N(C(=O)c2cn4cc([C@@H]5CCOC(C)(C)C5)ccc4c2C2(c4noc(=O)[nH]4)CC2)CC3)cc(C)c1F] | 3-(1-(6-((R)-2,2-dimethyltetrahydro-2H-pyran-4-yl)-2-((S)-2-(4-fluoro-3,5-dimethylphenyl)-4-methyl-3-(3-(3-methyl-[1,2,4]triazolo[4,3-a]pyridin-7-yl)-2-oxo-2,3-dihydro-1H-imidazol-1-yl)-4,5,6,7-tetrahydro-2H-pyrazolo[4,3-c]pyridine-5-carbonyl)indolizin-1-yl)cyclopropyl)-1,2,4-oxadiazol-5(4H)-one |
| 80 | 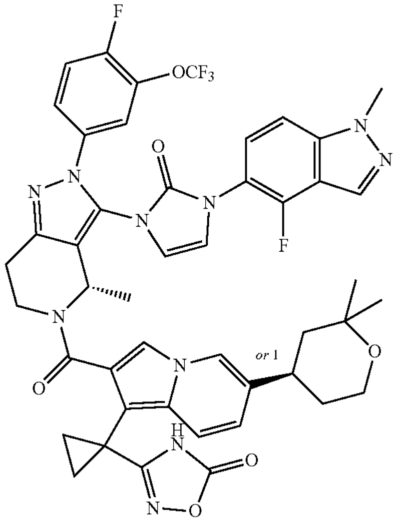 [SMILES: C[C@H]1c2c(nn(-c3ccc(F)c(OC(F)(F)F)c3)c2-n2ccn(-c3ccc4c(cnn4C)c3F)c2=O)CCN1C(=O)c1cn2cc([C@@H]3CCOC(C)(C)C3)ccc2c1C1(c2noc(=O)[nH]2)CC1] | 3-(1-(6-((R)-2,2-dimethyltetrahydro-2H-pyran-4-yl)-2-((S)-3-(3-(4-fluoro-1-methyl-1H-indazol-5-yl)-2-oxo-2,3-dihydro-1H-imidazol-1-yl)-2-(4-fluoro-3-(trifluoromethoxy)phenyl)-4-methyl-4,5,6,7-tetrahydro-2H-pyrazolo[4,3-c]pyridine-5-carbonyl)indolizin-1-yl)cyclopropyl)-1,2,4-oxadiazol-5(4H)-one |
| 81 | 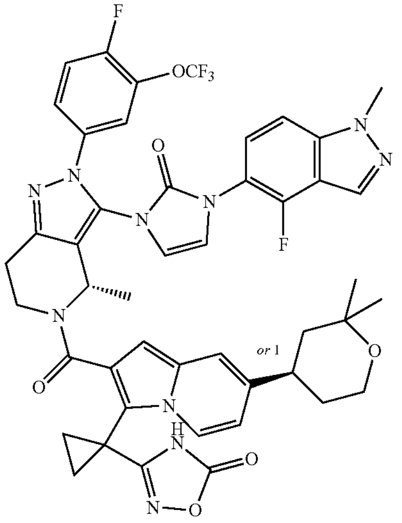 [SMILES: C[C@H]1c2c(nn(-c3ccc(F)c(OC(F)(F)F)c3)c2-n2ccn(-c3ccc4c(cnn4C)c3F)c2=O)CCN1C(=O)c1cc2cc([C@@H]3CCOC(C)(C)C3)ccn2c1C1(c2noc(=O)[nH]2)CC1] | 3-(1-(7-((R)-2,2-dimethyltetrahydro-2H-pyran-4-yl)-2-((S)-3-(3-(4-fluoro-1-methyl-1H-indazol-5-yl)-2-oxo-2,3-dihydro-2H-imidazol-1-yl)-2-(4-f1uoro-3-(trifluoromethoxy)phenyl)-4-methyl-4,5,6,7-tetrahydro-2H-pyrazolo[4,3-c]pyridine-5-carbonyl)indolizin-3-yl)cyclopropyl)-1,2,4-oxadiazol-5(4H)-one |

TABLE A-continued

| Cmpd No. | Structure | Chemical name |
|---|---|---|
| 82 | 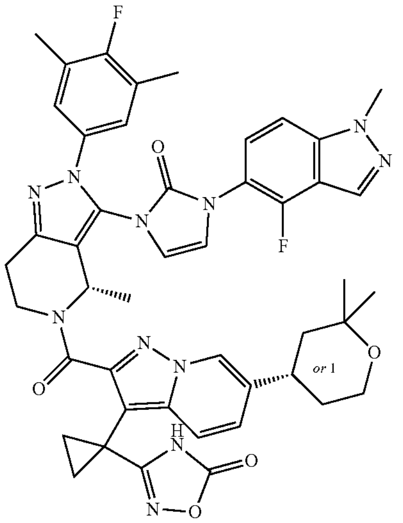 [SMILES: Cc1cc(-n2nc3c(c2-n2ccn(-c4ccc5c(cnn5C)c4F)c2=O)[C@H](C)N(C(=O)c2nn4cc([C@H]5CCOC(C)(C)C5)ccc4c2C2(c4noc(=O)[nH]4)CC2)CC3)cc(C)c1F] | 3-(1-(6-((S)-2,2-dimethyltetrahydro-2H-pyran-4 yl)-2-((S)-3-(3-(4-fluoro-1-methyl-1H-indazol-5 yl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)pyrazolo[1,5-a]pyridin-3-yl)cyclopropyl)-1,2,4-oxadiazol-5(4H)-one |
| 83 | 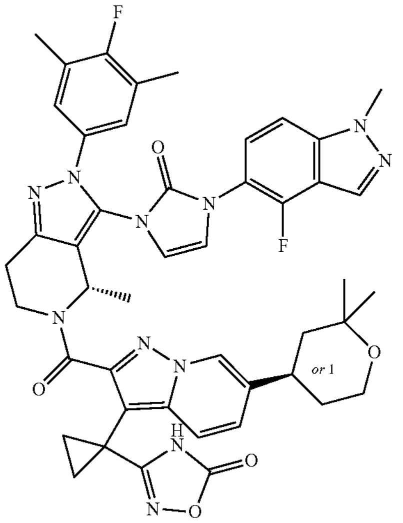 [SMILES: Cc1cc(-n2nc3c(c2-n2ccn(-c4ccc5c(cnn5C)c4F)c2=O)[C@H](C)N(C(=O)c2nn4cc([C@@H]5CCOC(C)(C)C5)ccc4c2C2(c4noc(=O)[nH]4)CC2)CC3)cc(C)c1F] | 3-(1-(6-((R)-2,2-dimethyltetrahydro-2H-pyran-4 yl)-2-((S)-3-(3-(4-fluoro-1-methyl-1H-indazol-5 yl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)pyrazolo[1,5-a]pyridin-3-yl)cyclopropyl)-1,2,4-oxadiazol-5(4H)-one |
| 84 | 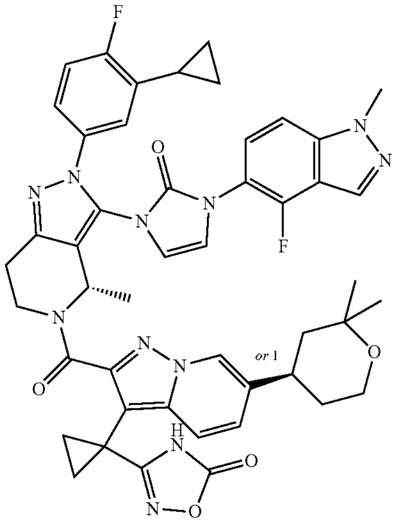 [SMILES: C[C@H]1c2c(nn(-c3ccc(F)c(C4CC4)c3)c2-n2ccn(-c3ccc4c(cnn4C)c3F)c2=O)CCN1C(=O)c1nn2cc([C@@H]3CCOC(C)(C)C3)ccc2c1C1(c2noc(=O)[nH]2)CC1] | 3-(1-(2-((S)-2-(3-cyclopropyl-4-fluorophenyl)-3-(3-(4-fluoro-1-methyl-1H-indazol-5-yl)-2-oxo-2,3-dihydro-1H-imidazol-1-yl)-4-methyl-4,5,6,7-tetrahydro-2H-pyrazolo[4,3-c]pyridine-5-carbonyl)-6-((R)-2,2-dimethyltetrahydro-2H-pyran-4-yl)pyrazolo[1,5-a]pyridin-3-yl)cyclopropy))-1,2,4-oxadiazol-5(4H)-one |

TABLE A-continued

| Cmpd No. | Structure | Chemical name |
| --- | --- | --- |
| 85 | 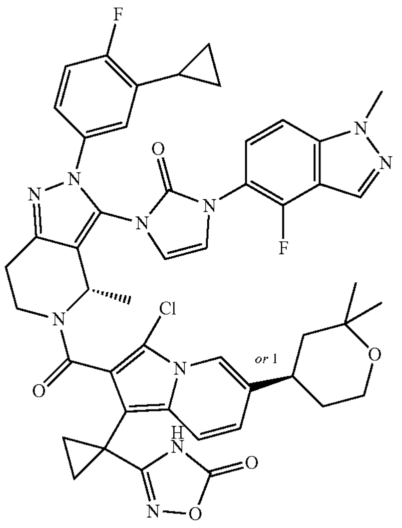 [SMILES: C[C@H]1c2c(nn(-c3ccc(F)c(C4CC4)c3)c2-n2ccn(-c3ccc4c(cnn4C)c3F)c2=O)CCN1C(=O)c1c(C2(c3noc(=O)[nH]3)CC2)c2ccc([C@@H]3CCOC(C)(C)C3)cn2c1Cl] | 3-(1-(3-chloro-2-((S)-2-(3-cyclopropyl-4-fluorophenyl)-3-(3-(4-fluoro-1-methyl-1H-indazol-5-yl)-2-oxo-2,3-dihydro-1H-imidazol-1-yl)-4-methyl-4,5,6,7-tetrahydro-2H-pyrazolo[4,3-c]pyridine-5-carbonyl)-6-((R)-2,2-dimethyltetrahydro-2H-pyran-4-yl)indolizin-1-yl)cyclopropyl)-1,2,4-oxadiazol-5(4H)-one |
| 86 | 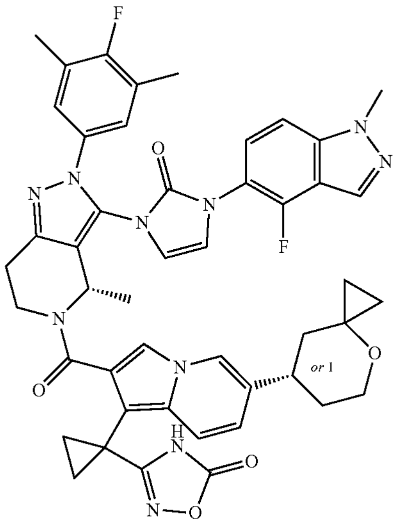 [SMILES: Cc1cc(-n2nc3c(c2-n2ccn(-c4ccc5c(cnn5C)c4F)c2=O)[C@H](C)N(C(=O)c2cn4cc([C@H]5CCOC6(CC6)C5)ccc4c2C2(c4noc(=O)[nH]4)CC2)CC3)cc(C)c1F] | 3-(1-(2-((S)-3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-6-((S)-4-oxaspiro[2.5]octan-7-yl)indolizin-1-yl)cyclopropyl)-1,2,4-oxadiazol-5(4H)-one |
| 87 | 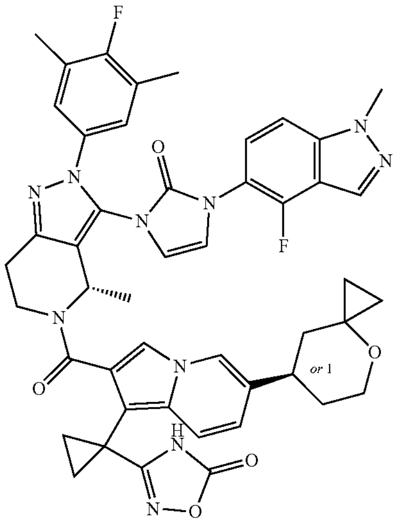 [SMILES: Cc1cc(-n2nc3c(c2-n2ccn(-c4ccc5c(cnn5C)c4F)c2=O)[C@H](C)N(C(=O)c2cn4cc([C@@H]5CCOC6(CC6)C5)ccc4c2C2(c4noc(=O)[nH]4)CC2)CC3)cc(C)c1F] | 3-(1-(2-((S)-3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-6-((R)-4-oxaspiro[2.5]octan-7-yl)indolizin-1-yl)cyclopropyl)-1,2,4-oxadiazol-5(4H)-one |

TABLE A-continued

| Cmpd No. | Structure | Chemical name |
|---|---|---|
| 88 | 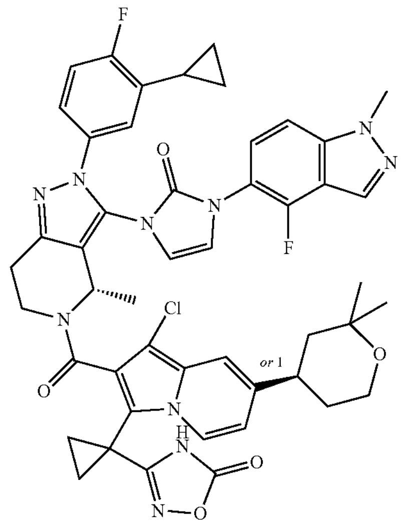 [SMILES: C[C@H]1c2c(nn(-c3ccc(F)c(C4CC4)c3)c2-n2ccn(-c3ccc4c(cnn4C)c3F)c2=O)CCN1C(=O)c1c(Cl)c2cc([C@@H]3CCOC(C)(C)C3)ccn2c1C1(c2noc(=O)[nH]2)CC1] | 3-(1-(1-chloro-2-((S)-2-(3-cyclopropyl-4-fluorophenyl)-3-(3-(4-fluoro-1-methyl-1H-indazol-5-yl)-2-oxo-2,3-dihydro-1H-imidazol-1-yl)-4-methyl-4,5,6,7-tetrahydro-2H-pyrazolo[4,3-c]pyridine-5-carbonyl)-7-((R)-2,2-dimethyltetrahydro-2H-pyran-4-yl)indolizin-3-yl)cyclopropyl)-1,2,4-oxadiazol-5(4H)-one |
| 89 | 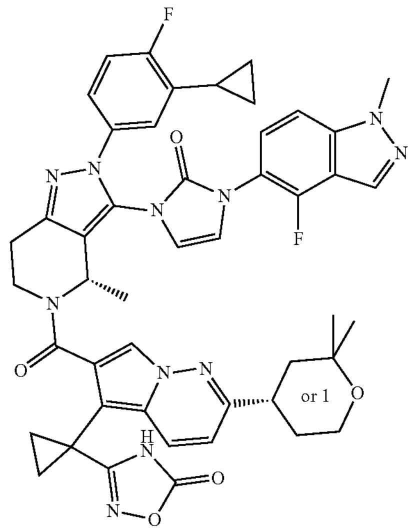 [SMILES: C[C@H]1c2c(nn(-c3ccc(F)c(C4CC4)c3)c2-n2ccn(-c3ccc4c(cnn4C)c3F)c2=O)CCN1C(=O)c1cn2nc([C@H]3CCOC(C)(C)C3)ccc2c1C1(c2noc(=O)[nH]2)CC1] | 3-(1-(6-((S)-2-(3-cyclopropyl-4-fluorophenyl)-3-(3-(4-fluoro-1-methyl-1H-indazol-5-yl)-2-oxo-2,3-dihydro-1H-imidazol-1-yl)-4-methyl-4,5,6,7-tetrahydro-2H-pyrazolo[4,3-c]pyridine-5-carbonyl)-2-((S)-2,2-dimethyltetrahydro-2H-pyran-4-yl)pyrrolo[1,2-b]pyridazin-5-yl)cyclopropyl)-1,2,4-oxadiazol-5(4H)-one |
| 90 | 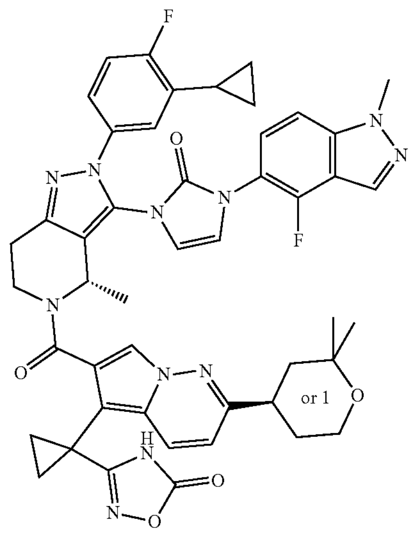 [SMILES: C[C@H]1c2c(nn(-c3ccc(F)c(C4CC4)c3)c2-n2ccn(-c3ccc4c(cnn4C)c3F)c2=O)CCN1C(=O)c1cn2nc([C@@H]3CCOC(C)(C)C3)ccc2c1C1(c2noc(=O)[nH]2)CC1] | 3-(1-(6-((S)-2-(3-cyclopropyl-4-fluorophenyl)-3-(3-(4-fluoro-1-methyl-1H-indazol-5-yl)-2-oxo-2,3-dihydro-1H-imidazol-1-yl)-4-methyl-4,5,6,7-tetrahydro-2H-pyrazolo[4,3-c]pyridine-5-carbonyl)-2-((R)-2,2-dimethyltetrahydro-2H-pyran-4-yl)pyrrolo[1,2-b]pyridazin-5-yl)cyclopropyl)-1,2,4-oxadiazol-5(4H)-one |

TABLE A-continued

| Cmpd No. | Structure | Chemical name |
|---|---|---|
| 91 | 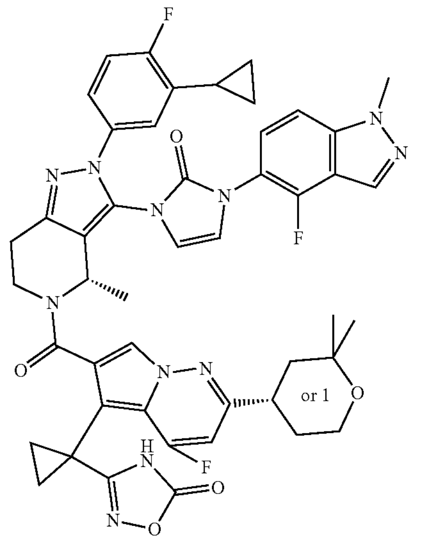 [SMILES: C[C@H]1c2c(nn(-c3ccc(F)c(C4CC4)c3)c2-n2ccn(-c3ccc4c(cnn4C)c3F)c2=O)CCN1C(=O)c1cn2nc([C@H]3CCOC(C)(C)C3)cc(F)c2c1C1(c2noc(=O)[nH]2)CC1] | 3-(1-(2-((S)-2-(3-cyclopropyl-4-fluorophenyl)-3-(3-(4-fluoro-1-methyl-1H-indazol-5-yl)-2-oxo-2,3-dihydro-1H-imidazol-1-yl)-4-methyl-4,5,6,7-tetrahydro-2H-pyrazolo[4,3-c]pyridine-5-carbonyl)-6-((S)-2,2-dimethyltetrahydro-2H-pyran-4-yl)-8-fluoroindolizin-1-yl)cyclopropyl)-1,2,4-oxadiazol-5(4H)-one |
| 92 | 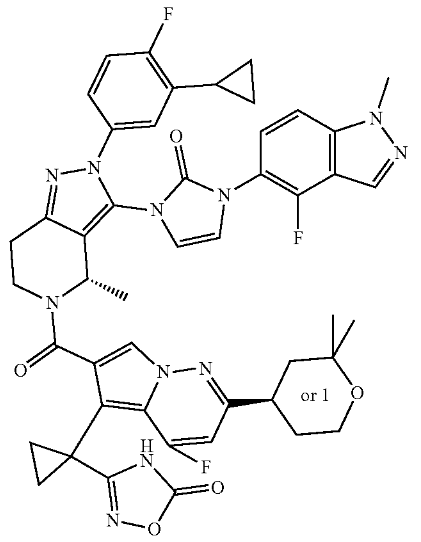 [SMILES: C[C@H]1c2c(nn(-c3ccc(F)c(C4CC4)c3)c2-n2ccn(-c3ccc4c(cnn4C)c3F)c2=O)CCN1C(=O)c1cn2nc([C@@H]3CCOC(C)(C)C3)cc(F)c2c1C1(c2noc(=O)[nH]2)CC1] | 3-(1-(2-((S)-2-(3-cyclopropyl-4-fluorophenyl)-3-(3-(4-fluoro-1-methyl-1H-indazol-5-yl)-2-oxo-2,3-dihydro-1H-imidazol-1-yl)-4-methyl-4,5,6,7-tetrahydro-2H-pyrazolo[4,3-c]pyridine-5-carbonyl)-6-((R)-2,2-dimethyltetrahydro-2H-pyran-4-yl)-8-fluoroindolizin-1-yl)cyclopropyl)-1,2,4-oxadiazol-5(4H)-one |
| 93 | 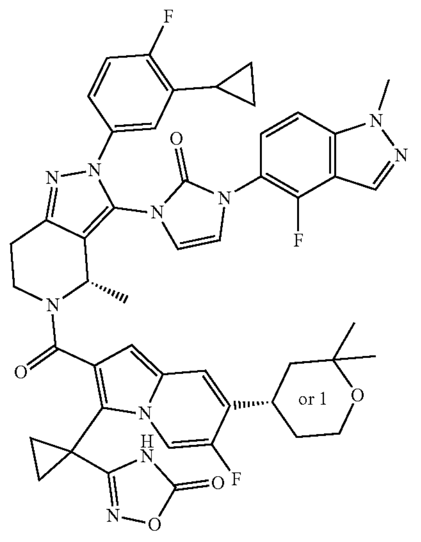 [SMILES: C[C@H]1c2c(nn(-c3ccc(F)c(C4CC4)c3)c2-n2ccn(-c3ccc4c(cnn4C)c3F)c2=O)CCN1C(=O)c1cc2cc([C@H]3CCOC(C)(C)C3)c(F)cn2c1C1(c2noc(=O)[nH]2)CC1] | 3-(1-(2-((S)-2-(3-cyclopropyl-4-fluorophenyl)-3-(3-(4-fluoro-1-methyl-1H-indazol-5-yl)-2-oxo-2,3-dihydro-1H-imidazol-1-yl)-4-methyl-4,5,6,7-tetrahydro-2H-pyrazolo[4,3-c]pyridine-5-carbonyl)-7-((S)-2,2-dimethyltetrahydro-2H-pyran-4-yl)-6-fluoroindolizin-3-yl)cyclopropyl)-1,2,4-oxadiazol-5(4H)-one |

TABLE A-continued

| Cmpd No. | Structure | Chemical name |
|---|---|---|
| 94 | 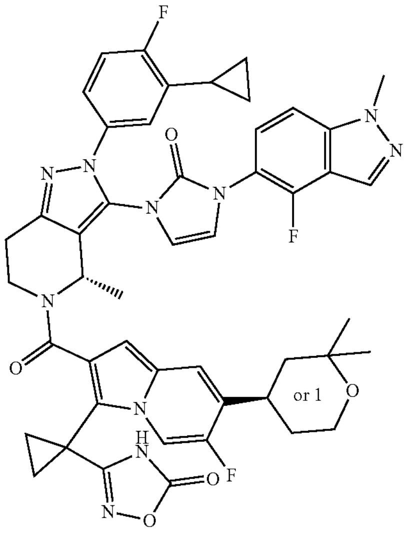 [SMILES: C[C@H]1c2c(nn(-c3ccc(F)c(C4CC4)c3)c2-n2ccn(-c3ccc4c(cnn4C)c3F)c2=O)CCN1C(=O)c1cc2cc([C@@H]3CCOC(C)(C)C3)c(F)cn2c1C1(c2noc(=O)[nH]2)CC1] | 3-(1-(2-((S)-2-(3-cyclopropyl-4-fluorophenyl)-3-(3-(4-fluoro-1-methyl-1H-indazol-5-yl)-2-oxo-2,3-dihydro-1H-imidazol-1-yl)-4-methyl-4,5,6,7-tetrahydro-2H-pyrazolo[4,3-c]pyridine-5-carbonyl)-7-((R)-2,2-dimethyltetrahydro-2H-pyran-4-yl)-6-fluoroindolizin-3-yl)cyclopropyl)-1,2,4-oxadiazol-5(4H)-one |
| 95 | 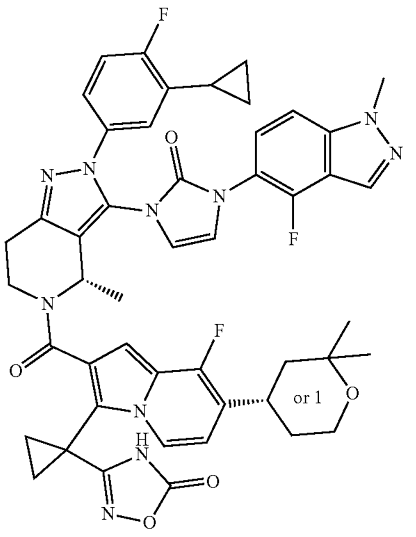 [SMILES: C[C@H]1c2c(nn(-c3ccc(F)c(C4CC4)c3)c2-n2ccn(-c3ccc4c(cnn4C)c3F)c2=O)CCN1C(=O)c1cc2c(F)c([C@H]3CCOC(C)(C)C3)ccn2c1C1(c2noc(=O)[nH]2)CC1] | 3-(1-(2-((S)-2-(3-cyclopropyl-4-fluorophenyl)-3-(3-(4-fluoro-1-methyl-1H-indazol-5-yl)-2-oxo-2,3-dihydro-1H-imidazol-1-yl)-4-methyl-4,5,6,7-tetrahydro-2H-pyrazolo[4,3-c]pyridine-5-carbonyl)-7-((S)-2,2-diniethyltetrahydro-2H-pyran-4-yl)-8-fluoroindolizin-3-yl)cyclopropyl)-1,2,4-oxadiazol-5(4H)-one |

TABLE A-continued

| Cmpd No. | Structure | Chemical name |
|---|---|---|
| 96 | 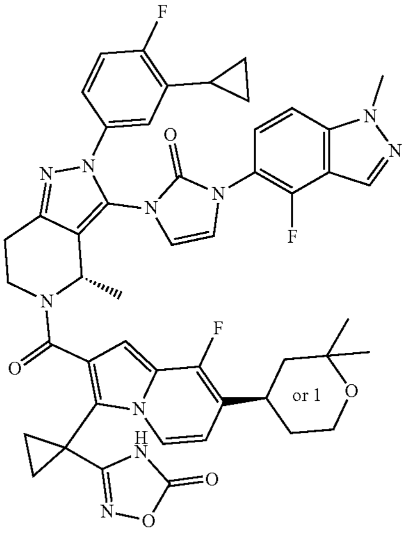 [SMILES: C[C@H]1c2c(nn(-c3ccc(F)c(C4CC4)c3)c2-n2ccn(-c3ccc4c(cnn4C)c3F)c2=O)CCN1C(=O)c1cc2c(F)c([C@@H]3CCOC(C)(C)C3)ccn2c1C1(c2noc(=O)[nH]2)CC1] | 3-(1-(2-((S)-2-(3-cyclopropyl-4-fluorophenyl)-3-(3-(4-fluoro-1-methyl-1H-indazol-5-yl)-2-oxo-2,3-dihydro-1H-imidazol-1-yl)-4-methyl-4,5,6,7-tetrahydro-2H-pyrazolo[4,3-c]pyridine-5-carbonyl)-7-((R)-2,2-dimethyltetrahydro-2H-pyran-4-yl)-8-fluoroindolizin-3-yl)cyclopropyl)-1,2,4-oxadiazol-5(4H)-one |
| 97 | 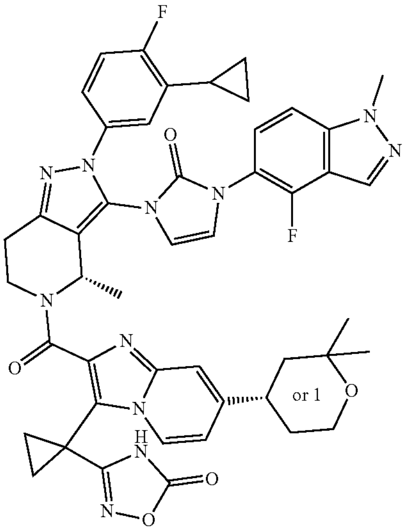 [SMILES: C[C@H]1c2c(nn(-c3ccc(F)c(C4CC4)c3)c2-n2ccn(-c3ccc4c(cnn4C)c3F)c2=O)CCN1C(=O)c1nc2cc([C@H]3CCOC(C)(C)C3)ccn2c1C1(c2noc(=O)[nH]2)CC1] | 3-(1-(2-((S)-2-(3-cyclopropyl-4-fluorophenyl)-3-(3-(4-fluoro-1-methyl-1H-indazol-5-yl)-2-oxo-2,3-dihydro-1H-imidazol-1-yl)-4-methyl-4,5,6,7-tetrahydro-2H-pyrazolo[4,3-c]pyridine-5-carbonyl)-7-((S)-2,2-dimethyltetrahydro-2H-pyran-4-yl)imidazo[1,2-a]pyridin-3-yl)cyclopropyl)-1,2,4-oxadiazol-5(4H)-one |
| 98 | 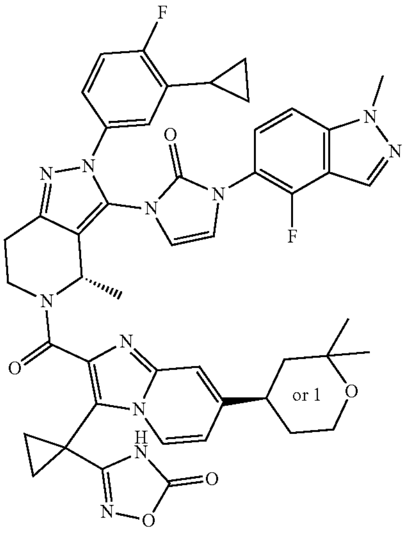 [SMILES: C[C@H]1c2c(nn(-c3ccc(F)c(C4CC4)c3)c2-n2ccn(-c3ccc4c(cnn4C)c3F)c2=O)CCN1C(=O)c1nc2cc([C@@H]3CCOC(C)(C)C3)ccn2c1C1(c2noc(=O)[nH]2)CC1] | 3-(1-(2-((S)-2-(3-cyclopropyl-4-fluorophenyl)-3-(3-(4-fluoro-1-methyl-1H-indazol-5-yl)-2-oxo-2,3-dihydro-1H-imidazol-1-yl)-4-methyl-4,5,6,7-tetrahydro-2H-pyrazolo[4,3-c]pyridine-5-carbonyl)-7-((R)-2,2-dimethyltetrahydro-2H-pyran-4-yl)imidazo[1,2-a]pyridin-3-yl)cyclopropyl)-1,2,4-oxadiazol-5(4H)-one |

TABLE A-continued

| Cmpd No. | Structure | Chemical name |
|---|---|---|
| 99 | 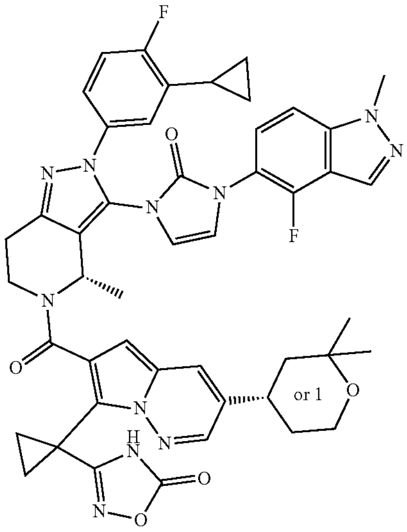 [SMILES: C[C@H]1c2c(nn(-c3ccc(F)c(C4CC4)c3)c2-n2ccn(-c3ccc4c(cnn4C)c3F)c2=O)CCN1C(=O)c1cc2cc([C@H]3CCOC(C)(C)C3)cnn2c1C1(c2noc(=O)[nH]2)CC1] | 3-(1-(6-((S)-2-(3-cyclopropyl-4-fluorophenyl)-3-(3-(4-fluoro-1-methyl-1H-indazol-5-yl)-2-oxo-2,3-dihydro-1H-imidazol-1-yl)-4-methyl-4,5,6,7-tetrahydro-2H-pyrazolo[4,3-c]pyridine-5-carbonyl)-3-((S)-2,2-dimethyltetrahydro-2H-pyran-4-yl)pyrrolo[1,2-b]pyridazin-7-yl)cyclopropy))-1,2,4-oxadiazol-5(4H)-one |
| 100 | 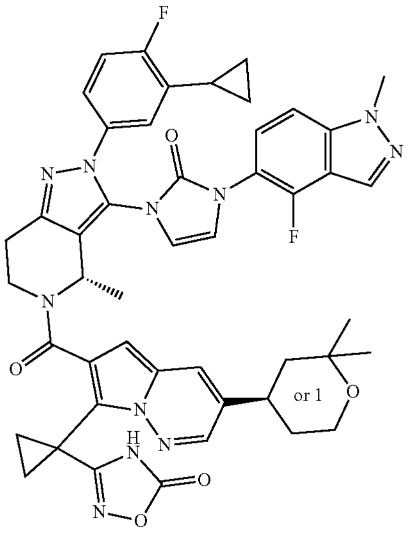 [SMILES: C[C@H]1c2c(nn(-c3ccc(F)c(C4CC4)c3)c2-n2ccn(-c3ccc4c(cnn4C)c3F)c2=O)CCN1C(=O)c1cc2cc([C@@H]3CCOC(C)(C)C3)cnn2c1C1(c2noc(=O)[nH]2)CC1] | 3-(1-(6-((S)-2-(3-cyclopropyl-4-fluorophenyl)-3-(3-(4-fluoro-1-methyl-1H-indazol-5-yl)-2-oxo-2,3-dihydro-1H-imidazol-1-yl)-4-methyl-4,5,6,7-tetrahydro-2H-pyrazolo[4,3-c]pyridine-5-carbonyl)-3-((R)-2,2-dimethyltetrahydro-2H-pyran-4-yl)pyrrolo[1,2-b]pyridazin-7-yl)cyclopropyl)-1,2,4-oxadiazol-5(4H)-one |

TABLE A-continued

| Cmpd No. | Structure | Chemical name |
|---|---|---|
| 101 | 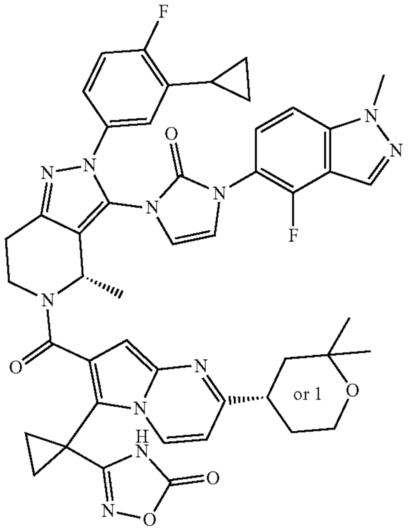 [SMILES: C[C@H]1c2c(nn(-c3ccc(F)c(C4CC4)c3)c2-n2ccn(-c3ccc4c(cnn4C)c3F)c2=O)CCN1C(=O)c1cc2nc([C@H]3CCOC(C)(C)C3)ccn2c1C1(c2noc(=O)[nH]2)CC1] | 3-(1-(7-((S)-2-(3-cyclopropyl-4-fluorophenyl)-3-(3-(4-fluoro-1-methyl-1H-indazol-5-yl)-2-oxo-2,3-dihydro-1H-imidazol-1-yl)-4-methyl-4,5,6,7-tetrahydro-2H-pyrazolo[4,3-c]pyridine-5-carbonyl)-2-((S)-2,2-dimethyltetrahydro-2H-pyran-4-yl)pyrrolo[1,2-a]pyrimidin-6-yl)cyclopropyl)-1,2,4-oxadiazol-5(4H)-one |
| 102 | 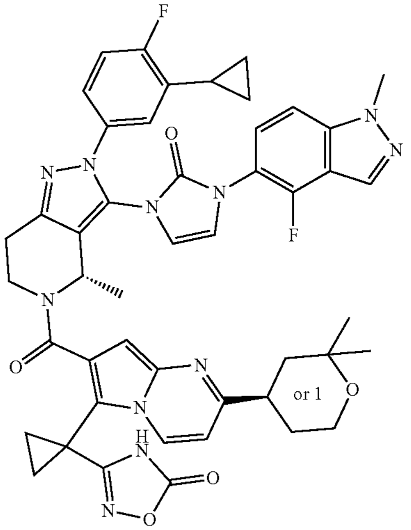 [SMILES: C[C@H]1c2c(nn(-c3ccc(F)c(C4CC4)c3)c2-n2ccn(-c3ccc4c(cnn4C)c3F)c2=O)CCN1C(=O)c1cc2nc([C@@H]3CCOC(C)(C)C3)ccn2c1C1(c2noc(=O)[nH]2)CC1] | 3-(1-(7-((S)-2-(3-cyclopropyl-4-fluorophenyl)-3-(3-(4-fluoro-1-methyl-1H-indazol-5-yl)-2-oxo-2,3-dihydro-1H-imidazol-1-yl)-4-methyl-4,5,6,7-tetrahydro-2H-pyrazolo[4,3-c]pyridine-5-carbonyl)-2-((R)-2,2-dimethyltetrahydro-2H-pyran-4-yl)pyrrolo[1,2-a]pyrimidin-6-yl)cyclopropy))-1,2,4-oxadiazol-5(4H)-one |
| 103 | 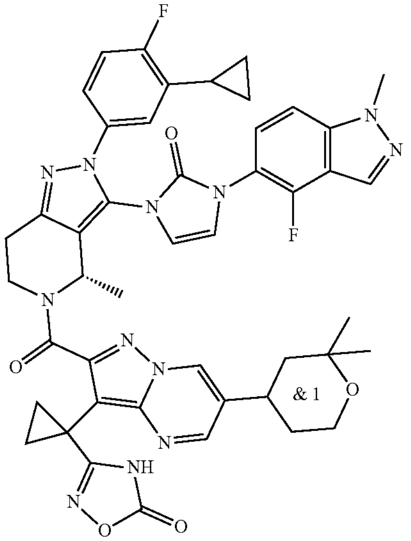 [SMILES: C[C@H]1c2c(nn(-c3ccc(F)c(C4CC4)c3)c2-n2ccn(-c3ccc4c(cnn4C)c3F)c2=O)CCN1C(=O)c1nn2cc(C3CCOC(C)(C)C3)cnc2c1C1(c2noc(=O)[nH]2)CC1] | 3-(1-(2-((S)-2-(3-cyclopropyl-4-fluorophenyl)-3-(3-(4-fluoro-1-methyl-1H-indazol-5-yl)-2-oxo-2,3-dihydro-1H-imidazol-1-yl)-4-methyl-4,5,6,7-tetrahydro-2H-pyrazolo[4,3-c]pyridine-5-carbonyl)-6-(2,2-dimethyltetrahydro-2H-pyran-4-yl)pyrazolo[1,5-a]pyrimidin-3-yl)cyclopropyl)-1,2,4-oxadiazol-5(4H)-one |

The compounds of the present application possess advantageous characteristics, as compared to known compounds, such as known GLP-1 agonists. For example, the compounds of the present application display more potent GLP-1 agonistic activity, more favorable pharmacokinetic properties (e.g., as measured by $C_{max}$, $T_{max}$, and/or AUC), and/or less interaction with other cellular targets (e.g., hepatic cellular transporter such as OATP1B1) and accordingly improved safety (e.g., drug-drug interaction). These beneficial properties of the compounds of the present application can be measured according to methods commonly available in the art, such as methods exemplified herein.

Due to the existence of double bonds, the compounds of the present application may be in cis or trans, or Z or E, configuration. It is understood that although one configuration may be depicted in the structure of the compounds or formulae of the present application, the present application also encompasses the other configuration. For example, the compounds or formulae of the present application may be depicted in cis or trans, or Z or E, configuration.

In one embodiment, a compound of the present application (e.g., a compound of any of the formulae or any individual compounds disclosed herein) is a pharmaceutically acceptable salt. In another embodiment, a compound of the present application (e.g., a compound of any of the formulae or any individual compounds disclosed herein) is a solvate. In another embodiment, a compound of the present application (e.g., a compound of any of the formulae or any individual compounds disclosed herein) is a hydrate.

The details of the application are set forth in the accompanying description below. Although methods and materials similar or equivalent to those described herein can be used in the practice or testing of the present application, illustrative methods and materials are now described. Other features, objects, and advantages of the application will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this application belongs. All patents and publications cited in this specification are incorporated herein by reference in their entireties.

Definitions

The articles "a" and "an" are used in this application to refer to one or more than one (i.e., at least one) of the grammatical object of the article. By way of example, "an element" means one element or more than one element.

The term "and/or" is used in this application to mean either "and" or "or" unless indicated otherwise.

The application also includes pharmaceutical compositions comprising an effective amount of a compound of the present application (e.g., a compound of any of the formulae or any individual compounds disclosed herein) and a pharmaceutically acceptable carrier.

The term "alkyl," as used herein, refers to saturated, straight or branched-chain hydrocarbon radicals containing, in certain embodiments, between one and six carbon atoms. Examples of $C_1$-$C_8$ alkyl radicals include, but are not limited to, methyl, ethyl, propyl, isopropyl, n-butyl, tert-butyl, neopentyl, n-hexyl, n-heptyl, and n-octyl radicals. Examples of $C_1$-$C_6$ alkyl radicals include, but are not limited to, methyl, ethyl, propyl, isopropyl, n-butyl, tert-butyl, neopentyl, and n-hexyl radicals.

The term "alkenyl," as used herein, denotes a monovalent group derived from a hydrocarbon moiety containing, in certain embodiments, from two to six carbon atoms having at least one carbon-carbon double bond. The double bond may or may not be the point of attachment to another group. Alkenyl groups include, but are not limited to, for example, ethenyl, propenyl, butenyl, 1-methyl-2-buten-1-yl and the like.

The term "alkoxy" refers to an —O-alkyl radical.

The terms "hal," "halo," and "halogen," as used herein, refer to an atom selected from fluorine, chlorine, bromine and iodine.

The term "aryl," as used herein, refers to a mono- or poly-cyclic carbocyclic ring system having one or more aromatic rings, fused or non-fused, including, but not limited to, phenyl, naphthyl, tetrahydronaphthyl, indanyl, indenyl and the like.

The term "aralkyl," as used herein, refers to an alkyl residue attached to an aryl ring. Examples include, but are not limited to, benzyl, phenethyl and the like.

The term "cycloalkyl," as used herein, denotes a monovalent group derived from a monocyclic or polycyclic saturated or partially unsaturated carbocyclic ring compound (fused, bridged, or spiro rings). Examples of $C_3$-$C_8$ cycloalkyl include, but not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo [2.2.1] heptyl, and bicyclo [2.2.2] octyl. Also contemplated is a monovalent group derived from a monocyclic or polycyclic carbocyclic ring compound having at least one carbon-carbon double bond by the removal of a single hydrogen atom. Examples of such groups include, but are not limited to, cyclopropenyl, cyclobutenyl, cyclopentenyl, cyclohexenyl, cycloheptenyl, cyclooctenyl, and the like.

The term "heteroaryl," as used herein, refers to a mono- or poly-cyclic (e.g., bi-, or tri-cyclic or more) fused or non-fused, radical or ring system having at least one aromatic ring, having from five to ten ring atoms of which one ring atoms is selected from S, O, and N; zero, one, or two ring atoms are additional heteroatoms independently selected from S, O, and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "heteroaralkyl" as used herein, refers to an alkyl residue attached to a heteroaryl ring. Examples include, but are not limited to, pyridinylmethyl, pyrimidinylethyl and the like.

The term "heterocyclyl" or "heterocycloalkyl," as used herein, refers to a saturated or unsaturated non-aromatic 3-, 4-, 5-, 6-, 7-, or 8-membered monocyclic, 7-, 8-, 9-, 10-, 11-, or 12-membered bicyclic (fused, bridged, or spiro rings), or 11-, 12, 13, or 14-membered tricyclic ring system (fused, bridged, or spiro rings), where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, and (iv) the nitrogen heteroatom may optionally be quaternized. Representative heterocycloalkyl groups include, but are not limited to, [1,3]dioxolanyl, pyrrolidinyl, pyrazolidinyl, pyrazolinyl, imidazolinyl, imidazolidinyl, piperidinyl, piperazinyl, 2-pyridone, oxazolidinyl, isoxazolidinyl, morpholinyl, tetrahydropyranyl, thiazolidinyl, isothiazolidinyl, tetrahydrofuryl, dioxanyl, oxetanyl, azetidinyl, thietanyl, oxiranyl, aziridinyl, thiiranyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl, 2-azaspiro[3.3]heptan-5-amine, 1-azaspiro[3.3]heptan-5-amine, 1-oxa-6-azaspiro[3.3]heptan-3-amine, 2-azaspiro[3.3]heptan-6-amine, 1-azaspiro[3.3]heptan-6-amine, 6-azaspiro[3.4]octan-2-amine, 5-azaspiro[3.4]octan-2-amine, 6-azaspiro[3.4]octan-1-amine, 5-azaspiro[3.4]octan-1-amine, 5-oxa-2-azaspiro[3.4]octan-7-amine, 7-amino-5-thia-2-azaspiro[3.4]octane 5,5-dioxide, 5-oxa-2-azaspiro[3.4]octan-8-amine, 8-amino-5-thia-2-azaspiro[3.4]octane 5,5-dioxide, and the like.

The term "alkylamino" refers to a group having the structure, e.g., NH($C_1$-$C_6$ alkyl), where $C_1$-$C_6$ alkyl is as previously defined.

The term "dialkylamino" refers to a group having the structure, e.g., N($C_1$-$C_6$ alkyl)$_2$, where $C_1$-$C_6$ alkyl is as previously defined.

In accordance with the application, any of the aryls, substituted aryls, heteroaryls and substituted heteroaryls described herein, can be any aromatic group. Aromatic groups can be substituted or unsubstituted.

As described herein, compounds of the application may optionally be substituted with one or more substituents, such as are illustrated generally above, or as exemplified by particular classes, subclasses, and species of the application. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. The terms "optionally substituted", "optionally substituted alkyl," "optionally substituted alkenyl," "optionally substituted cycloalkyl," "optionally substituted cycloalkenyl," "optionally substituted aryl", "optionally substituted heteroaryl," "optionally substituted aralkyl", "optionally substituted heteroaralkyl," "optionally substituted heterocyclyl," and any other optionally substituted group as used herein, refer to groups that are substituted or unsubstituted by independent replacement of one, two, or three or more of the hydrogen atoms thereon with substituents including, but not limited to: —F, —CI, —Br, —I, —OH, protected hydroxy, —$NO_2$, —CN, —$NH_2$, protected amino, —NH—$C_1$-$C_{12}$-alkyl, —NH—$C_2$-$C_{12}$-alkenyl, —NH—$C_2$-$C_{12}$-alkenyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkenyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkenyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_{12}$-alkenyl, —CONH—$C_2$-$C_{12}$-alkenyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-$C_{12}$-alkenyl, —$OCO_2$—$C_2$-$C_{12}$-alkenyl, —$OCO_2$—$C_3$-$C_{12}$-cycloalkyl, —$OCO_2$-aryl, —$OCO_2$-heteroaryl, —$OCO_2$-heterocycloalkyl, —$OCONH_2$, —OCONH—$C_1$-$C_{12}$-alkyl, —OCONH—$C_2$-$C_{12}$-alkenyl, —OCONH—$C_2$-$C_{12}$-alkenyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_{12}$-alkenyl, —NHC(O)—$C_2$-$C_{12}$-alkenyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_{12}$-alkenyl, —$NHCO_2$—$C_2$-$C_{12}$-alkenyl, —$NHCO_2$—$C_3$-$C_{12}$-cycloalkyl, —$NHCO_2$-aryl, —$NHCO_2$-heteroaryl, —$NHCO_2$-heterocycloalkyl, —NHC(O)$NH_2$, —NHC(O)NH—$C_1$-$C_{12}$-alkyl, —NHC(O)NH—$C_2$-$C_{12}$-alkenyl, —NHC(O)NH—$C_2$-$C_{12}$-alkenyl, —NHC(O)NH—$C_3$-$C_{12}$-cycloalkyl, —NHC(O)NH-aryl, —NHC(O)NH-heteroaryl, NHC(O)NH-heterocycloalkyl, —NHC(S)$NH_2$, —NHC(S)NH—$C_1$-$C_{12}$-alkyl, —NHC(S)NH—$C_2$-$C_{12}$-alkenyl, —NHC(S)NH—$C_2$-$C_{12}$-alkenyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)$NH_2$, —NHC(NH)NH— $C_1$-$C_{12}$-alkyl, —NHC(NH)NH—$C_2$-$C_{12}$-alkenyl, —NHC(NH)NH—$C_2$-$C_{12}$-alkenyl, —NHC(NH)NH—$C_3$-$C_{12}$-cycloalkyl, —NHC(NH)NH-aryl, —NHC(NH)NH-heteroaryl, —NHC(NH)NHheterocycloalkyl, —NHC(NH)—$C_1$-$C_{12}$-alkyl, —NHC(NH)—$C_2$-$C_{12}$-alkenyl, —NHC(NH)—$C_2$-$C_{12}$-alkenyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_{12}$-alkenyl, C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkenyl, —S(O)—$C_3$-$C_{12}$-cycloalkyl, —S(O)-aryl, —S(O)-heteroaryl, —S(O)-heterocycloalkyl-$SO_2NH_2$, —$SO_2NH$—$C_1$-$C_{12}$-alkyl, —$SO_2NH$—$C_2$-$C_{12}$-alkenyl, —$SO_2NH$—$C_2$-$C_{12}$-alkenyl, —$SO_2NH$—$C_3$-$C_{12}$-cycloalkyl, —$SO_2NH$-aryl, —$SO_2NH$-heteroaryl, —$SO_2NH$-heterocycloalkyl, —$NHSO_2$—$C_1$-$C_{12}$-alkyl, —$NHSO_2$—$C_2$-$C_{12}$-alkenyl, —$NHSO_2$—$C_2$-$C_{12}$-alkenyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_{12}$-alkenyl, —S—$C_2$-$C_{12}$-alkenyl, —S—$C_3$-$C_{12}$-cycloalkyl, —S-aryl, —S-heteroaryl, —S-heterocycloalkyl, or methylthiomethyl.

The term "carrier", as used in this application, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The compounds of the present application may form salts which are also within the scope of this application. Reference to a compound of the Formulae herein is understood to include reference to salts thereof, unless otherwise indicated.

Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumerate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

The compounds of the present application, for example, including the pharmaceutically acceptable salts, solvates, prodrugs, stereoisomers, or tautomers of the compounds, can exist in a solvated form with other solvent molecules or in an unsolvated form.

"Solvate" means solvent addition forms that contain either stoichiometric or non stoichiometric amounts of solvent. Some compounds or salts have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this application, as are positional isomers (such as, for example, 4-pyridyl and 3-pyridyl). For example, if a compound of Formula (I) incorporates a double bond or a fused ring, both the cis- and trans-forms, as well as mixtures, are embraced within the scope of the application. Individual stereoisomers of the compound of the application may, for example, be substantially free of other isomers, or may be admixed, for example, as racemates or with all other, or other selected, stereoisomers. The chiral centers of the present application can have the S or R configuration as defined by the IUPAC 1974 Recommendations. The use of the terms "salt", "solvate", "ester," "prodrug" and the like, is intended to equally apply to the salt, solvate, ester and prodrug of enantiomers, stereoisomers, rotamers, tautomers, positional isomers, racemates or prodrugs of the inventive compounds.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of the present application (e.g., a compound of any of the formulae or any individual compounds disclosed herein) may have one or more asymmetric carbon atom and may occur as racemates, racemic mixtures or as individual enantiomers or diastereomers.

In the present specification, the structural formula of the compound represents a certain isomer for convenience in some cases, but the present application includes all isomers, such as geometrical isomers, optical isomers based on an asymmetrical carbon, stereoisomers, tautomers, and the like.

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

The compounds of the application may contain asymmetric or chiral centers, and, therefore, exist in different stereoisomeric forms. It is intended that all stereoisomeric forms of the compounds of the application as well as mixtures thereof, including racemic mixtures, form part of the present application. In addition, the present application embraces all geometric and positional isomers. For example, if a compound of the application incorporates a double bond or a fused ring, both the cis- and trans-forms, as well as mixtures, are embraced within the scope of the application. Each compound herein disclosed includes all the enantiomers that conform to the general structure of the compound. The compound may be in a racemic or enantiomerically pure form, or any other form in terms of stereochemistry. The assay results may reflect the data collected for the racemic form, the enantiomerically pure form, or any other form in terms of stereochemistry.

A carbon atom bonded to four non-identical substituents is termed a "chiral center".

"Chiral isomer" means a compound with at least one chiral center. Compounds with more than one chiral center may exist either as an individual diastereomer or as a mixture of diastereomers, termed "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

In another embodiment of the application, the compound of the present application (e.g., a compound of any of the formulae or any individual compounds disclosed herein) is an enantiomer. In some embodiments the compound is the (S)-enantiomer. In other embodiments the compound is the (R)-enantiomer. In yet other embodiments, the compounds of the present application (e.g., a compound of any of the formulae or any individual compounds disclosed herein) may be (+) or (−) enantiomers. The compound may contain more than one stereocenter.

In another embodiment of the application, the compounds of the present application (e.g., a compound of any of the formulae or any individual compounds disclosed herein) are diastereomers. In some embodiments, the compounds are the syn diastereomer. In other embodiments, the compounds are the anti diastereomer.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Enantiomers can also be separated by use of a chiral HPLC column.

It is also possible that the compounds of the application may exist in different tautomeric forms, and all such forms are embraced within the scope of the application. Also, for example, all keto-enol and imine-enamine forms of the compounds are included in the application.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solid form, usually one tautomer predominates. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-imine.

The present application relates to a compound of the present application (e.g., a compound of any of the formulae or any individual compounds disclosed herein) or pharmaceutically acceptable salts, solvates, prodrugs, stereoisomers, or tautomers thereof, capable of modulating (e.g., activating or stimulating) GLP-1 receptor, which are useful for the treatment of diseases and disorders associated with modulation of GLP-1 receptor. The application further relates to compounds of the present application (e.g., a compound of any of the formulae or any individual compounds disclosed herein), or pharmaceutically acceptable salts, solvates, prodrugs, stereoisomers, or tautomers thereof, which are useful for modulating (e.g., activating or stimulating) GLP-1 receptor. In some embodiments, the GLP-1 receptor is wild-type GLP-1 receptor. In other embodiments, the GLP-1 receptor is a mutant GLP-1 receptor.

In some embodiments, the application provides a compound of the present application (e.g., a compound of any of the formulae or any individual compounds disclosed herein), wherein the compound possesses advantageous characteristics, such as increased potency, improved oral bioavailability, or desirable phamarcodynamic/pharmacokinetic profile, compared to one or more known GLP-1 receptor ligands (e.g., incretin or small molecule GLP-1 receptor agonists).

Potency of the agonist/activator/stimulator can be determined by $EC_{50}$ value. A compound with a lower $EC_{50}$ value, as determined under substantially similar conditions, is a more potent agonist/activator/stimulator relative to a compound with a higher $EC_{50}$ value.

The compounds of the present application can be converted to N-oxides by treatment with an oxidizing agent (e.g., 3-chloroperoxybenzoic acid (m-CPBA) and/or hydrogen peroxides) to afford other compounds of the present application. Thus, all shown and claimed nitrogen-containing compounds are considered, when allowed by valency and structure, to include both the compound as shown and its N-oxide derivative (which can be designated as N→O or $N^+$—$O^-$). Furthermore, in other instances, the nitrogens in the compounds of the present application can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compounds as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

The term "prodrug," as used in this application, means a compound which is convertible in vivo by metabolic means (e.g., by hydrolysis) to a disclosed compound.

Since prodrugs are known to enhance numerous desirable qualities of pharmaceuticals (e.g., solubility, bioavailability, manufacturing, etc.) the compounds of the present application (e.g., a compound of any of the formulae or any individual compounds disclosed herein), or pharmaceutically acceptable salts, solvates, prodrugs, stereoisomers, or tautomers thereof can be delivered in prodrug form. Thus, the present application is intended to cover prodrugs of a compound of the present application (e.g., a compound of any of the formulae or any individual compounds disclosed herein), or a pharmaceutically acceptable salt, solvate, prodrug, stereoisomer, or tautomer thereof, methods of delivering the same and compositions containing the same. "Prodrugs" are intended to include any covalently bonded carriers that release an active parent drug of the present application in vivo when such prodrug is administered to a mammalian subject. Prodrugs are prepared by modifying functional groups present in the compound in such a way that the modifications are cleaved, either in routine manipulation or in vivo, to the parent compound. Prodrugs include compounds of the application wherein a hydroxyl or amino, group is bonded to any group that, when the prodrug of the present application is administered to a mammalian subject, it cleaves to form a free hydroxyl or free amino group, respectively. Examples of prodrugs include, but are not limited to, acetate, formate, and benzoate derivatives of alcohol and amine functional groups in the compounds of each of the formulae described herein or a pharmaceutically acceptable salt, solvate, prodrug, stereoisomer, or tautomer thereof.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate.

As used herein, the term “analog” refers to a compound that is structurally similar to another compound but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

The application also comprehends isotopically-labeled compounds, which are identical to those recited in the each of the formulae described herein, but for the fact that one or more atoms are replaced by an atom having an atomic mass or mass number different from the atomic mass or mass number most commonly found in nature. Examples of isotopes that can be incorporated into compounds of the application include isotopes of hydrogen, carbon, nitrogen, fluorine, such as $^{3}H$, $^{11}C$, $^{14}C$, $^{2}H$ and $^{18}F$.

Compounds of the present application (e.g., a compound of any of the formulae or any individual compounds disclosed herein), or pharmaceutically acceptable salts, solvates, prodrugs, stereoisomers, or tautomers thereof, that contain the aforementioned isotopes and/or other isotopes of other atoms are within the scope of the present application. Isotopically-labeled compounds of the present application, for example those into which radioactive isotopes such as $^{3}H$, $^{14}C$ are incorporated, are useful in drug and/or substrate tissue distribution assays. Tritiated, i.e., $^{3}H$, and carbon-14, i.e., $^{14}C$, isotopes are useful for their ease of preparation and detectability. $^{11}C$ and $^{18}F$ isotopes are useful in PET (positron emission tomography). PET is useful in brain imaging. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances, isotopically labeled compounds of the present application (e.g., a compound of any of the formulae or any individual compounds disclosed herein), or pharmaceutically acceptable salts, solvates, prodrugs, stereoisomers, or tautomers thereof, can generally be prepared by carrying out the procedures disclosed in the Schemes and/or in the Examples described herein, by substituting a readily available isotopically labeled reagent for a non-isotopically labeled reagent. In one embodiment, the compound of the present application (e.g., a compound of any of the formulae or any individual compounds disclosed herein) or pharmaceutically acceptable salts, solvates, prodrugs, stereoisomers, or tautomers thereof, is not isotopically labelled.

The term “administer”, “administering”, or “administration” as used in this application refers to either directly administering a disclosed compound or pharmaceutically acceptable salt of the disclosed compound or a composition to a subject, or administering a prodrug, derivative or analog of the compound or pharmaceutically acceptable salt of the compound or a composition to the subject, which can form an equivalent amount of active compound within the subject’s body.

A “patient” or “subject” is a mammal, e.g., a human, mouse, rat, guinea pig, dog, cat, horse, cow, pig, or non-human primate, such as a monkey, chimpanzee, baboon or rhesus.

An “effective amount” or “therapeutically effective amount” when used in connection with a compound or pharmaceutical composition is an amount effective for treating or preventing a disease in a subject as described herein.

The term “treating” with regard to a subject, refers to improving at least one symptom of the subject’s disorder. Treating includes curing, improving, or at least partially ameliorating the disorder.

The compounds of the present application, or a pharmaceutically acceptable salt, solvate, prodrug, stereoisomer, or tautomer thereof, can also be used to prevent a disease, condition or disorder. As used herein, “preventing” or “prevent” describes reducing or eliminating the onset of the symptoms or complications of the disease, condition or disorder.

The term “disorder” is used in this application to mean, and is used interchangeably with, the terms disease, condition, or illness, unless otherwise indicated.

As used herein, the term “GLP-1 receptor-mediated” diseases or disorders means any disease or other deleterious condition in which GLP-1 receptor, or a mutant thereof, is known to play a role. Accordingly, another embodiment of the present application relates to treating or lessening the severity of one or more diseases in which GLP-1 receptor, or a mutant thereof, is known to play a role. Specifically, the present application relates to a method of treating or lessening the severity of a disease or condition as described herein, wherein said method comprises administering to a subject in need thereof a compounds of the present application (e.g., a compound of any of the formulae or any individual compounds disclosed herein), or pharmaceutically acceptable salts, solvates, prodrugs, stereoisomers, or tautomers thereof, or a composition according to the present application.

Methods for Preparing the Compounds

The compounds of the present application may be made by a variety of methods, including standard chemistry. Suitable synthetic routes are depicted in the Schemes given below.

The compounds of the present application (e.g., a compound of any of the formulae or any individual compounds disclosed herein) may be prepared by methods known in the art of organic synthesis as set forth in part by the following synthetic schemes. In the scheme described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, “Protective Groups in Organic Synthesis”, Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of the compounds of the present application.

Those skilled in the art will recognize if a stereocenter exists in the compounds of the present application (e.g., a compound of any of the formulae or any individual compounds disclosed herein). Accordingly, the present application includes both possible stereoisomers (unless specified in the synthesis) and includes not only racemic compound but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, “Stereochemistry of Organic Compounds” by E. L. Eliel, S. H. Wilen, and L. N. Mander (Wiley-Interscience, 1994).

The compounds described herein may be made from commercially available starting materials or synthesized using known organic, inorganic, and/or enzymatic processes.

The compounds of the present application can be prepared in a number of ways well known to those skilled in the art of organic synthesis. By way of example, the compounds of the present application can be synthesized using the methods described below, together with synthetic methods known in the art of synthetic organic chemistry, or variations thereon as appreciated by those skilled in the art. Preferred methods include but are not limited to those methods described below. The compounds of the present application (i.e., a compound of the present application (e.g., a compound of any of the formulae or any individual compounds disclosed herein)) can be synthesized by following the steps outlined in the examples, schemes, procedures, and/or synthesis described herein (e.g., Examples). Starting materials are either commercially available or made by known procedures in the reported literature or as illustrated.

A mixture of enantiomers, diastereomers, cis trans isomers resulting from the processes described above can be separated into their single components by chiral salt technique, chromatography using normal phase, reverse phase or chiral column, depending on the nature of the separation.

Analytical Methods, Materials, and Instrumentation

Unless otherwise noted, reagents and solvents were used as received from commercial suppliers. Proton nuclear magnetic resonance (NMR) spectra were obtained on either Bruker or Varian spectrometers at 400 MHz. Spectra are given in ppm (δ) and coupling constants, J, are reported in Hertz. Tetramethylsilane (TMS) was used as an internal standard. Liquid chromatography-mass spectrometry (LC/MS) were collected using a SHIMADZU LCMS-2020EV or Agilent 1260-6125B LCMS. Purity and low resolution mass spectral data were measured using Agilent 1260-6125B LCMS system (with Diode Array Detector, and Agilent G6125BA Mass spectrometer) or using Waters Acquity UPLC system (with Diode Array Detector, and Waters 3100 Mass Detector). The purity was characterized by UV wavelength 214 nm, 220 nm, 254 nm and ESI. Column: poroshell 120 EC-C18 2.7 μm 4.6×100 mm; Flow rate 0.8 mL/min; Solvent A (100/0.1 water/formic acid), Solvent B (100 acetonitrile); gradient: hold 5% B to 0.3 min, 5-95% B from 0.3 to 2 min, hold 95% B to 4.8 min, 95-5% B from 4.8 to 5.4 min, then hold 5% B to 6.5 min. Or, column: Acquity UPLC BEH C18 1.7 μm 2.1×50 mm; Flow rate 0.5 mL/min; Solvent A (0.1% formic acid water), Solvent B (acetonitrile); gradient: hold 5% B for 0.2 min, 5-95% B from 0.2 to 2.0 min, hold 95% B to 3.1 min, then 5% B at 3.5 min.

Abbreviations used in the following examples and elsewhere herein are:

DIEA N,N-diisopropylethylamine
DMF N,N-dimethylformamide
DMA N,N-dimethylacetamide
DMSO dimethylsulfoxide
DEAD DiethylAzodicarboxylate
EA ethyl acetate
IPA iso-propyl alcohol
IPE di-isopropyl ether
MeCN acetonitrile
THF tetrahydrofuran
m-CPBA 3-chlorobenzenecarboperoxoic acid
DCM dichloromethane
LC/MS liquid chromatography-mass spectrometry
MeOH methanol
MS mass spectrometry
PE petroleum ether
NMP N-methyl pyrrolidinone
NMR nuclear magnetic resonance
ppm parts per million
TEA triethylamine Biological Assays The biological activities of the compounds of the present application can be assessed with methods and assays known in the art. Exemplary methods are described in the Examples, such as GLP1R cAMP assay and human GLP-1 activity assay.

The compounds of the present application also possess favorable pharmacokinetic properties and/or activity profile against hepatic drug transporters (e.g., OATP1B1, OATP1B3), compared to known small molecule GLP-1 receptor agonists. These properties can be evaluated with methods and assays available in the art, such as those described and/or exemplified herein.

Methods of Using the Compounds

The compounds of the present application are useful for modulating (e.g., activating or stimulating) GLP-1 receptor. As such, the compounds of the present application are useful for the treatment of a disease or disorder associated with the GLP-1 receptor, including metabolic diseases such as diabetes and obesity, cardiovascular diseases, liver diseases such as NASH, kidney diseases, neurodegenerative diseases, and other diseases or disorders associated with the modulation of GLP-1 receptor. For example, a disease or disorder associated with the GLP-1 receptor includes, but is not limited to, diabetes (non-insulin-dependent diabetes mellitus (Type 2 diabetes) or insulin-dependent diabetes mellitus (Type 1 diabetes)), diabetic complication, obesity, impaired glucose tolerance, overweight condition, hyperlipidemia, hypercholesteremia, atherosclerosis, hypertension, coronary heart disease such as myocardial infarction and angina pectoris, congestive heart failure, cardiac arrhythmias, brain infarction, stroke, liver diseases such as nonalcoholic fatty liver disease (NAFLD) and nonalcoholic steatohepatitis (NASH), dementia, Parkinson's disease, and diabetic kidney disease.

"Diabetes" is a state or a disease in which the metabolism for generating and using glucose becomes deficient due to a failure in maintaining an appropriate blood glucose level in the body, and encompasses insulin-dependent diabetes mellitus (Type 1 diabetes) and non-insulin-dependent diabetes mellitus (Type 2 diabetes).

"Dementia" includes, for example, Alzheimer's disease, vascular dementia, and diabetic dementia.

"Diabetic complication" is a complication caused by diabetes or hyperglycemia, including ketoacidosis, infectious disease (e.g., skin infection, soft tissue infection, biliary system infection, respiratory system infection, urinary tract infection), microangiopathy (e.g., nephropathy, retinopathy), neuropathy (e.g., sensory nerve disorder, motor nerve disorder, autonomic nerve disorder), and gangrene. Major diabetes complexes include diabetic retinopathy, diabetic nephropathy, and diabetic neuropathy.

A liver disease (e.g., a liver disease associated with GLP-1 receptor) includes, but is not limited to, NASH, NAFLD, liver inflammation, liver fibrosis, cirrhosis, liver autoimmune diseases, autoimmune hepatitis, primary biliary cirrhosis, sclerosing cholangitis, autoimmune cholangitis, and alcoholic liver disease.

Another aspect of the application relates to a method of treating, preventing, inhibiting, or eliminating a disease or disorder associated with modulation of GLP-1 receptor (e.g., activation or stimulation of GLP-1 receptor). The method comprises administering to a subject in need of a treatment for diseases or disorders associated with modulation of GLP-1 receptor an effective amount a compound of the present application (e.g., a compound of any of the formulae or any individual compounds disclosed herein) or a pharmaceutically acceptable salt, solvate, prodrug, stereoisomer, or tautomer thereof or a pharmaceutical composition of a compound of the present application (e.g., a compound of any of the formulae or any individual compounds disclosed herein). In one embodiment, the GLP-1 receptor-mediated disorder is a disease or disorder described herein. In some embodiments, the GLP-1 receptor is wild-type GLP-1 receptor. In other embodiments, the GLP-1 receptor is mutant GLP-1 receptor.

Another aspect of the application relates to a method of modulating GLP-1 receptor, the method comprising administering to a subject in need thereof a therapeutically effective amount of a compound of the present application (e.g., a compound of any of the formulae or any individual compounds disclosed herein), or a pharmaceutically acceptable salt, solvate, prodrug, stereoisomer, or tautomer thereof, or a pharmaceutical composition of a compound of the present application (e.g., a compound of any of the formulae or any individual compounds disclosed herein). In one embodiment, modulating GLP-1 receptor is activating GLP-1 receptor. In some embodiments, the GLP-1 receptor is wild-type GLP-1 receptor. In other embodiments, the GLP-1 receptor is mutant GLP-1 receptor.

Another aspect of the application relates to a compound of the present application (e.g., a compound of any of the formulae or any individual compounds disclosed herein), or a pharmaceutically acceptable salt, solvate, prodrug, stereoisomer, or tautomer thereof, for use in a method of treating a GLP-1 receptor-mediated disease or disorder. In one embodiment, the GLP-1 receptor-mediated disorder is a disease or disorder described herein. In some embodiments, the GLP-1 receptor is wild-type GLP-1 receptor. In other embodiments, the GLP-1 receptor is mutant GLP-1 receptor.

In another aspect, the present application relates to a pharmaceutical composition of a compound of the present application (e.g., a compound of any of the formulae or any individual compounds disclosed herein), or a pharmaceutically acceptable salt, solvate, prodrug, stereoisomer, or tautomer thereof, for use in a method of treating a GLP-1 receptor-mediated disease or disorder. In one embodiment, the GLP-1 receptor-mediated disorder is a disease or disorder described herein. In some embodiments, the GLP-1 receptor is wild-type GLP-1 receptor. In other embodiments, the GLP-1 receptor is mutant GLP-1 receptor.

Another aspect of the application relates to a compound of the present application (e.g., a compound of any of the formulae or any individual compounds disclosed herein), or a pharmaceutically acceptable salt, solvate, prodrug, stereoisomer, or tautomer thereof, for use in modulating GLP-1 receptor. In one embodiment, modulating GLP-1 receptor is activating or stimulating GLP-1 receptor. In some embodiments, the GLP-1 receptor is wild-type GLP-1 receptor. In other embodiments, the GLP-1 receptor is mutant GLP-1 receptor.

In another aspect, the present application relates to a pharmaceutical composition of a compound of the present application (e.g., a compound of any of the formulae or any individual compounds disclosed herein), or a pharmaceutically acceptable salt, solvate, prodrug, stereoisomer, or tautomer thereof, for use in modulating GLP-1 receptor. In one embodiment, modulating GLP-1 receptor is activating or stimulating GLP-1 receptor. In some embodiments, the GLP-1 receptor is wild-type GLP-1 receptor. In other embodiments, the GLP-1 receptor is mutant GLP-1 receptor.

Another aspect of the application relates to the use of a compound of the present application (e.g., a compound of any of the formulae or any individual compounds disclosed herein), or a pharmaceutically acceptable salt, solvate, prodrug, stereoisomer, or tautomer thereof, in the manufacture of a medicament for treating a GLP-1 receptor-mediated disease or disorder. In one embodiment, the GLP-1 receptor-mediated disorder is a disease or disorder described herein. In some embodiments, the GLP-1 receptor is wild-type GLP-1 receptor. In other embodiments, the GLP-1 receptor is mutant GLP-1 receptor.

In another aspect, the present application relates to the use of a pharmaceutical composition of a compound of the present application (e.g., a compound of any of the formulae or any individual compounds disclosed herein), or a pharmaceutically acceptable salt, solvate, prodrug, stereoisomer, or tautomer thereof, in the manufacture of a medicament for treating a GLP-1 receptor-mediated disease or disorder. In one embodiment, the GLP-1 receptor-mediated disorder is a disease or disorder described herein. In some embodiments, the GLP-1 receptor is wild-type GLP-1 receptor. In other embodiments, the GLP-1 receptor is mutant GLP-1 receptor.

Another aspect of the application relates to the use of a compound of the present application (e.g., a compound of any of the formulae or any individual compounds disclosed herein), or a pharmaceutically acceptable salt, solvate, prodrug, stereoisomer, or tautomer thereof, in the manufacture of a medicament for modulating GLP-1 receptor. In one embodiment, modulating GLP-1 receptor is activating or stimulating GLP-1 receptor. In some embodiments, the GLP-1 receptor is wild-type GLP-1 receptor. In other embodiments, the GLP-1 receptor is mutant GLP-1 receptor.

In another aspect, the present application relates to the use of a pharmaceutical composition of a compound of the present application (e.g., a compound of any of the formulae or any individual compounds disclosed herein), or a pharmaceutically acceptable salt, solvate, prodrug, stereoisomer, or tautomer thereof, in the manufacture of a medicament for modulating GLP-1 receptor. In one embodiment, modulating GLP-1 receptor is activating or stimulating GLP-1 receptor. In some embodiments, the GLP-1 receptor is wild-type GLP-1 receptor. In other embodiments, the GLP-1 receptor is mutant GLP-1 receptor.

The disclosed compound of the application can be administered in effective amounts to treat or prevent a disorder and/or prevent the development thereof in subjects.

The compound of the application can be administered in therapeutically effective amounts in a combinational therapy with one or more therapeutic agents (pharmaceutical combinations) or modalities, e.g., non-drug therapies. For example, synergistic effects can occur with other anti-proliferative, anti-cancer, immunomodulatory or anti-inflammatory substances. In some embodiments, a compound of the present application (e.g., a compound of any of the formulae or any individual compounds disclosed herein) is administered in combination with an additional therapeutic agent selected from an anti-inflammatory agent, an immunomodulatory agent, a chemotherapeutic agent, an agent for treating cardiovascular disease, an agent for treating liver disease, an agent for treating lung disease, an agent for treating kidney disease, an agent for treating ocular disease, an agent for treating skin disease, an anti-viral agent, an agent for treating blood disorders, an agent for treating diabetes, and an agent for treating immunodeficiency disorders. Where the compound of the application is administered in conjunction with other therapies, dosages of the co-administered compounds will of course vary depending on the type of co-drug employed, on the specific drug employed, on the condition being treated and so forth.

Combination therapy includes the administration of the subject compound in further combination with other biologically active ingredients (such as, but not limited to, an anti-inflammatory agent, an immunomodulatory agent, chemotherapeutic agent, an agent for treating cardiovascular disease, an agent for treating liver disease, an anti-viral agent, an agent for treating blood disorders, an agent for treating diabetes, an agent for treating immunodeficiency disorders, and an agent for treating pain) and non-drug therapies (such as, but not limited to, surgery or radiation treatment). For instance, the compound of the application can be used in combination with other pharmaceutically active compounds, preferably compounds that are able to enhance the effect of the compound of the application. The compound of the application can be administered simultaneously (as a single preparation or separate preparation) or sequentially to the other drug therapy or treatment modality. In general, a combination therapy envisions administration of two or more drugs during a single cycle or course of therapy.

Pharmaceutical Compositions

The present application also provides pharmaceutical compositions comprising a compound of the present application (e.g., a compound of any of the formulae or any individual compounds disclosed herein), or a pharmaceutically acceptable salt, solvate, prodrug, stereoisomer, or tautomer thereof, in combination with at least one pharmaceutically acceptable excipient or carrier.

A "pharmaceutical composition" is a formulation containing the compound of the present application in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or a pharmaceutically acceptable salt, solvate, prodrug, stereoisomer, or tautomer thereof thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this application include powders, sprays, ointments, pastes, creams, lotions, gels, solutions, patches and inhalants. In one embodiment, the active compound is mixed under sterile conditions with a pharmaceutically acceptable carrier, and with any preservatives, buffers or propellants that are required.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical compositions of the application are formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A compound or pharmaceutical composition of the application can be administered to a subject in many of the well-known methods currently used for chemotherapeutic treatment. The dose chosen should be sufficient to constitute effective treatment but not as high as to cause unacceptable side effects. The state of the disease condition and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or modulatory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In one embodiment, the disease or disorder is a disease or disorder described herein.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compound (i.e., a compound of the present application (e.g., a compound of any of the formulae or any individual compounds disclosed herein)) of the present application may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compound into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compound is delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compound is formulated into ointments, salves, gels, or creams as generally known in the art.

The active compound can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the application are dictated by and directly dependent on the unique characteristics of the active compound and the particular therapeutic effect to be achieved.

In therapeutic applications, the dosages of the pharmaceutical compositions used in accordance with the application vary depending on the agent, the age, weight, and clinical condition of the recipient patient, and the experience and judgment of the clinician or practitioner administering the therapy, among other factors affecting the selected dosage. Dosages can range from about 0.01 mg/kg per day to about 5000 mg/kg per day. An effective amount of a pharmaceutical agent is that which provides an objectively identifiable improvement as noted by the clinician or other qualified observer. As used herein, the term "dosage effective manner" refers to amount of an active compound to produce the desired biological effect in a subject or cell.

The pharmaceutical compositions can be included in a container, pack, or dispenser together with instructions for administration.

As used herein, "pharmaceutically acceptable salts" refer to derivatives of the compound of the present application wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present application also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates) or crystal forms (polymorphs) as defined herein, of the same salt.

The compound of the present application can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., an acetate, propionate or other ester.

The compound of the present application can also be prepared as prodrugs, for example, pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.), the compound of the present application can be delivered in prodrug form. Thus, the present application is intended to cover prodrugs of the presently claimed compound, methods of delivering the same and compositions containing the same. "Prodrugs" are intended to include any covalently bonded carriers that release an active parent drug of the present application in vivo when such prodrug is administered to a subject. Prodrugs in the present application are prepared by modifying functional groups present in the compound in such a way that the modifications are cleaved, either in routine manipulation or in vivo, to the parent compound. Prodrugs include the compound of the present application wherein a hydroxy, amino, sulfhydryl, carboxy or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates and benzoate derivatives) and carbamates (e.g., N,N-dimethylaminocarbonyl) of hydroxy functional groups, esters (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in the compound of the application, and the like, See Bundegaard, H., *Design of Prodrugs*, p 1-92, Elsevier, New York-Oxford (1985).

The compound, or pharmaceutically acceptable salts, tautomers, prodrugs, solvates, metabolites, polymorphs, analogs or derivatives thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound or a pharmaceutically acceptable salt, solvate, prodrug, stereoisomer, or tautomer thereof is administered orally. One skilled in the art will recognize the advantages of certain routes of administration.

The dosage regimen utilizing the compound is selected in accordance with a variety of factors including type, species, age, weight, sex and medical condition of the patient; the severity of the condition to be treated; the route of administration; the renal and hepatic function of the patient; and the particular compound or pharmaceutically acceptable salt, solvate, prodrug, stereoisomer, or tautomer thereof employed. An ordinarily skilled physician or veterinarian can readily determine and prescribe the effective amount of the drug required to prevent, counter or arrest the progress of the condition.

Techniques for formulation and administration of the disclosed compound of the application can be found in *Remington: the Science and Practice of Pharmacy,* $19^{th}$ edition, Mack Publishing Co., Easton, Pa. (1995). In an embodiment, the compound described herein, and the pharmaceutically acceptable salts, solvates, prodrugs, stereoisomers, or tautomers thereof, are used in pharmaceutical preparations in combination with a pharmaceutically acceptable carrier or diluent. Suitable pharmaceutically acceptable carriers include inert solid fillers or diluents and sterile aqueous or organic solutions. The compound or pharmaceutically acceptable salts, solvates, prodrugs, stereoisomers, or tautomers thereof will be present in such pharmaceutical compositions in amounts sufficient to provide the desired dosage amount in the range described herein.

All percentages and ratios used herein, unless otherwise indicated, are by weight. Other features and advantages of the present application are apparent from the different examples. The provided examples illustrate different components and methodology useful in practicing the present application. The examples do not limit the claimed application. Based on the present application the skilled artisan can identify and employ other components and methodology useful for practicing the present application.

EXAMPLES

The application is further illustrated by the following examples and synthesis schemes, which are not to be construed as limiting this application in scope or spirit to the specific procedures herein described. It is to be understood that the examples are provided to illustrate certain embodiments and that no limitation to the scope of the application is intended thereby. It is to be further understood that resort may be had to various other embodiments, modifications, and equivalents thereof which may suggest themselves to those skilled in the art without departing from the spirit of the present application and/or scope of the appended claims.

Example 1: Synthesis of Intermediate 1

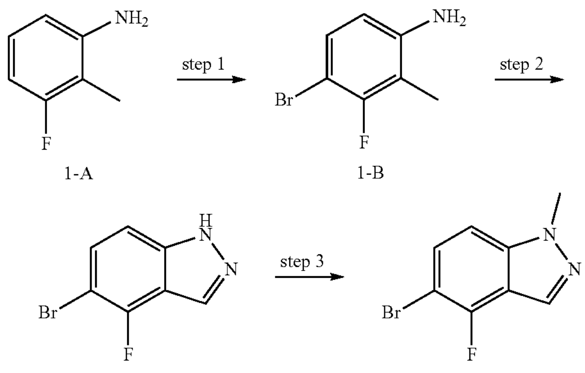

1-A 1-B 1-C Intermediate 1

Step 1: 1-B

To a solution of 1-A (20.0 g, 0.16 mol) in MeCN (500 mL) was added NBS (31.3 g, 0.176 mol) in portions at 10° C. The resulting mixture was warmed up to 25° C. and stirred for 30 min. After cooling down to 10° C., saturated aqueous $Na_2S_2O_3$ (500 mL) was added slowly into the reaction mixture. The organic layer was separated and the aqueous layer was extracted with ethyl acetate (300 mL×3). The combined organic layers were washed with water (100 mL×3) and brine (100 mL×3), dried over anhydrous sodium sulfate, filtered and concentrated to give a residue, which was washed with petroleum ether to afford 1-B (19.2 g, 58.88% yield). MS: m/z=204 (M+1).

Step 2: 1-C

To a solution of 1-B (19.2 g, 89.3 mmol) in AcOH (600 mL) was added $NaNO_2$ (7.39 g, 107 mmol) at 10° C. The mixture was stirred at 25° C. for 4 hr. After cooling down to 10° C., aqueous NaOH (50% w/w) was added slowly to the reaction mixture until pH=7-8. The aqueous layer was extracted with ethyl acetate (500 mL×3). The combined organic layers were washed with water (100 mL×3) and brine (100 mL×3), dried over anhydrous sodium sulfate, filtered and concentrated under vacuum. The residue was purified by flash chromatography (9% dichloromethane in ethyl acetate) to afford 1-C (9.2 g, 45.47% yield). MS: m/z=215 (M+1).

Step 3: Intermediate 1

To a solution of 1-C (9.2 g, 42.0 mmol) in DMF (50 mL) was added t-BuOK (4.7 g, 42.0 mmol) at 0° C. The resulting mixture was stirred at 25° C. for 40 min. $CH_3I$ (3.1 mL, 50.3 mmol) was added dropwise at 0° C. After stirring at 25° C. for 18 hr, the reaction mixture was quenched with saturated aqueous $NH_4Cl$ (200 mL) and the aqueous layer was extracted with ethyl acetate (300 mL×3). The combined organic layers were washed with saturated aqueous $NH_4Cl$ (100 mL×3), water (100 mL×3) and brine (100 mL×3), dried over anhydrous sodium sulfate, filtered and concentrated under vacuum. The residue was purified by flash chromatography (25% petroleum ether in ethyl acetate) to afford Intermediate 1 (5.5 g, 56.12% yield). $^1H$ NMR (400 MHz, $CDCl_3$) δ 8.02 (s, 1H), 7.45 (dd, J=8.8, 6.2 Hz, 1H), 7.07 (d, J=8.8 Hz, 1H), 4.07 (s, 3H) ppm; MS: m/z=229 (M+1).

Example 2: Synthesis of Intermediate 2

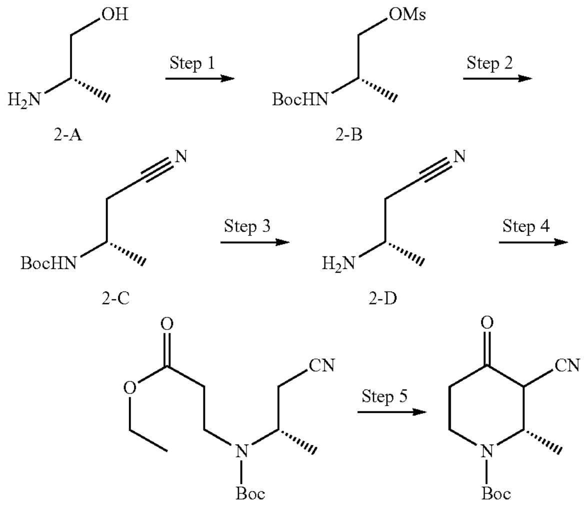

2-A 2-B 2-C 2-D 2-E Intermediate 2

Step 1: 2-B

To a stirring mixture of 2-A (28.23 g, 0.375 mol) in ethyl acetate (200 mL) was added $(Boc)_2O$ (86.13 g, 0.395 mol) dissolved in ethyl acetate (200 mL) dropwise at 0° C. for 30 min. Then, TMEDA (59.6 mL, 0.395 mol) in ethyl acetate (50 mL) was added dropwise at 0° C. MsCl (30.6 mL, 0.395 mol) was then added dropwise at 0° C. for 46 min. The reaction mixture was stirred at 0° C. for 3.2 hr. After filtration, the filtrate was concentrated to about half volume and poured into hexane (800 mL) and stirred at 0° C. for 2 hr. 2-B (79.6 g, 83.9% yield) was obtained after filtration. $^1H$ NMR (400 MHz, $CDCl_3$) δ 4.58 (m, 1H), 4.22 (m, 1H), 3.98 (m, 1H), 3.04 (s, 3H), 1.44 (s, 9H), 1.24 (d, J=6.9 Hz, 3H) ppm; MS: m/z=254 (M+1).

Step 2: 2-C

To a stirring mixture of sodium cyanide (47.2 g, 0.407 mol) in DMF (500 mL) was added TBAB (10.2 g, 31.3 mmol) and stirred at 35° C. for 2 hr. 2-B (79.6 g, 0.313 mol) was then added and stirred for another 48 hr. Water (500 mL) was added and the aqueous layer was extracted with ethyl acetate (1000 mL×3). The combined organic layers were dried over sodium sulfate, and concentrated to give 2-C (43 g, 74% yield). $^1$H NMR (400 MHz, $CDCl_3$) δ 4.68 (m, 1H), 3.95 (m, 1H), 2.80-2.63 (m, 1H), 1.45 (s, 9H), 1.31 (dd, J=11.8, 6.0 Hz, 3H) ppm; MS: m/z=185 (M+1).

Step 3: 2-D

To a mixture of 2-C (43 g, 0.232 mol) in THF (500 mL) was added methanesulfonic acid (37.6 mL, 0.580 mol) at 0° C. and stirred for 20 min. The reaction mixture was heated to 65° C. and stirred for 3 hr. The reaction mixture was then cooled to 25° C. and filtered. The cake was dissolved in DCM (200 mL) and the mixture was adjusted to pH~13 with aqueous sodium carbonate and NaOH (6 M). After separation, the aqueous layer was extracted with DCM (300 mL×3) and the combined organic layers were dried over sodium sulfate, concentrated to give 2-D (10.1 g, 51% yield). $^1$H NMR (400 MHz, $CDCl_3$) δ 3.39-3.26 (m, 1H), 2.40 (m, 2H), 1.24 (d, J=6.4 Hz, 3H) ppm; MS: m/z=85 (M+1).

Step 4: 2-E

To a solution of 2-D (10.1 g, 120.2 mmol) in ethanol (60 mL) was added ethyl acrylate (14.4 g, 144.2 mmol) and $Et_3N$ (20 mL, 144.2 mmol). The reaction solution was heated at 70° C. for 3 hr. After cooling to 25° C., N-methylpiperazine (4 mL, 36.1 mmol) and $(Boc)_2O$ (33.1 mL, 144.2 mmol) was added and was stirred at 25° C. for 14 hr. Water (100 mL) was added and the aqueous layer was extracted with toluene (100 mL×3). The combined organic layers were dried over sodium sulfate, concentrated to give 2-E (34.1 g, crude). MS: m/z=285 (M+1).

Step 5: Intermediate 2

To a mixture of 2-E (34.1 g) in THF (500 mL) was added t-BuOK (13.5 g, 120.2 mmol) at 25° C. and stirred for 2 hr. 2 N HCl (90 mL) was added and stirred for 30 min. The reaction solution was diluted with water (500 mL) and extracted with Ethyl acetate (500 mL×3). The combined organic layers were dried over sodium sulfate and concentrated. The residue was purified by silica gel column (PE/EA=20/1) to give Intermediate 2 (9.2 g, 32% yield). $^1$H NMR (400 MHz, $CDCl_3$) δ 5.17-4.97 (m, 1H), 4.36 (m, 1H), 3.80 (d, J=5.6 Hz, 1H), 3.24 (m, 1H), 2.53-2.45 (m, 2H), 1.49 (s, 9H), 1.35-1.31 (m, 3H) ppm; MS: m/z=329 (M+1).

Example 3: Synthesis of Intermediate 3

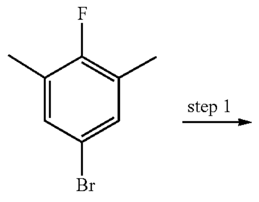

3-A

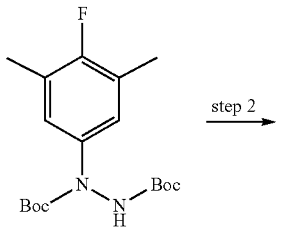

3-B

-continued

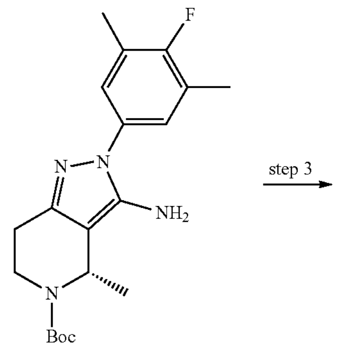

3-C

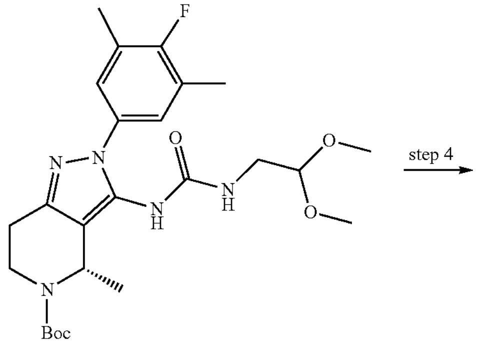

3-D

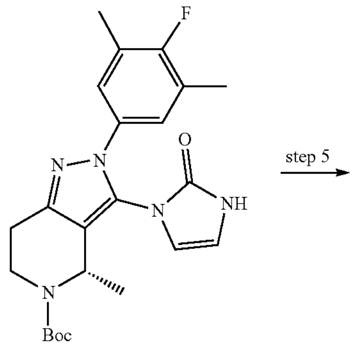

3-E

-continued

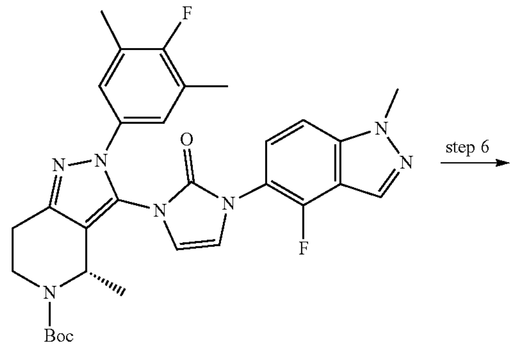

3-F

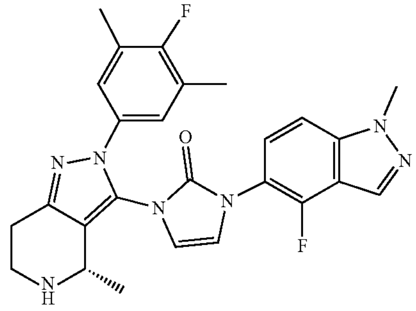

Intermediate 3

Step 1: 3-B

To a solution of 3-A (2 g, 9.85 mmol) in THF (20 mL) was added n-BuLi (2.5 M, 3.94 mL, 9.85 mmol) at −78° C. The reaction mixture was stirred at −70° C. for 1 hr. Di-tert-butyl-diazene-1,2-dicarboxylate (2.27 g, 9.85 mmol) was added, and the reaction mixture was stirred at −40° C. for 30 min and warmed up to 25° C. for another 2 hr. Aqueous $NH_4Cl$ (50 mL) was added, the aqueous layer was extracted with ethyl acetate (50 mL×2). The combined organic layers were dried over sodium sulfate, concentrated and purified by silica gel column (PE/EA=10/1) to give 3-B (2.58 g, 74% yield). $^1H$ NMR (400 MHz, $CDCl_3$) δ 7.17-6.92 (m, 2H), 2.22 (s, 6H), 1.53-1.46 (m, 18H) ppm; MS: m/z=439 (M−1).

Step 2: 3-C

To a solution of 3-B (2.58 g, 7.29 mmol) in NMP (20 mL) was added methanesulfonic acid (1.40 g, 14.58 mmol). The reaction mixture was heated up to 80° C. and stirred for 12 hr. After cooling down to room temperature, the reaction mixture was poured into toluene (20 mL) and adjust pH to ~9 with aqueous $K_2CO_3$. The organic layer was collected and dried over sodium sulfate. Then Intermediate 2 (1.73 g, 7.29 mmol) and pyridine hydrochloride (84.3 mg, 0.73 mmol) was added into the organic layer, the resulting mixture was heated at 90° C. for 1 hr. The reaction mixture was poured into water (40 mL) and adjust pH to ~9 with aqueous NaOH and extracted with ethyl acetate (50 mL×3). The combined organic layers were dried over sodium sulfate and concentrated to give a residue, which was purified by silica gel column (PE/EA=4/1) to give 3-C (1.80 g, 66% yield). MS: m/z=375 (M+1).

Step 3: 3-D

To a solution of N-(2,2-dimethoxyethyl)imidazole-1-carboxamide (1.29 g, 6.47 mmol) and 3-C (2.2 g, 5.88 mmol) in DMA (30 mL) was added t-BuOK (1.98 g, 17.65 mmol) at 25° C. The reaction mixture was stirred at 25° C. for 4 hr. The reaction mixture was poured into water (80 mL) and extracted with ethyl acetate (50 mL×3). The organic layer was washed with brine (50 mL×3), dried over sodium sulfate and concentrated to give a residue, which was purified by silica gel column (DCM/EA=3/1) to give 3-D (1.34 g, 45% yield). MS: m/z=506 (M+1).

Step 4: 3-E

To a solution of 3-D (1.29 g, 2.55 mmol) in THF (20 mL) was added methanesulfonic acid (196 mg, 2.04 mmol). The reaction mixture was stirred at 60° C. for 2 hr. Then the reaction mixture was cooled and adjust pH to ~9 with aqueous $K_3PO_4$. $Boc_2O$ (222.7 mg, 1.02 mmol) was added to the reaction mixture. The reaction mixture was stirred at 25° C. for 1 hr. Then the reaction mixture was poured into water (40 mL) and extracted with ethyl acetate (30 mL×3). The organic layer was washed with brine (20 mL×3), dried over sodium sulfate and concentrated to give a residue, which was purified by silica gel column to give 3-E (729 mg, 65% yield). MS: m/z=442 (M+1).

Step 5: 3-F

To a solution of 3-E (700 mg, 1.59 mmol), Intermediate 1 (727 mg, 3.17 mmol), (1S, 2S)-(+)-N,N-dimethylcyclohexane-1,2-diamine (112.7 mg, 0.79 mmol) and $K_2CO_3$ (657 mg, 4.76 mmol) in NMP (15 mL) was added CuI (60.5 mg, 0.32 mmol). The reaction mixture was stirred at 130° C. under argon for 3 hr. After cooling down to room temperature, the reaction mixture was poured into water (40 mL) and extracted with ethyl acetate (30 mL×3). The organic layer was washed with brine (20 mL×3), dried over sodium sulfate, concentrated and purified by silica gel column to give 3-F (774 mg, 82.6% yield). MS: m/z=590 (M+1).

Step 6: Intermediate 3

To a solution of 3-F (400 mg, 678.39 μmol) in DCM (3 mL) was added HCl/dioxane (4 M, 3 mL) at 25° C. The reaction mixture was stirred at 25° C. for 2 hr. The excess of solvent was removed under reduced pressure to give the crude product Intermediate 3 (396 mg, HCl salt). MS: m/z=490 (M+1).

Example 4: Synthesis of Intermediates 4-7
Intermediates 4-7 in Table 1 were made according to the procedure of Intermediate 3.
TABLE 1
| Name | Structure | $^1$H NMR and/or LC/MS data |
|---|---|---|
| Intermediate 4 | 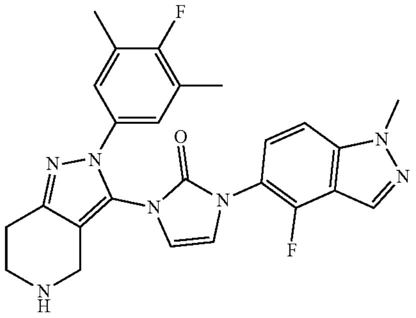 [SMILES: Cc1cc(-n2nc3c(c2-n2ccn(-c4ccc5c(cnn5C)c4F)c2=O)CNCC3)cc(C)c1F] | MS: m/z = 476.0 (M + 1) |
| Intermediate 5 | 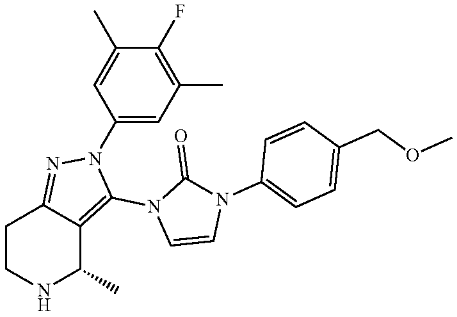 [SMILES: COCc1ccc(-n2ccn(-c3c4c(nn3-c3cc(C)c(F)c(C)c3)CCN[C@H]4C)c2=O)cc1] | MS: m/z = 462.2 (M + 1) |
| Intermediate 6 | 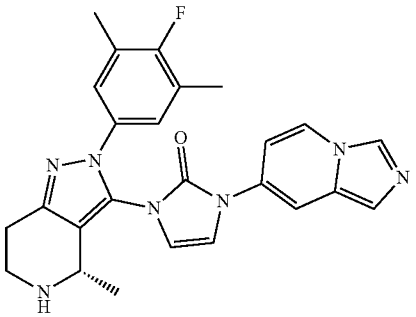 [SMILES: Cc1cc(-n2nc3c(c2-n2ccn(-c4ccn5cncc5c4)c2=O)[C@H](C)NCC3)cc(C)c1F] | MS: m/z = 458.2 (M + 1) |
| Intermediate 7 | 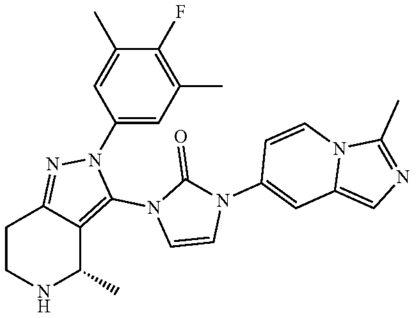 [SMILES: Cc1cc(-n2nc3c(c2-n2ccn(-c4ccn5c(C)ncc5c4)c2=O)[C@H](C)NCC3)cc(C)c1F] | MS: m/z = 472.2 (M + 1) |

Example 5: Synthesis of Intermediate 8
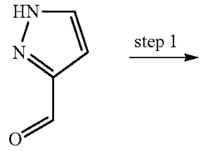
8-A
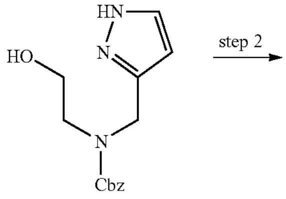
8-B
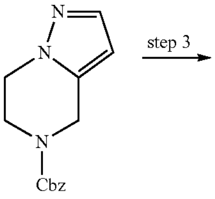
8-C
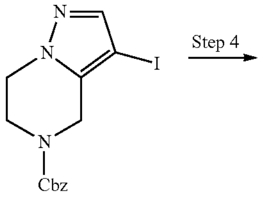
8-D
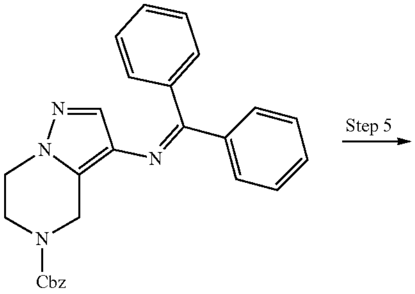
8-E
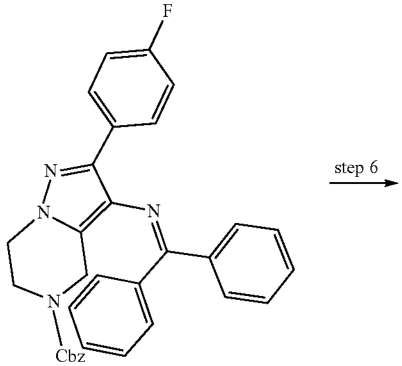
8-F
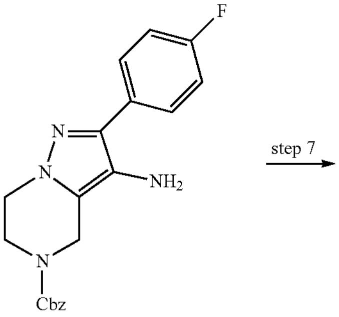
8-G
-continued
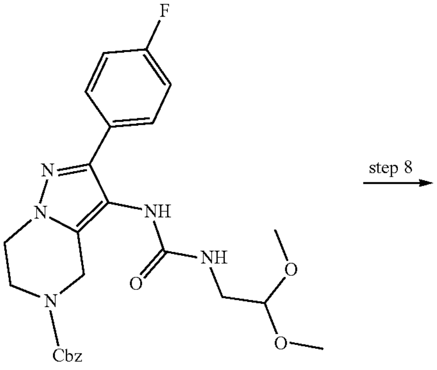
8-H
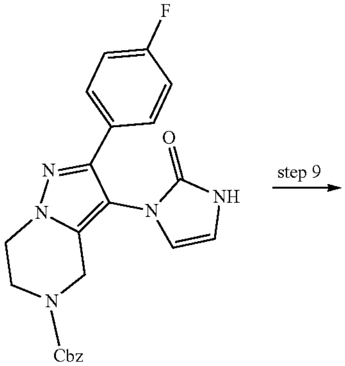
8-I
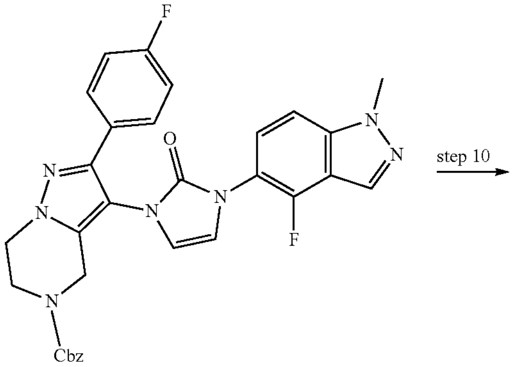
8-J
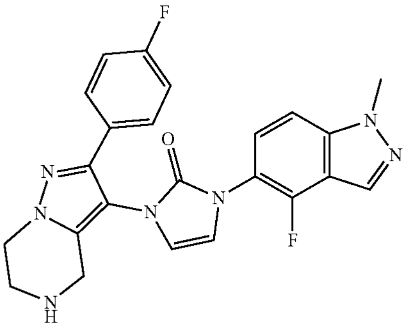
Intermediate 8
Step 1: 8-B
To a solution of 8-A (10 g, 104.07 mmol) in methanol (60 mL) was added 2-aminoethanol (7.63 g, 124.89 mmol) and stirred for 1 hr. Then sodium borohydride (4.72 g, 124.89 mmol) was added slowly at 0° C. The resulting mixture was stirred for another 1 hr before being poured into water (100 mL), and to which benzyl chloroformate (21.29 g, 124.80 mmol) was added dropwise. The resulting mixture was stirred for another 2 hr. The mixture was extracted with ethyl acetate (100 mL×3). The combined organic layers were washed with brine (100 mL), dried over sodium sulfate and concentrated to give a residue. The residue was purified by flash chromatography (DCM/MeOH=10/1) to give 8-B (16 g, 55.88% yield). 1H NMR (300 MHz, $CDCl_3$): δ 7.49 (d, J=7.5 Hz, 1H), 7.39-7.14 (m, 5H), 6.20 (d, J=52.6 Hz, 1H), 5.12 (d, J=7.1 Hz, 2H), 4.52 (s, 2H), 3.89-3.70 (m, 2H), 3.58 (d, J=4.9 Hz, 2H).

Step 2: 8-C

To a solution of 8-B (15 g, 54.49 mmol) and triphenylphosphine (42.87 g, 163.46 mmol) in THF (200 mL) was added di-tert-butyl azodicarboxylate (25.52 g, 110.8 mmol) in THE (200 mL) at 0° C. dropwise. The resulting mixture was stirred for 16 hr. The mixture was concentrated, and the residue was dissolved in DCM (50 mL) and TFA (30 mL). After stirring for 0.5 hr, the mixture was concentrated, re-dissolved in DCM (100 mL) and basified by saturated $NaHCO_3$ to pH 7~8. After separation, the organic layer was washed with brine (50 mL) and concentrated to give a crude product. The crude product was dissolved in DCM (30 mL) and petroleum ether was added until a white precipitate formed. The mixture was filtered, and the filtrate was concentrated and purified by flash chromatography (PE/EA=1/1) to give 8-C (10 g, 38.87 mmol, 71.33% yield). $^1$H NMR (300 MHz, $CDCl_3$): δ 7.51 (bs, 1H), 7.41-7.33 (m, 5H), 6.09 (d, J=10.7 Hz, 1H), 5.18 (s, 2H), 4.75 (s, 2H), 4.30-4.19 (m, 2H), 4.00-3.93 (m, 2H); MS: m/z=257.9 (M+1).

Step 3: 8-D

To a solution of 8-C (6 g, 23.32 mmol) in MeCN (150 mL) was added NIS (7.87 g, 34.98 mmol) in MeCN (150 mL) dropwise at 0° C. The mixture was stirred for 16 hr before being poured into water (100 mL) and extracted with ethyl acetate (100 mL×2). The combined organic layers were washed with saturated $Na_2SO_3$ solution (100 mL), brine (100 mL) and concentrated to give 8-D (8.2 g, 91.76% yield). MS: m/z=383.6 (M+1).

Step 4: 8-E

A mixture of 8-D (8 g, 20.88 mmol), diphenylmethanimine (7.57 g, 41.76 mmol), potassium tert-butoxide (7.03 g, 62.63 mmol), $Pd_2(dba)_3$ (1.91 g, 2.09 mmol) and xantphos (2.42 g, 4.18 mmol) in toluene (100 mL) was stirred and refluxed for 16 hr. The reaction mixture was filtered and the filtrate was concentrated. The residue was purified by flash chromatography (DCM/MeOH=15/1) to give 1,1-diphenyl-N-(4,5,6,7-tetrahydropyrazolo[1,5-a]pyrazin-3-yl)methanimine (3.3 g). $^1$H NMR (400 MHz, $CDCl_3$): δ 7.76-7.72 (m, 2H), 7.52-7.45 (m, 3H), 7.42-7.32 (m, 3H), 7.25-7.20 (m, 2H), 6.04 (s, 1H), 4.21 (s, 2H), 4.01 (t, J=5.5 Hz, 2H), 3.31-3.23 (m, 2H); MS: m/z=302.9 (M+1). The intermediate was dissolved in DCM (100 mL) and TEA (3.3 g, 32.7 mmol) was added, then benzyl chloroformate (2 g, 11.7 mmol) was added dropwise. After stirring for 1 hr, the mixture was washed with brine (100 mL), dried over sodium sulfate and concentrated. The crude product was purified by flash chromatography (PE/EA=1/1) to give 8-E (3.9 g, 42.79% yield). MS: m/z=436.7 (M+1).

Step 5: 8-F

A mixture of 8-E (2.16 g, 4.95 mmol), 1-bromo-4-fluorobenzene (1.73 g, 9.90 mmol), $Pd(OAc)_2$ (333.29 mg, 1.48 mmol), 1,10-phenanthroline (891.73 mg, 4.95 mmol) and $Cs_2CO_3$ (4.84 g, 14.85 mmol) in toluene (50 mL) was stirred at 140° C. for 12 hr. The reaction mixture was concentrated to give a crude product, which was purified by flash chromatography (PE/EA=1/1) to give 8-F (280 mg, 10.66% yield). MS: m/z=558.7 (M+1).

Step 6: 8-G

To a solution of 8-F (160 mg, 301.55 μmol) in ethyl acetate (2 mL) was added HCl/dioxane (4 M, 2 mL). The reaction mixture was stirred for 1 hr. The mixture was diluted with ethyl acetate (10 mL) and saturated aqueous $NaHCO_3$ (20 mL). The organic layer was washed with brine (20 mL), dried over sodium sulfate and concentrated. The residue was purified by flash chromatography (PE/EA=1/1) to give 8-G (110 mg, 99.56% yield). MS: m/z=367.2 (M+1).

Step 7: 8-H

To a solution of triphosgene (90 mg, 300.23 μmol) in THF (10 mL) was added 8-G (110 mg, 300.23 μmol) in THF (5 mL) at 0° C. followed by TEA (152 mg, 1.50 mmol) in THF (5 mL). The reaction mixture was stirred for 1 hr. Then 2,2-dimethoxyethanamine (158 mg, 1.50 mmol) in THF (5 mL) was added at 0° C. The reaction mixture was stirred for another 1 hr. The mixture was diluted with brine (10 mL) and extracted with ethyl acetate (10 mL). The organic layer was dried, concentrated to give 8-H (140 mg, 93.73% yield). MS: m/z=497.7 (M+1).

Step 8: 8-I

A solution of 8-H (140 mg, 281.40 μmol) in DCM (2 mL) was added HCl/dioxane (4 M, 1 mL). The resulting mixture was stirred for 2 hr. The reaction mixture was diluted with saturated aqueous $NaHCO_3$ (10 mL) and DCM (10 mL). The organic layer was dried over sodium sulfate and concentrated to give a crude product, which was purified by prep-TLC (PE/EA=1/2) to give 8-I (105 mg, 86.09% yield). MS: m/z=434.2 (M+1).

Step 9: 8-J

A mixture of 8-I (105 mg, 242.25 μmol), Intermediate 1 (83 mg, 363.38 μmol), (1S,2S)-N1,N2-dimethylcyclohexane-1,2-diamine (34 mg, 242.25 μmol), CuI (46 mg, 242.25 mol) and $K_2CO_3$ (100 mg, 726.75 μmol) in dioxane (5 mL) was stirred at 100° C. for 16 hr. The reaction mixture was concentrated to give a crude product, which was purified by flash chromatography (PE/EA=1/1) to give 8-J (55 mg, 39.04% yield). MS: m/z=582.1 (M+1).

Step 10: Intermediate 8

To a solution of 8-J (55 mg, 94.57 μmol) in DCM (2 mL) was added a solution of boron trichloride in DCM (2 mL, 1 M) at 0° C. and the resulting mixture was stirred for 2 hr. The reaction was quenched with MeOH (2 mL), and diluted with saturated aqueous $NaHCO_3$ (20 mL) and DCM (10 mL).

After separation, the organic layer was washed with brine, dried over sodium sulfate and concentrated to give Intermediate 8 (45 mg, crude). MS: m/z=448.2 (M+1).

Example 6a: Syntheis of Intermediate 9

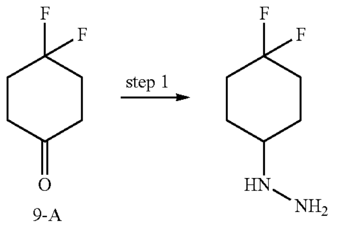

9-A

Intermediate 9

A mixture of 9-A (7.83 g, 58.38 mmol), tert-butyl N-aminocarbamate (7.72 g, 58.38 mmol) and hexane (100 mL) was stirred to reflux for 1 hr. White solid was filtered and washed with hexane. To this solid was added 1 M borane solution in THF (58.35 mL) to obtain a clear mixture, which was stirred at room temperature until the evolution of hydrogen ceased. 6 M HCl (58.35 mL) was added and the mixture was heated to reflux for 45 min. The mixture was concentrated in vacuo and washed with THE to give Intermediate 9 (9.36 g, 99% yield, HCl salt). $^1$H NMR (400 MHz, DMSO) δ 7.15 (bs, 5H), 3.09 (t, J=9.4 Hz, 1H), 2.16-1.94 (m, 4H), 1.94-1.72 (m, 2H), 1.57 (m, 2H); MS: m/z=151.0 (M+1).

Example 6b: Synthesis of Intermediate 10

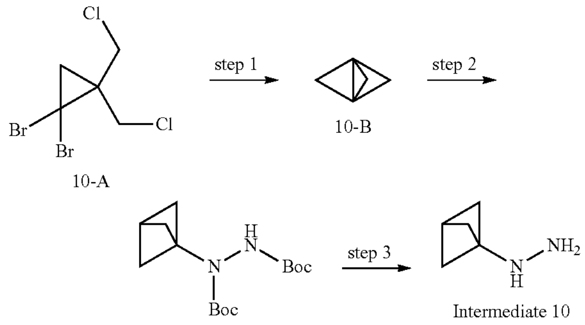

10-A

10-B

10-C

Intermediate 10

Step 1: 10-B

To a stirred and cooled mixture (−50° C.) of 10-A (20 g, 67.38 mmol) in pentane (15 mL) and diethyl ether (3 mL) in a 500 mL 3-neck RBF (attached with nitrogen line, thermometer, and addition funnel) was added an ether solution of methyllithium lithium bromide complex (1 M, 161.72 mL) slowly. After the addition was completed, the mixture was allowed to warm to 0° C. After 2 hr, the addition funnel was swapped out for a distillation head with attached 200 mL RBF in a −78° C. bath. A vacuum was slowly applied to the system and the distillate collected. A solution of 10-B (130 mL, about 0.3 M) in diethyl ether was obtained, which was used into the next step without further purification. $^1$H NMR (300 MHz, $CDCl_3$) δ 1.93 (s, 6H).

Step 2: 10-C

Under a nitrogen atmosphere, $Mn(dpm)_3$ (435.41 mg, 720.0 μmol) was dissolved in isopropanol (200 mL) and cooled to 0° C. A solution of phenylsilane (3.90 g, 36.0 mmol) and tert-butyl (NE)-N-tert-butoxycarbonyliminocarbamate (12.43 g, 54.0 mmol) in DCM (200 mL) were added, followed by 10-B (0.3 M, 120 mL) in ether/pentane. The resulting mixture was stirred at 0° C. for 21 hr. The reaction was quenched by addition of water (200 mL) and brine (500 mL). The mixture was stirred for 5 min and extracted with ethyl acetate. The organic layer was dried over $MgSO_4$, filtered and concentrated to give a residue, which was purified by silica gel column (PE/EA=10/1) to give 10-C (8.3 g, 77.27% yield). $^1$H NMR (400 MHz, DMSO-$d_6$) δ 9.00 (s, 1H), 2.37 (s, 1H), 1.92 (s, 6H), 1.40 (s, 18H).

Step 3: Intermediate 10

To a solution of 10-C (8.3 g, 27.82 mmol) in DCM (20 mL) was added HCl/dioxane (4 M, 69.54 mL) at 25° C. The reaction was stirred at 25° C. for 16 hr. After filtration, the solid was collected and dried to give Intermediate 10 (3.3 g, 69.35% yield, HCl salt).

Example 7: Synthesis of Intermediate 11

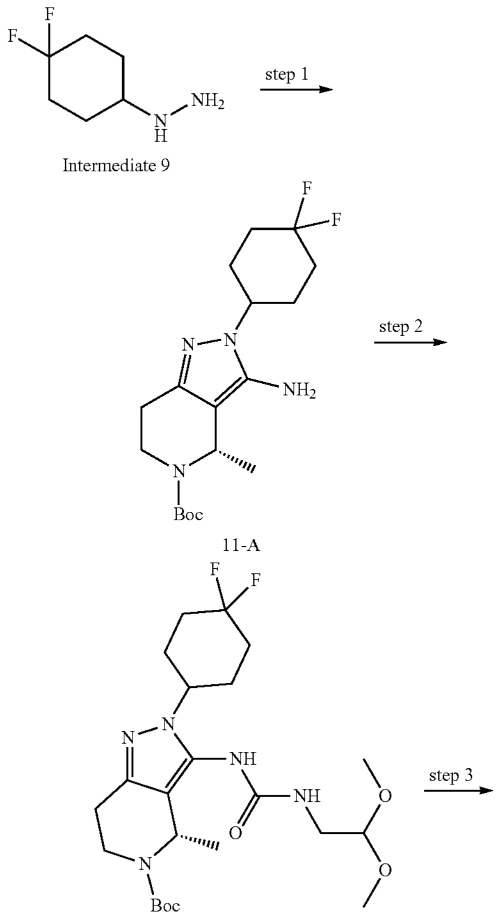

Intermediate 9

11-A

11-B

-continued

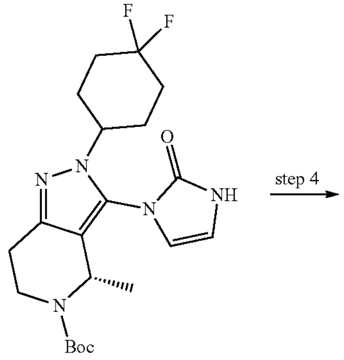

11-C

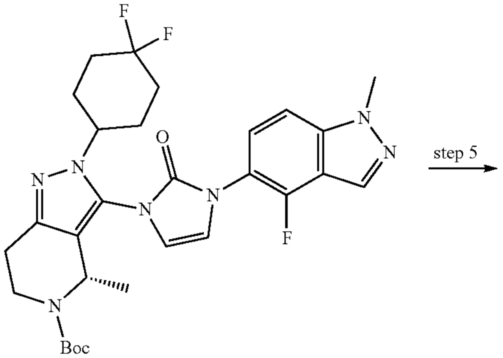

11-D

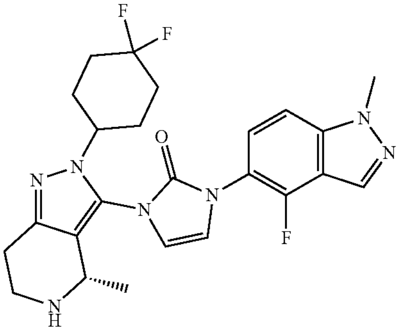

Intermediate 11

Step 1: 11-A

To a solution of Intermediate 2 (1.2 g, 5.04 mmol) in ethanol (11 mL) was added Intermediate 9 (1.12 g, 5.04 mmol) and HCl (2 M, 4 mL) at 25° C. The resulting mixture was warmed to 50° C. and stirred for 1 hr. The mixture was quenched with saturated aqueous $K_2CO_3$ and extracted with ethyl acetate (50 mL×3). The organic layers were dried over sodium sulfate and filtered. The filtrate was concentrated in vacuo to give the crude product, which was purified by combi-flash eluting with DCM/MeOH=20/1 to afford 11-A (0.998 g, 53% yield). MS: m/z=371.0 (M+1).

Step 2: 11-B

To a solution of triphosgene (480 mg, 1.62 mmol) in THF (66 mL) were added 11-A (600 mg, 1.62 mmol) and triethylamine (819 mg, 8.1 mmol). The resulting mixture was warmed up to room temperature and stirred for 1 hr. Then the reaction was cooled to 0° C., 2,2-dimethoxyethanamine (851 mg, 8.1 mmol) was added, the mixture was warmed up to room temperature and stirred at for further 3 hr. The reaction mixture was filtered and the filtrate was concentrated in vacuo to give 11-B (1.46 g, crude). MS: m/z=501.8 (M+1).

Step 3: 11-C

To a solution of 11-B (1.36 g) in DCM (14 mL) was added HCl in dioxane (4 M, 7.46 mL). The reaction mixture was stirred at 25° C. for 16 hr. Then the reaction mixture was adjusted to pH~10 with aqueous NaOH. $Boc_2O$ (710 mg, 3.25 mmol) was added and the reaction mixture was stirred at 25° C. for 4 hr. The reaction mixture was poured into water (15 mL) and extracted with ethyl acetate (15 mL×3). The organic layer was washed with brine (15 mL), dried over sodium sulfate and concentrated under reduced pressure. The crude product was purified by silica gel column (DCM/methanol=20/1) to give 11-C (378 mg, 31% yield). MS: m/z=437.8 (M+1).

Step 4: 11-D

To a solution of Intermediate 1 (275.37 mg, 1.20 mmol), 11-C (338 mg, 1.0 mmol), (1S,2S)-N1,N2-dimethylcyclohexane-1,2-diamine (342.02 mg, 2.40 mmol) and CuI (228.97 mg, 1.20 mmol) in dioxane (17 mL) was added $K_2CO_3$ (332.33 mg, 2.40 mmol). The reaction mixture was stirred at 100° C. under argon for 16 hr. The resulting mixture was filtered and the filtrate was concentrated in vacuo to give a residue, which was purified by combi-flash (eluted with DCM/methanol=20/1) to afford 11-D (309 mg, 52% yield). MS: m/z=585.7 (M+1).

Step 5: Intermediate 11

A mixture of 11-D (309 mg, 0.527 mmol) and HCl in dioxane (4 M, 10.55 mL) was stirred for 0.5 hr. The solvent was removed under reduced pressure to give Intermediate 11 (250 mg, 97% yield). MS: m/z=485.8 (M+1).

Example 8: Synthesis of Intermediates 12-16
Intermediates 12-16 in Table 2 were made according to the procedure of Intermediate 11.
TABLE 2
| Name | Structure | $^1$H NMR and/or LC/MS data |
| --- | --- | --- |
| Intermediate 12 | 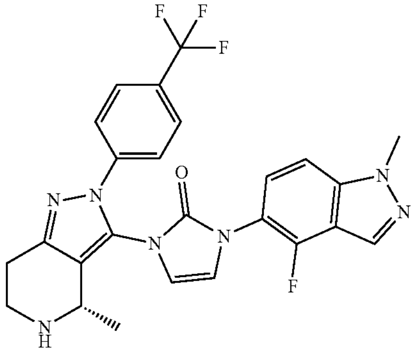 [SMILES: C[C@@H]1NCCc2nn(-c3ccc(C(F)(F)F)cc3)c(-n3ccn(-c4ccc5c(cnn5C)c4F)c3=O)c21] | MS: m/z = 512.2 (M + 1). |
| Intermediate 13 | 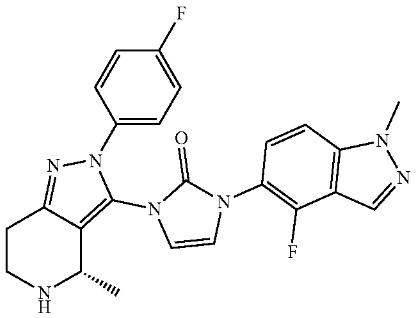 [SMILES: C[C@@H]1NCCc2nn(-c3ccc(F)cc3)c(-n3ccn(-c4ccc5c(cnn5C)c4F)c3=O)c21] | MS: m/z = 462.2 (M + 1). |
| Intermediate 14 | 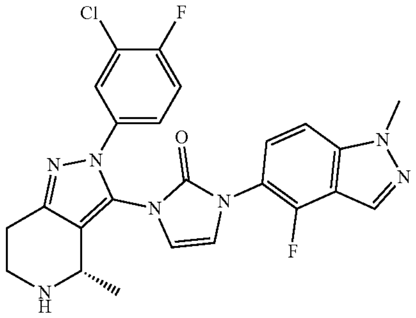 [SMILES: C[C@@H]1NCCc2nn(-c3ccc(F)c(Cl)c3)c(-n3ccn(-c4ccc5c(cnn5C)c4F)c3=O)c21] | MS: m/z = 496.1 (M + 1). |
| Intermediate 15 | 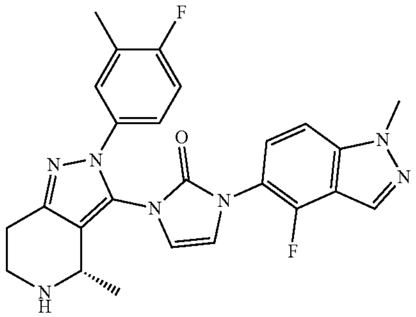 [SMILES: Cc1cc(-n2nc3c(c2-n2ccn(-c4ccc5c(cnn5C)c4F)c2=O)[C@H](C)NCC3)ccc1F] | MS: m/z = 476.2 (M + 1). |

TABLE 2-continued
| Name | Structure | $^1$H NMR and/or LC/MS data |
|---|---|---|
| Intermediate 16 | 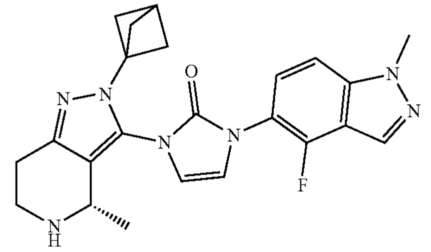 [SMILES: C[C@@H]1NCCc2nn(C34CC(C3)C4)c(-n3ccn(-c4ccc5c(cnn5C)c4F)c3=O)c21] | MS: m/z = 433.9 (M + 1). |
Example 9: Synthesis of Intermediate 17
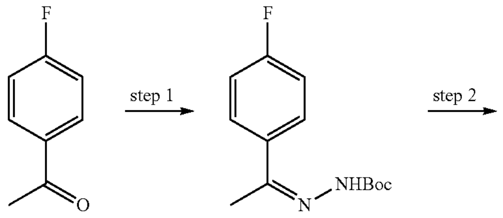
17-A 17-B
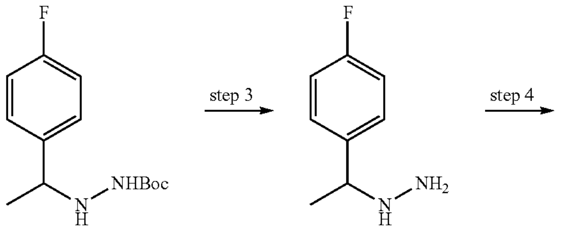
17-C 17-D
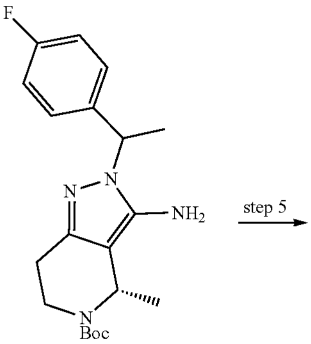
17-E
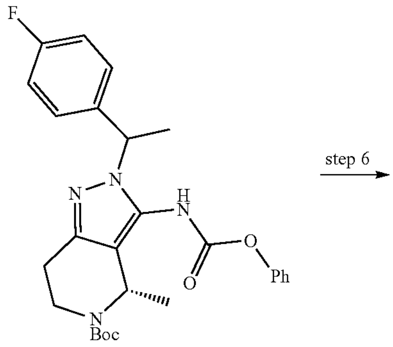
17-F
-continued
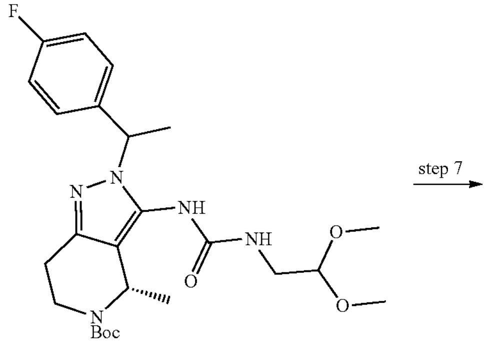
17-G
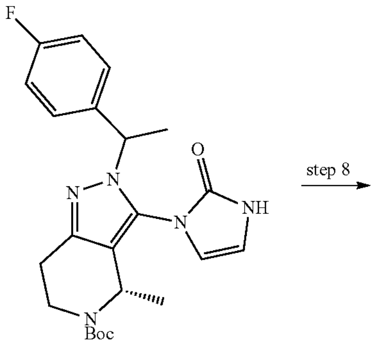
17-H
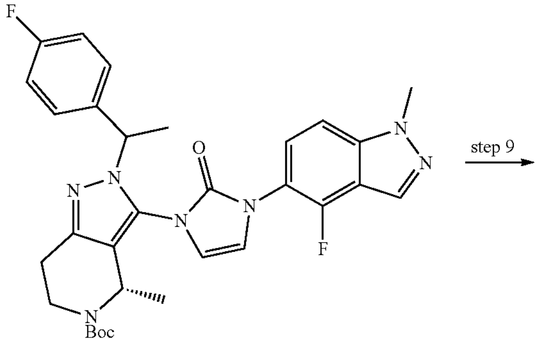
17-I -continued

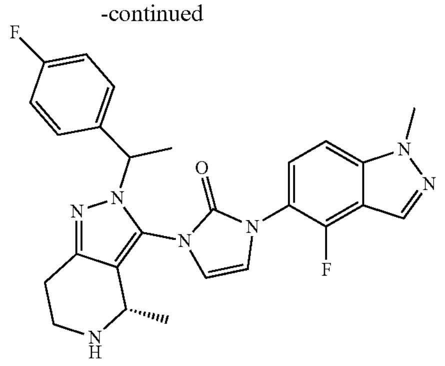

Intermediate 17

Step 1: 17-B

To a solution of 17-A (10 g, 72.39 mmol) in isopropyl alcohol (80 mL) was added tert-butyl N-amino carbamate (9.57 g, 72.39 mmol) at 25° C. The resulting mixture was heated to 90° C. for 2 hr. To the reaction mixture was added petroleum ether (160 mL) at 25° C. and the resulting mixture was stirred for 10 minutes and filtered, the residue was washed by petroleum ether (40 mL×2) and dried to afford 17-B (12 g, 65% yield). MS: m/z=197.2 (M+1-56).

Step 2: 17-C

To a solution of 17-B (10 g, 39.64 mmol) in methanol (150 mL) was added Palladium (843 mg, 7.93 mmol) at 25° C. under a hydrogen atmosphere. The resulting mixture was stirred at 25° C. for 3 hr. The reaction was filtered and concentrated under reduced pressure to afford 17-C (9 g, 89% yield). MS: m/z=277.2 (M+23).

Step 3: 17-D

To a solution of 17-C (1 g, 3.93 mmol) in DCM (15 mL) was added HCl/dioxane (4 M, 2 mL) at 25° C., the mixture was stirred for 18 hr. The reaction mixture was concentrated under reduced pressure to afford 17-D (0.72 g, 95% yield, HCl salt). MS: m/z=155 (M+1).

Step 4: 17-E

To a mixture of 17-D (1.1 g, 7.13 mmol, HCl salt) in ethanol (50 mL) was added N-ethyl-N-isopropyl-propan-2-amine (1.38 g, 10.70 mmol) at 25° C. and stirred for 3 minutes, then Intermediate 2 (1.70 g, 7.13 mmol) was added to the mixture. The resulting mixture was stirred at 70° C. for 3 hr. The reaction mixture was concentrated and purified with flash (30% Ethyl acetate in Petroleum ether) to afford 17-E (1.5 g, 56% yield). MS: m/z=375.3 (M+1).

Step 5: 17-F

To a solution of 17-E (450 mg, 1.20 mmol), DIEA (465 mg, 3.61 mmol) in THF (5 mL) was added phenyl carbonochloridate (376 mg, 2.40 mmol), and the reaction was stirred at 25° C. for 2 hr. The reaction was concentrated to give 17-F (590 mg, crude). MS: m/z=495, (M+1).

Step 6: 17-G

Crude 17-F (590 mg, 1.2 mmol) was dissolved in 5 mL of pyridine, to which 2,2-dimethoxyethanamine (379 mg, 3.61 mmol) was added. The mixture was stirred at 25° C. for 3 hr. The reaction was concentrated to give 17-G (3 g, crude). MS: m/z=506 (M+1).

Step 7: 17-H

To a solution of crude 17-G (3 g) in THF (5 mL) was treated with methanesulfonic acid (569 mg, 5.93 mmol). The solution was stirred at 60° C. for 2 hr. Aqueous $K_3PO_4$ was added to adjusted pH~9, and then $Boc_2O$ (388 mg, 1.78 mmol) was added, and the reaction was stirred at 25° C. for 16 hr. The reaction was poured into water and extracted with ethyl acetate (20 mL×3), the organic layer was dried over sodium sulfate and concentrated to give a residue. The residue was purified by prep-TLC (DCM/MeOH=10/1) to give 17-H (300 mg, 56.5% yield over 3 steps). MS: m/z=442.1, (M+1).

Step 8: 17-I

To a solution of 17-H (300 mg, 679.5 μmol) and Intermediate 1 in NMP (2 mL) was added N1,N2-dimethylcyclohexane-1,2-diamine (82 mg, 579.84 μmol), CuI (69 mg, 362.4 μmol) and $K_2CO_3$ (300 mg, 2.17 mmol), the reaction was heated at 130° C. for 3 hr. The reaction was diluted with 10 mL of ethyl acetate and washed with brine (10 mL×5). The organic layer was dried, concentrated and purified by column chromatography (PE/EA=5/3) to give 17-I (320 mg, 75.9% yield). MS: m/z=590.2, (M+1).

Step 9: Intermediate 17

To a solution of 17-I (320 mg, 542.71 μmol) in DCM (4 mL) was added TFA (6.19 g, 54.27 mmol, 4.2 mL), the reaction was stirred at 25° C. for 16 hr. Solvent was removed, the residue was treated with 5 mL of toluene and concentrated, and repeated three times to give Intermediate 17 (250 mg, 89% yield, TFA salt). MS: m/z=490.1 (M+1).

Example 10: Synthesis of Intermediate 18

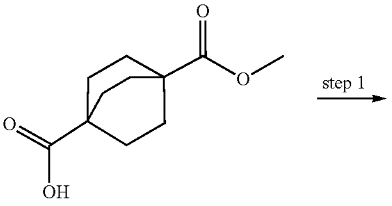

18-A

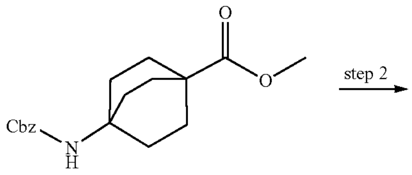

18-B

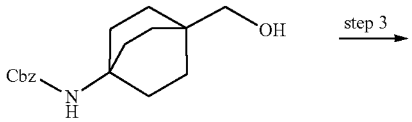

18-C

-continued

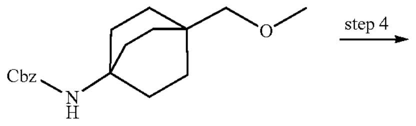

18-D

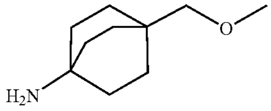

Intermediate 18

Step 1: 18-B

To a solution of 18-A (6 g, 28.27 mmol) in toluene (50 mL) was added benzyl alcohol (3.06 g, 28.27 mmol, 2.91 mL), DPPA (10.31 g, 42.41 mmol), triethylamine (7.15 g, 70.68 mmol). The mixture was stirred at 90° C. for 20 hr. The mixture was diluted with ethyl acetate (200 mL) and washed with aqueous $NaHCO_3$ (100 mL×2). The organic phase was dried over sodium sulfate and concentrated under reduced pressure. The crude was purified by chromatographic column (PE/EA=2/1) to give 18-B (5.8 g, 58.18% yield). MS: m/z=317.8 (M+1).

Step 2: 18-C

To a solution of 18-B (5 g, 15.75 mmol) in THF (50 mL) was added sodium borohydride (5.96 g, 157.54 mmol). The resulting mixture was stirred for 18 hr and quenched with 100 mL HCl (1M) and extracted with ethyl acetate (200 mL×3), the combined organic phases were dried with sodium sulfate, concentrated under reduced pressure to give 18-C (5.3 g, crude). MS: m/z=289.9 (M+1).

Step 3: 18-D

To a mixture of 18-C (1.5 g, 5.19 mmol), silver trifluoromethanesulfonate (2 g, 7.78 mmol) and DCM (22.5 mL) was added MeI (1.1 g, 7.78 mmol) dropwise at 0° C. The reaction mixture was stirred for 3 hr. The resulting mixture was filtered and the filtrate was concentrated in vacuo to give the crude product, which was purified by combi-flash (PE/EA=2/1) to afford 18-D (323 mg, 20% yield). $^1$H NMR (400 MHz, DMSO) δ 7.51-7.20 (m, 5H), 6.93 (s, 1H), 4.95 (s, 2H), 3.20 (s, 3H), 2.93 (s, 2H), 1.73 (dd, J=9.8, 6.2 Hz, 6H), 1.42 (dd, J=9.8, 6.2 Hz, 6H); MS: m/z=303.9 (M+1).

Step 4: Intermediate 18

A mixture of 18-D (323 mg, 1.06 mmol), Pd/C (40 mg) and methanol (10 mL) was stirred at under $H_2$ for 18 hr. The reaction was filtered and the filtrate was concentrated in vacuo to afford Intermediate 18 (190 mg, crude). MS: m/z=170.2 (M+1).

Example 11: Synthesis of Intermediate 19

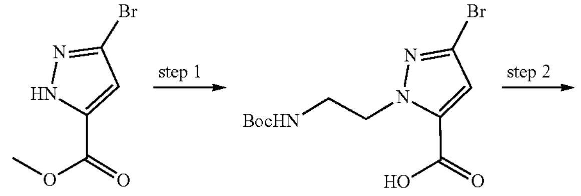

19-A 19-B

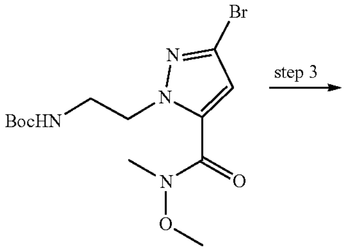

19-C

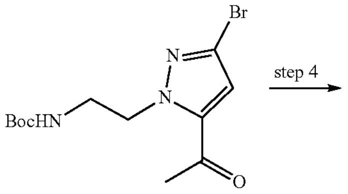

19-D

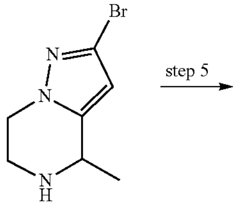

19-E

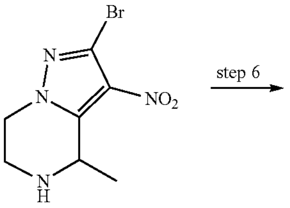

19-F

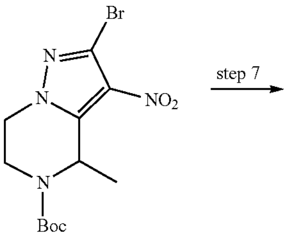

19-G

-continued

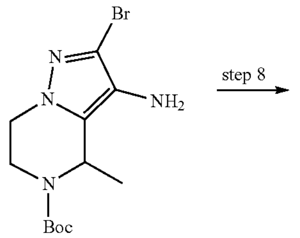

19-H

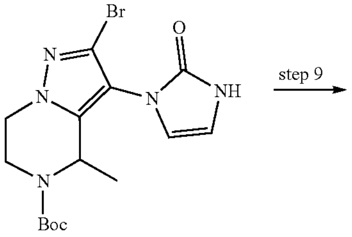

19-I

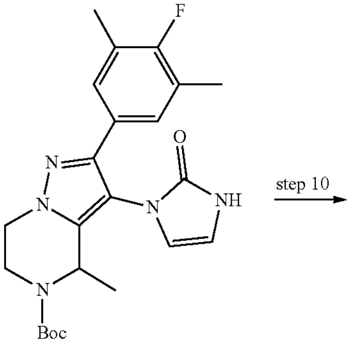

19-J

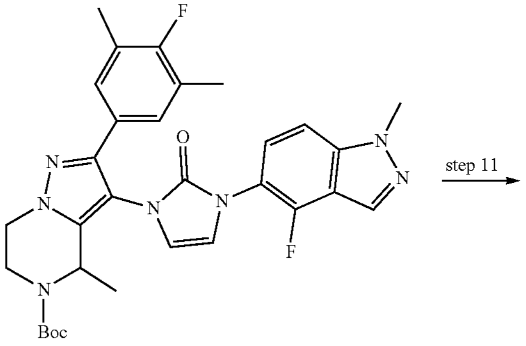

19-K

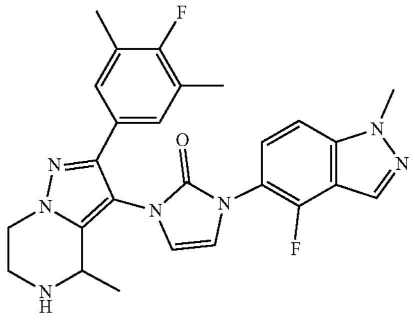

Intermediate 19

Step 1: 19-B

To a solution of 19-A (5 g, 24.39 mmol), DEAD (5.10 g, 29.27 mmol) and tert-butyl N-(2-aminoethyl)carbamate (4.69 g, 29.27 mmol) in THF (50 mL) was added $Ph_3P$ (7.68 g, 29.27 mmol) at 0° C. for 0.5 hr. Then the mixture was stirred for 4 hr before MeOH (50 mL), water (12 mL) and NaOH (1.95 g, 48.78 mmol) were added, which was then stirred further for 1 hr. The mixture was concentrated, water (50 mL) was added, the mixture was extracted with ethyl acetate (50 mL×3). The aqueous phase was acidized (1 M HCl) to pH~3 and extracted with ethyl acetate (50 mL×3), dried over sodium sulfate, filtered and concentrated to give 19-B (8.1 g, 24.24 mmol, 99.4% yield).

Step 2: 19-C

To a mixture of 19-B (8.1 g, 24.24 mmol), N-methoxymethanamine (1.48 g, 15.18 mmol, HCl salt) in DCM (100 mL) was added TEA (7.36 g, 72.72 mmol, 10.14 mL) and HATU (9.22 g, 24.24 mmol) at 30° C. The reaction solution was stirred for 2 hr at 30° C. Then, ethyl acetate (100 mL) was added and the mixture reaction was washed with $H_2O$ (100 mL×3), dried over sodium sulfate, filtered and concentrated. The crude product was purified by silica gel chromatography (PE/EA=5/1-1/1) to obtain 19-C (7.7 g, 20.41 mmol, 84.21% yield).

Step 3: 19-D

To a solution of 19-C (7 g, 18.56 mmol) in THF (50 mL) was added MeMgBr (1 M, 92.78 mL) at 0° C. Then the mixture was stirred for 2 hr at 25° C. The mixture was concentrated and purified by column chromatography (EA/PE=1/10-1/1) to give 19-D (6 g, 18.06 mmol, 97.34% yield). MS: m/z=232.0 (M+1-100).

Step 4: 19-E

To a mixture of 19-D (6 g, 18.06 mmol) in methanol (5 mL) was added HCl/dioxane (4 M, 40 mL) at 0° C. and stirred for 1 hr, the reaction mixture was concentrated to give white solid. Then, DCM (40 mL) and TEA (18.28 g, 180.62 mmol, 25.17 mL) were added, $NaBH_3CN$ (4.54 g, 72.25 mmol) was added at 0° C. and stirred for 2 hr. The solution was concentrated and purified by silica gel chromatography (DCM/MeOH=50/1-10/1, v/v) to obtain 19-E (3.1 g, 14.35 mmol, 79.43% yield).

Step 5: 19-F

To a mixture of 19-E (3.1 g, 14.35 mmol) in $H_2SO_4$ (40 mL) was added $KNO_3$ (7.25 g, 71.73 mmol) at 0° C. The reaction solution was stirred for 5 hr at 45° C. Then, the solution was poured into ice-water (200 mL) and the yellow solid was generated and filtered. Then the solid was dissolved in HCl/MeOH (4 M, 50 mL) and refluxed for 2 hr. The mixture was concentrated to obtain 19-F (2 g, 7.66 mmol, 53.40% yield).

Step 6: 19-G

To a mixture of 19-F (1.8 g, 6.89 mmol) and TEA (2.09 g, 20.68 mmol, 2.88 mL) in DCM (30 mL) was added $Boc_2O$ (1.81 g, 8.27 mmol) at 25° C., and stirred for 2 hr. Then, the solution was concentrated. The crude product was purified by silica gel chromatography (PE/EA=10/1-4/1) to obtain 19-G (2.0 g, 5.54 mmol, 80.31% yield).

Step 7: 19-H

To a mixture of 19-G (1.5 g, 4.15 mmol) and $NH_4Cl$ (2.22 g, 41.53 mmol) in ethanol (50 mL) and water (50 mL) was added Zn (1.36 g, 20.76 mmol) at 25° C. The mixture was stirred for 1 hr, filtered and concentrated. The crude product was purified by silica gel chromatography (PE/EA=10/1-2/1) to obtain 19-H (1.1 g, 3.32 mmol, 79.97% yield).

Step 8: 19-I

To a mixture of 19-H (800 mg, 2.42 mmol) and bis (trichloromethyl) carbonate (2.15 g, 7.25 mmol) in DCM (10 mL) was added TEA (977.66 mg, 9.66 mmol, 1.35 mL) at −78° C. and stirred for 1 hr. 2,2-dimethoxyethanamine (1.27 g, 12.08 mmol, 1.32 mL) was added and stirred at 0° C. for 30 min. The mixture was concentrated to give a residue, which was dissolved in THE (20 mL) and trifluoromethanesulfonic acid (724.99 mg, 4.83 mmol, 423.97 μL) was added at 30° C. The reaction solution was stirred for 2 hr at 70° C. $Boc_2O$ (1.05 g, 4.83 mmol, 1.11 mL) was added and stirred at 25° C. for 1 hr. The mixture was filtered and concentrated. The residue was purified by column chromatography on silica gel (EA/PE=1/1-1/0) to give 19-I (600 mg, 1.51 mmol, 62.37% yield).

Step 9: 19-J

To a mixture of 19-I (68.91 mg, 173.03 μmol) and (4-fluoro-3,5-dimethyl-phenyl)boronic acid (37.78 mg, 224.94 μmol) in dioxane (4 mL) and $H_2O$ (1 mL) was added $Pd(dppf)Cl_2$ (12.66 mg, 17.30 μmol) and $K_2CO_3$ (71.74 mg, 519.10 μmol) at 30° C. The reaction solution was stirred for 2 hr at 100° C. The mixture was filtered and concentrated. The residue was purified by column chromatography on silica gel (EA/PE=1/1-1/0) to give 19-J (70 mg, 158.55 μmol, 91.63% yield).

Step 10: 19-K

To a mixture of 19-J (70 mg, 158.55 μmol), Intermediate 1 (62.26 mg, 271.80 mol), $K_2CO_3$ (75.13 mg, 543.60 μmol) and CuI (17.25 mg, 90.60 μmol) in NMP (5 mL) was stirred at 80° C. for 6 hr. Then, the solution was concentrated and purified by silica gel chromatography (PE/EA/TEA=4/1/0.01-1/1:0.01) to obtain 19-K (68 mg, 115.33 μmol, 72.7% yield). MS: m/z=590.4 (M+1).

Step 11: Intermediate 19

19-K (50 mg, 84.80 μmol) was dissolved in HCl/dioxane (4 M, 2 mL) and stirred at 25° C. for 16 hr. The reaction was then concentrated to give Intermediate 19 (45 mg, 95% yield). MS: m/z=490.1 (M+1).

Example 12: Synthesis of Intermediates 20-24

Intermediates 20-24 in Table 3 were made according to the procedure of Intermediate 19.

TABLE 3

| Name | Structure | $^1$H NMR and/or LC/MS data |
|---|---|---|
| Intermediate 20 | 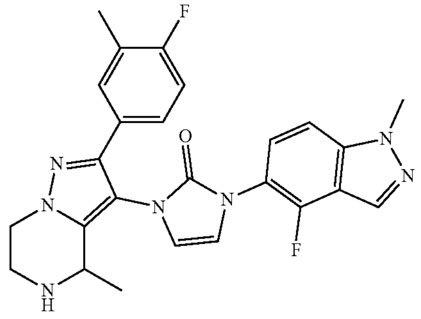 [SMILES: Cc1cc(-c2nn3c(c2-n2ccn(-c4ccc5c(cnn5C)c4F)c2=O)C(C)NCC3)ccc1F] | MS: m/z = 476 (M + 1). |
| Intermediate 21 | 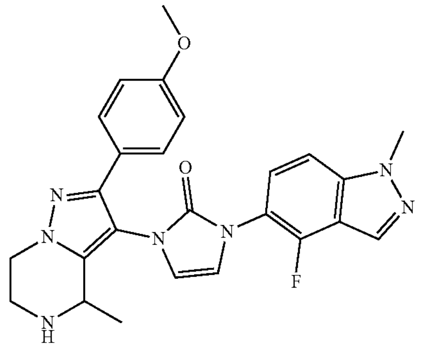 [SMILES: COc1ccc(-c2nn3c(c2-n2ccn(-c4ccc5c(cnn5C)c4F)c2=O)C(C)NCC3)cc1] | MS: m/z = 474 (M + 1). |

TABLE 3-continued
| Name | Structure | $^1H$ NMR and/or LC/MS data |
|---|---|---|
| Intermediate 22 | 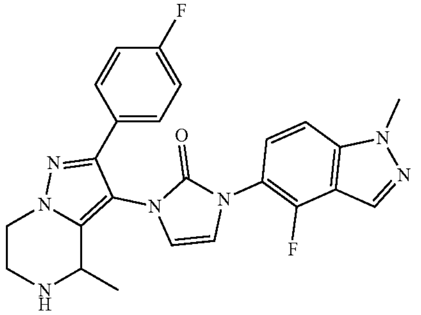 [SMILES: CC1NCCn2nc(-c3ccc(F)cc3)c(-n3ccn(-c4ccc5c(cnn5C)c4F)c3=O)c21] | MS: m/z = 462.1 (M + 1). |
| Intermediate 23 | 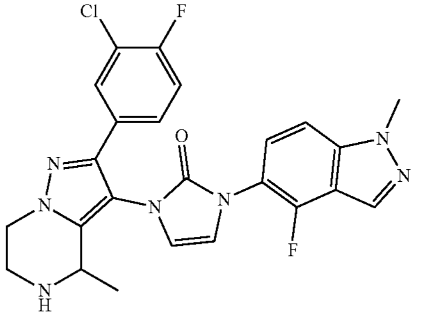 [SMILES: CC1NCCn2nc(-c3ccc(F)c(Cl)c3)c(-n3ccn(-c4ccc5c(cnn5C)c4F)c3=O)c21] | MS: m/z = 496.1 (M + 1) |
| Intermediate 24 | 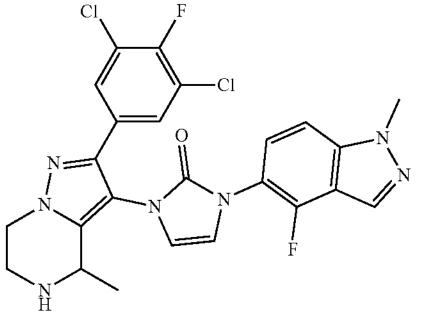 [SMILES: CC1NCCn2nc(-c3cc(Cl)c(F)c(Cl)c3)c(-n3ccn(-c4ccc5c(cnn5C)c4F)c3=O)c21] | MS: m/z = 530.1 (M + 1) |
Example 13: Synthesis of Intermediate 25
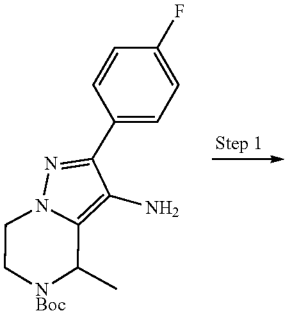
25-A
-continued
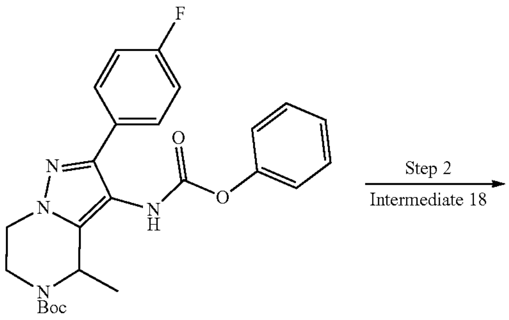
25-B -continued

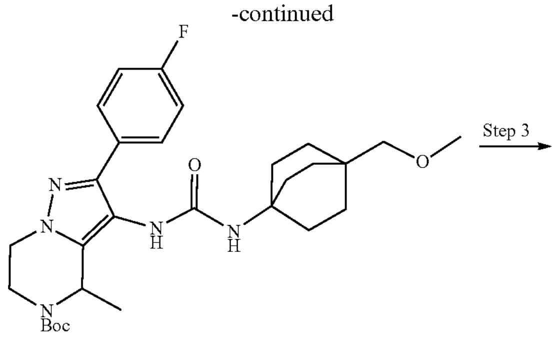

25-C

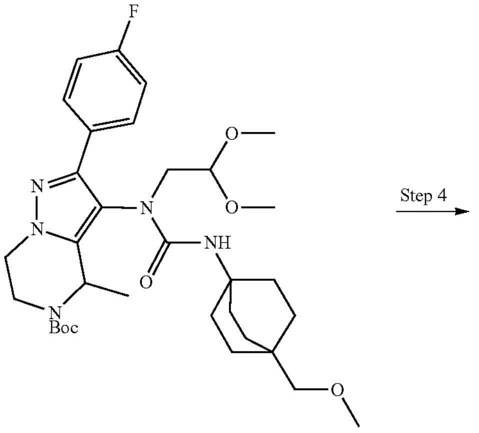

25-D

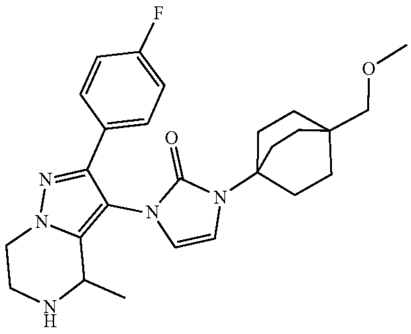

Intermediate 25

Step 1: 25-B

To a solution of 25-A (intermediate for Intermediate 22, 0.26 g, 750.58 μmol), DIEA (291 mg, 2.25 mmol) in THF (5 mL) was added phenyl carbonochloridate (153 mg, 975.76 μmol). The reaction was stirred at 0° C. for 2 hr. The reaction was concentrated to give 25-B (0.4 g, crude). MS: m/z=467.1 (M+1).

Step 2: 25-C

To a solution of 25-B (0.4 g) in pyridine (8 mL) was added Intermediate 18 (290 mg, 1.71 mmol), the reaction was stirred at 20° C. for 15 hr. The mixture was concentrated to give a residue, which was purified by silica gel column (PE/EA=1/1) to give 25-C (0.33 g, 71% yield). MS: m/z=542.2 (M+1).

Step 3: 25-D

To a solution of 25-C (0.3 g, 553.86 μmol) in dioxane (10 mL) was added 2-bromo-1,1-dimethoxy-ethane (2.8 g, 16.62 mmol, 2 mL), t-BuOK (620 mg, 5.54 mmol) and 18-crown-6 (586 mg, 2.22 mmol). The reaction was sealed in a tube and heated at 120° C. for 36 hr. The solvent was removed, and the residue was diluted with 20 mL of ethyl acetate. The organic layer was washed with water (5 mL×2), dried over sodium sulfate and concentrated to give the crude product. The crude product was purified by flash column chromatography (PE/EA=1/1) to give 25-D (0.18 g, 52% yield). MS: m/z=630.4 (M+1).

Step 4: Intermediate 25

To a solution of 25-D (0.18 g, 285.82 μmol) in ethyl acetate (2 mL) was added HCl (2 M, 1.4 mL). The reaction was stirred at 25° C. for 6 hr. The reaction was concentrated to give a residue, which was purified by reverse-phase column (55% MeCN in water) to give Intermediate 25 (0.08 g, 56% yield). MS: m/z=466.2 (M+1).

Example 14: Synthesis of Intermediates 19-P1 and 19-P2

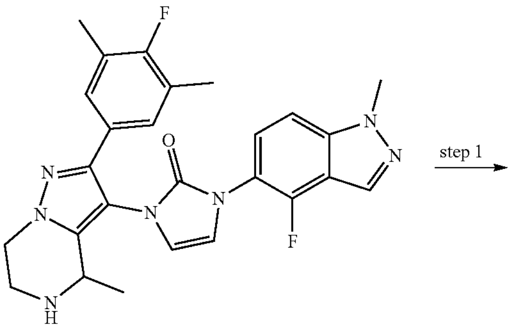

intermediate 19

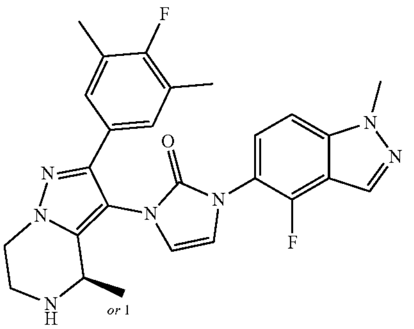

+ intermediate 19-P1

-continued

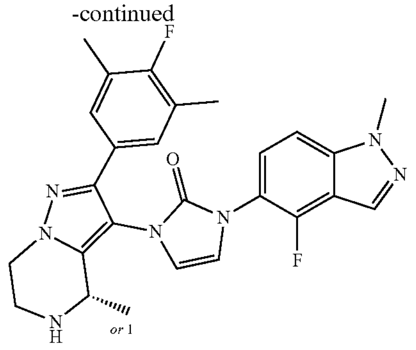

intermediate 19-P2

Intermediate 19 (45 mg) was separated by SFC (Column: Daicel CHIRALPAK OD-H 250 mm×20 mm I.D. 5 μm; Mobile phase: $C_{02}$/MeOH (0.2% $NH_4$—OH)=65/35; Flow rate: 50 g/min; Wave length: UV 214 nm; Temperature: 35° C.) to give Intermediate 19-P1 (23 mg) and Intermediate 19-P2 (16 mg).

Example 15: Isolation of Intermediates 17-P1, 17-P2, 20-P1, 20-P2, 22-P1, 22-P2, 23-P1, 23-P2, 24-P1, 24-P2, 25-P1, and 25-P2

Compounds in Table 4 were obtained by SFC separation as Intermediate 19-P1 and Intermediate 19-P2.

TABLE 4

| Name | Structure | Chiral separation condition |
|---|---|---|
| Intermediate 17-P1 | 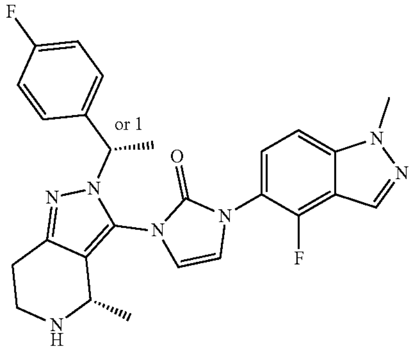 [SMILES: C[C@@H]1NCCc2nn([C@@H](C)c3ccc(F)cc3)c(-n3ccn(-c4ccc5c(cnn5C)c4F)c3=O)c21] | Column: Daicel CHIRALPAK IC-H 250 mm × 20 mm I.D., 5 μm; Mobile phase: $CO_2$/MeOH (0.2% $NH_4$•OH) = 56/44; Flow rate: 50 g/min; Wave length: UV 214 nm; Temperature: 35° C. |
| Intermediate 17-P2 | 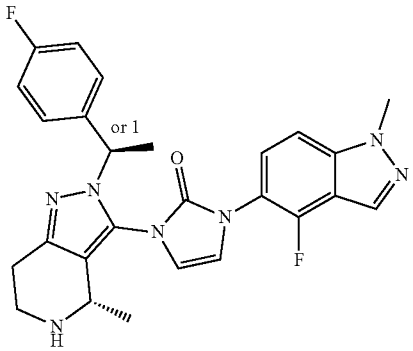 [SMILES: C[C@@H]1NCCc2nn([C@H](C)c3ccc(F)cc3)c(-n3ccn(-c4ccc5c(cnn5C)c4F)c3=O)c21] | |
| Intermediate 20-P1 | 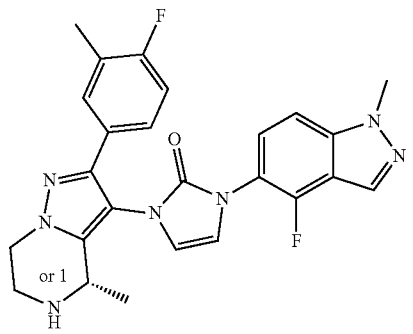 [SMILES: Cc1cc(-c2nn3c(c2-n2ccn(-c4ccc5c(cnn5C)c4F)c2=O)[C@H](C)NCC3)ccc1F] | Column: Daicel CHIRALPAK OD-H 250 mm × 20 mm I.D., 5 μm; Mobile phase: $CO_2$/MeOH (0.2% $NH_4$•OH) = 65/35; Flow rate: 50 g/min; Wavelength: UV 214 nm; Temperature: 35° C. |

TABLE 4-continued
| Name | Structure | Chiral separation condition |
|---|---|---|
| Intermediate 20-P2 | 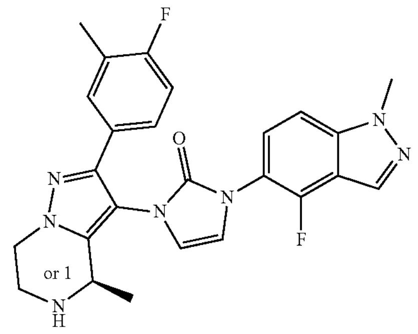 [SMILES: Cc1cc(-c2nn3c(c2-n2ccn(-c4ccc5c(cnn5C)c4F)c2=O)[C@@H](C)NCC3)ccc1F] | |
| Intermediate 22-P1 | 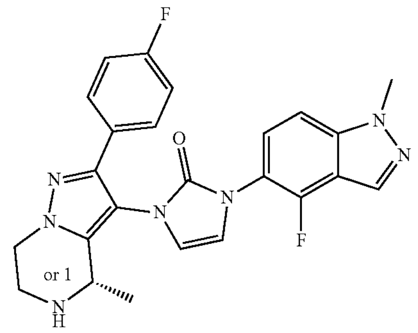 [SMILES: C[C@@H]1NCCn2nc(-c3ccc(F)cc3)c(-n3ccn(-c4ccc5c(cnn5C)c4F)c3=O)c21] | Column: CHIRALPAK OD-H 250 mm × 20 mm, 5 μm; Modifier: 50% methanol (0.2% DEA); Total Flow: 40 g/min; Wavelength: UV 214 nm; Temperature: 35° C. |
| Intermediate 22-P2 | 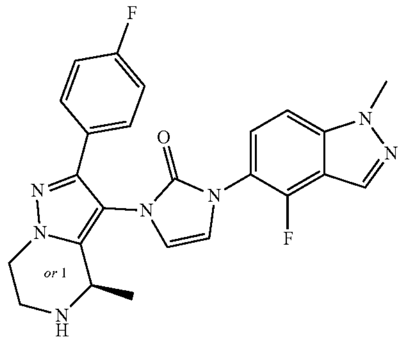 [SMILES: C[C@H]1NCCn2nc(-c3ccc(F)cc3)c(-n3ccn(-c4ccc5c(cnn5C)c4F)c3=O)c21] | |
| Intermediate 23-P1 | 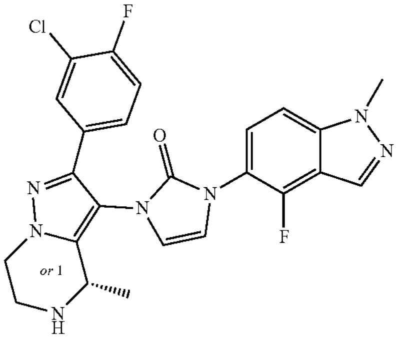 [SMILES: C[C@@H]1NCCn2nc(-c3ccc(F)c(Cl)c3)c(-n3ccn(-c4ccc5c(cnn5C)c4F)c3=O)c21] | Column: Daicel CHIRALPAK OD-H 250 mm × 20 mm I.D., 5 μm; Mobile phase: $CO_2$/MeOH (0.2% $NH_4$•OH) = 70/30; Flow rate: 50 g/min; Wave length: UV 214 nm; Temperature: 35° C. |

TABLE 4-continued

| Name | Structure | Chiral separation condition |
| --- | --- | --- |
| Intermediate 23-P2 | 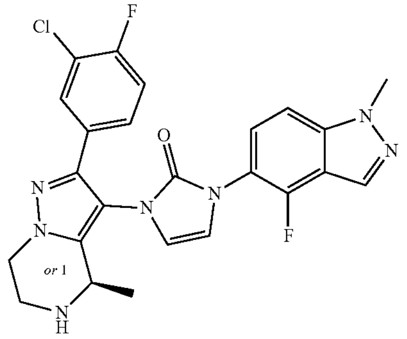 [SMILES: C[C@H]1NCCn2nc(-c3ccc(F)c(Cl)c3)c(-n3ccn(-c4ccc5c(cnn5C)c4F)c3=O)c21] | |
| Intermediate 24-P1 | 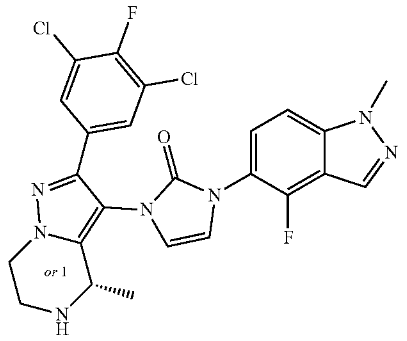 [SMILES: C[C@@H]1NCCn2nc(-c3cc(Cl)c(F)c(Cl)c3)c(-n3ccn(-c4ccc5c(cnn5C)c4F)c3=O)c21] | Column: Daicel CHIRALPAK OZ-H 250 mm × 20 mm I.D., 5 μm; Mobile phase: $CO_2$/MeOH (0.2% $NH_4$•OH) = 70/30; Flow rate: 50 g/min; Wavelength: UV 214 nm; Temperature: 35° C. |
| Intermediate 24-P2 | 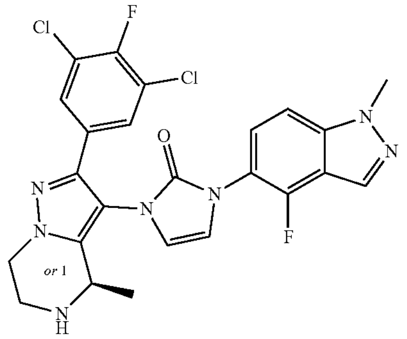 [SMILES: C[C@H]1NCCn2nc(-c3cc(Cl)c(F)c(Cl)c3)c(-n3ccn(-c4ccc5c(cnn5C)c4F)c3=O)c21] | |
| Intermediate 25-P1 | 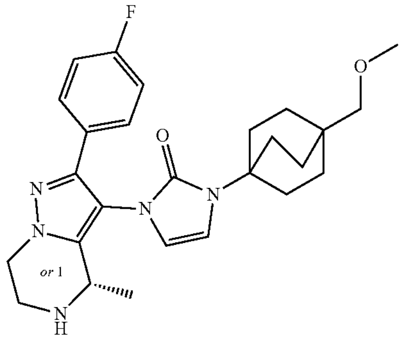 [SMILES: COCC12CCC(n3ccn(-c4c(-c5ccc(F)cc5)nn5c4[C@H](C)NCC5)c3=O)(CC1)CC2] | Column: Daicel CHIRALPAK OD-H 250 mm × 20 mm I.D., 5 μm; Mobile phase: $CO_2$/MeOH (0.2% $NH_4$•OH) = 80/20; Flow rate: 50 g/min; Wave length: UV 214 nm; Temperature: 35° C. |

TABLE 4-continued

| Name | Structure | Chiral separation condition |
|---|---|---|
| Intermediate 25-P2 | 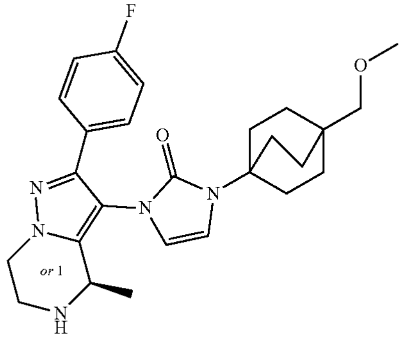 [SMILES: COCC12CCC(n3ccn(-c4c(-c5ccc(F)cc5)nn5c4[C@@H](C)NCC5)c3=O)(CC1)CC2] | |

Example 16: Synthesis of Intermediate 26

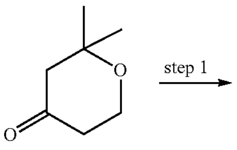

26-A

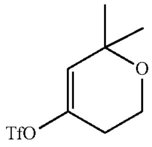

and/or

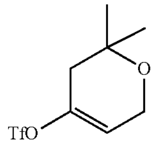

Intermediate 26

To a solution of 26-A (25 g, 195.05 mmol) in THF (250 mL) was added LDA (2 M, 117.03 mL) at −70° C. for 0.5 hr. The mixture was stirred at −70° C. for 0.5 hr, and then 1,1,1-trifluoro-N-phenyl-N-(trifluoromethylsulfonyl) methanesulfonamide (76.65 g, 214.56 mmol) in THE (250 mL) was added to the reaction mixture at −60° C. for 1 hr. After the addition, the temperature was raised to 25° C. slowly. The mixture was stirred at 25° C. for 16 hr. The reaction mixture was quenched by aqueous $NH_4Cl$ (200 mL) and extracted by ethyl acetate (300 mL×2). The combined organic layers were washed with brine (200 mL), dried over sodium sulfate and concentrated with a rotary evaporator to obtain Intermediate 26 (95 g, crude).

Example 17: Synthesis of Intermediate 27

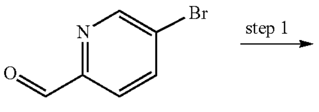

27-A

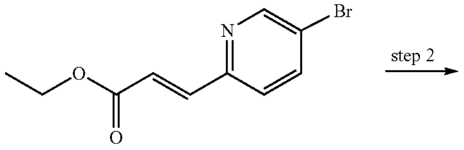

27-B

-continued

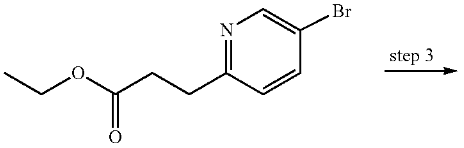

27-C

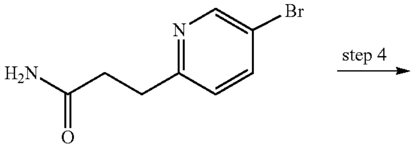

27-D

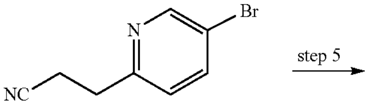

27-E

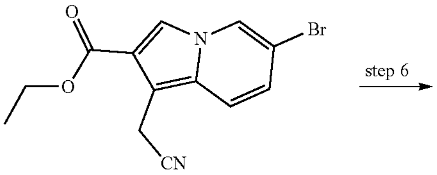

27-F

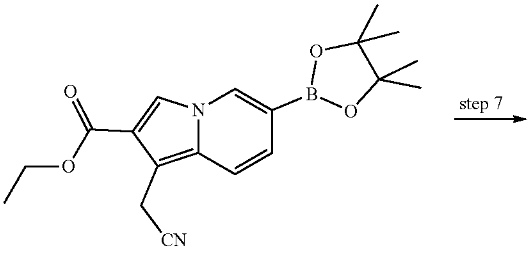

27-G

-continued

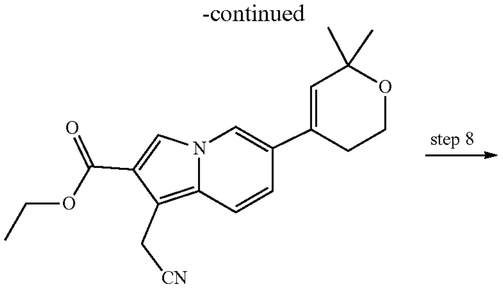

27-H

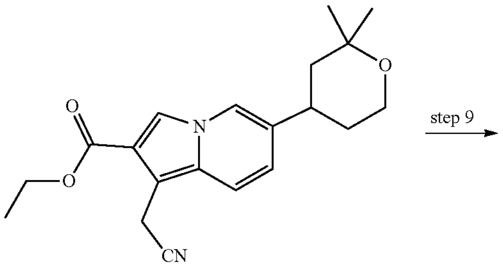

27-I

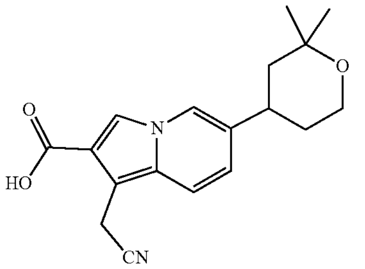

Intermediate 27

Step 1: 27-B

To a solution of 27-A (25 g, 134.40 mmol) in DCM (100 mL) was added ethyl 2-(triphenyl-phosphanylidene)acetate (46.82 g, 134.40 mmol). The reaction was stirred at 0° C. for 2 hr. Solvent was removed under reduced pressure to give a solid, which was then washed by PE/EA=10/1 (100 mL) to afford the crude product. The crude product was purified by silica gel chromatography (PE/EA=10/1-5/1) to give 27-B (26.5 g, 77% yield). MS: m/z=256.0 (M+1, ESI).

Step 2: 27-C

To a solution of 27-B (30 g, 117.14 mmol) in MeOH (300 mL) was added $NaBH_4$ (5.32 g, 140.57 mmol) and $NiCl_2$ (1.52 g, 11.71 mmol). The reaction mixture was stirred for 1 hr. The mixture was diluted with water (200 mL), extracted with EA (200 mL×3). The combined organic layers were washed with brine, dried over sodium sulfate, filtered and concentrated to give 27-C (25 g, 82% yield). MS: m/z=258.0 (M+1).

Step 3: 27-D

To a solution of 27-C (25 g, 96.86 mmol) in MeOH (200 mL) was added $NH_3.H_2O$ (1.13 kg, 30%). The reaction mixture was stirred for 16 hr. Solvent was removed under vacuum to give 27-D (20 g, 90% yield). MS: m/z=229.0 (M+1).

Step 4: 27-E

To a solution of 27-D (20 g, 87.31 mmol) in dry dioxane (200 mL) was added TFAA (36.6 g, 174.62 mmol, 24.61 mL) and pyridine (17.2 g, 218.27 mmol, 17.65 mL) at 0° C. The reaction mixture was stirred at 0° C. for 1 hr. The reaction was diluted with $H_2O$ (200 mL) and extracted with ethyl acetate (200 mL×3). The combined organic layers were washed with brine, dried over sodium sulfate, filtered and concentrated to give the crude product, which was purified by flash chromatography (PE/EA=3/1) to give 27-E (16 g, 87% yield). MS: m/z=211.0 (M+1).

Step 5: 27-F

To a solution of 27-E (15 g, 71.07 mmol) in MeCN (200 mL) was added ethyl 3-bromo-2-oxo-propanoate (27.7 g, 142.14 mmol, 17.77 mL) and $NaHCO_3$ (11.9 g, 142.14 mmol). The mixture was stirred at 90° C. for 16 hr. The mixture was filtered, and the filtrate was concentrated in vacuum to give a residue, which was purified by silica gel chromatography (PE/EA=4/1) to give 27-F (1.0 g, 5% yield).

Step 6: 27-G

A mixture of 4,4,5,5-tetramethyl-2-(4,4,5,5-tetramethyl-1,3,2-dioxaborolan-2-yl)-1,3,2-dioxaborolane (298 mg, 1.17 mmol), 27-F (300 mg, 976.75 μmol), $Pd(dppf)Cl_2$ (71.47 mg, 97.67 μmol), and potassium acetate (192 mg, 1.95 mmol) in dioxane (5 mL) was stirred at 90° C. for 8 hr. The mixture was concentrated in vacuum, the residue was added to water (20 mL), and extracted with ethyl acetate (20 mL×2). The combined organic layers were washed with brine (20 mL×2), dried over sodium sulfate, concentrated to give 27-G (320 mg). MS: m/z=355.1 (M+1).

Step 7: 27-H

A mixture of 27-G (320 mg, 903.43 μmol), Intermediate 26 (470 mg, 1.81 mmol), potassium carbonate (375 mg, 2.71 mmol), $Pd(dppf)Cl_2$ (66 mg, 90.34 μmol) in dioxane (3 mL) and water (1 mL) was stirred at 110° C. for 2 hr. The mixture was concentrated and the residue was added to water (20 mL), extracted with ethyl acetate (20 mL×2). The combined organic layers were washed with brine (20 mL×2), dried over sodium sulfate, concentrated and purified by column chromatography on silica gel (PE/EA=8/1) to give 27-H (200 mg, 59% yield). MS: m/z=339.1 (M+1).

Step 8: 27-I

To a solution of 27-H (150 mg, 443.26 μmol) in MeOH (3 mL) was added Pd/C (47 mg, 10%), the mixture was stirred at 25° C. for 1 hr under $H_2$. The mixture was filtered, and the filtrate was concentrated to give 27-I (145 mg). MS: m/z=341.1 (M+1).

Step 9: Intermediate 27

To a solution of 27-I (180 mg, 528.77 μmol) in methanol (5 mL) was added sodium hydroxide solution (5 M, 1.06 mL), and stirred at 50° C. for 3 hr. The reaction mixture was adjusted to pH~3 with HCl (1 M). The solution was extracted with ethyl acetate (10 mL×3), and the combined organic layers were dried over sodium sulfate and concentrated to give a residue, which was purified by reverse-phase column (35% MeCN in $H_2O$) to give Intermediate 27 (98 mg, 59% yield). MS: m/z=313.2 (M+1).

Example 18: Synthesis of Intermediate 28

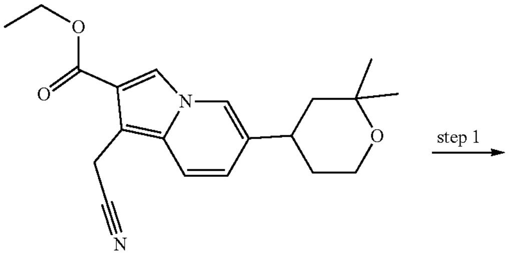

27-I

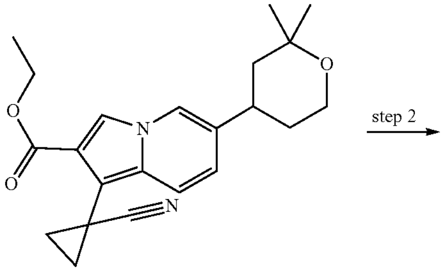

28-A

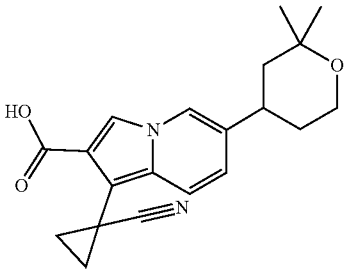

Intermediate 28

Step 1: 28-A

To a solution of 27-I (330 mg, 969.40 μmol) and 1,3,2-dioxathiolane 2,2-dioxide (361 mg, 2.91 mmol) in DMPU (10 mL) was added KHMDS (1 M, 7.76 mL) dropwise at 0° C. The reaction mixture was stirred for 1 hr at 0° C. Saturated $NH_4Cl$ solution (10 mL) was added to quench the reaction. The reaction mixture was diluted with water (30 mL) and extracted with ethyl acetate (30 mL×3). The organic phase was washed with aqueous LiCl (10 mL×3), followed by brine (15 mL), dried over anhydrous sodium sulfate and concentrated to dryness. The crude product was purified by flash column chromatography (PE/EA=1/1) to give 28-A (200 mg, 56% yield). MS: m/z=367.2 (M+1).

Step 2: Intermediate 28

To a solution of 28-A (81 mg, 221.04 μmol) in MeOH (3 mL) was added aqueous NaOH (2 M, 6 mL), and stirred at 50° C. for 2 hr. The reaction mixture was extracted with ethyl acetate (10 mL×2). Then the aqueous solution was adjusted to pH~3 with HCl (1 M). The solution was extracted with ethyl acetate (10 mL×3) and the combined organic phase was dried over sodium sulfate and concentrated to give Intermediate 28 (80 mg, crude). MS: m/z=339.1 (M+1).

Example 19: Synthesis of Intermediate 29

Intermediate 29 in Table 5 was made according to the procedure of Intermediate 28.

TABLE 5

| Name | Structure | $^1H$ NMR and/or LC/MS data |
|---|---|---|
| Intermediate 29 | 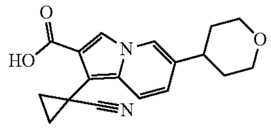 [SMILES: N#CC1(c2c(C(=O)O)cn3cc(C4CCOCC4)ccc23)CC1] | MS: m/z = 311 (M + 1). |

Example 20: Synthesis of Intermediate 30

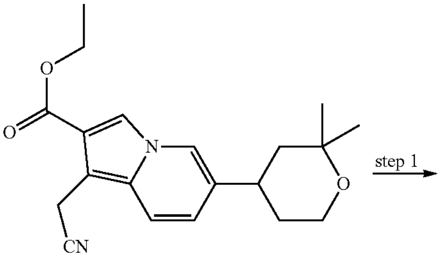

30-A

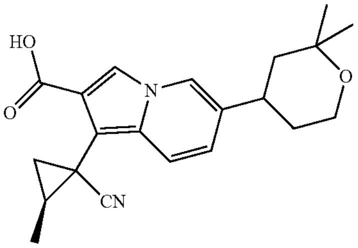

Intermediate 30

To a solution of KHMDS (1 M, 7.05 mL) was added 30-A (300 mg, 881.28 μmol) and (4R)-4-methyl-1,3,2-dioxathiolane 2,2-dioxide (122 mg, 881.28 μmol) in THF (5 mL) at 0° C. The mixture was stirred at 0° C. for 2 hr. The mixture was poured into aqueous $NH_4Cl$ (20 mL), extracted with ethyl acetate (20 mL×2). The combined organic layers were washed with brine (20 mL×2), dried over sodium sulfate, concentrated in vacuum to give Intermediate 30 (300 mg, 96% yield). MS: m/z=353.1 (M+1).

Example 21a: Synthesis of Intermediate 31

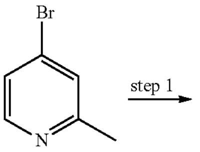

31-A

-continued

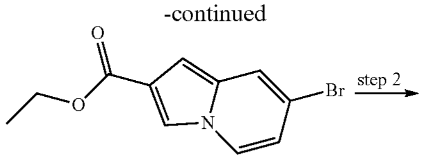

31-B

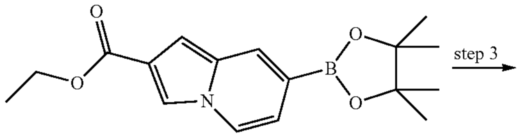

31-C

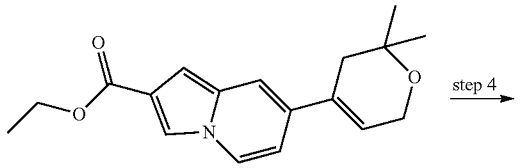

31-D

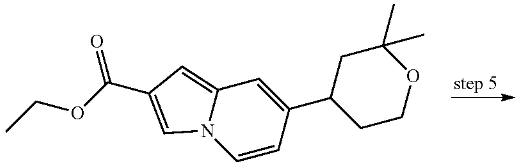

31-E

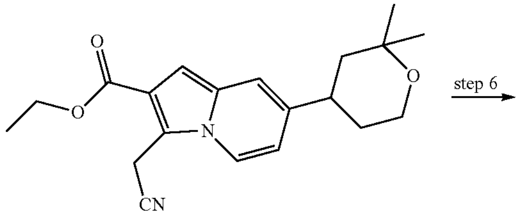

31-F

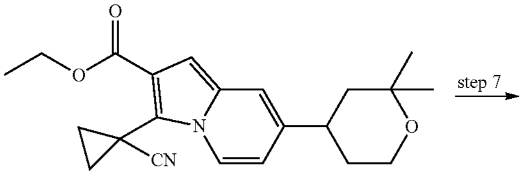

31-G

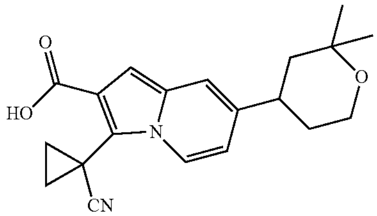

Intermediate 31

Step 1: 31-B

To a solution of 31-A (15 g, 87.20 mmol, 10.34 mL) in MeCN (100 mL) was added sodium bicarbonate (14.65 g, 174.40 mmol) and ethyl 3-bromo-2-oxo-propanoate (25.51 g, 130.80 mmol, 16.35 mL). The mixture was stirred at 90° C. for 16 hr. The mixture was filtered and the filtrate was concentrated in vacuum. The residue was diluted with $H_2O$ (50 mL), extracted with ethyl acetate (50 mL×3), dried over anhydrous sodium sulfate and concentrated to dryness. The crude product was purified by silica gel chromatography (PE/EA=10/1) to give 31-B (2.6 g, 11% yield). MS: m/z=268.1 (M+1).

Step 2: 31-C

A mixture of 31-B (2.43 g, 9.06 mmol), 4,4,5,5-tetramethyl-2-(4,4,5,5-tetramethyl-1,3,2-dioxaborolan-2-yl)-1,3,2-dioxaborolane (2.99 g, 11.78 mmol), KOAc (1.78 g, 18.13 mmol) and Pd(dppf)$Cl_2$ (663 mg, 906.36 μmol) in dioxane (30 mL) was stirred at 90° C. for 16 hr. The mixture was filtered and the filtrate was concentrated in vacuum to give 31-C (2.5 g, crude). MS: m/z=316.2 (M+1).

Step 3: 31-D

To a solution of 31-C (2.5 g, 7.93 mmol) in dioxane (20 mL) and water (5 mL) was added $K_2CO_3$ (2.19 g, 15.86 mmol), Pd(dppf)$Cl_2$ (580 mg, 793.22 μmol), and Intermediate 26 (4.13 g, 15.86 mmol), the mixture was stirred at 90° C. for 1 hr. The reaction mixture was concentrated in vacuum. The residue was diluted with ethyl acetate (50 mL), washed with water (50 mL) and brine (50 mL), dried over sodium sulfate, concentrated in vacuum and purified by column chromatography on silica gel (PE/EA=3/1) to give 31-D (2.1 g, 88% yield). MS: m/z=300.1 (M+1).

Step 4: 31-E

To a solution of 31-D (1.3 g, 4.34 mmol) in methanol (30 mL) was added Pd/C (10%, 50% wet, 400 mg) under hydrogen. The reaction was stirred at 25° C. for 2 hr at 15 psi. The mixture was filtered and the filtrate was concentrated to give 31-E (1.2 g, 92% yield). MS: m/z=302.1 (M+1).

Step 5: 31-F

To a mixture of 31-E (1.1 g, 3.65 mmol), 2-bromoacetonitrile (482 mg, 4.01 mmol, 279.99 μL), ferrous sulfate heptahydrate (508 mg, 1.82 mmol) and NaI (547 mg, 3.65 mmol) in DMSO (10 mL) was added hydrogen peroxide (1.88 mL, 30%) dropwise. The reaction mixture was stirred at 0° C. for 20 min. The reaction was diluted with water (20 mL) and extracted with ethyl acetate (20 mL×3). The combined organic phase was washed with brine, dried over sodium sulfate and concentrated. The residue was purified by silica gel column (PE/EA=4/1) to give 31-F (530 mg, 43% yield). MS: m/z=341.3 (M+1).

Step 6: 31-G

To a solution of 31-F (220 mg, 646.27 μmol) in DMPU (3 mL) was added 1,3,2-dioxathiolane 2,2-dioxide (241 mg, 1.94 mmol), then LiHMDS (1 M, 5.82 mL) was added to the mixture slowly at 0° C. The mixture was stirred at 0° C. for 2 hr. The mixture was poured into water (10 mL), extracted with ethyl acetate (10 mL×2). The combined organic layers were washed with brine (10 mL×10), dried over sodium sulfate and concentrated to give a residue, which was purified by column chromatography on silica gel (EA/PE=1/5) to give 31-G (135 mg, 57% yield). MS: m/z=367.1 (M+1).

Step 7: Intermediate 31

To a solution of 31-G (135 mg, 368.40 μmol) in MeOH (2 mL) was added NaOH (5 M, 1.47 mL). The mixture was stirred at 50° C. for 3 hr. The mixture was concentrated in vacuum and the residue was added to HCl (1 M, 10 mL), extracted with ethyl acetate (10 mL×2). The combined organic layers were washed with brine (10 mL×2), dried over sodium sulfate, concentrated in vacuum to give Intermediate 31 (65 mg, 50% yield). MS: m/z=339.1 (M+1).

Example 21b: Synthesis of Intermediate 32

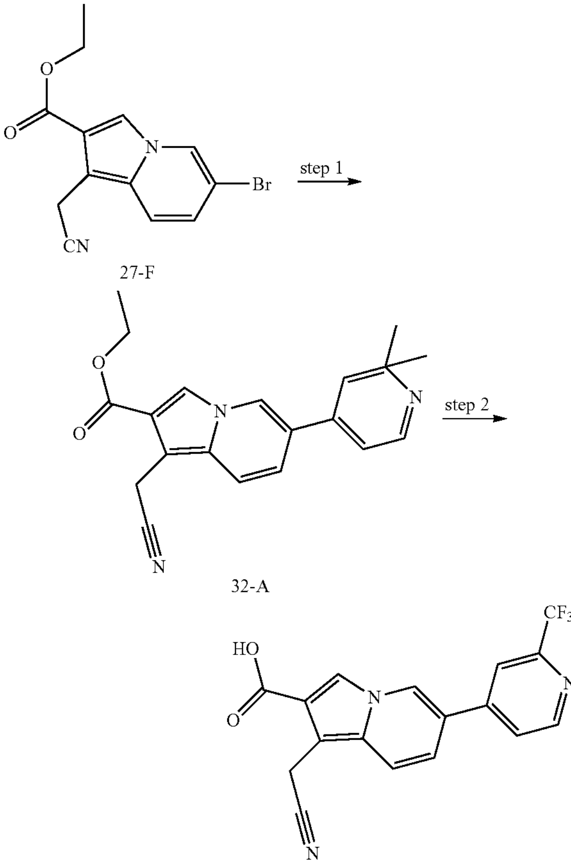

27-F

32-A

Intermediate 32

Step 1: 32-A

To a solution of ethyl 27-F (10 mg, 32.56 μmol) in dioxane (2 mL) was added 4-(4,4,5,5-tetramethyl-1,3,2-dioxaborolan-2-yl)-2-(trifluoromethyl)pyridine (9 mg, 32.56 μmol), Pd(dppf)$Cl_2$ (3 mg, 3.2 μmol) and $K_2CO_3$ (9 mg, 65.12 μmol). The mixture was stirred at 90° C. for 16 hr. The mixture was concentrated in vacuum to give a residue, which was then diluted with water (20 mL), extracted with ethyl acetate (20 mL×3). The organic phase was washed with brine, dried over sodium sulfate and concentrated in vacuum. The crude was purified by flash chromatography (PE/EA=2/1) to give 32-A (10 mg, 82% yield). MS: m/z=374.1 (M+1).

Step 2: Intermediate 32

To a solution of 32-A (10 mg, 26.79 μmol) in MeOH (1 mL) was added NaOH (5 M, 535.72 μL), the reaction mixture was stirred at 25° C. for 2 hr. The mixture was concentrated and adjusted to pH~5 with 1 N HCl. The mixture was filtered, and the filter cake was washed with $H_2O$ (0.5 mL) and dried on vacuum to give Intermediate 32 (8 mg, 87% yield). MS: m/z=346.2 (M+1).

Example 22: Synthesis of Intermediate 33

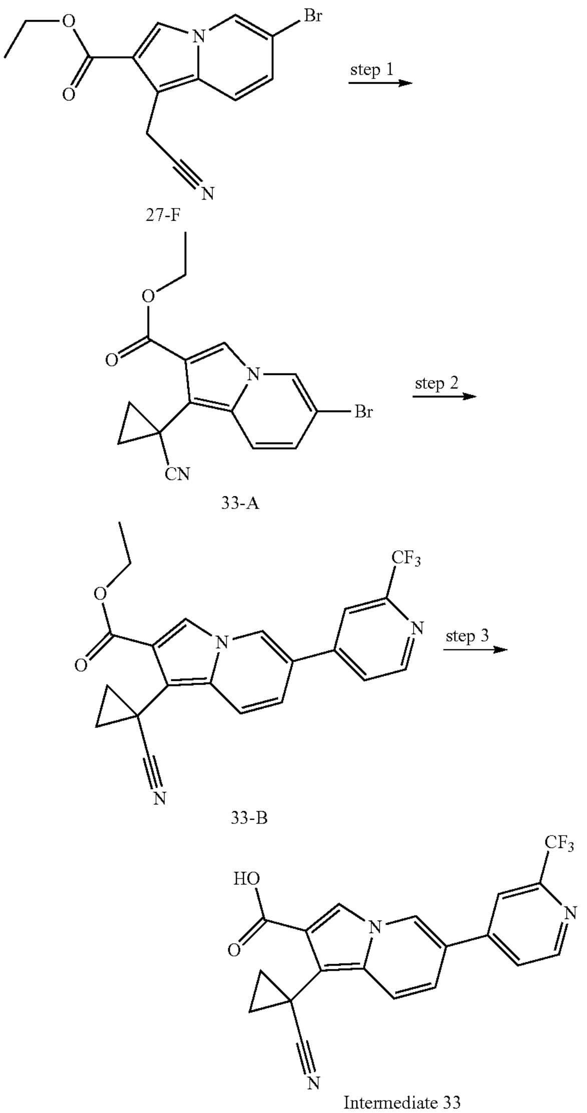

27-F

33-A

33-B

Intermediate 33

Step 1: 33-A

To a three-neck flask was added LiHMDS (1 M, 1.63 mL) and cooled to −40° C., then 27-F (100 mg, 325.58 μmol) and 1,3,2-dioxathiolane 2,2-dioxide (60 mg, 488.37 μmol) in THF (2 mL) was added. The mixture was stirred at −40° C. for 2 hr. The reaction mixture was extracted with ethyl acetate (20 mL×2). The combined organic layers were washed with brine (10 mL×2), dried over sodium sulfate, concentrated in vacuum to give the crude product. The crude was purified by silica gel chromatography (PE/EA=4/1) to give 33-A (20 mg, 18% yield). MS: m/z=333.0 (M+1).

Step 2: 33-B

To a solution of 33-A (15 mg, 45.02 μmol) in dioxane (5 mL) and water (0.5 mL) was added $K_2CO_3$ (18 mg, 135.06 μmol), 4-(4,4,5,5-tetramethyl-1,3,2-dioxaborolan-2-yl)-2-(trifluoromethyl)pyridine (12 mg, 45.02 μmol) and Pd(dppf) $Cl_2$ (32 mg, 45.02 μmol). The mixture was stirred at 90° C. for 2 hr. Dioxane was removed in vacuum and the crude was diluted with water (20 mL), extracted with ethyl acetate (20 mL×3). The organic layer was washed with brine, dried over sodium sulfate and concentrated in vacuum. The crude was purified by prep-TLC (PE/EA=1/1) to give 33-B (15 mg, 83% yield). MS: m/z=400.1 (M+1).

Step 3: Intermediate 33

To a solution of 33-B (15 mg, 37.56 μmol) in THF (1 mL) and MeOH (1 mL) was added NaOH (6 M, 2.0 mL). The reaction mixture was stirred at 25° C. for 2 hr. The mixture was concentrated and adjusted to pH~5 with 1 N HCl. The reaction mixture was extracted with ethyl acetate (20 mL×3), the combined organic layers were washed with brine (10 mL), dried over sodium sulfate and concentrated in vacuum to give Intermediate 33 (13 mg, 93% yield). MS: m/z=372.0 (M+1).

Example 23: Isolation of Intermediate 27-P1 and Intermediate 27-P2

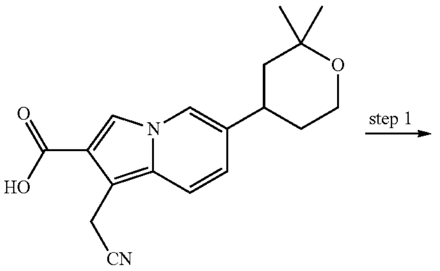

Intermediate 27

-continued

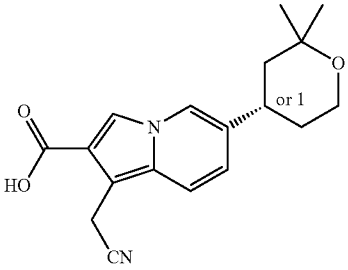

Intermediate 27-P1

+

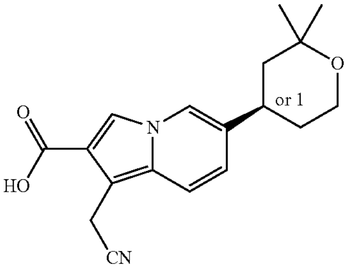

Intermediate 27-P2

Intermediate 27 (100 mg) was separated by SFC (Column: Daicel CHIRALPAK AD-H 0.46 cm I.D.×15 cm L, 5 μm; Mobile phase: HEP/EtOH (0.1% DEA)=60/40; Flow rate: 0.5 mL; Wave length: UV 254 nm; Temperature: 25° C.) to give Intermediate 27-P1 (40 mg) and Intermediate 27-P2 (40 mg).

Example 24: Syntheis and Isolation of Intermediates 28-P1, 28-P2, 30-P1, 30-P2, 30-P3, 30-P4, 31-P1, and 31-P2

Compounds in Table 6 were obtained by SFC separation as described in Intermediate 27-P1 and Intermediate 27-P2.

TABLE 6

| Name | Structure | Chiral separation condition |
|---|---|---|
| Intermediate 28-P1 | 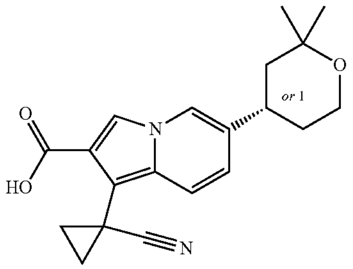 [SMILES: CC1(C)C[C@@H](c2ccc3c(C4(C#N)CC4)c(C(=O)O)cn3c2)CCO1] | Column: AD-H, 0.46 cm I.D. × 15 cm L; Mobile Phase: A/B: HEP/ETOH (0.1% DEA) = 60/40; Flow rate: 0.5 mL; Column Temp: 25° C. |
| Intermediate 28-P2 | 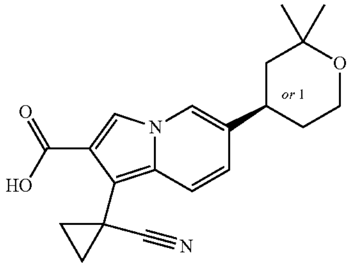 [SMILES: CC1(C)C[C@H](c2ccc3c(C4(C#N)CC4)c(C(=O)O)cn3c2)CCO1] | |

TABLE 6-continued

| Name | Structure | Chiral separation condition |
| --- | --- | --- |
| Intermediate 30-P1 and Intermediate 30-P2 (mixture) | | Column: Daicel CHIRALPAK IG-H 250 mm x 20 mm I.D., 5 μm; Mobile phase: $CO_2$/MeOH (0.2% $NH_4$•OH) = 60/40; Flow rate: 50 g/min; Wavelength: UV 214 nm; Temperature: 35° C. |
| Intermediate 30-P3 | 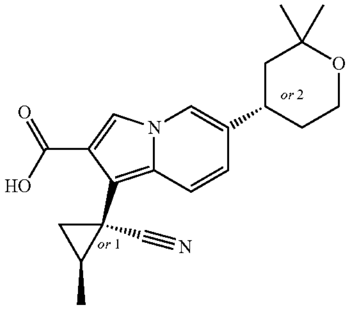 [SMILES: C[C@H]1C[C@@]1(C#N)c1c(C(=O)O)cn2cc([C@H]3CCOC(C)(C)C3)ccc12] | |
| Intermediate 30-P4 | 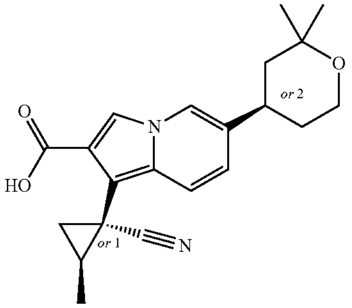 [SMILES: C[C@H]1C[C@@]1(C#N)c1c(C(=O)O)cn2cc([C@@H]3CCOC(C)(C)C3)ccc12] | |
| Intermediate 30-P1 | 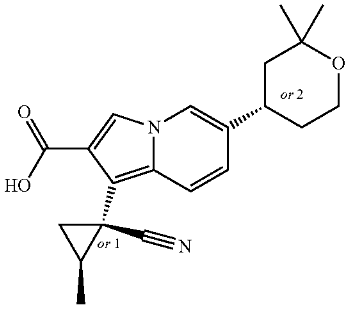 [SMILES: C[C@H]1C[C@]1(C#N)c1c(C(=O)O)cn2cc([C@H]3CCOC(C)(C)C3)ccc12] | Column: Daicel CHIRALPAK IG-H 250 mm x 20 mm I.D., 5 μm; Mobile phase: $CO_2$/MeOH (0.2% $NH_4$•OH) = 70/30; Flow rate: 50 g/min; Wavelength: UV 214 nm; Temperature: 35° C. |
| Intermediate 30-P2 | 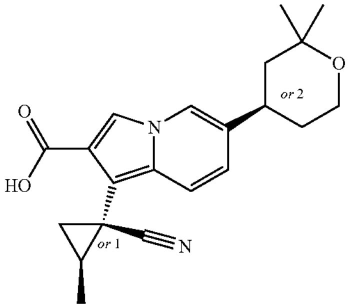 [SMILES: C[C@H]1C[C@]1(C#N)c1c(C(=O)O)cn2cc([C@@H]3CCOC(C)(C)C3)ccc12] | |
| Intermediate 31-P1 | 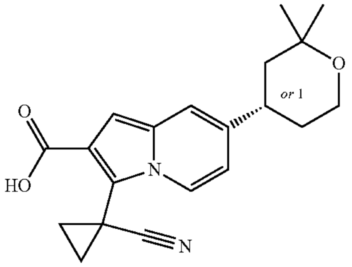 [SMILES: CC1(C)C[C@@H](c2ccn3c(C4(C#N)CC4)c(C(=O)O)cc3c2)CCO1] | Column: Daicel CHIRALPAK IG-H 50 mm x 20 mm I.D., 5 μm; Mobile phase: $CO_2$/MeOH (0.2% $NH_4$•OH) = 50/50; Flow rate: 40 g/min; Wavelength: UV 214 nm; Temperature: 35° C. |

TABLE 6-continued

| Name | Structure | Chiral separation condition |
|---|---|---|
| Intermediate 31-P2 | 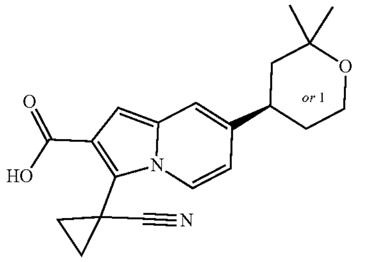 [SMILES: CC1(C)C[C@H](c2ccn3c(C4(C#N)CC4)c(C(=O)O)cc3c2)CCO1] | |

Example 25: Synthesis of Intermediate 34

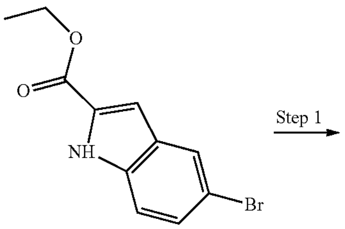

34-A

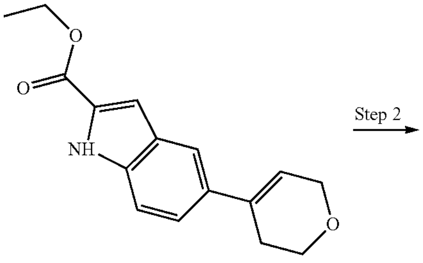

34-B

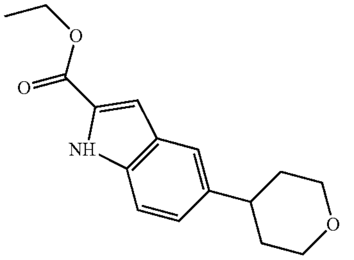

intermediate 34

Step 1: 34-B

To a solution of 34-A (10 g, 37.30 mmol) and 2-(3,6-dihydro-2H-pyran-4-yl)-4,4,5,5-tetramethyl-1,3,2-dioxaborolane (7.84 g, 37.30 mmol) in dioxane (100 mL) and water (10 mL) was added $K_2CO_3$ (10.29 g, 74.60 mmol) and Pd(dppf)$Cl_2$ (2.73 g, 3.73 mmol). The reaction was stirred at 90° C. for 4 hr. The reaction was cooled, diluted with 200 mL ethyl acetate and 100 mL water. The solid was filtered and the organic layer was dried over anhydrous sodium sulfate and concentrated to give a residue, which was combined with the solid to give 34-B (6 g, 59% yield). MS: m/z=272.2 (M+1).

Step 2: Intermediate 34

To a solution of 34-B (5 g, 18.43 mmol) in DMF (25 mL) and MeOH (25 mL) was added Pd/C (10%, 50% wet, 1 g). The mixture was stirred under $H_2$ at 15 psi for 4 hr. The mixture was filtered and the filtrate was concentrated to give a residue, which was purified by silica gel column chromatography (PE/EA=9/1) to give Intermediate 34 (3.8 g, 72% yield). MS: m/z=274.1 (M+1).

Example 26: Synthesis of Intermediates 35 and 36

Intermediates 35-36 in Table 7 were made according to the procedure of Intermediate 34.

TABLE 7

| Name | Structure | $^1$H NMR and/or LC/MS data |
|---|---|---|
| Intermediate 35 | 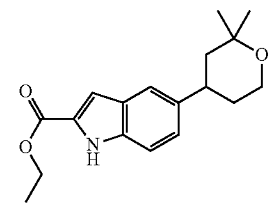 [SMILES: CCOC(=O)c1cc2cc(C3CCOC(C)(C)C3)ccc2[nH]1] | MS: m/z = 302 (M + 1) |
| Intermediate 36 | 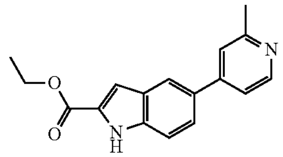 [SMILES: CCOC(=O)c1cc2cc(-c3ccnc(C)c3)ccc2[nH]1] | MS: m/z = 281.1 (M + 1) |

Example 27: Synthesis of Intermediate 37

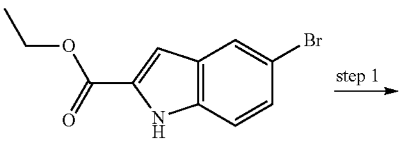

34-A

-continued

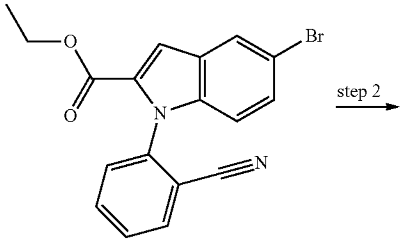

37-A

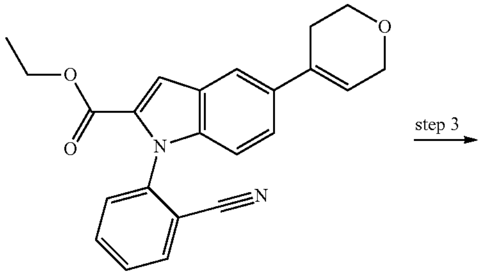

37-B

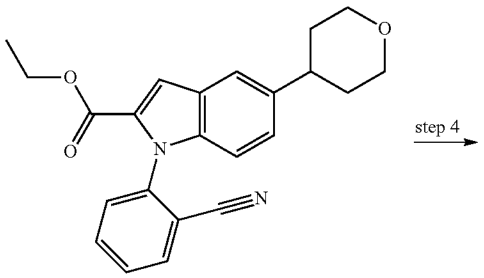

37-C

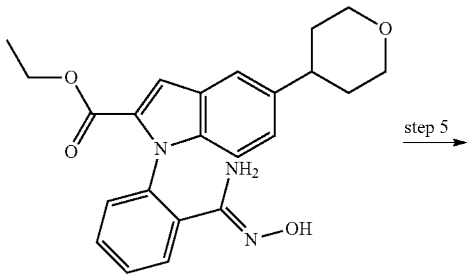

37-D

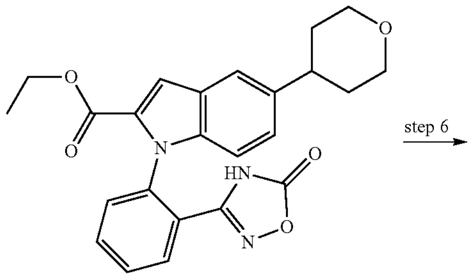

37-E

-continued

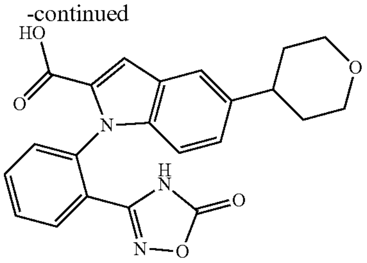

Intermediate 37

Step 1: 37-A

To a solution of 34-A (5.0 g, 18.65 mmol) in DMSO (50 mL) was added 2-fluorobenzonitrile (6.78 g, 55.95 mmol, 6.05 mL) and potassium tert-butoxide (6.28 g, 55.95 mmol). The mixture was stirred at 140° C. for 16 hr. The mixture was cooled to 25° C., poured into water, extracted with ethyl acetate (30 mL×2). The combined organic layers were washed with water (30 mL×2) and brine (30 mL), concentrated in vacuum and purified by column chromatography on silica gel (PE/EA=20/1 to 10/1) to give 37-A (2.5 g, 36% yield). MS: m/z=369 (M+1).

Step 2: 37-B

To a solution of 37-A (1.3 g, 3.52 mmol) in dioxane (10 mL) was added 2-(3,6-dihydro-2H-pyran-4-yl)-4,4,5,5-tetramethyl-1,3,2-dioxaborolane (887.62 mg, 4.23 mmol), Pd(dppf)$Cl_2$ (257.39 mg, 352.10 μmol), sodium carbonate (559.78 mg, 5.28 mmol) and water (2 mL). The mixture was stirred at 90° C. for 1 hr. The mixture was filtered, the filtrate was concentrated in vacuum and purified by column chromatography on silica gel (PE/EA=10/1) to give 37-B (1.22 g, 88% yield). MS: m/z=373 (M+1).

Step 3: 37-C

To a solution of 37-B (600 mg, 1.52 mmol) in EtOH (10 mL) was added Pd/C (60 mg, 10%, 55% wet). The mixture was stirred at 25° C. for 30 min under hydrogen. The mixture was filtered, and the filtrate was concentrated in vacuum to give 37-C (560 mg, crude). MS: m/z=375 (M+1).

Step 4: 37-D

To a solution of 37-C (200 mg, 534.14 μmol) in DMSO (5 mL) was added hydroxylamine hydrochloride (185.59 mg, 2.67 mmol) and sodium bicarbonate (224.37 mg, 2.67 mmol). The mixture was stirred at 60° C. for 4 hr. The mixture was poured into water, extracted with ethyl acetate (10 mL×2). The combined organic layers were washed with water (10 mL) and brine (10 mL), dried over sodium sulfate, concentrated in vacuum to give 37-D (200 mg, crude). MS: m/z=408 (M+1).

Step 5: 37-E

To a solution of 37-D (200 mg, 343.59 μmol) in DMSO (5 mL) was added di(imidazol-1-yl)methanone (111 mg, 687 μmol) and 2,3,4,6,7,8,9,10-octahydropyrimido[1,2-a]azepine (104 mg, 687 μmol). The mixture was stirred at 25° C. for 3 hr. The mixture was poured into water and extracted with ethyl acetate (10 mL×2). The combined organic layers were washed with water (10 mL) and brine (10 mL), dried over sodium sulfate, and concentrated to give 37-E (120 mg, crude). MS: m/z=434, (M+1).

Step 6: Intermediate 37

To a solution of 37-E (120 mg, 229 μmol) in MeOH (5 mL) was added NaOH (2 M, 1.15 mL). The mixture was stirred at 60° C. for 1 hr. The mixture was concentrated and to the residue was added water (10 mL). The mixture was extracted with ethyl acetate (10 mL×2), and the water phase was neutralized with aqueous HCl, extracted with ethyl acetate (10 mL×2). The combined organic layers were washed with brine (10 mL), dried over sodium sulfate, and concentrated in vacuum to give Intermediate 37 (90 mg, 67% yield). MS: m/z=406, (M+1).

Example 28: Synthesis of Intermediate 38

Intermediate 38 in Table 8 was made according to the procedure of Intermediate 37.

TABLE 8

| Name | Structure | $^1$H NMR and/or LC/MS data |
|---|---|---|
| Intermediate 38 | 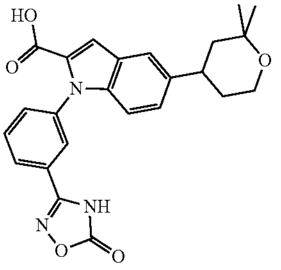 [SMILES: CC1(C)CC(c2ccc3c(c2)cc(C(=O)O)n3-c2cccc(-c3noc(=O)[nH]3)c2)CCO1] | MS: m/z = 434 (M + 1). |

Example 29: Synthesis of Intermediate 39

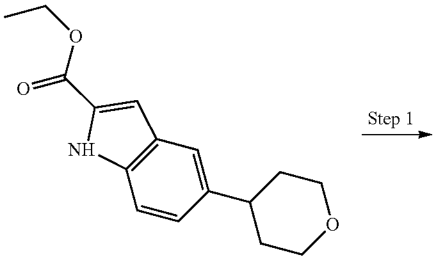

intermediate 34

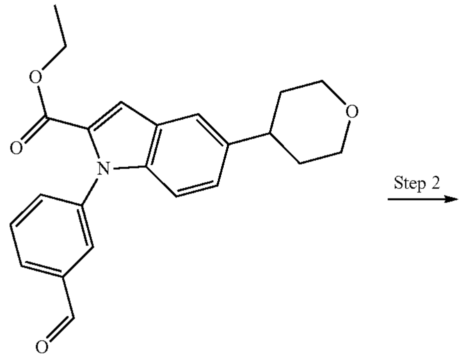

39-A

-continued

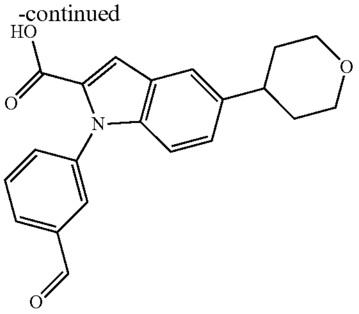

Intermediate 39

Step 1: 39-A

To a solution of Intermediate 34 (300 mg, 1.10 mmol) in DCM (6 mL) was added 4 Å molecular sieves (500 mg), (3-formylphenyl)boronic acid (247 mg, 1.65 mmol), DIEA (355 mg, 2.74 mmol, 477.94 μL) and $Cu(OAc)_2$ (218 mg, 1.10 mmol). The mixture was stirred at 35° C. under oxygen for 16 hr. Water (50 mL) was added to quench the reaction. The resulting solution was extracted with ethyl acetate (50 mL×2), and the combined organic layers were washed with brine, dried over anhydrous sodium sulfate, and concentrated to give a residue. The residue was purified by silica gel chromatography (PE/EA=20/1) to give 39-A (290 mg, 70% yield). MS: m/z=400.1 (M+23).

Step 2: Intermediate 39

To a solution of 39-A (290 mg, 768.35 μmol) in MeOH (6 mL) was dropwise added 2 M NaOH (2 mL) at 0° C. The reaction solution was stirred at 25° C. for 16 hr. The mixture was concentrated to give a residue, which was then diluted with water (20 mL), adjusted to pH 3-4 with 6 M HCl at 0° C. and extracted with ethyl acetate (20 mL×3). The combined organic layers were dried over anhydrous sodium sulfate and concentrated to give Intermediate 39 (245 mg, 91% yield). MS: m/z=350.2 (M+1).

Example 30: Synthesis of Intermediate 40

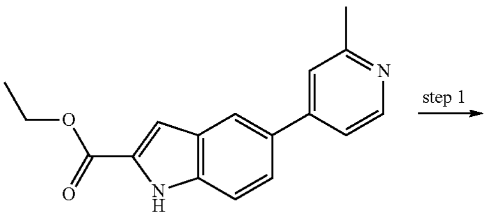

Intermediate 36

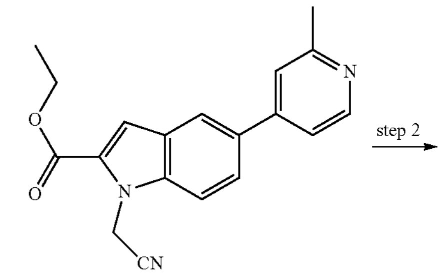

40-A

-continued

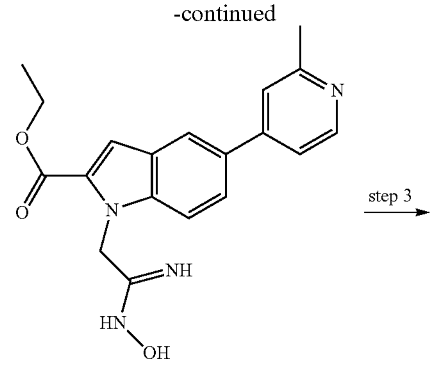

40-B

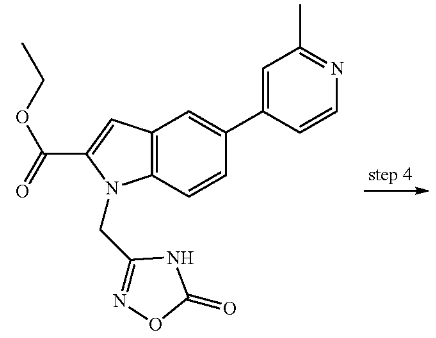

40-C

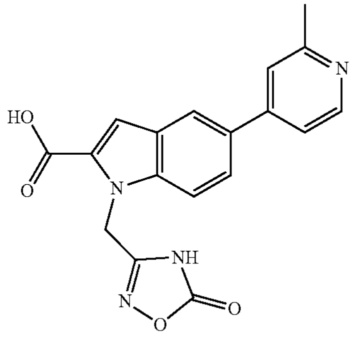

Intermediate 40

Step 1: 40-A

To a solution of Intermediate 36 (1.1 g, 3.92 mmol) in DMF (10 mL) was added potassium bis(trimethylsilyl) amide (0.5 M, 15.70 mL) in an ice-water bath, which was then stirred for 1 hr at 25° C. 2-chloroacetonitrile (888.77 mg, 11.77 mmol, 740.64 μL) was added and the resulting solution was stirred at 25° C. for 16 hr. To the mixture was added saturated aqueous $NH_4Cl$ (50 mL) and extracted with ethyl acetate (20 mL×3), the combined organic layers were dried over sodium sulfate and concentrated under reduced pressure. The residue was purified by silica gel column (PE/EA=2/1) to give 40-A (1.1 g, 87.78% yield). MS: m/z=319.9 (M+1).

Step 2: 40-B

To a solution of 40-A (1.1 g, 3.44 mmol) in ethanol (15 mL) was added hydroxylamine hydrochloride (718.07 mg, 10.33 mmol) and DIPEA (1.34 g, 10.33 mmol). The mixture was stirred at 80° C. for 16 hr. The reaction mixture was concentrated under vacuum to give a crude product, which was purified by column chromatography (PE/EA=1/1) to give 40-B (1.1 g, 90.63% yield). MS: m/z=353.1 (M+1).

Step 3: 40-C

To a solution of 40-B (1.1 g, 3.12 mmol) in DMSO (10 mL) was added di(imidazol-1-yl)methanone (1.01 g, 6.24 mmol) and 2,3,4,6,7,8,9,10-octahydropyrimido[1,2-a]azepine (950.44 mg, 6.24 mmol, 931.80 μL). The reaction mixture was stirred at 25° C. for 3 hr. The reaction mixture was cooled to 0° C., quenched with saturated aqueous $NH_4Cl$ (25 mL) and extracted with ethyl acetate (15 mL×3). The combined organic layers were dried over sodium sulfate and concentrated under vacuum to give 40-C (1 g, 84.66% yield). MS: m/z=378.8 (M+1).

Step 4: Intermediate 40

To a solution of 40-C (500 mg, 1.32 mmol) in water (5 mL), THE (5 mL) and methanol (5 mL) was added lithium hydroxide hydrate (277.26 mg, 6.61 mmol). The resulting solution was stirred at 25° C. for 16 hr. About half volume of methanol was removed in vacuum and HCl (1 M) was added to the residue until pH~5. The resulting mixture was extracted with ethyl acetate (20 mL×2), and the combined organic layers were dried over sodium sulfate and concentrated under reduced pressure to give Intermediate 40 (400 mg, 86.41% yield). MS: m/z=351.1 (M+1).

Example 31: Synthesis of Intermediate 41

Intermediate 41 in Table 9 was made according to the procedure of Intermediate 40.

TABLE 9

| Name | Structure | $^1$H NMR and/or LC/MS data |
|---|---|---|
| Intermediate 41 | 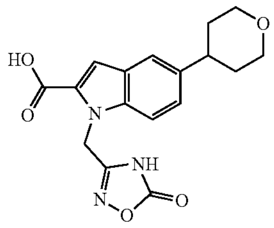 [SMILES: O=C(O)c1cc2cc(C3CCOCC3)ccc2n1Cc1noc(=O)[nH]1] | MS: m/z = 344.0 (M + 1). |

Example 32: Synthesis of Intermediate 42

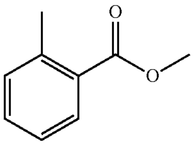

42-A

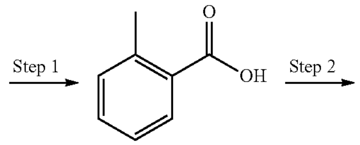

42-B

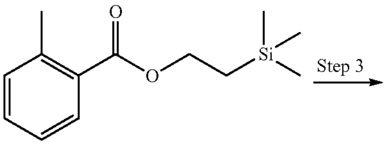

42-C

-continued

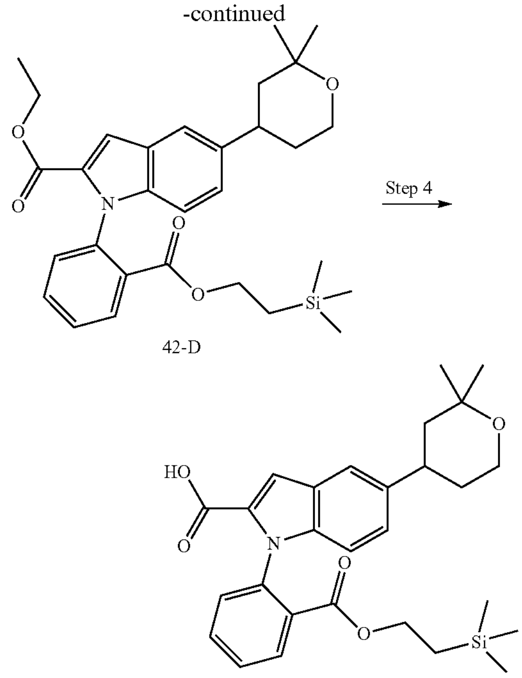

42-D

Intermediate 42

Step 1: 42-B

To a mixture of 42-A (7.0 g, 26.71 mmol) in EtOH/$H_2O$ (60 mL, 5/1) was added NaOH (2.14 g, 53.43 mmol). After stirred at 25° C. for 2 hr, the volatile fractions were removed under reduced pressure. The residue was diluted with water (100 mL) and pH was adjusted to ~5 by HCl (1M). The mixture was extracted with ethyl acetate (250 mL×2). The combined organic layers were washed with water (100 mL), brine (100 mL), dried over sodium sulfate and filtered. The filtrate was concentrated under reduced pressure to afford 42-B (7.1 g, crude). MS: m/z=249.0 (M+1).

Step 2: 42-C

To a mixture of 42-B (7.00 g, 28.22 mmol) and 2-(trimethylsilyl)ethan-1-ol (4.00 g, 33.87 mmol) in DMF (70 mL) was added HOBT (4.58 g, 33.87 mmol), EDCI (6.50 g, 33.87 mmol) and DIPEA (10.94 g, 84.67 mmol). After stirred at 25° C. for 4 hr, the mixture was poured into water (100 mL) and extracted with ethyl acetate (250 mL×2). The combined organic layers were washed with water (100 mL), brine (100 mL), dried over sodium sulfate and filtered. The filtrate was concentrated under reduced pressure. The residue was purified by silica gel column (PE/EA=50/1) to afford 42-C (7.3 g, 74.27% yield). $^1$H NMR (400 MHz, $CDCl_3$) δ 7.99-7.97 (m, 1H), 7.79-7.76 (m, 1H), 7.41-7.37 (m, 1H), 7.16-7.13 (m, 1H), 4.45-4.41 (m, 2H), 1.18-1.14 (m, 2H), 0.02 (s, 9H) ppm.

Step 3: 42-D

To a mixture of Intermediate 35 (2.40 g, 7.96 mmol), 42-C (3.33 g, 9.56 mmol) and N,N-dimethylethane-1,2-diamine (140.40 mg, 1.59 mmol) in dioxane (30 mL) was added CuI (151.66 mg, 0.80 mmol) and $K_3PO_4$ (4.22 g, 19.91 mmol). The resulting mixture was stirred in sealed tube at 110° C. for 40 hr. After cooling to 25° C., the reaction mixture was poured into ice-water (50 mL) and extracted with ethyl acetate (50 mL×2). The combined organic layers were washed with water (50 mL), brine (50 mL), dried over sodium sulfate and filtered. The filtrate was concentrated under reduced pressure. The residue was purified by silica gel column (PE/EA=20/1) to afford 42-D (400 mg, 9.63% yield). MS: m/z=522.3 (M+1).

Step 4: Intermediate 42

To a mixture of 42-D (400 mg, 0.77 mmol) in EtOH/$H_2O$ (12 mL, 5/1) was added NaOH (61.60 mg, 1.54 mmol). After stirred at 25° C. for 2 hr, the resulting mixture was poured into ice-water (50 mL) and extracted with ethyl acetate (50 mL×2). The combined organic layers were washed with water (50 mL), brine (50 mL), dried over sodium sulfate and filtered. The filtrate was concentrated under reduced pressure to afford Intermediate 42 (190 mg, crude). MS: m/z=494.5 (M+1).

Example 33: Synthesis of Intermediate 43

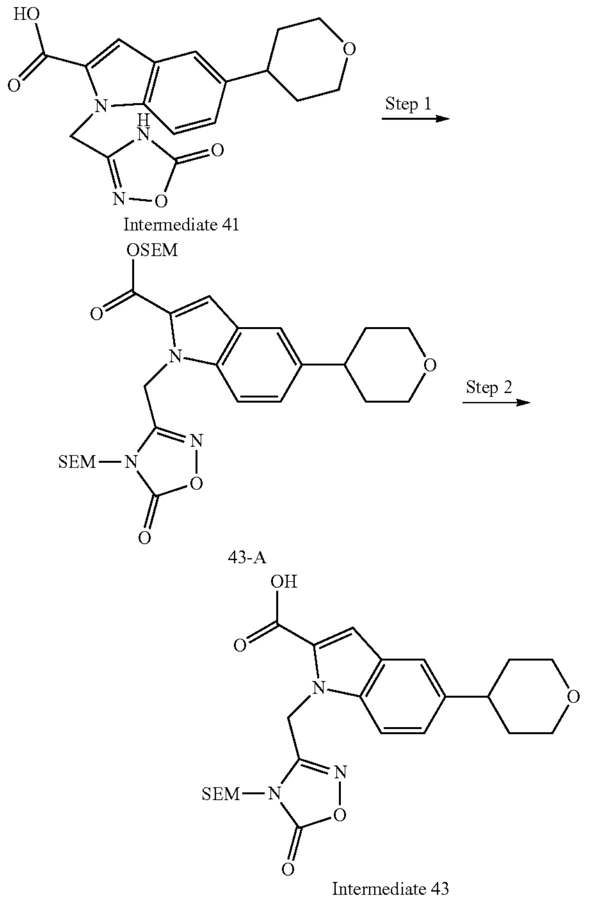

Intermediate 41

43-A

Intermediate 43

Step 1: 43-A

To a solution of Intermediate 41 (0.1 g, 291.26 μmol) in THF (10 mL) was added DIEA (188 mg, 1.46 mmol) and 2-(chloromethoxy)ethyl-trimethyl-silane (107 mg, 640.78 μmol). The reaction was stirred at 0° C. for 1 hr. The mixture was poured into water (10 mL), extracted with ethyl acetate (20 mL×2). The combined organic layers were washed with brine, dried over sodium sulfate and concentrated to give 43-A (0.17 g, crude). MS: m/z=626.3 (M+23).

Step 2: Intermediate 43

To a solution of 43-A (0.17 g, 281.53 μmol) in DMSO (5 mL) was added $MgBr_2$ (518 mg, 2.82 mmol). The reaction was stirred at 40° C. for 8 hr. The reaction was diluted with water (5 mL) and extracted with ethyl acetate (10 mL×3). The combined organic phase was washed with brine, dried over sodium sulfate and concentrated to give Intermediate 43 (0.12 g, 90% yield). MS: m/z=496.2 (M+23).

Example 34: Synthesis of Intermediate 44

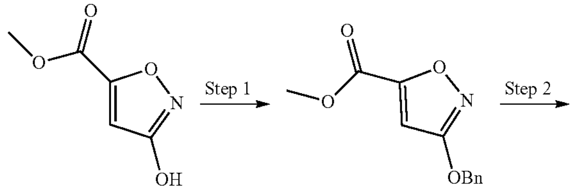

44-A 44-B

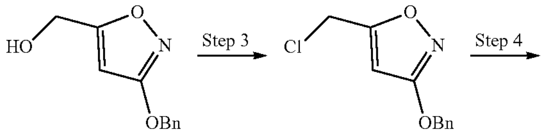

44-C 44-D

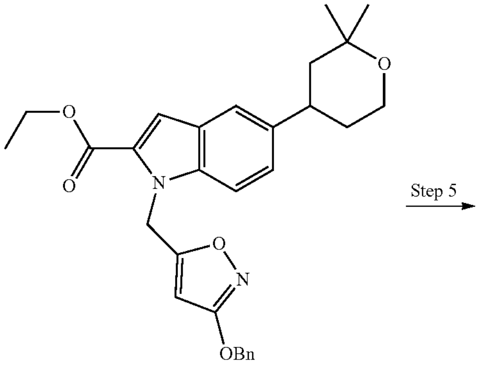

44-E

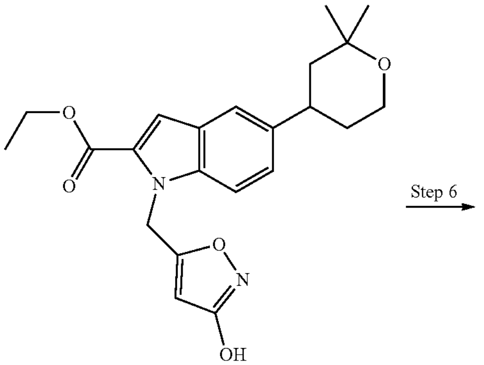

44-F

-continued

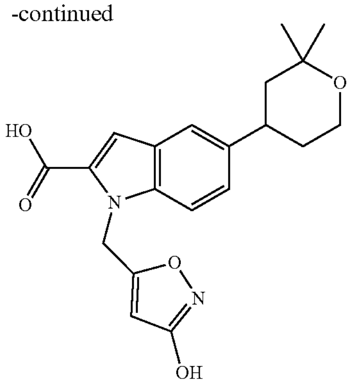

Intermediate 44

Step 1: 44-B

To a solution of 44-A (4 g, 27.95 mmol) in DMF (5 mL) and acetonitrile (35 mL) was added potassium carbonate (7.73 g, 55.91 mmol, 3.37 mL). The reaction mixture was stirred for 15 min at 25° C. Then bromomethylbenzene (5.26 g, 30.75 mmol, 3.65 mL) was added dropwise. The reaction mixture was stirred for 5 hr at 25° C. The reaction mixture was concentrated, diluted with water (15 mL) and extracted with ethyl acetate (10 mL×3). The combined organic phase was washed with brine (10 mL), dried over anhydrous sodium sulfate and concentrated to give a residue. The residue was purified by FCC (Gradient: 15-30% EA in PE) to give 44-B (4.72 g, 72% yield). MS: m/z=234.1 (M+1).

Step 2: 44-C

To a solution of 44-B (3 g, 12.86 mmol) in MeOH (30 mL) was added sodium borohydride (973.31 mg, 25.73 mmol) slowly. The reaction mixture was stirred for 5 hr at 25° C. The reaction mixture was concentrated, diluted with water (20 mL) and extracted with ethyl acetate (15 mL×3). The combined organic phase was washed with brine (15 mL), dried over anhydrous sodium sulfate and concentrated to give 44-C (3.2 g, 97% yield). MS: m/z=206.1 (M+1).

Step 3: 44-D

A solution of 44-C (856 mg, 4.17 mmol) in thionyl chloride (10 mL) was heat at 80° C. for 16 hr. The reaction mixture was concentrated to dryness, and extracted with ethyl acetate (5 mL×3) from water (10 mL). The combined organic phase was washed with brine (5 mL), dried over anhydrous sodium sulfate, and concentrated to give a residue. The residue was purified by FCC (Gradient: 5-10% EAin PE) to give 44-D (466 mg, 50% yield). MS: m/z=224.1 (M+1).

Step 4: 44-E

To a solution of Intermediate 35 (270 mg, 894.23 μmol) in DMF (5 mL) was added cesium carbonate (437 mg, 1.34 mmol) and stirred for 10 min at 25° C. Then 44-D (200 mg, 894.23 μmol) was added and the reaction mixture was stirred for 5 hr at 60° C. The reaction mixture was poured into water (15 mL) and extracted with ethyl acetate (5 mL×3). The combined organic phase was washed with brine (5 mL), dried over anhydrous sodium sulfate, and concentrated to give a residue. The residue was purified by FCC (Gradient: 20% EA in PE) to give 44-E (414 mg, 95% yield). MS: m/z=489.1 (M+1).

Step 5: 44-F

A solution of 44-E (414 mg, 847.36 μmol) in TFA (5 mL) was heated at 60° C. for 24 hr. The reaction mixture was concentrated and purified by FCC (Gradient: 30% EA in PE) to give 44-F (125 mg, 37% yield). MS: m/z=399.1 (M+1).

Step 6: Intermediate 44

To a solution of 44-F (125 mg, 313.71 μmol) in THF (3 mL) was added sodium hydroxide solution (25%, 30 μL). The reaction mixture was stirred for 16 hr at 25° C. The reaction mixture was concentrated and then water (5 mL) was added and adjusted pH to 2-3 with 2 M HCl. The aqueous phase was extracted with DCM (3 mL×3). The combined organic phase was washed with brine (3 mL), dried over anhydrous sodium sulfate, and concentrated to dryness. The residue was purified by prep-TLC (Gradient: 33.3% EA in PE with 1% HCOOH) to give Intermediate 44 (62 mg, 54% yield). MS: m/z=371.1 (M+1).

Example 35: Synthesis of Intermediate 45

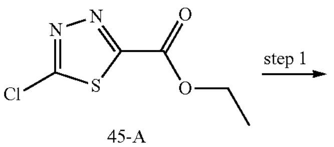

45-A

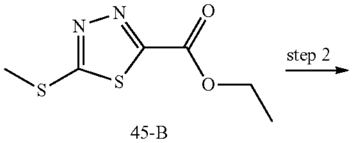

45-B

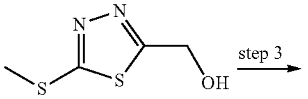

45-C

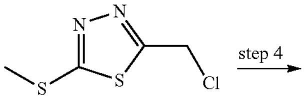

45-D

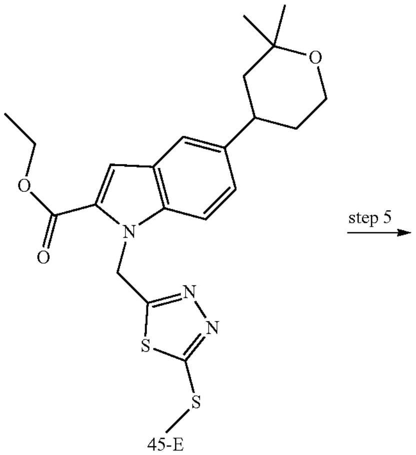

45-E

-continued

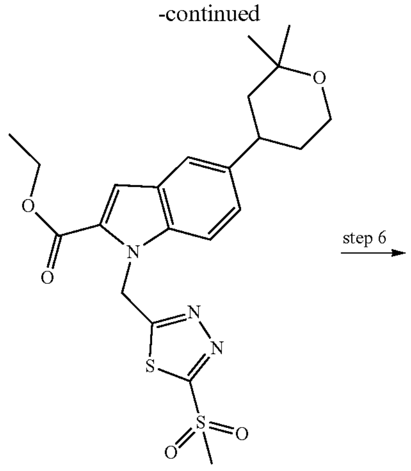

45-E

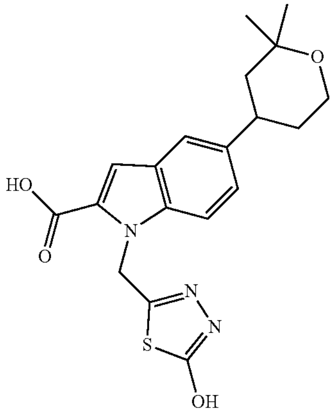

Intermediate 45

Step 1: 45-B

To a solution of 45-A (1 g, 5.19 mmol) in THF (10 mL) was added sodium thiomethoxide (730 mg, 10.42 mmol), and stirred overnight. The mixture was diluted with $H_2O$ (20 mL) and extracted with ethyl acetate (30 mL×3). The combined organic layers were washed with brine (20 mL) and dried over sodium sulfate and concentrated. The crude product was purified by silica gel column (PE/EA=10/1) to give 45-B (200 mg, yield 18.87%). MS: m/z=204.9 (M+1).

Step 2: 45-C

To a solution of 45-B (200 mg, 0.98 mmol) in THF (5 mL) was added $LiAlH_4$ (44.6 mg, 1.17 mmol) at 0° C. The mixture was stirred at 0° C. for 3 hr. The reaction was quenched with $H_2O$ (10 mL) and extracted with DCM (30 mL×3). The combined organic layers were washed with brine (30 mL) and dried over $MgSO_4$, filtered and concentrated to give 45-C (60 mg, crude). MS: m/z=163.0 (M+1).

Step 3: 45-D

To a solution of 45-C (60 mg, 0.37 mmol) in DCM (3 mL) was added methanesulfonyl chloride (32 mg, 0.28 mmol) and DMAP (67.78 mg, 0.56 mmol), and the mixture was stirred overnight. The reaction mixture was poured into $H_2O$ (10 mL) and extracted with DCM (30 mL×3). The combined organic layers were washed with brine (30 mL), dried over $MgSO_4$, filtered and concentrated. The crude product was purified by silica gel column (PE/EA=10/1) to give 45-D (50 mg, yield 74.87%). MS: m/z=180.8 (M+1).

Step 4: 45-E

To a solution of 45-D (50 mg, 0.28 mmol) and Intermediate 35 (100 mg, 0.33 mmol) in MeCN (2 mL) was added cesium carbonate (180.34 mg, 0.55 mmol), and the mixture was stirred for 16 hr. The mixture was filtered, and the filtrate was diluted with $H_2O$ (30 mL) and extracted with DCM (30 mL×3). The combined organic layers were washed with brine (30 mL×2), dried over $MgSO_4$, filtered and concentrated. The crude product was purified by silica gel column (PE/EA=5/1) to give 45-E (80 mg, yield 65.05%). MS: m/z=445.7 (M+1).

Step 5: 45-F

To a solution of 45-E (80 mg, 179.53 μmol) in DCM (2 mL) was added m-CPBA (91.12 mg, 448.84 μmol, 85% purity) and stirred for 16 hr. The reaction was quenched with aqueous $Na_2S_2O_3$ (3 mL) and extracted with DCM (30 mL×3). The combined organic layers were washed with brine (30 mL×2), dried over $MgSO_4$, filtered and concentrated. The crude product was purified by silica gel column (PE/EA=10/1) to give 45-F (40 mg, yield 46.65%). MS: m/z=477.6 (M+1).

Step 6: Intermediate 45

To a solution of 45-F (40 mg, 83.75 μmol) in THF (1 mL) was added aqueous lithium hydroxide (3 M, 0.1 mL) dropwise at 0° C. The mixture was stirred at 60° C. for 2 hr. The mixture was filtered and filtrate was concentrated to give Intermediate 45 (20 mg, crude). MS: m/z=387.7 (M+1).

Example 36: Synthesis of Intermediate 46

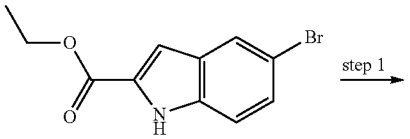

34-A

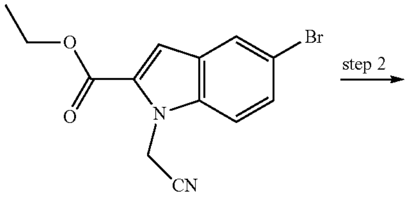

46-A

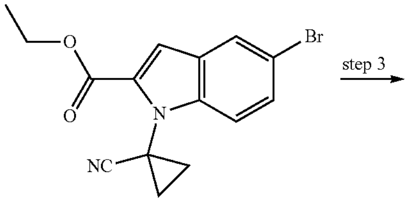

46-B

-continued

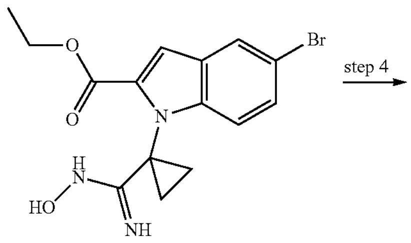

46-C

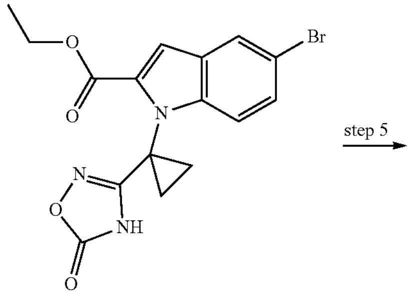

46-D

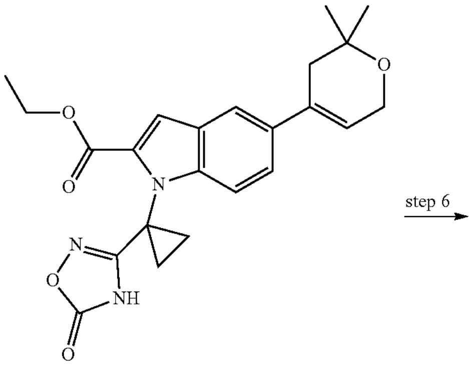

46-E

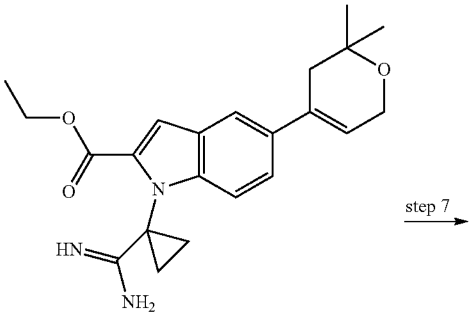

46-F

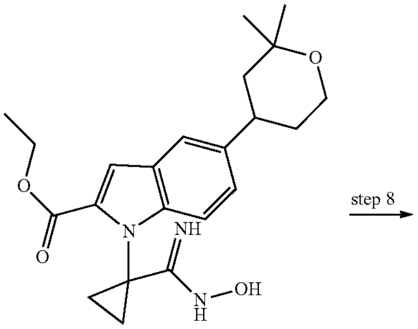

46-G

-continued

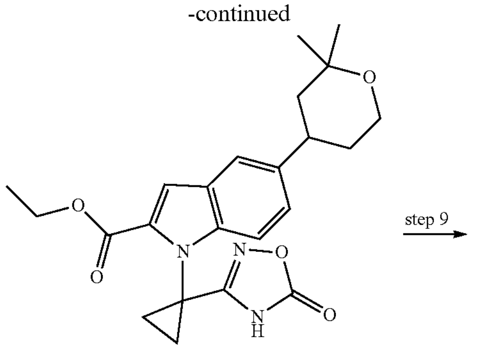

46-H

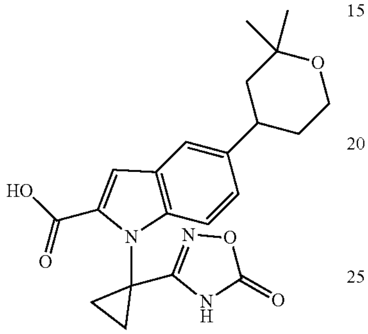

Intermediate 46

Step 1: 46-A

A mixture of 34-A (10 g, 37.30 mmol) in DMF (50 mL) under nitrogen atmosphere was added sodium hydride (60% dispersion in mineral oil, 857.49 mg, 37.30 mmol), and the reaction mixture was stirred for 1 hr at 25° C. before 2-chloroacetonitrile (2.82 g, 37.30 mmol) was added slowly. The resulting mixture was stirred for further 18 hr. The reaction mixture was quenched with water (250 mL) and extracted with ethyl acetate (450 mL×3). The combined organic layers were dried over sodium sulfate and concentrated to give a residue, which was purified by column chromatography (PE/EA=5/1) to give 46-A (9 g, 78.56% yield). $^1$H NMR (400 MHz, $CDCl_3$) δ 7.88 (d, J=1.7 Hz, 1H), 7.65-7.50 (m, 1H), 7.42-7.29 (m, 2H), 5.62 (s, 2H), 4.45 (q, J=7.1 Hz, 2H), 1.46 (t, J=7.1 Hz, 3H).

Step 2: 46-B

A mixture of 46-A (7.2 g, 23.44 mmol) and 1,3,2-dioxathiolane 2,2-dioxide (7.27 g, 58.60 mmol) in THF (50 mL) under nitrogen atmosphere was cooled to 5° C. and then lithium bis(trimethylsilyl)amide (1 M, 23.44 mL) was added dropwise. The reaction mixture was stirred at this temperature for 0.5 hr. The reaction mixture was quenched with saturated aqueous $NH_4Cl$ and extracted with ethyl acetate (300 mL×3). The combined organic layers were dried over sodium sulfate and concentrated under vacuum to give a residue, which was purified by column chromatography (PE/EA=5/1) to give 46-B (4.5 g, 57.62% yield). MS: m/z=332.9 (M+1).

Step 3: 46-C

A mixture of 46-B (2 g, 6.0 mmol), sodium bicarbonate (2.52 g, 30.01 mmol) and hydroxylamine hydrochloride (2.09 g, 30.01 mmol) in DMSO (50 mL) was heated at 50° C. for 3 hr. The reaction mixture was cooled to room temperature, quenched with water and extracted with ethyl acetate (100 mL×3). The combined organic layers were dried over sodium sulfate and concentrated under vacuum to give a residue, which was purified by column chromatography (PE/EA=3/1) to give 46-C (2.0 g, 90.98% yield). MS: m/z=365.8 (M+1).

Step 4: 46-D

A mixture of 46-C (2.66 g, 7.26 mmol) in DMSO (30 mL) was added 1,1'-carbonyldiimidazole (2.36 g, 14.53 mmol) and 1,8-diazabicyclo[5.4.0]undec-7-ene (2.21 g, 14.53 mmol). The mixture was stirred at 25° C. for 3 hr. The reaction mixture was cooled to 0° C. and quenched with saturated aqueous $NH_4Cl$ (50 mL) and extracted with ethyl acetate (50 mL×3). The combined organic layers were dried over sodium sulfate and concentrated under vacuum to give 46-D (2.2 g, 77.23% yield). MS: m/z=391.6 (M+1).

Step 5: 46-E

A mixture of Intermediate 26 (2.6 g, 9.99 mmol), 4,4,5,5-tetramethyl-2-(4,4,5,5-tetramethyl-1,3,2-dioxaborolan-2-yl)-1,3,2-dioxaborolane (2.54 g, 9.99 mmol) and Potassium Acetate (1.96 g, 19.98 mmol) in dioxane (25 mL) was degassed for 15 min, and to which was added cyclopentyl (diphenyl)phosphane; dichloromethane; dichloropalladium; iron (244.77 mg, 299.73 μmol). The reaction mixture was degassed again for 15 min, and then heated at 80° C. for 16 hr. The mixture was cooled, filtered and washed with MTBE (10 mL×4). The organic extracts were combined, concentrated, and to which was added aqueous 2M NaOH solution (26 mL) under an ice bath. The basic aqueous solution was extracted with MTBE (10 mL×3) and the organic extracts were discarded. The aqueous phase was cooled and adjusted to pH~3-5 with concentrated HCl. The mixture was extracted with ethyl acetate (50 mL×3), and the combined organic layers were washed with water (100 mL) and brine (100 mL), dried over sodium sulfate, filtered and concentrated. The crude product was purified by column chromatography (0-15% EA in hexane) to give 2-(6,6-dimethyl-2,5-dihydropyran-4-yl)-4,4,5,5-tetramethyl-1,3,2-dioxaborolane (1.5 g, 6.3 mmol).

A mixture of 2-(6,6-dimethyl-2,5-dihydropyran-4-yl)-4,4,5,5-tetramethyl-1,3,2-dioxaborolane (1.5 g, 6.3 mmol), Intermediate 46-D (2 g, 5.10 mmol) and $Na_2CO_3$ (1.08 g, 10.20 mmol) and Pd(dppf)$Cl_2$ (416.43 mg, 509.94 μmol) in dioxane (15 mL) and water (5 mL) under nitrogen atmosphere was heated at 90° C. for 16 hr. The mixture was concentrated and purified by column chromatography (DCM/MeOH=50/1) to give 46-E (2.5 g, crude). MS: m/z=423.8 (M+1).

Step 6: 46-F

A mixture of 46-E (2.5 g, 6.38 mmol), Rh/C (1.5 g) in methanol (30 mL) under $H_2$ atmosphere (1 atm) was stirred at 25° C. for 16 hr. The mixture was filtered and the filtrate was concentrated under reduced pressure. To the residue in methanol was added Pd/C (1.5 g), and the mixture was stirred at 25° C. for 16 hr under $H_2$ atmosphere (1 atm). The mixture was filtered and concentrated to a residue, which was purified by column chromatography (DCM/MeOH=3/1) to give 46-F (700 mg, 28.63% yield). MS: m/z=383.9 (M+1).

Step 7: 46-G

A mixture of 46-F (700 mg, 1.83 mmol) and hydroxylamine hydrochloride (634.23 mg, 9.13 mmol) and TEA (1.85 g, 18.25 mmol) in ethanol (10 mL) was stirred at 25° C. for 16 hr. The reaction mixture was concentrated under vacuum and the residue was purified by column chromatography (PE/EA=1/1) to give 46-G (450 mg, 61.71% yield). MS: m/z=399.9 (M+1).

Step 8: 46-H

To a mixture of 46-G (450 mg, 1.13 mmol) in DMSO (5 mL) was added 2,3,4,6,7,8,9,10-octahydropyrimido[1,2-a]azepine (342.98 mg, 2.25 mmol) and di(imidazol-1-yl)methanone (365.31 mg, 2.25 mmol). The reaction mixture was stirred at 25° C. for 3 hr. The reaction mixture was cooled to 0° C. and quenched with saturated aqueous $NH_4Cl$ (15 mL) and extracted with ethyl acetate (15 mL×3). The combined organic layers were dried over sodium sulfate and concentrated under vacuum to give 46-H (440 mg, 91.80% yield). MS: m/z=425.7 (M+1).

Step 9: Intermediate 46

To a solution of 46-H (440 mg, 1.03 mmol) in methanol (2 mL), water (2 mL) and THE (2 mL) was added lithium hydroxide hydrate (216.98 mg, 5.17 mmol). The resulting solution was stirred at 50° C. for 16 hr. Solvent was removed under vacuum, and the residue was diluted with water (15 mL) and adjusted to pH=3-5 with HCl (1 M). The mixture was extracted with ethyl acetate (20 mL×2), and the combined organic layers were dried over sodium sulfate and concentrated under reduced pressure to give Intermediate 46 (385 mg, 93.68% yield). MS: m/z=419.8 (M+23).

Example 37: Isolation of Intermediate 35-P1 and Intermediate 35-P2

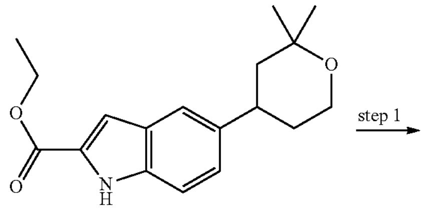

Intermediate 35

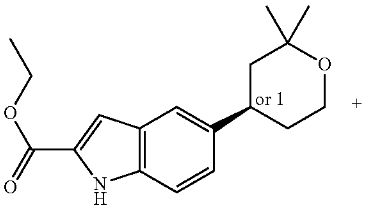

Intermediate 35-P1

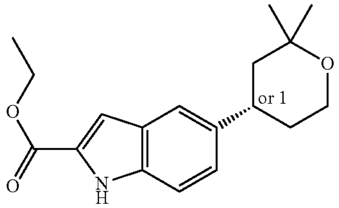

Intermediate 35-P2

Intermediate 35 (5.3 g) was separated by SFC (Column: CHIRALPAK @IE 4.6×250 mm 5 μm; Mobile phase: Hexane/EtOH=30/70; Column temperature: 25° C.; Flow rate: 1 mL/min) to give Intermediate 35-P1 (Rt=10.94 min) and Intermediate 35-P2 (2.5 g, Rt=21.33 min).

Example 38: Isolation of Intermediates 46-P1 and 46-P2

Compounds in Table 10 were obtained by SFC separation as Intermediate 35-P1 and Intermediate 35-P2.

TABLE 10

| Name | Structure | Chiral separation condition: |
| --- | --- | --- |
| Intermediate 46-P1 | 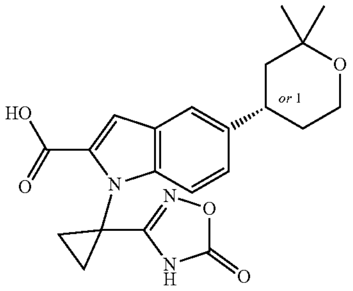 [SMILES: CC1(C)C[C@@H](c2ccc3c(c2)cc(C(=O)O)n3C2(c3noc(=O)[nH]3)CC2)CCO1] | Column: Daicel CHIRALPAK OJ-H 250 mm × 20 mm I.D., 51 μm; Mobile phase: $CO_2$/MeOH (0.1% DEA) = 84/16; Flow rate: 50 g/min; Wave length: UV 214 nm; Temperature: 35° C. |

TABLE 10-continued

| Name | Structure | Chiral separation condition: |
|---|---|---|
| Intermediate 46-P2 | 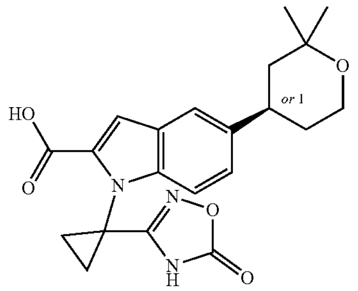 [SMILES: CC1(C)C[C@H](c2ccc3c(c2)cc(C(=O)O)n3C2(c3noc(=O)[nH]3)CC2)CCO1] | |

Example 39: Synthesis of Intermediate 47

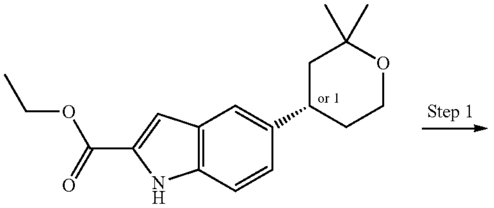

Intermedaite 35-P2

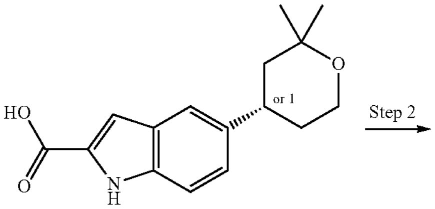

47-A

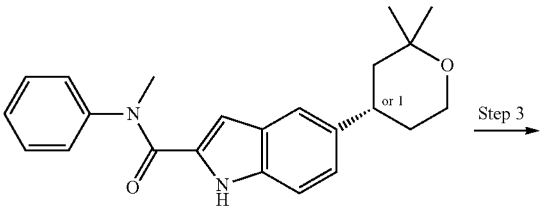

47-B

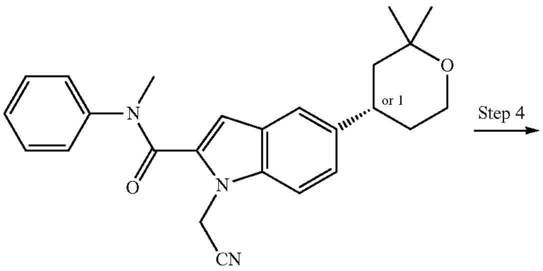

47-B

-continued

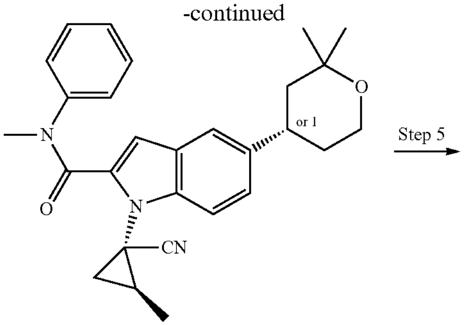

47-D

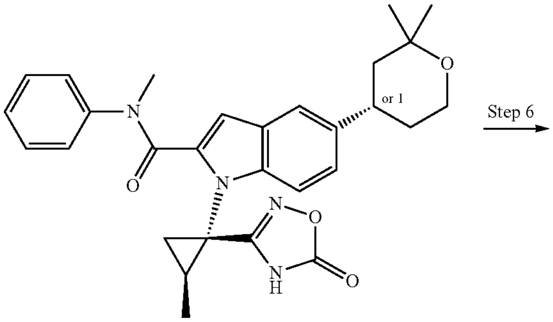

47-E

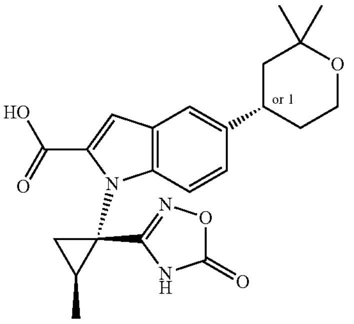

Intermediate 47

Step 1: 47-A

To a solution of Intermediate 35-P2 (1.5 g, 4.98 mmol) in methanol (20 mL) and water (10 mL) was added sodium hydroxide (597.21 mg, 14.93 mmol). The mixture was stirred at 60° C. for 3 hr. About half volume of methanol was removed in vacuum and 1 M HCl was added to the residue until pH~1. The resulting mixture was extracted with ethyl acetate (50 mL×2). The combined organic layers were dried over sodium sulfate and concentrated under reduced pressure to give 47-A (1.30 g, 95.56% yield). MS: m/z=274 (M+1).

Step 2: 47-B

To a solution of 47-A (1.30 g, 4.76 mmol) in DMA (30 mL) was added thionyl chloride (679.19 mg, 5.71 mmol) in an ice-water bath. After addition, the resulting mixture was warmed up to 25° C. and stirred for 3 hr. To the resulting mixture was added TEA (1.44 g, 14.27 mmol) and N-methylaniline (611.57 mg, 5.71 mmol) in ice-water bath. The mixture was warmed up to 25° C. and stirred for 16 hr. Water (20 mL) was added to the reaction mixture. After filtration, the solid was collected, washed with water (10 mL) and dried under vacuum to give 47-B (1.52 g, 88.17% yield). MS: m/z=363 (M+1).

Step 3: 47-C

To a suspension of sodium hydride (503.17 mg, 12.58 mmol, 60% dispersion in mineral oil) in 1,3-dimethylimidazolidin-2-one (40 mL) was added 47-B (1.52 g, 4.19 mmol) in ice-water bath. After addition, the resulting mixture was warmed to 25° C. and stirred for 1 hr. 2-chloroacetonitrile (474.90 mg, 6.29 mmol) was added and the resulting solution was stirred at 25° C. for 16 hr. To the resulting mixture saturated aqueous $NH_4Cl$ (80 mL) was added and the aqueous layer was extracted with ethyl acetate (40 mL×3). The combined organic layers were dried over sodium sulfate and concentrated under reduced pressure to give 47-C (1.68 g, crude). MS: m/z=402 (M+1).

Step 4: 47-D

To a solution of 47-C (1.68 g, 4.18 mmol), (4R)-4-methyl-1,3,2-dioxathiolane 2,2-dioxide (1.73 g, 12.55 mmol) in DMPU (20 mL) was added LiHMDS (1 M, 33.47 mL) under ice-water cooling (<15° C.). The resulting solution was stirred at 15° C. for 4 hr. The reaction was quenched by saturated aqueous $NH_4Cl$ (30 mL) and the aqueous layer was extracted with ethyl acetate (30 mL×3). The combined organic layers were washed with water (20 mL), brine (15 mL), dried over sodium sulfate and concentration under reduced pressure. The residue was purified by silica gel column (PE/EA=3/1) to give 47-D (380 mg, 20.57% yield). MS: m/z=442 (M+1).

Step 5: 47-E

To a solution of 47-D (380 mg, 860.58 μmol), hydroxylamine hydrochloride (598.02 mg, 8.61 mmol) in DMSO (10 mL) was added sodium bicarbonate (722.89 mg, 8.61 mmol). The resulting mixture was heated at 60° C. for 5 hr before ethyl acetate (70 mL) was added. The organic layer was separated and washed with water (20 mL), brine (20 mL), dried over sodium sulfate and concentrated under reduced pressure. The residue was dissolved in DMSO (10 mL), to which was added CDI (279.08 mg, 1.72 mmol) and DBU (327.02 mg, 2.15 mmol). The mixture was stirred for 4 hr at 25° C. After that, saturated aqueous $NH_4Cl$ (20 mL) was added, the aqueous layer was extracted with ethyl acetate (30 mL×3). The combined organic layers were washed with brine (20 mL), dried over sodium sulfate and concentrated under reduced pressure. The residue was purified by silica gel column (PE/EA=1/1) to give 47-E (220 mg, 51.07% yield). $^1H$ NMR (400 MHz, $CDCl_3$) δ 11.14 (s, 1H), 7.60-7.23 (m, 5H), 7.06 (t, J=28.0 Hz, 4H), 4.13-3.97 (m, 3H), 3.82-3.63 (m, 2H), 3.48 (s, 3H), 2.86 (s, 1H), 1.98 (s, 3H), 1.88-1.66 (m, 2H), 1.49-1.33 (m, 2H), 1.18 (M, 6H) ppm; MS: m/z=501 (M+1).

Step 6: Intermediate 47

To a solution of 47-E (220.00 mg, 439.48 μmol) in methoxy ethanol (3 mL) was added potassium hydroxide (246.57 mg, 4.39 mmol). The reaction mixture was heated at 100° C. for 3 hr. After cooling down, to the resulting mixture was added HCl (6 M) in ice-water bath until pH~5. The reaction mixture was stirred at 25° C. for 10 min and the aqueous layer was extracted with ethyl acetate (15 mL×3). The combined organic layers were washed with water (10 mL), brine (10 mL), dried over sodium sulfate and concentrated under reduced pressure to give Intermediate 47 (270 mg, crude). MS: m/z=412 (M+1).

Example 40: Synthesis of Intermediates 48 and 49

The compounds in Table 11 were made according to the procedure of Intermediate 47.

TABLE 11

| Name | Structure | $^1H$ NMR and/or LC/MS data |
|---|---|---|
| Intermediate 48 (As for 47-D) | 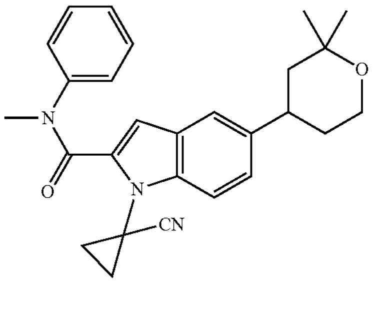 [SMILES: CN(C(=O)c1cc2cc(C3CCOC(C)(C)C3)ccc2n1C1(C#N)CC1)c1ccccc1] | MS: m/z = 428 (M + 1) |

TABLE 11-continued

| Name | Structure | $^1$H NMR and/or LC/MS data |
| --- | --- | --- |
| Intermediate 49 | 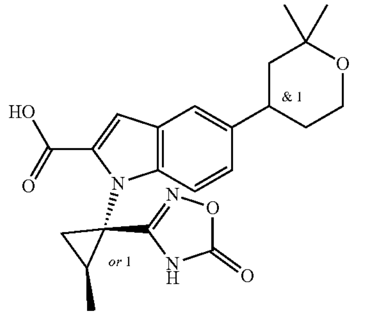 [SMILES: C[C@H]1C[C@]1(c1noc(=O)[nH]1)n1c(C(=O)O)cc2cc(C3CCOC(C)(C)C3)ccc21] | MS: m/z = 412 (M + 1). |

Example 41: Synthesis of Intermediate 50

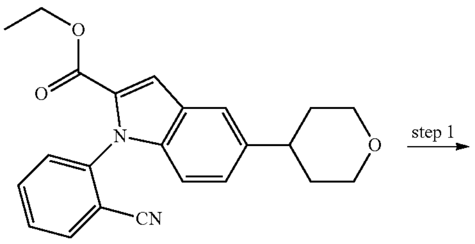

37-C

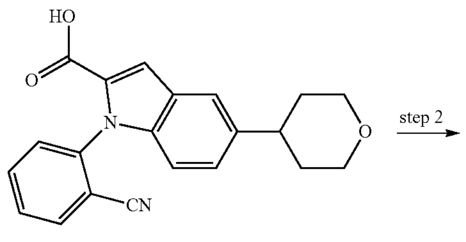

50-A

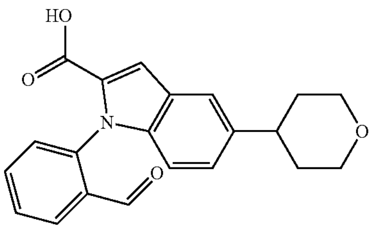

Intermediate 50

Step 1: 50-A

To a solution of 37-C (1 g, 2.67 mmol) in THF (30 mL) was added NaOH (13.35 mmol, 10% aqueous solution), the reaction was stirred at 20° C. for 16 hr. Most of the solvent was evaporated, and the residue was diluted with 5 mL of water, and charged with con. HCl until pH~3. The mixture was filtered and the solid was dissolved in 10 mL of THF, dried over sodium sulfate and concentrated to give 50-A (760 mg, 82% yield). MS: m/z=347.1 (M+1).

Step 2: Intermediate 50

To a solution of 50-A (380 mg, 1.10 mmol) in THF (5 mL) was added Dibal-H (1 M, 4.39 mL), and stirred at 20° C. for 48 hr. The reaction was poured into 5 mL of 1 M HCl and extracted with ethyl acetate (5 mL×3), the organic layers were dried over sodium sulfate, and concentrated to give a residue. The residue was purified by reverse-phase (ACN: 0.1% HCOOH in $H_2O$=50:50) to give Intermediate 50 (190 mg, 50% yield). MS: m/z=350.2 (M+1).

Example 42: Synthesis of Intermediate 51-P1 and Intermediate 51-P2

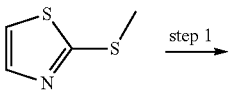

51-A

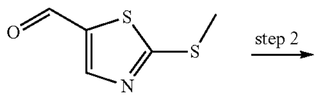

51-B

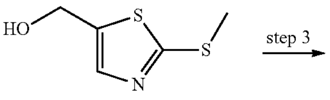

51-C

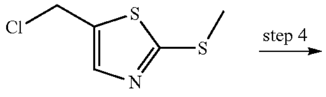

51-D

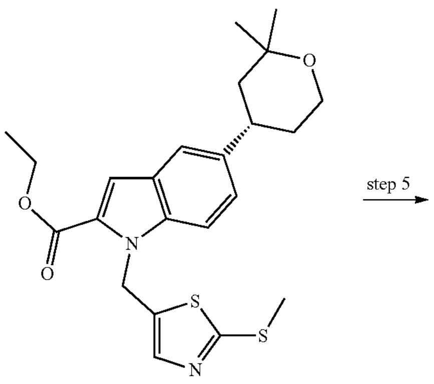

51-E

-continued

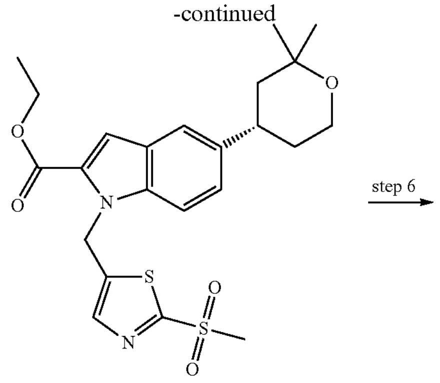

51-F

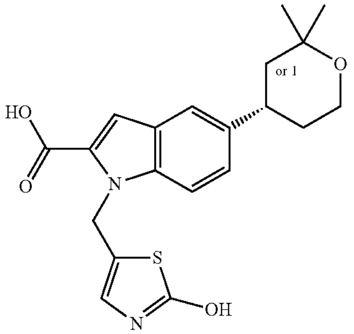

Intermedaite 51-P1

+

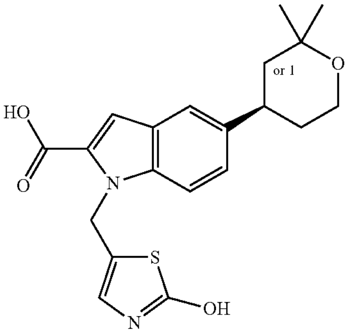

Intermedaite 51-P1

Step 1: 51-B

To a solution of 51-A (1 g, 7.62 mmol) in THF (10 mL) was added n-BuLi (2.4 M, 6.35 mL) dropwise at −78° C. The reaction mixture was warmed to −60° C. and stirred for 1 hr. Then, to the resulting mixture was added DMF (5.57 g, 76.21 mmol) and stirred at −60° C. for 2 hr. The reaction was diluted with water (10 mL) and extracted with ethyl acetate (50 mL×3). The combined organic layers were dried with anhydrous sodium sulfate, filtered and concentrated in vacuum. The residue was purified by silica gel column chromatography (EA/DCM=1/5) to give 51-B (1.1 g, 6.91 mmol, 90.65% yield). MS: m/z=159.9 (M+1).

Step 2: 51-C

To a mixture of $LiBH_4$ (276.33 mg, 12.56 mmol) in THF (10 mL) was added dropwise a solution of 51-B (1 g, 6.28 mmol) in THF (10 mL) at 25° C. The resulting mixture was stirred for 18 hr before diluting with HCl (1M, 1 mL). The mixture was adjusted to pH~8 with saturated aqueous $NaHCO_3$, and extracted with DCM (10 mL×3). The combined organic layers were dried over anhydrous sodium sulfate, filtered and concentrated in vacuum. The residue was purified by silica gel column chromatography (EA/DCM=1/3) to give 51-C (0.9 g, 5.58 mmol, 88.87% yield). MS: m/z=161.9 (M+1).

Step 3: 51-D

To a mixture of 51-C (1 g, 6.20 mmol) and DMAP (1.14 g, 9.30 mmol) in DCM (2 mL) was added MsCl (78.45 mg, 6.82 mmol) dropwise in an ice bath. After stirred for 18 hr, the resulting mixture was concentrated. The residue was purified by silica gel column chromatography (EA/DCM=1/5) to give 51-D (390 mg, 2.17 mmol, 35.0% yield). $^1H$ NMR (400 MHz, $CDCl_3$) δ 7.47 (s, 1H), 4.80 (d, J=0.5 Hz, 2H), 2.70 (s, 3H).

Step 4: 51-E

To a suspension of $Cs_2CO_3$ (108.17 mg, 331.81 μmol) in MeCN (5 mL) in an ice bath was added Intermediate 35 (50 mg, 165.90 mol). After stirring for 1 hr, 51-D (29.81 mg, 165.90 mol) was added and the resulting mixture was stirred for 16 hr. The mixture was diluted with ice-water (20 mL) and extracted with ethyl acetate (20 mL×3). The combined organic layers were dried over sodium sulfate and concentrated under reduced pressure. The residue was purified by silica gel column (PE/EA=5/1) to give 51-E (50 mg, 112.46 μmol, 67.79% yield). MS: m/z=444.9 (M+1).

Step 5: 51-F

51-E (800 mg, 1.8 mmol) in DCM (20 mL) is mixed portionwise under stirring with mCPBA (776.28 mg, 85% purity) under an argon atmosphere and at 0° C. The reaction was stirred for 30 minutes at 0° C., then 18 hr at 25° C. The mixture was washed with $NaHCO_3$ (2 M), water and brine. The organic phase was dried over sodium sulfate and concentrated to give a residue, which was purified by column chromatography (PE/EA=1/1) to give 51-F (600 mg, 70% yield). MS: m/z=476.9 (M+1).

Step 6: Intermediate 51-P1 and Intermediate 51-P2

The mixture of 51-F (600 mg, 1.26 mmol), NaOH (503.56 mg, 12.59 mmol) in THE (3 mL) and $H_2O$ (3 mL) in a sealed tube was heated at 60° C. for 18 hr. Solvent was removed under vacuum, and the residue was diluted with water (3 mL), adjusted to pH=3-5 with HCl (1 M). The solid was collected by filtration and dried, which was separated by chiral prep-HPLC (Column: OJ-H, 20×250 mm; Flow: 40 g/min; Solvent: MeOH ($NH_4OH$ 0.2%): $CO_2$=30:70; Time: 7.94 min, 12.42 min) to afford Intermediate 51-P1 (150 mg, 388.13 μmol, 30.83% yield, RT=5.13 min) and Intermediate 51-P2 (150 mg, 388.13 μmol, 30.83% yield, RT=7.27 min).

Intermediate 51-P1: 1H NMR (400 MHz, DMSO) δ 13.08 (bs, 1H), 11.03 (d, J=2.2 Hz, 1H), 7.68 (d, J=8.7 Hz, 1H), 7.52 (s, 1H), 7.27 (dd, J=8.7, 1.5 Hz, 1H), 7.21 (s, 1H), 7.02 (d, J=2.6 Hz, 1H), 5.64 (s, 2H), 3.71 (d, J=7.3 Hz, 2H), 3.02 (t, J=12.4 Hz, 1H), 1.69 (d, J=12.8 Hz, 2H), 1.64-1.46 (m, 2H), 1.32-1.24 (m, 3H), 1.19 (s, 3H). MS: m/z=387 (M+1).

Intermediate 51-P2: 1H NMR (400 MHz, DMSO) δ 13.03 (bs, 1H), 11.03 (s, 1H), 7.68 (d, J=8.8 Hz, 1H), 7.52 (s, 1H), 7.27 (d, J=8.6 Hz, 1H), 7.21 (s, 1H), 7.02 (s, 1H), 5.64 (s, 2H), 3.72 (d, J=7.7 Hz, 2H), 3.01 (d, J=12.8 Hz, 2H), 1.68 (s, 2H), 1.56 (dt, J=26.0, 10.9 Hz, 2H), 1.26 (d, J=12.3 Hz, 3H), 1.19 (s, 3H).

Example 43: Synthesis of Intermediate 52

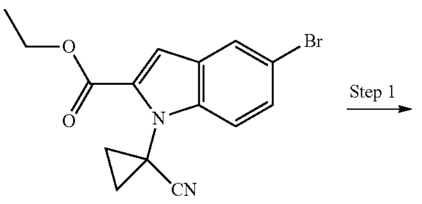

46-B

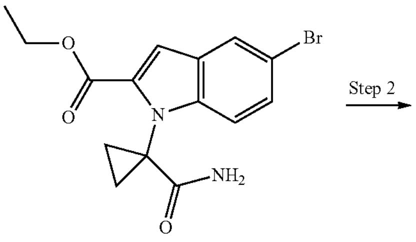

52-A

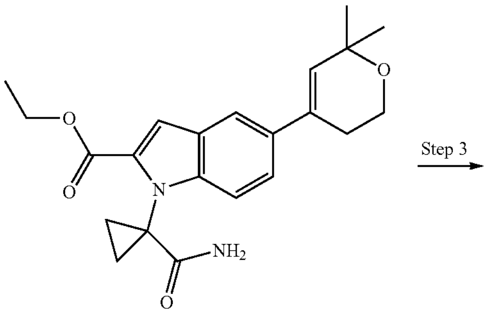

52-B

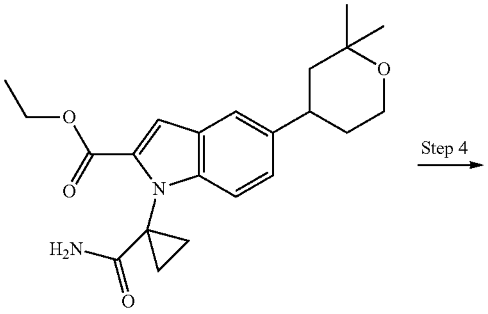

52-C

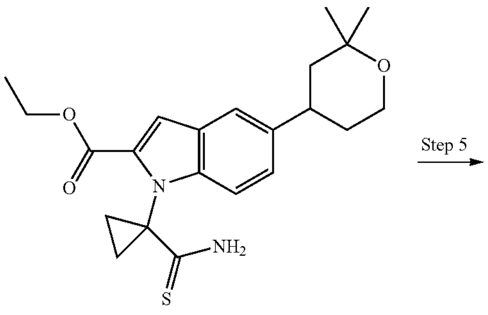

52-D

-continued

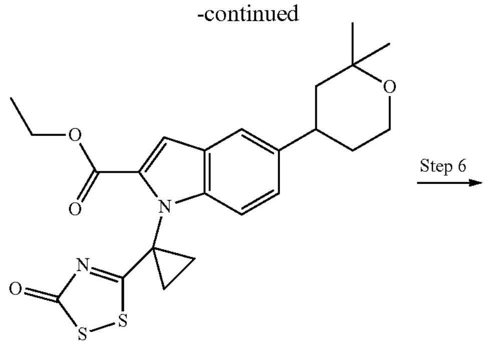

52-E

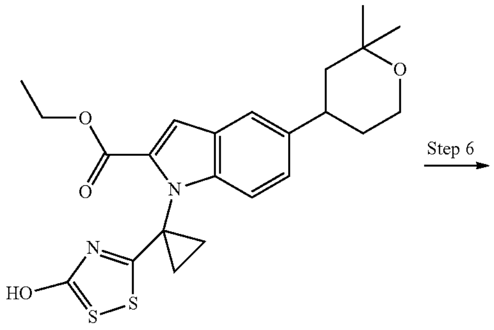

52-F

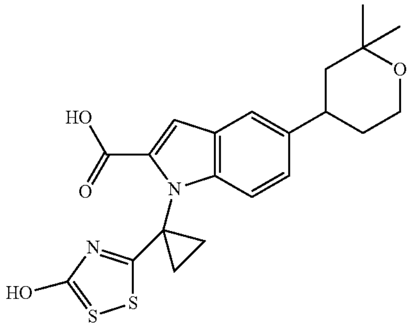

Intermediate 52

Step 1: 52-A

A mixture of ethyl 46-B (2 g, 6.0 mmol), sodium bicarbonate (2.52 g, 30.01 mmol, 1.17 mL) and hydroxylamine hydrochloride (2.09 g, 30.01 mmol, 1.25 mL) in DMSO (50 mL) was heated at 50° C. for 3 hrs. The reaction mixture was cooled to room temperature and quenched with water and extracted with ethyl acetate (100 mL×3). The combined organic layer was dried over sodium sulfate and concentrated under vacuum to give a residue. The residue (with crude from another batch together) was purified by column chromatography (PE/EA=3/1) to give 52-A (1.32 g, byproduct).

Step 2: 52-B

A mixture of ethyl 52-A (1.1 g, 3.13 mmol), 2-(6,6-dimethyl-2,5-dihydropyran-4-yl)-4,4,5,5-tetramethyl-1,3,2-dioxaborolane (447.52 mg, 1.88 mmol), sodium carbonate (663.95 mg), and 1,1'-Bis(diphenylphosphino)ferrocene palladium(II)dichloride (458.36 mg, 626.43 mol) in dioxane (10 mL) and water (3 mL) was heated at 90° C. for 18 hrs. The solvent was removed under vacuum to give a crude product. The crude product was purified by column chromatography (PE/EA=1/10) to give 52-B (1 g, 83.48% yield).

Step 3: 52-C

A mixture of 52-B (1 g, 2.62 mmol) in methanol (15 mL) was added Pd/C (10%, 556.51 mg), the mixture was stirred under the atmosphere of hydrogen with a balloon for 18 hrs. The reaction mixture was filtered and the filtered cake was washed with methanol. The filtrate was concentrated under vacuum to give a residue, which was purified by column chromatography (PE/EA=1/10) to give 52-C (1 g, 2.60 mmol, 99.48% yield).

Step 4: 52-D

A mixture of 52-C (160 mg, 416.16 μmol) and phosphorus pentasulfide (370.0 mg, 832.32 μmol) in THF (3 mL) was heated at 50° C. for 18 hrs. The solvent was removed under vacuum to give a crude product, which was purified by column chromatography (PE/EA=3/1) to obtain 52-D (130 mg, 78% yield). MS: m/z=400.8 (M+1).

Step 5: 52-E

A mixture of 52-D (100 mg, 249.67 μmol) in THF (3 mL) was added S-chloro chloromethanethioate (163.51 mg, 1.25 mmol) slowly at 25° C., and the mixture was stirred for 2 hr. The mixture was quenched with water and extracted with DCM (20 mL×2). The combined organic layer was dried over sodium sulfate and concentrated under vacuum to give a residue, which was purified by combi-flash (PE/EA=5/1) to afford 52-E (75 mg, 65.5% yield). MS: m/z=458.9 (M+1).

Step 6: 52-F

To a mixture of 52-E (257 mg, 0.56 mmol) and dioxane (10 mL) was added a solution of triphenylphosphine (146.99 mg, 0.56 mmol) in dioxane (5 mL) at 10° C., and the reaction stirred for 10 minutes. Azidotrimethylsilane (129 mg, 1.12 mmol) was added and the reaction mixture was stirred 120° C. for 3 hr. Solvent was removed under reduced pressure, the residue was purified by combi-flash (DCM/methanol=15/1) to afford 52-F (60 mg, 24%). MS: m/z=441.8 (M+1).

Step 7: Intermediate 52

A mixture of 52-F (60 mg, 0.136 mmol) in KOH (2 M, 2 mL) and THF (5 mL) was stirred at 70° C. for 18 hr. Most solvent was removed under reduced pressure, and the mixture was adjusted to pH=5-6 and extracted with ethyl acetate (10 mL×3). The combined organic phase was dried over sodium sulfate and then filtered. The filtrate was concentrated in vacuo to afford Intermediate 52 (60 mg, crude). MS: m/z=413.8 (M+1).

Example 44: Synthesis of Intermediate 53

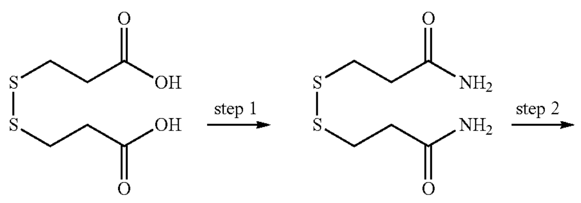

53-A 53-B

-continued

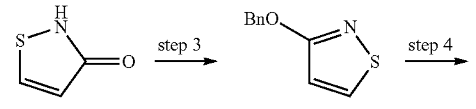

53-C 53-D

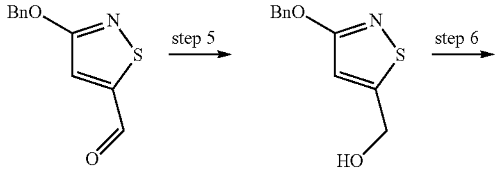

53-E 53-F

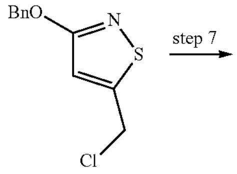

53-G

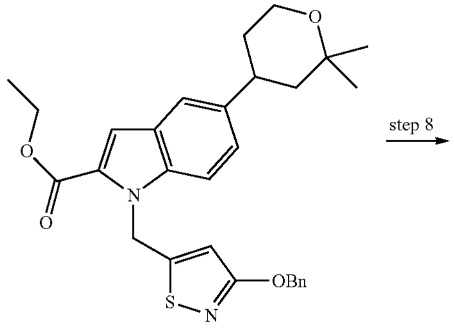

53-H

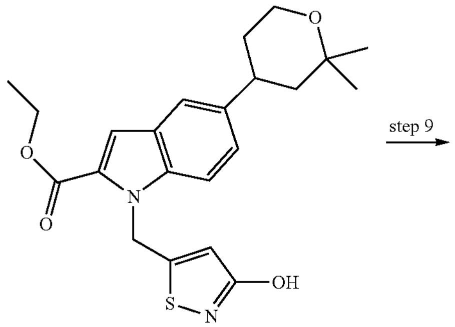

53-I

-continued

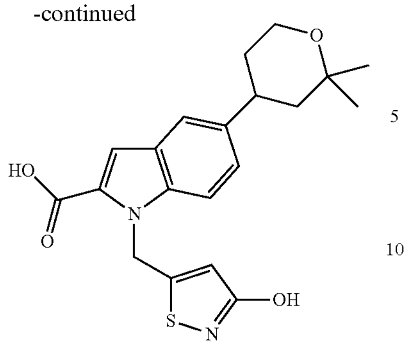

Intermedaite 53

Step 1: 53-B

A mixture of 53-A (11 g, 52.31 mmol) in thionyl chloride (180.40 g, 1.52 mol, 110.0 mL) was stirred at 70° C. for 16 hr. The mixture was concentrated to dryness, and dissolved in DCM (100 mL). $NH_3H_2O$ (100 mL) was added in an ice-water bath, and the reaction was warmed up to 25° C. and stirred for 0.5 hr. The mixture was concentrated under reduced pressure to afford 53-B (16.26 g, crude). MS: m/z=208.9 (M+1).

Step 2: 53-C

To a solution of 53-B (16.26 g) in DCE (160 mL) was added sulfuryl chloride (15.81 g, 117 mmol) at 0° C. very slowly. Then the reaction mixture was stirred at 25° C. for 3 hr. The resulting mixture was concentrated in vacuum, and the residue was treated with ethyl acetate (100 mL) and $H_2O$ (100 mL). The aqueous layer was then extracted with ethyl acetate (200 mL×2). The combined organics were washed with brine (200 mL), dried over anhydrous sodium sulfate, filtered and concentrated in vacuum. The residue was purified by column chromatography on silica gel (DCM/MeOH=10/1) to give 53-C (7.3 g, 92% yield). MS: m/z=102.0 (M+1).

Step 3: 53-D

To a solution of 53-C (7.3 g, 72.19 mmol) in DMF (50 mL) at 0° C. was added $K_2CO_3$ (19.95 g, 144.37 mmol) followed by benzyl bromide (14.2 mL, 83.01 mmol). The reaction mixture was allowed to stir for 24 hr at 25° C. The reaction mixture was diluted with $H_2O$ (200 mL) and extracted with $Et_2O$. The organic layer was washed with brine, dried over sodium sulfate, and evaporated to give a crude product, which was purified by column flash chromatography (heptane/EA=4/1) to give 53-D (3.78 g, 27% yield). $^1H$ NMR (400 MHz, $CDCl_3$) δ 8.48 (d, J=4.7 Hz, 1H), 7.49 (dd, J=7.7, 1.0 Hz, 2H), 7.45-7.32 (m, 3H), 6.67 (d, J=4.7 Hz, 1H), 5.45 (s, 2H); MS: m/z=191.9 (M+1).

Step 4:53-E

To freshly prepared LDA (0.58 mmol) in $Et_2O$ (4.5 mL) at −78° C. under $N_2$ was added 53-D (500 mg, 2.61 mol) in $Et_2O$ (0.3 mL). After 15 min, DMF (213 mg, 2.92 mmol) in $Et_2O$ (0.2 mL) was added and stirring at −78° C. for 15 min. The reaction mixture was quenched with saturated $NH_4Cl$ and extracted with ethyl acetate. The organic layer was washed with brine, dried over sodium sulfate, and evaporated to give a residue, which was purified by combi-flash (PE/EA=4/1) to afford 53-E (100 mg, 17% yield). $^1H$ NMR (400 MHz, $CDCl_3$) δ 10.05 (s, 1H), 7.53-7.33 (m, 5H), 7.17 (s, 1H), 5.46 (s, 2H); MS: m/z=220.1 (M+1).

Step 5: 53-F

To a solution of 53-E (259 mg, 1.18 mmol) in methanol (10 mL) was added sodium borohydride (67 mg, 1.77 mmol). The mixture was stirred at 25° C. for 0.5 hr. The solvent was removed, and the residue was purified by combi-flash (DCM/methanol=20/1) to afford 53-F (159 mg, 60% yield). MS: m/z=221.9 (M+1).

Step 6: 53-G

To a solution of 53-F (110 mg, 0.497 mmol) in DCM (2 mL) was added thionyl chloride (177 mg, 1.49 mmol) at 25° C. The reaction was stirred for 2 hr. The reaction mixture was concentrated in vacuo to afford 53-G (110 mg, crude). MS: m/z=239.9 (M+1).

Step 7: 53-H

A mixture of Intermediate 35, 53-G (109 mg, 0.456 mmol), $Cs_2CO_3$ (297 mg, 0.912 mmol) and DMF (5 mL) was stirred at 60° C. for 3 hr. Water (20 mL) was added and extracted with ethyl acetate (20 mL×3). The organic phase was dried over sodium sulfate and then filtered. The filtrate was concentrated in vacuo and purified by combi-flash (DCM/methanol=20/1) to afford 53-H (112 mg, 48% yield). MS: m/z=504.7 (M+1).

Step 8: 53-I

A mixture of 53-H (107 mg, 0.212 mmol) and TFA (5 mL) was stirred at 50° C. for 2 hr. The reaction mixture was concentrated in vacuo to give 53-I (80 mg, 91% yield). MS: m/z=414.8 (M+1).

Step 9: Intermediate 53

A mixture of 53-H (84 mg, 0.202 mmol) in NaOH (2 M, 5 mL) and THE (5 mL) was stirred at 25° C. for 2 hr. Most solvent was removed, and the mixture was adjusted to pH=5-6 and extracted with ethyl acetate (30 mL×3). The organic phase was dried over sodium sulfate and then filtered. The filtrate was concentrated in vacuo to give Intermediate 53 (60 mg, 76% yield). MS: m/z=386.7 (M+1).

Example 45: Synthesis of Intermediate 54

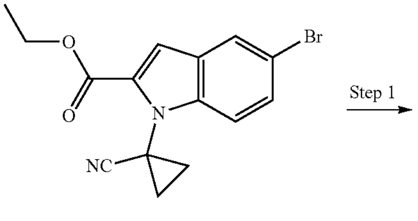

46-B

-continued

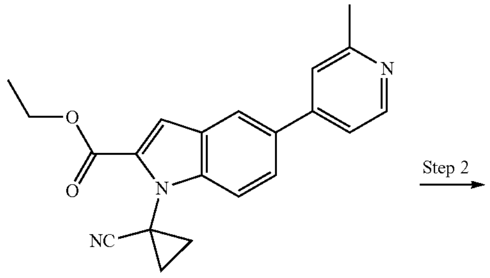

54-A

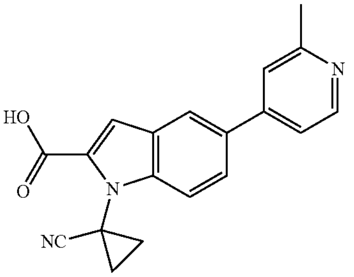

Intermediate 54

Step 1: 54-A

A 20 mL microwave reaction tube was charged with 46-B (600 mg, 1.80 mmol), (2-methyl-4-pyridyl)boronic acid (295.94 mg, 2.16 mmol), $K_2CO_3$, (746.65 mg, 5.40 mmol) and cyclopentyl(diphenyl)phosphane; dichiorornethane; dichioropalladiun; iron (147.06 ng, 180.08 μmol) in water (3 mL) and dioxane (12 mL). After $O_2$ was purged by bubbling $N_2$ into the reaction solution, the tube was sealed and heated at 120° C. for 50 min in a Biotage microwave reactor. The reaction was cooled to 25° C., diluted with ethyl acetate and filtered. The filtrate was concentrated under reduced pressure. The crude product was purified by flash chromatography (EA in PE, 0-50%) to afford 54-A (590 mg, 1.71 mmol, 87.59% yield). MS: m/z=346.2 (M+1).

Step 2: Intermediate 54

A mixture of 54-A (550 mg, 1.59 mmol) and lithium hydroxide hydrate (267.29 mg, 6.37 mmol) in THF (6 mL) and water (1 mL) was stirred at 25° C. for 24 hr. The reaction mixture was acidified with 1 M HCl and concentrated. The crude product was purified by FCC (Methanol in DCM, 0-10%) to give Intermediate 54 (300 mg, 945.36 μmol, 59.37% yield). MS: m/z=318.1 (M+1).

Example 46: Synthesis of Compound 1

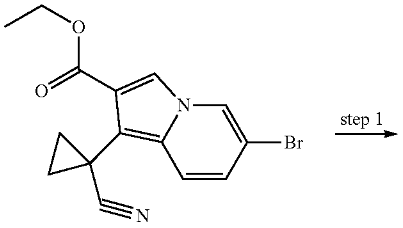

33-A

-continued

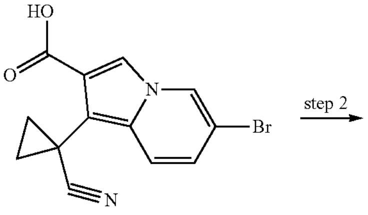

1-1

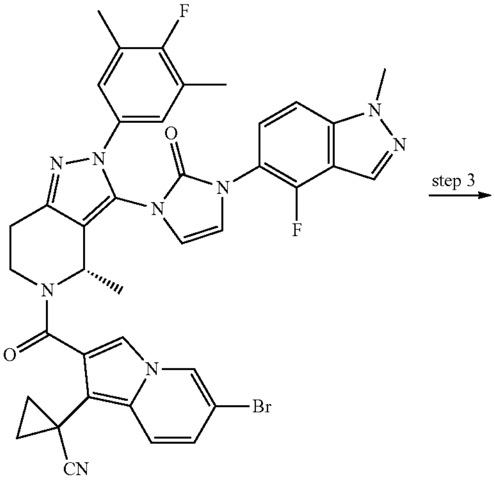

1-2

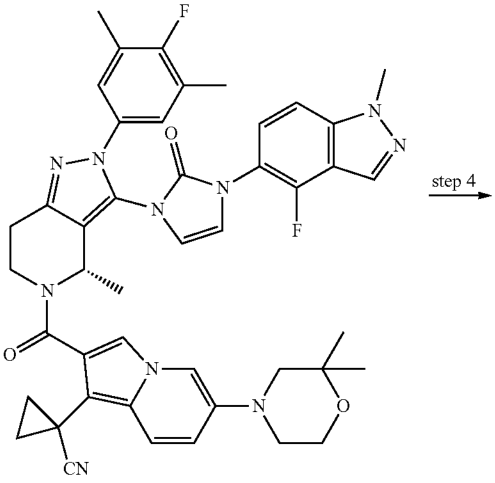

1-3

-continued

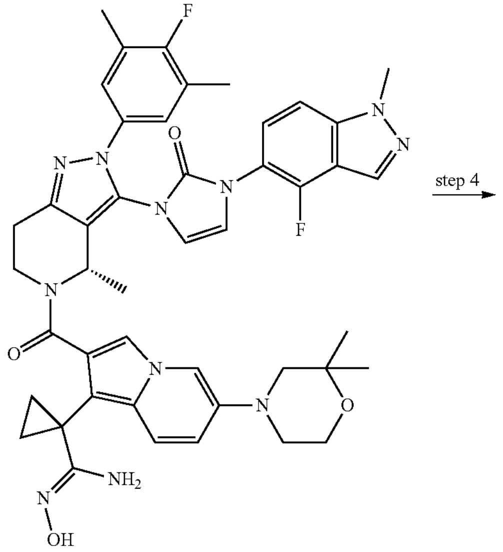

1-4

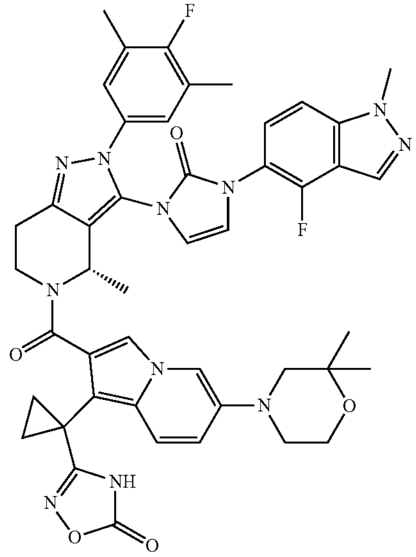

Compound 1

Step 1: 1-1

To a solution of 33-A (30 mg, 90.04 µmol) in MeOH (5 mL) was added NaOH (6 M, 2 mL). The reaction mixture was stirred at 25° C. for 2 hr. MeOH was removed, the mixture was adjusted to pH~5 with HCl (1M), the mixture was extracted with ethyl acetate (20 mL×3). The combined organic layers were washed with brine (10 mL), dried over sodium sulfate, concentrated in vacuum to give 1-1 (25 mg, 91% yield). MS: m/z=305.0 (M+1).

Step 2: 1-2

To a solution of 1-1 (25 mg, 81.93 µmol), Intermediate 3 (40 mg, 81.93 µmol) and HATU (46 mg, 122.9 µmol) in DMF (2 mL) was added DIEA (52 mg, 409.67 µmol). The reaction mixture was stirred for 1 hr at 25° C. The mixture was diluted with water (20 mL) and extracted with ethyl acetate (20 mL×3). The combined organic phase was washed with brine (30 mL), filtered. The filtrate was concentrated and purified by prep-TLC (DCM/MeOH=10/1) to give 1-2 (30 mg, 47% yield). MS: m/z=776.1 (M+1).

Step 3: 1-3

To a solution of 1-2 (30 mg, 38.63 µmol) in toluene (5 mL) was added 2,2-dimethylmorpholine (22 mg, 193.14 µmol), t-BuONa (11 mg, 115.89 µmol), Jonephos (3 mg, 7.73 µmol) and $Pd_2(dba)_3$ (4 mg, 3.86 µmol). The mixture was stirred at 100° C. for 16 hr. The reaction mixture was extracted with ethyl acetate (50 mL×2), the combined organic layers were washed with brine (50 mL×2), dried over sodium sulfate, concentrated in vacuum. The crude was purified by prep-TLC (DCM/MeOH=10/1) to give 1-3 (10 mg, 32% yield). MS: m/z=811.3 (M+1).

Step 4: 1-4

To a solution of 1-3 (10 mg, 12.33 µmol) in DMSO (2 mL) was added $NH_2OH$ HCl (25 mg, 369.96 µmol) and $NaHCO_3$ (31 mg, 369.96 µmol). The mixture was stirred at 60° C. for 16 hr. The reaction mixture was diluted with ethyl acetate (20 mL), washed with brine (10 mL×2), dried over anhydrous sodium sulfate and filtered. The filtrate was concentrated to give 1-4 (10 mg, 96% yield). MS: m/z=844.3 (M+1).

Step 5: Compound 1

To a solution of 1-4 (10 mg, 11.85 µmol) in DMSO (3 mL) was added DBU (15 mg, 59.25 µmol) and CDI (8 mg, 59.25 µmol). The reaction mixture was stirred for 2 hr at 25° C. The reaction was concentrated and purified by prep-HPLC (Chromatographic columns: Xbridge 5µ C18 150×19 mm Mobile Phase: MeCN—$H_2O$ (0.1% FA)) to give Compound 1 (1.0 mg, 9.70% yield). $^1H$ NMR (400 MHz, $CD_3OD$) δ 8.15 (d, J=21.6 Hz, 1H), 7.66-7.40 (m, 5H), 7.16 (d, J=6.0 Hz, 2H), 6.88-6.64 (m, 4H), 5.34-5.20 (m, 1H), 4.11 (s, 3H), 3.87-3.77 (m, 2H), 3.62-3.47 (m, 2H), 2.97-2.65 (m, 6H), 2.27 (s, 6H), 1.47-1.43 (m, 4H), 1.33-1.29 (m, 9H); MS: m/z=870.2 (M+1).

Example 47: Synthesis of Compound 2

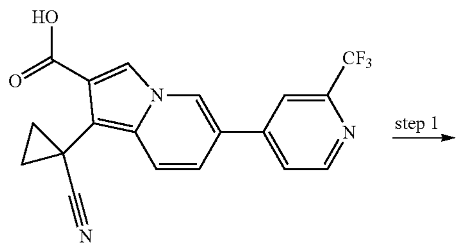

Intermediate 33

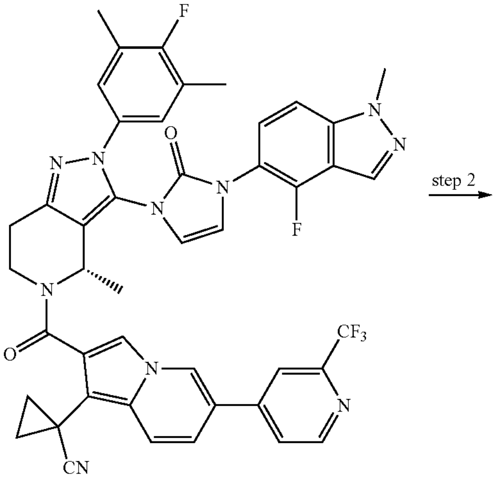

1-3

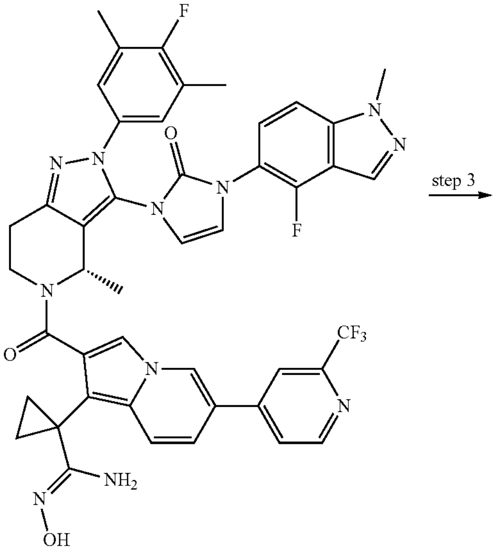

2-2

-continued

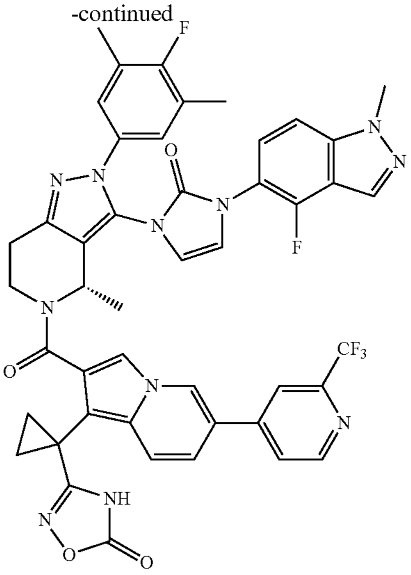

Compound 2

Step 1: 2-1

To a solution of Intermediate 33 (13 mg, 35.01 μmol), Intermediate 3 (17 mg, 35.01 μmol) and HATU (19 mg, 52.52 μmol) in DMF (2 mL) was added DIEA (90 mg, 700.22 mol). The mixture was stirred for 1 hr at 25° C. The reaction mixture was diluted with water (20 mL) and extracted with ethyl acetate (20 mL×3). The combined organic layers were washed with brine (30 mL) and filtered. The filtrate was concentrated and purified by prep-TLC (DCM/MeOH=10/1) to give 2-1 (12 mg, 41% yield). MS: m/z=843.2 (M+1).

Step 2: 2-2

To a solution of 2-1 (12 mg, 14.24 μmol) in DMSO (1 mL) was added $NaHCO_3$ (23 mg, 284.76 μmol) and $NH_2OH.HCl$ (19 mg, 284.76 μmol). The mixture was stirred at 60° C. for 16 hr. The reaction mixture was diluted with ethyl acetate (20 mL), washed with brine (10 mL×2), dried over anhydrous sodium sulfate and filtered. The filtrate was concentrated to dryness to give 2-2 (10 mg, 80% yield). MS: m/z=876.2 (M+1).

Step 3: Compound 2

To a solution of 2-2 (10 mg, 11.42 μmol) in DMSO (1 mL) was added CDI (2 mg, 11.42 μmol) and DBU (3 mg, 11.42 μmol). The reaction mixture was stirred for 2 hr at 25° C. The reaction mixture was diluted with ethyl acetate (20 mL), washed with water (10 mL×3) and brine (10 mL), dried over anhydrous sodium sulfate and filtered. The filtrate was concentrated and purified by prep-HPLC (Chromatographic columns: Xbridge 5μ C18 150×19 mm Mobile Phase: MeCN—$H_2O$ (0.1% $NH_4OH$)) to give Compound 2 (1.1 mg, 11% yield). $^1H$ NMR (400 MHz, $CD_3OD$) δ 8.81-8.65 (m, 2H), 8.16-7.84 (m, 3H), 7.69-7.64 (m, 2H), 7.48-7.43 (m, 1H), 7.33-7.13 (m, 4H), 6.86-6.62 (m, 2H), 5.33-5.17 (m, 1H), 4.10-4.00 (m, 3H), 3.61-3.46 (m, 2H), 2.86-2.63 (m, 2H), 2.25 (s, 6H), 1.75-1.71 (m, 2H), 1.45-1.39 (m, 2H), 1.27 (s, 3H); MS: m/z=902.2, (M+1).

Example 48: Synthesis of Compounds 3-23
The compounds in Table 12 were made according to the procedure of Compound 2.
TABLE 12
| Name | Structure | $^1$H NMR and/or LC/MS data |
|---|---|---|
| Compound 3 (from Intermediate 3 and 30-P2) | 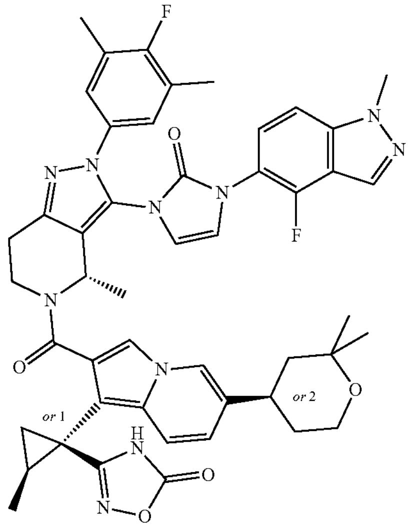 [SMILES: Cc1cc(-n2nc3c(c2-n2ccn(-c4ccc5c(cnn5C)c4F)c2=O)[C@H](C)N(C(=O)c2cn4cc([C@@H]5CCOC(C)(C)C5)ccc4c2[C@@]2(c4noc(=O)[nH]4)C[C@@H]2C)CC3)cc(C)c1F] | MS: m/z = 883.1 (M + 1); $^1$H NMR (400 MHz, $CD_3OD$) δ 8.20-8.00 (m, 2H), 7.65 (s, 1H), 7.44-7.53 (m, 2H), 7.16 (d, J = 6.0 Hz, 2H), 6.69-6.89 (m, 3H), 5.81 (s, 1H), 4.12 (s, 3H), 3.83-3.87 (m, 2H), 3.48-3.63 (m, 3H), 2.98-2.79 (m, 2H), 2.29 (s, 6H), 2.03-1.93 (m, 2H), 1.77-1.46 (m, 7H), 1.35-0.99 (m, 11H). |
| Compound 4 (from intermediate 3 and 30-P1) | 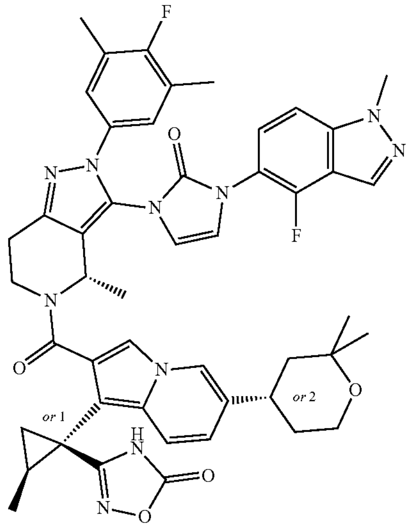 [SMILES: Cc1cc(-n2nc3c(c2-n2ccn(-c4ccc5c(cnn5C)c4F)c2=O)[C@H](C)N(C(=O)c2cn4cc([C@H]5CCOC(C)(C)C5)ccc4c2[C@@]2(c4noc(=O)[nH]4)C[C@@H]2C)CC3)cc(C)c1F] | MS: m/z = 883.1 (M + 1); $^1$H NMR (400 MHz, $CD_3OD$) δ 8.20-8.00 (m, 2H), 7.65 (s, 1H), 7.44-7.53 (m, 2H), 7.16 (d, J = 6.0 Hz, 2H), 6.69-6.89 (m, 3H), 5.81 (s, 1H), 4.12 (s, 3H), 3.83-3.87 (m, 2H), 3.48-3.63 (m, 3H), 2.98-2.79 (m, 2H), 2.29 (s, 6H), 2.03-1.93 (m, 2H), 1.77-1.46 (m, 7H), 1.35-0.99 (m, 11H). |

TABLE 12-continued

| Name | Structure | $^1$H NMR and/or LC/MS data |
|---|---|---|
| Compound 5 (from intermediate 3 and 30-P3) | 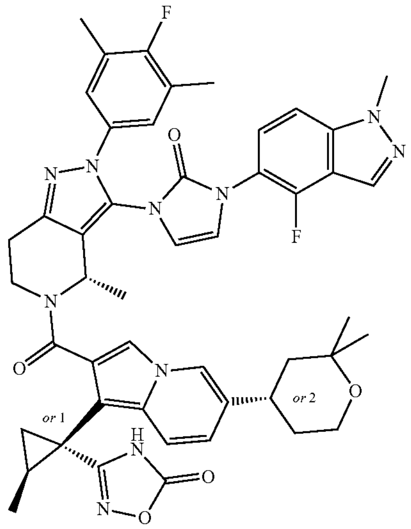 [SMILES: Cc1cc(-n2nc3c(c2-n2ccn(-c4ccc5c(cnn5C)c4F)c2=O)[C@H](C)N(C(=O)c2cn4cc([C@H]5CCOC(C)(C)C5)ccc4c2[C@]2(c4noc(=O)[nH]4)C[C@@H]2C)CC3)cc(C)c1F] | MS: m/z = 883.1 (M + 1); $^1$H NMR (400 MHz, $CD_3OD$) δ 8.20-8.00 (m, 2H), 7.65 (s, 1H), 7.44-7.53 (m, 2H), 7.16 (d, J = 6.0 Hz, 2H), 6.69-6.89 (m, 3H), 5.81 (s, 1H), 4.12 (s, 3H), 3.83-3.87 (m, 2H), 3.48-3.63 (m, 3H), 2.98-2.79 (m, 2H), 2.29 (s, 6H), 2.03-1.93 (m, 2H), 1.77-1.46 (m, 7H), 1.35-0.99 (m, 11H). |
| Compound 6 (from intermediate 3 and 30-P4) | 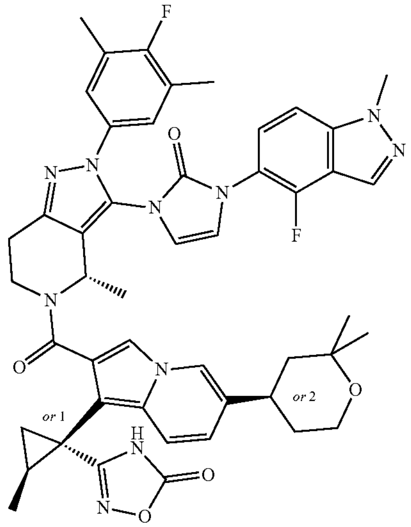 [SMILES: Cc1cc(-n2nc3c(c2-n2ccn(-c4ccc5c(cnn5C)c4F)c2=O)[C@H](C)N(C(=O)c2cn4cc([C@@H]5CCOC(C)(C)C5)ccc4c2[C@]2(c4noc(=O)[nH]4)C[C@@H]2C)CC3)cc(C)c1F] | MS: m/z = 883.1 (M + 1); $^1$H NMR (400 MHz, $CD_3OD$) δ 8.20-8.00 (m, 2H), 7.65 (s, 1H), 7.44-7.53 (m, 2H), 7.16 (d, J = 6.0 Hz, 2H), 6.69-6.89 (m, 3H), 5.81 (s, 1H), 4.12 (s, 3H), 3.83-3.87 (m, 2H), 3.48-3.63 (m, 3H), 2.98-2.79 (m, 2H), 2.29 (s, 6H), 2.03-1.93 (m, 2H), 1.77-1.46 (m, 7H), 1.35-0.99 (m, 11H). |
| Compound 7 (from intermediate 22-P1 and 54) | 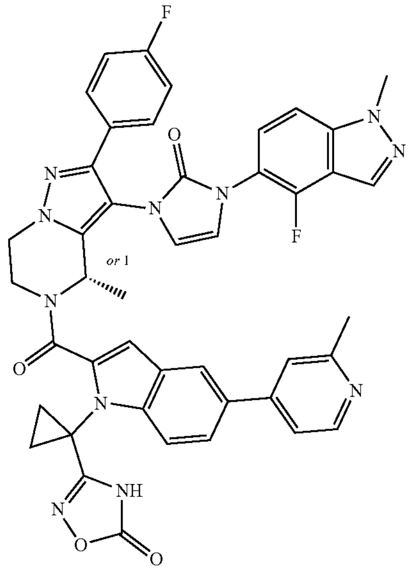 [SMILES: Cc1cc(-c2ccc3c(c2)cc(C(=O)N2CCn4nc(-c5ccc(F)cc5)c(-n5ccn(-c6ccc7c(cnn7C)c6F)c5=O)c4[C@@H]2C)n3C2(c3noc(=O)[nH]3)CC2)ccn1] | MS: m/z = 820 (M + 1); $^1$H NMR (400 MHz, $CDCl_3$) δ 10.93 (s, 1H), 8.62-8.54 (m, 1H), 8.18-8.11 (m, 1H), 8.07-8.00 (m, 1H), 7.97 (s, 1H), 7.83-7.75 (m, 2H), 7.73-7.67 (m, 2H), 7.60 (m, 4H), 7.15-7.05 (m, 2H), 6.87-6.79 (m, 1H), 6.71-6.52 (m, 1H), 6.34-6.21 (m, 1H), 4.54-4.39 (m, 2H), 4.13 (s, 3H), 3.83 (m, 2H), 2.69 (s, 3H), 1.65 (d, J = 6.9 Hz, 3H), 1.25 (m, 4H). |

TABLE 12-continued
| Name | Structure | $^1H$ NMR and/or LC/MS data |
| --- | --- | --- |
| Compound 8 (from intermediate 12 and 28-P2) | 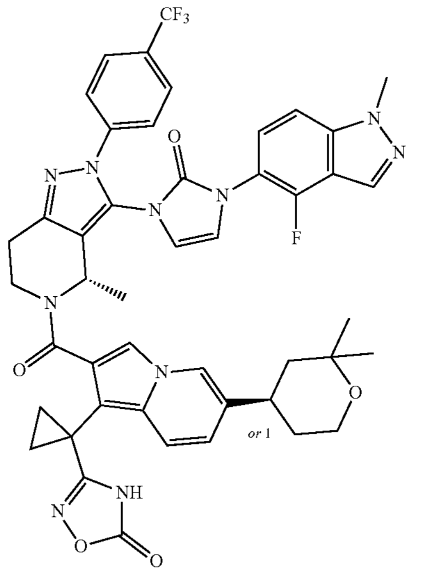 [SMILES: C[C@H]1c2c(nn(-c3ccc(C(F)(F)F)cc3)c2-n2ccn(-c3ccc4c(cnn4C)c3F)c2=O)CCN1C(=O)c1cn2cc([C@@H]3CCOC(C)(C)C3)ccc2c1C1(c2noc(=O)[nH]2)CC1] | MS: m/z = 891.2 (M + 1); $^1H$ NMR (400 MHz, $CD_3OD$) δ 8.18-8.05 (m, 2H), 7.83-7.78 (m, 2H), 7.66-7.41 (m, 5H), 7.32-7.29 (m, 1H), 6.96 (s, 1H), 6.89-6.82 (m, 1H), 6.73-6.71 (m, 1H), 5.92-5.88 (m, 1H), 5.25-5.17 (m, 1H), 4.30-4.26 (m, 1H), 4.10 (d, J = 9.6 Hz, 3H), 3.86-3.73 (m, 2H), 3.58-3.51 (m, 1H), 2.99-2.84 (m, 2H), 1.80-1.22 (m, 17H). |
| Compound 9 (from intermediate 3 and 31-P1) | 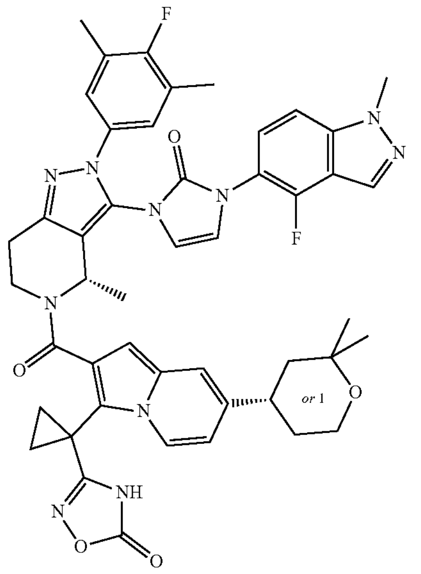 [SMILES: Cc1cc(-n2nc3c(c2-n2ccn(-c4ccc5c(cnn5C)c4F)c2=O)[C@H](C)N(C(=O)c2cc4cc([C@H]5CCOC(C)(C)C5)ccn4c2C2(c4noc(=O)[nH]4)CC2)CC3)cc(C)c1F] | MS: m/z = 869.2 (M + 1); $^1H$ NMR (400 MHz, $CD_3OD$) δ 8.18-8.09 (m, 2H), 7.52 (d, J = 9.2 Hz, 1H), 7.46-7.41 (m, 1H), 7.31-7.25 (m, 1H), 7.17-7.12 (m, 2H), 6.89 (d, J = 2.8 Hz, 1H), 6.79 (s, 1H), 6.73-6.68 (m, 1H), 5.87-5.83 (m, 1H), 4.10 (d, J = 14.2 Hz, 3H), 3.88-3.74 (m, 2H), 3.48 (s, 2H), 3.02-2.81 (m, 3H), 2.27 (d, J = 9.6 Hz, 6H), 1.81-1.24 (m, 17H). |

TABLE 12-continued
| Name | Structure | $^1$H NMR and/or LC/MS data |
|---|---|---|
| Compound 10 (from intermediate 3 and 31-P2) | 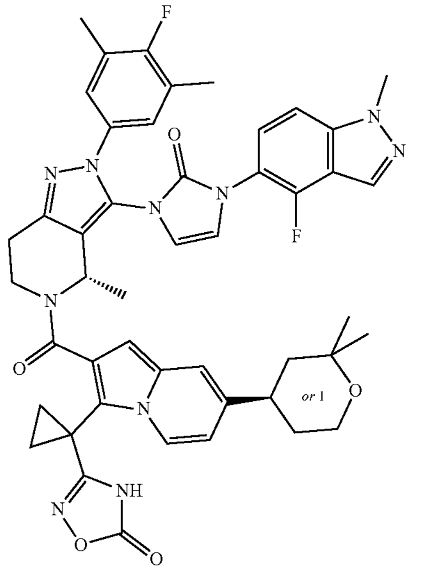 [SMILES: Cc1cc(-n2nc3c(c2-n2ccn(-c4ccc5c(cnn5C)c4F)c2=O)[C@H](C)N(C(=O)c2cc4cc([C@@H]5CCOC(C)(C)C5)ccn4c2C2(c4noc(=O)[nH]4)CC2)CC3)cc(C)c1F] | MS: m/z = 869.2 (M + 1); $^1$H NMR (400 MHz, $CD_3OD$) δ 8.18-8.09 (m, 2H), 7.52 (d, J = 9.2 Hz, 1H), 7.46-7.41 (m, 1H), 7.31-7.25 (m, 1H), 7.17-7.12 (m, 2H), 6.89 (d, J = 2.8 Hz, 1H), 6.79 (s, 1H), 6.73-6.68 (m, 1H), 5.87-5.83 (m, 1H), 4.10 (d, J = 14.2 Hz, 3H), 3.88-3.74 (m, 2H), 3.48 (s, 2H), 3.02-2.81 (m, 3H), 2.27 (d, J = 9.6 Hz, 6H), 1.81-1.24 (m, 17H). |
| Compound 11 (from intermediate 13 and 28-P2) | 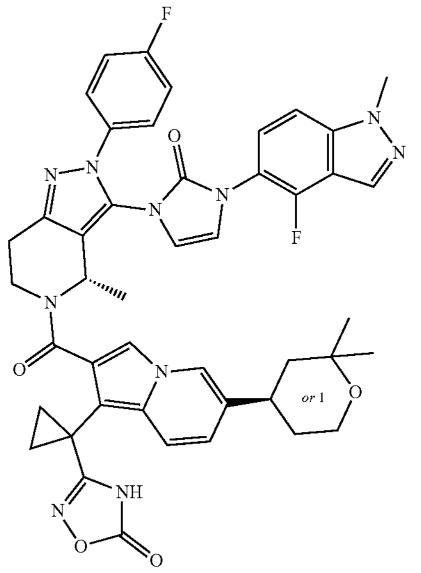 [SMILES: C[C@H]1c2c(nn(-c3ccc(F)cc3)c2-n2ccn(-c3ccc4c(cnn4C)c3F)c2=O)CCN1C(=O)c1cn2cc([C@@H]3CCOC(C)(C)C3)ccc2c1C1(c2noc(=O)[nH]2)CC1] | MS: m/z = 841.2 (M + 1); $^1$H NMR (400 MHz, DMSO-$d_6$) δ 11.97 (s, 1H), 8.30 (s, 1H), 8.13 (s, 1H), 7.69 (s, 1H), 7.63 (d, J = 8.8 Hz, 1H), 7.56-7.40 (m, 3H), 7.44-7.31 (m, 2H), 7.07 (s, 1H), 6.99-6.71 (m, 2H), 5.68 (d, J = 6.8 Hz, 1H), 4.90 (d, J = 80.4 Hz, 1H), 4.11 (s, 3H), 3.71 (d, J = 7.2 Hz, 2H), 3.63-3.61 (m, 2H), 3.27-3.13 (m, 1H), 2.99-2.70 (m, 3H), 1.77-1.61 (m, 2H), 1.62-1.36 (m, 4H), 1.40-1.21 (m, 6H), 1.19 (s, 3H). |

TABLE 12-continued
| Name | Structure | $^1$H NMR and/or LC/MS data |
| --- | --- | --- |
| Compound 12 (from intermediate 14 and 28-P2) | 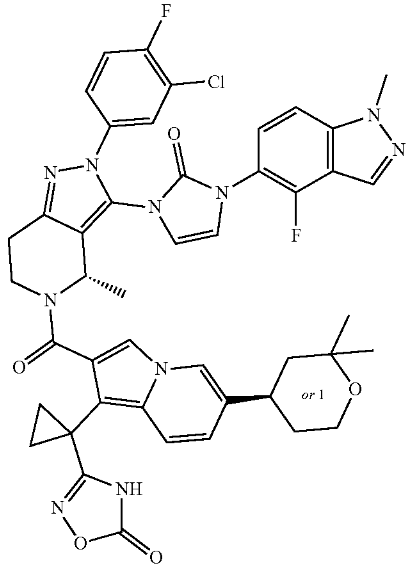 | MS: m/z = 875.2 (M + 1); $^1$H NMR (400 MHz, DMSO-$d_6$) δ 11.91 (s, 1H), 8.30 (s, 1H), 8.13 (s, 1H), 7.73-7.53 (m, 3H), 7.50-7.30 (m, 3H), 7.09 (d, J = 30.8 Hz, 1H), 7.00-6.69 (m, 2H), 5.70 (d, J = 7.2 Hz, 1H), 4.89 (d, J = 75.6 Hz, 1H), 4.11 (s, 3H), 3.71 (d, J = 7.2 Hz, 2H), 3.49-3.38 (m, 2H), 3.28-3.11 (m, 1H), 2.98-2.70 (m, 3H), 1.70 (d, J = 9.2 Hz, 2H), 1.61-1.38 (m, 4H), 1.38-1.20 (m, 6H), 1.19 (s, 3H). |
| Compound 13 (from intermediate 15 and 28-P2) | 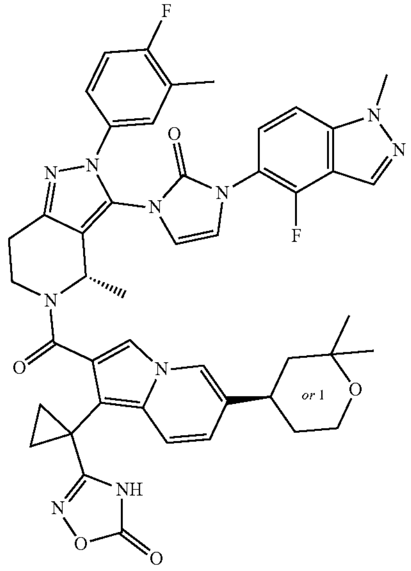 | MS: m/z = 855.3 (M + 1); $^1$H NMR (400 MHz, DMSO-$d_6$) δ 11.93 (s, 1H), 8.31 (s, 1H), 8.13 (s, 1H), 7.69 (s, 1H), 7.64 (d, J = 8.8 Hz, 1H), 7.53-7.40 (m, 2H), 7.40-7.19 (m, 3H), 7.08 (s, 1H), 6.97 (s, 1H), 6.86 (d, J = 8.8 Hz, 1H), 5.66 (d, J = 6.0 Hz, 1H), 5.01 (s, 0.5H), 4.78 (s, 0.5H), 4.11 (s, 3H), 3.71 (d, J = 7.2 Hz, 2H), 2.96-2.67 (m, 4H), 2.27 (s, 3H), 1.76-1.63 (m, 2H), 1.60-1.38 (m, 4H), 1.38-1.1 (m, 11H). |

TABLE 12-continued
| Name | Structure | $^1H$ NMR and/or LC/MS data |
| --- | --- | --- |
| Compound 14 (from intermediate 22-P1 and 28-P2) | 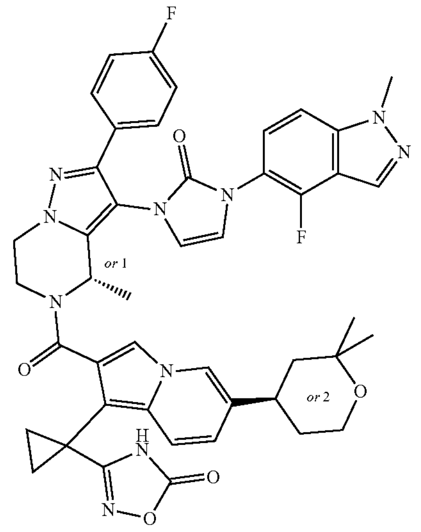 [SMILES: C[C@H]1c2c(-n3ccn(-c4ccc5c(cnn5C)c4F)c3=O)c(-c3ccc(F)cc3)nn2CCN1C(=O)c1cn2cc([C@@H]3CCOC(C)(C)C3)ccc2c1C1(c2noc(=O)[nH]2)CC1] | MS: m/z = 841.2 (M + 1); $^1H$ NMR (400 MHz, DMSO-$d_6$) δ 8.30 (s, 1H), 8.09 (s, 1H), 7.70 (s, 1H), 7.58-7.55 (m, 3H), 7.45 (d, J = 10.0 Hz, 2H), 7.34-7.18 (m, 2H), 7.06 (s, 1H), 6.85 (d, J = 9.6 Hz, 2H), 5.77-5.75 (m, 1H), 4.22-4.12 (m, 5H), 3.70-3.68 (m, 4H), 2.88-2.84 (m, 1H), 2.67 (s, 1H), 2.33 (s, 1H), 1.68 (d, J = 13.6 Hz, 2H), 1.62-1.33 (m, 6H), 1.26-1.18 (m, 6H). |
| Compound 15 (from intermediate 3 and 32) | 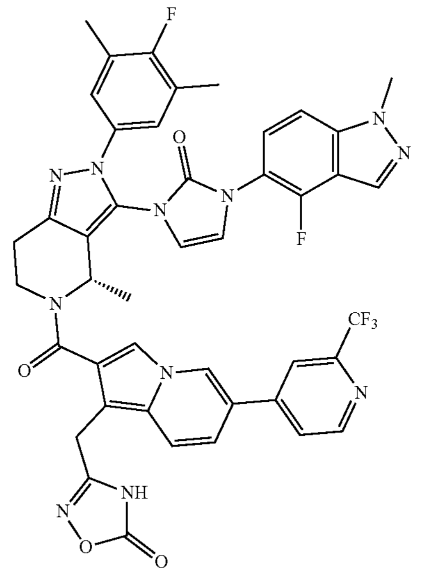 [SMILES: Cc1cc(-n2nc3c(c2-n2ccn(-c4ccc5c(cnn5C)c4F)c2=O)[C@H](C)N(C(=O)c2cn4cc(-c5ccnc(C(F)(F)F)c5)ccc4c2Cc2noc(=O)[nH]2)CC3)cc(C)c1F] | MS: m/z = 876.3 (M + 1); $^1H$ NMR (400 MHz, $CD_3OD$) δ 8.87-8.76 (m, 1H), 8.49 (s, 3H), 8.18-7.82 (m, 3H), 7.67 (d, J = 9.6 Hz, 1H), 7.50-7.06 (m, 4H), 6.88-6.64 (m, 2H), 5.34-5.32 (m, 1H), 4.11-4.02 (m, 3H), 3.18-2.88 (m, 2H), 2.27 (s, 3H), 2.18 (t, J = 7.6 Hz, 1H), 2.04-2.00 (m, 1H), 1.63-1.55 (m, 1H), 1.48-1.47 (m, 1H), 1.29 (s, 6H). |

TABLE 12-continued
| Name | Structure | $^1$H NMR and/or LC/MS data |
|---|---|---|
| Compound 16 (from intermediate 6 and 28-P1) | 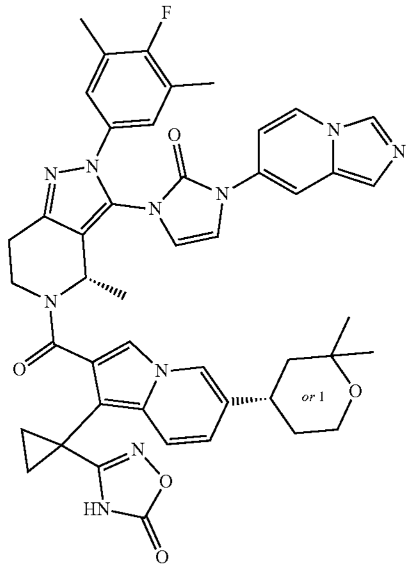 [SMILES: Cc1cc(-n2nc3c(c2-n2ccn(-c4ccn5cncc5c4)c2=O)[C@H](C)N(C(=O)c2cn4cc([C@H]5CCOC(C)(C)C5)ccc4c2C2(c4noc(=O)[nH]4)CC2)CC3)cc(C)c1F] | MS: m/z = 837 (M + 1, ESI); $^1$H NMR (400 MHz, $CD_3OD$) δ 8.50 (s, 2H), 8.38-8.22 (m, 2H), 8.12-7.76 (m, 1H), 7.50 (m, 3H), 7.18-7.04 (m, 3H), 6.96-6.74 (m, 2H), 3.95-3.61 (m, 2H), 3.07-2.73 (m, 3H), 2.24 (s, 6H), 1.54-1.11 (m, 17H). |
| Compound 17 (from intermediate 7 and 28-P2) | 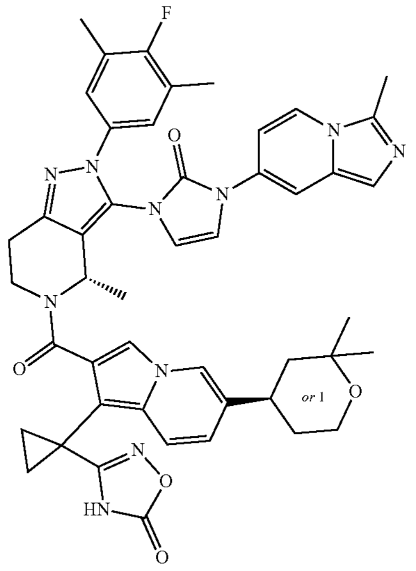 [SMILES: Cc1cc(-n2nc3c(c2-n2ccn(-c4ccn5c(C)ncc5c4)c2=O)[C@H](C)N(C(=O)c2cn4cc([C@@H]5CCOC(C)(C)C5)ccc4c2C2(c4noc(=O)[nH]4)CC2)CC3)cc(C)c1F] | MS: m/z = 851.3 (M + 1); $^1$H NMR (400 MHz, $CD_3OD$) δ 8.10-8.04 (m, 2H), 7.60 (s, 1H), 7.60-7.49 (m, 2H), 7.33-7.26 (m, 2 H), 7.15 (s, 1H), 7.13 (s, 1H), 7.07 (m, 1H), 6.88-6.81 (m, 2H), 6.66 (s, 1H), 5.86-5.83 (m, 1 H), 5.19-5.17 (m, 1H), 4.25-4.23 (m, 1 H), 3.83-3.76 (m, 3H), 2.89-2.86 (m, 4 H), 2.63 (s, 3H), 2.23 (s, 6H), 1.77-1.21 (m, 14H). |

TABLE 12-continued
| Name | Structure | $^1$H NMR and/or LC/MS data |
|---|---|---|
| Compound 18 (from intermediate 7 and 28-P1) | 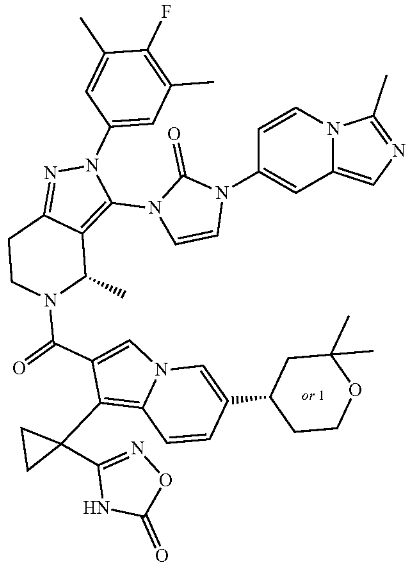 [SMILES: Cc1cc(-n2nc3c(c2-n2ccn(-c4ccn5c(C)ncc5c4)c2=O)[C@H](C)N(C(=O)c2cn4cc([C@H]5CCOC(C)(C)C5)ccc4c2C2(c4noc(=O)[nH]4)CC2)CC3)cc(C)c1F] | MS: m/z = 851.3 (M + 1); $^1$H NMR (400 MHz, $CD_3OD$) δ 8.10-8.04 (m, 2H), 7.60 (s, 1H), 7.60-7.49 (m, 2H), 7.33-7.26 (m, 2 H), 7.15 (s, 1H), 7.13 (s, 1H), 7.07 (m, 1H), 6.88-6.81 (m, 2H), 6.66 (s, 1H), 5.86-5.83 (m, 1 H), 5.19-5.17 (m, 1H), 4.25-4.23 (m, 1 H), 3.83-3.76 (m, 3H), 2.89-2.86 (m, 4 H), 2.63 (s, 3H), 2.23 (s, 6H), 1.77-1.21 (m, 14H). |
| Compound 19 (from intermediate 3 and 28-P2) | 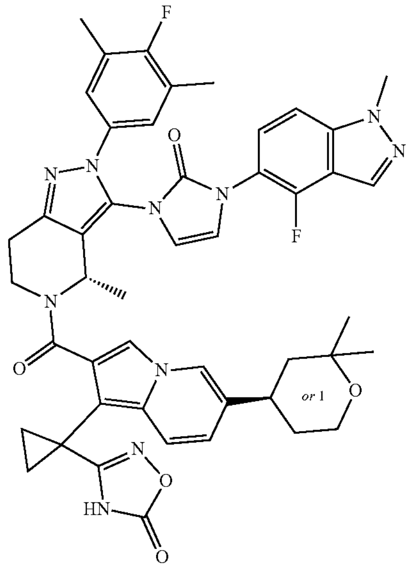 [SMILES: Cc1cc(-n2nc3c(c2-n2ccn(-c4ccc5c(cnn5C)c4F)c2=O)[C@H](C)N(C(=O)c2cn4cc([C@@H]5CCOC(C)(C)C5)ccc4c2C2(c4noc(=O)[nH]4)CC2)CC3)cc(C)c1F] | MS: m/z = 869.3 (M + 1); $^1$H NMR (400 MHz, $CD_3OD$) δ 8.14 (d, J = 28.0 Hz, 1H), 8.00 (d, J = 28.0 Hz, 1H), 7.59 (d, J = 16.0 Hz, H), 7.54-7.43 (m, 2H), 7.28 (s, 1H), 7.16 (d, J = 4.0 Hz, 2H), 6.89-6.78 (m, 2H), 6.64 (d, J = 24.0 Hz, 1H), 5.87 (s, 1H), 4.26 (d, J = 12.0 Hz, 1H), 4.10 (d, J = 12.0 Hz, 3H), 3.86-3.76 (m, 2H), 3.54-3.48 (m, 1H), 2.89-2.85 (m, 3H), 2.28 (s, 6H), 1.87-1.62 (m, 3H), 1.59-1.54 (m, 2H), 1.47-1.42 (m, 4H), 1.37-1.23 (m, 8H). |

TABLE 12-continued
| Name | Structure | $^1$H NMR and/or LC/MS data |
| --- | --- | --- |
| Compound 20 (from intermediate 3 and 28-P1) | 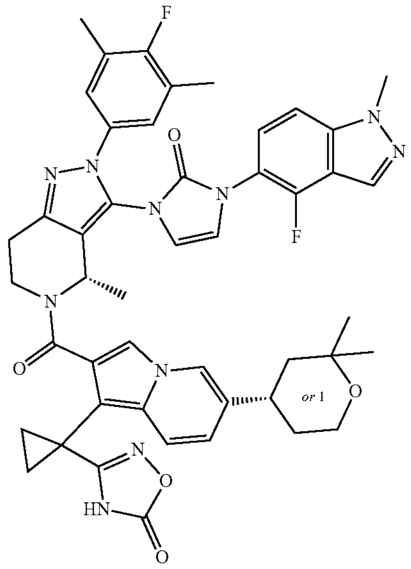 [SMILES: Cc1cc(-n2nc3c(c2-n2ccn(-c4ccc5c(cnn5C)c4F)c2=O)[C@H](C)N(C(=O)c2cn4cc([C@H]5CCOC(C)(C)C5)ccc4c2C2(c4noc(=O)[nH]4)CC2)CC3)cc(C)c1F] | MS: m/z = 869.3, (M + 1); $^1$H NMR (400 MHz, $CD_3OD$) δ 8.15 (d, J = 28.0 Hz, 1H), 8.01 (d, J = 28.0 Hz, 1H), 7.59 (d, J = 16.0 Hz, 1H), 7.52-7.42 (m, 2H), 7.28 (s, 1H), 7.17 (d, J = 4.0 Hz, 2H), 6.89-6.78 (m, 2H), 6.64 (d, J = 24.0 Hz, 1H), 5.86 (d, J = 4.0 Hz, 1H), 4.26 (d, J = 8.0 Hz, 1H), 4.10 (d, J = 12.0 Hz, 3H), 3.91-3.70 (m, 2H), 3.54-3.48 (m, 1H), 2.89-2.85 (m, 3H), 2.28-2.26 (m, 6H), 1.77-1.69 (m, 3H), 1.57-1.54 (m, 2H), 1.50-1.40 (m, 4H), 1.39-1.03 (m, 8H). |
| Compound 21 (from intermediate 3 and 27-P2) | 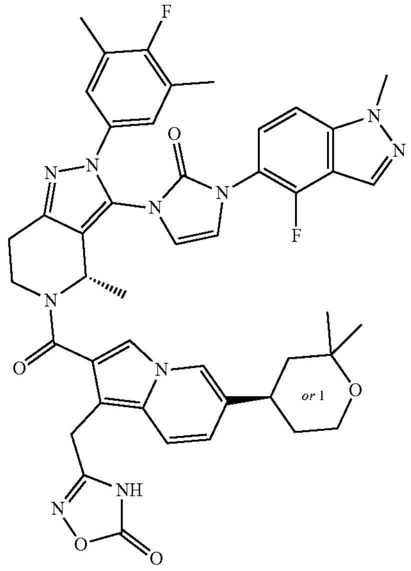 [SMILES: Cc1cc(-n2nc3c(c2-n2ccn(-c4ccc5c(cnn5C)c4F)c2=O)[C@H](C)N(C(=O)c2cn4cc([C@@H]5CCOC(C)(C)C5)ccc4c2Cc2noc(=O)[nH]2)CC3)cc(C)c1F] | MS: m/z = 843.3, (M + 1); $^1$H NMIR (400 MHz, $CD_3OD$) δ 8.15 (d, J = 16.4 Hz, 1 H), 8.00 (d, J = 13.2 Hz, 1 H), 7.68 (s, 1 H), 7.51-7.44 (m, 2 H), 7.31 (s, 1 H), 7.18 (s, 2 H), 6.88-6.77 (m, 2 H), 6.66 (s, 0.5 H), 6.54 (s, 0.5 H), 5.79 (s, 1H), 4.11-4.07 (m, 4 H), 3.87-3.75 (m, 3H), 3.01-2.80 (m, 5 H), 2.28 (s, 6 H), 1.77-1.46 (m, 8 H), 1.33-1.25 (m, 6H). |

TABLE 12-continued
| Name | Structure | $^1$H NMR and/or LC/MS data |
|---|---|---|
| Compound 22 (from intermediate 3 and 27-P1) | 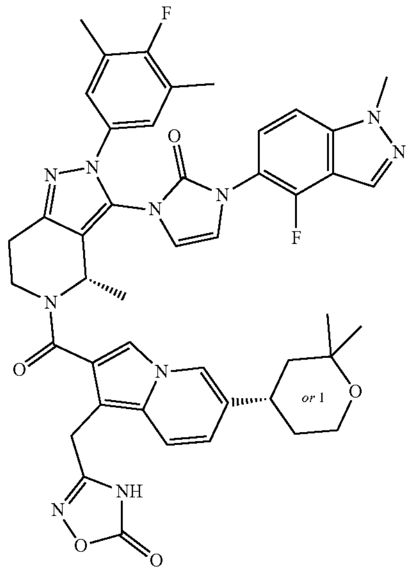 [SMILES: Cc1cc(-n2nc3c(c2-n2ccn(-c4ccc5c(cnn5C)c4F)c2=O)[C@H](C)N(C(=O)c2cn4cc([C@H]5CCOC(C)(C)C5)ccc4c2Cc2noc(=O)[nH]2)CC3)cc(C)c1F] | MS: m/z = 843.3, (M + 1); $^1$H NMR (400 MHz, $CD_3OD$) δ 8.15 (d, J = 16.4 Hz, 1 H), 8.00 (d, J = 12.0 Hz, 1 H), 7.67 (s, 1 H), 7.51-7.44 (m, 2 H), 7.32 (s, 1 H), 7.18 (s, 2 H), 6.88-6.77 (m, 2 H), 6.66 (s, 0.5 H), 6.55 (s, 0.5 H), 5.79 (s, 1H), 4.10-4.07 (m, 4 H), 3.87-3.75 (m, 3H), 3.01-2.80 (m, 5 H), 2.28 (s, 6 H), 1.77-1.46 (m, 8 H), 1.33-1.25 (m, 6H). |
| Compound 23 (from intermediate 22 and 29) | 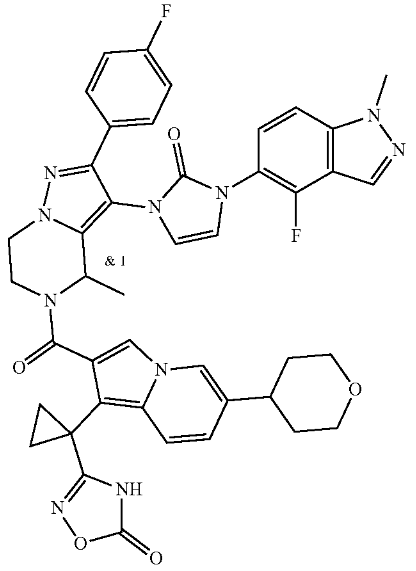 [SMILES: CC1c2c(-n3ccn(-c4ccc5c(cnn5C)c4F)c3=O)c(-c3ccc(F)cc3)nn2CCN1C(=O)c1cn2cc(C3CCOCC3)ccc2c1C1(c2noc(=O)[nH]2)CC1] | MS: m/z = 813.2 (M + 1); $^1$H NMR (400 MHz, DMSO-$d_6$) δ 11.86 (s, 1H), 8.30 (s, 1H), 8.09 (s, 1H), 7.74 (s, 1H), 7.68-7.50 (m, 3H), 7.47 (d, J = 9.6 Hz, 1H), 7.27 (t, J = 8.4 Hz, 2H), 7.06 (s, 1H), 6.87 (d, J = 9.2 Hz, 2H), 5.79 (s, 1H), 4.39-4.16 (m, 2H), 4.12 (s, 3H), 4.03-3.67 (m, 3H), 3.52-3.43 (m, 4H), 2.70 (s, 1H), 1.79-1.46 (m, 5H), 1.39 (d, J = 6.8 Hz, 3H), 1.34-1.17 (m, 2H). |
Example 49: Synthesis of Compound 24
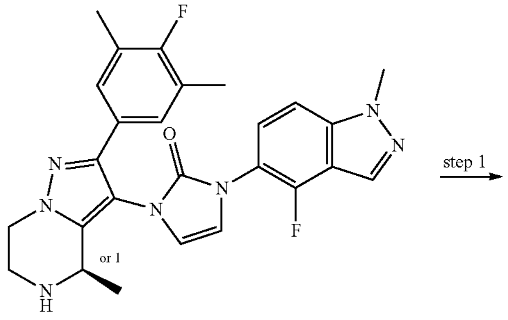
Intermediate 19-P1

-continued

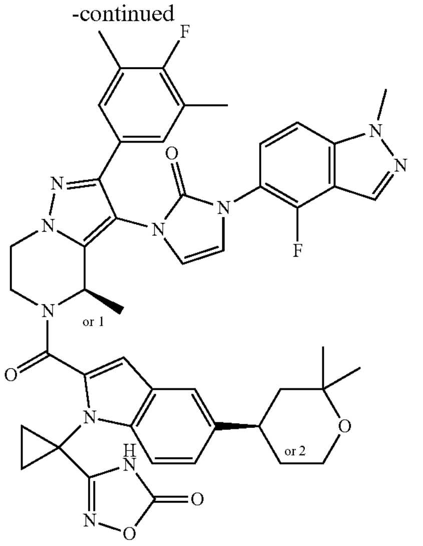

Compound 24

To a solution of Intermediate 19-P1 (11 mg, 22.47 μmol), Intermediate 46-P2 (10 mg, 25.16 μmol) and HATU (13 mg, 33.71 μmol) in NMP (2 mL) was added DIEA (15 mg, 112.36 μmol). The reaction mixture was stirred for 16 hr at 25° C. The mixture was concentrated and purified by reverse-phase column (MeCN: 0.5% FA in $H_2O$=60:40) to give Compound 24 (3.2 mg, 16% yield). $^1$H NMR (400 MHz, DMSO-$d_6$) δ 12.13 (s, 1H), 8.31 (s, 1H), 7.63-7.50 (m, 4H), 7.25-7.24 (m, 3H), 7.06 (s, 1H), 6.91-6.82 (m, 2H), 5.65 (s, 1H), 4.33 (s, 2H), 4.11 (s, 3H), 3.90 (s, 2H), 3.72 (d, J=7.6 Hz, 2H), 3.04 (s, 1H), 2.23 (s, 6H), 1.67-1.63 (m, 6H), 1.62-1.37 (m, 5H), 1.28-1.23 (m, 3H), 1.18 (s, 3H); MS: m/z=869.3 (M+1).

Example 50: Synthesis of Compounds 25-52

The compounds in Table 13 were made according to the procedure of Compound 24.

TABLE 13

| Name | Structure | $^1$H NMR and/or LC/MS data |
| --- | --- | --- |
| Compound 25 (from intermediate 19-P2 and 46-P2) | 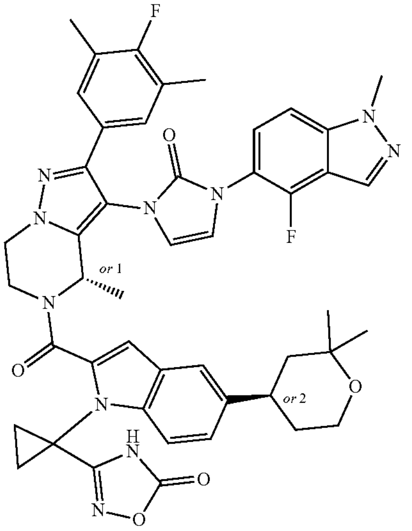 [SMILES: Cc1cc(-c2nn3c(c2-n2ccn(-c4ccc5c(cnn5C)c4F)c2=O)[C@H](C)N(C(=O)c2cc4cc([C@@H]5CCOC(C)(C)C5)ccc4n2C2(c4noc(=O)[nH]4)CC2)CC3)cc(C)c1F] | MS: m/z = 869.3, (M + 1); $^1$H NMR (400 MHz, DMSO-$d_6$) δ 12.13 (s, 1H), 8.31 (s, 1H), 7.63-7.49 (m, 4H), 7.25 (s, 3H), 7.06 (s, 1H), 6.91-6.81 (m, 2H), 5.64 (s, 1H), 4.34 (s, 2H), 4.12 (s, 3H), 3.90 (s, 2H), 3.72 (d, J = 7.6 Hz, 2H), 3.05 (s, 1H), 2.23 (s, 6H), 2.00-1.98 (m, 1H), 1.89-1.36 (m, 10H), 1.30-1.14 (m, 6H). |

TABLE 13-continued
| Name | Structure | $^1$H NMR and/or LC/MS data |
| --- | --- | --- |
| Compound 26 (from intermediate 20-P1 and 46-P2) | 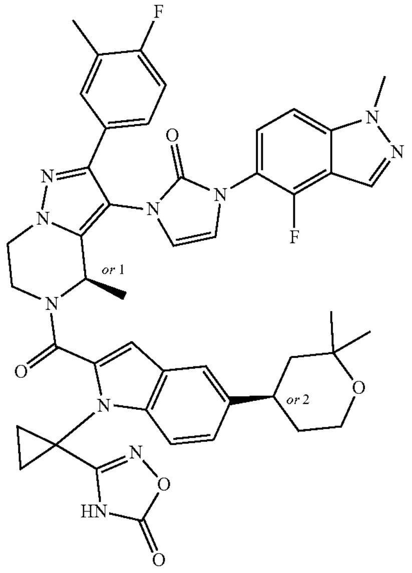 [SMILES: Cc1cc(-c2nn3c(c2-n2ccn(-c4ccc5c(cnn5C)c4F)c2=O)[C@@H](C)N(C(=O)c2cc4cc([C@@H]5CCOC(C)(C)C5)ccc4n2C2(c4noc(=O)[nH]4)CC2)CC3)ccc1F] | MS: m/z = 855 (M + 1); $^1$H NMR (400 MHz, DMSO-d6) δ 12.14 (s, 1H), 8.31 (s, 1H), 7.53-7.49 (m, 6H), 7.23-7.21 (m, 2H), 7.07 (s, 1H), 6.88-6.86 (m, 2H), 5.65-5.63 (m, 1H), 4.55-4.31 (m, 2H), 4.12 (s, 3H), 3.95-3.70 (m, 4H), 3.06 (m, 1H), 2.26 (s, 3H), 1.86-1.42 (m, 11H), 1.28 (s, 3H), 1.19 (s, 3H). |
| Compound 27 (from intermediate 20-P2 and 46-P2) | 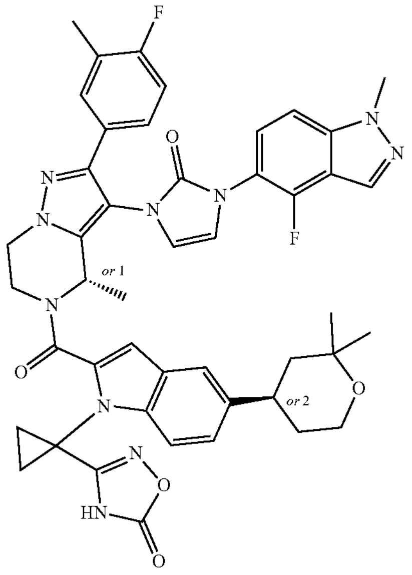 [SMILES: Cc1cc(-c2nn3c(c2-n2ccn(-c4ccc5c(cnn5C)c4F)c2=O)[C@H](C)N(C(=O)c2cc4cc([C@@H]5CCOC(C)(C)C5)ccc4n2C2(c4noc(=O)[nH]4)CC2)CC3)ccc1F] | MS: m/z = 855 (M + 1); $^1$H NMR (400 MHz, DMSO-d6) δ 12.14 (s, 1H), 8.31 (s, 1H), 7.53-7.49 (m, 6H), 7.23-7.21 (m, 2H), 7.07 (s, 1H), 6.88-6.86 (m, 2H), 5.65-5.63 (m, 1H), 4.55-4.31 (m, 2H), 4.12 (s, 3H), 3.95-3.70 (m, 4H), 3.06 (m, IH), 2.26 (s, 3H), 1.86-1.42 (m, 11H), 1.28 (s, 3H), 1.19 (s, 3H). |

TABLE 13-continued
| Name | Structure | $^1$H NMR and/or LC/MS data |
| --- | --- | --- |
| Compound 28 (from intermediate 21 and 46-P2) | 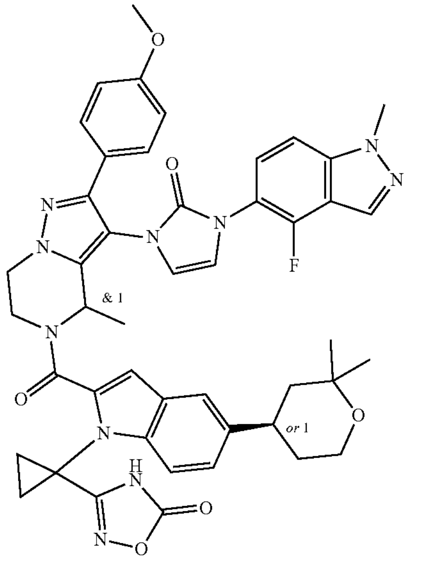 [SMILES: COc1ccc(-c2nn3c(c2-n2ccn(-c4ccc5c(cnn5C)c4F)c2=O)C(C)N(C(=O)c2cc4cc([C@@H]5CCOC(C)(C)C5)ccc4n2C2(c4noc(=O)[nH]4)CC2)CC3)cc1] | MS: m/z = 853 (M + 1); 1H NMR (400 MHz, DMSO-d6) δ 12.06 (s, 1H), 8.31 (s, 1H), 7.69-7.38 (m, 6H), 7.33-7.10 (m, 2H), 7.06-6.95 (m, 2H), 6.85-6.83 (m, 2H), 5.66-5.64 (m, 1H), 4.12 (s, 3H), 3.78 (s, 3H), 3.75-3.66 (m, 3H), 3.08-3.04 (m, 4H), 1.65-1.55 (m, 11H), 1.28 (s, 3H), 1.18 (s, 3H). |
| Compound 29 (from intermediate 25-P1 and 46-P2) | 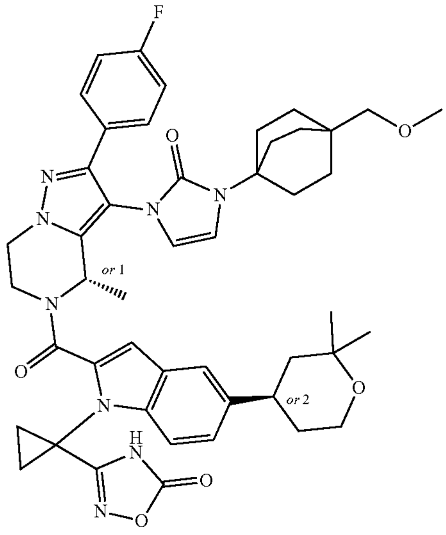 [SMILES: COCC12CCC(n3ccn(-c4c(-c5ccc(F)cc5)nn5c4[C@H](C)N(C(=O)c4cc6cc([C@@H]7CCOC(C)(C)C7)ccc6n4C4(c6noc(=O)[nH]6)CC4)CC5)c3=O)(CC1)CC2] | MS: m/z = 845.3 (M + 1); $^1$H NMR (400 MHz, DMSO-$d_6$) δ 12.08 (s, 1H), 7.47-7.45 (m, 4H), 7.22 (t, J = 8.0 Hz, 3H), 6.86 (s, 1H), 6.71 (s, 1H), 6.48 (s, 1H), 5.82-5.46 (m, 1H), 4.76-4.01 (m, 3H), 3.93-3.78 (m, 1H), 3.72 (d, J = 8.0 Hz, 2H), 3.22 (s, 3H), 3.09-3.01 (m, 1H), 2.98 (s, 2H), 2.87 (s, 1H), 2.94-2.12 (m, 5H), 1.87-1.62 (m, 6H), 1.61-1 45 (m, 9H), 1.36-1.23 (m, 6H), 1.22-1.11 (m, 4H). |

TABLE 13-continued
| Name | Structure | $^1H$ NMR and/or LC/MS data |
|---|---|---|
| Compound 30 (from intermediate 3 and 38) | 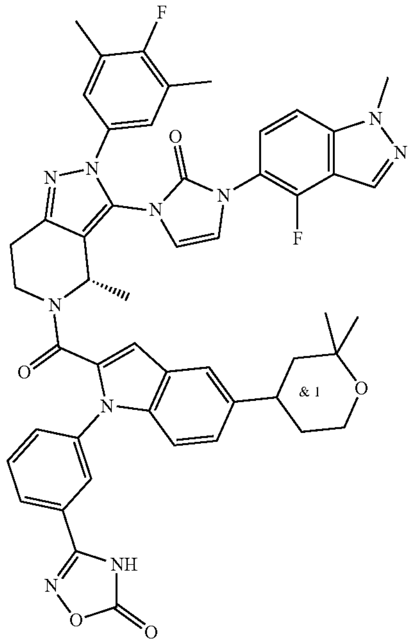 [SMILES: Cc1cc(-n2nc3c(c2-n2ccn(-c4ccc5c(cnn5C)c4F)c2=O)[C@H](C)N(C(=O)c2cc4cc(C5CCOC(C)(C)C5)ccc4n2-c2cccc(-c4noc(=O)[nH]4)c2)CC3)cc(C)c1F] | MS: m/z = 905 (M + 1); $^1H$ NMR (400 MHz, DMSO-$d_6$) δ 13.08 (s, 1H), 8.29 (s, 1H), 7.85-7.75 (m, 3H), 7.70-7.35 (m, 6H), 7.27-6.86 (m, 6H), 5.50-5.42 (m, 1H), 4.10 (s, 3H), 3.78-3.64 (m, 2H), 3.53-3.49 (m, 1H), 3.30-2.68 (m, 4H), 2.24 (s, 6H), 1.79-1.52 (m, 4H), 1.29-1.12 (m, 9H). |
| Compound 31 (from intermediate 22-P1 and 46-P1) | 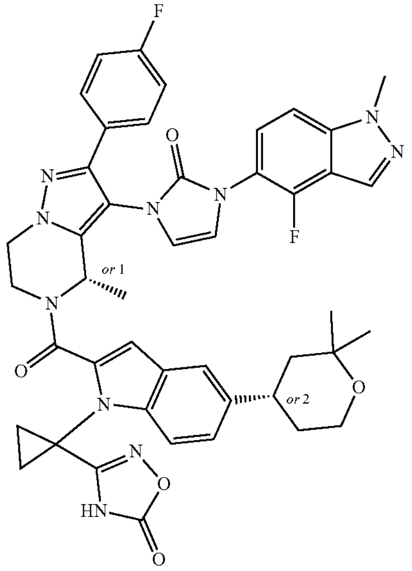 [SMILES: C[C@H]1c2c(-n3ccn(-c4ccc5c(cnn5C)c4F)c3=O)c(-c3ccc(F)cc3)nn2CCN1C(=O)c1cc2cc([C@H]3CCOC(C)(C)C3)ccc2n1C1(c2noc(=O)[nH]2)CC1] | MS: m/z = 841.5 (M + 1); $^1H$ NMR (400 MHz, DMSO-$d_6$) δ 12.15 (s, 1H), 8.30 (s, 1H), 7.69-7.53 (m, 3H), 7.53-7.45 (m, 2H), 7.35-7.17 (m, 3H), 7.06 (s, 1H), 6.92-6.80 (m, 2H), 5.92-5.61 (m, 1H), 4.26-4.58 (m, 3H), 4.12(s, 3H), 3.88 (s, 1H), 3.72 (d, J = 7.6 Hz, 2H), 3.05 (t, J = 12.0 Hz, 1H), 1.88-1.61 (m, 5H), 1.61-1.50 (m, 2H), 1.47-1.34 (m, 3H), 1.28 (s, 3H), 1.23-1.13 (m, 4H). |

TABLE 13-continued
| Name | Structure | $^1$H NMR and/or LC/MS data |
|---|---|---|
| Compound 32 (from intermediate 22-P2 and 46-P1) | 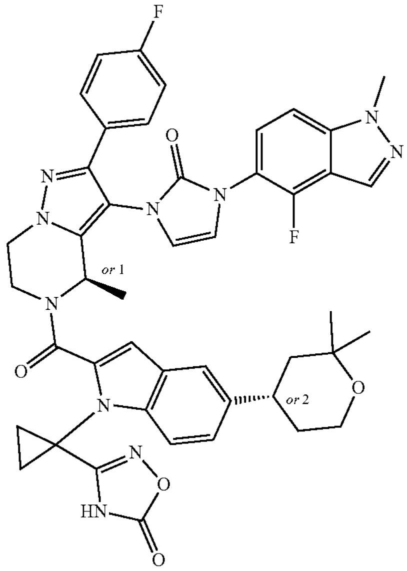 [SMILES: C[C@@H]1c2c(-n3ccn(-c4ccc5c(cnn5C)c4F)c3=O)c(-c3ccc(F)cc3)nn2CCN1C(=O)c1cc2cc([C@H]3CCOC(C)(C)C3)ccc2n1C1(c2noc(=O)[nH]2)CC1] | MS: m/z = 841.5 (M + 1); $^1$H NMR (400 MHz, DMSO-$d_6$) δ 12.10 (s, 1H), 8.30 (s, 1H), 7.69-7.53 (m, 3H), 7.49 (d, J = 7.6 Hz, 1H), 7.33-7.17 (m, 3H), 7.06 (s, 1H), 6.92-6.80 (m, 2H), 5.87-5.56 (m, 1H), 4.23-4.62 (m, 3H), 4.11 (s, 3H), 3.88 (s, 1H), 3.72 (d, J = 7.6 Hz, 2H), 3.05 (t, J = 12.0 Hz, 1H), 1.89-1.63 (m, 5H), 1.60-1.50 (m, 2H), 1.46-1 34 (m, 3H), 1.28 (s, 3H), 1.23-1.10 (m, 4H). |
| Compound 33 (from intermediate 22-P1 and 46-P2) | 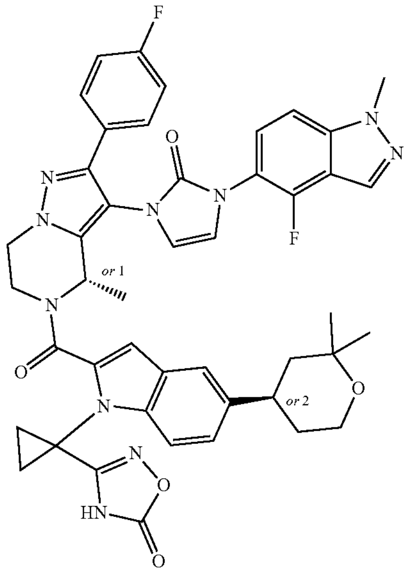 [SMILES: C[C@H]1c2c(-n3ccn(-c4ccc5c(cnn5C)c4F)c3=O)c(-c3ccc(F)cc3)nn2CCN1C(=O)c1cc2cc([C@@H]3CCOC(C)(C)C3)ccc2n1C1(c2noc(=O)[nH]2)CC1] | MS: m/z = 841.3 (M + 1); $^1$H NMR (400 MHz, DMSO-$d_6$) δ 12.10 (s, 1H), 8.30 (s, 1H), 7.69-7.51 (m, 3H), 7.48 (d, J = 8.4 Hz, 1H), 7.33-7.18 (m, 3H), 7.06 (s, 1H), 6.86 (s, 2H), 5.87-5.56 (m, 1H), 4.23-4.63 (m, 3H), 4.11 (s, 3H), 3.88 (s, 1H), 3.72 (d, J = 7.6 Hz, 2H), 3.03 (t, J = 12.0 Hz, 1H), 1.91-1.34 (m, 10H), 1.33-1.10 (m, 7H). |

TABLE 13-continued
| Name | Structure | $^1$H NMR and/or LC/MS data |
|---|---|---|
| Compound 34 (from intermediate 22-P2 and 46-P2) | 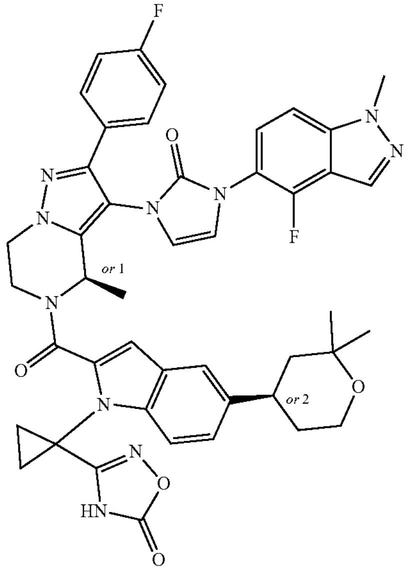 [SMILES: C[C@@H]1c2c(-n3ccn(-c4ccc5c(cnn5C)c4F)c3=O)c(-c3ccc(F)cc3)nn2CCN1C(=O)c1cc2cc([C@@H]3CCOC(C)(C)C3)ccc2n1C1(c2noc(=O)[nH]2)CC1] | MS: m/z = 841.2 (M + 1); $^1$H NMR (400 MHz, DMSO-$d_6$) δ 12.17 (s, 1H), 8.30 (s, 1H), 7.68-7.54 (m, 3H), 7.48 (d, J = 8.0 Hz, 1H), 7.34-7.18 (m, 3H), 7.05 (s, 1H), 6.87 (s, J = 15.6 Hz, 2H), 5.82 (s, 1H), 5.66 (s, 1H), 4.23-4.63 (m, 3H), 4.11 (s, 3H), 3.89 (s, 1H), 3.72 (d, J = 7.6 Hz, 2H), 3.04 (t, J = 12.8 Hz, 1H), 1.91-1.38 (m, 10H), 1.37-1.10 (m, 7H). |
| Compound 35 (from intermediate 4 and 45) | 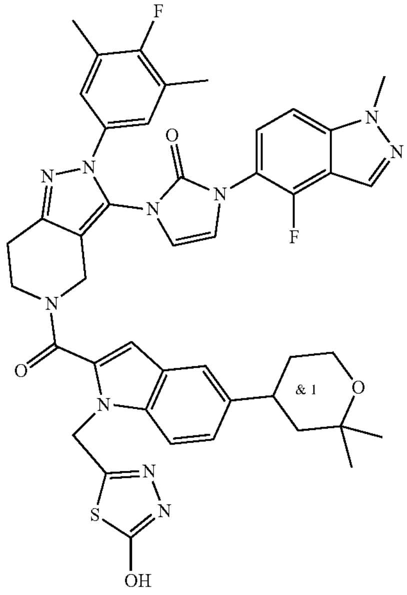 [SMILES: Cc1cc(-n2nc3c(c2-n2ccn(-c4ccc5c(cnn5C)c4F)c2=O)CN(C(=O)c2cc4cc(C5CCOC(C)(C)C5)ccc4n2Cc2nnc(O)s2)CC3)cc(C)c1F] | MS: m/z = 844.5 (M + 1); $^1$H NMR (400 MHz, DMSO) δ 8.29 (s, 2H), 7.61-7.51 (m, 4H), 7.32-7.05 (m, 3H), 6.92 (s, 2H), 5.53 (s, 2H), 4.70 (s, 2H), 4.10 (s, 3H), 4.00 (s, 1H), 3.71 (d, J = 8.3 Hz, 2H), 3.08-2.76 (m, 4H), 2.24 (s, 6H), 1.80-1.62 (m, 2H), 1.54-1.48 (m, 2H), 1.34-1.12 (m, 6H). |

TABLE 13-continued
| Name | Structure | $^1$H NMR and/or LC/MS data |
| --- | --- | --- |
| Compound 36 (from intermediate 4 and 44) | 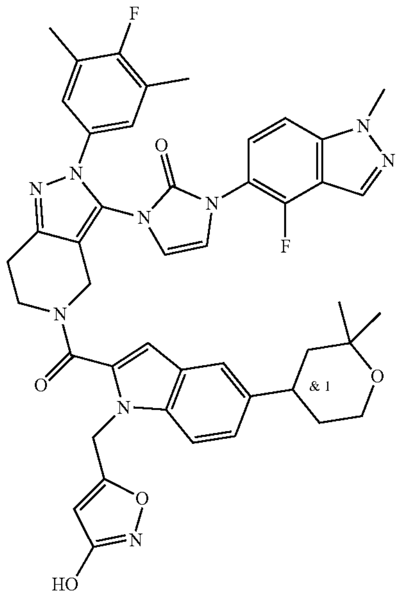 [SMILES: Cc1cc(-n2nc3c(c2-n2ccn(-c4ccc5c(cnn5C)c4F)c2=O)CN(C(=O)c2cc4cc(C5CCOC(C)(C)C5)ccc4n2Cc2cc(O)no2)CC3)cc(C)c1F] | MS: m/z = 828.3 (M + 1); $^1$H NMR (400 MHz, $CD_3OD$) δ 8.15 (s, 1H), 7.53-7.36 (m, 4H), 7.24 (d, J = 8.0 Hz, 1H), 7.14 (d, J = 6.0 Hz, 2H), 6.87 (s, 1H), 6.65 (s, 2H), 5.54 (s, 2H), 4.79 (s, 2H), 4.59 (s, 1H), 4.10 (s, 3H), 3.84-3.75 (m, 3H), 3.08-3.05 (m, 2H), 2.95 (s, 2H), 2.28 (s, 6H), 1.76-1.58 (m, 4H), 1.36 (s, 3H), 1.25 (s, 3H). |
| Compound 37 (from intermediate 4 and 37) | 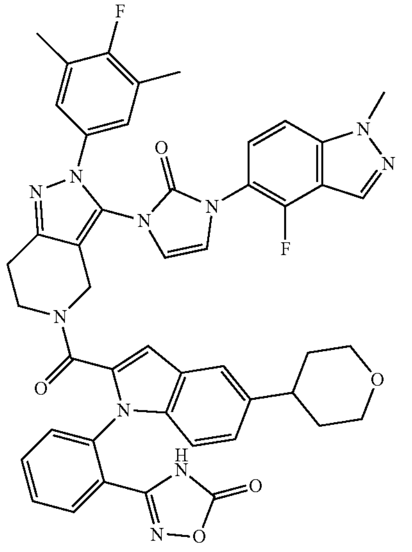 [SMILES: Cc1cc(-n2nc3c(c2-n2ccn(-c4ccc5c(cnn5C)c4F)c2=O)CN(C(=O)c2cc4cc(C5CCOCC5)ccc4n2-c2ccccc2-c2noc(=O)[nH]2)CC3)cc(C)c1F] | MS: m/z = 863 (M + 1); 1H NMR (400 MHz, $CD_3OD$) δ 8.16 (s, 1H), 7.77-7.74 (m, 3H), 7.68-7.62 (m, 2H), 7.58 (br, 2H), 7.50-7.43 (m, 2H), 7.18-7.13 (m, 3H), 7.04 (br, 1H), 6.97-6.94 (m, 1H), 6.71-6.65 (m, 2H), 4.41 (s, 3H), 4.05 (d, J = 12 Hz, 3H), 3.61-3.34 (m, 6H), 3 26-2.79 (m, 3H), 2.28 (s, 6H), 1.92-1.75 (m, 4H). |

TABLE 13-continued
| Name | Structure | $^1$H NMR and/or LC/MS data |
|---|---|---|
| Compound 38 (from intermediate 17-P2 and 46-P2) | 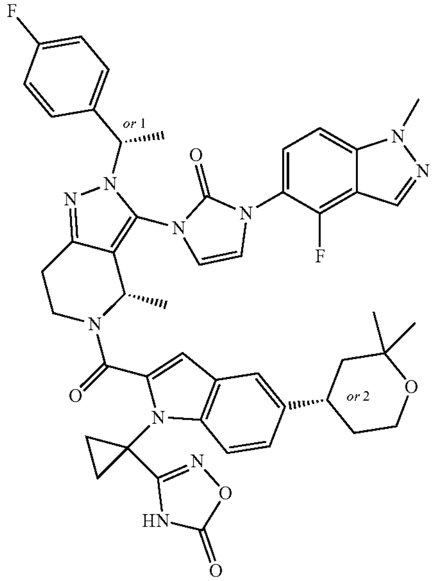 [SMILES: C[C@H]1c2c(nn([C@@H](C)c3ccc(F)cc3)c2-n2ccn(-c3ccc4c(cnn4C)c3F)c2=O)CCN1C(=O)c1cc2cc([C@H]3CCOC(C)(C)C3)ccc2n1C1(c2noc(=O)[nH]2)CC1] | MS: m/z = 869.3, (M + 1); $^1$H NMR (400 MHz, $CD_3OD$) δ 8.19 (s, 1H), 7.52-6.75 (m, 12H), 5.45-5.23 (m, 2H), 4.12 (s, 3H), 3.85-3.75 (m, 2H), 3.55-3.50 (m, 1H), 3.12-3.10 (m, 2H), 2.90-2.85 (m, 2H), 1.95-1.05 (m, 20H). |
| Compound 39 (from intermediate 17-P1 and 46-P1) | 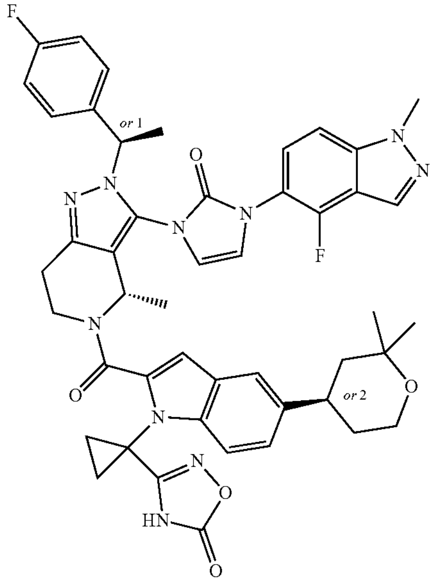 [SMILES: C[C@H](c1ccc(F)cc1)n1nc2c(c1-n1ccn(-c3ccc4c(cnn4C)c3F)c1=O)[C@H](C)N(C(=O)c1cc3cc([C@@H]4CCOC(C)(C)C4)ccc3n1C1(c3noc(=O)[nH]3)CC1)CC2] | MS: m/z = 869.3, (M + 1); $^1$H NMR (400 MHz, $CD_3OD$) δ 8.19 (s, 1H), 7.52-6.75 (m, 12H), 5.45-5.23 (m, 2H), 4.12 (s, 3H), 3.85-3.75 (m, 2H), 3.55-3.50 (m, 1H), 3.12-3.10 (m, 2H), 2.90-2.85 (m, 2H), 1.95-1.05 (m, 20H). |

TABLE 13-continued
| Name | Structure | $^1$H NMR and/or LC/MS data |
| --- | --- | --- |
| Compound 40 (from intermediate 17-P1 and 46-P2) | 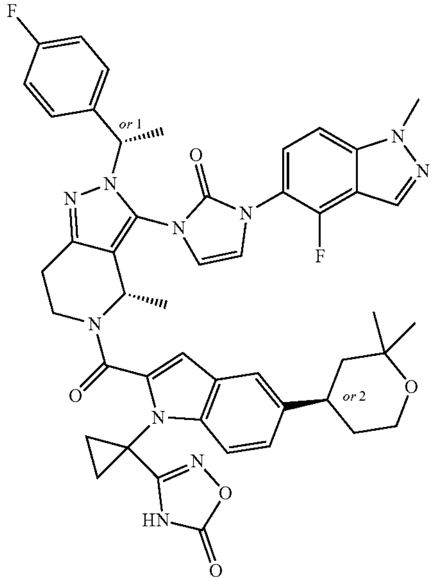 [SMILES: C[C@H]1c2c(nn([C@@H](C)c3ccc(F)cc3)c2-n2ccn(-c3ccc4c(cnn4C)c3F)c2=O)CCN1C(=O)c1cc2cc([C@@H]3CCOC(C)(C)C3)ccc2n1C1(c2noc(=O)[nH]2)CC1] | MS: m/z = 869.3, (M + 1); $^1$H NMR (400 MHz, $CD_3OD$) δ 8.19 (s, 1H), 7.52-6.75 (m, 12H), 5.45-5.23 (m, 2H), 4.12(s, 3H), 3.85-3.75 (m, 2H), 3.55-3.50 (m, 1H), 3.12-3.10 (m, 2H), 2.90-2.85 (m, 2H), 1.95-1.05 (m, 20H). |
| Compound 41 (from intermediate 17-P2 and 46-P1) | 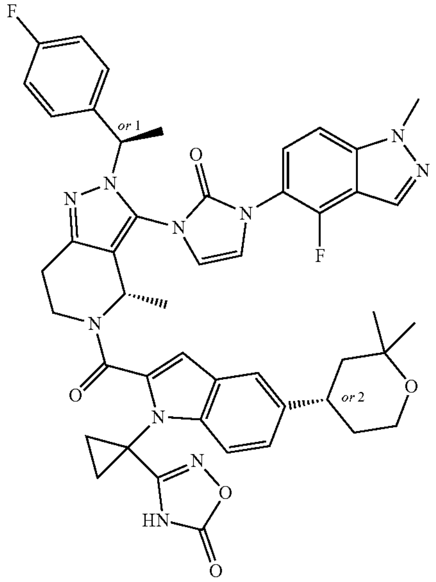 [SMILES: C[C@H](c1ccc(F)cc1)n1nc2c(c1-n1ccn(-c3ccc4c(cnn4C)c3F)c1=O)[C@H](C)N(C(=O)c1cc3cc([C@H]4CCOC(C)(C)C4)ccc3n1C1(c3noc(=O)[nH]3)CC1)CC2] | MS: m/z = 869.3, (M + 1); $^1$H NMR (400 MHz, $CD_3OD$) δ 8.19 (s, 1H), 7.52-6.75 (m, 12H), 5.45-5.23 (m, 2H),4.12(s, 3H), 3.85-3.75 (m, 2H), 3.55-3.50 (m, 1H), 3.12-3.10 (m, 2H), 2.90-2.85 (m, 2H), 1.95-1.05 (m, 20H). |

TABLE 13-continued
| Name | Structure | $^1$H NMR and/or LC/MS data |
| --- | --- | --- |
| Compound 42 (from intermediate 4 and 53) | 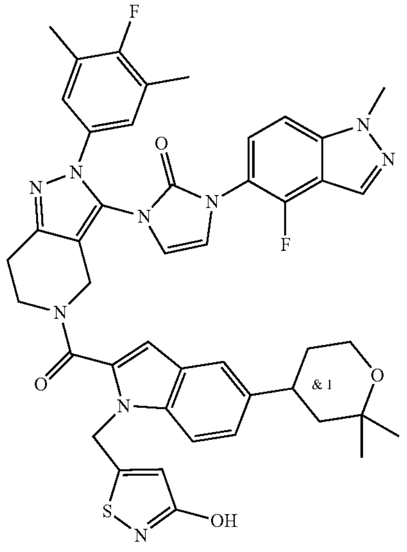 [SMILES: Cc1cc(-n2nc3c(c2-n2ccn(-c4ccc5c(cnn5C)c4F)c2=O)CN(C(=O)c2cc4cc(C5CCOC(C)(C)C5)ccc4n2Cc2cc(O)ns2)CC3)cc(C)c1F] | MS: m/z = 843.5 (M + 1); $^1$H NMR (400 MHz, DMSO) δ 8.29 (s, 2H), 7.72-7.56 (m, 2H), 7.49 (s, 2H), 7.21 (d, J = 8.6 Hz, 1H), 7.13 (d, J = 5.3 Hz, 2H), 7.03 (s, 1H), 6.92 (s, 1H), 6.55 (s, 1H), 5.72 (s, 2H), 4.72 (s, 2H), 4.11 (s, 3H), 4.00 (s, 1H), 3.71 (d, J = 8.5 Hz, 2H), 3.11-2.81 (m, 4H), 2.25 (s, 6H), 1.82-1.61 (m, 2H), 1.60-1.43 (m, 2H), 1.34-1.07 (m, 6H). |
| Compound 43 (from intermediate 11 and 46-P1) | 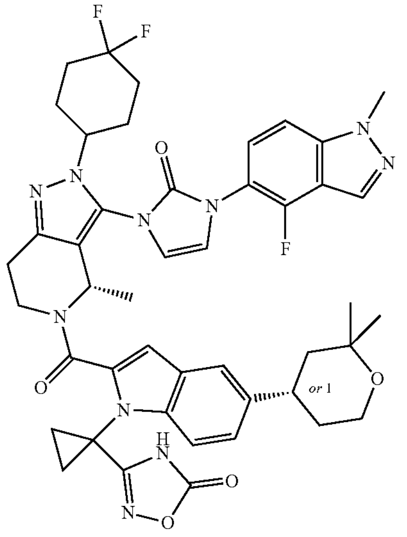 [SMILES: C[C@H]1c2c(nn(C3CCC(F)(F)CC3)c2-n2ccn(-c3ccc4c(cnn4C)c3F)c2=O)CCN1C(=O)c1cc2cc([C@H]3CCOC(C)(C)C3)ccc2n1C1(c2noc(=O)[nH]2)CC1] | MS: m/z = 864.5 (M + 1); $^1$H NMR (400 MHz, DMSO-d6) δ 12.12 (s, 1H), 8.30 (s, 1H), 7.72-7.40 (m, 4H), 7.27-6.93 (m, 3H), 6.73 (d, J = 26.3 Hz, 1H), 5.45 (s, 1H), 4.24 (s, 2H), 4.13 (s, 3H), 3.72 (d, J = 7.7 Hz, 2H), 3.49 (s, 1H), 3.11-2.89 (m, 2H), 2.83-2.64 (m, 1H), 2.28-1.88 (m, 8H), 1.88-1.40 (m, 8H), 1.28-1.19 (m, 9H). |

TABLE 13-continued
| Name | Structure | $^1$H NMR and/or LC/MS data |
| --- | --- | --- |
| Compound 44 (from intermediate 11 and 46-P2) | 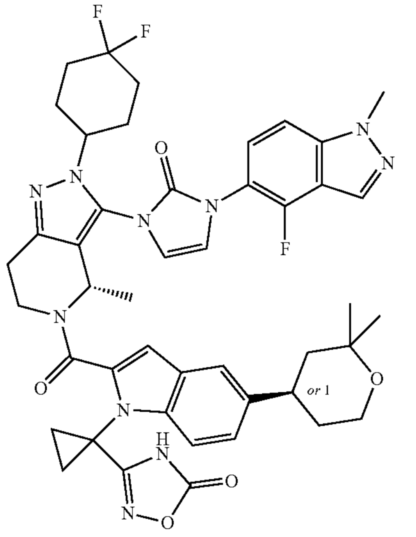 [SMILES: C[C@H]1c2c(nn(C3CCC(F)(F)CC3)c2-n2ccn(-c3ccc4c(cnn4C)c3F)c2=O)CCN1C(=O)c1cc2cc([C@@H]3CCOC(C)(C)C3)ccc2n1C1(c2noc(=O)[nH]2)CC1] | MS: m/z = 864.5 (M + 1); $^1$H NMR (400 MHz, DMSO-d6) δ 12.13 (s, 1H), 8.30 (s, 1H), 7.80-7.42 (m, 4H), 7.33-7.14 (m, 2H), 7.12-6.92 (m, 1H), 6.73 (d, J = 26.3 Hz, 1H), 5.44 (s, 1H), 4.24 (s, 2H), 4.13 (s, 3H), 3.72 (d, J = 7.7 Hz, 2H), 3.43 (s, 1H), 3.04 (t, J = 12.5 Hz, 2H), 2.85-2.60 (m, 1H), 2.30-1.85 (m, 8H), 1.85-1.37 (m, 8H), 1.36-1.05 (m, 9H). |
| Compound 45 (from intermediate 3 and 51-P1) | 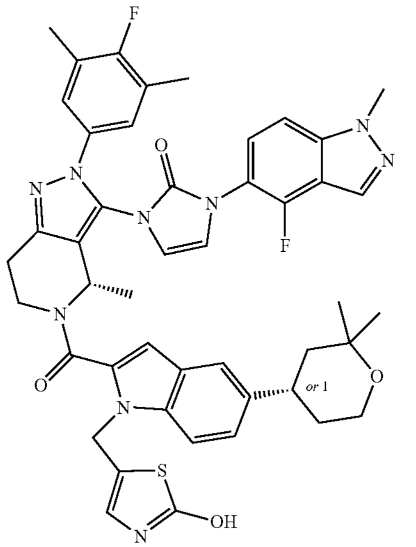 [SMILES: Cc1cc(-n2nc3c(c2-n2ccn(-c4ccc5c(cnn5C)c4F)c2=O)[C@H](C)N(C(=O)c2cc4cc([C@H]5CCOC(C)(C)C5)ccc4n2Cc2cnc(O)s2)CC3)cc(C)c1F] | MS: m/z = 857.6 (M + 1); 1H NMR (400 MHz, DMSO) δ 11.08-10.86(m, 1H), 8.35-8.24 (m, 1H), 7.70-7.54 (m, 2H), 7.52-7.34 (m, 2H), 7.30-6.75 (m, 7H), 5.65-4.97 (m, 3H), 4.12 (s, 3H), 3.72 (d, J = 8.1 Hz, 2H), 3.60-3.25 (m, 1H), 3.10-2.75 (m, 2H), 2.30-2.15 (m, 6H), 1.75-1.66 (m, 2H), 1.65-1.45 (m, 3H), 1.45-1.34 (m, 2H), 1.27 (s, 3H), 1.18 (s, 3H). |

TABLE 13-continued
| Name | Structure | $^1H$ NMR and/or LC/MS data |
|---|---|---|
| Compound 46 (from intermediate 3 and 51-P2) | 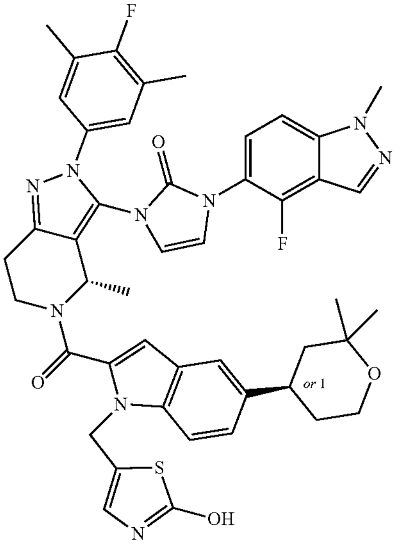 [SMILES: Cc1cc(-n2nc3c(c2-n2ccn(-c4ccc5c(cnn5C)c4F)c2=O)[C@H](C)N(C(=O)c2cc4cc([C@@H]5CCOC(C)(C)C5)ccc4n2Cc2cnc(O)s2)CC3)cc(C)c1F] | MS: m/z = 857.7 (M + 1); 1H NMR (400 MHz, DMSO) δ 11.12-10.82 (m, 1H), 8.35-8 24 (m, 1H), 7.70-7.54 (m, 2H), 7.52-7.34 (m, 2H), 7.30-6.75 (m, 7H), 5.65-4.97 (m, 3H), 4.12 (s, 3H), 3.72 (d, J = 8.1 Hz, 2H), 3.60-3.25 (m, 1H), 3.10-2.75 (m, 2H), 2.30-2.15 (m, 6H), 1.75-1.66 (m, 2H), 1.65-1.45 (m, 3H), 1.45-1.34 (m, 2H), 1.27 (s, 3H), 1.18 (s, 3H). |
| Compound 47 (from intermediate 3 and 45) | 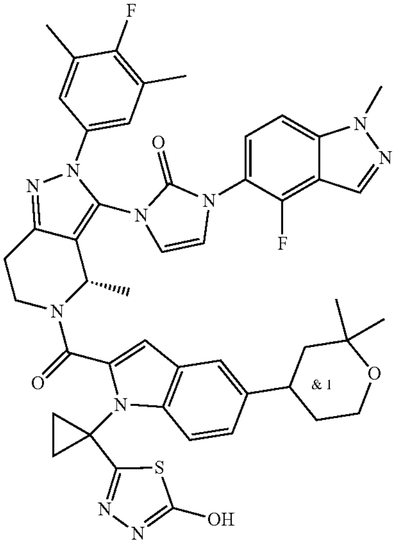 [SMILES: Cc1cc(-n2nc3c(c2-n2ccn(-c4ccc5c(cnn5C)c4F)c2=O)[C@H](C)N(C(=O)c2cc4cc(C5CCOC(C)(C)C5)ccc4n2C2(c4nnc(O)s4)CC2)CC3)cc(C)c1F] | MS: m/z = 884.5 (M + 1); $^1H$ NMR (400 MHz, $CDCl_3$) δ 12.79 (s, 1H), 8.07 (s, 1H), 7.54 (s, 1H), 7.38 (d, J = 8.6 Hz, 1H), 7.29 (s, 1H), 7.26 (d, J = 6.9 Hz, 1H), 7.20 (d, J = 8.6 Hz, 1H), 7.14 (d, J = 8.9 Hz, 1H), 7.09 (d, J = 6.1 Hz, 2H), 6.72 (s, 1H), 6.68 (s, 1H), 6.53 (d, J = 2.9 Hz, 1H), 5.37 (q, J = 6.6 Hz, 1H), 4.99 (dd, J = 12.8, 4.4 Hz, 1H), 4.07 (s, 3H), 3.94-3.83 (m, 2H), 3.20-3.02 (m, 2H), 2.92-2.76 (m, 2H), 2.44-2.38 (m, 1H), 2.26 (s, 6H), 2.00-1.90 (m, 2H), 1.87-1.76 (m, 4H), 1.66 (d, J = 6.8 Hz, 3H), 1.36 (s, 3H), 1.30 (s, 3H). |

TABLE 13-continued
| Name | Structure | $^1$H NMR and/or LC/MS data |
| --- | --- | --- |
| Compound 48 (from intermediate 3 and 52) | 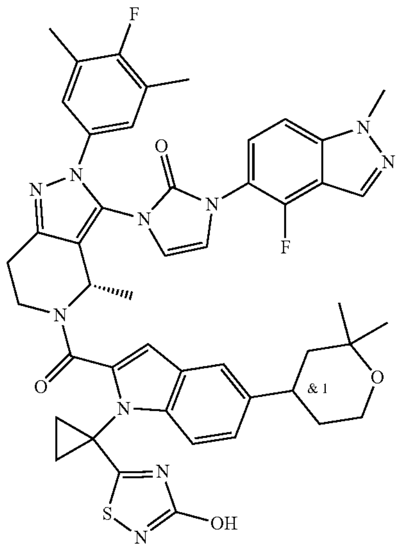 [SMILES: Cc1cc(-n2nc3c(c2-n2ccn(-c4ccc5c(cnn5C)c4F)c2=O)[C@H](C)N(C(=O)c2cc4cc(C5CCOC(C)(C)C5)ccc4n2C2(c4nc(O)ns4)CC2)CC3)cc(C)c1F] | MS: m/z = 885.3 (M + 1); $^1$H NMR (400 MHz, DMSO) δ 12.49 (brs, 1H), 8.31 (s, 1H), 7.64 (d, J = 8.3 Hz, 2H), 7.56 (s, 1H), 7.53-7.35 (m, 2H), 7.32-7.14 (m, 3H), 7.08 (s, 1H), 6.89 (m, 2H), 5.49 (d, J = 6.8 Hz, 1H), 4.30 (d, J = 9.5 Hz, 1H), 4.11 (s, 3H), 3.73 (d, J = 8.1 Hz, 2H), 3.55 (m, 1H), 3.12-2.74 (m, 3H), 2.26 (s, 6H), 2.12-1.45 (m, 7H), 1.42-1.09 (m, 10H). |
| Compound 49 (from intermediate 23-P2 and 46-P2) | 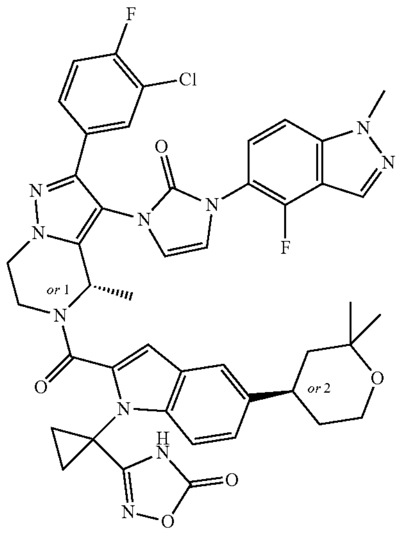 [SMILES: C[C@H]1c2c(-n3ccn(-c4ccc5c(cnn5C)c4F)c3=O)c(-c3ccc(F)c(Cl)c3)nn2CCN1C(=O)c1cc2cc([C@@H]3CCOC(C)(C)C3)ccc2n1C1(c2noc(=O)[nH]2)CC1] | MS: m/z = 875.1 (M + 1); $^1$H NMR (400 MHz, DMSO-$d_6$) δ 8.30 (s, 1H), 7.66-7.42 (m, 6H), 7.21 (s, 1H), 7.09 (s, 1H), 6.96-6.79 (m, 2H), 5.68 (s, 1H), 4.50 (s, 1H), 4.34 (s, 2H), 4.11 (s, 3H), 3.86 (s, 2H), 3.73 (d, J = 7.6 Hz, 2H), 1.80-1.55 (m, 8H), 1.43 (s, 3H), 1.31-1.20 (m, 3H), 1.18 (s, 3H). |

TABLE 13-continued
| Name | Structure | $^1$H NMR and/or LC/MS data |
|---|---|---|
| Compound 50 (from intermediate 23-P1 and 46-P2) | 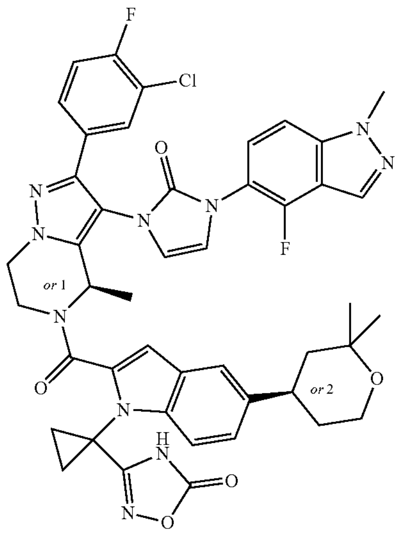 [SMILES: C[C@@H]1c2c(-n3ccn(-c4ccc5c(cnn5C)c4F)c3=O)c(-c3ccc(F)c(Cl)c3)nn2CCN1C(=O)c1cc2cc([C@@H]3CCOC(C)(C)C3)ccc2n1C1(c2noc(=O)[nH]2)CC1] | MS: m/z = 875.2 (M+ 1); $^1$H NMR (400 MHz, DMSO-$d_6$) δ 8.30 (s, 1H), 7.77-7.39 (m, 6H), 7.22 (s, 1H), 7.09 (s, 1H), 6.92 (s, 1H), 6.83 (s, 1H), 5.84 (s, 1H), 5.70 (s, 1H), 4.51 (s, 1H), 4.32 (s, 2H), 4.11 (s, 311), 3.82 (s, 2H), 3.72 (d, J = 7.6 Hz, 2H), 1.94-1.45 (m, 8H), 1.42 (s, 3H), 1.31-1.21 (m, 3H), 1.18 (s, 3H). |
| Compound 51 (from intermediate 24-P2 and 46-P2) | 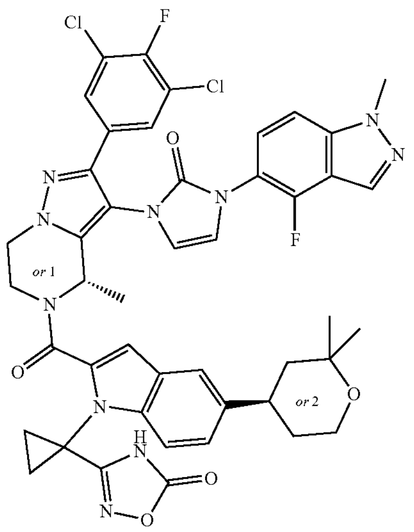 [SMILES: C[C@H]1c2c(-n3ccn(-c4ccc5c(cnn5C)c4F)c3=O)c(-c3cc(Cl)c(F)c(Cl)c3)nn2CCN1C(=O)c1cc2cc([C@@H]3CCOC(C)(C)C3)ccc2n1C1(c2noc(=O)[nH]2)CC1] | MS: m/z = 909.1 (M + 1); $^1$H NMR (400 MHz, DMSO-$d_6$) δ 12.18 (s, 1H), 8.31 (s, 1H), 7.64 (s, 3H), 7.56-7.43 (m, 3H), 7.23 (d, J = 7.2 Hz, 1H), 7.13 (s, 1H), 7.00-6.83 (m, 2H), 5.67 (s, 1H), 4.61-4.30 (m, 3H), 4.11(s, 3H), 3.88 (s, 2H), 3.72 (d, J = 7.6 Hz, 3H), 1.91-1.05 (m, 17H). |

TABLE 13-continued

| Name | Structure | $^1$H NMR and/or LC/MS data |
|---|---|---|
| Compound 52 (from intermediate 24-P1 and 46-P2) | 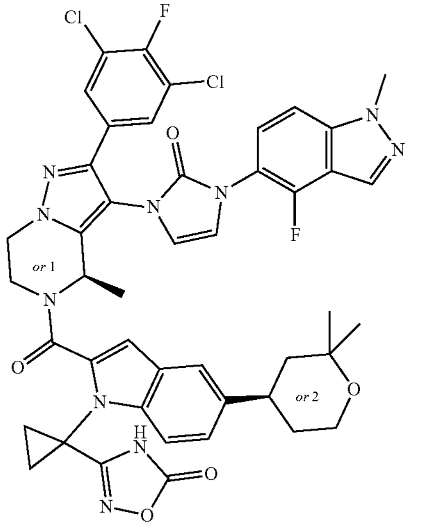 [SMILES: C[C@@H]1c2c(-n3ccn(-c4ccc5c(cnn5C)c4F)c3=O)c(-c3cc(Cl)c(F)c(Cl)c3)nn2CCN1C(=O)c1cc2cc([C@@H]3CCOC(C)(C)C3)ccc2n1C1(c2noc(=O)[nH]2)CC1] | MS: m/z = 909.1 (M + 1); $^1$H NMR (400 MHz, DMSO-$d_6$) δ 12.21 (s, 1H), 8.31 (s, 1H), 7.63 (s, 3H), 7.56-7.41 (m, 3H), 7.23 (d, J = 6.8 Hz, 1H), 7.13 (s, 1H), 6.95 (s, 1H), 6.86 (s, 1H), 5.70 (s, 1H), 4.59-4.27 (m, 3H), 4.11 (s, 3H), 3.86 (s, 2H), 3.73 (d, J = 7.6 Hz, 1H), 1.84-1.07 (m, 17H). |

Example 51: Synthesis of Compound 53

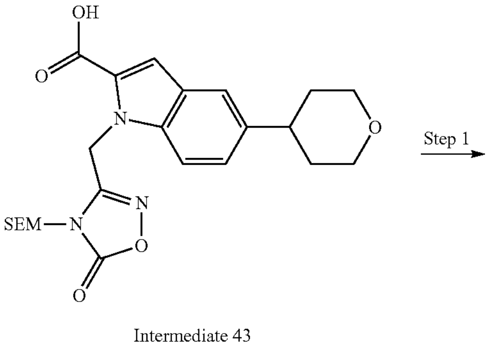

Intermediate 43

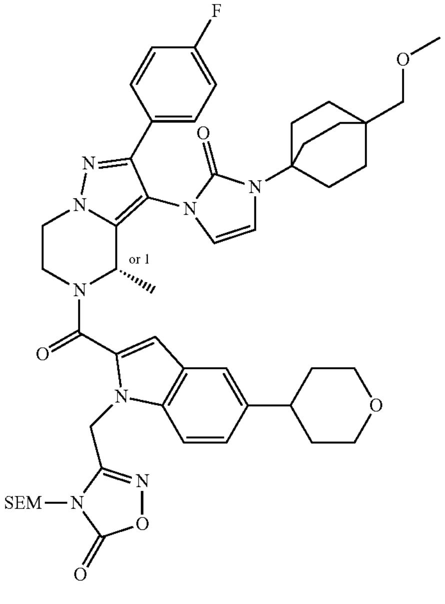

53-1

-continued

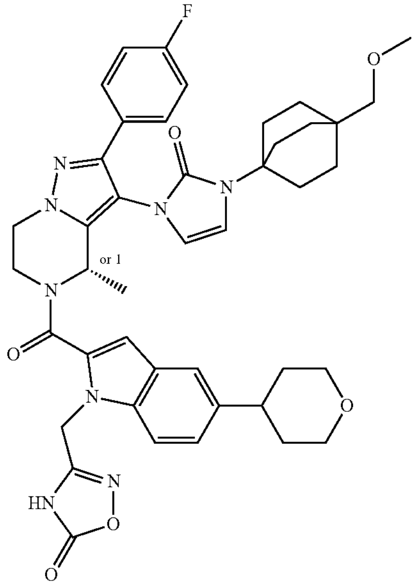

Compound 53

Step 1: 53-1

To a solution of Intermediate 43 (17 mg, 35.44 μmol), Intermediate 25-P2 (15 mg, 32.22 μmol) and HATU (18 mg, 48.33 μmol) in DMF (2 mL) was added DIEA (21 mg, 161.10 mol). The reaction was stirred at 20° C. for 3 hr. The mixture was concentrated and purified by reverse-phase column (70% MeCN in water) to give 53-1 (0.02 g, 67% yield). MS: m/z=921.3 (M+1).

Step 2: Compound 53

To a solution of 53-1 (0.02 g, 21.71 μmol) in THF (2 mL) was added $CH_3COOH$ (52 mg, 868.49 μmol) and TBAF (1 M, 868 μL). The reaction was stirred at 80° C. for 72 hr. The mixture was concentrated and purified by reverse-phase column (65% MeCN in water) to give Compound 53 (7 mg, 41% yield). $^1H$ NMR (400 MHz, $CD_3OD$) δ 7.46 (s, 1H), 7.41-7.38 (m, 2H), 7.19 (d, J=8.4 Hz, 1H), 6.98 (t, J=8.4 Hz, 2H), 6.84 (s, 1H), 6.51 (s, 2H), 6.22 (s, 1H), 5.63 (s, 1H), 5.35 (s, 2H), 4.51 (s, 2H), 4.21 (s, 1H), 3.97 (d, J=10.8 Hz, 2H), 3.73 (s, 1H), 3.50 (td, J=10.8, 3.6 Hz, 2H), 3.19 (s, 3H), 2.92 (s, 2H), 2.87-2.75 (m, 1H), 1.94 (s, 6H), 1.78-1.67 (m, 3H), 1.42 (s, 6H), 1.38-1.19 (m, 4H); MS: m/z=791.3 (M+1).

Example 52: Synthesis of Compound 54

The compound in Table 14 was made according to the procedure of Compound 53.

TABLE 14

| Name | Structure | $^1H$ NMR and/or LC/MS data |
|---|---|---|
| Compound 54 (from intermediate 3 and 42) | 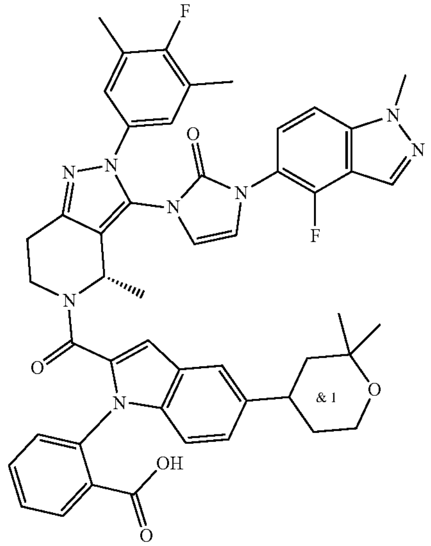 [SMILES: Cc1cc(-n2nc3c(c2-n2ccn(-c4ccc5c(cnn5C)c4F)c2=O)[C@H](C)N(C(=O)c2cc4cc(C5CCOC(C)(C)C5)ccc4n2-c2ccccc2C(=O)O)CC3)cc(C)c1F] | MS: m/z = 865.2 (M + 1); $^1H$ NMR (400 MHz, DMSO-$d_6$) δ 8.29 (s, 1H), 7.96-7.94 (m, 1H), 7.77-7.73 (m, 1H), 7.62-7.54 (m, 4H), 7.44-7.40 (m, 1H), 7.17-7.11 (m, 3H), 7.02-6.96 (m, 2H), 6.90-6.86 (m, 2H), 5.48-5.43 (m, 1H), 4.69-4.66 (m, 1H), 4.10 (s, 3H), 3.74-3.72 (m, 3H), 2.74-2.68 (m, 3H), 2.25 (s, 6H), 1.71-1.50 (m, 5H), 1.28 (s, 3H), 1.19 (s, 3H), 1.18-1.11 (m, 2H). |

Example 53: Synthesis of Compound 55

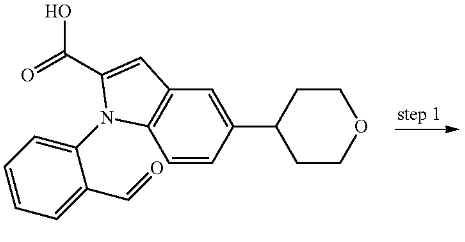

Intermediate 50

-continued

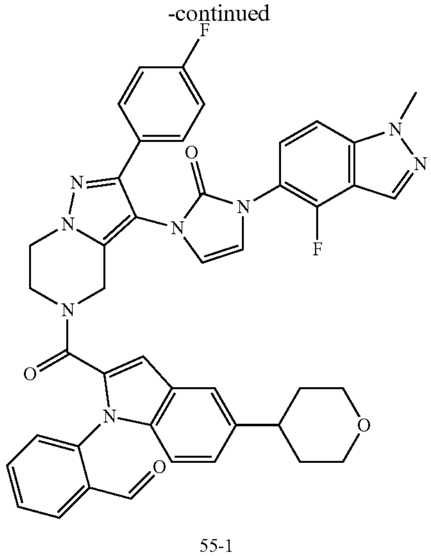

55-1

-continued

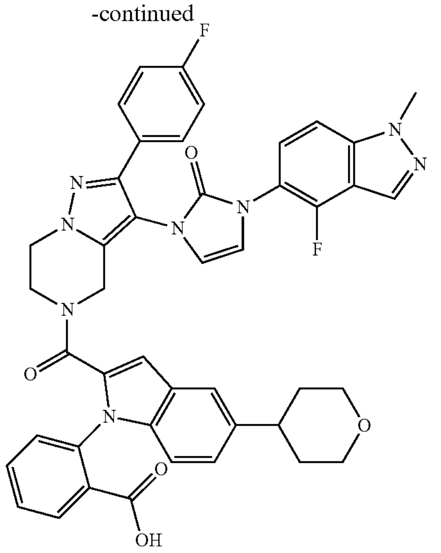

Compound 55

Step 1: 55-1

To a solution of Intermediate 8 (20 mg, 44.70 μmol) in DMF (2 mL) was added Intermediate 50 (18 mg, 53.64

μmol), HATU (34 mg, 89.40 μmol) and DIEA (29 mg, 223.49 mol). The reaction was stirred at 15° C. for 4 hr. The reaction was diluted with ethyl acetate (10 mL), and ethyl acetate layer was washed with brine (5 mL×5), dried over sodium sulfate and concentrated to give a residue, which was purified by reverse phase (0.1% FA in water:MeCN=44:56) to give 55-1 (12 mg, 34% yield). MS: m/z=801.2 (M+23).

Step 2: Compound 55

To a solution of 55-1 (12 mg, 15.41 μmol) in dioxane/$H_2O$ (3:1, 3 mL) was added 2-methylbut-2-ene (5.40 mg, 77.04 μmol), $KH_2PO_4$ (6 mg, 46.22 μmol) and $NaClO_2$ (4 mg, 46.22 mol). The reaction was stirred at 20° C. for 4 hr. The mixture was concentrated and purified by reverse phase (0.1 FA in water:MeCN=43:57) to give Compound 55 (3.7 mg, 30% yield). $^1H$ NMR (400 MHz, MeOD) δ 8.28 (s, 1H), 8.15 (s, 1H), 7.93 (d, J=8.0 Hz, 1H), 7.67-7.47 (m, 7H), 7.16-7.12 (m, 3H), 7.01-6.99 (m, 2H), 6.84 (s, 1H), 6.67 (s, 1H), 4.62-4.44 (m, 2H), 4.21-4.20 (m, 2H), 4.10-4.03 (m, 4H), 3.58 (t, J=11.2 Hz, 2H), 2.88-2.86 (m, 1H), 1.86-1.79 (m, 4H); MS: m/z=795.2 (M+1).

Example 54: Synthesis of Compounds 56 and 57

The compounds in Table 15 were made according to the procedure of Compound 55.

TABLE 15

| Name | Structure | $^1H$ NMR and/or LC/MS data |
|---|---|---|
| Compound 56 (from intermediate 3 and 39) | 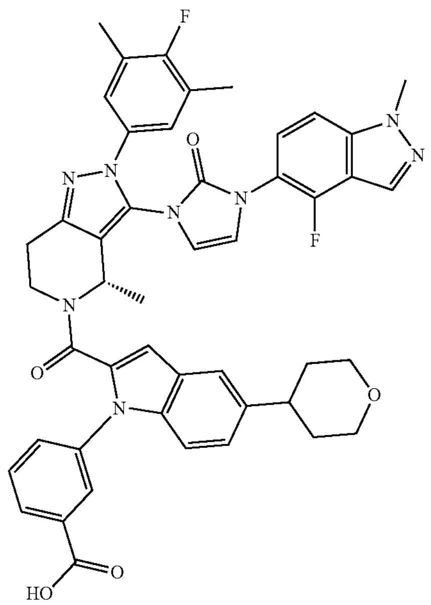 [SMILES: Cc1cc(-n2nc3c(c2-n2ccn(-c4ccc5c(cnn5C)c4F)c2=O)[C@H](C)N(C(=O)c2cc4cc(C5CCOCC5)ccc4n2-c2cccc(C(=O)O)c2)CC3)cc(C)c1F] | MS: m/z = 837.3 (M + 1); $^1H$ NMR (400 MHz, DMSO-$d_6$) δ 13.36 (s, 1H), 8.29-8.19 (m, 1H), 7.97-7.81 (m, 2H), 7.66-7.58 (m, 4H), 7.44-7.42 (m, 1H), 7.31 (d, J = 8.8 Hz, 1H), 7.21 (d, J = 8.4 Hz, 1H), 7.15 (d, J = 5.6 Hz, 1H), 7.03 (s, 2H), 6.97 (s, 1H), 6.90 (s, 1H), 5.47 (d, J = 6.4 Hz, 1H), 4.23 (s, 1H), 4.10 (s, 3H), 3.97 (d, J = 9.2 Hz, 2H), 3.45 (s, 3H), 2.85-2.67 (m, 3H), 2.24 (s, 6H), 1.75 (s, 4H), 1.31-1.10 (m, 3H). |

TABLE 15-continued

| Name | Structure | $^1$H NMR and/or LC/MS data |
|---|---|---|
| Compound 57 (from intermediate 5 and 50) | 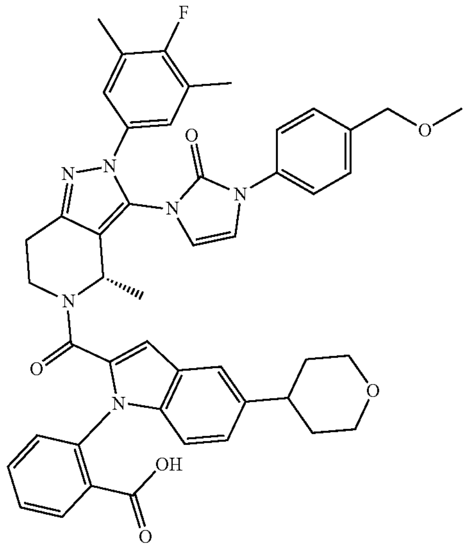 [SMILES: COCc1ccc(-n2ccn(-c3c4c(nn3-c3cc(C)c(F)c(C)c3)CCN(C(=O)c3cc5cc(C6CCOCC6)ccc5n3-c3ccccc3C(=O)O)[C@H]4C)c2=O)cc1] | MS: m/z = 809.3 (M + 1); $^1$H NMR (400 MHz, DMSO-$d_6$) δ 13.0 (s, 1H), 7.97-7.89 (m, 1H), 7.74-7.68 (m, 1H), 7.61 (d, J = 8.4 Hz, 2H), 7.57-7.50 (m, 2H), 7 40 (d, J = 7.6 Hz, 2H), 7.28 (s, 1H), 7.13 (s, 2H), 6.99-6.92 (m, 2H), 6.89-6.82 (m, 1H), 5.46-5.42 (m, 1H), 5.34-5.30 (m, 1H), 4.57-4.48 (m, 2H), 4.41 (s, 2H), 3.97 (d, J = 9.6 Hz, 2H), 3.49-3.43 (m, 2H), 3.33 (s, 3H), 3.28 (s, 2H), 2.89-2.81 (m, 2H), 2.48 (s, 6H), 2.19 (s, 4H), 1.78-1.70 (m, 3H). |

Example 55: Synthesis of Compound 58

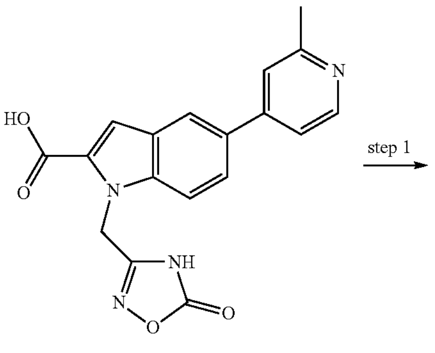

Intermediate 40

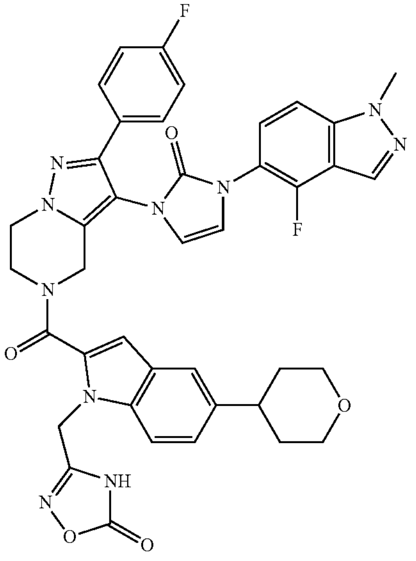

Compound 58

To a mixture of Intermediate 8 (40 mg, 89.40 µmol), intermediate 40 (46.98 mg, 134.10 µmol), EDCI (34.28 mg, 178.80 µmol), HOBT (18.12 mg, 134.10 µmol) and DCM (1.5 mL) was added TEA (27.14 mg, 268.19 µmol) at 25° C. The mixture was stirred overnight. The resulting mixture was diluted with water (10 mL) and extracted with ethyl acetate (20 mL×3). The organic phase was dried over sodium sulfate and then filtered. The crude product was further purified by Prep-HPLC (Waters2545, column: Gemini-C18 150×21.2 mm, 5 µm; mobile phase: MeCN—$H_2O$ (0.1% FA), MeCN from 25% to 40%) to afford Compound 58 (15.5 mg, 22%). $^1$H NMR (400 MHz, DMSO) δ 8.47 (d, J=5.2 Hz, 1H), 8.26 (s, 1H), 8.13 (d, J=13.2 Hz, 2H), 7.75 (s, 2H), 7.70-7.45 (m, 5H), 7.31-7.22 (m, 2H), 7.10 (s, 1H), 7.00 (s, 1H), 6.79 (s, 1H), 5.48 (s, 2H), 4.90 (s, 2H), 4.39 (s, 2H), 4.25 (s, 2H), 4.09 (s, 3H), 2.54 (s, 3H); MS: m/z=779.5 (M+1).

Example 56: Synthesis of Compound 59

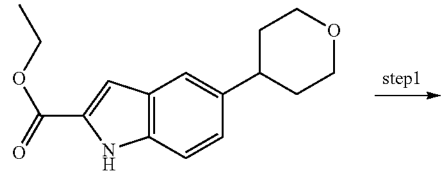

Intermedaite 34

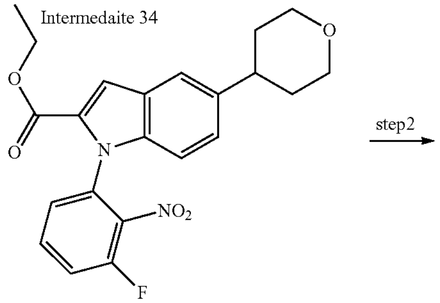

59-1

-continued
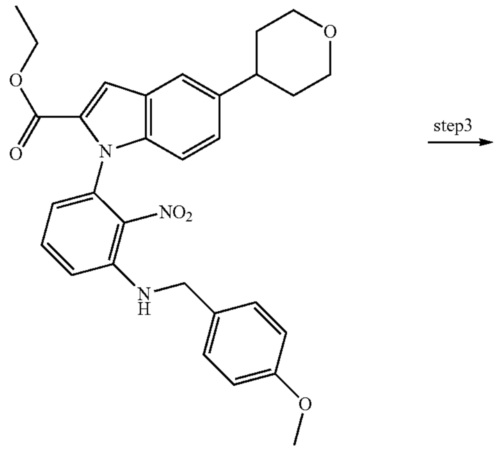
59-2
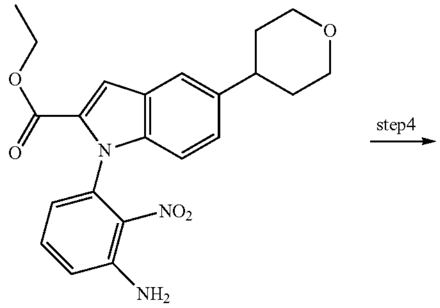
59-3
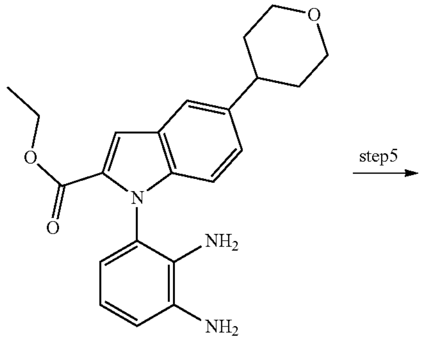
59-4
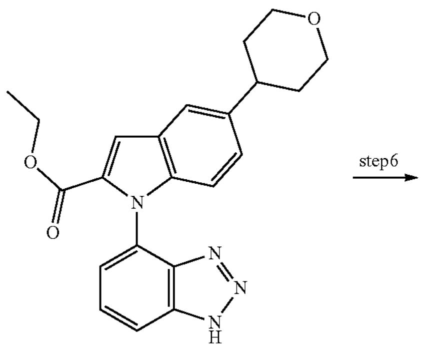
59-5
-continued
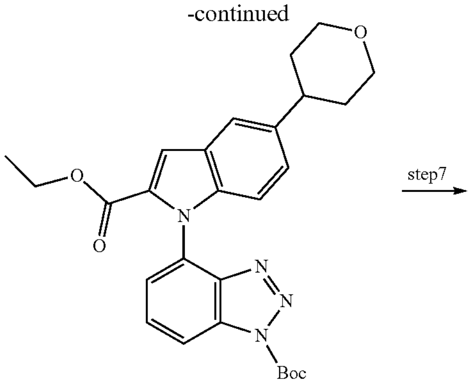
59-6
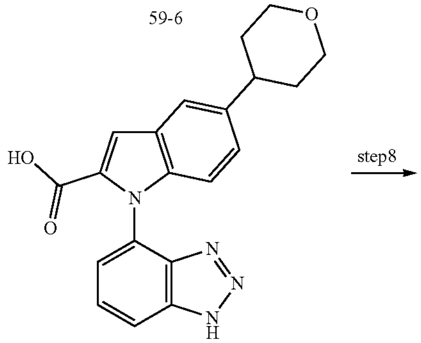
59-7
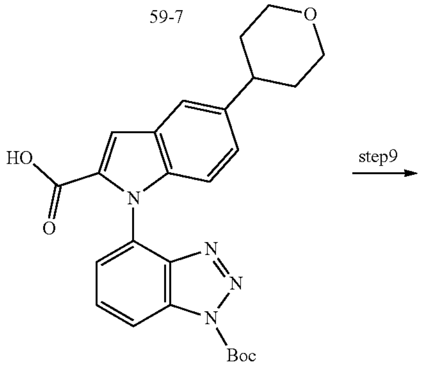
59-6
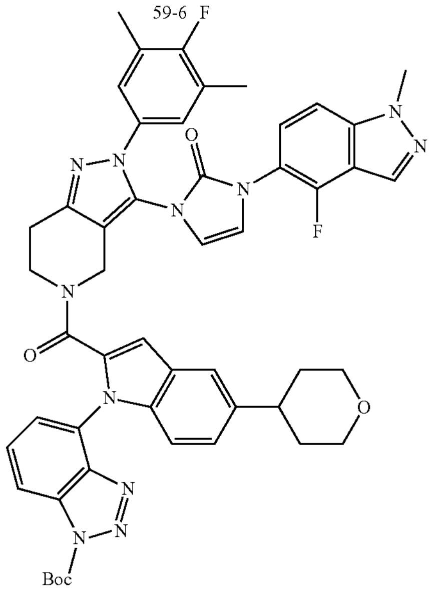
59-9

-continued

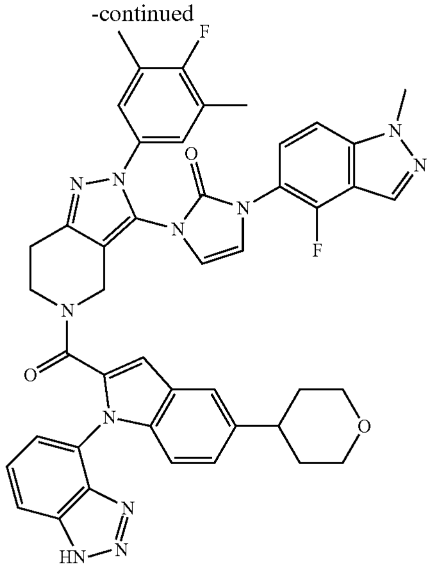

Compound 59

Step 1: 59-1

To a suspension of sodium hydride (840 mg, 21 mmol, 60% in mineral oil) in dry DMF (30 mL) was added Intermediate 34 (3.7 g, 0.014 mol). The solution was stirred at 20° C. for 10 min. Then 1,3-difluoro-2-nitrobenzene (2.16 g, 0.014 mol) was added into the reaction mixture, and the reaction was heated at 100° C. for 2 hr. The reaction was quenched with 50 mL of saturated $NH_4Cl$ solution and extracted with ethyl acetate (80 mL×3). The organic phase was washed by water (30 mL×3) and brine (30 mL), dried over sodium sulfate, and concentrated to give 59-1 (5.56 g, crude). MS: m/z=413 (M+1).

Step 2: 59-2

To a solution of 59-1 (5.56 g, 0.013 mol) in DMF (30 mL) was added (4-methoxyphenyl)methanamine (1.85 g, 0.013 mol) and $K_2CO_3$ (9.88 g, 0.072 mol). The reaction was heated at 80° C. for 1 hr. The reaction was diluted with 50 mL of ethyl acetate, washed with brine (30 mL×3) and dried over sodium sulfate, and concentrated under depressed pressure to give 59-2 (3.2 g, 47% yield). MS: m/z=530.1 (M+1).

Step 3: 59-3

To a solution of 59-2 (3.2 g, 0.006 mol) in DCM (20 mL) was added TFA (10 mL). The reaction was stirred at 40° C. for 2 hr. The reaction was diluted with 20 mL of water and extracted with DCM (30 mL×3). The organic phase was dried over sodium sulfate and concentrated to give a residue, which was purified by silica gel chromatography (PE/EA=10/1 to 2/1) to give 59-3 (2.16 g, 88% yield). MS: m/z=410 (M+1).

Step 4: 59-4

To a solution of 59-3 (2.16 g, 0.005 mol) in MeOH (40 mL) and $H_2O$ (10 mL) was added reductive Fe (2.96 g, 0.052 mol) and $NH_4Cl$ (5.34 g, 0.1 mol), the reaction was heated at 80° C. for 4 hr. The reaction was filtered, concentrated and diluted with 30 mL of water. The aqueous phase was extracted with ethyl acetate (30 mL×3). The organic layer was dried over sodium sulfate and concentrated to give 59-4 (950 mg, crude). MS: m/z=380.2 (M+1).

Step 5: 59-5

To a solution of 59-4 (950 mg, 2.5 mmol) in AcOH (10 mL) and $H_2O$ (5 mL) was added $NaNO_2$ (276 mg, 4 mmol) at 0° C. The reaction was stirred at 0° C. for 1 hr. The reaction was concentrated, diluted with 10 mL of water, the aqueous phase was extracted with ethyl acetate (10 mL×3). Then the organic layer was dried over sodium sulfate and concentrated to give a residue, which was purified by silica gel chromatography (DCM/MeOH=100/1 to 40/1) to give 59-5 (422 mg, 43% yield). MS: m/z=391.2 (M+1).

Step 6: 59-6

To a solution of 59-5 (422 mg, 1.08 mmol) in dioxane (2 mL) was added $(Boc)_2O$ (306 mg, 1.41 mmol), NaOH (43 mg, 1.08 mmol) and DMAP (2 mg, 16.37 μmol). The reaction was stirred at 25° C. for 2 hr. The reaction was quenched by water (5 ml), and the mixture was then extracted by ethyl acetate (10 mL×3). The organic phase was washed by brine, dried over sodium sulfate and concentrated to give 59-6 (500 mg, 94% yield). MS: m/z=391.2 (M+1-100).

Step 7: 59-7

To a solution of 59-6 (500 mg, 1.02 mmol) in MeOH (5 mL) was added NaOH (122 mg, 3.06 mmol). The reaction was heated at 60° C. for 2 hr. The reaction was concentrated, diluted with 5 mL of water, the aqueous phase was washed with ethyl acetate (3 mL×3), and then adjusted to pH~6 by HCl (1 M). The mixture was extracted with ethyl acetate (5 mL×3), and the organic layer was dried over sodium sulfate, filtered and concentrated to give 59-7 (200 mg, 54% yield). MS: m/z=363.2 (M+1).

Step 8: 59-8

To a solution of 59-7 (200 mg, 551.91 μmol) in water (2 mL) and dioxane (8 mL) was added $(Boc)_2O$ (180.68 mg, 827.86 μmol), NaOH (22.08 mg, 551.91 μmol) and DMAP (2 mg, 16.37 μmol). The reaction was stirred at 20° C. for 2 hr. The reaction was concentrated, diluted with 5 mL of water, the aqueous phase was extracted with ethyl acetate (5 mL×3). The organic layer was dried over sodium sulfate, filtered and concentrated to give a residue, which was purified by prep-TLC (DCM/MeOH=20/1) to give 59-8 (48.7 mg, 19% yield). MS: m/z=485.0 (M+23).

Step 9: 59-9

To a solution of 59-8 (48.7 mg, 0.11 mmol) in DMF (5 mL) was added Intermediate 4 (50 mg, 0.11 mmol) and HATU (63 mg, 0.17 mmol). The solution was stirred for 5 min, then DIEA (204 mg, 2.2 mmol) was introduced into the solution. The reaction was stirred at 25° C. for 16 hr. The reaction was diluted with 50 mL of ethyl acetate and washed with brine (20 mL×3), dried over sodium sulfate and concentrated to give 59-9 (65 mg, crude). MS: m/z=820.2, (M+1-100).

Step 10: Compound 59

To a solution of 59-9 (65 mg, 70.6 mmoL) in DCM (5 mL) was added TFA (1 mL). The reaction mixture was stirred at 20° C. for 2 hr. The reaction mixture was concentrated to give a residue, which was purified by prep-HPLC (Chromatographic columns: ACQUITY BEH C18, 50×2.1 mm, 1.7μ. Mobile Phase: MeCN—$H_2O$ (0.05% FA) Gradient: 5%-95%) to give Compound 59 (8 mg, 9% yield). $^1H$ NMR (400 MHz, $CD_3OD$) δ 8.18 (s, 1H), 7.84-7.83 (m, 1H), 7.67-7.63 (m, 2H), 7.55 (d, J=7.2 Hz, 1H), 7.50-7.47 (m, 1H), 7.43-7.14 (m, 5H), 6.72-6.70 (m, 3H), 4.14-4.04 (m, 5H), 3.67-3.56 (m, 3H), 3.52-3.49 (m, 1H), 2.93-2.91 (m, 3H), 2.31 (s, 6H), 1.88-1.86 (m, 4H). MS: m/z=820.2 (M+1).

Example 57: Synthesis of Compounds 60 and 61

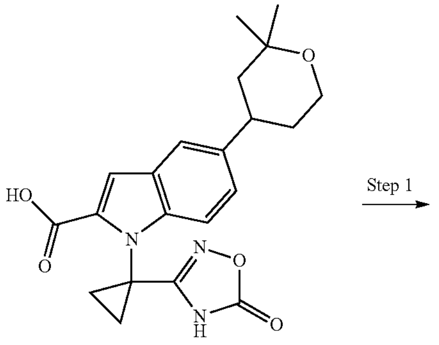

Intermediate 46

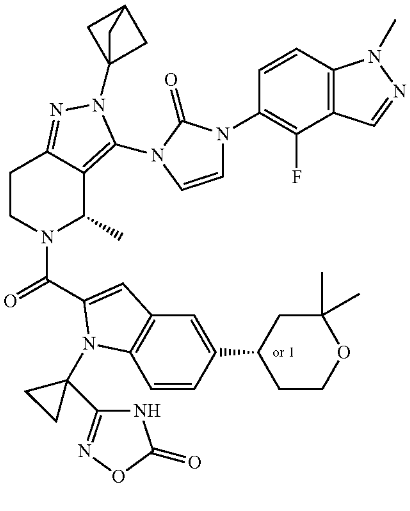

+

Compound 60

-continued

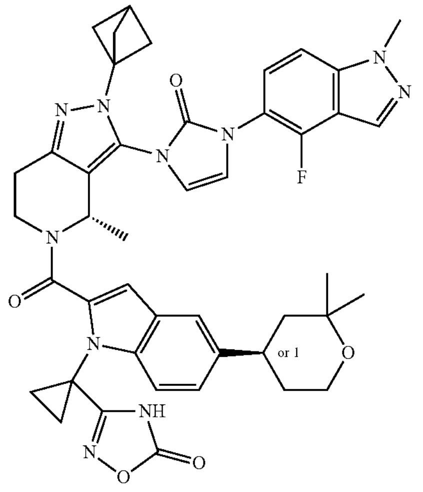

Compound 61

To a solution of Intermediate 46 (100 mg, 251.62 μmol) in DMF (3 mL) was added DIEA (260.16 mg, 2.01 mmol), N,N,N',N'-tetramethyl-1-(3-oxido-2,3-dihydrotriazolo[4,5-b]pyridin-3-ium-1-yl)methanediamine hexafluorophosphate (192.36 mg, 503.24 mol) and Intermediate 16 (118.25 mg, 251.62 μmol). The resulting solution was stirred at 25° C. for 16 hr. The mixture was diluted with water (5 mL) and the aqueous layer was extracted with ethyl acetate (5 mL×3). The combined organic layers were washed with brine (5 mL), dried over sodium sulfate and concentration to give a residue, which was purified by prep-HPLC (chromatographic column: Gemini-C18 150×21.2 mm, 5 μm; mobile phase: MeCN—$H_2O$ (0.1% TFA); gradient: 60-70%) to give a mixture of diasteromers. The mixture was further separated by SFC to give two desired isomers. The isomers were separately further purified by prep-HPLC (chromatographic column: Gemini-C18 150×21.2 mm, 5 μm; mobile phase: MeCN—$H_2O$ (0.1% TFA); gradient: 50-70%) to give:

Compound 60 (SFC chromatographic column: chiralpak-OD (4.6 mm×250 mm), mobile phase: 70% $CO_2$-30% MeOH (0.2% $NH_3H_2O$); Flow: 2.5 mL/min; retention time: 16.28 min, 30.0 mg, 14.67% yield); $^1H$ NMR (400 MHz, DMSO) δ 12.10 (s, 1H), 8.32 (s, 1H), 7.80-7.38 (m, 4H), 7.37-6.91 (m, 3H), 6.91-6.59 (m, 1H), 5.78-5.28 (m, 1H), 5.18-4.56 (m, 1H), 4.51-4.21 (m, 1H), 4.13 (s, 3H), 3.71-3.67 (m, 2H), 3.59-3.34 (m, 1H), 3.13-2.64 (m, 3H), 2.63-2.55 (m, 1H), 2.18 (s, 6H), 1.98-1.40 (m, 8H), 1.34-1.23 (m, 5H), 1.19 (s, 3H); MS: m/z=812.6 (M+1).

Compound 61 (SFC chromatographic column: chiralpak-OD (4.6 mm×250 mm); mobile phase: 70% $CO_2$-30% MeOH (0.2% $NH_3H_2O$); Flow: 2.5 mL/min, retention time: 20.43 min, 30.0 mg, 14.67% yield); $^1H$ NMR (400 MHz, DMSO) δ 12.11 (s, 1H), 8.32 (s, 1H), 7.82-7.37 (m, 4H), 7.32-6.89 (m, 3H), 6.89-6.56 (m, 1H), 5.77-5.31 (m, 1H), 5.20-4.50 (m, 1H), 4.50-4.19 (m, 1H), 4.13 (s, 3H), 3.72 (d, J=8.1 Hz, 2H), 3.57-3.34 (m, 1H), 3.12-2.63 (m, 3H), 2.59 (d, J=3.2 Hz, 1H), 2.18 (s, 6H), 1.91-1.42 (m, 8H), 1.34-1.22 (m, 5H), 1.19 (s, 3H); MS: m/z=812.6 (M+1).

Example 58: Synthesis of Compounds 62 and 63

The compounds in Table 16 were made according to the procedure of Compound 60 and Compound 61.

TABLE 16

| Name | Structure | $^1H$ NMR and/or LC/MS data |
|---|---|---|
| Compound 62 (from intermediate 25-P1 and 49) | 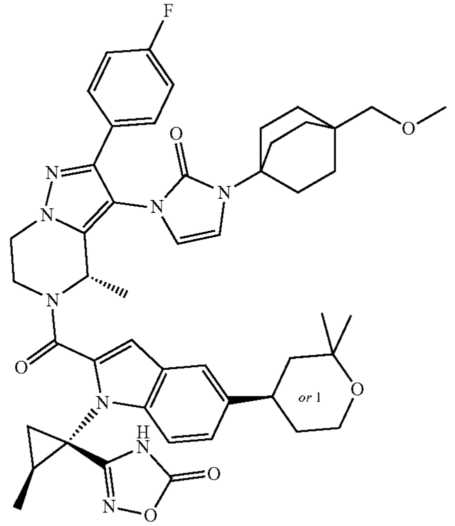 [SMILES: COCC12CCC(n3ccn(-c4c(-c5ccc(F)cc5)nn5c4[C@H](C)N(C(=O)c4cc6cc([C@@H]7CCOC(C)(C)C7)ccc6n4[C@@]4(c6noc(=O)[nH]6)C[C@@H]4C)CC5)c3=O)(CC1)CC2] | $^1H$ NMR (400 MHz, $CD_3OD$) δ 8.52 (s, 3H), 7.52-7.51 (m, 2H), 7.29 (d, J = 7.6 Hz, 1H), 7.13-7.08 (m, 2H), 6.91-6.32 (m, 2H), 5.82 (s, 1H), 5.48 (s, 1H), 5.28-5.26 (m, 1H), 4.81 (s, 1H), 4.62 (s, 1H), 4.35-4.33 (m, 1H), 4.20-4.16 (m, 1H), 3.93-3.82 (m, 1H), 3.24-3.07 (m, 3H), 2.36 (t, J =7.6 Hz, 1H), 2.21-2.19 (m, 1H), 2.07-2.04 (m, 5H), 1.78-1.54 (m, 8H), 1.38-1.29 (m, 16H), 0.92 (t, J = 6.0 Hz, 2H). Chiral separation condition Column: Daicel CHIRALPAK OD-H 250 mm x 20 mm I.D. 5 μm, Mobile phase: $CO_2$/MeOH (0.2% $NH_4$•OH) = 70/30; Flow rate: 50 g/min; Wave length: UV 214 nm; Temperature: 35° C. (retention time, 5.809 min) |
| Compound 63 (from intermediate 25-P1 and 49) | 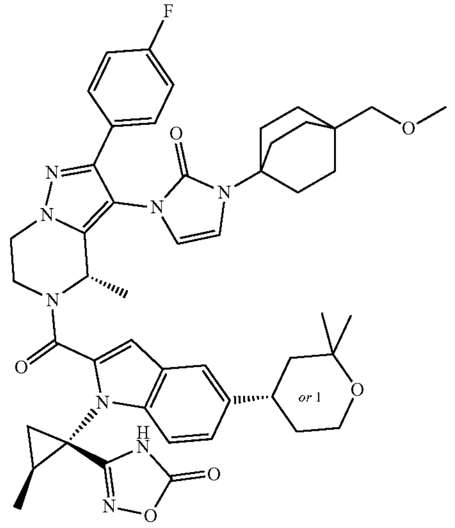 [SMILES: COCC12CCC(n3ccn(-c4c(-c5ccc(F)cc5)nn5c4[C@H](C)N(C(=O)c4cc6cc([C@H]7CCOC(C)(C)C7)ccc6n4[C@@]4(c6noc(=O)[nH]6)C[C@@H]4C)CC5)c3=O)(CC1)CC2] | $^1H$ NMR (400 MHz, $CD_3OD$) δ 8.49 (s, 4H), 7.52-7.48 (m, 2H), 7.26 (d, J = 8.4 Hz, 1H), 7.11-7.06 (m, 2H), 6.89-6.81 (m, 1H), 6.54-6.27 (m, 2H), 5.78 (s, 1H), 5.50 (s, 1H), 4.40-4.29 (m, 2H), 4.18-4.13 (m, 1H), 3.91-3.79 (m, 3H), 3.13-2.92 (m, 4H), 2.33 (t, J = 7.2 Hz, 1H), 2.22-2.14 (m, 3H), 2.04-2.01 (m, 2H), 1.76-1.52 (m, 10H), 1.36-1.26 (m, 12H), 0.89 (t, J = 6.4 Hz, 2H). Chiral separation condition: Column: Daicel CHIRALPAK OD-H 250 mm x 20 mm I.D. 5 μm; Mobile phase: $CO_2$/MeOH (0.2% $NH_4$•OH) = 70/30; Flow rate: 50 g/min; Wave length: UV 214 nm; Temperature: 35° C. (retention time, 3.274 min). |

Example 59: Synthesis of Compound 64

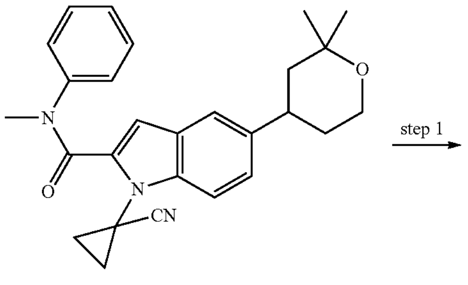

Intermediate 48

-continued

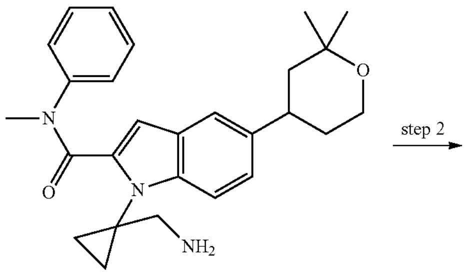

64-1

-continued

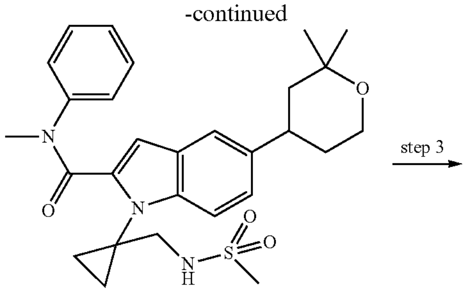

64-2

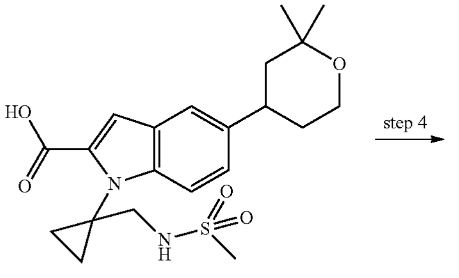

64-3

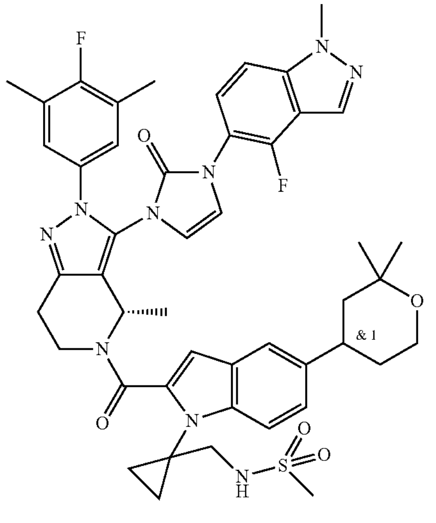

Compound 64

Step 1: 64-1

To a solution of Intermediate 48 (300.0 mg, 0.70 mmol) in MeOH (10 mL) was added Raney Nickel (20.0 mg). The resulting mixture was stirred at 35° C. for 5 hr under $H_2$ atmosphere. The reaction mixture was filtered and the filtrate was concentrated in vacuo. The residue was purified by silica gel column (PE/EA=1/1 to DCM/MeOH=10/1) to afford 64-1 (200.0 mg, 66.04%). MS: m/z=432.3 (M+1).

Step 2: 64-2

To a solution of 64-1 (200.0 mg, 0.46 mmol) in DCM (5 mL) was added MsCl (106.12 mg, 0.93 mmol) and DIEA (119.79 mg, 0.93 mmol). After stirred at 25° C. for 1 hr, the mixture was poured into ice-water (50 mL) and extracted with DCM (50 mL×2). The combined organic layers were washed with water (50 mL), brine (50 mL), dried over sodium sulfate and filtered. The filtrate was concentrated and purified by silica gel column (PE/EA=1/1) to afford 64-2 (210.0 mg, 88.91%). MS: m/z=510.2 (M+1).

Step 3: 64-3

To a solution of 64-2 (210.0 mg, 0.41 mmol) in 2-Methoxyethanol (5 mL), $H_2O$ (1 mL) was added KOH (462.39 mg, 8.24 mmol). The resulting mixture was heated up to 100° C. and stirred for 60 hr. The reaction mixture was concentrated under vacuum. The residue was diluted with water (20 mL) and adjusted to pH~3 with HCl (concentrated). The aqueous mixture was extracted with ethyl acetate (50 mL×2). The combined organic layers were washed with water (50 mL), brine (50 mL), dried over sodium sulfate and filtered. The filtrate was concentrated under reduced pressure. The residue was purified by silica gel column (PE/EA=2/1 to DCM/MeOH=10/1) to afford 64-3 (160.0 mg, 92.34%). MS: m/z=421.2 (M+1).

Step 4: Compound 64

To a solution of 64-3 (160.0 mg, 0.38 mmol), Intermediate 3 (240.15 mg, 0.46 mmol, HCl salt) in Pyridine (10 mL) was added EDCI (146.10 mg, 0.76 mmol). After stirred at 25° C. for 16 hr, the solvent was removed in vacuo. The residue was diluted with water (50 mL) and extracted with ethyl acetate (50 mL×2). The combined organic layers were washed with water (50 mL), brine (50 mL), dried over sodium sulfate and filtered. The filtrate was concentrated under reduced pressure. The residue was purified by prepHPLC (0.1% FA) to afford Compound 64 (120.0 mg, 35.36%). $^1$H NMR (400 MHz, DMSO-$d_6$) δ 8.31 (s, 1H), 7.67-7.63 (m, 2H), 7.50-7.45 (m, 2H), 7.22-7.17 (m, 3H), 7.08-7.07 (m, 1H), 6.96 (s, 1H), 6.73 (s, 1H), 4.12-4.08 (m, 3H), 3.73-3.66 (m, 3H), 3.53-3.40 (m, 1H), 3.06-3.03 (m, 2H), 2.44-2.43 (m, 3H), 2.26-2.22 (m, 6H), 1.69-1.50 (m, 5H), 1.41-1.40 (m, 2H), 1.28 (s, 3H), 1.19 (s, 3H), 1.09-1.03 (m, 2H); MS: m/z=892.4 (M+1).

Example 60: Synthesis of Intermediate 55

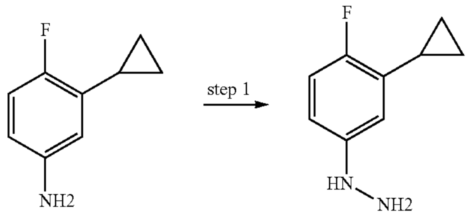

55-A Intermediate 55

To a mixture of 55-A (900 mg, 5.95 mmol) in HCl (concentrated, 30 mL) was added $NaNO_2$ (492.89 mg, 7.14 mmol) in water (60 mL) at 0° C. for 0.5 hr. The mixture was stirred for 1 hr at 0° C. Then, to the mixture was added $SnCl_2$ (3.39 g, 17.86 mmol) in HCl (concentrated, 50 mL) at 0° C. for 1 hr. The reaction solution was stirred for 0.5 hr at 0° C., and quenched with water (150 mL) at 0° C. The reaction mixture was neutralized with saturated aqueous NaOH until the pH~8, and to which ethyl acetate (200 mL) was added. Then the mixture was filtered and the organic layer was washed with brine (80 mL), dried over sodium sulfate and concentrated to give Intermediate 55 (500 mg, crude).

The compound in Table 17 was made according to the procedure of Intermediate 55.

TABLE 17

| Name | Structure | $^1$H NMR and/or LC/MS data |
|---|---|---|
| Intermediate 56 | 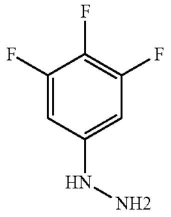 [SMILES: NNc1cc(F)c(F)c(F)c1] | MS: m/z = 163.1 (M + 1). |

Example 61: Synthesis of Intermediate 57

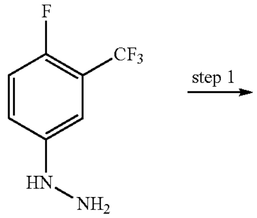

57-A

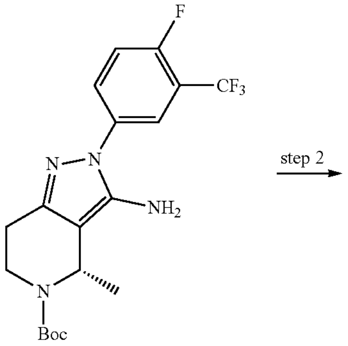

57-B

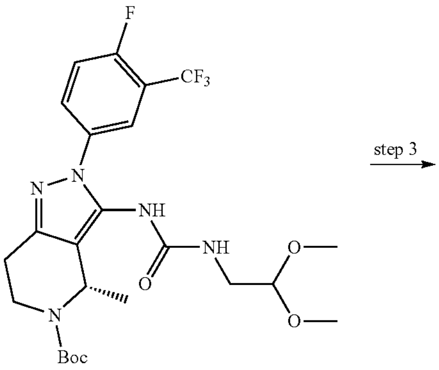

57-C

-continued

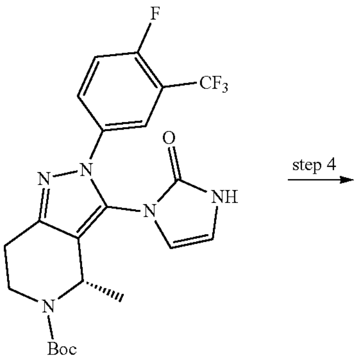

57-D

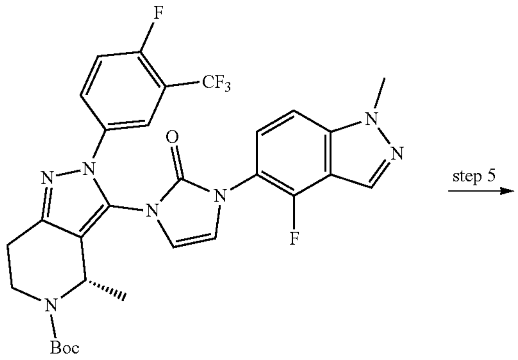

57-E

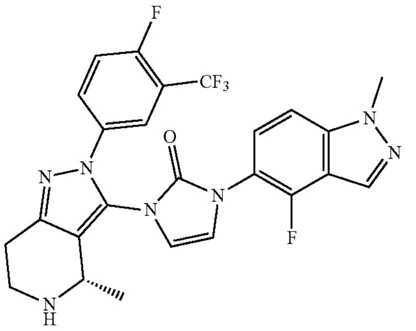

Intermediate 57

Step 1: 57-B

To a mixture of Intermediate 2 (700 mg, 2.94 mmol) in ethanol (20 mL) was added 57-A (812.88 mg, 3.53 mmol, HCl salt) and $H_2O$ (264.62 mg, 14.69 mmol) at 25° C. The reaction solution was stirred for 2 hr at 80° C. The mixture was concentrated to give a residue, to which was added $H_2O$ (50 mL) and extracted with ethyl acetate (50 mL×2). The combined organic layers were washed with brine (60 mL), dried over sodium sulfate and concentrated to give a crude product. The crude product was purified by silica gel chromatography (PE/EA=2/1) to give 57-B (750 mg, 1.81 mmol, 61.61% yield). MS: m/z=163.1 (M+1).

Step 2: 57-C

To a mixture of 57-B (750 mg, 1.81 mmol) and DIEA (1.17 g, 9.05 mmol, 1.58 mL) in THF (16 mL) was added phenyl carbonochloridate (368.37 mg, 2.35 mmol, 294.70 μL) at 25° C. The reaction solution was stirred for 1 hr at 25° C. Then, 2,2-dimethoxyethanamine (761.12 mg, 7.24 mmol, 788.73 μL) was added to the reaction mixture at 25° C. The reaction solution was stirred for 1 hr at 25° C. The solution was concentrated with a rotary evaporator to give 57-C (950 mg, crude). MS: m/z=546.3 (M+1).

Step 3: 57-D

To a mixture of 57-C (950 mg) in THF (15 mL) was added $CF_3SO_3H$ (214.46 mg, 2.61 mmol) at 25° C. The reaction mixture was stirred for 2 hr at 60° C. Then, $(Boc)_2O$ (570.09 mg, 2.61 mmol) and TEA (528.65 mg, 5.22 mmol, 728.17 μL) were added at 25° C. The reaction mixture was stirred for 2 hr at 25° C. The mixture was concentrated to give a residue, which was purified by silica gel chromatography (PE/EA=1/1) to obtain 57-D (500 mg, 1.04 mmol, 59.64% yield). MS: m/z=482.2 (M+1).

Step 4: 57-E

To a mixture of 57-E (500 mg, 1.04 mmol), Intermediate 1 (309.24 mg, 1.35 mmol) and (1S,2S)-N1,N2-dimethylcyclohexane-1,2-diamine (73.86 mg, 519.27 μmol, 81.89 L) in NMP (6 mL) was added $K_2CO_3$ (430.60 mg, 3.12 mmol) and CuI (98.90 mg, 519.27 μmol) at 25° C. After $O_2$ was purged by bubbling $N_2$ into the reaction solution, the reaction mixture was stirred for 2.5 hr at 135° C. The mixture was quenched with $H_2O$ (50 mL) and extracted by ethyl acetate (50 mL×2). The combined organic layers were washed with brine (40 mL), dried over sodium sulfate and concentrated to give a residue, which was purified by silica gel chromatography (PE/EA=1/1) to give 57-E (380 mg, 603.58 μmol, 58.12% yield). MS: m/z=630.3 (M+1).

Step 5: Intermediate 57

To a solution of 57-E (0.13 g, 206.49 μmol) in MeOH (4 mL) was added HCl (4 M in MeOH, 1.03 mL), and the mixture was stirred at 25° C. for 6 hr. The reaction was concentrated to Intermediate 57 (0.11 g, 194.37 μmol, 94.13% yield, HCl salt). MS: m/z=530.1 (M+1).

The compounds in Table 18 were made according to the procedure of Intermediate 57.

TABLE 18

| Name | Structure | $^1H$ NMR and/or LC/MS data |
|---|---|---|
| Intermediate 58 | 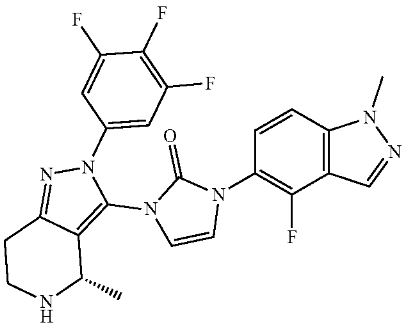 [SMILES: C[C@@H]1NCCc2nn(-c3cc(F)c(F)c(F)c3)c(-n3ccn(-c4ccc5c(cnn5C)c4F)c3=O)c21] | MS: m/z = 498.0 (M + 1). |
| Intermediate 59 | 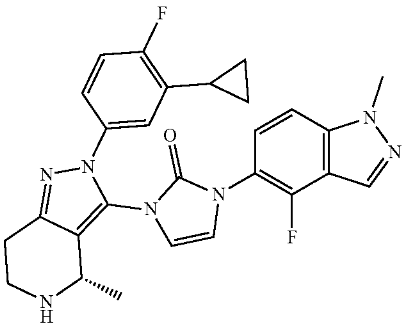 [SMILES: C[C@@H]1NCCc2nn(-c3ccc(F)c(C4CC4)c3)c(-n3ccn(-c4ccc5c(cnn5C)c4F)c3=O)c21] | MS: m/z = 502.2 (M + 1). |

The compound in Table 19 was made according to the procedure of Intermediate 11.

TABLE 19

| Name | Structure | $^1H$ NMR and/or LC/MS data |
|---|---|---|
| Intermediate 60 | 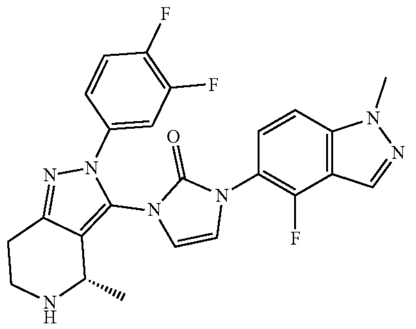 [SMILES: C[C@@H]1NCCc2nn(-c3ccc(F)c(F)c3)c(-n3ccn(-c4ccc5c(cnn5C)c4F)c3=O)c21] | MS: m/z = 480.1 (M + 1). |

The compounds in Table 20 were made according to the procedure of Intermediate 19-Pt and Intermediate 19-P2.

TABLE 20

| Name | Structure | Chiral separation condition: |
|---|---|---|
| Intermediate 61-P1 | 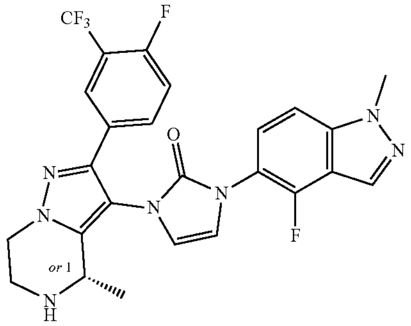 [SMILES: C[C@@H]1NCCn2nc(-c3ccc(F)c(C(F)(F)F)c3)c(-n3ccn(-c4ccc5c(cnn5C)c4F)c3=O)c21] | Column: Daicel CHIRALPAK OZ-H 250 mm × 20 mm I.D. 5 μm; Mobile phase: $CO_2$/MeOH (0.2% NH4•OH) = 80/20; Flow rate: 50 g/min; Wavelength: UV 214 nm; Temperature: 35° C. |
| Intermediate 61-P2 | 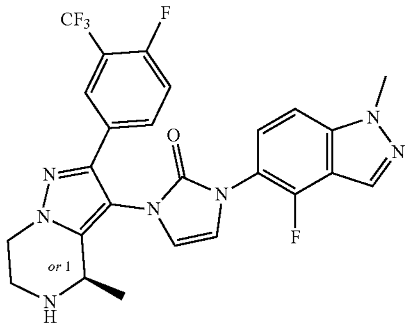 [SMILES: C[C@H]1NCCn2nc(-c3ccc(F)c(C(F)(F)F)c3)c(-n3ccn(-c4ccc5c(cnn5C)c4F)c3=O)c21] | |

The compounds in Table 21 were made according to the procedure of Compound 24.
TABLE 21
| Name | Structure | $^1H$ NMR and/or LC/MS data |
| --- | --- | --- |
| Compound 65 (from intermediate 61-P1 and 46-P2) | 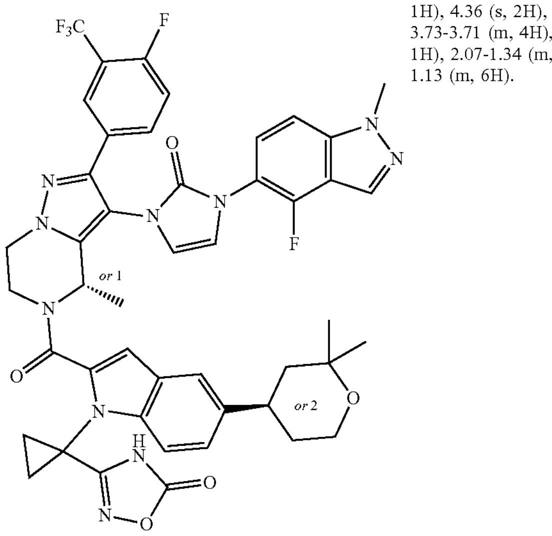 | MS: m/z = 909.3 (M + 1); $^1H$ NMR (400 MHz, DMSO-d6) δ 8.30 (s, 1H), 7.95 (s, 1H), 7.80 (s, 1H), 7.65-7.63 (m, 2H), 7.49-7.41 (m, 2H), 7.22 (d, J = 7.2 Hz, 1H), 7.11 (s, 1H), 6.94 (s, 1H), 6.86 (s, 1H), 5.69 (s, 1H), 4.36 (s, 2H), 4.11 (s, 3H), 3.73-3.71 (m, 4H), 3.04 (s, 1H), 2.07-1.34 (m, 11H), 1.33-1.13 (m, 6H). |
| Compound 66 (from intermediate 61-P2 and 46-P2) | 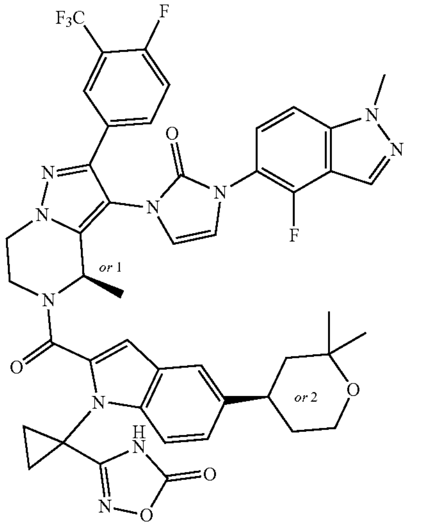 [SMILES: C[C@@H]1c2c(-n3ccn(-c4ccc5c(cnn5C)c4F)c3=O)c(-c3ccc(F)c(C(F)(F)F)c3)nn2CCN1C(=O)c1cc2cc([C@@H]3CCOC(C)(C)C3)ccc2n1C1(c2noc(=O)[nH]2)CC1] | MS: m/z = 909.3, (M + 1); $^1H$ NMR (400 MHz, DMSO-d6) δ 8.30 (s, 1H), 7.96 (s, 1H), 7.80 (s, 1H), 7.66-7.64 (m, 2H), 7.50-7.48 (m, 2H), 7.24 (s, 1H), 7.11 (s, 1H), 6.93-6.89 (m, 2H), 5.69 (s, 1H), 4.37 (s, 2H), 4.11 (s, 3H), 3.72 (d, J = 7.6 Hz, 4H), 3 04 (s, 1H), 2.03-1.38 (m, 11H), 1.31-1.13 (m, 6H). |

The compounds in Table 22 were made according to the procedure of Compound 2.

TABLE 22

| Name | Structure | $^1$H NMR and/or LC/MS data |
|---|---|---|
| Compound 67 (from intermediate 14 and 31-P2) | 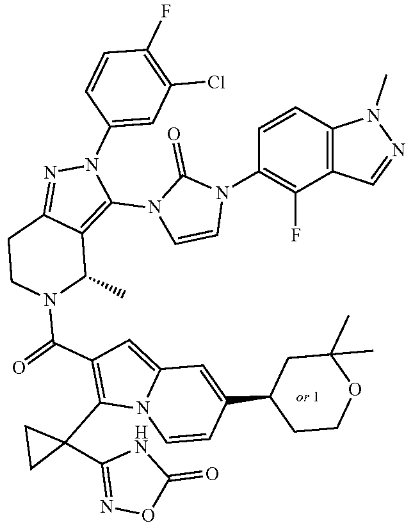 | MS: m/z = 875.1 (M + 1); $^1$H NMR (400 MHz, DMSO-d6) δ 12.0 (s, 1H), 8.30-8.23 (m, 1H), 8.16-8.14 (m, 1H), 7.65-7.55 (m, 3H), 7.48-7.43 (m, 2H), 7.29-7.27 (m, 1H), 7.13-6.95 (m, 2H), 6.71 (d, J = 7.6 Hz, 1H), 6.42 (s, 1H), 5.68-5.67 (m, 1H), 4.11-4.04 (m, 4H), 3.72-3.70 (m, 2H), 3.43-3.38 (m, 1H), 2.96-2.90 (m, 1H), 2.71-2.67 (m, 2H), 1.75-1.61 (m, 4H), 1.50-1.44 (m, 4H), 1.33 (d, J = 6.8 Hz, 3H), 1.26-1.24 (m, 3H), 1.19-1.16 (m, 3H). |
| Compound 68 (from intermediate 19-P1 and 31-P2) | 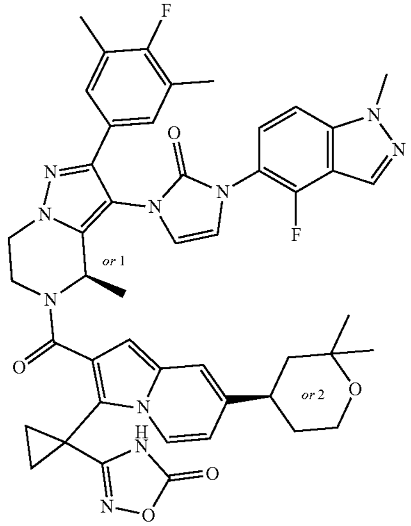 [SMILES: Cc1cc(-c2nn3c(c2-n2ccn(-c4ccc5c(cnn5C)c4F)c2=O)[C@@H](C)N(C(=O)c2cc4cc([C@@H]5CCOC(C)(C)C5)ccn4c2C2(c4noc(=O)[nH]4)CC2)CC3)cc(C)c1F] | MS: m/z = 869.2 (M + 1); $^1$H NMR (400 MHz, DMSO-d6) δ 12.01 (s, 1H), 8.31 (s, 1H), 8.16 (d, J = 7.2 Hz, 1H), 7.65 (d, J = 9.2 Hz, 1H), 7.54 (t, J = 7.6 Hz, 1H), 7.30-7.24 (m, 3H), 7.06 (s, 1H), 6.82 (s, 1H), 6.72 (d, J = 6.8 Hz, 1H), 6.48 (s, 1H), 5.78 (s, 1H), 4.17-4.12 (m, 5H), 3.72-3.70 (m, 4H), 2.97-2.90 (m, 2H), 2.23 (s, 5H), 1.67-1.19 (m, 17H). |
| Compound 69 (from intermediate 19-P1 and 28-P2) | 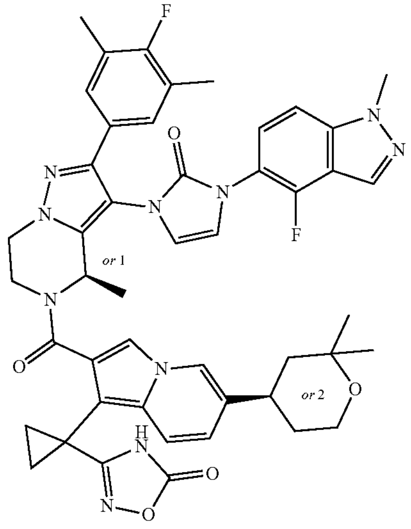 [SMILES: Cc1cc(-c2nn3c(c2-n2ccn(-c4ccc5c(cnn5C)c4F)c2=O)[C@@H](C)N(C(=O)c2cn4cc([C@@H]5CCOC(C)(C)C5)ccc4c2C2(c4noc(=O)[nH]4)CC2)CC3)cc(C)c1F] | MS: m/z = 869.2 (M + 1); $^1$H NMR (400 MHz, DMSO-d6) δ 11.84 (s, 1H), 8.31 (s, 1H), 8.09 (s, 1H), 7.72 (s, 1H), 7.63 (s, 1H), 7.54 (s, 1H), 7.46 (d, J = 9.2 Hz, 1H), 7.24 (s, 2H), 7.06 (s, 1H), 6.86 (d, J = 9.2 Hz, 1H), 6.81 (s, 1H), 5.78 (s, 1H), 4.21 (s, 2H), 4.12 (s, 3H), 3.71 (s, 4H), 2.90 (s, 1H), 2.23 (s, 6H), 1.69 (d, J = 9.6 Hz, 2H), 1.60-1.34 (m, 7H), 1.26-1.18 (m, 8H). |

TABLE 22-continued

| Name | Structure | $^1$H NMR and/or LC/MS data |
|---|---|---|
| Compound 70 (from intermediate 60 and 28-P2) | 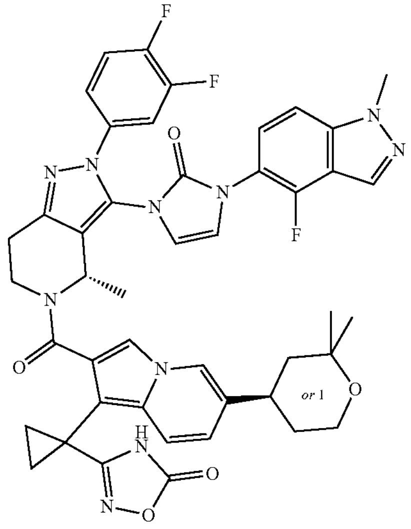 [SMILES: C[C@H]1c2c(nn(-c3ccc(F)c(F)c3)c2-n2ccn(-c3ccc4c(cnn4C)c3F)c2=O)CCN1C(=O)c1cn2cc([C@@H]3CCOC(C)(C)C3)ccc2c1C1(c2noc(=O)[nH]2)CC1] | MS: m/z = 859.3 (M + 1); $^1$H NMR (400 MHz, DMSO-d6) δ 11.89 (s, 1H), 8.30-8.12 (m, 2H), 7.69-7.28 (m, 7H), 7.12-7.04 (m, 2H), 5.68 (s, 1H), 5.01-4.79 (m, 1H), 4.11 (s, 3H), 3.72-3.70 (m, 2H), 2.90-2.59 (m, 4H), 1.71-1.19(m, 17H). |
| Compound 71 (from intermediate 57 and 28-P2) | 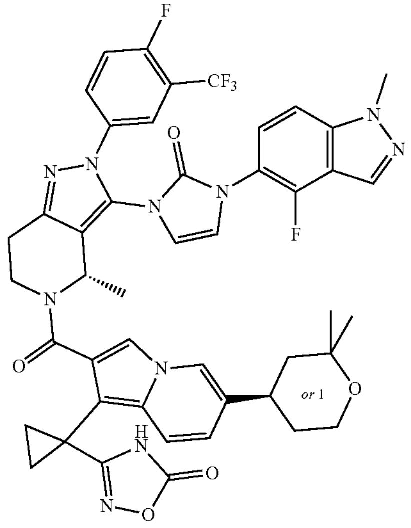 | MS: m/z = 909.2 (M + 1); $^1$H NMR (400 MHz, DMSO) δ 11.94 (s, 1H), 8.29 (s, 1H), 8.11 (s, 1H), 7.90-7.61 (m, 4H), 7.45 (d, J = 8.4 Hz, 2H), 7.27-6.91 (m, 2H), 6.85 (d, J = 8.0 Hz, 1H), 5.70 (s, 1H), 4.90 (d, J = 74.8 Hz, 1H), 4.11 (s, 3H), 3.70 (s, 2H), 3.26-3.08 (m, 1H), 2.98-2.69 (m, 3H), 1.98-0.82 (m, 17H). |
| Compound 72 (from intermediate 58 and 31-P2) | 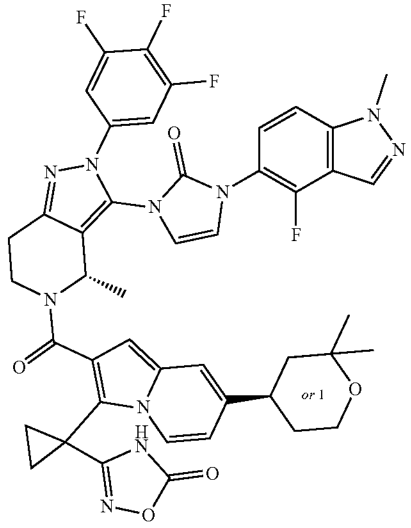 [SMILES: C[C@H]1c2c(nn(-c3cc(F)c(F)c(F)c3)c2-n2ccn(-c3ccc4c(cnn4C)c3F)c2=O)CCN1C(=O)c1cc2cc([C@@H]3CCOC(C)(C)C3)ccn2c1C1(c2noc(=O)[nH]2)CC1] | MS: m/z = 877.2 (M + 1); $^1$H NMR (400 MHz, DMSO-d6) δ 12.0 s 1H 8.30 s 1H 8.15 d J = 7.2 Hz, 1H), 7.64 (d, J = 8.8 Hz, 1H), 7.51-7.47 (m, 1H), 7.42-7.30 (m, 3H), 7.17 (d, J = 2.8 Hz, 1H), 7.08 (s, 1H), 6.71 (d, J = 7.6 Hz, 1H), 6.42 (s, 1H), 5.69 (s, 1H), 4.99-4.82 (m, 1H),4.11-4.04 (m, 4H), 3.71 (d, J = 8.0 Hz, 2H), 2.93-2.66 (m, 4H), 1.67-1.17 (m, 17H). |

TABLE 22-continued

| Name | Structure | $^1$H NMR and/or LC/MS data |
|---|---|---|
| Compound 73 (from intermediate 59 and 31-P2) | 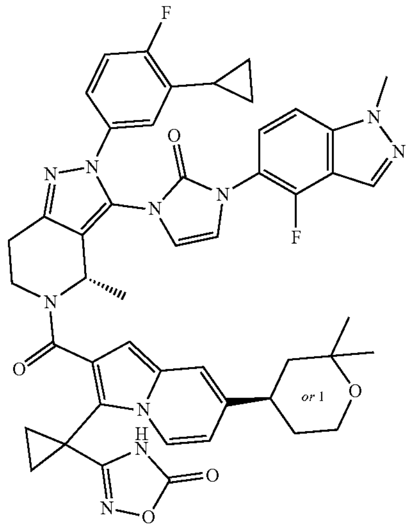 [SMILES: C[C@H]1c2c(nn(-c3ccc(F)c(C4CC4)c3)c2-n2ccn(-c3ccc4c(cnn4C)c3F)c2=O)CCN1C(=O)c1cc2cc([C@@H]3CCOC(C)(C)C3)ccn2c1C1(c2noc(=O)[nH]2)CC1] | MS: m/z = 881.3 (M + 1); $^1$H NMR (400 MHz, DMSO-d6) δ 8.30(s, 1H), 8.10 (d, J = 7.2 Hz, 1H), 7.64 (d, J = 8.8 Hz, 1H), 7.49-7.40 (m, 1H), 7.28-7.22 (m, 3H), 7.09 (s, 1H), 7.03-6.76 (m, 3H), 6.69 (d, J = 6.8 Hz, 1H), 6.38 (s, 1H), 5.65-5.62 (m,1H), 4.09-4.07 (m, 3H), 3.71 (d, J = 8.0 Hz, 2H), 2.93 (s, 1H), 2.67-2.65 (m, 2H), 2.13-1.98 (m, 2H), 1.73-1.48 (m, 6H), 1.34-1.17 (m, 12H), 1.01-0.98 (m, 2H), 0.67-0.63 (m, 2H). |
| Compound 74 (from intermediate 57 and 31-P2) | 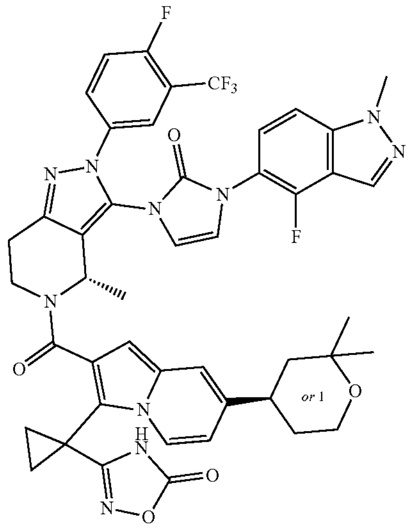 [SMILES: C[C@H]1c2c(nn(-c3ccc(F)c(C(F)(F)F)c3)c2-n2ccn(-c3ccc4c(cnn4C)c3F)c2=O)CCN1C(=O)c1cc2cc([C@@H]3CCOC(C)(C)C3)ccn2c1C1(c2noc(=O)[nH]2)CC1] | MS: m/z = 909 (M + 1); $^1$H NMR (400 MHz, DMSO-d6) δ 8.29(s, 1H), 8.15 (d, J = 7.2 Hz, 1H), 7.89-7.61 (m, 5H), 7.43 (m, 1H), 7.30(s, 1H), 7.15 (d, J = 2.4 Hz, 1H), 6.71 (d, J = 6.9 Hz, 1H), 6.42 (s, 1H), 5.74-5.64 (m, 1H), 4.11 (s, 3H), 3.68-3.57 (m, 6H), 2.93 (m, 1H), 1.45-1.09 (m, 17H). |
| Compound 75 (from intermediate 58 and 28-P2) | 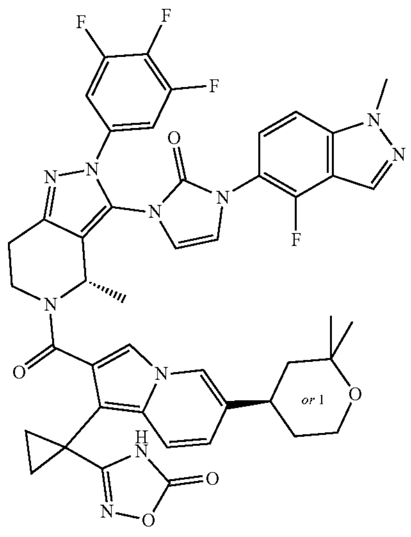 [SMILES: C[C@H]1c2c(nn(-c3cc(F)c(F)c(F)c3)c2-n2ccn(-c3ccc4c(cnn4C)c3F)c2=O)CCN1C(=O)c1cn2cc([C@@H]3CCOC(C)(C)C3)ccc2c1C1(c2noc(=O)[nH]2)CC1] | MS: m/z = 877.2 (M + 1); $^1$H NMR (400 MHz, CD3OD) δ 8.16 (d, J = 23.6 Hz, 1H), 8.02 (d, J = 19.6 Hz, 1H), 7.59 (d, J = 17.6 Hz, 1H), 7.43-7.51 (m, 3H), 7.30 (d, J = 2.4 Hz, 2H), 7.03-6.92 (m, 1H), 6.91-6.83 (m, 1H), 6.76 (d, J = 13.2 Hz, 1H), 5.88 (s, 1H), 4.26 (s, 1H), 4.11 (d, J = 8.8 Hz, 3H), 3.82-3.87 (m, 2H), 2.80-3.12 (m, 4H), 1.57-1.77 (m, 4H), 1.48-1.10 (m, 13H). |

TABLE 22-continued

| Name | Structure | $^1$H NMR and/or LC/MS data |
|---|---|---|
| Compound 76 (from intermediate 59 and 28-P2) | 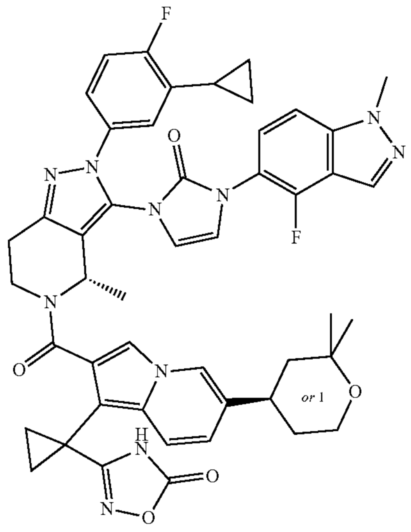 [SMILES: C[C@H]1c2c(nn(-c3ccc(F)c(C4CC4)c3)c2-n2ccn(-c3ccc4c(cnn4C)c3F)c2=O)CCN1C(=O)c1cn2cc([C@@H]3CCOC(C)(C)C3)ccc2c1C1(c2noc(=O)[nH]2)CC1] | MS: m/z = 881.2 (M + 1); $^1$H NMR (400 MHz, DMSO-d6) δ 8.30 (s, 1H), 8.12 (s, 1H), 7.72-7.61 (m, 2H), 7.45 (d, J = 8.4 Hz, 2H), 7.28 (s, 2H), 7.10 (s, 1H), 6.98-6.85 (m, 3H), 5.66 (s, 1H), 4.11 (s, 3H), 3.70 (s, 2H), 2.90 (s, 1H), 2.75 (s, 2H), 2.08 (s, 1H), 1.69 (s, 2H), 1.54-1.44 (m, 4H), 1.33-1.18 (m, 13H), 0.99 (s, 2H), 0.64 (s, 2H). |
| Compound 77 (from intermediate 15 and 31-P2) | 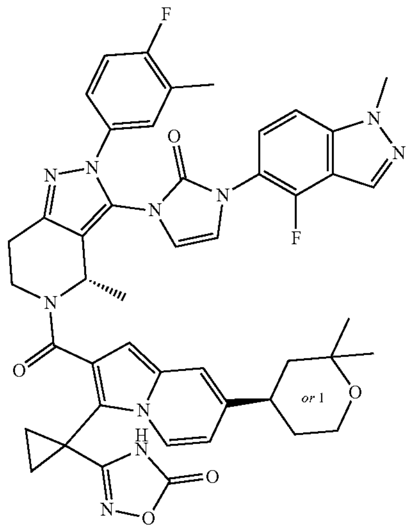 | MS: m/z = 855.3 (M + 1); $^1$H NMR (400 MHz, DMSO-d6) δ 12.03 (br, 1H), 8.30 (s, 1H), 8.15 (d, J = 7.2 Hz, 1H), 7.63 (d, J = 8.4 Hz, 1H), 7.48-7.21 (m, 5H), 7.08 (d, J = 2.8 Hz, 1H), 6.97 (s, 1H), 6.71 (d, J = 7.2 Hz, 1H), 6.42 (s, 1H), 5.68-5.66 (m, 1H), 4.10 (s, 3H), 3.73-3.70 (m, 2H), 3.45-3.30 (m, 2H), 3.00-2.85 (m, 2H), 2.71-2.69 (m, 1H), 2.27 (s, 3H), 1.80-1.11 (m, 17H). |
| Compound 78 (from intermediate 60 and 31-P2) | 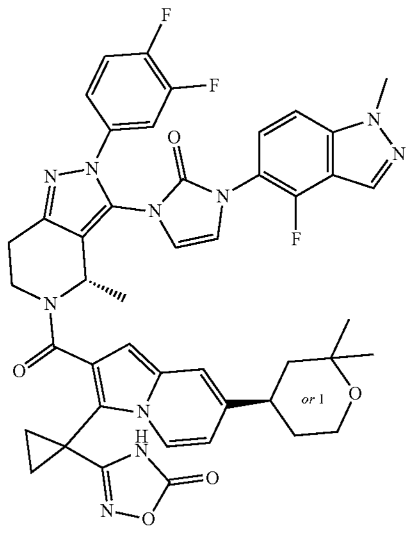 | MS: m/z = 859.3 (M + 1); $^1$H NMR (400 MHz, DMSO-d6) δ 8.26 (s, 1H), 8.12-8.11 (m, 1H), 7.64-7.47 (m, 4H), 7.28-7.03 (m, 4H), 6.70 (d, J = 6.8, 1H), 6.40 (s, 1H), 5.67-5.66 (m, 1H), 4.10-4.06 (m, 4H), 3.71-3.69 (m, 2H), 2.95-2.89 (m, 2H), 2.68 (s, 2H), 1.74-1.43 (m, 8H), 1.32 (d, J = 6.4, 3H), 1.25-1.22 (m, 3H), 1.18-1.16 (m, 3H). |

Example 62: Synthesis of Intermediate 62

Intermediate 62 in Table 23 was made according to the procedure of Intermediate 3.

TABLE 23

| Name | Structure | $^1$H NMR and/or LC/MS data |
| --- | --- | --- |
| Intermediate 62 | 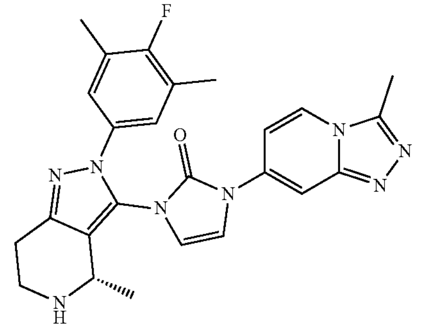 [SMILES: Cc1cc(-n2nc3c(c2-n2ccn(-c4ccn5c(C)nnc5c4)c2=O)[C@H](C)NCC3)cc(C)c1F] | MS: m/z = 473.1 (M + 1). |

Example 63: Synthesis of Intermediate 63

Intermediate 63 in Table 24 was made according to the procedure of Intermediate 55.

TABLE 24

| Name | Structure | $^1$H NMR and/or LC/MS data |
| --- | --- | --- |
| Intermediate 63 | 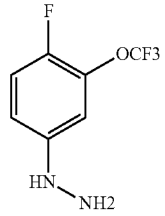 [SMILES: NNc1ccc(F)c(OC(F)(F)F)c1] | MS: m/z = 211.1 (M + 1). |

Example 64: Synthesis of Intermediate 64

Intermediate 64 in Table 25 was made according to the procedure of Intermediate 57.

TABLE 25

| Name | Structure | $^1$H NMR and/or LC/MS data |
| --- | --- | --- |
| Intermediate 64 | 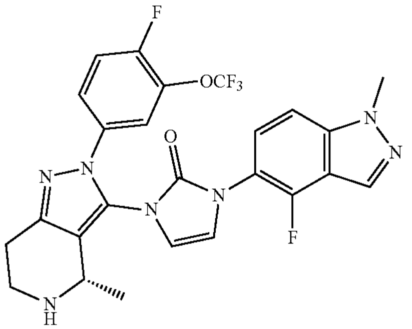 [SMILES: C[C@@H]1NCCc2nn(-c3ccc(F)c(OC(F)(F)F)c3)c(-n3ccn(-c4ccc5c(cnn5C)c4F)c3=O)c21] | MS: m/z = 546.1 (M + 1). |

Example 65: Synthesis of Intermediate 65

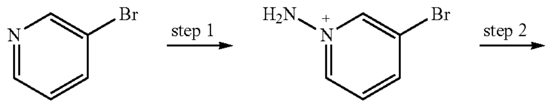

65-A 65-B

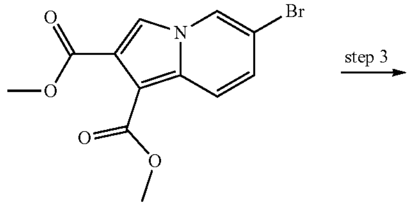

65-C

-continued

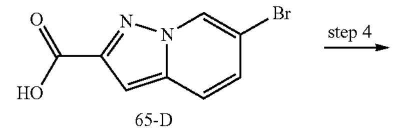

65-D

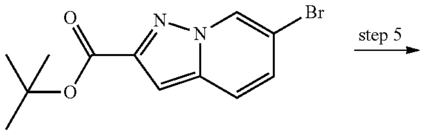

65-E

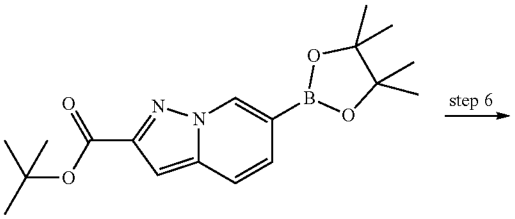

65-F

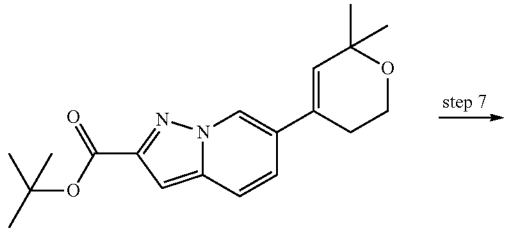

65-G

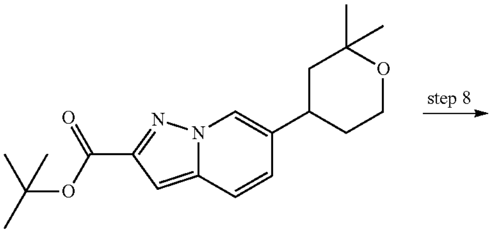

65-H

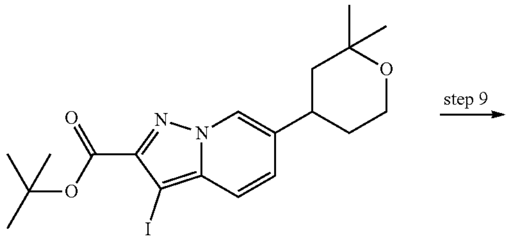

65-I

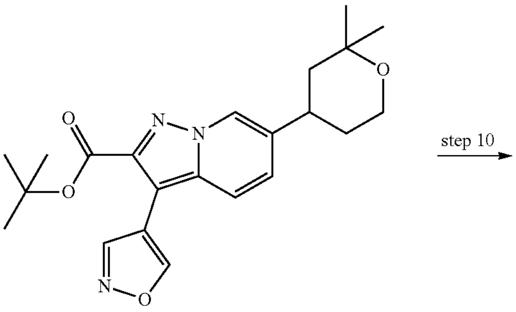

65-J

-continued

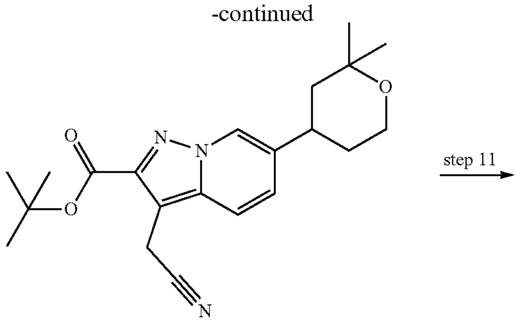

65-K

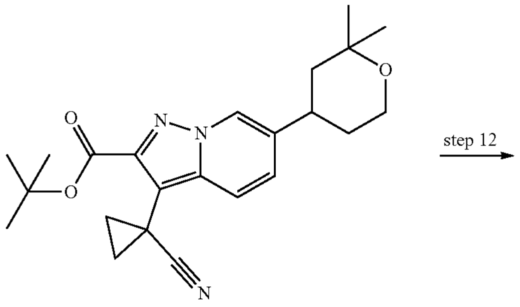

65-L

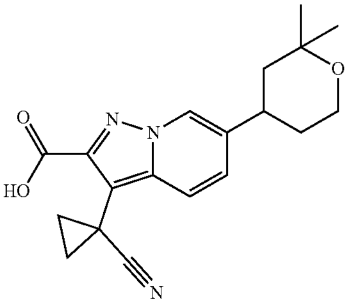

Intermediate 65

Step 1: 65-B

To a solution of Hydroxylamine-O-sulfonic acid (107.37 g, 949.39 mmol) in 300 mL of cold water was added 65-A (100 g, 632.93 mmol, 61.73 mL) at 25° C. The mixture was heated at 90° C. for 40 minutes, after cooling to room temperature, potassium carbonate (138 g) was added, followed by the removal of water by evaporation in vacuum. The residue was treated with 300 mL of ethanol and the insoluble precipitate was removed by filtration. The filtrate was treated with 140 mL of 57% hydroiodic acid and stored at −20° C. The solids were then collected by filtration to give 65-B (40 g, 132.48 mmol, 20.9% yield, HI salt), which is used in the next step without further purification.

Step 2: 65-C

To a freshly prepared solution of 65-B (40 g, 132.48 mmol, HI salt) in DMF (300 mL) was added dimethyl but-2-ynedioate (65.33 g, 459.72 mmol) and $K_2CO_3$ (63.54 g, 459.72 mmol). The mixture was stirred at 25° C. for 12 hrs. The mixture was filtered and concentrated to give a residue, which was purified by column chromatography on silica gel (EA/PE=1/10-1/3) to give 65-C (20 g, 63.88 mmol, 27.8% yield).

Step 3: 65-D

A mixture of 65-C (20 g, 63.88 mmol) in conc. $H_2SO_4$ (50 mL) and Water (50 mL) was stirred for 3 hrs at 100° C. After cooling to 0° C., pH 8 was attained with an aqueous solution of 8 M sodium hydroxide. Then, 6 M hydrochloric acid was added till pH=3, the mixture was extracted with DCM (100 mL/3), the combined organic phases were dried over anhydrous magnesium sulfate, filtered, and concentrated. The precipitate was collected by filtration, washed with MTBE to give 65-D (12 g, 49.78 mmol, 77.9% yield).

Step 4: 65-E

To a mixture of 65-D (2 g, 8.30 mmol) in THF (30 mL) and DCM (30 mL) was added oxalyl dichloride (1.58 g, 12.45 mmol) at 0° C. under the $N_2$ atmosphere for 0.5 hr, then DMF (64 μL) was added and stirred for 1 hr before t-BuONa (7.97 g, 82.97 mmol) was added. The reaction solution was stirred for 1.5 hrs at 25° C. Then, water (20 mL) was added and the solution was concentrated with a rotary evaporator. Ethyl acetate (80 mL) was added and the organic phase was dried over $Na_2SO_4$, filtered and concentrated to give a residue, which was purified by silica gel chromatography (PE/EA=10/1-1/2) to obtain 65-E (1.6 g, 5.38 mmol, 64.9% yield).

Step 5: 65-F

To a mixture of 65-E (1.6 g, 5.38 mmol), 4,4,5,5-tetramethyl-2-(4,4,5,5-tetramethyl-1,3,2-dioxaborolan-2-yl)-1,3,2-dioxaborolane (1.37 g, 5.38 mmol) in dioxane (20 mL) was added KOAc (1.59 g, 16.15 mmol) and Pd(dppf)$Cl_2$ (393.99 mg, 538.45 μmol) at 30° C. under N2 atmosphere. The reaction was stirred for 2 hrs at 100° C. Then, the mixture was filtered and concentrated to give 65-F (1.85 g, crude), which was used for the next step without further purification. MS: m/z=345.3 (M+1).

Step 6: 65-G

To a mixture of Intermediate 26 (2.34 g, 9.01 mmol), 65-F (1.55 g, crude) in water (2 mL) and dioxane (10 mL) was added Pd(dppf)$Cl_2$ (3.29 g, 4.50 mmol) and $K_2CO_3$ (622.34 mg, 4.50 mmol) at 30° C. The reaction mixture was stirred for 2 hrs at 100° C. The mixture was filtered and concentrated to give a residue, which was purified by silica gel chromatography (PE/PE=10/1-3/1) to obtain 65-G (1.3 g, 3.96 mmol, 87.9% yield). MS: m/z=329.2 (M+1).

Step 7: 65-H

To a mixture of 65-G (1.3 g, 3.96 mmol) in Methanol (100 mL) was added Pd/C (130 mg) at 25° C. The reaction solution was stirred for 4 hrs at 25° C. under $H_2$ atmosphere. Then, the mixture was filtered and concentrated to give 65-H (1.32 g, crude), which was used for the next step without further purification. MS: m/z=331.2 (M+1).

Step 8: 65-I

To a mixture of 65-H (1.3 g, crude), $NaHCO_3$ (661.03 mg, 7.87 mmol) in MeCN (40 mL) was added NIS (1.06 g, 4.72 mmol) at 0° C. The reaction solution was stirred for 0.5 hr at 0° C. Then, the solution was concentrated to give a residue, which was purified by silica gel chromatography (PE/EA=10/1-3/1) to obtain 65-I (1.7 g, 3.73 mmol, 94.7% yield).

Step 9: 65-J

A 30 mL microwave reaction tube was charged with 65-I (1.55 g, 3.40 mmol), 4-(4,4,5,5-tetramethyl-1,3,2-dioxaborolan-2-yl)isoxazole (662.45 mg, 3.40 mmol), Pd(dppf)$Cl_2$ (248.54 mg, 339.68 μmol) and KF (986.76 mg, 16.98 mmol) in DMSO (10 mL) and Water (1 mL). After $O_2$ was purged by bubbling $N_2$ into the reaction solution, the tube was sealed and heated at 90° C. for 45 minutes in a Biotage microwave reactor. The reaction was cooled to room temperature, filtered, diluted with EA (50 mL), and the organic phase was washed with water (30 mL), dried over $Na_2SO_4$, filtered and concentrated to give a residue, which was purified by flash chromatography (0-100%, EA/PE) to deliver 65-J (1 g, 2.52 mmol, 74.1% yield).

Step 10: 65-K

A 30 mL microwave reaction tube was charged with 65-J (1 g, 2.52 mmol) and KF (1.46 g, 25.16 mmol) in Methanol (10 mL) and Water (2 mL). After $O_2$ was purged by bubbling N2 into the reaction solution, the tube was sealed and heated at 100° C. for 45 minutes in a Biotage microwave reactor. The reaction was cooled to room temperature, and concentrated to give a residue, which was purified by flash chromatography (0-100%, EA/PE) to deliver 65-K (800 mg, 2.17 mmol, 86.1% yield). MS: m/z=314.2 (M−55).

Step 11: 65-L

To a mixture of 65-K (800 mg, 2.17 mmol), 1,3,2-dioxathiolane 2,2-dioxide (290.63 mg, 2.38 mmol) in THF (50 mL) was added LiHDMS (1 M, 10.82 mL) at 0° C. The reaction solution was stirred for 0.5 hr at 0° C. Then, sat. $NH_4Cl$ (5 mL) was added and the organic phase was separated and concentrated with a rotary evaporator. The crude product was purified by silica gel chromatography (PE/EA=4/1) to obtain 65-L (700 mg, 1.77 mmol, 81.7% yield). MS: m/z=340.2 (M−55).

Step 12: Intermediate 65

A mixture of 65-L (700 mg, 1.77 mmol) in HCl/dioxane (4 M, 20 mL) was stirred for 4 hrs at 35° C. The mixture was concentrated and purified by prep-HPLC (column: XBridge® Prep C18 5 μm 19×150 mm; A: 0.2% $HCO_2H$ water, B: acetonitrile; gradient: 5-95% B; GT: 16 min; flow rate: 15 mL/min) to give Intermediate 65 (102 mg).

Example 66: Synthesis of Intermediate 66

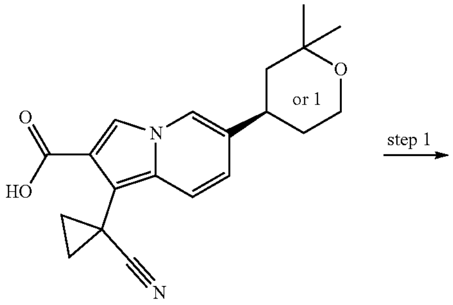

Intermediate 28-P2

-continued

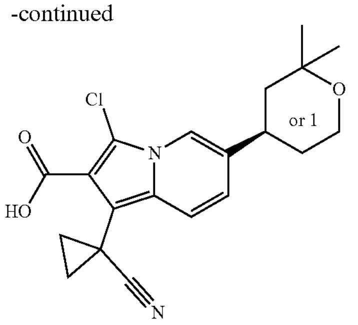

Intermediate 66

To a solution of Intermediate 28-P2 (50 mg, 147.75 μmol) in MeCN (4 mL) was added NCS (30 mg, 221.63 μmol). The mixture was stirred at 25° C. for 1 hr. The reaction mixture was diluted with EA (20 mL), washed with brine (10 mL×2), dried over anhydrous $Na_2SO_4$, and filtered. The filtrate was concentrated and purified by reverse-phase column (45% MeCN in $H_2O$ (0.1% FA)) to give Intermediate 66 (25 mg, 45% yield). MS: m/z=373.1 (M+1).

Example 67: Synthesis of Intermediate 67

Intermediate 67 in Table 26 was made according to the procedure of Intermediate 66.

TABLE 26

| Name | Structure | $^1$H NMR and/or LC/MS data |
|---|---|---|
| Intermediate 67 | 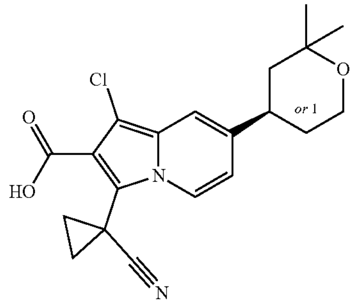 [SMILES: CC1(C)C[C@H](c2ccn3c(C4(C#N)CC4)c(C(=O)O)c(Cl)c3c2)CCO1] | MS: m/z = 373.1 (M + 1). |

Example 68: Synthesis of Intermediate 68

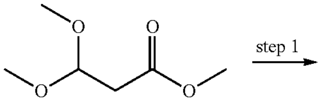

68-A

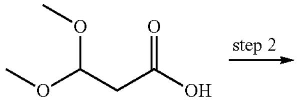

68-B

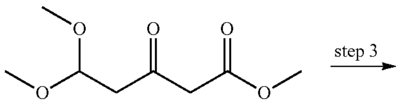

68-C

-continued

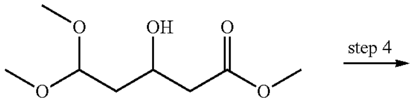

68-D

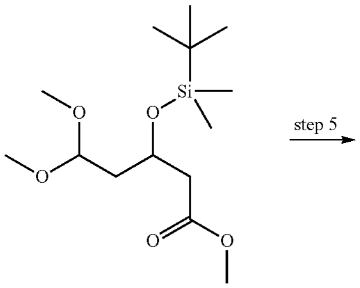

68-E

-continued

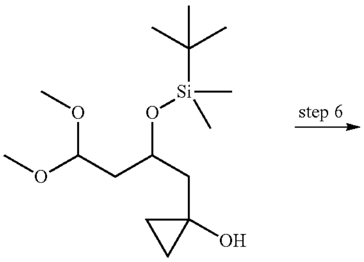

68-F

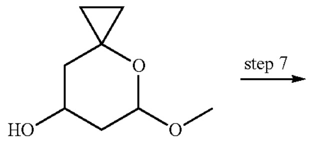

68-G

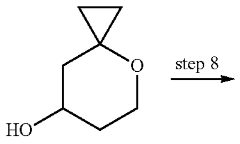

68-H

-continued

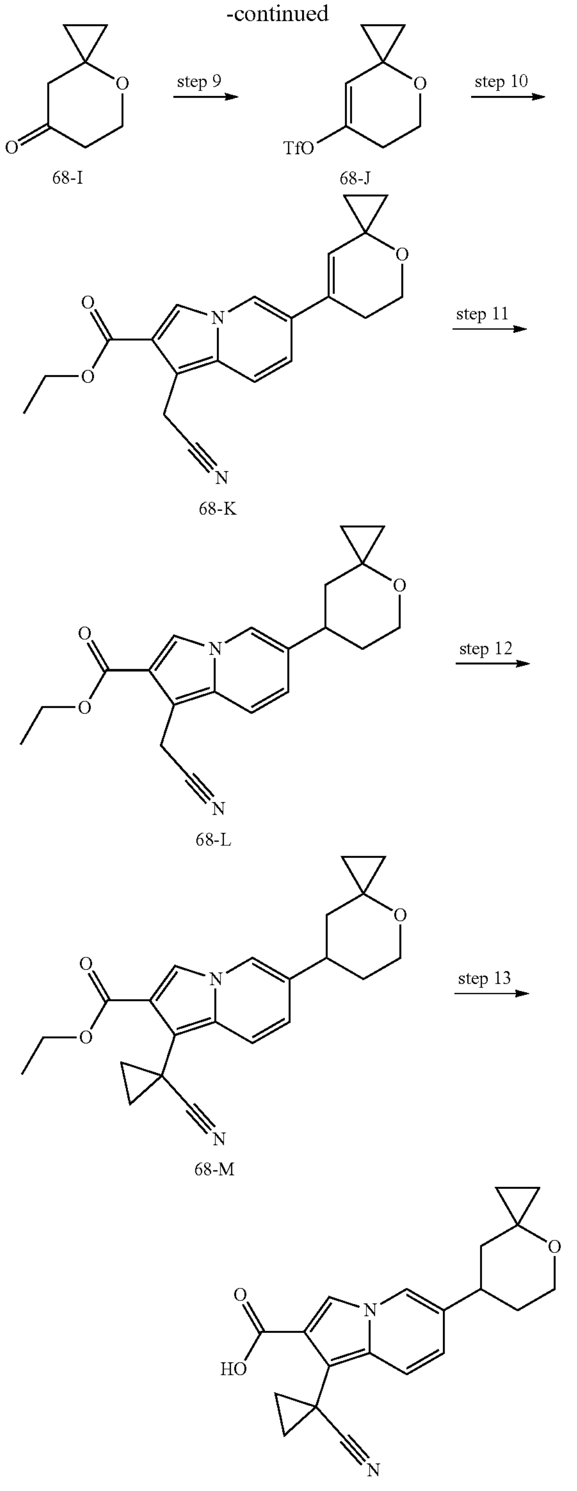

68-I

68-J

68-K

68-L

68-M

Intermediate 68

Step 1: 68-B

To a solution of 68-A (50 g, 337.48 mmol) in MeOH (200 mL) was added LiOH (aq.) (4 M, 168.74 mL), the mixture was stirred at 80° C. for 2 hrs. The reaction mixture was neutralized with citric acid, extracted with DCM (200 mL×10). The combined organic layers were washed with water, dried over sodium sulfate, and concentrated in vacuum to give 68-B (28.5 g, 62.96% yield).

Step 2: 68-C

To a solution of 68-B (23 g, 171.48 mmol) in THF (200 mL) was added the suspension of CDI (33.37 g, 205.77 mmol) in THF (100 mL) dropwise. The mixture was stirred at 25° C. for 2 hrs. At the same time, another flask with potassium 3-methoxy-3-oxopropanoate (40.17 g, 257.21 mmol) and $MgCl_2$ (17.96 g, 188.62 mmol) in 200 mL of THF was stirred at 25° C. for 2 hrs. The imidazoline solution was then transferred into the latter solution dropwise and the resulting mixture was stirred at 25° C. for 16 hrs. The mixture was acidified with 60 mL of aqueous HCl (2M) and extracted with EA (300 mL×3). The combined organic layers were washed with sat. $NaHCO_3$ aqueous solution, brine, dried over sodium sulfate and concentrated in vacuum to give 68-C (25 g, 76.7% yield).

Step 3: 68-D

To a solution of 68-C (25 g, 131.45 mmol) in MeOH (200 mL) was added $NaBH_4$ (4.97 g, 131.45 mmol) slowly at 0° C. The mixture was stirred at 0° C. for 1 hr. The mixture was quenched with aqueous HCl (1 M, 30 mL), then 200 mL of water was added to the mixture. The reaction mixture was extracted with EA (100 mL×5), dried over sodium sulfate, and concentrated in vacuum to give 68-D (14 g, 55.4% yield).

Step 4: 68-E

To a solution of 68-D (14 g, 72.84 mmol) in DMF (100 mL) was added imidazole (9.92 g, 145.67 mmol) and TBSCl (14.27 g, 94.69 mmol). The mixture was stirred at 25° C. for 16 hrs. The mixture was added into water, and extracted with EA (100 mL×2). The combined organic layers were washed with brine (100 mL×2), dried over sodium sulfate, and concentrated in vacuum to give a residue, which was purified by column chromatography on silica gel (EA in PE, 0-10%) to give 68-E (11 g, 49.3% yield).

Step 5: 68-F

To a solution of 68-E (11 g, 35.89 mmol) in THF (100 mL) was added Titanium isopropoxide (2.04 g, 7.18 mmol). Ethyl magnesium bromide (1 M, 107.68 mL) was then added dropwise by a syringe pump over 1 hr at 0° C. The mixture was stirred at 0° C. for 2 hrs. The mixture was quenched with aqueous HCl (1 M, 30 mL), then to which 200 mL of water was added. The reaction mixture was extracted with EA (100 mL×5), the combined organic layers were dried over sodium sulfate, and concentrated to give a residue, which was purified by column chromatography on silica gel (EA in PE, 0-10%) to give 68-F (10.5 g, 96.1% yield).

Step 6: 68-G

To a solution of 68-F (10.5 g, 34.48 mmol) in MeOH (100 mL) was added p-toluenesulfonic acid monohydrate (6.56 g, 34.48 mmol). The mixture was stirred at 25° C. for 16 hrs. The mixture was added to water (100 mL), and concentrated in vacuum to remove MeOH. The residue was extracted with DCM (30 mL×6), the combined organic layers were washed with water (100 mL), dried over sodium sulfate, and concentrated in vacuum to give 68-G (4.8 g, 88.0% yield).

Step 7: 68-H

To a solution of 68-G (4.8 g, 30.34 mmol) in DCM (100 mL) was added bis(trimethylsilyl)trifluoroacetamide (5.86 g, 22.76 mmol), which was stirred at 25° C. for 2 hrs. The mixture was then cooled down to −10° C. Triethyl silane (14.11 g, 121.37 mmol, 19.39 mL) was added followed by Boron trifluoride diethyl etherate (10.77 g, 75.86 mmol, 9.53 mL). The mixture was then allowed to warm to 0° C. slowly and stirred at 0° C. for 30 minutes. The mixture was added to water (200 mL), and extracted with DCM (50 mL×6). The combined organic layers were washed with water (200 mL), dried over sodium sulfate, and concentrated in vacuum to give 68-H (3.8 g, 97.7% yield).

Step 8: 68-I

To a solution of oxalyl dichloride (4.89 g, 38.54 mmol, 3.35 mL) in 30 mL of DCM at −78° C. was added DMSO (5.79 g, 74.12 mmol, 5.26 mL) in 10 mL of DCM dropwise. The mixture was stirred for 20 minutes and 68-H (3.8 g, 29.65 mmol) in 10 mL of DCM was added dropwise. The mixture was stirred at −78° C. for 20 minutes, TEA (15.0 g, 148.24 mmol, 20.66 mL) was then added and the mixture was warmed slowly to 25° C. for 30 minutes. The mixture was poured into water (50 mL), extracted with DCM (50 mL×6). The combined organic layers were washed with water (100 mL), dried over sodium sulfate, and concentrated in vacuum to give a residue, which was purified by column chromatography on silica gel (PE/EA=20/1-10/1) to give 68-I (2.0 g, 53.5% yield).

Step 9: 68-J

To a solution of 68-I (2.0 g, 15.85 mmol) in THF (20 mL) was added LDA (2 M, 15.85 mL) dropwise at −78° C., and was stirred at this temperature for 30 minutes. Then 1,1,1-trifluoro-N-phenyl-N-(trifluoromethylsulfonyl)methanesulfonamide (6.23 g, 17.44 mmol) in THE (20 mL) was added to the mixture dropwise (keeping temperature below −60° C.). The mixture was warmed to 25° C. slowly and stirred for 16 hrs. The mixture was poured into water (50 mL), extracted with EA (30 mL×2). The combined organic layers were washed with brine (50 mL), dried over sodium sulfate, and concentrated to give 68-J (6.0 g, crude), which was used for the next step without further purification.

Step 10: 68-K

To a solution of 27-F (530 mg, 1.73 mmol) in dioxane (10 mL) was added 4,4,5,5-tetramethyl-2-(4,4,5,5-tetramethyl-1,3,2-dioxaborolan-2-yl)-1,3,2-dioxaborolane (569.65 mg, 2.24 mmol), $Pd(dppf)Cl_2$ (126.26 mg, 172.56 μmol) and $K_2CO_3$ (476.97 mg, 3.45 mmol). The mixture was stirred at 90° C. for 2 hrs. The mixture was filtered and concentrated in vacuum. The residue was dissolved in dioxane (10 mL), to which 68-J (877.64 mg), $K_2CO_3$ (476.97 mg, 3.45 mmol), $Pd(dppf)Cl_2$ (126.26 mg, 172.56 μmol) and water (4 mL) was added. The mixture was stirred at 90° C. for 1 hr under nitrogen atmosphere. The mixture was added into water, extracted with EA (20 mL×2). The combined organic layers were washed with brine (20 mL), dried over sodium sulfate, and concentrated in vacuum to give a residue, which was purified by column chromatography on silica gel (PE/EA=10/1-5/1) to give 68-K (300 mg, 51.7% yield). MS: m/z=337 (M+1).

Step 11: 68-L

To a solution of 68-K (300 mg, 891.84 μmol) in EA (5 mL) was added Pd/C (30 mg, 55% wet, 10%). The mixture was stirred at 25° C. for 30 minutes under hydrogen atmosphere. The mixture was filtered and concentrated in vacuum to give 68-L (240 mg, 79.5% yield). MS: m/z=339.1 (M+1).

Step 12: 68-M

To a solution of LiHMDS (1 M, 7.09 mL) in THF (10 mL) was added the mixture of 68-L (240 mg, 709.22 μmol) and 1,3,2-dioxathiolane 2,2-dioxide (264.08 mg, 2.13 mmol) in THE dropwise at 0° C. The mixture was stirred at 25° C. for 2 hrs. The mixture was added into water, extracted with EA (5 mL×2). The combined organic layers were washed with brine (5 mL×2), dried over sodium sulfate, and concentrated in vacuum to give a residue, which was purified by column chromatography on silica gel (PE/EA=10/1-5/1) to give 68-M (110 mg, 31.1% yield). MS: m/z=365.1 (M+1).

Step 13: Intermediate 68

To a solution of 68-M (110 mg, 220.34 μmol) in Methanol (5 mL) was added aqueous NaOH (4 M, 550.85 μL). The mixture was stirred at 60° C. for 1 hr. The mixture was neutralized with aqueous HCl, extracted with EA (5 mL×2). The combined organic layers were washed with brine (5 mL), dried over sodium sulfate, and concentrated in vacuum to give a residue, which was purified by reverse phase chromatography (MeCN in $H_2O$, 0-70%) to give Intermediate 68 (52 mg, 70.2% yield). MS: m/z=337.1 (M+1).

Example 69: Synthesis of Intermediate 69

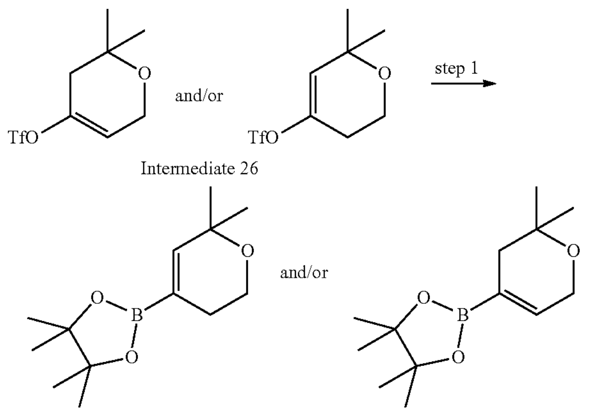

and/or

Intermediate 26 and/or

Intermediate 69

A suspension of Intermediate 26 (25 g, 90.07 mmol) 4,4,5,5-tetranethyl-2-(4,4,5,5-tetramethyl-1,3,2-dioxaborolan-2-yl-1,3,2-dioxaborolane (26.84 g, 105.68 mmol), potassium acetate (14.14 g, 144.10 mmol), $Pd(dppf)Cl_2$ (2.11 g, 2.88 mmol) in dioxane (300 mL) was stirred at 100° C. for 6 hrs. The reaction mixture was filtered and concentrated to give Intermediate 69 (45 g, crude), which was used for the next step without further purification.

Example 70: Synthesis of Intermediate 70

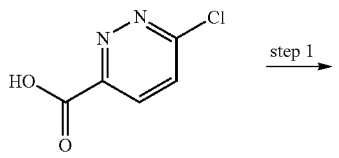

70-A

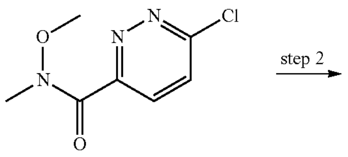

70-B

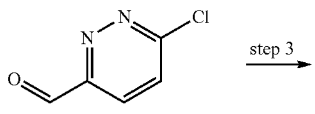

70-C

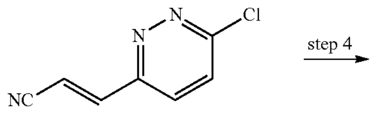

70-D

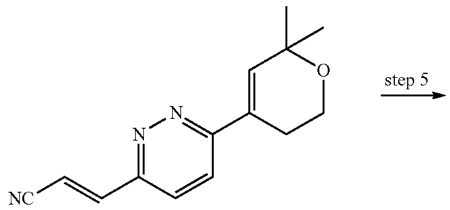

70-E

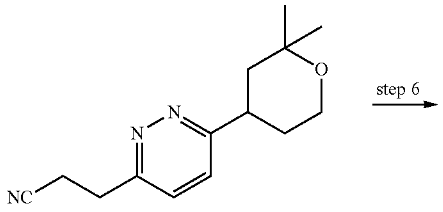

70-F

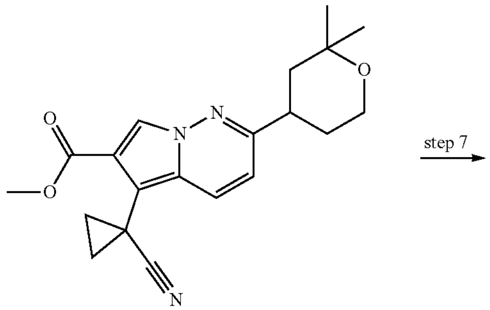

70-G

-continued

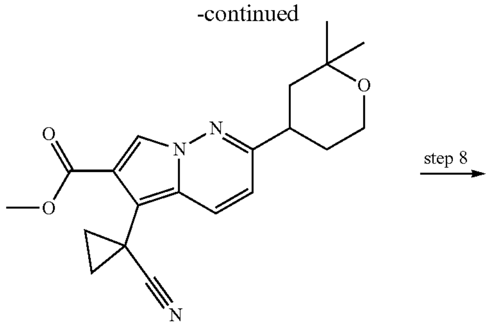

70-H

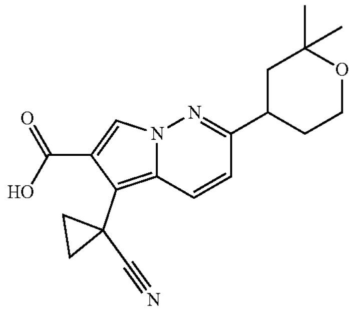

Intermediate 70

Step 1: 70-B

To a solution of 70-A (10 g, 63.07 mmol), N-methoxymethanamine (6.77 g, 69.38 mmol, HCl salt) and DIPEA (20.38 g, 157.69 mmol, 27.47 mL) in DCM (200 mL) was added HATU (31.18 g, 82.0 mmol) at 0° C., and the resulting solution was stirred overnight. The reaction mixture was washed with water (100 mL), and brine (100 mL). The organic layer was dried over $Na_2SO_4$, filtered and evaporated to afford a residue, which was purified by flash chromatography (EA in PE, 0-35%) to obtain 70-B (11 g, 54.56 mmol, 86.5% yield). MS: m/z=202.1 (M+1).

Step 2: 70-C

To a mixture of 70-B (11 g, 54.56 mmol) in THF (200 mL) was added Diisobutylaluminum hydride (1 M, 81.84 mL) at 0° C. and stirred for 1 hr. The reaction mixture was quenched with $NH_4Cl$ solution (50 mL). The mixture was filtered, the filtrate was extracted with EA (50 mL×3). The combined organic layers were washed with brine (50 mL×3), dried over $Na_2SO_4$, filtered and concentrated to deliver 70-C (3.9 g, 27.36 mmol, 50.1% yield). MS: m/z=143.1 (M+1).

Step 3: 70-D

To a solution of 70-C (3.9 g, 27.36 mmol) in DCM (150 mL) was added 2-(triphenyl-phosphanylidene)acetonitrile (8.24 g, 27.36 mmol) and stirred at 25° C. for 3 hrs. The reaction mixture was concentrated and purified by flash chromatography on silica gel (EA in PE, 0-30%) to give 70-D (4.1 g, 24.76 mmol, 90.7% yield). MS: m/z=166.1 (M+1).

Step 4: 70-E

A suspension of 70-D (4.1 g, 24.76 mmol), Intermediate 69 (7.01 g, 29.71 mmol), $K_2CO_3$ (6.84 g, 49.52 mmol), Pd(dppf)Cl2 (905.91 mg, 1.24 mmol) in $H_2O$ (30 mL) and dioxane (150 mL) was stirred at 100° C. under $N_2$ atmosphere for 3 hrs. The reaction mixture was concentrated and the residue was purified by flash chromatography on silica gel (EA/PE=1/10-3/1) to give 70-E (2.3 g, 9.53 mmol, 38.5% yield). MS: m/z=242.2 (M+1).

Step 5: 70-F

To a solution of 70-E (2.3 g, 9.53 mmol) in EA (200 mL) was added Pd/C (231.54 mg) tinder hydrogen atmosphere, and the reaction mixture was stirred at 25° C. for 48 hrs. The reaction mixture was filtered, and the filtrate was concentrated to give a residue, which was purified by flash chromatography on silica gel (EA/PE=1/10-1/1) to give 70-F (0.8 g, 3.26 mmol, 34.2% yield). MS: m/z=246.2 (M+1).

Step 6: 70-G

A 30 mL microwave reaction tube was charged with methyl 3-bromo-2-oxo-propanoate (790.99 mg, 4.24 mmol), 70-F (0.8 g, 3.26 mmol) and sodium bicarbonate (547.92 mg, 6.52 mmol) in MeCN (10 ml). After $O_2$ was purged by bubbling $N_2$ into the reaction solution, the tube was sealed and heated at 120° C. for 1 hr in a Biotage microwave reactor. The reaction was cooled to room temperature, and the reaction mixture was filtered and concentrated under reduced pressure to give a residue, which was purified by flash chromatography on silica gel (EA/PE=1/10-1/3) to give 70-G (280 mg, 855.28 μmol, 26.2% yield). MS: m/z=328.2 (M+1).

Step 7: 70-H

To a solution of 70-G (280 mg, 855.28 μmol), 1,3,2-dioxathiolane 2,2-dioxide (318.46 mg, 2.57 mmol) and DMPU (219.24 mg, 1.71 mmol) in THF (5 mL) was added LiHMDS (1 M, 5.13 mL), and stirred for 0.2 hr at 0° C. The reaction was quenched with $NH_4Cl$ solution (10 mL). The mixture was extracted with EA (20 mL×3). The combined organic layers were washed with brine (20 mL×3), dried over $Na_2SO_4$, filtered and concentrated to give a residue, which was purified by flash chromatography on silica gel (EA/PE=1/10-1/3) to give 70-H (130 mg, 367.84 μmol, 43.0% yield). MS: m/z=354.2 (M+1).

Step 8: Intermediate 70

To a mixture of 70-H (130 mg, 367.84 μmol) in water (1 mL), THE (4 mL) and MeOH (4 mL) was added NaOH (73.57 mg, 1.84 mmol) at 25° C. The mixture was stirred for 3 hrs at 50° C. The reaction mixture was cooled to room temperature and adjusted to pH~5 with aqueous HCl (1 M). The mixture was extracted with EA (20 mL×3). The combined organic layers were concentrated with a rotary evaporator to give Intermediate 70 (63 mg). MS: m/z=340.2 (M+1).

Example 71: Synthesis of Intermediate 71

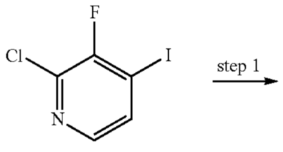

71-A

-continued

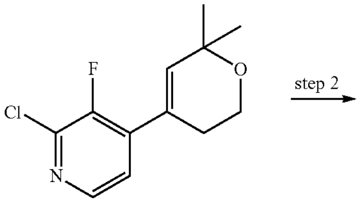

71-B

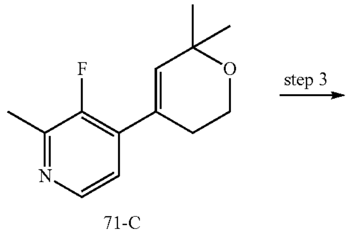

71-C

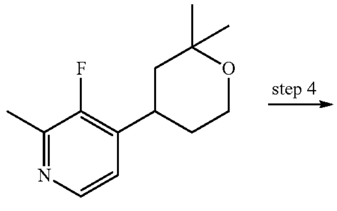

71-D

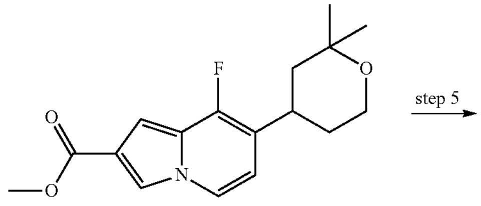

71-E

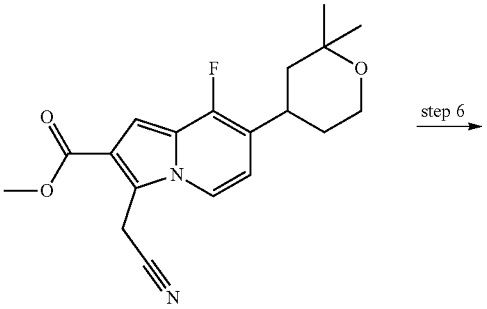

71-F

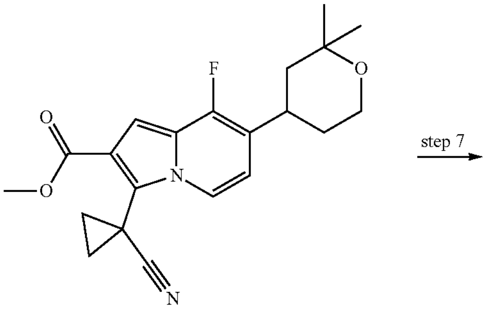

71-G

-continued

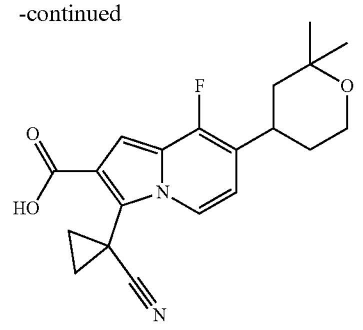

Intermediate 71

Step 1: 71-B

A suspension of Intermediate 69 (26.64 g, 55.94 mmol), 71-A (12 g, 46.61 mmol), $K_2CO_3$ (12.88 g, 93.23 mmol), Pd(dppf)$Cl_2$ (1.02 g, 1.40 mmol) in $H_2O$ (40 mL) and dioxane (160 mL) was stirred at 70° C. for 2 hrs. The reaction mixture was concentrated to give a residue, which was purified by flash chromatography on silica gel (EA in PE, 0-10%) to give 71-B (8.3 g, 34.34 mmol, 73.7% yield). MS: m/z=242.1 (M+1).

Step 2: 71-C

A suspension of 71-B (5.8 g, 24.0 mmol), methylboronic acid (4.31 g, 71.99 mmol), $K_2CO_3$ (9.95 g, 71.99 mmol), $Pd(PPh_3)_4$ (1.39 g, 1.20 mmol) in dioxane (60 mL) was stirred at 105° C. for 2 hrs. The reaction mixture was concentrated, and the residue was purified by flash chromatography on silica gel (EA in PE, 0-15%) to give 71-C (5 g, 22.60 mmol, 94.2% yield). MS: m/z=222.2 (M+1).

Step 3: 71-D

To a solution of 71-C (5 g, 22.60 mmol) in MeOH (60 mL) was added Pd/C (548.88 mg) under hydrogen atmosphere. The reaction mixture was stirred at 25° C. for 16 hrs. The reaction mixture was filtered, and the filtrate was concentrated to give 71-D (4.5 g, 20.15 mmol, 89.2% yield). MS: m/z=224.2 (M+1).

Step 4: 71-E

A 30 mL microwave reaction tube was charged with methyl 3-bromo-2-oxo-propanoate (7.52 g, 40.31 mmol, 4.42 mL), 71-D (4.5 g, 20.15 mmol) and sodium bicarbonate (6.77 g, 80.61 mmol) in MeCN (20 mL). After $O_2$ was purged by bubbling $N_2$ into the reaction solution, the tube was sealed and heated at 100° C. for 0.75 hr in a Biotage microwave reactor. The reaction was cooled to room temperature, and the reaction mixture was filtered and concentrated to give a residue, which was purified by flash chromatography on silica gel (EA in PE, 0-10%) to give 71-F (1.5 g, 4.91 mmol, 24.4% yield), MS: m/z=306.2 (M+1).

Step 5: 71-F

To a solution of 71-E (1.5 g, 4.91 mmol) in DMSO (4 mL) and water (0.8 mL) was added 2-bromoacetonitrile (1.77 g, 14.74 mmol), NaI (736.34 mg, 4.91 mmol), $Fe_2SO_4$. $7H_2O$ (1.21 g, 4.91 mmol), then $H_2O_2$ (30%, 1.39 g) was added dropwise at 0° C. After addition, the mixture was stirred for 20 minutes. The reaction mixture was quenched with water (100 mL) and extracted with EA (50 mL×3). The combined organic layers were washed with aqueous $Na_2SO_3$ (80 mL), brine (80 mL), dried over $Na_2SO_4$, filtered and concentrated to give a residue, which was purified by combi-flash (EA in PE, 0-20%) to give 71-F (880 mg, 2.56 mmol, 52.0% yield). MS: m/z=345.2 (M+1).

Step 6: 71-G

To a solution of 71-F (880 mg, 2.56 mmol), 1,3,2-dioxathiolane 2,2-dioxide (951.47 mg, 7.67 mmol) and DMPU (655.03 mg, 5.11 mmol) in THF (5 mL) was added LiHMDS (1 M, 15.33 ml, and stirred for 0.2 hr at 0° C. The reaction was quenched with aqueous $NH_4Cl$ (10 mL). The mixture was extracted with EA (20 mL×3). The combined organic layers were washed with brine (20 ml×3), dried over $Na_2SO_4$, filtered and concentrated to give a residue, which was purified by flash chromatography on silica gel (EA/PE=1/10-1/3) to give 71-G (560 mg, 1.51 mmol, 59.2% yield). MS: m/z=371.2 (M+1).

Step 7: Intermediate 71

To a solution of 71-G (560 mg, 1.51 mmol) in DMSO (6 mL) was added Potassium fluoride (2.64 g, 45.35 mmol). The mixture was heated at 130° C. in a Biotage microwave reactor for 3 hrs. The reaction mixture was poured into water (20 mL) and extracted with EA (30 mL×3). The aqueous layer was adjusted to pH 4~5 with aqueous HCl (1 M) and extracted with EA (30 mL×3). The combined organic layers were washed with brine (50 mL), dried over $Na_2SO_4$, filtered and concentrated to give Intermediate 71 (400 mg, crude). MS: m/z=357.2 (M+1).

Example 72: Synthesis of Intermediate 72

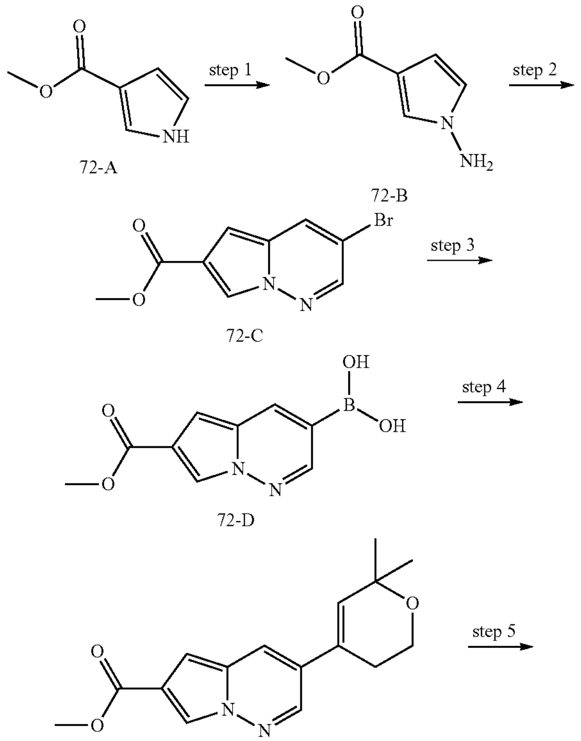

72-A

72-B

72-C

72-D

72-E

-continued

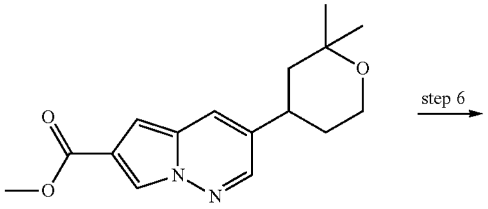

72-F

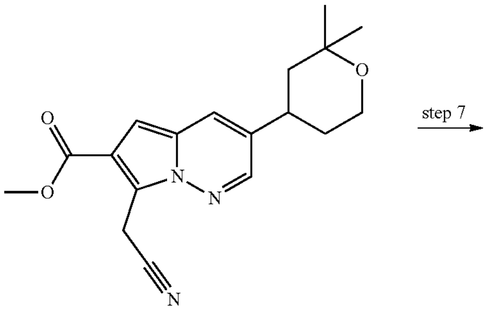

72-G

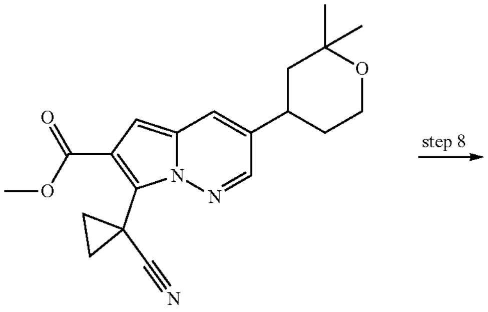

72-H

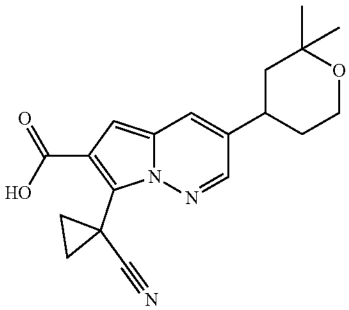

Intermediate 72

Step 1: 72-B

To a solution of 72-A (10 g, 79.92 mmol) in DMF (70 mL) was added NaH (4.16 g, 103.90 mmol, 60%), and the reaction was stirred for 0.3 hr at 25° C., before 0-(2,4-dinitrophenyl)hydroxylamine (23.87 g, 119.88 mmol) was added. The reaction was stirred at 25° C. for another 12 hrs. The reaction was quenched with saturated aqueous $Na_2S_2O_3$, diluted with water, and extracted with EA. The organic layer was dried, filtered, and concentrated to give a residue, which was purified by silica gel column chromatography (EA in PE, 0-100%) to afford 72-B (7 g, 49.95 mmol, 62.5% yield).

Step 2: 72-C

A mixture of 72-B (5 g, 35.68 mmol), 2-bromopropanedial (10.77 g, 71.36 mmol) in $H_3PO_4$ (10 mL) and dioxane (30 mL) was stirred for 1 hr at 25° C. Water (50 mL) and EA (100 mL) were added, and the organic phase was separated and concentrated to give a residue, which was purified by silica gel chromatography (PE/EA=100/1-10/1) to give 72-C (2.5 g, 9.80 mmol, 27.5% yield). MS: m/z=255.3 (M+1).

Step 3: 72-D

To a mixture of 72-C (1.5 g, 5.88 mmol), 4,4,5,5-tetramethyl-2-(4,4,5,5-tetramethyl-1,3,2-dioxaborolan-2-yl)-1,3,2-dioxaborolane (1.79 g, 7.06 mmol) in dioxane (15 mL) was added KOAc (1.73 g, 17.64 mmol) and Pd(dppf)$Cl_2$ (4.30 g, 5.88 mmol) at 30° C. The reaction was stirred for 2 hrs at 100° C. Then, the solution was concentrated to give a residue, which was purified by silica gel chromatography (PE/EA=10/1-1/1) to give 72-D (1.31 g, crude).

Step 4: 72-E

To a mixture of 72-D (1.31 g, crude), Intermediate 26 (2.32 g, 8.93 mmol) in water (5 mL) and dioxane (50 mL) was added $K_2CO_3$ (2.47 g, 17.86 mmol) and Pd(dppf)$Cl_2$ (435.72 mg, 595.48 μmol) at 30° C. The reaction was stirred for 2 hrs at 100° C. The mixture was filtered, and the filtrate was evaporated to give a residue, which was purified by silica gel chromatography (PE/EA=10/1-1/1) to give 72-E (1.5 g, 5.24 mmol, 88.0% yield). MS: m/z=287.2 (M+1).

Step 5: 72-F

To a mixture of 72-E (1.3 g, 4.54 mmol) in Methanol (100 mL) was added Pd/C (100 mg) at 25° C. The reaction was stirred for 12 hrs at 25° C. under $H_2$ atmosphere. Then, the mixture was filtered and concentrated to give 72-F (1.2 g, 4.16 mmol, 91.7% yield). MS: m/z=289.2 (M+1).

Step 6: 72-G

To a solution of 72-F (1 g, 3.47 mmol) in DMSO (10 mL) and Water (2 mL) was added 2-bromoacetonitrile (2.08 g, 17.34 mmol), $H_2O_2$ (30%, 1.18 g), $FeSO_4$. $7H_2O$ (964.19 mg, 3.47 mmol). Then, NaI (519.85 mg, 3.47 mmol) was added. After addition, the mixture was stirred for 10 minutes. The reaction mixture was quenched with water (100 mL) and extracted with EA (50 mL×3). The combined organic layers were washed with aqueous $Na_2SO_3$ (80 mL), brine (80 mL), dried over $Na_2SO_4$, filtered and concentrated to give a residue, which was purified by combi flash (EA in PE, 0-20%) to give 72-G (201 mg, 17.7% yield). MS: m/z=328.1 (M+1).

Step 7: 72-H

To a mixture of 72-G (200 mg, 610.92 μmol), 1,3,2-dioxathiolane 2,2-dioxide (90.99 mg, 733.10 μmol) and DMPU (156.60 mg, 1.22 mmol) in THF (10 mL) was added LiHDMS (1 M, 3.05 mL) at 0° C. The reaction solution was stirred for 15 minutes at 0° C. Aqueous $NH_4Cl$ (50 mL) and EA (100 mL) were added, the organic phase was dried over $Na_2SO_4$, filtered and concentrated to give a residue, which was purified by silica gel chromatography (PE/EA=4/1-1/1) to give 72-H (128 mg, 59.3% yield).

Step 8: Intermediate 72

A mixture of 72-H (128 mg, 362.18 μmol) and LiOH (86.74 mg, 3.62 mmol) in THF (5 mL), Methanol (5 mL) and Water (1 mL) was stirred for 4 hrs at 40° C. Then, the solution was concentrated with a rotary evaporator. The crude product was purified by prep-HPLC (column: XBridge® Prep C18 5 μm 19×150 mm; A: 0.2% $HCO_2H$ water, B: acetonitrile; gradient: 5-95% B; GT: 16 min; flow rate: 15 mL/min) to give Intermediate 72 (122 mg).

Example 73: Synthesis of Intermediate 73

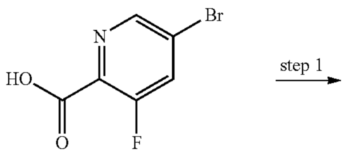

73-A

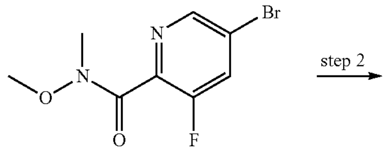

73-B

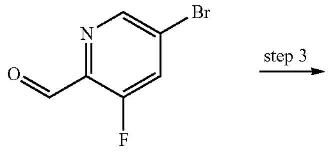

73-C

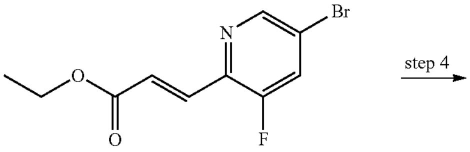

73-D

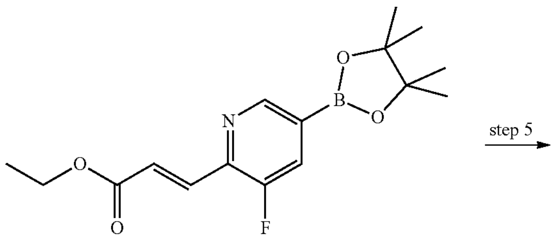

73-E

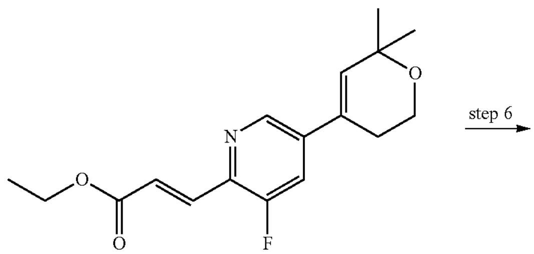

73-F

-continued

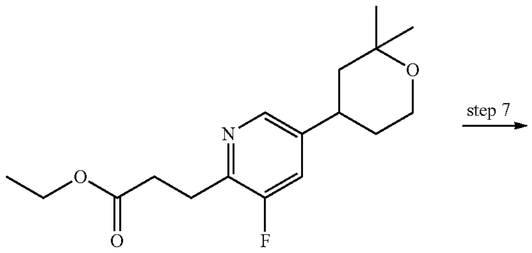

73-G

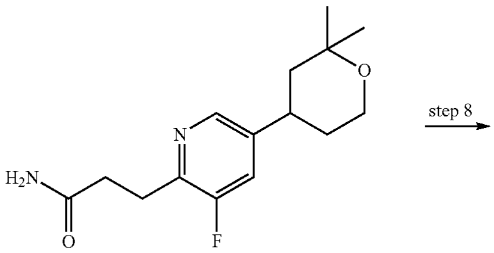

73-H

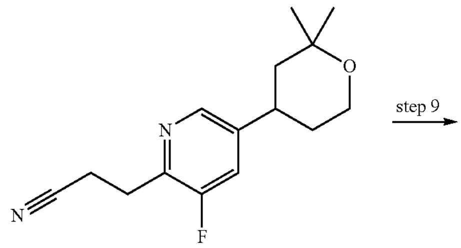

73-I

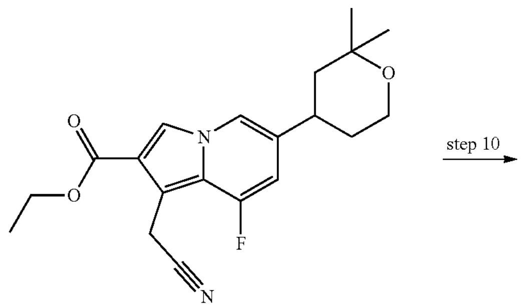

73-J

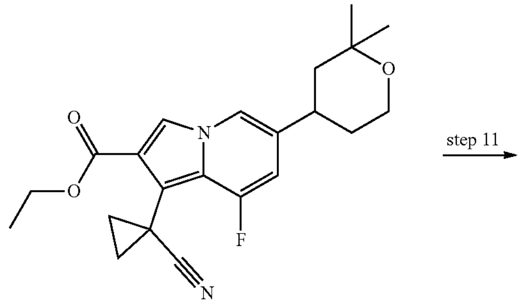

73-K

-continued

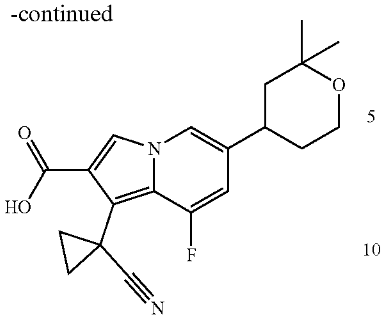

Intermediate 73

Step 1: 73-B

To a mixture of 73-A (13 g, 59.10 mmol), N-methoxymethanamine (11.52 g, 118.20 mmol, HCl salt) and HATU (67.42 g, 125.27 mmol) in DCM (160 mL) was added TEA (17.94 g, 177.27 mmol, 16.90 mL), and stirred for 2 hrs. The resulting mixture was diluted with water (300 mL) and extracted with EA (300 mL). The separated organic layer was washed with water (300 mL×3) and brine, dried over $Na_2SO_4$, filtered and concentrated to give 73-B (13 g, 83.6% yield).

Step 2: 73-C

To a mixture of 73-B (13 g, 49.42 mmol) in THF (150 mL) was added Diisobutylaluminum hydride (1 M, 98.84 mL) at 0° C. and stirred for 40 minutes. The reaction mixture was quenched with $NH_4Cl$ solution (50 mL). The mixture was filtered, the filtrate was extracted with EA (30 mL×3). The combined organic layers were washed with brine (30 mL×3), dried over $Na_2SO_4$, filtered and concentrated to deliver 73-C (11 g, crude). MS: m/z=203.9 (M+1).

Step 3: 73-D

To a solution of 71-C (11 g, crude) in DCM (150 mL) was added ethyl 2-(triphenyl-phosphanylidene)acetate (18.79 g, 53.92 mmol) and stirred at 25° C. for 3 hrs. The reaction mixture was concentrated and purified by flash chromatography on silica gel (PE/EA=20/1-5/1) to give 73-D (6.8 g, 46.0% yield). MS: m/z=274.0 (M+1).

Step 4: 73-E

A suspension of 73-D (6.8 g, 24.81 mmol), 4,4,5,5-tetramethyl-2-(4,4,5,5-tetramethyl-1,3,2-dioxaborolan-2-yl)-1,3,2-dioxaborolane (7.56 g, 29.77 mmol), potassium acetate (3.65 g, 37.21 mmol), Pd(dppf)$Cl_2$ (907.67 g, 1.24 mmol) in dioxane (100 mL) was stirred at 100° C. for 6 hrs. The reaction mixture was filtered and concentrated. The residue was purified by flash chromatography on silica gel (EA/PE=1/20-2/1) to give 73-E (12 g, crude).

Step 5: 73-F

A suspension of 73-E (12 g, crude), Intermediate 26 (17.5 g, 33.63 mmol), $K_2CO_3$ (6.2 g, 44.84 mmol), Pd(dppf)$Cl_2$ (820.22 mg, 1.12 mmol) in dioxane (200 mL) and water (40 mL) was stirred at 100° C. for 6 hrs. The reaction mixture was concentrated, and the residue was purified by flash chromatography on silica gel (EA/PE=1/10-5/1) to give 73-F (6.5 g, 21.29 mmol, 94.9% yield). MS: m/z=306.2 (M+1).

Step 6: 73-G

To a solution of 73-F (6.5 g, 21.29 mmol) in Methanol (100 mL) was added Pd/C (517.07 mg) under hydrogen atmosphere. The reaction mixture was stirred at 25° C. for 24 hrs. The reaction mixture was filtered, and the filtrate was concentrated to give 73-G (6.5 g, 21.01 mmol, 98.7% yield). MS: m/z=310.2 (M+1).

Step 7: 73-H

To a mixture of 73-G (6.5 g, 21.01 mmol) in Methanol (100 mL) was added aqueous ammonium hydroxide (28%, 25.78 mL) at 25° C. The reaction solution was stirred for 24 hrs at 25° C. Then, methanol was removed with a rotary evaporator. The mixture was extracted with EA (30 mL×3). The combined organic layers were washed with $NaHCO_3$ (30 mL×3), dried over $Na_2SO_4$, filtered and concentrated to give 73-H (3 g, 10.70 mmol, 50.9% yield). MS: m/z=281.2 (M+1).

Step 8: 73-I

To a solution of 73-H (3 g, 10.70 mmol) in dry dioxane (30 mL) was added TFAA (4.50 g, 21.40 mmol, 3.02 mL) and Pyridine (2.12 g, 26.75 mmol, 2.16 mL) at 25° C. The reaction mixture was stirred at 25° C. for 2 hrs. The solution was concentrated to give a residue, which was purified by flash chromatography on silica gel (EA in PE, 0-20%) to give 73-I (2 g, 7.62 mmol, 71.3% yield). MS: m/z=263.2 (M+1).

Step 9: 73-J

To a mixture of 73-I (1.5 g, 5.72 mmol), ethyl 3-bromo-2-oxo-propanoate (1.67 g, 8.58 mmol, 1.07 mL) in MeCN (10 mL) was added $NaHCO_3$ (2.40 g, 28.59 mmol) at 25° C. The reaction solution was stirred for 8 hrs at 100° C. The solution was concentrated to give a residue, which was purified by silica gel chromatography (PE/EA=4/1) to give 73-J (500 mg, 1.40 mmol, 24.4% yield).

Step 10: 73-K

To a solution of 73-J (130 mg, 362.72 μmol) and 1,3,2-dioxathiolane 2,2-dioxide (54.02 mg, 435.26 μmol) in THF (5 mL) was added LiHMDS (1 M, 1.81 mL) dropwise at 0° C. The reaction mixture was stirred for 2 hrs at 0° C., before quenching with aqueous $NH_4Cl$ (10 mL). Then, water (20 mL) was added, and the mixture was extracted with EA (20 mL×3), the combined organic phases were washed with saturated aqueous $NaHCO_3$ (10 mL×3), followed by brine (10 mL), dried over anhydrous $Na_2SO_4$, and filtered. The filtrate was concentrated to give a residue, which was purified by flash chromatography (20% EA in PE) to give 73-K (56 mg, 145.67 μmol, 40.2% yield).

Step 11: Intermediate 73

To a mixture of 73-K (55 mg, 143.06 μmol) in THF (3 mL), Water (1 mL) and Methanol (3 mL) was added NaOH (22.89 mg, 572.26 μmol) and heated at 50° C. for 2 hrs. After cooling to room temperature, the mixture was concentrated and acidified with aqueous HCl (1 M) to pH=3. The white solid was collected by filtration and washed with water to give Intermediate 73 (49.5 mg, 138.89 μmol, 97.1% yield).

Example 74: Synthesis of Intermediate 74

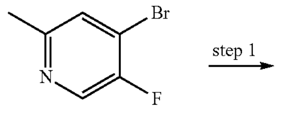

74-A

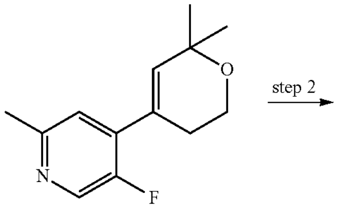

74-B

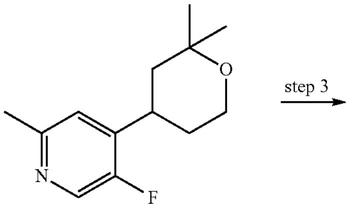

74-C

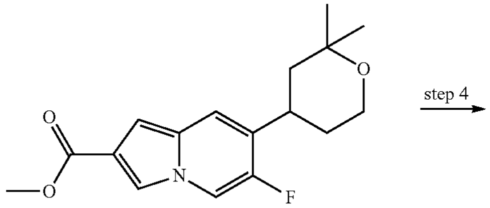

74-D

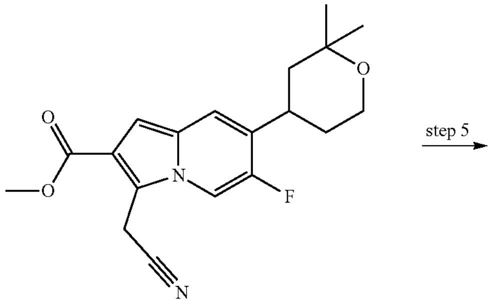

74-E

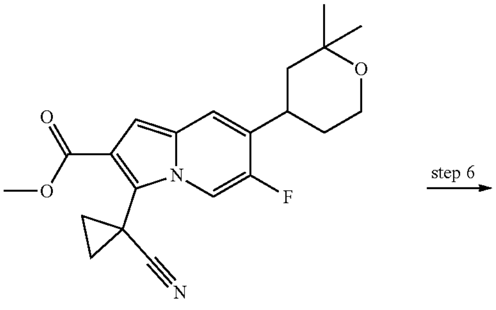

74-F

-continued

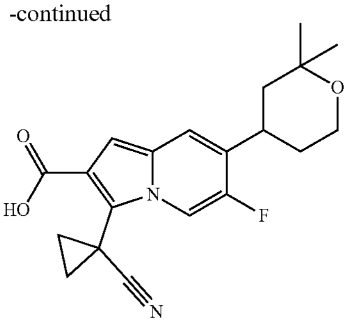

Intermediate 74

Step 1: 74-B

A solution of 74-A (5 g, 26.31 mmol), Intermediate 69 (8.15 g, 34.21 mmol), $K_2CO_3$ (7.27 g, 52.63 mmol), Pd(dppf)$Cl_2$ (962.70 mg, 1.32 mmol) in $H_2O$ (10 mL) and dioxane (50 mL) was stirred at 100° C. for 2 hrs. The reaction mixture was concentrated, and the residue was purified by flash chromatography on silica gel (EA/PE=1/10-1/4) to give 74-B (5.1 g, 23.05 mmol, 87.6% yield). MS: m/z=222.2 (M+1).

Step 2: 74-C

To a solution of 74-B (5.1 g, 23.05 mmol) in EtOH (100 mL) was added Pd/C (559.85 mg) under $H_2$ atmosphere. The reaction mixture was stirred at 25° C. for 48 hrs. The reaction mixture was filtered, and the filtrate was concentrated to give 74-C (5.2 g, crude). MS: m/z=224.2 (M+1).

Step 3: 74-D

A mixture of methyl 3-bromo-2-oxo-propanoate (5.01 g, 26.87 mmol, 2.95 mL), 74-C (3 g, 13.44 mmol) and sodium bicarbonate (2.82 g, 33.59 mmol) in MeCN (20 mL) was sealed and heated at 120° C. for 1 hr in a Biotage microwave reactor. The reaction was cooled to room temperature, filtered and concentrated to give a residue, which was purified by flash chromatography on silica gel (EA in PE, 0-10%) to give 74-D (520 mg, 1.70 mmol, 12.7% yield). MS: m/z=306.2 (M+1).

Step 4: 74-E

To a solution of 74-D (425 mg, 1.39 mmol) in DMSO (4 mL) and Water (0.8 mL) was added 2-bromoacetonitrile (417.38 mg, 3.48 mmol), NaI (104.31 mg, 695.94 mol), and $Fe_2SO_4$. $7H_2O$ (171.76 mg, 695.94 μmol). Then, $H_2O_2$ (30%, 789.07 mg) was added at 0° C. dropwise. After addition, the mixture was stirred for 15 minutes. The reaction was quenched with water (50 mL) and extracted with EA (30 mLx3). The combined organic layers were washed with aqueous $Na_2SO_3$ (80 mL), brine (80 mL), dried over $Na_2SO_4$, filtered and concentrated to give a residue, which was purified by combi flash (EA in PE, 0-15%) to give 74-E (100 mg, 290.38 μmol, 20.9% yield). $^1$H NMR (400 MHz, DMSO-$d_6$) δ 8.54 (d, J=7.0 Hz, 1H), 7.44 (d, J=7.7 Hz, 1H), 6.81 (s, 1H), 4.56 (s, 2H), 3.77 (s, 3H), 3.66 (dd, J=8.7, 1.9 Hz, 2H), 3.08 (t, J=12.3 Hz, 1H), 1.66 (dd, J=13.2, 3.4 Hz, 2H), 1.58-1.39 (m, 2H), 1.20 (s, 3H), 1.12 (s, 3H). MS: m/z=345.2 (M+1).

Step 5: 74-F

To a solution of 74-E (100 mg, 290.38 μmol), 1,3,2-dioxathiolane 2,2-dioxide (108.12 mg, 871.13 μmol) and DMPU (74.44 mg, 580.76 μmol) in THF (3 mL) was added LiHMDS (1 M, 1.74 mL) at 0° C. The reaction was stirred for 0.2 hr before quenching with aqueous $NH_4Cl$ (50 mL). The mixture was extracted with EA (30 mL×3). The combined organic layers were washed with brine (50 mL), dried over $Na_2SO_4$, filtered and concentrated to give a residue, which was purified by silica gel (EA in PE, 0-15%) to give 74-F (43 mg, 116.09 mol, 40.0% yield). $^1H$ NMR (400 MHz, DMSO-$d_6$) δ 8.57 (d, J=6.7 Hz, 1H), 7.54 (d, J=7.6 Hz, 1H), 6.88 (s, 1H), 3.85 (s, 3H), 3.74 (d, J=8.6 Hz, 2H), 3.25-3.18 (m, 1H); 1.99 (q, J=4.6 Hz, 2H), 1.73 (d, J=12.4 Hz, 2H), 1.62-1.42 (m, 4H), 1.32-1.17 (m, 6H). MS: m/z=371.2 (M+1).

Step 6: Intermediate 74

To a solution of 74-F (43 mg, 116.09 μmol) in DMSO (2 mL) and $H_2O$ (0.5 mL) was added Potassium fluoride (202.34 mg, 3.48 mmol), the mixture was stirred for 1 hr at 130° C. in a Biotage microwave reactor. The reaction was quenched with water (50 mL) and extracted with EA (30 mL). The aqueous phase was acidified with aqueous HCl (1 M) to pH=3-4 and extracted with EA (30 mL×2). The organic layers were washed with brine (50 mL), dried over $Na_2SO_4$, filtered and concentrated to give Intermediate 74 (36 mg, 101 μmol, 87% yield). MS: m/z=357.2 (M+1).

Example 75: Synthesis of Intermediate 75

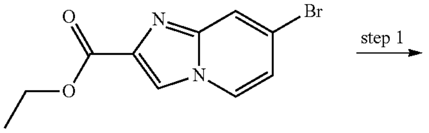

75-A

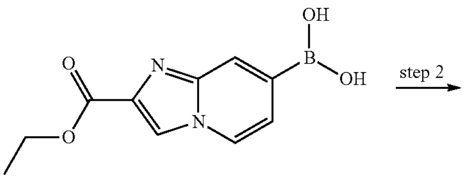

75-B

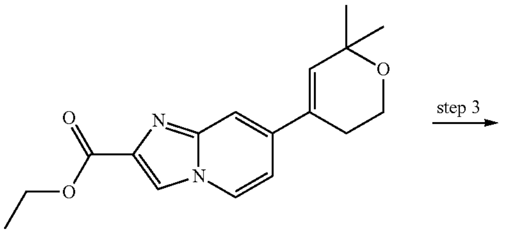

75-C

-continued

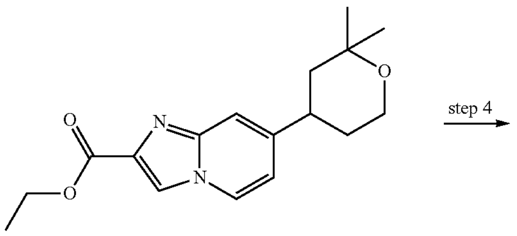

75-D

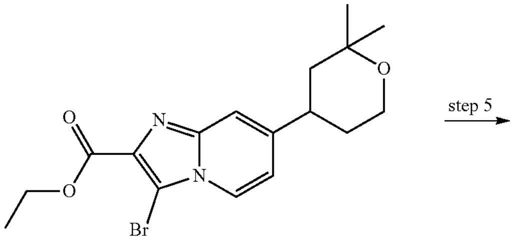

75-E

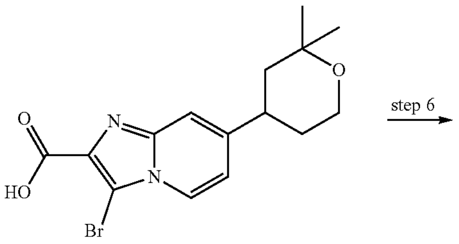

75-F

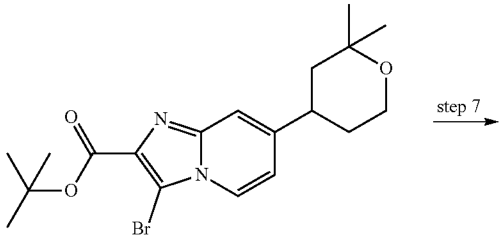

75-G

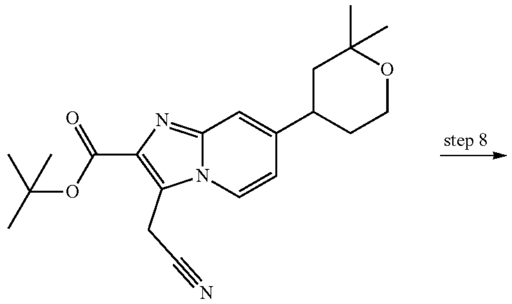

75-H

-continued

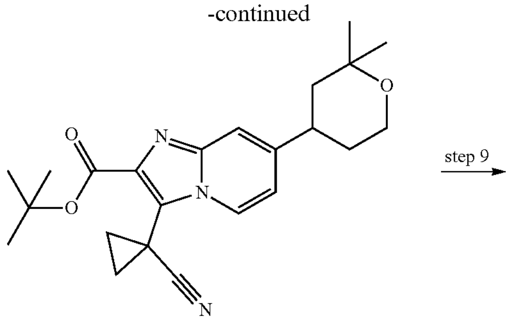

75-I

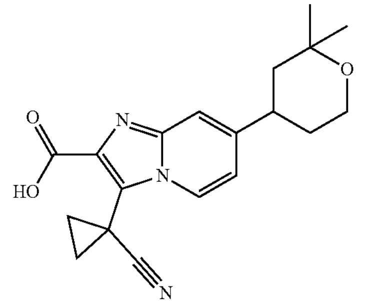

Intermediate 75

Step 1: 75-B

To a mixture of 75-A (10.8 g, 40.13 mmol), 4,4,5,5-tetramethyl-2-(4,4,5,5-tetramethyl-1,3,2-dioxaborolan-2-yl)-1,3,2-dioxaborolane (11.21 g, 44.15 mmol) and KOAc (5.91 g, 60.20 mmol) in dioxane (100 mL) was added 1,1'-Bis(diphenylphosphino)ferrocene-palladium(II)dichloride dichloromethane complex (655.51 mg, 802.69 μmol) at 25° C. The reaction solution was stirred at 100° C. for 6 hrs and concentrated to give a residue. The residue was diluted with $H_2O$ (200 mL) and extracted with EA (200 mL×2). The combined organic layers were washed with brine (150 mL), dried over $Na_2SO_4$ and concentrated to give 75-B (10 g, crude). MS: m/z=235.2 (M+1).

Step 2: 75-C

To a mixture of 75-B (10 g, crude), Intermediate 26 (16.68 g, 64.10 mmol) and $K_2CO_3$ (11.81 g, 85.46 mmol) in dioxane (160 mL) and Water (40 mL) was added 1,1'-Bis (diphenylphosphino)ferrocene-palladium(II)dichloride dichloromethane complex (1.05 g, 1.28 mmol) at 25° C. The reaction solution was stirred at 100° C. for 2 hrs and concentrated to give a residue. The residue was diluted with $H_2O$ (150 mL) and extracted with EA (150 mL×2). The combined organic layers were washed with brine (150 mL), dried over $Na_2SO_4$ and concentrated to give a residue, which was purified by silica gel chromatography (PE/EA=1/1) to give 75-C (9.2 g, 30.63 mmol, 71.7% yield). MS: m/z=301.2 (M+1).

Step 3: 75-D

To a mixture of 75-C (9.2 g, 30.63 mmol) in Methanol (180 mL) was added Pd/C (920 mg) at 25° C. The reaction mixture was stirred for 3 hrs at 25° C. under $H_2$ atmosphere. Then, the mixture was filtered and concentrated to give 75-D (9 g, crude). MS: m/z=303.2 (M+1).

Step 4: 75-E

To a solution of 75-D (9 g) in MeCN (100 mL) was added NBS (6.89 g, 38.69 mmol, 3.28 mL) at 25° C. The reaction mixture was stirred at 25° C. for 0.5 hr and concentrated to give a crude. The crude mixture was diluted with $H_2O$ (80 mL) and extracted with EA (150 mL×2). The combined organic layers were washed with brine (80 mL), dried over $Na_2SO_4$ and concentrated to give a residue, which was purified by silica gel chromatography (PE/EA=1/1) to give 75-E (9 g, 23.61 mmol, 79.3% yield). MS: m/z=381.1 (M+1).

Step 5: 75-F

To a mixture of 75-E (9 g, 23.61 mmol) in Water (8 mL), THE (32 mL) and Methanol (32 mL) was added NaOH (2.83 g, 70.82 mmol) at 25° C. The reaction solution was stirred at 25° C. for 1 hr. Then, the solution was treated with aqueous citric acid (1.0 M) until pH=5 and concentrated with a rotary evaporator to give 75-F (9 g, crude). MS: m/z=353.1 (M+1).

Step 6: 75-G

To a mixture of 75-F (4 g) in THF (80 mL) was added Oxalyl chloride (2.87 g, 22.65 mmol, 1.97 mL) at 0° C. The reaction mixture was stirred at 0° C. for 0.5 hr before sodium tert-butoxide (10.88 g, 113.25 mmol) was added. The reaction was stirred for another 1.5 hrs at 25° C. The reaction was quenched with aqueous $NH_4Cl$ and extracted with EA (80 mL×2). The combined organic layers were washed with brine (80 mL), dried over $Na_2SO_4$ and concentrated to give a residue, which was purified by silica gel chromatography (PE/EA=1/1) to afford 75-G (2.6 g, 6.35 mmol, 56.1% yield). MS: m/z=409.1 (M+1).

Step 7: 75-H

To a mixture of 75-G (2.6 g, 6.35 mmol), 4-(4,4,5,5-tetramethyl-1,3,2-dioxaborolan-2-yl)isoxazole (2.48 g, 12.7 mmol) and Pd(dppf)$Cl_2$ (259.16 mg, 317.6 μmol) in Water (4 mL) and DMSO (16 mL) was added KF (3.69 g, 63.52 mmol) at 25° C. The reaction was stirred at 90° C. for 3 hrs in a Biotage microwave reactor. The reaction was quenched with $H_2O$ (50 mL) and extracted with EA (50 mL). aThe mixture was concentrated, diluted with $H_2O$ (80 mL), and extracted with EA (80 mL×2). The combined organic layers were washed with brine (80 mL), dried over $Na_2SO_4$ and concentrated to give a residue, which was purified by silica gel chromatography (PE/EA=1/2) to give 75-H (1 g, 2.71 mmol, 42.6% yield). MS: m/z=370.3 (M+1).

Step 8: 75-I

To a mixture of 75-H (450 mg, 1.22 mmol), 1,3,2-dioxathiolane 2,2-dioxide (151.17 mg, 1.22 mmol) and DMPU (312.22 mg, 2.44 mmol) in THF (15 mL) was added LiHMDS (1 M, 6.09 mL) at 0° C. The reaction solution was stirred for 0.2 hr at 0° C. before quenching with $H_2O$ (40 mL). The mixture was extracted with EA (40 mL×2), and the combined organic layers were washed with brine (50 mL), dried over $Na_2SO_4$ and concentrated to give 75-I (500 mg, crude).

Step 9: Intermediate 75

To a solution of 75-I (500 mg, crude) in MeCN (4 mL) was added trifluoroacetic acid (4 mL) at 25° C. The mixture was stirred for 1.5 hrs at 70° C. The mixture was concentrated and purified by prep-HPLC (column: XBridge® Prep C18 5 μm 19×150 mm; A: 0.2% $HCO_2H$ water, B: acetonitrile; gradient: 5-95% B; GT: 16 min; flow rate: 15 mL/min) to give Intermediate 75 (165 mg, 486.17 μmol, 38.5% yield). MS: m/z=340.2 (M+1).

Example 76: Synthesis of Intermediate 76

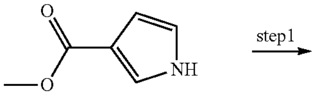

76-A

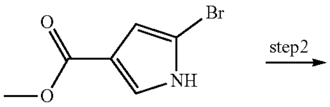

76-B

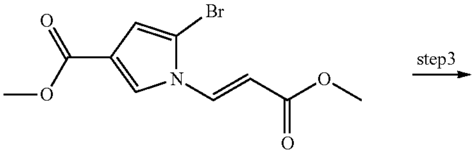

76-C

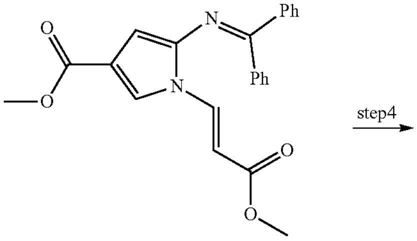

76-D

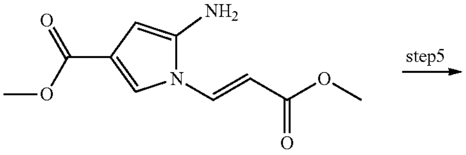

76-E

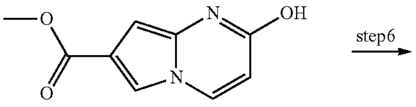

76-F

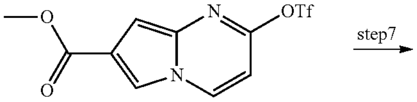

76-G

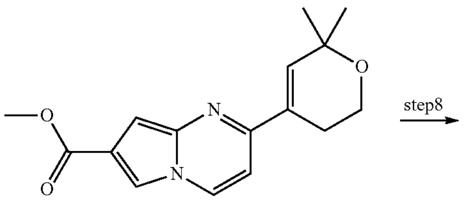

76-H

-continued

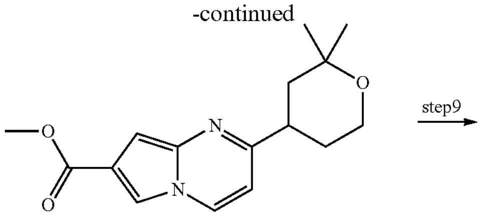

76-I

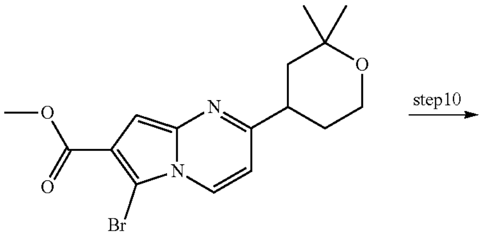

76-J

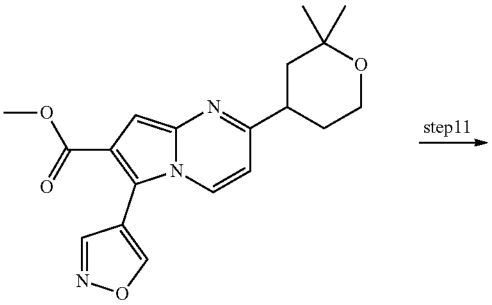

76-K

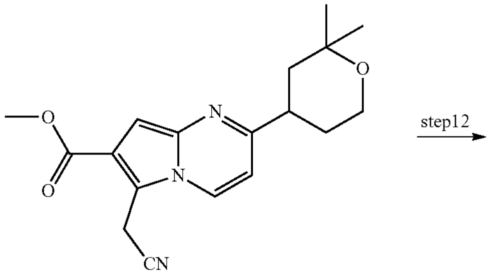

76-L

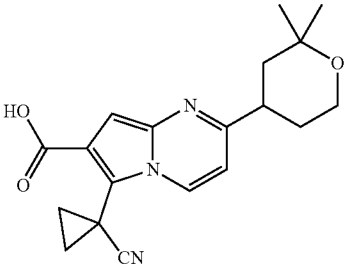

Intermediate 76

Step 1: 76-B

To a mixture of 76-A (25 g, 199.80 mmol) in THF (125 mL) was added 1-bromopyrrolidine-2,5-dione (37.3 g, 209.79 mmol) in THF (125 mL) dropwise at 0° C. The reaction was stirred at 0° C. for 0.5 hr, and was concentrated to give a residue. The residue was purified by silica gel column (PE/EA=6/1) to give 76-B (35.9 g, 88% yield). MS: m/z=203.9 (M+1).

Step 2: 76-C

To a mixture of 76-B (35.9 g, 175.96 mmol) and methyl prop-2-ynoate (19.2 g, 228.75 mmol, 20.4 mL) in THF (300 mL) was added TBAF (1 M, 88 mL) dropwise. The reaction was stirred at 20° C. for 1 hr. The reaction was concentrated to give a residue, which was purified by silica gel column (PE/EA=8/1) to give 76-C (40 g, 79% yield). MS: m/z=288.0 (M+1).

Step 3: 76-D

To a solution of 76-C (14.0 g, 48.60 mmol) in toluene (280 mL) was added diphenylmethanimine (13.2 g, 72.89 mmol), $Pd_2(dba)_3$ (2.22 g, 2.43 mmol), xantphos (2.8 g, 4.86 mmol) and $Cs_2CO_3$ (31.7 g, 97.19 mmol). The reaction mixture was stirred at 120° C. for 16 hrs. The reaction mixture was diluted with water (200 mL), extracted with EA (200 mL×3). The combined organic phases were dried over anhydrous $Na_2SO_4$ and concentrated to give a residue, which was purified by silica gel column (PE/EA=8/1) to give 76-D (10 g, 53% yield). MS: m/z=389.1 (M+1).

Step 4: 76-E

To a solution of 76-D (10 g, 25.75 mmol) in dioxane (10 mL) was added HCl (4 M in dioxane, 64.38 mL). The reaction was stirred at 25° C. for 10 hrs. The reaction mixture was concentrated to give a residue, which was diluted with MeOH (20 mL). After stirring for 20 minutes, 76-E (4.3 g, 74% yield) was filter out. MS: m/z=225.1 (M+1).

Step 5: 76-F

To a solution of 76-E (4.3 g, 19.18 mmol) in MeOH (40 mL) was added NaOMe (2.1 g, 38.36 mmol), and the mixture was stirred at 80° C. for 4 hrs. The reaction mixture was concentrated, to which water (20 mL) was added, and the mixture was neutralized with concentrated HCl. After stirring for 10 minutes, 76-F (2.2 g, 60% yield) was filter out. MS: m/z=193.1 (M+1).

Step 6: 76-G

To a mixture of 76-F (1.5 g, 7.81 mmol) and 1,1,1-trifluoro-N-phenyl-N-(trifluoromethylsulfonyl)methane-sulfonamide (5.58 g, 15.61 mmol) in DCM (60 mL) was added DBU (3.56 g, 23.42 mmol), and the mixture was stirred at 0° C. for 0.5 hr. The reaction mixture was concentrated to give a residue, which was purified by silica gel column (PE/EA=8/1) to give 76-G (1.5 g, 59% yield). MS: m/z=325.0 (M+1).

Step 7: 76-H

To a solution of 76-G (1.5 g, 4.63 mmol) in dioxane (50 mL) and water (10 mL) was added Intermediate 69 (1.65 g, 6.94 mmol), $Pd(dppf)Cl_2$ (0.15 g, 462.63 μmol), and $K_2CO_3$ (1.92 g, 13.88 mmol). The mixture was stirred at 80° C. for 3 hrs under $N_2$ atmosphere. The mixture was concentrated to give a residue, which was purified by flash chromatography (PE/EA=4/1) to give 76-H (1.0 g, 75% yield). MS: m/z=287.1 (M+1).

Step 8: 76-I

To a solution of 76-H (1.0 g, 3.49 mmol) in MeOH (25 mL) and THE (25 mL) was added Pd/C (10%, 50% wet, 0.2 g). The reaction was stirred at 25° C. for 0.5 hr under hydrogen atmosphere. The reaction mixture was filtered and concentrated to give a residue, which was purified by flash chromatography (PE/EA=4/1) to give 76-I (0.37 g, 1.28 mmol, 37% yield). MS: m/z=289.1 (M+1).

Step 9: 76-J

To a mixture of 76-I (0.3 g, 1.04 mmol) in THF (20 mL) was slowly added 1-bromopyrrolidine-2,5-dione (185.18 mg, 1.04 mmol) at 0° C. The reaction was stirred at 0° C. for 30 minutes. The reaction was concentrated to give a residue, which was purified by flash chromatography (PE/EA=5/1) to give 76-J (0.32 g, 84% yield). MS: m/z=367.1 (M+1).

Step 10: 76-K

To a solution of 76-J (0.32 g, 871.4 μmol) in dioxane (2.5 mL) and water (0.5 mL) was added 4-(4,4,5,5-tetramethyl-1,3,2-dioxaborolan-2-yl)isoxazole (340 mg, 1.74 mmol), $Pd(dppf)Cl_2$ (0.01 g, 261.4 μmol), and $K_2CO_3$ (361 mg, 2.61 mmol). The mixture was stirred at 75° C. for 4 hrs under $N_2$ atmosphere. The mixture was concentrated to give a residue, which was purified by flash chromatography (PE/EA=4/1) to give 76-K (0.24 g, 77.5% yield). MS: m/z=356.2 (M+1).

Step 11: 76-L

To a solution of 76-K (0.24 g, 675.3 μmol) in MeOH (15 mL) was added KF (588.5 mg, 10.13 mmol) in $H_2O$ (3 mL). The mixture was stirred at 90° C. for 30 minutes in a microwave reactor. The reaction was concentrated to give a residue, which was purified by flash chromatography (PE/EA=2/1) to give 76-L (0.065 g, 30.7% yield). MS: m/z=328.1 (M+1).

Step 12: Intermediate 76

To a solution of 76-L (0.065 g, 207.44 μmol) and 1,3,2-dioxathiolane 2,2-dioxide (128.73 mg, 1.04 mmol) in DMI (4 mL) was added KHMDS (1 M, 2.1 mL) dropwise at 0° C. The reaction was stirred for 3 hrs at 0° C. before water (0.5 mL) was added. The mixture was stirred at 20° C. for another 2 hrs. The mixture was concentrated and purified by reverse-phase column (0.1% FA in water/MeCN=100/0~0/100) to give Intermediate 76 (0.045 g, 64% yield). MS: m/z=340.1 (M+1).

Example 77: Synthesis of Intermediate 77

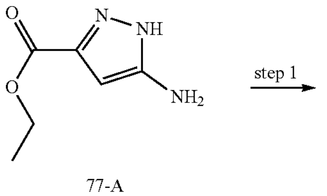

77-A

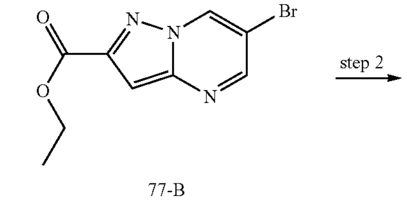

77-B

-continued

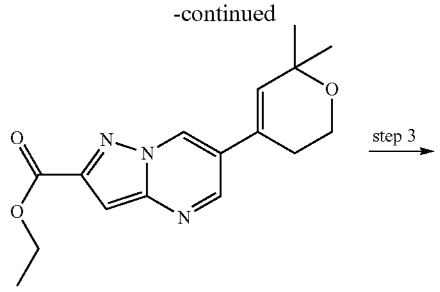

77-C

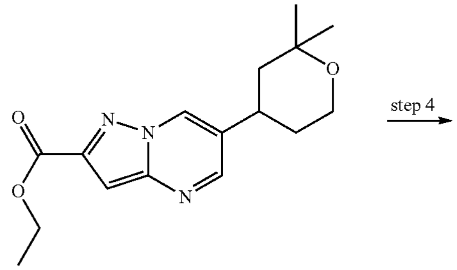

77-D

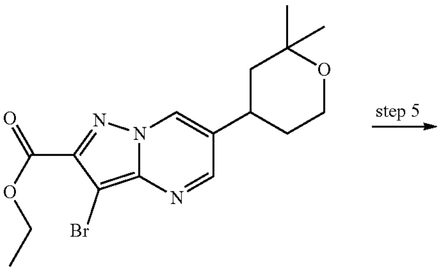

77-E

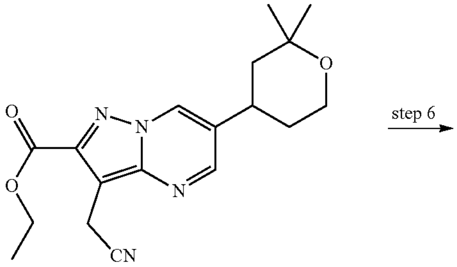

77-F

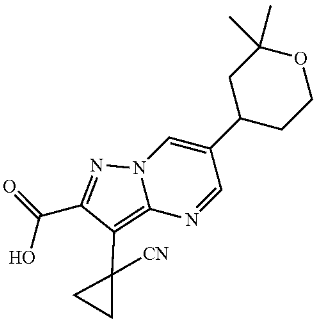

Intermediate 77

Step 1: 77-B

To a solution of 77-A (5 g, 32.23 mmol) and 2-bromopropanedial (5.35 g, 35.45 mmol) in methanol (4 mL) was added AcOH (16 mL). The reaction mixture was stirred for 16 hrs. The mixture was poured into water (200 mL) and extracted with EA (200 mL×2). The combined organic layers were washed with aqueous $NaHCO_3$ (200 mL) and brine (200 mL), dried over sodium sulfate, and concentrated to give a residue, which was purified by chromatography on silica gel (PE/EA=4/1) to give 77-B (6.2 g, 71% yield). MS: m/z=269.9 (M+1).

Step 2: 77-C

A mixture of 77-B (6.2 g, 22.96 mmol), Intermediate 69 (6.01 g, 25.25 mmol), $K_2CO_3$ (9.52 g, 68.87 mmol, 4.16 mL) and Pd(dppf)$Cl_2$ (1.68 g, 2.30 mmol) in dioxane (16 mL) and water (4 mL) was stirred at 90° C. for 3 hrs under $N_2$ atmosphere. Dioxane was removed in vacuum to give a residue, which was diluted with water (20 mL), extracted with EA (20 mL×3), washed with brine, dried over $Na_2SO_4$ and concentrated in vacuum. The crude was purified by flash chromatography (PE/EA=5/1) to give 77-C (5.4 g, 78% yield). MS: m/z=302.1 (M+1).

Step 3: 77-D

To a solution of 77-C (4 g, 13.27 mmol) in methanol (30 mL) and THE (30 mL) was added Pd/C (800 mg). The reaction mixture was stirred for 1 hr under $H_2$ atmosphere. The mixture was filtered and concentrated to give a residue, which was purified by flash chromatography (PE/EA=4/1) to give 77-D (1.8 g, 45% yield). MS: m/z=304.1 (M+1).

Step 4: 77-E

To a mixture of 77-D (1.8 g, 5.93 mmol) in THF (20 mL) was slowly added 1-bromopyrrolidine-2,5-dione (1.37 g, 7.71 mmol). The reaction was stirred at 25° C. for 2 hrs before water (50 mL) was added. The mixture was extracted with EA (30 mL×3), and the combined organic phases were washed with brine (100 mL), dried and concentrated to give a residue, which was purified by flash chromatography (PE/EA=3/1) to give 77-E (1.95 g, 86% yield). MS: m/z=382.1 (M+1).

Step 5: 77-F

To a solution of 77-E (1.95 g, 5.1 mmol) in DMSO (4 mL) and water (275 μL) was added 4-(4,4,5,5-tetramethyl-1,3,2-dioxaborolan-2-yl)isoxazole (1.99 g, 10.2 mmol), KF (889 mg, 15.3 mmol), and Pd(dppf)$Cl_2$ (373 mg, 510 μmol). The mixture was stirred at 130° C. for 8 hrs under $N_2$ atmosphere. The mixture was filtered through a Celite pad and the filtrate was diluted with brine (20 mL). The aqueous layer was extracted with EA (30 mL×2). The combined organic layers were dried over $Na_2SO_4$ and concentrated to give a residue, which was purified by flash chromatography (PE/EA=1/1) to give 77-F (800 mg, 45.8% yield). MS: m/z=343.2 (M+1).

Step 6: Intermediate 77

To a solution of 77-F (300 mg, 876.19 μmol) and 1,3,2-dioxathiolane 2,2-dioxide (326 mg, 2.63 mmol) in THF (6 mL) was added KHMDS (1 M, 5.26 mL) dropwise at 0° C. The reaction was stirred for 1 hr at 0° C. before water (0.5 mL) was added. The mixture was stirred at 20° C. for another 2 hrs. Aqueous $NH_4Cl$ (10 mL) was added to quench the reaction, and then water (50 mL) was added. The mixture was extracted with EA (15 mL×3), the combined organic phases were washed with aqueous $NaHCO_3$ (10 mL×3), brine (10 mL×2), dried over anhydrous $Na_2SO_4$, and concentrated to give a residue, which was purified by prep-HPLC (Column: Xbridge prep C18 5 μm OBD 19*150 mm; Condition: A: water (0.1% FA); B: Acetonitrile; 10-20% B in 8 min, hold at 100% B at for 2 min, back to 5% B with 0.5 min, stop at 13 min. Flow rate: 20 ml/min; Detector: 214/254 nm) to give Intermediate 77 (20 mg, 6.7% yield). MS: m/z=341.1 (M+1).

Example 78: Synthesis of Intermediate 68-P1 and Intermediate 68-P2

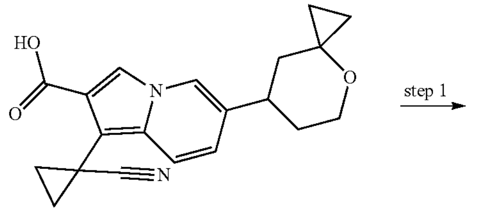

Intermediate 68

-continued

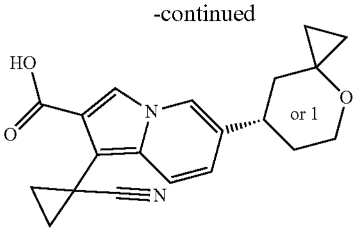

Intermediate 68-P1

+

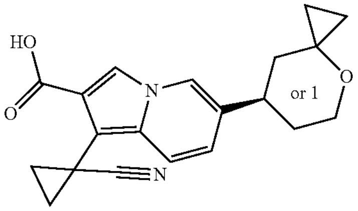

Intermediate 68-P2

Intermediate 68 (52 mg) was separated by SFC (Column: CHIRALPAK IG, 250 mm×20 mm I.D., 5 μm; Mobile phase: $CO_2$/{MeOH/ACN=1/1[0.2% $NH_3$ (7M Solution in MeOH)]}=55/45; Wave length: UV 214 nm; Column temperature: 35° C.; Flow rate: 45 g/min) to give Intermediate 68-P1 (17 mg) and Intermediate 68-P2 (18 mg).

The intermediates in Table 27 below were made according to the procedure of Intermediate 68-P1 and Intermediate 68-P2.

TABLE 27

| Name | Structure | Chiral separation condition: |
|---|---|---|
| Intermediate 65-P1 | 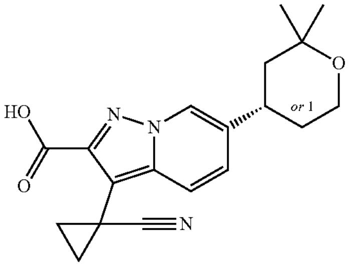 [SMILES: CC1(C)C[C@@H](c2ccc3c(C4(C#N)CC4)c(C(=O)O)nn3c2)CCO1] | Column: Daicel ChiralPak AD-H 250 mm * 30 mm I.D., 5 μm; Mobile phase: $CO_2$/EtOH(0.1% DEA) = 60:40; Flow rate: 50 g/min; Wave length: UV 254 nm; Temperature: 40° C. |
| Intermediate 65-P2 | 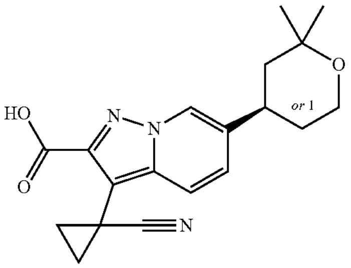 [SMILES: CC1(C)C[C@H](c2ccc3c(C4(C#N)CC4)c(C(=O)O)nn3c2)CCO1] | |

TABLE 27-continued

| Name | Structure | Chiral separation condition: |
| --- | --- | --- |
| Intermediate 70-P1 | 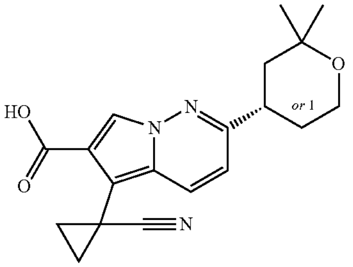 [SMILES: CC1(C)C[C@@H](c2ccc3c(C4(C#N)CC4)c(C(=O)O)cn3n2)CCO1] | Column: Daicel ChiralPak AD-H 250 mm * 30 mm I.D., 5 μm; Mobile phase: $CO_2$/EtOH(0.1% DEA) = 60:40; Flow rate: 50 g/min; Wave length: UV 254 nm; Temperature: 40° C. |
| Intermediate 70-P2 | 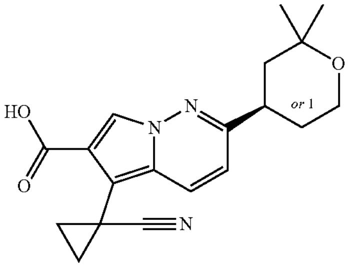 [SMILES: CC1(C)C[C@H](c2ccc3c(C4(C#N)CC4)c(C(=O)O)cn3n2)CCO1] | |
| Intermediate 71-P1 | 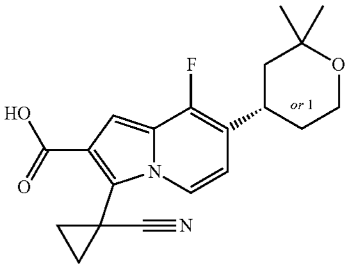 [SMILES: CC1(C)C[C@@H](c2ccn3c(C4(C#N)CC4)c(C(=O)O)cc3c2F)CCO1] | Column: Daicel ChiralPak AD-H 250 mm * 30 mm I.D., 5 μm; Mobile phase: $CO_2$/MeOH(0.1% DEA) = 65:35; Flow rate: 50 g/min; Wave length: UV 254 nm; Temperature: 40° C. |
| Intermediate 71-P2 | 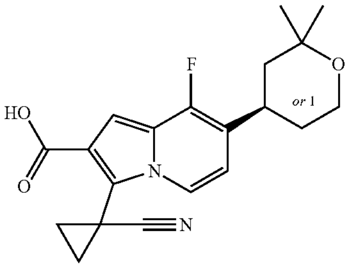 [SMILES: CC1(C)C[C@H](c2ccn3c(C4(C#N)CC4)c(C(=O)O)cc3c2F)CCO1] | |
| Intermediate 72-P1 | 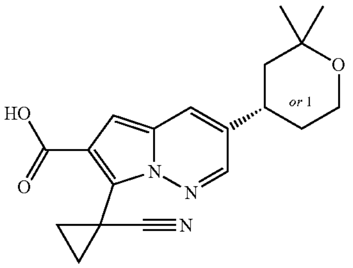 [SMILES: CC1(C)C[C@@H](c2cnn3c(C4(C#N)CC4)c(C(=O)O)cc3c2)CCO1] | Column: Daicel ChiralPak AD-H 250 mm * 30 mm I.D., 5 μm; Mobile phase: $CO_2$/EtOH(0.1% DEA) = 60:40; Flow rate: 50 g/min; Wave length: UV 254 nm; Temperature: 40° C. |

TABLE 27-continued

| Name | Structure | Chiral separation condition: |
|---|---|---|
| Intermediate 72-P2 | 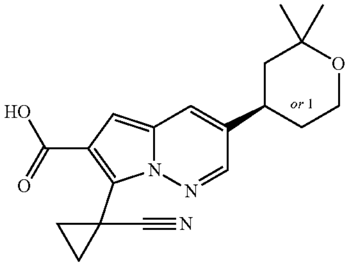 [SMILES: CC1(C)C[C@H](c2cnn3c(C4(C#N)CC4)c(C(=O)O)cc3c2)CCO1] | |
| Intermediate 73-P1 | 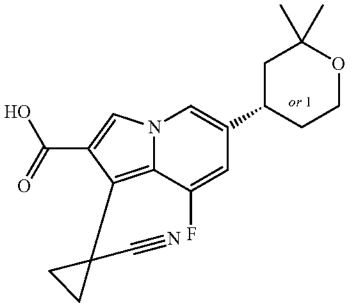 [SMILES: CC1(C)C[C@@H](c2cc(F)c3c(C4(C#N)CC4)c(C(=O)O)cn3c2)CCO1] | Column: Daicel ChiralPak AD-H 250 mm * 30 mm I.D., 5 μm; Mobile phase: $CO_2$/IPA(0.1% DEA) = 65:35; Flow rate: 50 g/min; Wave length: UV 254 nm; Temperature: 40° C. |
| Intermediate 73-P2 | 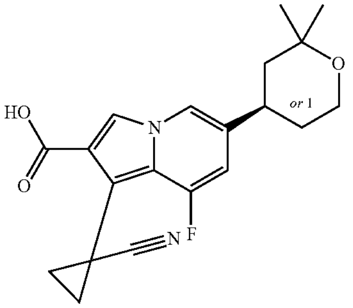 [SMILES: CC1(C)C[C@H](c2cc(F)c3c(C4(C#N)CC4)c(C(=O)O)cn3c2)CCO1] | |
| Intermediate 74-P1 | 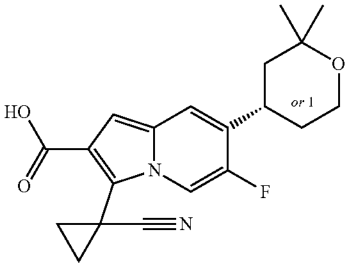 [SMILES: CC1(C)C[C@@H](c2cc3cc(C(=O)O)c(C4(C#N)CC4)n3cc2F)CCO1] | Column: Daicel ChiralPak AD-H 250 mm * 30 mm I.D., 5 μm; Mobile phase: $CO_2$/EtOH(0.1% DEA) = 65:35; Flow rate: 50 g/min; Wavelength: UV 254 nm; Temperature: 40° C. |
| Intermediate 74-P2 | 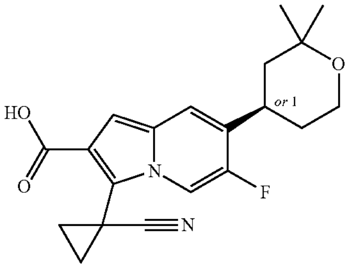 [SMILES: CC1(C)C[C@H](c2cc3cc(C(=O)O)c(C4(C#N)CC4)n3cc2F)CCO1] | |

TABLE 27-continued

| Name | Structure | Chiral separation condition: |
|---|---|---|
| Intermediate 75-P1 | 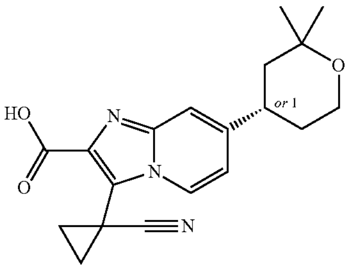 [SMILES: CC1(C)C[C@@H](c2ccn3c(C4(C#N)CC4)c(C(=O)O)nc3c2)CCO1] | Column: Daicel ChiralPak IG-H 250 mm * 30 mm I.D., 5 μm; Mobile phase: $CO_2$/EtOH(0.1% DEA) = 60:40; Flow rate: 50 g/min; Wave length: UV 254 nm; Temperature: 40° C. |
| Intermediate 75-P2 | 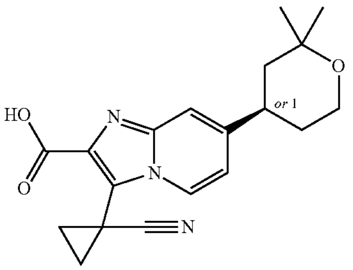 [SMILES: CC1(C)C[C@H](c2ccn3c(C4(C#N)CC4)c(C(=O)O)nc3c2)CCO1] | |
| Intermediate 76-P1 | 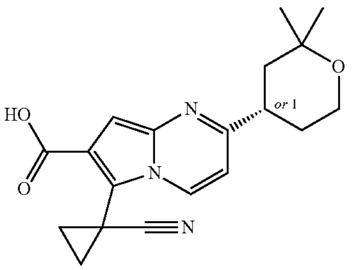 [SMILES: CC1(C)C[C@@H](c2ccn3c(C4(C#N)CC4)c(C(=O)O)cc3n2)CCO1] | Column: Daicel ChiralPak OZ-H 250 mm × 20 mm ID., 5 μm; Mobile phase: $CO_2$/MeOH (0.2% $NH_3$ (7M Solution in MeOH)) = 80:20; Flow rate: 50 g/min; Wave length: UV 214 nm; Temperature: 35° C. |
| Intermediate 76-P2 | 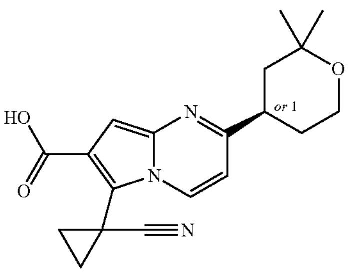 [SMILES: CC1(C)C[C@H](c2ccn3c(C4(C#N)CC4)c(C(=O)O)cc3n2)CCO1] | |

Example 79: Synthesis of Compounds 79-103

The compounds in Table 28 were made according to the procedure of Compound 2.

TABLE 28

| Name | Structure | $^1H$ NMR and/or LC/MS data |
|---|---|---|
| Compound 79 (from intermediate 62 and 28-P2) | 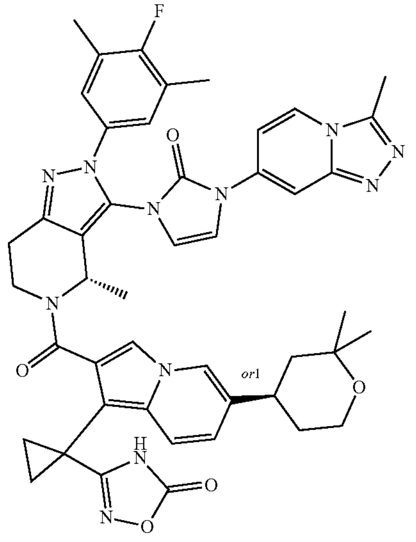 [SMILES: Cc1cc(-n2nc3c(c2-n2ccn(-c4ccn5c(C)nnc5c4)c2=O)[C@H](C)N(C(=O)c2cn4cc([C@@H]5CCOC(C)(C)C5)ccc4c2C2(c4noc(=O)[nH]4)CC2)CC3)cc(C)c1F] | MS: m/z = 852.2 (M + 1); $^1H$ NMR (400 MHz, $CD_3OD$) δ 8.48 (s, 1H), 8.36-8.29 (m, 1H), 8.01 (s, 1H), 7.95-7.87 (m, 1H), 7.58-7.46 (m, 2H), 7.38-7.32 (m, 1H), 7.13 (d, J = 6.0 Hz, 2H), 6.87-6.81 (m, 2H), 5.32 (t, J = 4.4 Hz, 1H), 3.84-3.78 (m, 1H), 3.46 (s, 2H), 3.11 (s, 1H), 2.78-2.74 (m, 3H), 2.29-2.19 (m, 9H), 2.01-1.92 (m, 4H), 1.58 (s, 3H), 1.33 (s, 6H), 0.89-0.86 (m, 4H). |
| Compound 80 (from intermediate 64 and 28-P2) | 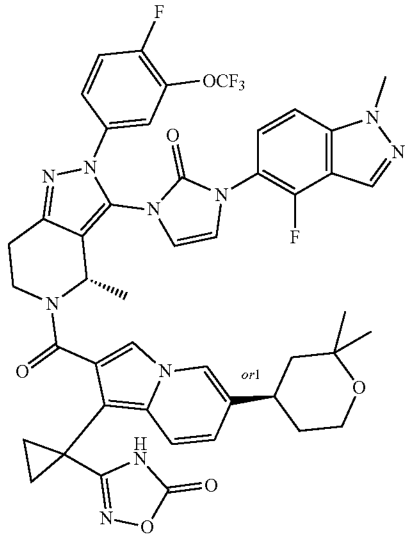 [SMILES: C[C@H]1c2c(nn(-c3ccc(F)c(OC(F)(F)F)c3)c2-n2ccn(-c3ccc4c(cnn4C)c3F)c2=O)CCN1C(=O)c1cn2cc([C@@H]3CCOC(C)(C)C3)ccc2c1C1(c2noc(=O)[nH]2)CC1] | MS: m/z = 925.2 (M + 1); $^1H$ NMR (400 MHz, DMSO-$d_6$) δ 11.97 (s, 1H), 8.29-8.25 (m, 1H), 8.11 (m, 1H), 7.74-7.57 (m, 5H), 7.44 (d, J = 9.2 Hz, 1H), 7.30 z (s, 1H), 7.13-6.95 (m, 2H), 6.85 (d, J = 9.2 Hz, 1H), 5.69 (m, 1H), 4.98-4.79 (m, 1H), 4.11 (s, 3H), 3.70 (d, J = 9.6 Hz, 2H), 2.92-2.73 (m, 4H), 1.71-1.19 (m, 17H). |

TABLE 28-continued

| Name | Structure | $^1H$ NMR and/or LC/MS data |
|---|---|---|
| Compound 81 (from intermediate 64 and 31-P2) | 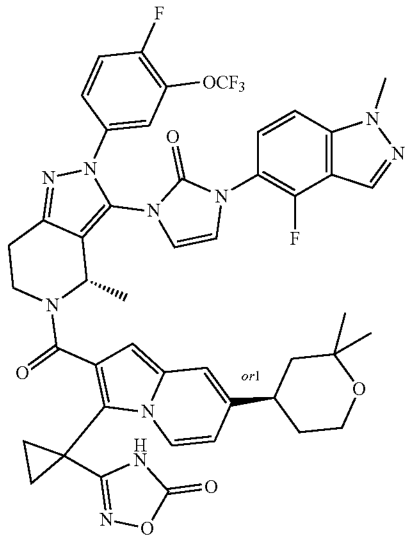 [SMILES: C[C@H]1c2c(nn(-c3ccc(F)c(OC(F)(F)F)c3)c2-n2ccn(-c3ccc4c(cnn4C)c3F)c2=O)CCN1C(=O)c1cc2cc([C@@H]3CCOC(C)(C)C3)ccn2c1C1(c2noc(=O)[nH]2)CC1] | MS: m/z = 925.2 (M + 1); $^1H$ NMR (400 MHz, DMSO-$d_6$) δ 12.05 (s, 1H), 8.29 (s, 1H), 8.13-8.10 (m, 1H), 7.74-7.42 (m, 5H), 7.29-7.26 (m, 1H), 7.14-7.07 (m, 1H), 6.95-6.84 (m, 1H), 6.70 (d, J = 7.2 Hz, 1H), 6.39 (s, 1H), 5.68-5.67 (m, 1H), 5.02-4.81 (m, 1H), 4.11 (s, 3H), 3.70 (d, J = 9.6 Hz, 2H), 2.97-2.89 (m, 2H), 2.72-2.67 (m, 2H), 1.71-1.17 (m, 17H). |
| Compound 82 (from intermediate 3 and 65-P1) | 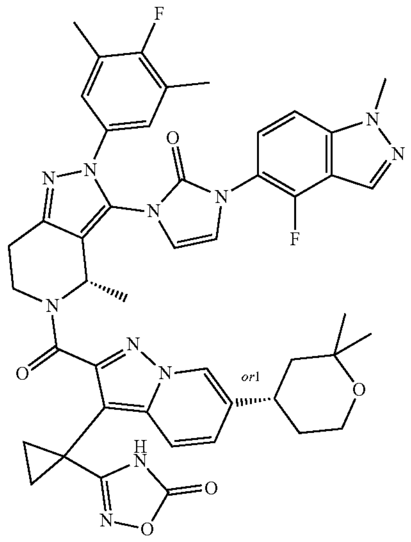 [SMILES: Cc1cc(-n2nc3c(c2-n2ccn(-c4ccc5c(cnn5C)c4F)c2=O)[C@H](C)N(C(=O)c2nn4cc([C@H]5CCOC(C)(C)C5)ccc4c2C2(c4noc(=O)[nH]4)CC2)CC3)cc(C)c1F] | MS: m/z = 870.3 (M + 1); $^1H$ NMR (400 MHz, DMSO) δ 11.92 (s, 1H), 8.58 (s, 1H), 8.31 (s, 1H), 7.71 (d, J = 9.6 Hz, 1H), 7.64 (d, J = 9.2 Hz, 1H), 7.47 (t, J = 7.2 Hz, 1H), 7.38 (d, J = 13.6 Hz, 1H), 7.16 (d, J = 6.4 Hz, 2H), 7.17-7.08 (m, 1H), 6.97 (s, 1H), 5.69 (q, J = 6.4 Hz, 1H), 5.00-4.80 (m, 1H), 4.12 (s, 3H), 4.04 (s, 1H), 3.75-3.68 (m, 2H), 3.14-3.03 (m, 2H), 2.78-2.68 (m, 2H), 2.25 (s, 6H), 1.78-1.65 (m, 2H), 1.62-1.47 (m, 4H), 1.40-1.30 (m, 4H), 1.28 (s, 3H), 1.20 (s, 3H). |
| Compound 83 (from intermediate 3 and 65-P2) | 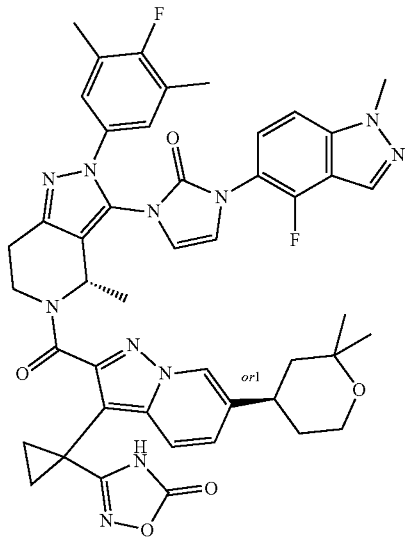 [SMILES: Cc1cc(-n2nc3c(c2-n2ccn(-c4ccc5c(cnn5C)c4F)c2=O)[C@H](C)N(C(=O)c2nn4cc([C@@H]5CCOC(C)(C)C5)ccc4c2C2(c4noc(=O)[nH]4)CC2)CC3)cc(C)c1F] | MS: m/z = 870.2 (M + 1); $^1H$ NMR (400 MHz, DMSO) δ 11.92(s, 1H), 8.55 (s, 1H), 8.28 (s, 1H), 7.70 (d, J = 9.6 Hz, 1H), 7.65 (d, J = 9.2 Hz, 1H), 7.47 (t, J = 7.2 Hz, 1H), 7.35 (d, J = 8.8 Hz, 1H), 7.17 (d, J = 6.4 Hz, 2H), 7.17-7.08 (m, 1H), 6.97 (s, 1H), 5.69 (q, J = 6.4 Hz, 1H), 5.00-4.80 (m, 1H), 4.10 (s, 3H), 4.04 (s, 1H), 3.75-3.68 (m, 2H), 3.14-3.03 (m, 2H), 2.78-2.68 (m, 2H), 2.23 (s, 6H), 1.77-1.65 (m, 2H), 1.61-1.47 (m, 4H), 1.39-1.30 (m, 4H), 1.28 (s, 3H), 1.20 (s, 3H). |

TABLE 28-continued
| Name | Structure | $^1$H NMR and/or LC/MS data |
|---|---|---|
| Compound 84 (from intermediate 59 and 65-P2) | 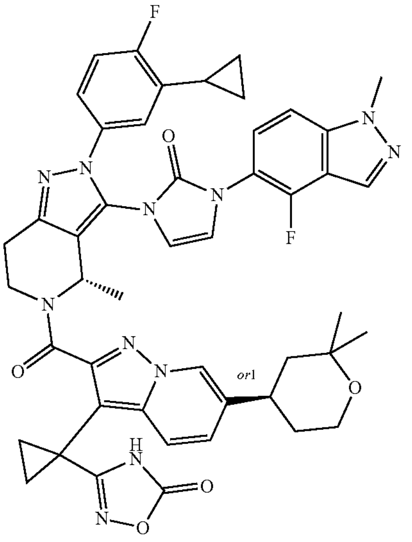 | MS: m/z = 882.2 (M + 1); $^1$H NMR (400 MHz, DMSO-$d_6$) δ 11.92 (s, 1H), 8.58-8.54 (s, 1H), 8.31 (s, 1H), 7.74-7.62 (m, 2H), 7.47-7.36 (m, 2H), 7.33-7.26 (m, 2H), 7.10 (d, J = 3.2 Hz, 1H), 7.01-6.88 (m, 2H), 5.71-5.60 (m, 1H), 4.10-4.08 (m, 3H), 3.73-3.71 (m, 2H), 3.47-3.39 (m, 1H), 3.13-3.02 (m, 2H), 2.74 (s, 2H), 2.08-2.06 (m, 2H), 1.71 (s, 3H), 1.61-1.56 (m, 3H), 1.39-1.31 (m, 4H), 1.26-1.24 (m, 3H), 1.22-1.14 (m, 3H), 1.00 (d, J = 8.8 Hz, 2H), 0.65 (d, J = 15.6 Hz, 2H). |
| Compound 85 (from intermediate 59 and 66) | 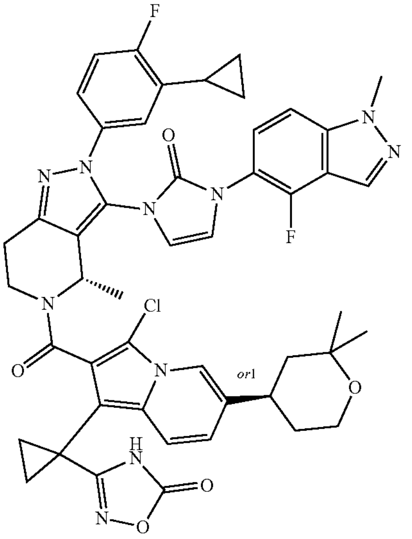 [SMILES: C[C@H]1c2c(nn(-c3ccc(F)c(C4CC4)c3)c2-n2ccn(-c3ccc4c(cnn4C)c3F)c2=O)CCN1C(=O)c1c(C2(c3noc(=O)[nH]3)CC2)c2ccc([C@@H]3CCOC(C)(C)C3)cn2c1Cl] | MS: m/z = 915.2 (M + 1); $^1$H NMR (400 MHz, DMSO-$d_6$) δ 8.30-8.24 (m, 1H), 7.96 (s, 1H), 7.71-7.63 (m, 2H), 7.61-7.41 (m, 2H), 7.28 (s, 2H), 7.10 (s, 1H), 7.04-6.98 (m, 2H), 5.72 (d, J = 21.2 Hz, 1H), 4.10 (d, J = 14.2 Hz, 3H), 3.72 (s, 2H), 3.08 (s, 3H), 2.08 (s, 2H), 1.72-1.51 (m, 7H), 1.38-1.20 (m, 11H), 0.93-0.89 (m, 2H), 0.64 (s, 2H). |

TABLE 28-continued
| Name | Structure | $^1$H NMR and/or LC/MS data |
|---|---|---|
| Compound 86 (from intermediate 3 and 68-P1) | 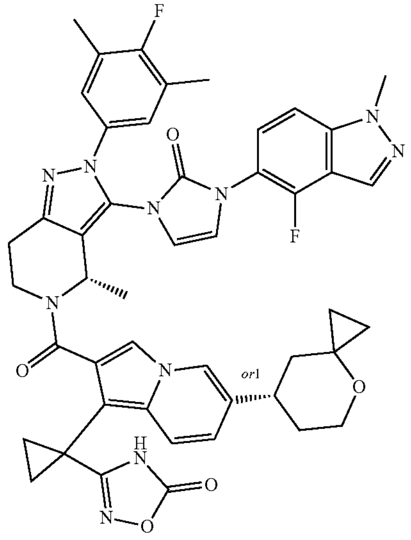 [SMILES: Cc1cc(-n2nc3c(c2-n2ccn(-c4ccc5c(cnn5C)c4F)c2=O)[C@H](C)N(C(=O)c2cn4cc([C@H]5CCOC6(CC6)C5)ccc4c2C2(c4noc(=O)[nH]4)CC2)CC3)cc(C)c1F] | MS: m/z = 867 (M + 1); $^1$H NMR (400 MHz, MeOD) δ 8.27-7.87 (m, 2H), 7.72-7.25 (m, 4H), 7.21-7.09 (m, 2H), 7.01-6.49 (m, 3H), 5.38-5.10 (m, 1H), 4.20-4.02 (m, 3H), 4.01-3.41 (m, 3H), 3.23-2.69 (m, 3H), 2.28 (d, J = 8.3 Hz, 7H), 1.62-1.18 (m, 11H), 0.91-0.40 (m, 4H). |
| Compound 87 (from intermediate 3 and 68-P2) | 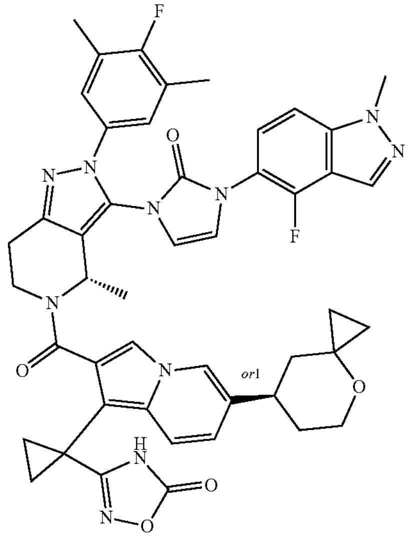 [SMILES: Cc1cc(-n2nc3c(c2-n2ccn(-c4ccc5c(cnn5C)c4F)c2=O)[C@H](C)N(C(=O)c2cn4cc([C@@H]5CCOC6(CC6)C5)ccc4c2C2(c4noc(=O)[nH]4)CC2)CC3)cc(C)c1F] | MS: m/z = 867 (M + 1); $^1$H NMR (400 MHz, MeOD) δ 8.26-7.98 (m, 2H), 7.67-7.23 (m, 4H), 7.17 (d, J = 6.4 Hz, 2H), 6.95-6.56 (m, 3H), 5.34-5.07 (m, 1H), 4.11 (d, J = 10.2 Hz, 3H), 4.01-3.53 (m, 3H), 3.08-2.72 (m, 3H), 2.28 (d, J = 5.2 Hz, 7H), 1.49-1.26 (m, 11H), 0.86-0.43 (m, 4H). |
| Compound 88 (from intermediate 59 and 67) | 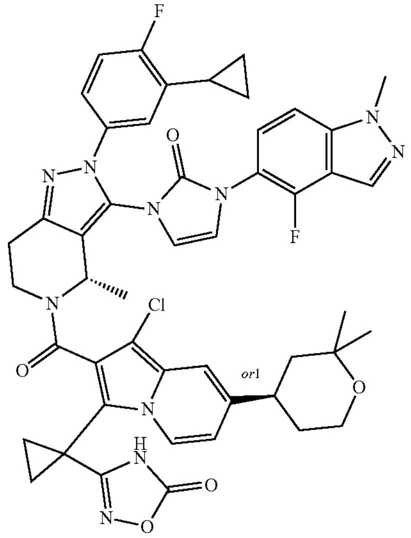 [SMILES: C[C@H]1c2c(nn(-c3ccc(F)c(C4CC4)c3)c2-n2ccn(-c3ccc4c(cnn4C)c3F)c2=O)CCN1C(=O)c1c(Cl)c2cc([C@@H]3CCOC(C)(C)C3)ccn2c1C1(c2noc(=O)[nH]2)CC1] | MS: m/z = 915.2 (M + 1); $^1$H NMR (400 MHz, DMSO-$d_6$) δ 8.17-8.08 (m, 2H), 7.52-7.40 (m, 2H), 7.26-7.07 (m, 3H), 7.00-6.98 (m, 1H), 6.91-6.90 (m, 1H), 6.82-6.67 (m, 2H), 5.91-5.89 (m, 1H), 4.11-4.07 (m, 3H), 3.87-3.79 (m, 2H), 3.60-3.47 (m, 2H), 3.12-2.65 (m, 3H), 2.18-2.01 (m, 2H), 1.76-1.47 (m, 8H), 1.35-1.25 (m, 8H), 1.01-0.95 (m, 2H), 0.69-0.65(m, 2H). |

TABLE 28-continued
| Name | Structure | $^1$H NMR and/or LC/MS data |
|---|---|---|
| Compound 89 (from intermediate 59 and 70-P1) | 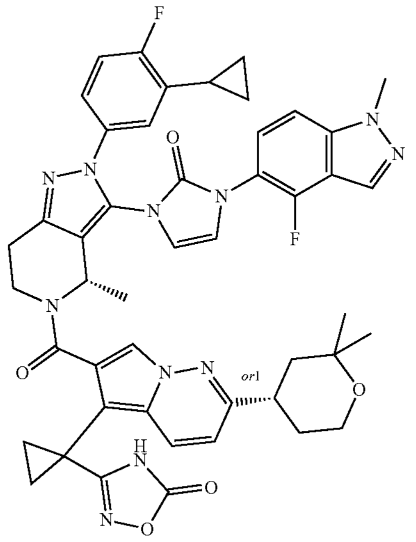 [SMILES: C[C@H]1c2c(nn(-c3ccc(F)c(C4CC4)c3)c2-n2ccn(-c3ccc4c(cnn4C)c3F)c2=O)CCN1C(=O)c1cn2nc([C@H]3CCOC(C)(C)C3)ccc2c1C1(c2noc(=O)[nH]2)CC1] | MS: m/z = 882.2 (M + 1); $^1$H NMR (400 MHz, DMSO-$d_6$) δ 8.28-8.22 (m, 1H), 7.99-7.97 (m, 2H), 7.63-7.61 (m, 1H), 7.50-7.48(m,1H), 7.28-7.26 (m, 2H), 7.07 (s, 1H), 6.96-6.82 (m, 3H), 5.63-5.62 (m, 1H), 4.09 (s, 3H), 3.71-3.69 (m, 2H), 3.15-3.13 (m, 2H), 2.85-2.65 (m, 3H), 2.06-2.05 (m, 1H), 1.75-1.50 (m, 8H), 1.30-1.17 (m, 9H), 1.01-0.92 (m, 2H), 0.62-0.60 (m, 2H). |
| Compound 90 (from intermediate 59 and 70-P2) | 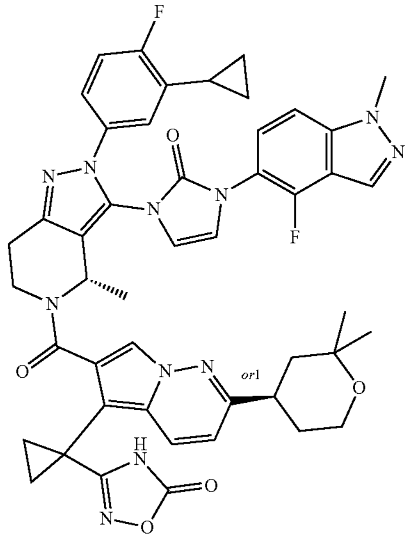 [SMILES: C[C@H]1c2c(nn(-c3ccc(F)c(C4CC4)c3)c2-n2ccn(-c3ccc4c(cnn4C)c3F)c2=O)CCN1C(=O)c1cn2nc([C@@H]3CCOC(C)(C)C3)ccc2c1C1(c2noc(=O)[nH]2)CC1] | MS: m/z = 882.2 (M + 1); $^1$H NMR (400 MHz, DMSO) δ 11.89 (br, 1H) 8.32-8.19 (m 1H) 8.03-7.93 (m 2H), 7.71-7.52 (m, 1H), 7.49-7.38 (m, 1H), 7.34-7.17 (m, 2H), 7.08 (s, 1H), 7.01-6.78 (m, 3H), 5.63 (d, J = 7.0 Hz, 1H), 4.10 (s, 3H), 3.78-3.62 (m, 2H), 3.22-3.01 (m, 2H), 2.93-2.55 (m, 3H), 2.06 (s, 1H), 1.84-1.36 (m, 8H), 1.30 (d, J = 6.7 Hz, 3H), 1.25 (s, 3H), 1.18 (s, 3H), 1.04-0.85 (m, 2H), 0.72-0.54 (m, 2H). |

TABLE 28-continued
| Name | Structure | $^1$H NMR and/or LC/MS data |
|---|---|---|
| Compound 91 (from intermediate 59 and 73-P1) | 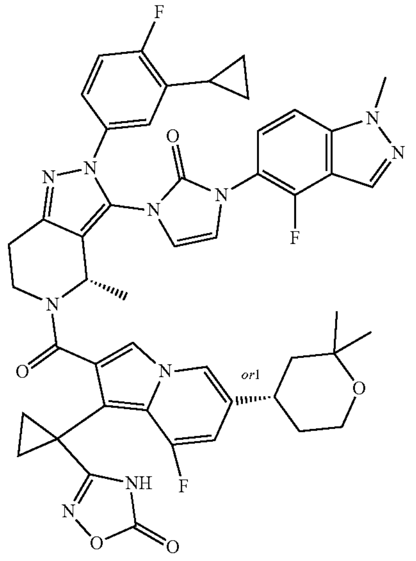 [SMILES: C[C@H]1c2c(nn(-c3ccc(F)c(C4CC4)c3)c2-n2ccn(-c3ccc4c(cnn4C)c3F)c2=O)CCN1C(=O)c1cn2cc([C@H]3CCOC(C)(C)C3)cc(F)c2c1C1(c2noc(=O)[nH]2)CC1] | MS: m/z = 899.2 (M + 1); $^1$H NMR (400 MHz, DMSO-$d_6$) δ 8.30-8.23 (m, 1H), 7.99 (s, 1H), 7.75 (s, 1H), 7.63-7.57 (m, 1H), 7.46 (s, 1H), 7.29 (d, J = 8.4 Hz, 2H), 7.09 (s, 1H), 6.98-6.94 (m, 2H), 6.70 (d, J = 13.2 Hz, 1H), 5.65 (d, J = 6.4 Hz, 1H), 4.11 (s, 3H), 3.71 (s, 2H), 3.17 (s, 2H), 2.91 (s, 1H), 2.70 (s, 2H), 2.07-1.98 (m, 2H), 1.76-1.65 (m, 2H), 1.47 (s, 4H), 1.32 (d, J = 6.0 Hz, 2H), 1.25-1.18 (m, 8H), 1.04-0.94 (m, 2H), 0.70-0.59 (m, 2H). |
| Compound 92 (from intermediate 59 and 73-P2) | 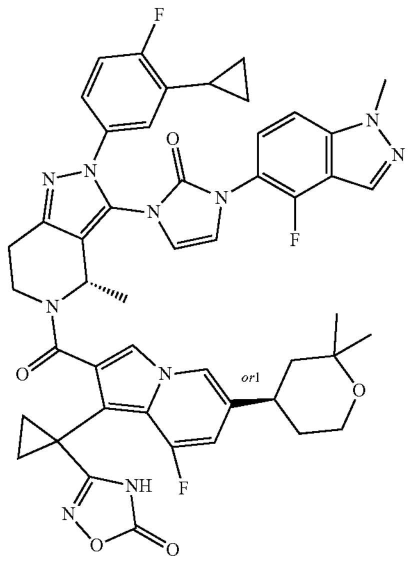 [SMILES: C[C@H]1c2c(nn(-c3ccc(F)c(C4CC4)c3)c2-n2ccn(-c3ccc4c(cnn4C)c3F)c2=O)CCN1C(=O)c1cn2cc([C@@H]3CCOC(C)(C)C3)cc(F)c2c1C1(c2noc(=O)[nH]2)CC1] | MS: m/z = 899.2 (M + 1); $^1$H NMR (400 MHz, DMSO-$d_6$) δ 11.88 (br, 1H), 8.30-8.24 (m, 1H), 8.00 (s, 1H), 7.78 (s, 1H), 7.63-7.58 (m, 1H), 7.48-7.41 (m, 1H), 7.29-7.27 (m, 2H), 7.10 (s, 1H), 6.95 (d, J = 6.0 Hz, 2H), 6.73 (d, J = 13.0 Hz, 1H), 5.65 (d, J = 6.4 Hz, 1H), 4.11 (s, 3H), 3.71 (s, 2H), 2.90 (s, 1H), 2.74 (s, 2H), 2.06 (s, 2H), 1.73 (s, 2H), 1.49-1.45 (m, 5H), 1.33 (d, J = 6.2 Hz, 3H), 1.25-1.19 (m, 8H), 1.01-0.98 (m, 2H), 0.63 (s, 2H). |

TABLE 28-continued
| Name | Structure | $^1$H NMR and/or LC/MS data |
| --- | --- | --- |
| Compound 93 (from intermediate 59 and 74-P1) | 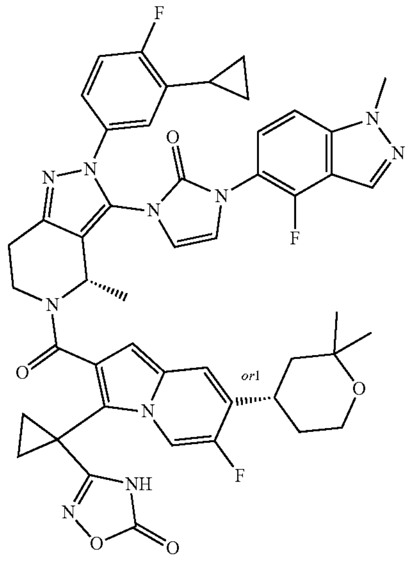 [SMILES: C[C@H]1c2c(nn(-c3ccc(F)c(C4CC4)c3)c2-n2ccn(-c3ccc4c(cnn4C)c3F)c2=O)CCN1C(=O)c1cc2cc([C@H]3CCOC(C)(C)C3)c(F)cn2c1C1(c2noc(=O)[nH]2)CC1] | MS: m/z = 899.2 (M + 1); $^1$H NMR (400 MHz, MeOD) δ 8.18-8.11 (m, 2H), 7.52-7.37 (m, 3H), 7.29-7.10 (m, 2H), 7.01-6.91 (m, 2H), 6.76 (d, J = 38 Hz, 1H), 6.58 (d, J = 12.4 Hz, 1H), 5.86-5.84 (m, 1H), 5.12-5.08 (m, 1H), 4.98-4.94 (m, 1H), 4.28-4.23 (m, 1H), 4.10 (d, J = 12.4 Hz, 2H), 3.92-3.77 (m, 3H), 2.90-2.78 (m, 3H), 2.17-2.06 (m, 2H), 1.84-1.24 (m, 15H), 1.03-0.98 (m, 2H), 0.73-0.68 (m, 2H). |
| Compound 94 (from intermediate 59 and 74-P2) | 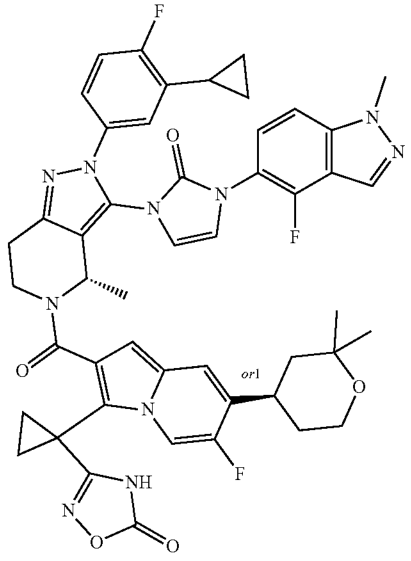 [SMILES: C[C@H]1c2c(nn(-c3ccc(F)c(C4CC4)c3)c2-n2ccn(-c3ccc4c(cnn4C)c3F)c2=O)CCN1C(=O)c1cc2cc([C@@H]3CCOC(C)(C)C3)c(F)cn2c1C1(c2noc(=O)[nH]2)CC1] | MS: m/z = 899.2 (M + 1); $^1$H NMR (400 MHz, MeOD) δ 8.18-8.11 (m, 2H), 7.52-7.37 (m, 3H), 7.29-7.10 (m, 2H), 7.01-6.91 (m, 2H), 6.76 (d, J = 37.2 Hz, 1H), 6.58 (d, J = 12.4 Hz, 1H), 5.86-5.84 (m, 1H), 5.12-5.08 (m, 1H), 4.98-4.94 (m, 1H), 4.28-4.23 (m, 1H), 4.10 (d, J = 12.4 Hz, 2H), 3.92-3.77 (m, 3H), 2.90-2.78 (m, 3H), 2.17-2.06 (m, 2H), 1.84-1.24 (m, 15H), 1.03-0.98 (m, 2H), 0.73-0.68 (m, 2H). |

TABLE 28-continued
| Name | Structure | $^1$H NMR and/or LC/MS data |
| --- | --- | --- |
| Compound 95 (from intermediate 59 and 71-P1) | 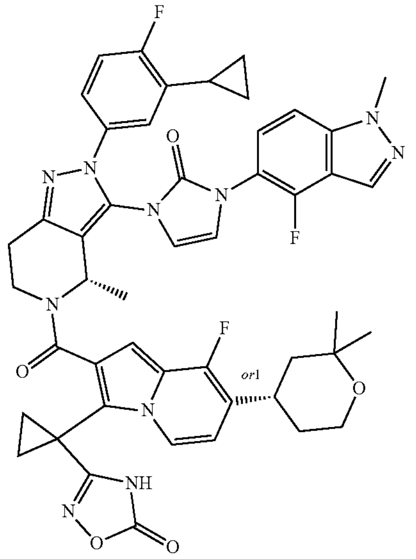 [SMILES: C[C@H]1c2c(nn(-c3ccc(F)c(C4CC4)c3)c2-n2ccn(-c3ccc4c(cnn4C)c3F)c2=O)CCN1C(=O)c1cc2c(F)c([C@H]3CCOC(C)(C)C3)ccn2c1C1(c2noc(=O)[nH]2)CC1] | MS: m/z = 899.2 (M + 1); $^1$H NMR (400 MHz, DMSO) δ 12.04 (br, 1H), 8.30 (s, 1H), 8.09 (d, J = 7.1 Hz, 1H), 7.77-7.61 (m, 2H), 7.50-7.39 (m, 1H), 7.34-7.22 (m, 2H), 7.10-6.91 (m, 2H), 6.78 (t, J = 7.0 Hz, 1H), 6.58 (s, 1H), 5.66 (d, J = 6.4 Hz, 1H), 4.14-3.94 (m, 4H), 3.79-3.66 (m, 2H), 3.47-3.35 (m, 2H), 2.13-2.02 (m, 1H), 1.61-1.17 (m, 19H), 1.03-0.95 (m, 2H), 0.71-0.59 (m, 2H). |
| Compound 96 (from intermediate 59 and 71-P2) | 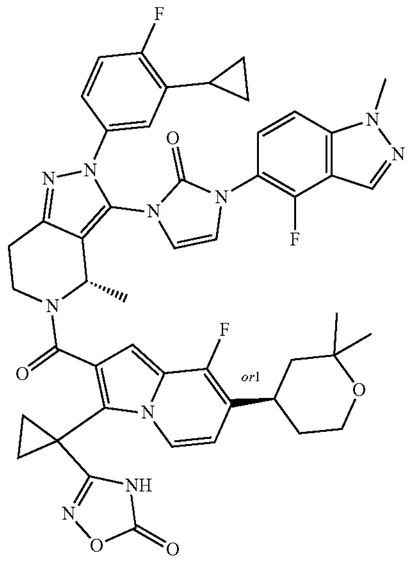 [SMILES: C[C@H]1c2c(nn(-c3ccc(F)c(C4CC4)c3)c2-n2ccn(-c3ccc4c(cnn4C)c3F)c2=O)CCN1C(=O)c1cc2c(F)c([C@@H]3CCOC(C)(C)C3)ccn2c1C1(c2noc(=O)[nH]2)CC1] | MS: m/z = 899.2 (M + 1); $^1$H NMR (400 MHz, DMSO) δ 12.04 (br, 1H), 8.30 (s, 1H), 8.08 (d, J = 7.3 Hz, 1H), 7.76-7.51 (m, 2H), 7.49-7.37 (m, 1H), 7.33-7.23 (m, 2H), 7.11-6.91 (m, 2H), 6.78 (t, J = 7.0 Hz, 1H), 6.57 (s, 1H), 5.71-5.62 (m, 1H), 4.14-3.94 (m, 4H), 3.80-3.72 (m, 2H), 3.45-3.36 (m, 2H), 2.13-2.03 (m, 1H), 1.61-1.20 (m, 19H), 1.04-0.95 (m, 2H), 0.70-0.58 (m, 2H). |

TABLE 28-continued
| Name | Structure | $^1$H NMR and/or LC/MS data |
|---|---|---|
| Compound 97 (from intermediate 59 and 75-P1) | 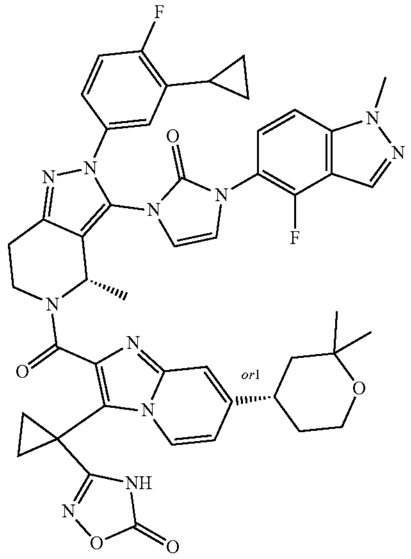 [SMILES: C[C@H]1c2c(nn(-c3ccc(F)c(C4CC4)c3)c2-n2ccn(-c3ccc4c(cnn4C)c3F)c2=O)CCN1C(=O)c1nc2cc([C@H]3CCOC(C)(C)C3)ccn2c1C1(c2noc(=O)[nH]2)CC1] | MS: m/z = 888.2 (M + 1); $^1$H NMIR (400 MHz, MeOD) δ 8.41-8.36 (m, 1H), 8.18-8.11 (m, 1H), 7.53-7.41 (m, 2H), 7.29-7.00 (m, 4H), 6.95-6.91 (m, 1H), 6.81 (s, 1H), 6.67 (d, J = 32 Hz, 1H), 5.88-5.85 (m, 1H), 4.29-4.23 (m, 1H), 4.10 (d, J = 12.4 Hz, 2H), 3.89-3.81 (m, 2H), 3.56-3.48 (m, 1H), 3.34-3.31 (m, 1H), 3.19-2.93 (m, 3H), 2.79-2.74 (m, 1H), 2.15-2.09 (m, 1H), 1.86-1.25 (m, 16H), 1.03-0.98 (m, 2H), 0.73-0.68 (m, 2H). |
| Compound 98 (from intermediate 59 and 75-P2) | 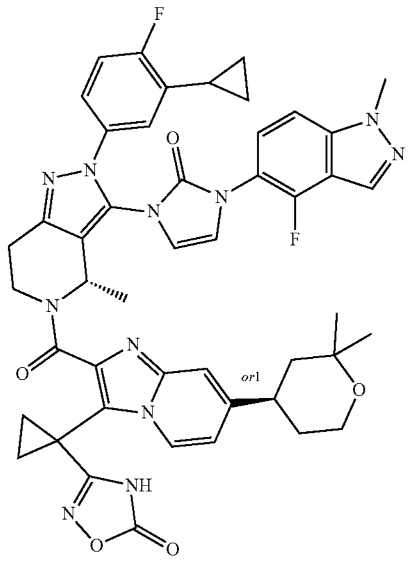 [SMILES: C[C@H]1c2c(nn(-c3ccc(F)c(C4CC4)c3)c2-n2ccn(-c3ccc4c(cnn4C)c3F)c2=O)CCN1C(=O)c1nc2cc([C@@H]3CCOC(C)(C)C3)ccn2c1C1(c2noc(=O)[nH]2)CC1] | MS: m/z = 888.2 (M + 1); $^1$H NMR (400 MHz, MeOD) δ 8.41-8.36 (m, 1H), 8.18-8.11 (m, 1H), 7.53-7.41 (m, 2H), 7.29-7.00 (m, 4H), 6.95-6.91 (m, 1H), 6.81 (s, 1H), 6.67 (d, J = 32 Hz, 1H), 5.88-5.85 (m, 1H), 4.29-4.23 (m, 1H), 4.10 (d, J = 12.4 Hz, 2H), 3.89-3.81 (m, 2H), 3.56-3.48 (m, 1H), 3.34-3.31 (m, 1H), 3.19-2.93 (m, 3H), 2.79-2.74 (m, 1H), 2.15-2.09 (m, 1H), 1.86-1.25 (m, 16H), 1.03-0.98 (m, 2H), 0.73-0.68 (m, 2H). |

TABLE 28-continued
| Name | Structure | $^1$H NMR and/or LC/MS data |
|---|---|---|
| Compound 99 (from intermediate 59 and 72-P1) | 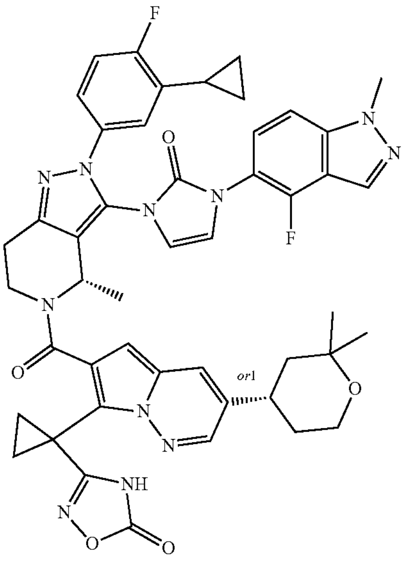 [SMILES: C[C@H]1c2c(nn(-c3ccc(F)c(C4CC4)c3)c2-n2ccn(-c3ccc4c(cnn4C)c3F)c2=O)CCN1C(=O)c1cc2cc([C@H]3CCOC(C)(C)C3)cnn2c1C1(c2noc(=O)[nH]2)CC1] | MS: m/z = 888.2 (M + 1); $^1$H NMR (400 MHz, DMSO-$d_6$) δ 12.14 (s, 1H), 8.34-8.14 (m, 2H), 7.79 (s, 1H), 7.64 (d, J = 9.2 Hz, 1H), 7.47-7.43 (m, 1H), 7.32-7.23 (m, 2H), 7.09 (d, J = 2.8 Hz, 1H), 6.99-6.94 (m, 2H), 6.53 (s, 1H), 5.68-5.63 (m, 1H), 5.00-4.82 (m, 1H), 4.11-4.04 (m, 3H), 3.73-3.70 (m, 2H), 3.11-2.98 (m, 2H), 2.67-2.63 (m, 2H), 2.08-2.05 (m, 1H), 1.73-0.63 (m, 21H). |
| Compound 100 (from intermediate 59 and 72-P2) | 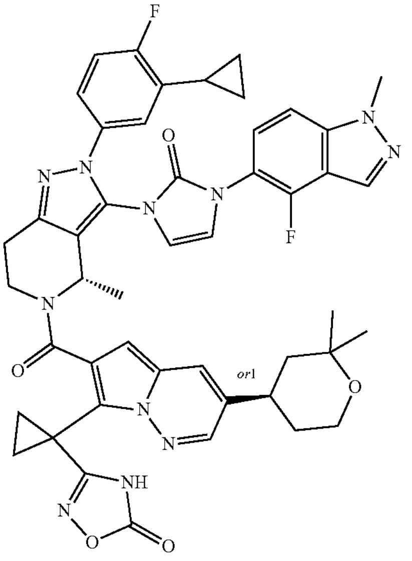 [SMILES: C[C@H]1c2c(nn(-c3ccc(F)c(C4CC4)c3)c2-n2ccn(-c3ccc4c(cnn4C)c3F)c2=O)CCN1C(=O)c1cc2cc([C@@H]3CCOC(C)(C)C3)cnn2c1C1(c2noc(=O)[nH]2)CC1] | MS: m/z = 888.2 (M + 1); $^1$H NMR (400 MHz, DMSO-$d_6$) δ 12.14 (s, 1H) 8.34-8.14 (m 2H) 7.79 (s 1H) 7.64 (d, J = 9.2 Hz, 1H), 7.47-7.43 (m, 1H), 7.32-7.23 (m, 2H), 7.09 (d, J = 2.8 Hz, 1H), 6.99-6.94 (m, 2H), 6.53 (s, 1H), 5.68-5.63 (m, 1H), 5.00-4.82(m, 1H), 4.11-4.04 (m, 3H), 3.73-3.70 (m, 2H), 3.11-2.98 (m, 2H), 2.67-2.63 (m, 2H), 2.08-2.05 (m, 1H), 1.73-0.63 (m, 21H). |

TABLE 28-continued

| Name | Structure | $^1$H NMR and/or LC/MS data |
| --- | --- | --- |
| Compound 101 (from intermediate 59 and 76-P1) | 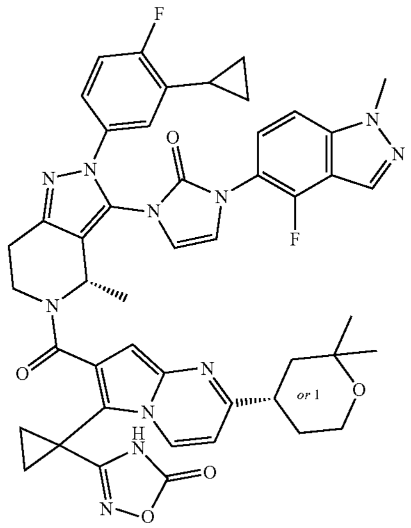 [SMILES: C[C@H]1c2c(nn(-c3ccc(F)c(C4CC4)c3)c2-n2ccn(-c3ccc4c(cnn4C)c3F)c2=O)CCN1C(=O)c1cc2nc([C@H]3CCOC(C)(C)C3)ccn2c1C1(c2noc(=O)[nH]2)CC1] | MS: m/z = 882.3 (M + 1); $^1$H NMR (400 MHz, DMSO-$d_6$) δ 12.03 (s, 1H), 8.61 (d, J = 7.2 Hz, 1H), 8.30(s, 1H), 7.64 (d, J = 8.8 Hz, 1H), 7.45 (t, J = 7.6 Hz, 1H), 7.36-7.20 (m, 2H), 7.10 (d, J = 3.2 Hz, 1H), 7.00-6.92 (m, 2H), 6.86 (d, J = 7.2 Hz, 1H), 6.51 (s, 1H), 5.64 (q, J = 6.0 Hz, 1H), 4.94-4.74 (m, 1H), 4.11 (s, 3H), 4.03-3.91 (m, 1H), 3.76-3.67 (m, 2H), 3.44-3.30 (m, 2H), 3.18-3.07 (m, 1H), 2.86-2.65 (m, 2H), 2.13-2.01 (m, 1H), 1.83-1.71 (m, 2H), 1.71-1.50 (m, 4H), 1.34 (d, J = 6.8 Hz, 3H), 1.27 (s, 3H), 1.19 (s, 3H), 1.04-0.94 (m, 2H), 0.70-0.60 (m, 2H). |
| Compound 102 (from intermediate 59 and 76-P2) | 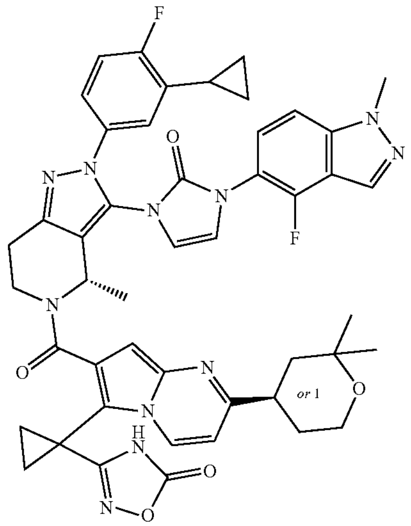 [SMILES: C[C@H]1c2c(nn(-c3ccc(F)c(C4CC4)c3)c2-n2ccn(-c3ccc4c(cnn4C)c3F)c2=O)CCN1C(=O)c1cc2nc([C@@H]3CCOC(C)(C)C3)ccn2c1C1(c2noc(=O)[nH]2)CC1] | MS: m/z = 882.3 (M + 1); $^1$H NMR (400 MHz, DMSO-$d_6$) δ 12.03 (s, 1H), 8.61 (d, J = 7.2 Hz, 1H), 8.30 (s, 1H), 7.64 (d, J = 8.8 Hz, 1H), 7.45 (t, J = 7.6 Hz, 1H), 7.36-7.22 (m, 2H), 7.10 (d, J = 2.8 Hz, 1H), 7.02-6.90 (m, 2H), 6.86 (d, J = 7.2 Hz, 1H), 6.52 (s, 1H), 5.64 (q, J = 6.0 Hz, 1H), 4.93-4.73 (m, 1H), 4.12 (s, 3H), 4.02-3.91 (m, 1H), 3.80-3.61 (m, 2H), 3.48-3.33 (m, 2H), 3.19-3.01 (m, 1H), 2.81-2.63 (m, 2H), 2.15-2.02 (m, 1H), 1.86-1.72 (m, 2H), 1.72-1.50 (m, 4H), 1.34 (d, J = 6.8 Hz, 3H), 1.26 (s, 3H), 1.18 (s, 3H), 1.07-0.94 (m, 2H), 0.73-0.55 (m, 2H). |
| Compound 103 (from intermediate 59 and 77) | 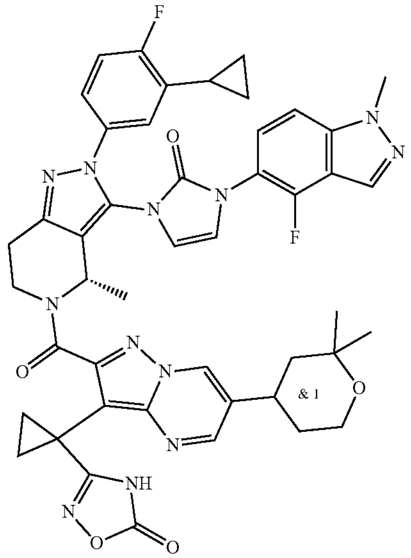 [SMILES: C[C@H]1c2c(nn(-c3ccc(F)c(C4CC4)c3)c2-n2ccn(-c3ccc4c(cnn4C)c3F)c2=O)CCN1C(=O)c1nn2cc(C3CCOC(C)(C)C3)cnc2c1C1(c2noc(=O)[nH]2)CC1] | MS: m/z = 883.2 (M + 1); $^1$H NMR (400 MHz, DMSO-$d_6$) δ 11.97 (br, 1H), 9.01-8.98 (m, 1H), 8.69 (m, 1H), 8.30 (m, 1H), 7.65-7.55 (m, 1H), 7.46-7.43 (m, 1H), 7.29-7.23 (m, 2H), 7.09 (d, J = 2.8 Hz, 1H), 7.01-6.90 (m, 2H), 5.68-5.64 (m, 1H), 4.97-4.76 (m, 1H), 4.11-4.02 (m, 3H), 3.74-3.71 (m, 2H), 3.45-3.38 (m, 1H), 3.26-3.13 (m, 2H), 2.80-2.67 (m, 2H), 2.08-2.06 (m, 1H), 1.75-1.13 (m, 16H), 1.00-0.94 (m, 2H), 0.67-0.60 (m, 2H). |

Example 80: h-GLP-1 Activity Assay

Human GLP-1 agonizing activity was detected in HEK293 cells with stable expression of human GLP-1 by Cisbio cAMP Gs dynamic kit (Catalog #62AM4PEC) according to manufacturer's protocol. Briefly, cells were collected and resuspended in assay buffer containing 0.1% BSA and 0.5 mM of IBMX at concentration to $2.5\times10^5$ cells/mL. Two μL 5× compound solution and 8 μL cell suspension were added to each well of low-volume 384 white assay plate. After 30 min incubation at 37° C., 5 μL cAMP-d2 working solution and 5 μL anti-cAMP antibody-cryptate were added to each well, and incubate at room temperature for 1 hr. Series dilution of cAMP was used as standard. Human GLP-1 (7-37) was used as positive control and 10 nM human GLP-1 was set as 100% response. HTRF signals were read at 665 and 615 nm with EnVision plate reader and calculated cAMP concentration by intrapolation to the standard curve. The $EC_{50}$ value of the tested compounds was calculated by fitting the dose response curve using a 4-parameter non-linear regression routine and relative $EC_{50}$ was presented in Table 29.

As shown in Table 29, the compounds exhibit potent h-GLP-1 agonism activity ("A" means >0 nM and ≤20 nM; "B" means >20 nM and ≤100 nM; "C" means >100 nM).

TABLE 29 h-GLP-1 activity of compounds of the application

| Compound No. | h-GLP-1 Activity ($EC_{50}$, nM) |
|---|---|
| 1 | A |
| 2 | A |
| 3 | A |
| 4 | B |
| 5 | A |
| 6 | B |
| 7 | A |
| 8 | A |
| 9 | B |
| 10 | A |
| 11 | A |
| 12 | A |
| 13 | A |
| 14 | A |
| 15 | A |
| 16 | B |
| 17 | A |
| 18 | A |
| 19 | A |
| 20 | B |
| 21 | A |
| 22 | B |
| 23 | B |
| 24 | A |
| 25 | C |
| 26 | A |
| 27 | C |
| 28 | B |
| 29 | B |
| 30 | B |
| 31 | C |
| 32 | C |
| 33 | A |
| 34 | C |
| 35 | C |
| 36 | C |
| 37 | C |
| 38 | A |
| 39 | C |
| 40 | A |
| 41 | C |
| 42 | C |
| 43 | C |
| 44 | A |
| 45 | C |
| 46 | B |
| 47 | A |
| 48 | A |
| 49 | A |
| 50 | C |
| 51 | A |
| 52 | C |
| 53 | C |
| 54 | A |
| 55 | C |
| 56 | A |
| 57 | C |
| 58 | A |
| 59 | C |
| 60 | A |
| 61 | B |
| 62 | B |
| 63 | C |
| 64 | C |
| 65 | A |
| 66 | C |
| 67 | A |
| 68 | A |
| 69 | A |
| 70 | A |
| 71 | A |
| 72 | A |
| 73 | A |
| 74 | A |
| 75 | A |
| 76 | A |
| 77 | A |
| 78 | A |
| 79 | A |
| 80 | A |
| 81 | A |
| 82 | B |
| 83 | A |
| 84 | A |
| 85 | B |
| 86 | A |
| 87 | A |
| 88 | C |
| 89 | B |
| 90 | A |
| 91 | A |
| 92 | A |
| 93 | A |
| 94 | B |
| 95 | C |
| 96 | A |
| 97 | C |
| 98 | B |
| 99 | A |
| 100 | B |
| 101 | C |
| 102 | A |
| 103 | A |

Example 81: Pharmacokinetics of the Compounds of the Application

Compounds of the present application were formulated in 10% DMSO/10% Cremophor EL/15% PEG400/65% 100 mM Glycine-NaOH pH 10, and administered via oral gavage (PO) at the dosages of 5 or 10 mg per kilogram body weight in fasted SD rats. Plasma samples were collected at 0.25, 0.5, 1, 2, 4, 6, 8, and 24 hours post dosing. Compound concentration was determined by LC-MS and pharmacokinetics parameters were calculated by WinNonlin 8.2 using Non-Compartmental Analysis model. PK parameters of representative compounds were listed in Table 30.

TABLE 30

| | PO parameters | | | |
|---|---|---|---|---|
| Cmpd No | Dose (mg/kg) | $C_{max}$ (ng/mL) | AUC (ng · hr/mL) | F (%) |
| Ref. Cmpd 1 | 10 | 571 | 4528 | 10 |
| 19 | 5 | 572 | 2998 | 26 |
| 73 | 5 | 1700 | 10193 | 90 |
| 76 | 5 | 962 | 5321 | 30 |
| 90 | 5 | 1370 | 3338 | 59 |
| 91 | 5 | 738 | 2661 | 22 |

Ref. Cmpd 1:

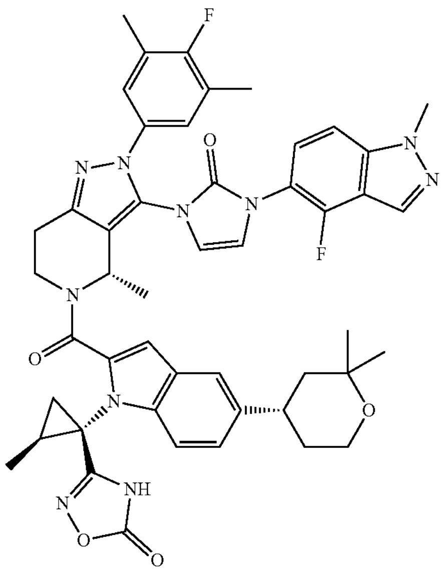 [SMILES: Cc1cc(-n2nc3c(c2-n2ccn(-c4ccc5c(cnn5C)c4F)c2=O)[C@H](C)N(C(=O)c2cc4cc([C@H]5CCOC(C)(C)C5)ccc4n2[C@@]2(c4noc(=O)[nH]4)C[C@@H]2C)CC3)cc(C)c1F]

Example 82: OATP1B1 Inhibition Assay

HEK293 cells over-expressing human OATP1B1 were used for determining the inhibitory effect of compounds of the application on OATP1B1-mediated transportation. Cells were seeded at a density of 400,000 cells per well in 24-well plates. When reaching confluence of 80~90%, cells were washed with pre-warmed assay buffer and then pre-incubated with serially diluted test compounds or negative control (NC) or positive inhibitor (PC, Rifampicin) for 30 min, followed by coincubation with the same test compound and OATP1B1 substrate estradiol 17-β-D-glucuronide for 10 min. Cells were washed with pre-cooled buffer, and lysed by freeze-thaw cycles. After extraction by mixture of 4-volume of methanol, the substrate concentration was determined by LC-MS/MS, and protein concentration was determined by BCA method. The substrate transport velocity U is calculated as $U=C_{lysate}/(P*T)$, where $C_{lysate}$ is substrate concentration in lysate, P is protein concentration in lysate, and T is incubation time. Relative transport activity Y is calculated as $Y=U_{TA}/U_{NC}$. The $IC_{50}$ value of the tested compounds was calculated by fitting Y to compound concentration using a 4-parameter non-linear regression routine in Prism.

TABLE 31

| $IC_{50}$ of OATP1B1 of Representative Compounds of the Application | |
|---|---|
| Cmpd No. | $IC_{50}$ (μM) |
| Ref. Cmpd 1 | <1 |
| 10 | >1 |
| 19 | >1 |
| 73 | >1 |
| 76 | >1 |
| 90 | >1 |
| 91 | >1 |

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A compound of Formula (I):

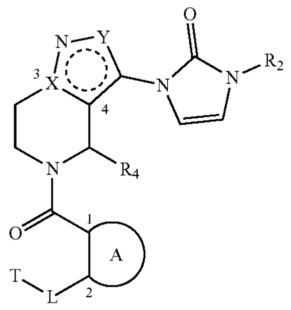

(I)

or a pharmaceutically acceptable salt, stereoisomer, or tautomer thereof, wherein:

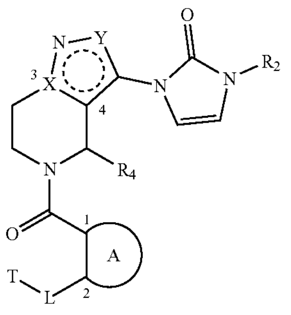

is

-continued

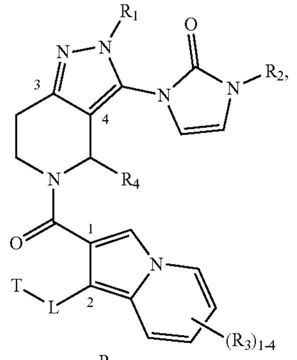

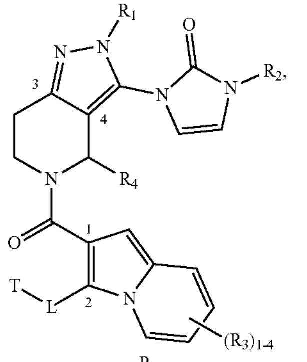

or

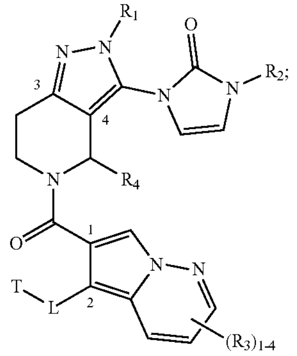

L is —$CR^5R^6$—;

$R_1$ is phenyl, wherein the phenyl is optionally substituted with 1 or more substituents independently selected from the group consisting of halogen, CN, $NO_2$, $C_1$-$C_6$ alkyl, $C_1$-$C_6$ haloalkyl, $NH_2$, $NHC_1$-$C_6$ alkyl, $N(C_1$-$C_6$ alkyl$)_2$, OH, $OC_1$-$C_6$ alkyl, $OC_1$-$C_6$ haloalkyl, and $C_3$-$C_6$ cycloalkyl;

$R_2$ is heteroaryl;

wherein the heteroaryl comprises 1 or 2 5- or 6-membered rings;

wherein the heteroaryl comprises 1, 2, or 3 heteroatoms independently selected from the group consisting of N, O, and S;

wherein the heteroaryl is optionally substituted with 1 or more substituents independently selected from the group consisting of halogen, CN, $NO_2$, $C_1$-$C_6$ alkyl, $C_1$-$C_6$ haloalkyl, $NH_2$, $NHC_1$-$C_6$ alkyl, $N(C_1$-$C_6$ alkyl$)_2$, OH, $OC_1$-$C_6$ alkyl, and $OC_1$-$C_6$ haloalkyl; and wherein each $C_1$-$C_6$ alkyl substituent of the heteroaryl is optionally and independently substituted with 1 or more independently selected $OC_1$-$C_6$ alkyl substituents;

each $R_3$ is independently halogen, $C_3$-$C_{10}$ cycloalkyl, heterocyclyl, phenyl, or heteroaryl;

wherein each $C_3$-$C_{10}$ cycloalkyl is independently a monocyclic, bridged, or spirocyclic cycloalkyl;

wherein each heterocyclyl independently comprises 1 or 2 3- to 6-membered rings;

wherein each heteroaryl independently comprises 1 or 2 5- or 6-membered rings;

wherein each heterocyclyl or heteroaryl independently comprises 1, 2, or 3 heteroatoms independently selected from the group consisting of N, O, and S; and wherein each $C_3$-$C_{10}$ cycloalkyl, heterocyclyl, phenyl, or heteroaryl is optionally and independently substituted with 1 or more substituents independently selected from the group consisting of halogen, CN, $NO_2$, $C_1$-$C_6$ alkyl, $C_1$-$C_6$ haloalkyl, $NH_2$, $NHC_1$-$C_6$ alkyl, $N(C_1$-$C_6$ alkyl$)_2$, OH, $OC_1$-$C_6$ alkyl, and $OC_1$-$C_6$ haloalkyl;

$R_4$ is CN, $C_1$-$C_6$ alkyl, $C_1$-$C_6$ haloalkyl, $NHC_1$-$C_6$ alkyl, $N(C_1$-$C_6$ alkyl$)_2$, $OC_1$-$C_6$ alkyl, or $OC_1$-$C_6$ haloalkyl;

$R_5$ and $R_6$, together with the carbon atom to which they are attached, form a $C_3$-$C_6$ cycloalkyl, wherein the $C_3$-$C_6$ cycloalkyl is optionally substituted with 1 or more substituents independently selected from the group consisting of halogen, $C_1$-$C_6$ alkyl, $C_1$-$C_6$ haloalkyl, OH, $OC_1$-$C_6$ alkyl, and $OC_1$-$C_6$ haloalkyl; and T is heteroaryl;

wherein the heteroaryl comprises 1 5- or 6-membered ring;

wherein the heteroaryl comprises 1, 2, or 3 heteroatoms independently selected from the group consisting of N, O, and S;

wherein the heteroaryl is optionally substituted with 1 or more substituents independently selected from the group consisting of halogen, $C_1$-$C_6$ alkyl, $C_1$-$C_6$ haloalkyl, OH, $OC_1$-$C_6$ alkyl, and $OC_1$-$C_6$ haloalkyl; and wherein each $C_1$-$C_6$ alkyl substituent of the heteroaryl is optionally and independently substituted with 1 or more independently selected $OC_1$-$C_6$ alkyl substituents;

with the proviso that at least 1 $R_3$ is $C_3$-$C_{10}$ cycloalkyl, heterocyclyl, phenyl, or heteroaryl.

2. The compound of claim 1, or a pharmaceutically acceptable salt, stereoisomer, or tautomer thereof, wherein:

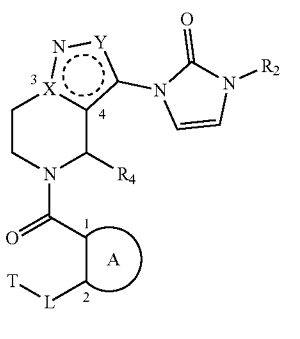

is

-continued

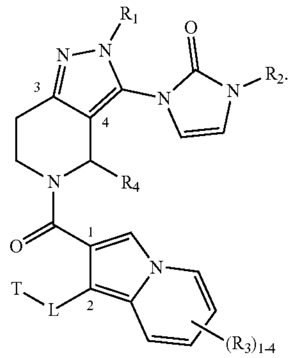

3. The compound of claim 1, or a pharmaceutically acceptable salt, stereoisomer, or tautomer thereof, wherein:

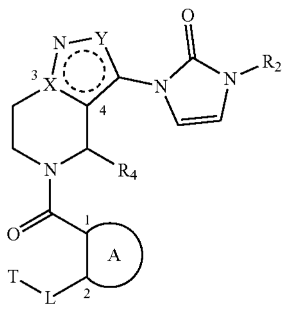

is

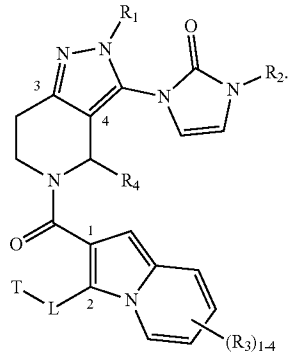

4. The compound of claim 1, or a pharmaceutically acceptable salt, stereoisomer, or tautomer thereof, wherein:

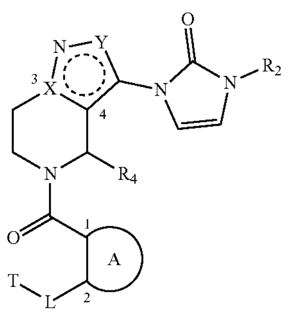

is

-continued

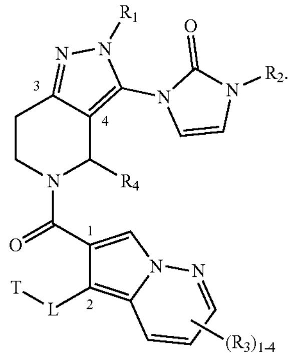

5. The compound of claim 1, or a pharmaceutically acceptable salt, stereoisomer, or tautomer thereof, wherein $R_1$ is phenyl, wherein the phenyl is optionally substituted with 1 or more substituents independently selected from the group consisting of halogen, $C_1$-$C_6$ alkyl, and $C_3$-$C_6$ cycloalkyl.

6. The compound of claim 1, or a pharmaceutically acceptable salt, stereoisomer, or tautomer thereof, wherein $R_2$ is heteroaryl;

wherein the heteroaryl comprises 2 5- or 6-membered rings;

wherein the heteroaryl comprises 1, 2, or 3 heteroatoms independently selected from the group consisting of N, O, and S; and wherein the heteroaryl is optionally substituted with 1 or more substituents independently selected from the group consisting of halogen and $C_1$-$C_6$ alkyl.

7. The compound of claim 6, or a pharmaceutically acceptable salt, stereoisomer, or tautomer thereof, wherein $R_2$ is indazolyl.

8. The compound of claim 1, or a pharmaceutically acceptable salt, stereoisomer, or tautomer thereof, wherein $R_4$ is straight-chain $C_1$-$C_6$ alkyl or branched $C_3$-$C_6$ alkyl.

9. The compound of claim 8, or a pharmaceutically acceptable salt, stereoisomer, or tautomer thereof, wherein $R_4$ is $CH_3$.

10. The compound of claim 1, or a pharmaceutically acceptable salt, stereoisomer, or tautomer thereof, wherein $R_5$ and $R_6$, together with the carbon atom to which they are attached, form a cyclopropyl.

11. The compound of claim 1, or a pharmaceutically acceptable salt, stereoisomer, or tautomer thereof, wherein T is oxadiazolyl substituted with OH.

12. The compound of claim 1, wherein the compound is of Formula (Ib1), Formula (Ib2), Formula (Ib3), Formula (Ib4), Formula (Ib5), Formula (Ib6), Formula (Ib7), Formula (Ib8), Formula (Ib9), Formula (Ib10), or Formula (Ib11):

(Ib1)
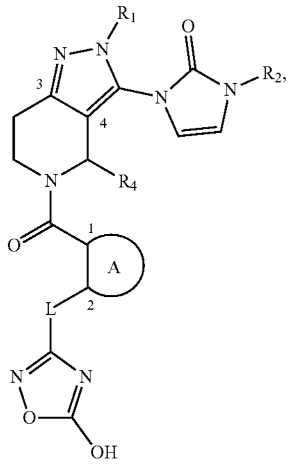
(Ib2)
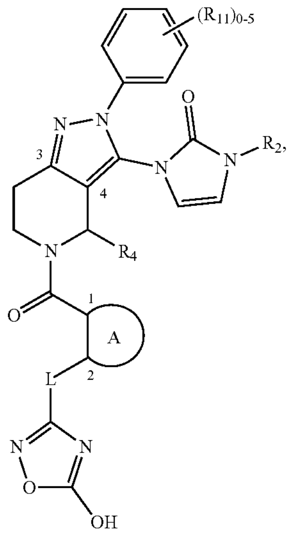
(Ib3)
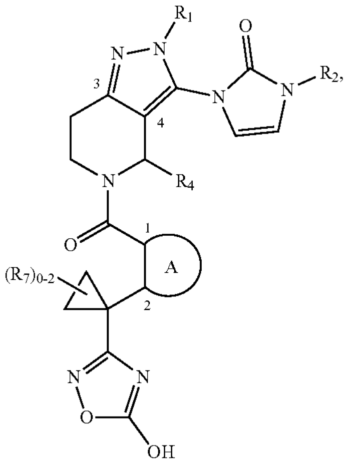
-continued
(Ib4)
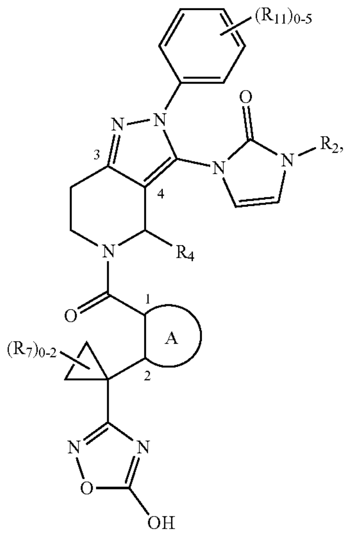
(Ib5)
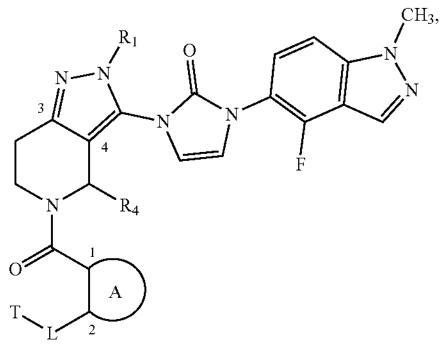
(Ib6)
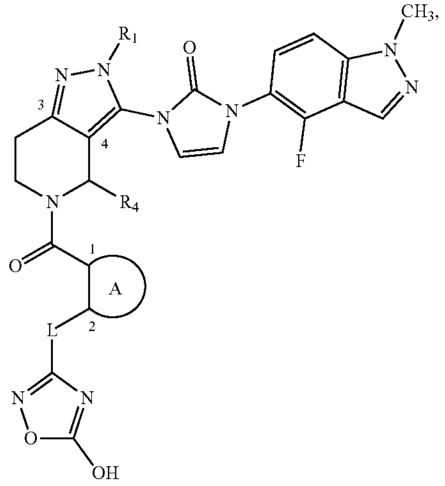

-continued (Ib7)

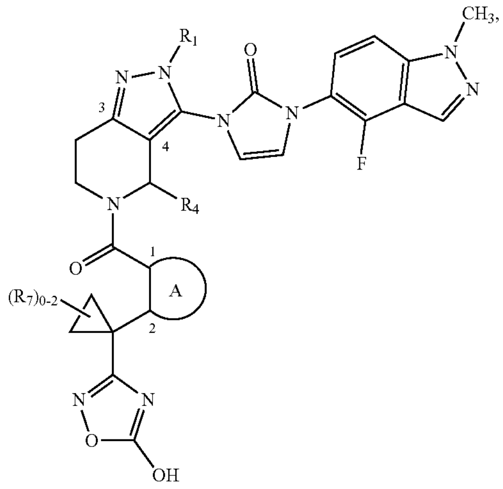

(Ib8)

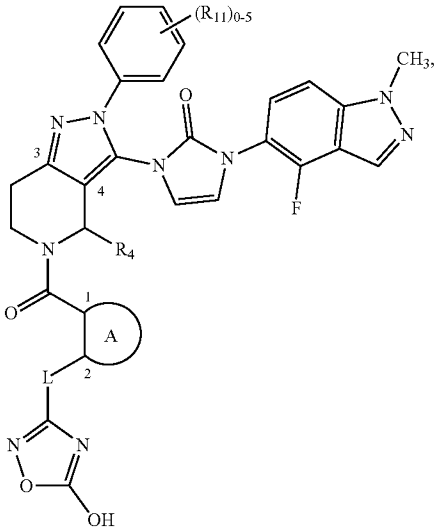

(Ib9)

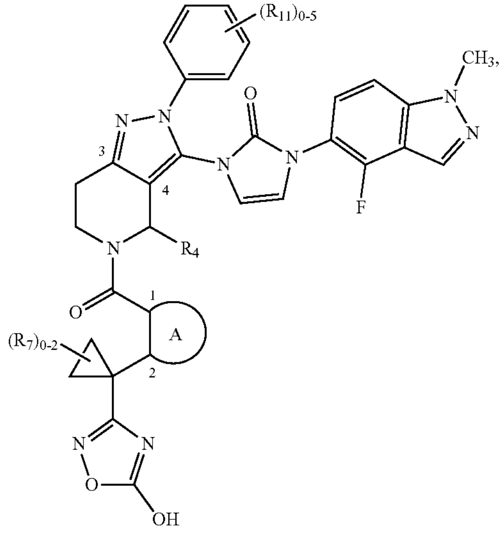

-continued (Ib10)

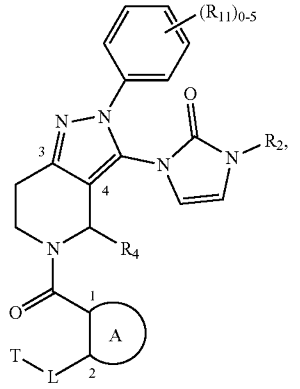

or (Ib11)

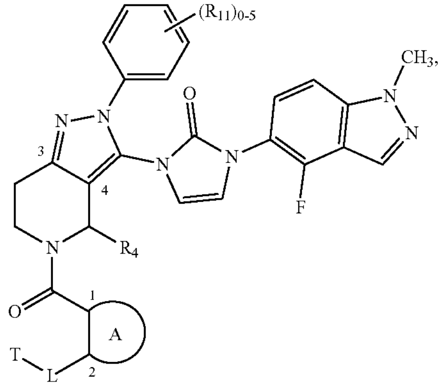

or a pharmaceutically acceptable salt, stereoisomer, or tautomer thereof, wherein:

each $R_7$ is independently halogen, $C_1$-$C_6$ alkyl, $C_1$-$C_6$ haloalkyl, OH, $OC_1$-$C_6$ alkyl, or $OC_1$-$C_6$ haloalkyl; and each $R_{11}$ is independently halogen, CN, $NO_2$, $C_1$-$C_6$ alkyl, $C_1$-$C_6$ haloalkyl, $NH_2$, $NHC_1$-$C_6$ alkyl, $N(C_1$-$C_6$ alkyl$)_2$, OH, $OC_1$-$C_6$ alkyl, $OC_1$-$C_6$ haloalkyl, or $C_3$-$C_6$ cycloalkyl.

13. The compound of claim 12, wherein the compound is of Formula (Ib9):

(Ib9)

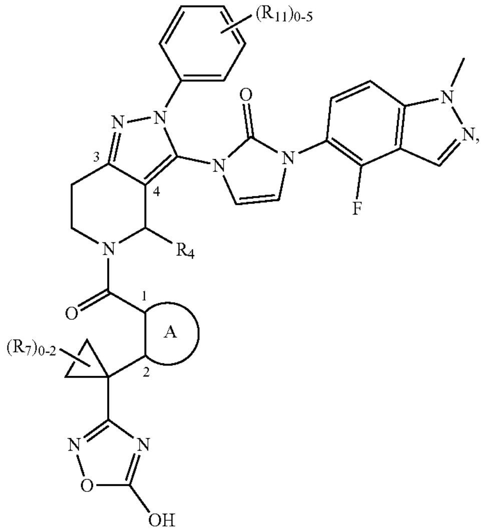

or a pharmaceutically acceptable salt, stereoisomer, or tautomer thereof.
14. The compound of claim 1, wherein the compound is selected from the group consisting of:
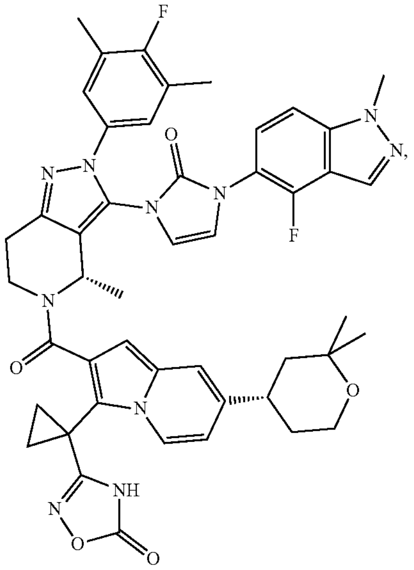
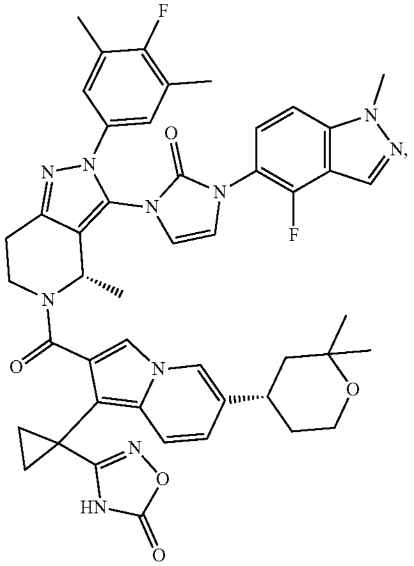
-continued
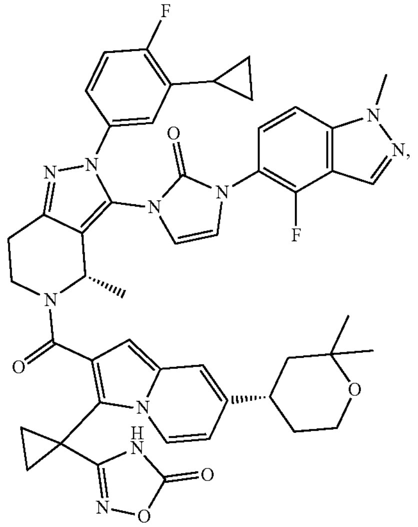
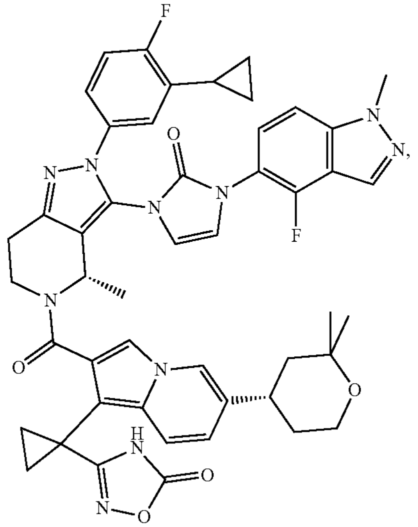
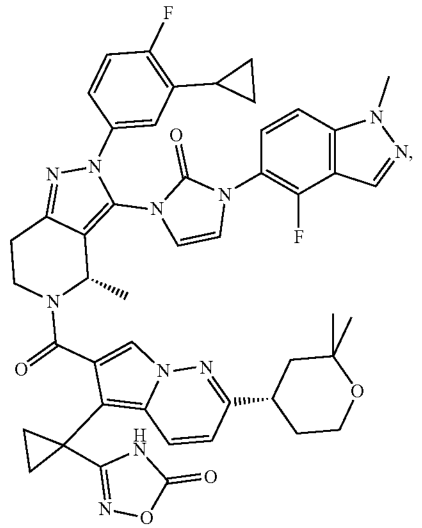
and -continued
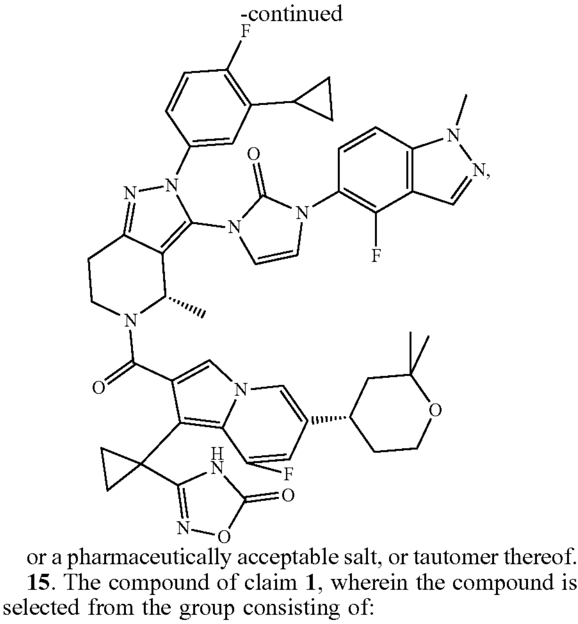
or a pharmaceutically acceptable salt, or tautomer thereof.
15. The compound of claim 1, wherein the compound is selected from the group consisting of:
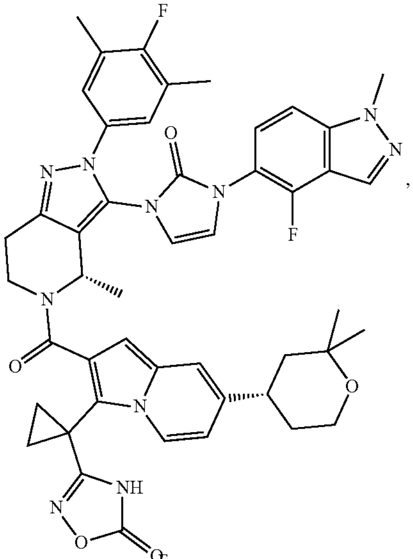
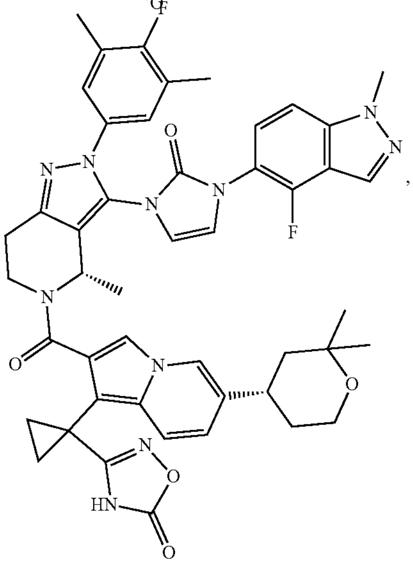
-continued
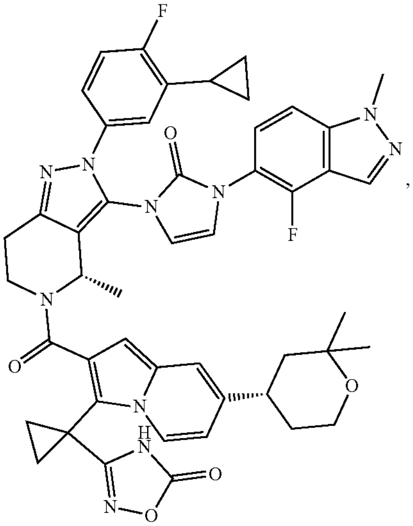
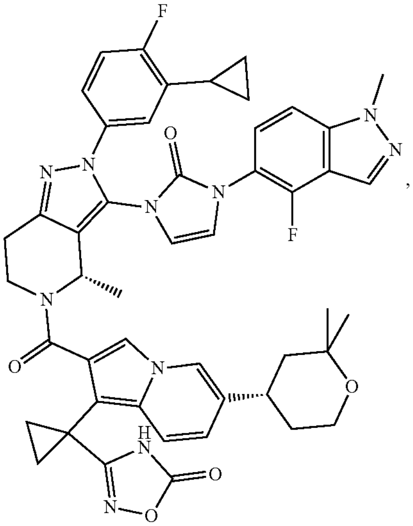
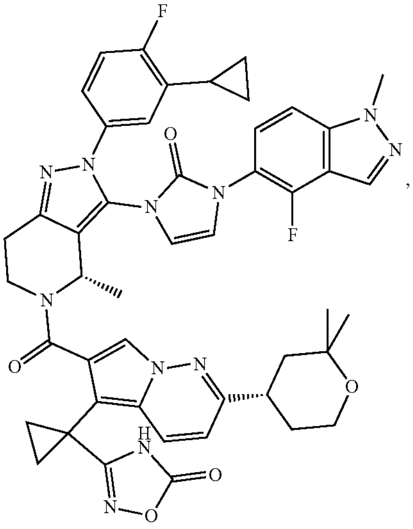

-continued
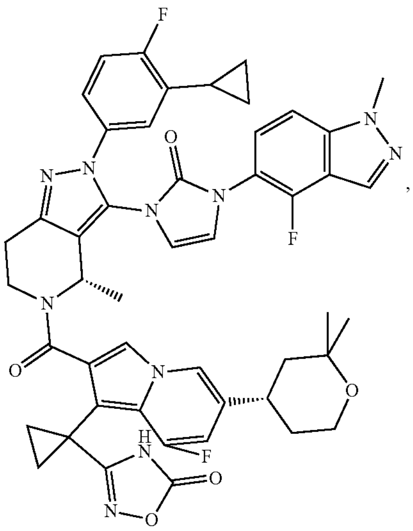
,
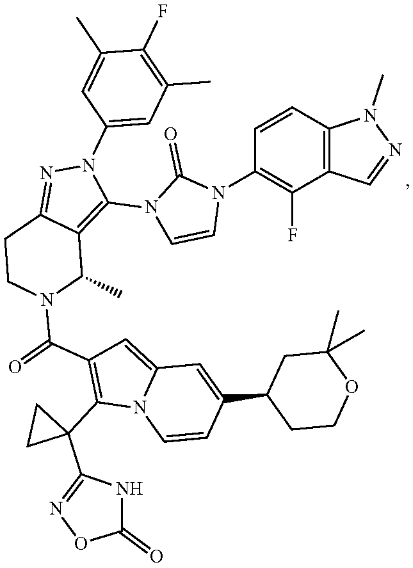
,
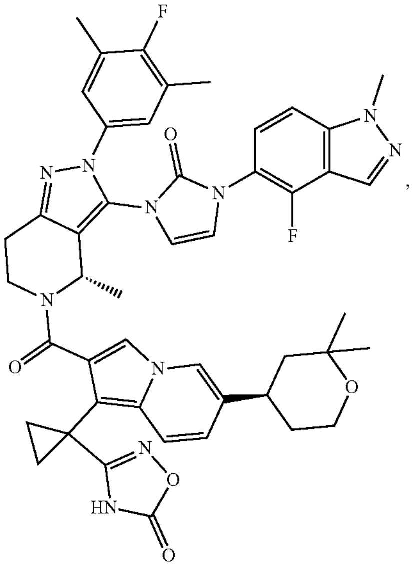
,
-continued
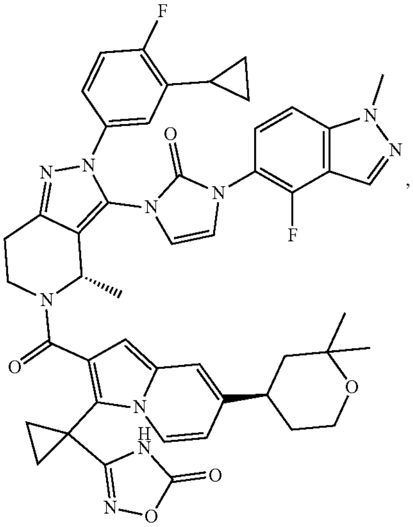
,
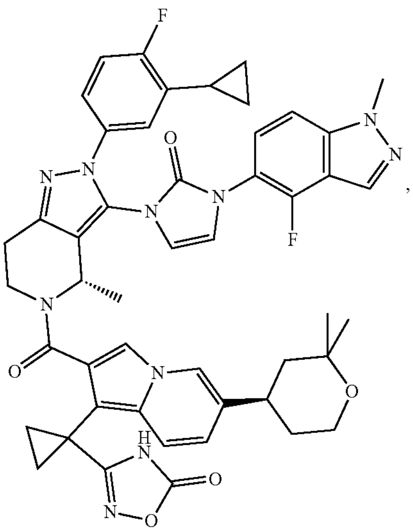
,
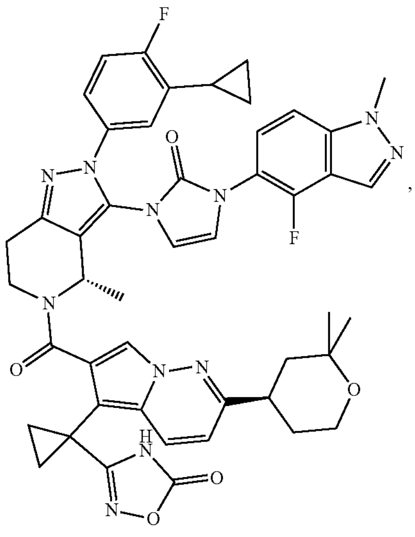
, and -continued
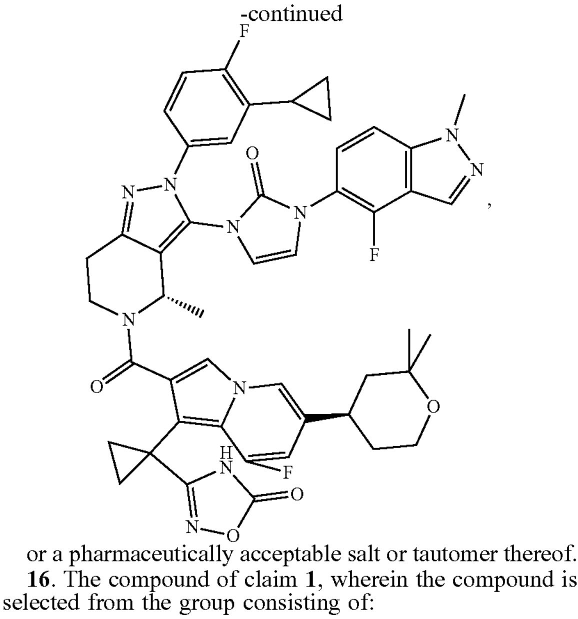
,
or a pharmaceutically acceptable salt or tautomer thereof.
16. The compound of claim 1, wherein the compound is selected from the group consisting of:
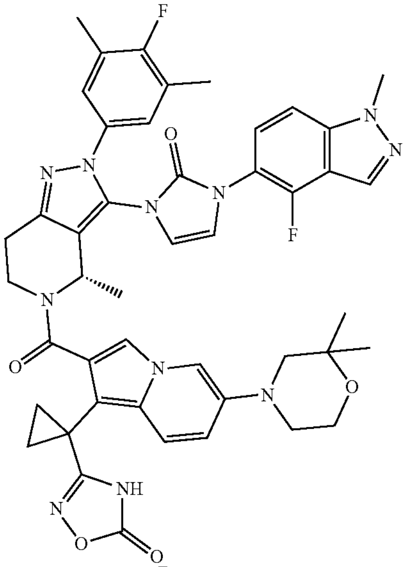
,
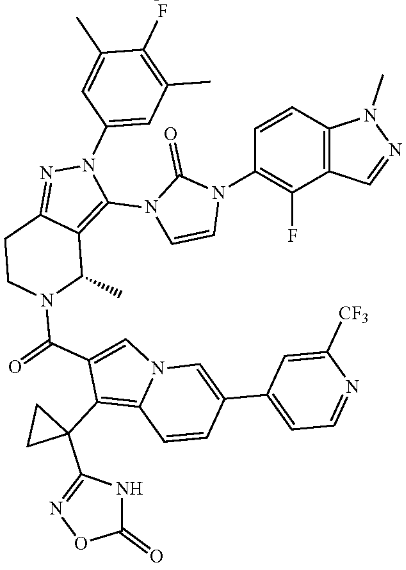
,
-continued
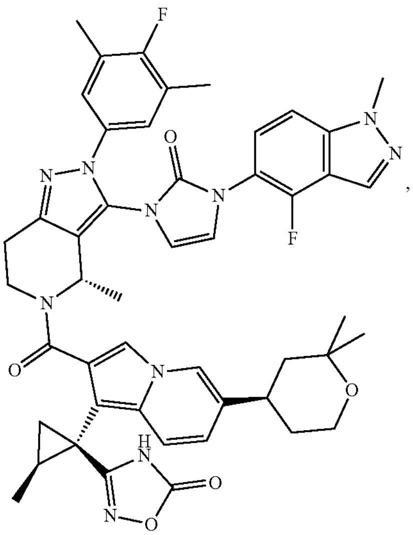
,
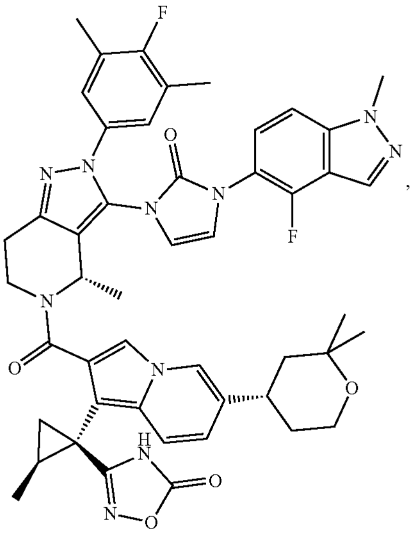
,
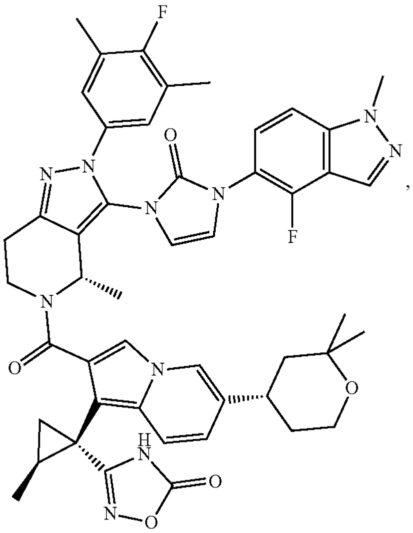
, -continued
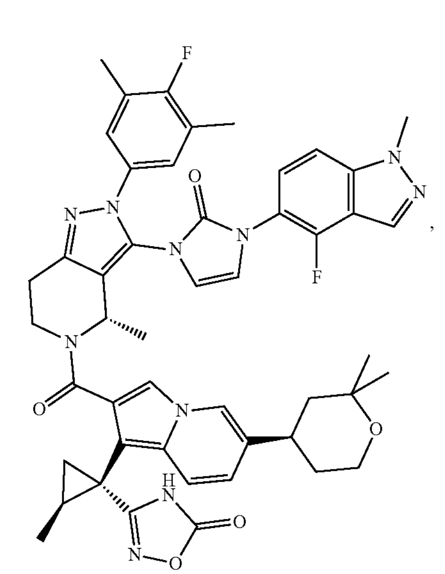
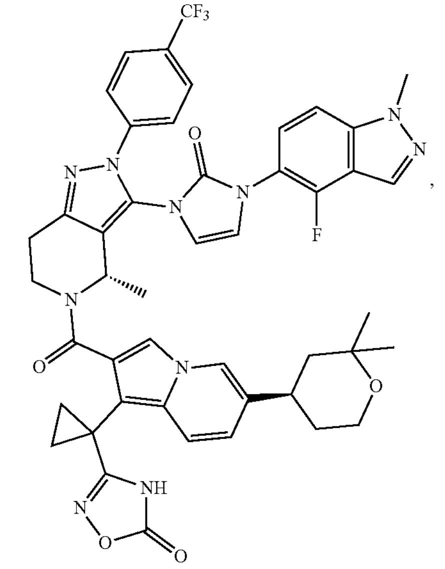
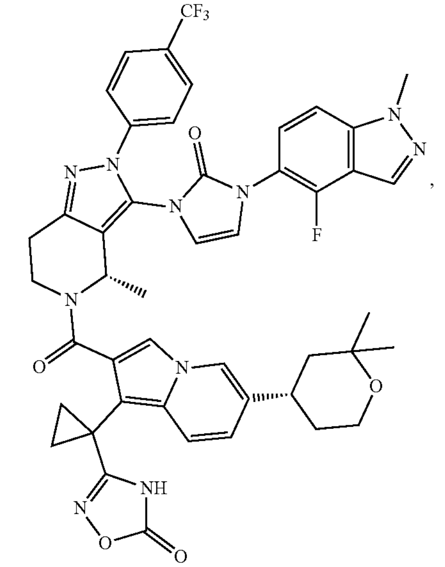
-continued
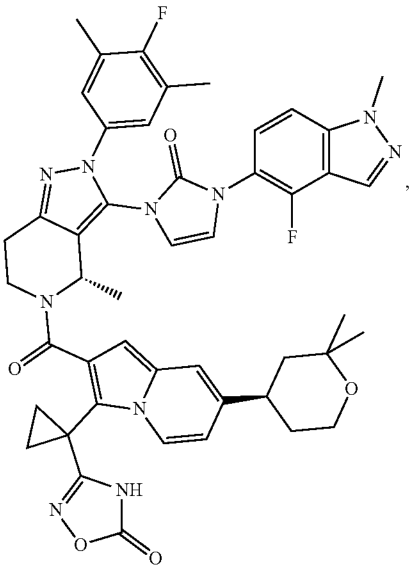
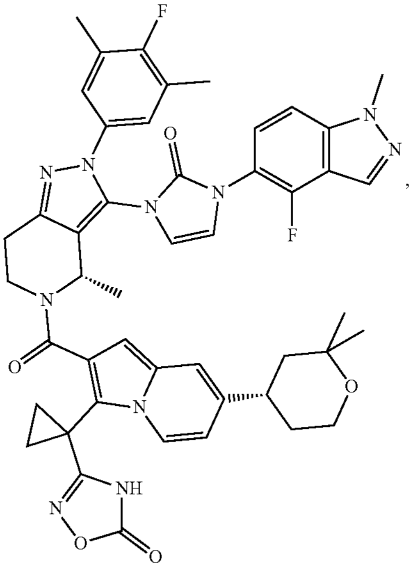
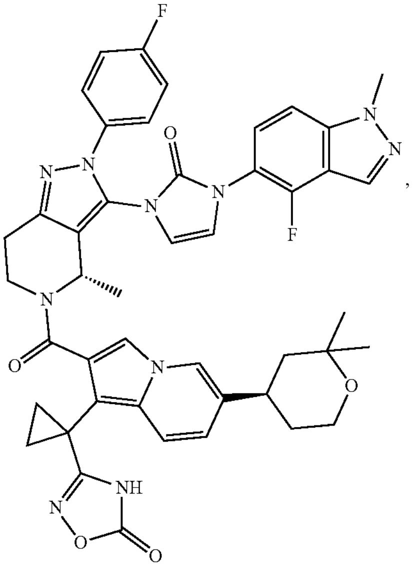

-continued
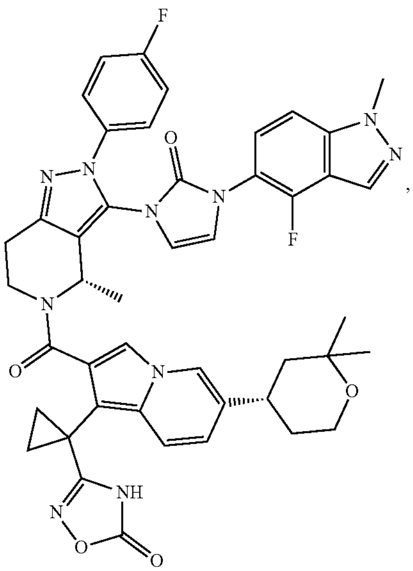
,
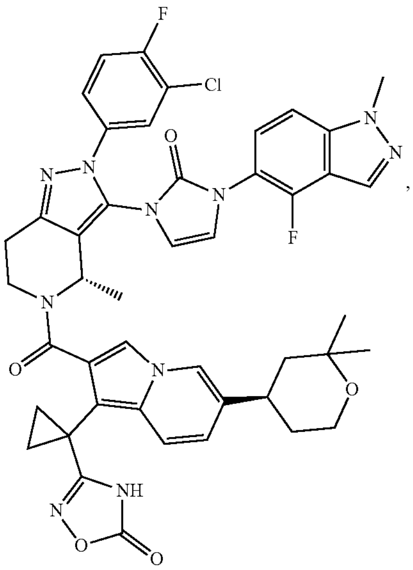
,
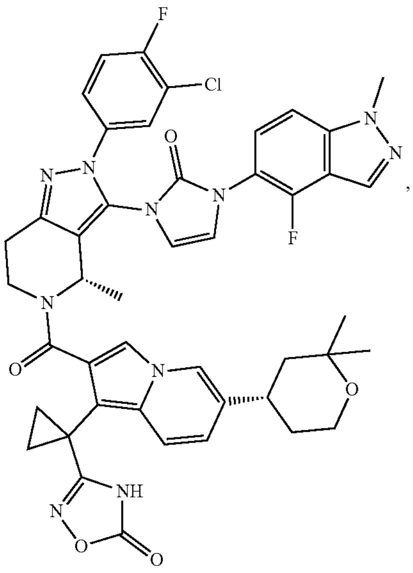
,
-continued
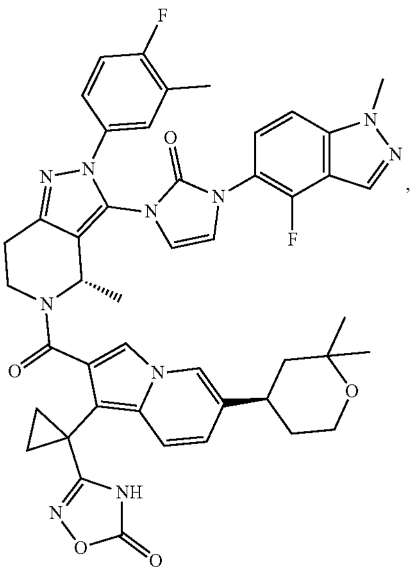
,
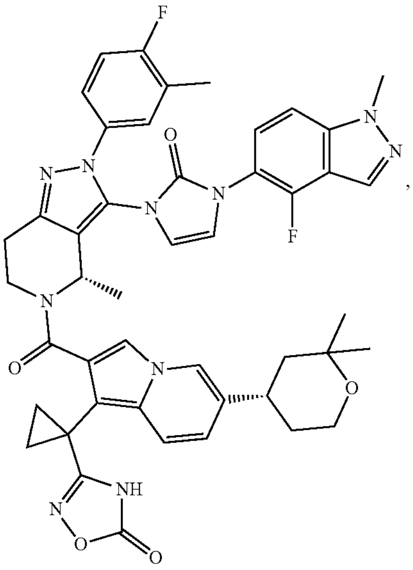
,
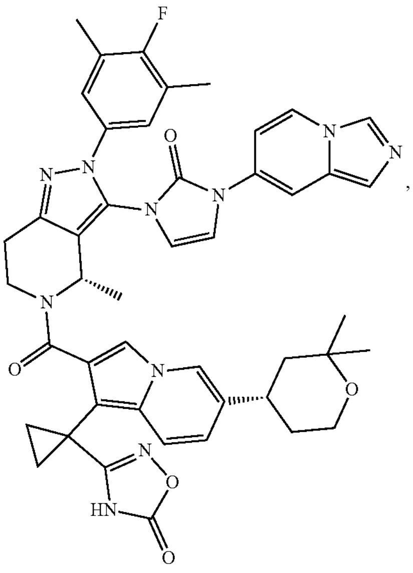
, -continued
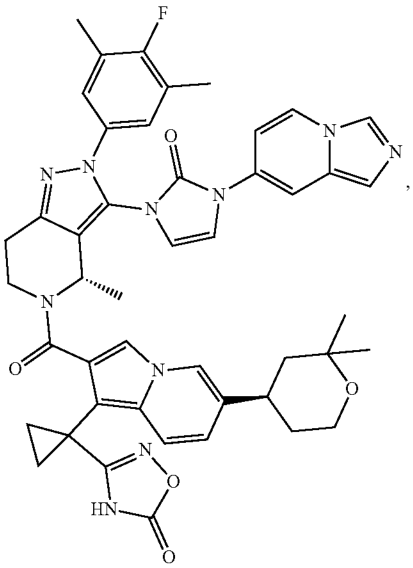
,
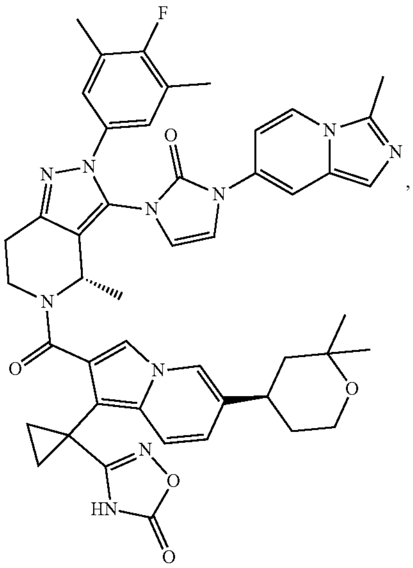
,
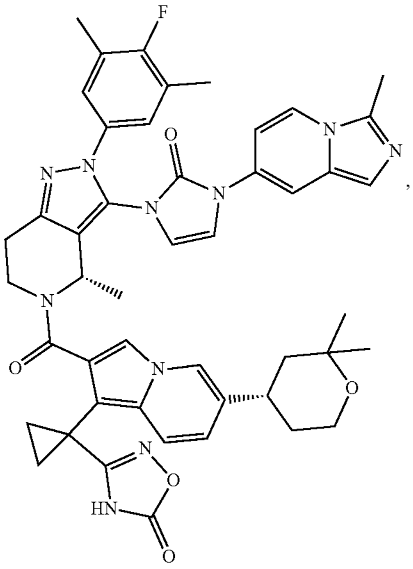
,
-continued
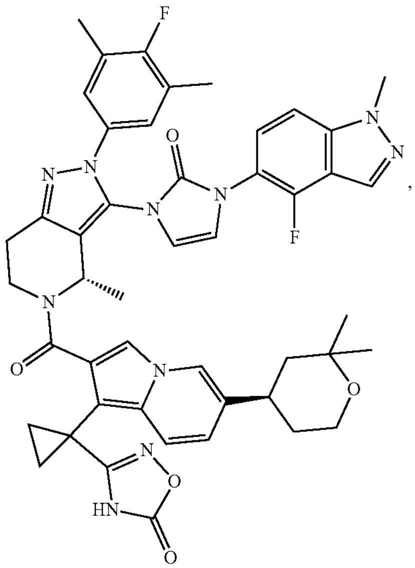
,
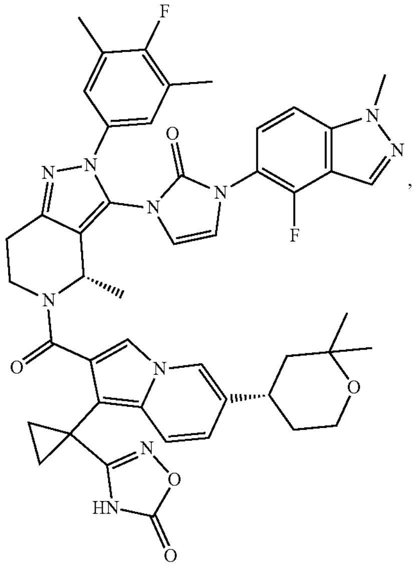
,
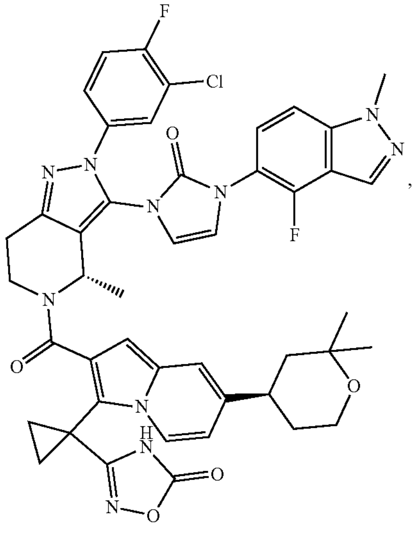
, -continued
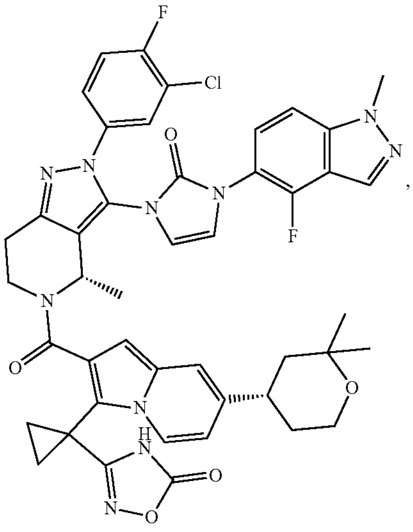
,
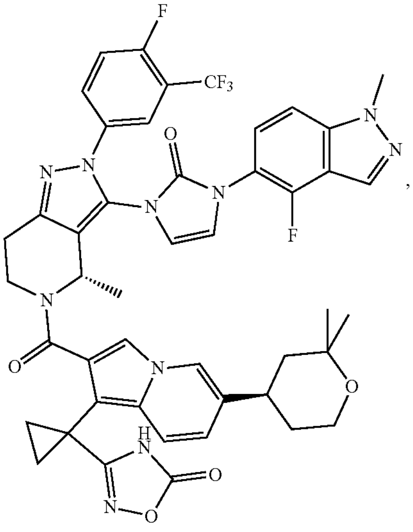
,
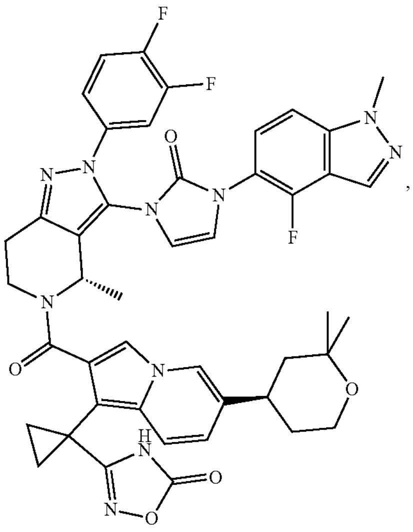
,
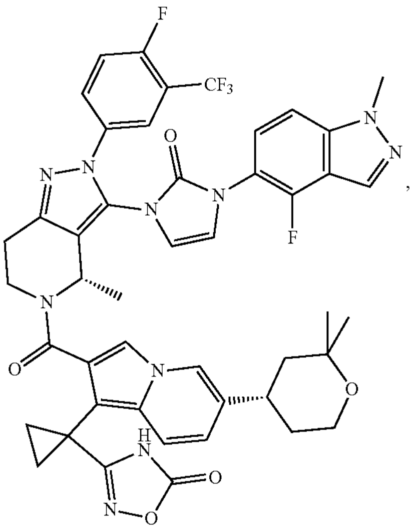
,
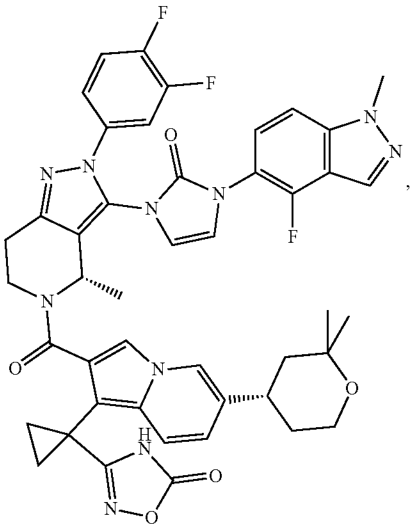
,
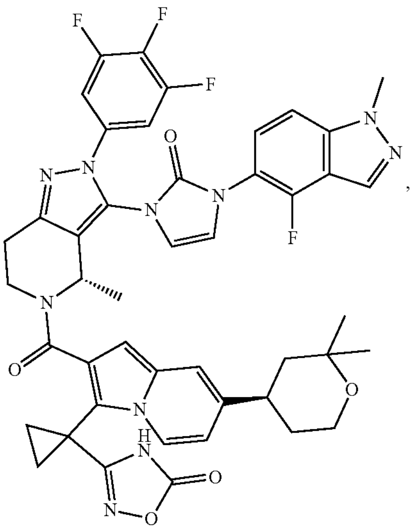
,

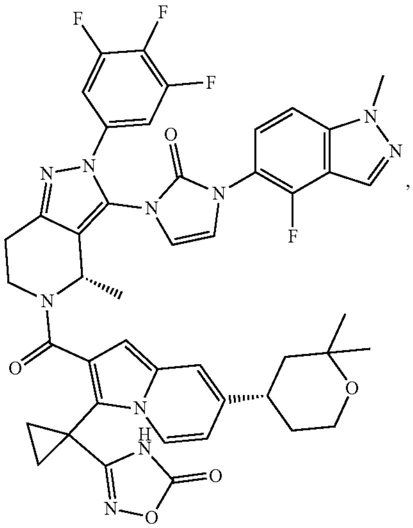
,
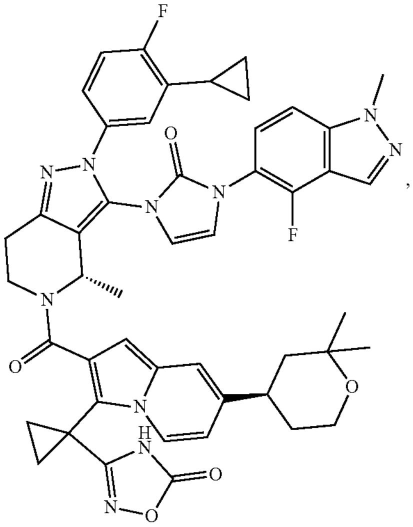
,
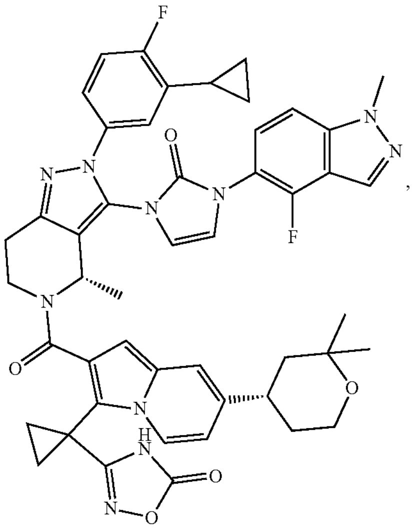
,
-continued
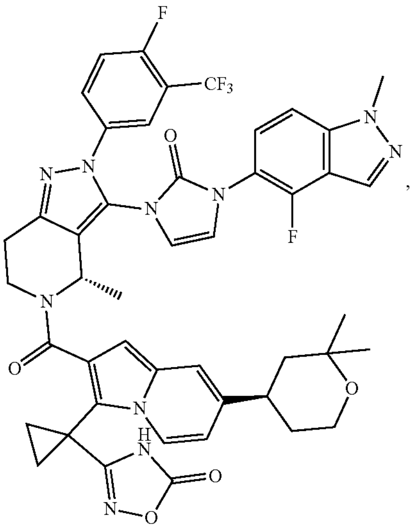
,
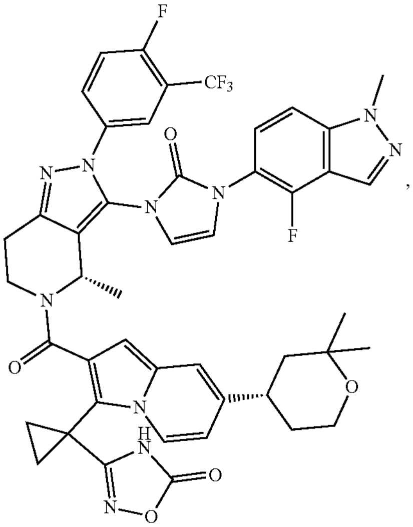
,
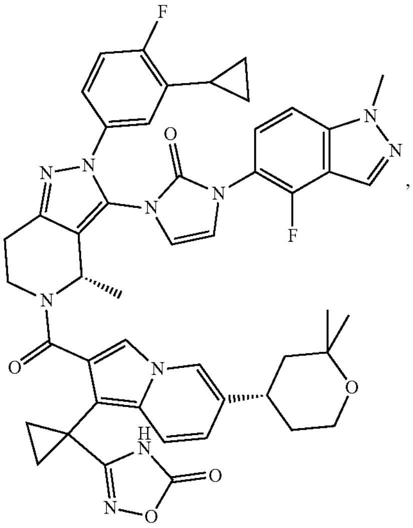
, -continued
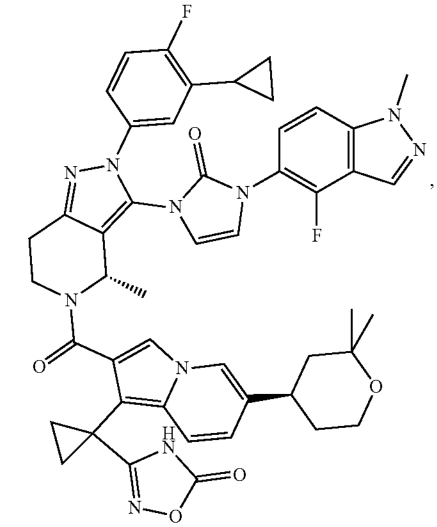
,
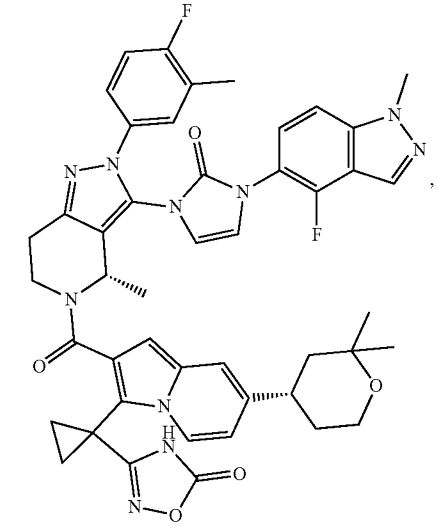
,
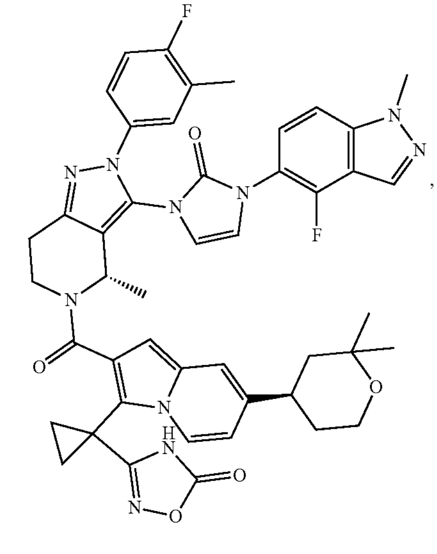
,
-continued
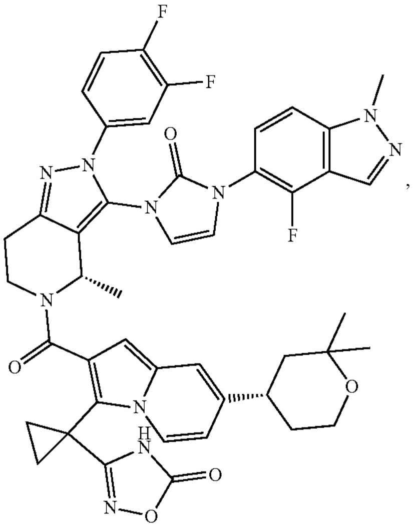
,
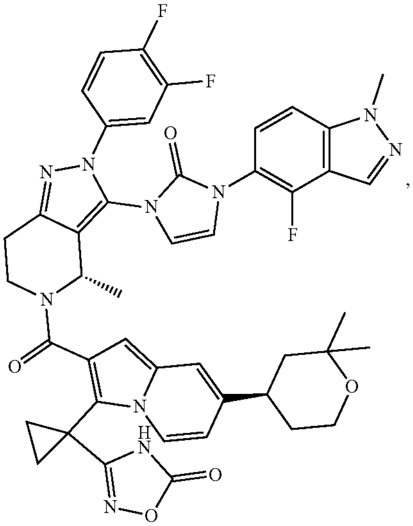
,
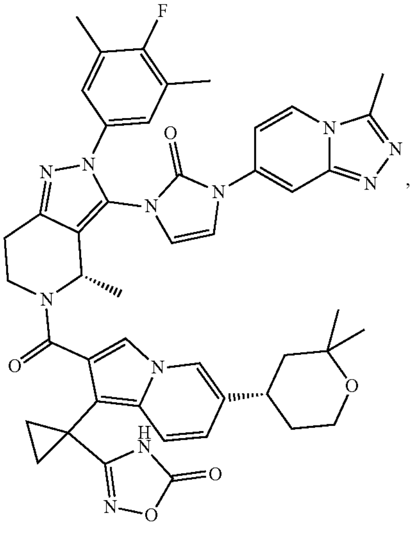
, -continued
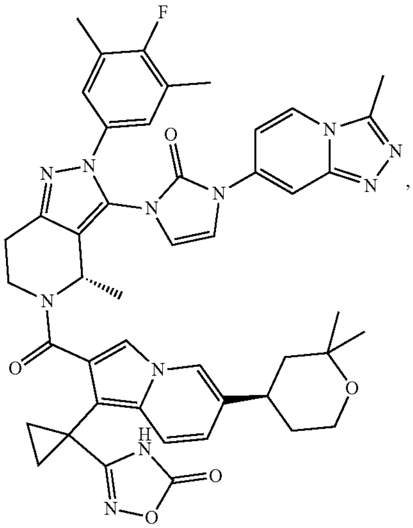
,
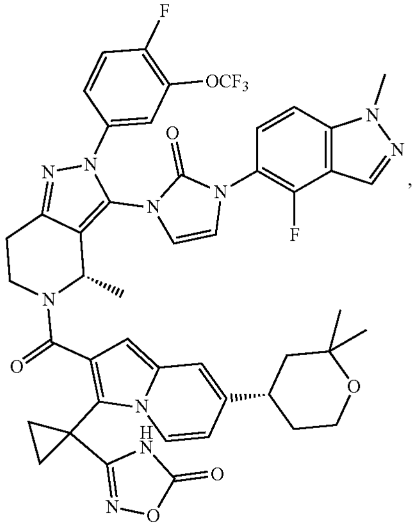
,
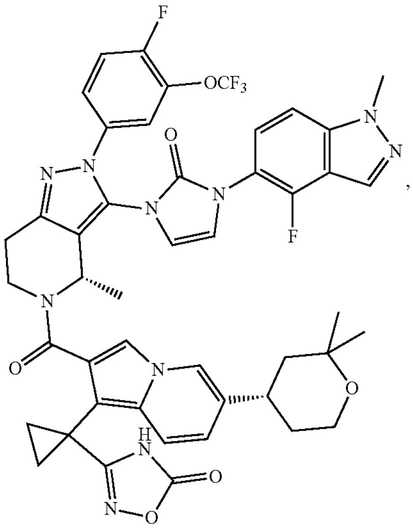
,
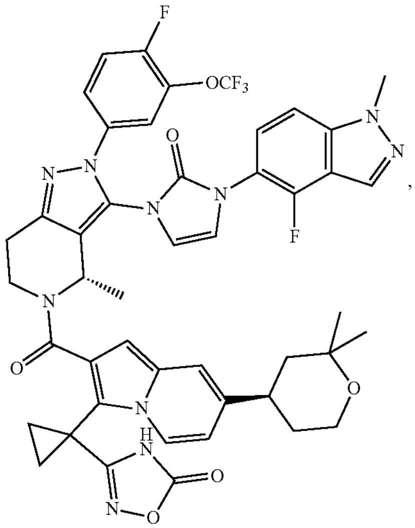
,
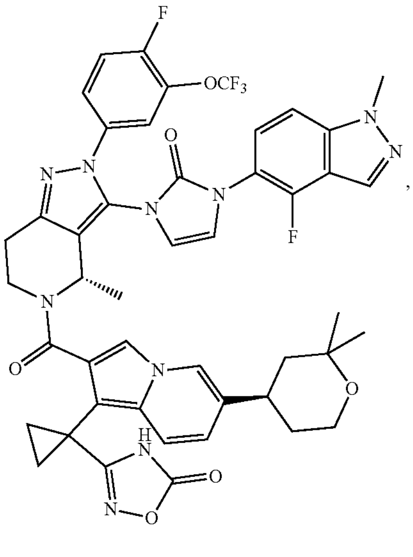
,
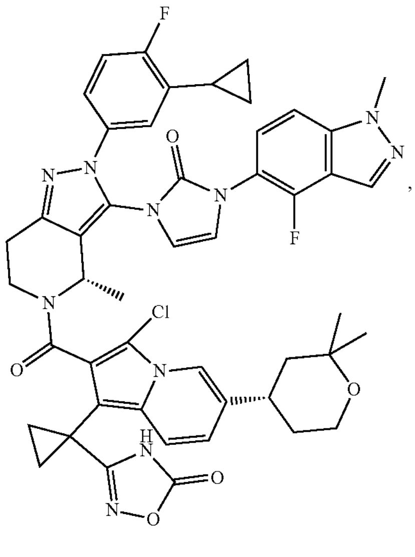
,
-continued -continued
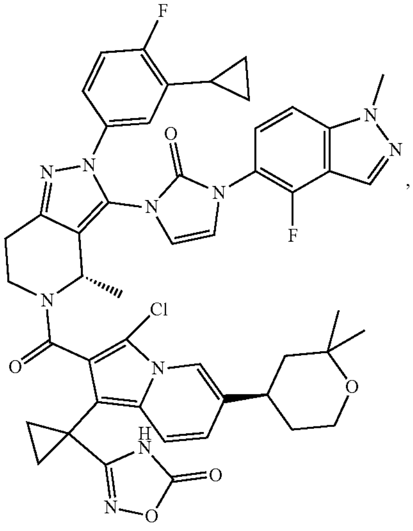,
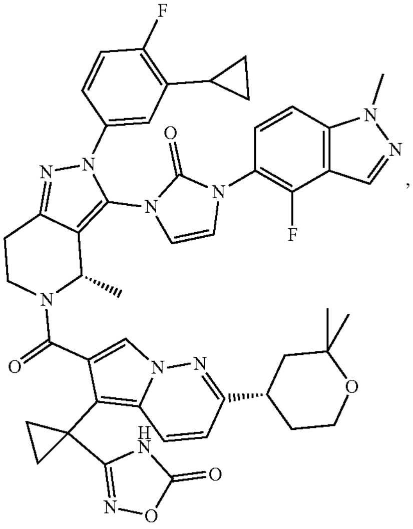,
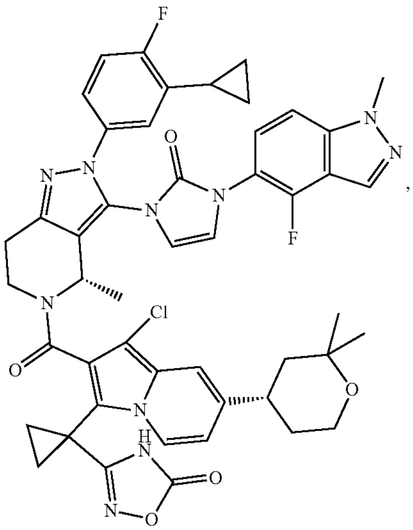,
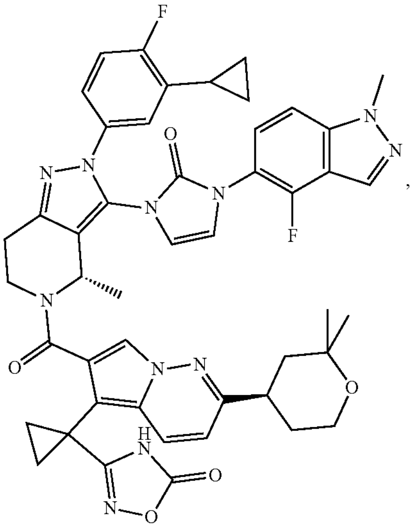,
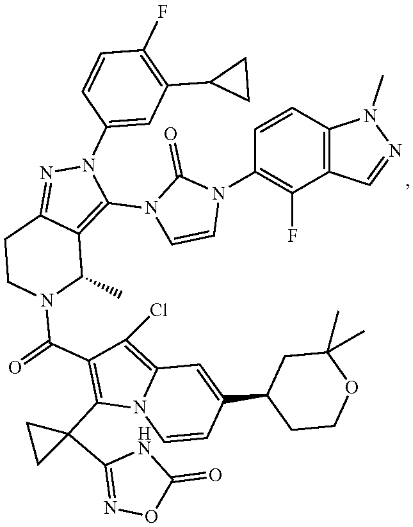,
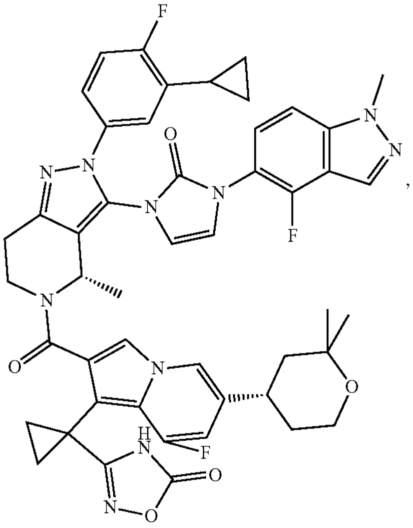, -continued
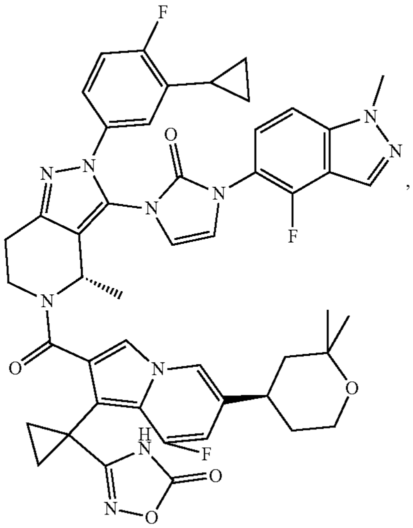
,
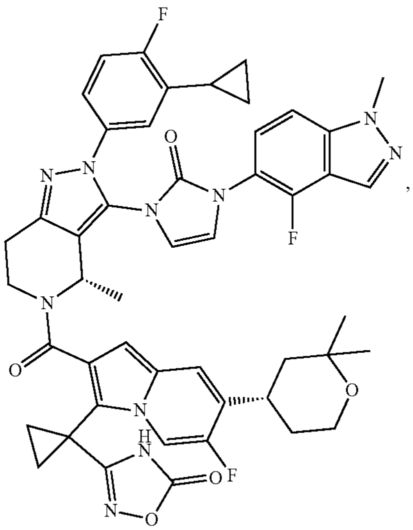
,
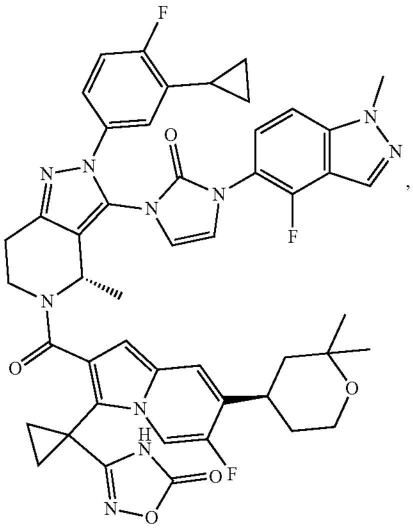
,
-continued
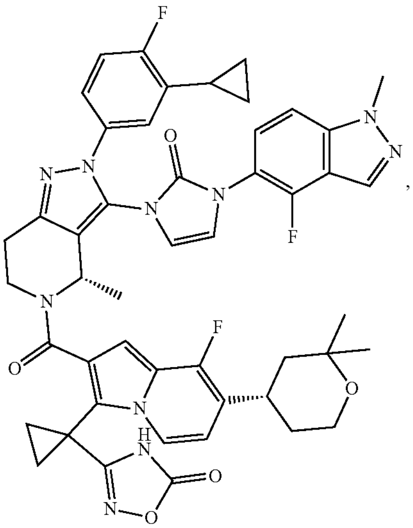
,
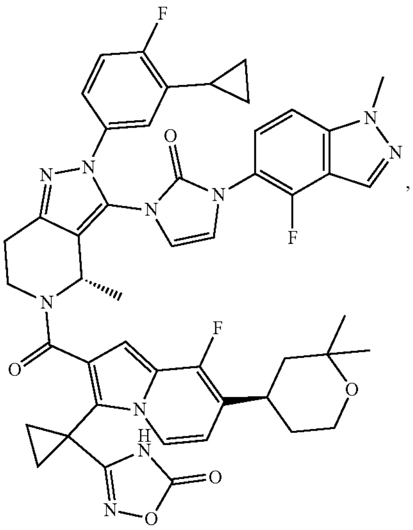
,
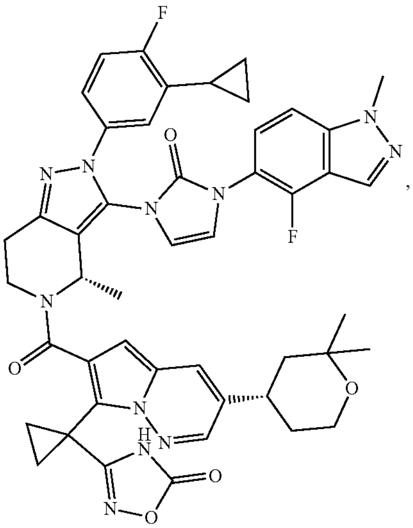
, -continued

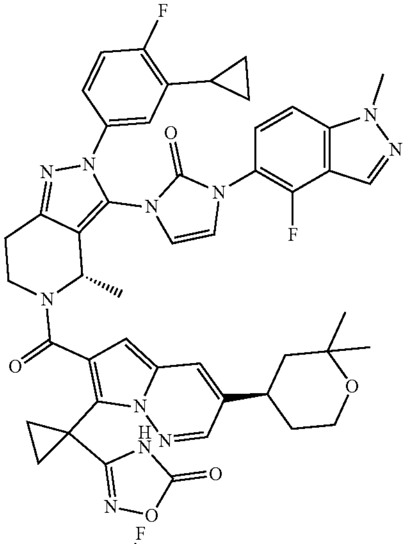

,

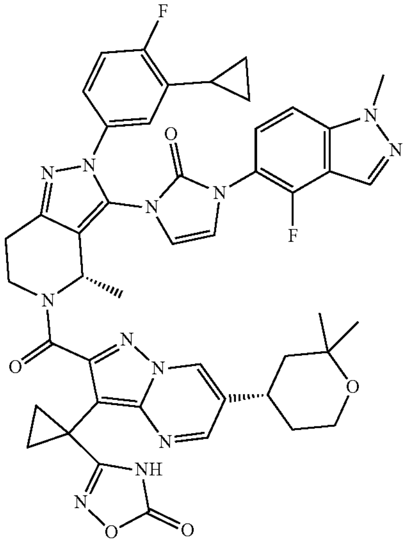

, and

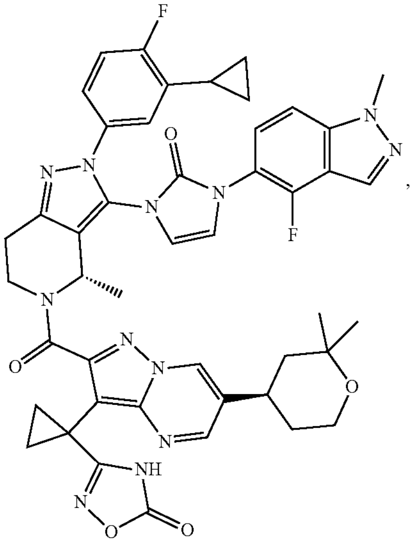

, or a pharmaceutically acceptable salt or tautomer thereof.

17. A pharmaceutical composition comprising the compound of claim 1, or a pharmaceutically acceptable salt, stereoisomer, or tautomer thereof, and a pharmaceutically acceptable diluent, carrier, or excipient.

18. A pharmaceutical composition comprising the compound of claim 16, or a pharmaceutically acceptable salt, stereoisomer, or tautomer thereof, and a pharmaceutically acceptable diluent, carrier, or excipient.

19. A pharmaceutical composition comprising the compound of claim 14, or a pharmaceutically acceptable salt, stereoisomer, or tautomer thereof, and a pharmaceutically acceptable diluent, carrier, or excipient.

20. A method for modulating glucagon-like peptide-1 receptor activity in a subject in need thereof, wherein the method comprises administering to the subject a therapeutically effective amount of the compound of claim 1, or a pharmaceutically acceptable salt, stereoisomer, or tautomer thereof.

21. The method of claim 20, wherein the subject has a glucagon-like peptide-1 receptor-mediated condition, disease, or disorder selected from the group consisting of Alzheimer's disease, atherosclerosis, a cardiac arrhythmia, congestive heart failure, coronary heart disease, dementia, diabetes, diabetic kidney disease, hypercholesterolemia, hyperlipidemia, hypertension, hypertriglyceridemia, a liver disease, obesity, Parkinson's disease, and stroke.

22. A method for modulating glucagon-like peptide-1 receptor activity in a subject in need thereof, wherein the method comprises administering to the subject a therapeutically effective amount of the compound of claim 16, or a pharmaceutically acceptable salt, stereoisomer, or tautomer thereof.

23. The method of claim 22, wherein the subject has a glucagon-like peptide-1 receptor-mediated condition, disease, or disorder selected from the group consisting of Alzheimer's disease, atherosclerosis, a cardiac arrhythmia, congestive heart failure, coronary heart disease, dementia, diabetes, diabetic kidney disease, hypercholesterolemia, hyperlipidemia, hypertension, hypertriglyceridemia, a liver disease, obesity, Parkinson's disease, and stroke.

24. A method for modulating glucagon-like peptide-1 receptor activity in a subject in need thereof, wherein the method comprises administering to the subject a therapeutically effective amount of the compound of claim 14, or a pharmaceutically acceptable salt, stereoisomer, or tautomer thereof.

25. The method of claim 24, wherein the subject has a glucagon-like peptide-1 receptor-mediated condition, disease, or disorder selected from the group consisting of Alzheimer's disease, atherosclerosis, a cardiac arrhythmia, congestive heart failure, coronary heart disease, dementia, diabetes, diabetic kidney disease, hypercholesterolemia, hyperlipidemia, hypertension, hypertriglyceridemia, a liver disease, obesity, Parkinson's disease, and stroke.

* * * * *

UNITED STATES PATENT AND TRADEMARK OFFICE

CERTIFICATE OF CORRECTION

PATENT NO. : 11,584,751 B1
APPLICATION NO. : 17/516932
DATED : February 21, 2023
INVENTOR(S) : Ren et al.

It is certified that error appears in the above-identified patent and that said Letters Patent is hereby corrected as shown below:

On the Title Page

Item (72), replace:
"(72) Inventors: Zaifang Ren, Shanghai (CN); Xuefeng Sun, Shanghai (CN); Jingye Zhou, Shanghai (CN); Qing Xu, Shanghai (CN)"

With:
--(72) Inventors: Zaifang Ren, Shanghai (CN); Xuefeng Sun, Shanghai (CN); Jingye Zhou, Shanghai (CN)--

The first or sole Notice should read --

Subject to any disclaimer, the term of this patent is extended or adjusted under 35 U.S.C. 154(b) by 0 days.

Signed and Sealed this
Seventeenth Day of October, 2023

Katherine Kelly Vidal

Katherine Kelly Vidal
*Director of the United States Patent and Trademark Office*